United States Patent
Huang et al.

(10) Patent No.: US 12,404,239 B2
(45) Date of Patent: Sep. 2, 2025

(54) MODULATORS OF BCL6 AS LIGAND DIRECTED DEGRADERS

(71) Applicants: Celgene Corporation, Summit, NJ (US); Bristol-Myers Squibb Company, Princeton, NJ (US)

(72) Inventors: Dehua Huang, San Diego, CA (US); Matthew David Alexander, San Diego, CA (US); Brandon Wade Whitefield, San Diego, CA (US); Hunter Paul Shunatona, San Diego, CA (US); Dharmpal S. Dodd, Escondido, CA (US); Deborah S. Mortensen, San Diego, CA (US); Giulianna Miseo, San Diego, CA (US); Natalie Holmberg-Douglas, San Diego, CA (US); Jayce Rhodes, San Diego, CA (US); Jennifer Griffin, San Diego, CA (US)

(73) Assignees: Celgene Corporation, Princeton, NJ (US); Bristol-Myers Squibb Company, Princeton, NJ (US)

( * ) Notice: Subject to any disclaimer, the term of this patent is extended or adjusted under 35 U.S.C. 154(b) by 274 days.

(21) Appl. No.: 18/140,129

(22) Filed: Apr. 27, 2023

(65) Prior Publication Data
US 2024/0025851 A1    Jan. 25, 2024

Related U.S. Application Data

(60) Provisional application No. 63/336,104, filed on Apr. 28, 2022.

(51) Int. Cl.
C07D 209/34    (2006.01)
(52) U.S. Cl.
CPC ................. *C07D 209/34* (2013.01)

(58) Field of Classification Search
CPC .................................................. C07D 209/34
USPC ............................................................ 514/418
See application file for complete search history.

(56) References Cited

U.S. PATENT DOCUMENTS 7,534,798 B2 *    5/2009    Balan .................. C07D 413/12
                                                              544/328
2021/0330672 A1    10/2021    Franken et al.

OTHER PUBLICATIONS

International Search Report and Written Opinion in PCT/US2023/020129 dated Aug. 10, 2023, Applicant: Celgene Corporation, Examiner: Gerda Flanter, 11 pages.
Kamada et al., "Discovery of a B-Cell Lymphoma 6 Protein-Protein Interaction Inhibitor by a Biophysics-Driven Fragment-Based Approach," J. Med. Chem., 2017, 60(10):4358-4368.
Teng et al., "Rationally Designed Covalent BCL6 Inhibitor that Targets a Tyrosine Residue in the Homodimer Interface," ACS Med. Chem. Lett., 2020, 11(6): 1269-1273.
Bellenie et al., "Achieving In Vivo Target Depletion through the Discovery and Optimization of Benzimidazolone BCL6 Degraders," J. Med. Chem., 2020, 63:4047-4068.
Kerres et al., "Chemically Induced Degradation of the Oncogenic Transcription Factor BCL6," Cell Reports, 2007, 20:2860-2875.
McCoull et al., "Development of a Novel B-Cell Lymphoma 6 (BCL6) Protac to Provide Insight into Small Molecule Targeting of BCL6," ACS Chem. Biol., 2018, 13:3131-3141.
U.S. Appl. No. 19/076,183, filed Mar. 11, 2025, Inventors: Dehua Huang et al., now abandoned.

* cited by examiner

*Primary Examiner* — Niloofar Rahmani
(74) *Attorney, Agent, or Firm* — McNeill PLLC

(57)    ABSTRACT

Provided herein are compounds and compositions thereof for modulating BCL6. In some embodiments, the compounds and compositions are provided for treatment of cancer or an autoimmune disease.

10 Claims, No Drawings

MODULATORS OF BCL6 AS LIGAND DIRECTED DEGRADERS

CROSS-REFERENCE TO RELATED APPLICATIONS

This application claims the benefit of priority of U.S. Provisional Application No. 63/336,104, filed on Apr. 28, 2022, which is incorporated herein by reference herein in its entirety for any purpose.

FIELD

The present disclosure relates generally to compounds, compositions, and methods for their preparation and use of the compounds and compositions for treating cancer or an autoimmune disease.

BACKGROUND

BCL6 (B cell lymphoma 6) is a member of the BTB/POZ-zinc finger family that contains an N-terminal BTB/POZ domain and a zinc finger at the C-terminus. As a transcription factor for T follicular helper (Tfh) cells, BCL6 is required for germinal center (GC) formation of naïve B cells and hence antibody affinity maturation. BCL6 was initially discovered as an oncogene in diffuse large B-cell lymphomas (DLBCLs) and its role has been implicated in many types of diseases including B-acute lymphoblastic leukemia, chronic myeloid leukemia, breast cancer, and non-small lung cancer (NSCLC) (Cardenas et al., *Clin Cancer Res* 2017, 23, 885-893). The N-terminal BTB/POZ domain binds to and recruits of co-repressor molecules such as SMRT, NCOR1, and BCOR, to form class I and II histone deacetylase complexes, and the C-terminal zinc fingers bind to specific DNA recognition sequences (Yang et al., *Cell Dev. Biol.* 2019, 7, 272). Upon binding to its target genes and forming complexes, BCL6 reduces RNA expression of its targets, including several key tumor suppressors. Overexpression of BCL6, common in malignancies such as Non-Hodgkin's lymphoma (NHL), leads to ectopic repression of cell cycle and DNA repair checkpoint proteins, causing unrestricted cell proliferation and tumorgenesis.

GC responses are known to result in increased production of pathogenic autoantibodies which are responsible for several diseases, suggesting that methods to suppress or degrade BCL6 hold potential therapeutic applicability. Structural characterization of the cocrystal structures of the BCL6 BTB/POZ domain and co-repressors has shown that binding occurs at the lateral grooves formed by the interface between BCL6 BTB/POZ homodimers (Melnick et al., *Mol. Cell Biol.* 2002, 22, 1804-1818; Ghetu et al., *Mol. Cell.* 2008, 29, 384-391). Since then, specific ligands that bind to this site have been investigated, purposed to exploit the binding affinity towards the lateral grooves to render BCL6 as a druggable target.

Protein degradation is a highly regulated and essential process that maintains cellular homeostasis. Selective identification and removal of damaged, misfolded, or excess proteins is achieved through the ubiquitin-proteasome pathway (UPP). The UPP is central to the regulation of almost all cellular processes. Ubiquitination of the protein is accomplished by an E3 ubiquitin ligase that binds to a protein and adds ubiquitin molecules to the protein, thus marking the protein for proteasome degradation.

Harnessing the UPP for therapeutic use has received significant interest (Zhou et al., *Mol. Cell* 2000, 6, 751-756). One promising therapy uses proteolysis targeting chimeras, commonly referred to as PROTACs, to effect removal of unwanted proteins by protein degradation (Scheepstra et al., *Comp. Struct. Biotech. J.* 2019, 17, 160-176). PROTACS are ligand directed degraders that bring together an E3 ligase and a target protein that is to be degraded. These bivalent molecules usually consist of an E3 ligase ligand connected through a linker moiety to small molecule that binds to the target protein. A PROTAC positions the E3 ligase at the appropriate distance and orientation to the target protein, allowing the latter to be ubiquitinated. The ubiquitinated target protein is subsequently recognized by the proteasome, where it is degraded.

Accordingly, in one aspect, provided herein are compounds that target BCL6 for degradation.

SUMMARY

Described herein, in certain embodiments, are compounds and compositions thereof for modulating BCL6. In various embodiments, the compounds and compositions thereof may be used for treatment of cancer.

The present embodiments can be understood more fully by reference to the detailed description and examples, which are intended to exemplify non-limiting embodiments.

Embodiment 1. A compound of Formula (IA):

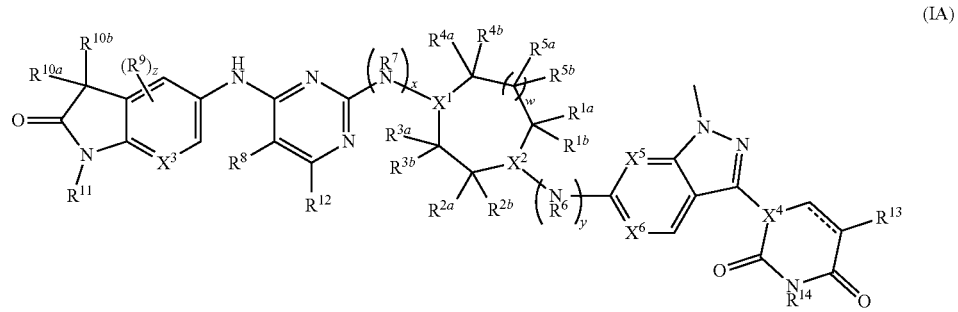

(IA)

or a pharmaceutically acceptable salt thereof, wherein:

$X^1$ and $X^2$ are each independently N or CH, provided that at least one of $X^1$ and $X^2$ is N;

$R^{1a}$ and $R^{1b}$ are each independently H, halo, or $C_1$-$C_6$ alkyl;

$R^{2a}$ and $R^{2b}$ are each independently H, $C_1$-$C_6$ alkyl, —O($C_1$-$C_6$ alkyl), —OH, halo, $C_1$-$C_6$ haloalkyl, or $C_1$-$C_6$ alkyl-OH, or $R^{2a}$ and $R^{2b}$ are taken together with the carbon atom to which they are attached to form a spiro $C_3$-$C_5$ cycloalkyl, or $R^{2a}$ and $R^{2b}$ are taken together to form oxo;

or $R^{1a}$ and $R^{2a}$ are taken together to form a bridging $C_2$-$C_3$ alkylene;

$R^{3a}$ and $R^{3b}$ are each independently H, halo, or $C_1$-$C_6$ alkyl;

$R^{4a}$ and $R^{4b}$ are each independently H, halo, or $C_1$-$C_6$ alkyl, or $R^{4a}$ and $R^{4b}$ are taken together with the carbon atom to which they are attached to form a spiro $C_3$-$C_5$ cycloalkyl;

$R^{5a}$ and $R^{5b}$ are each independently H, halo, or $C_1$-$C_6$ alkyl;

w is 0 or 1;

$R^6$ is H or $C_1$-$C_6$ alkyl;

$R^7$ is H or $C_1$-$C_6$ alkyl;

x and y are each independently 0 or 1, provided that x and y are not both 1;

$R^8$ is Cl or —CN;

$R^9$ is F;

$X^3$ is N or CH;

z is 0 or 1;

$R^{10a}$ and $R^{10b}$ are each independently H or halo;

$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;

$R^{12}$ is H, halo, or $C_1$-$C_6$ alkyl;

$R^{13}$ is H or halo;

$R^{14}$ is H or $C_1$-$C_6$ alkyl;

$X^4$ is N or $CR^{15}$;

$R^{15}$ is H or $C_1$-$C_6$ alkyl;

$X^5$ and $X^6$ are each independently N or CH; and

=== is a single or double bond;

wherein one or more hydrogen atoms in the compound are optionally replaced by deuterium.

Embodiment 2. The compound of embodiment 1, or a pharmaceutically acceptable salt thereof, wherein the compound is of Formula (I):

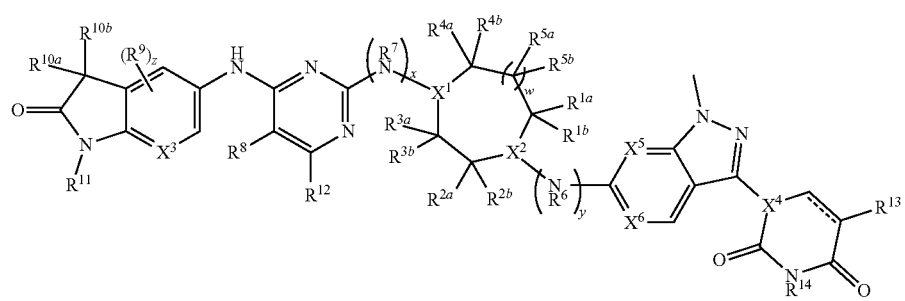

(I)

wherein:

$X^1$ and $X^2$ are each independently N or CH, provided that at least one of $X^1$ and $X^2$ is N;

$R^{1a}$ and $R^{1b}$ are each independently H, halo, or $C_1$-$C_6$ alkyl;

$R^{2a}$ and $R^{2b}$ are each independently H, $C_1$-$C_6$ alkyl, —OH, halo, or $C_1$-$C_6$ alkyl-OH, or $R^{2a}$ and $R^{2b}$ are taken together with the carbon atom to which they are attached to form a spiro $C_3$-$C_5$ cycloalkyl, or $R^{2a}$ and $R^{2b}$ are taken together to form oxo;

or $R^{1a}$ and $R^{2a}$ are taken together to form a bridging $C_2$-$C_3$ alkylene;

$R^{3a}$ and $R^{3b}$ are each independently H, halo, or $C_1$-$C_6$ alkyl;

$R^{4a}$ and $R^{4b}$ are each independently H, halo, or $C_1$-$C_6$ alkyl, or $R^{4a}$ and $R^{4b}$ are taken together with the carbon atom to which they are attached to form a spiro $C_3$-$C_5$ cycloalkyl;

$R^{5a}$ and $R^{5b}$ are each independently H, halo, or $C_1$-$C_6$ alkyl;

w is 0 or 1;

$R^6$ is H or $C_1$-$C_6$ alkyl;

$R^7$ is H or $C_1$-$C_6$ alkyl;

x and y are each independently 0 or 1, provided that x and y are not both 1;

$R^8$ is Cl or —CN;

$R^9$ is F;

$X^3$ is N or CH;

z is 0 or 1;

$R^{10a}$ and $R^{10b}$ are each independently H or halo;

$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;

$R^{12}$ is H, halo, or $C_1$-$C_6$ alkyl;

$R^{13}$ is H or halo;

$R^{14}$ is H or $C_1$-$C_6$ alkyl;

$X^4$ is N or $CR^{15}$;

$R^{15}$ is H or $C_1$-$C_6$ alkyl;

$X^5$ and $X^6$ are each independently N or CH; and

=== is a single or double bond;

wherein one or more hydrogen atoms in the compound are optionally replaced by deuterium.

Embodiment 3. The compound of embodiment 1 or 2, or a pharmaceutically acceptable salt thereof, wherein:

$X^1$ is CH and $X^2$ is N; or $X^1$ is N and $X^2$ is CH.

Embodiment 4. The compound of embodiment 1 or 2, or a pharmaceutically acceptable salt thereof, wherein:

$X^1$ and $X^2$ are each N.

Embodiment 5. The compound of any one of embodiments 1-4, or a pharmaceutically acceptable salt thereof, wherein:

$R^{1a}$ and $R^{1b}$ are each independently H, halo, or $C_1$-$C_3$ alkyl.

Embodiment 6. The compound of any one of embodiments 1-5, or a pharmaceutically acceptable salt thereof, wherein:
  $R^{2a}$ and $R^{2b}$ are each independently H, $C_1$-$C_3$ alkyl, —OH, halo, or $C_1$-$C_3$ alkyl-OH,
  or $R^{2a}$ and $R^{2b}$ are taken together with the carbon atom to which they are attached to form a spiro $C_3$-$C_4$ cycloalkyl,
  or $R^{2a}$ and $R^{2b}$ are taken together to form oxo.

Embodiment 7. The compound of any one of embodiments 1-6, or a pharmaceutically acceptable salt thereof, wherein:
  $R^{3a}$ and $R^{3b}$ are each independently H, halo, or $C_1$-$C_3$ alkyl.

Embodiment 8. The compound of any one of embodiments 1-7, or a pharmaceutically acceptable salt thereof, wherein:
  $R^{4a}$ and $R^{4b}$ are each independently H, halo, or $C_1$-$C_3$ alkyl,
  or $R^{4a}$ and $R^{4b}$ are taken together with the carbon atom to which they are attached to form a spiro $C_3$-$C_4$ cycloalkyl.

Embodiment 9. The compound of embodiment 8, or a pharmaceutically acceptable salt thereof, wherein:
  $R^{5a}$ and $R^{5b}$ are each independently H, halo, or $C_1$-$C_3$ alkyl.

Embodiment 10. The compound of any one of embodiments 1-9, or a pharmaceutically acceptable salt thereof, wherein

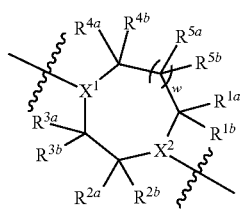

is:

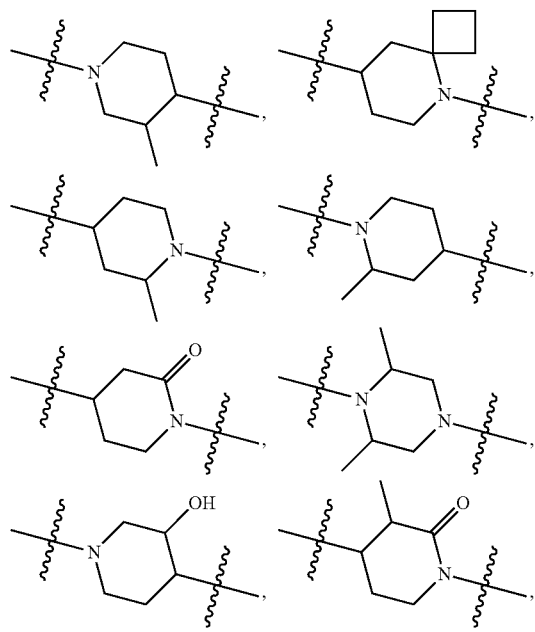

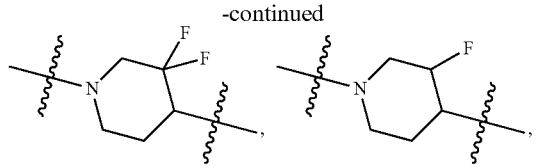

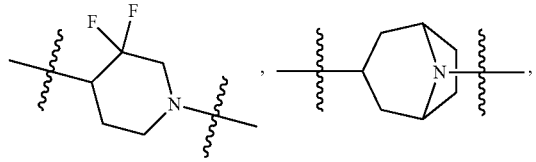

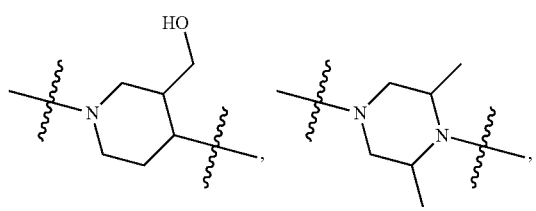

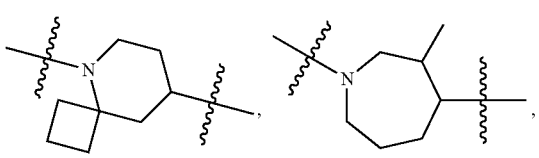

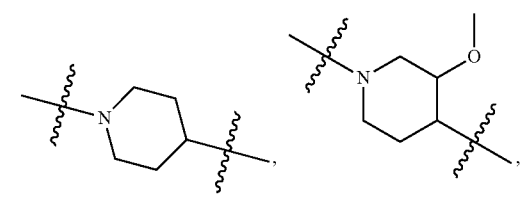

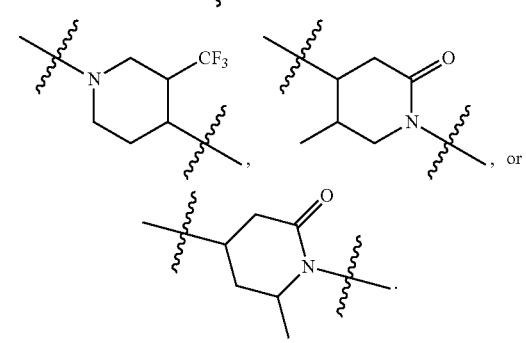

Embodiment 11. The compound of any one of embodiments 1-10, or a pharmaceutically acceptable salt thereof, wherein:
  $R^{11}$ is H, $C_1$-$C_3$ alkyl, —($C_1$-$C_3$ alkylene)-(6-membered heterocyclyl), —($C_1$-$C_3$ alkylene)-O($C_1$-$C_3$ alkyl), $C_1$-$C_5$ haloalkyl, $C_1$-$C_5$ alkyl-OH, or —($C_1$-$C_3$ alkylene)-NH($C_1$-$C_3$ alkyl), wherein the heterocyclyl contains 1-2 heteroatoms selected from N and O.

Embodiment 12. The compound of any one of embodiments 1-11, or a pharmaceutically acceptable salt thereof, wherein is:
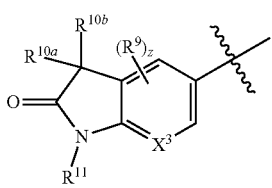
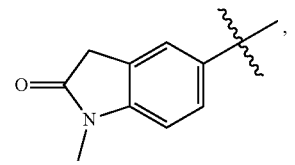 , 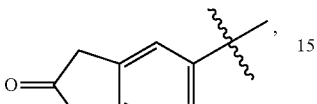 ,
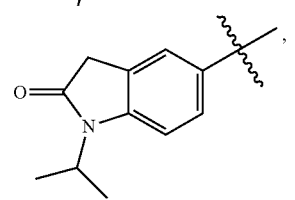 , 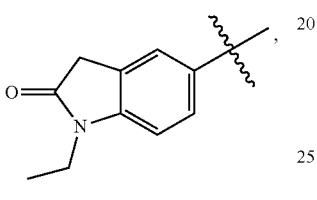 ,
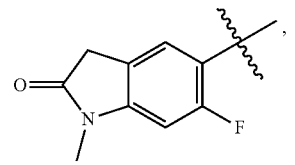 , 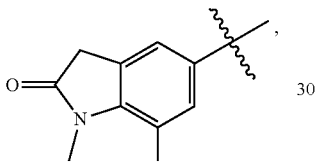 ,
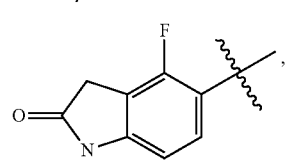 , 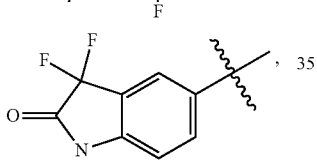 ,
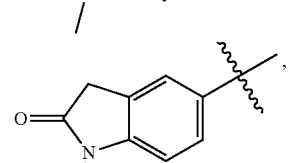 , 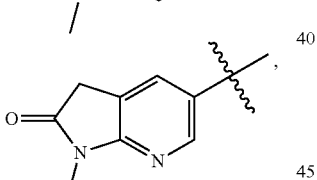 ,
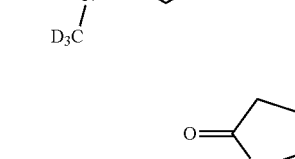
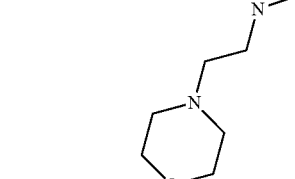
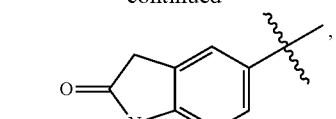 ,
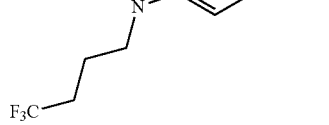 ,
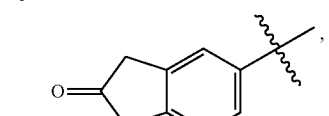 ,
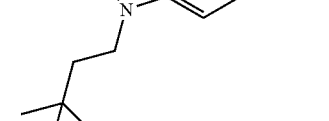 ,
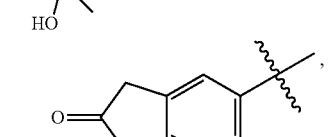 ,
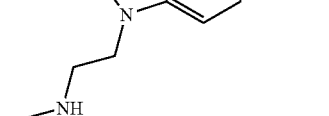 ,
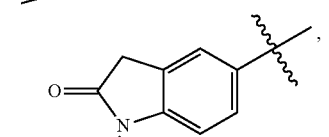 , or
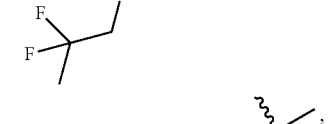 .
Embodiment 13. The compound of any one of claims 1-12, or a pharmaceutically acceptable salt thereof, wherein is:
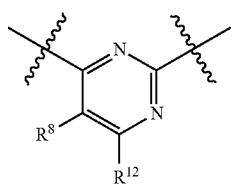
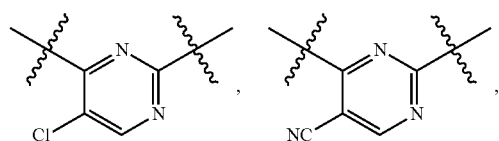
, or .
Embodiment 14. The compound of any one of embodiments 1-13, or a pharmaceutically acceptable salt thereof, wherein
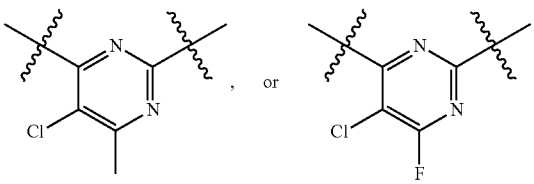
is:
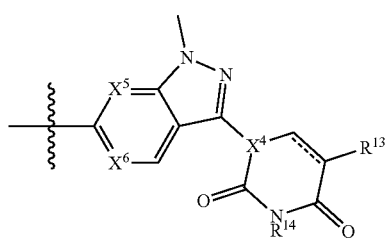
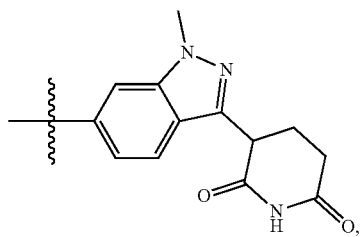
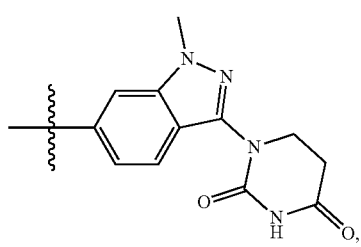
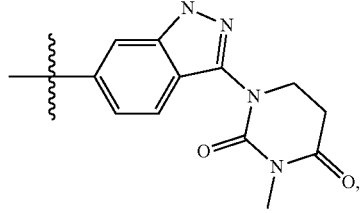
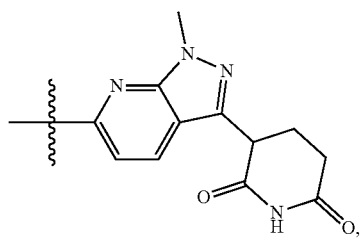
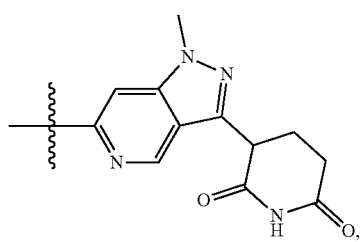
,
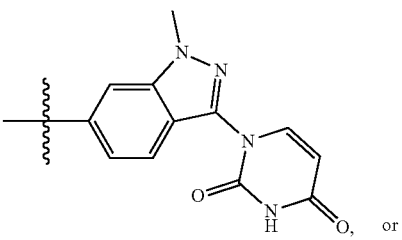
, or
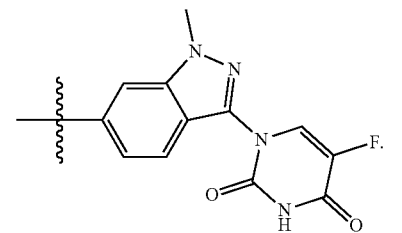
Embodiment 15. The compound of any one of embodiments 1-14, or a pharmaceutically acceptable salt thereof, wherein the compound is of Formula (II), (III), or (IV):

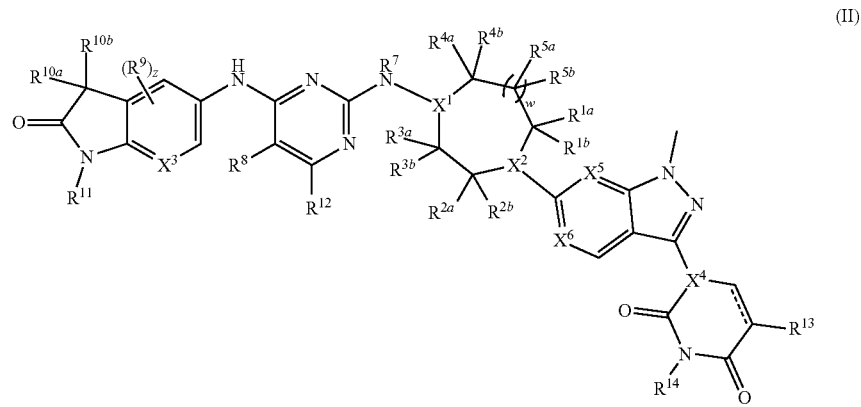
(II)
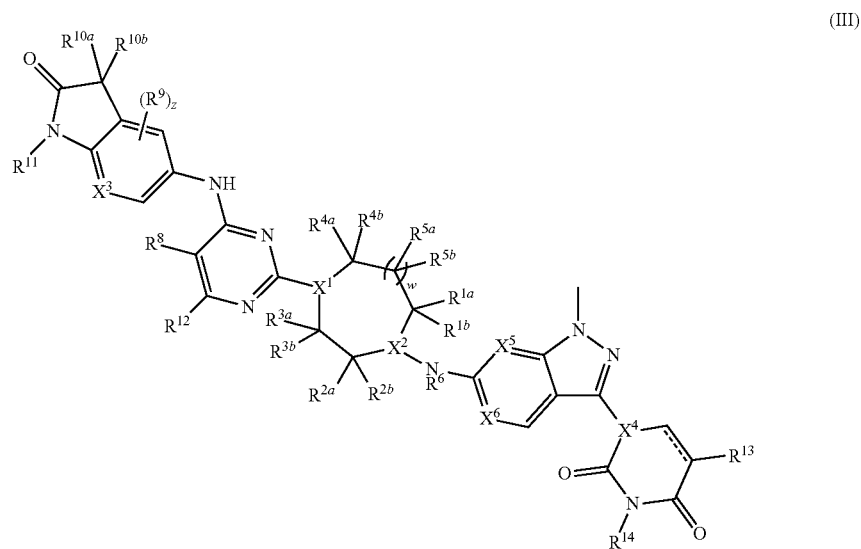
(III)
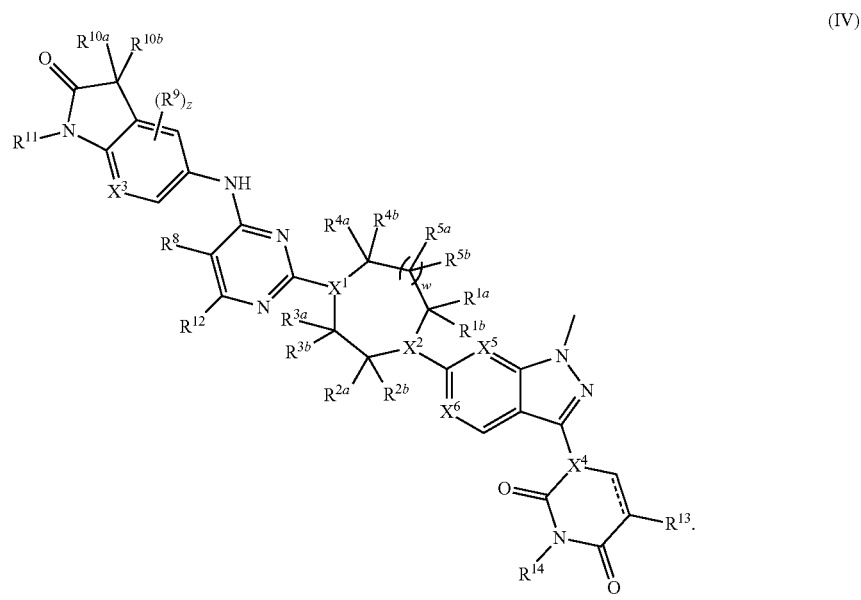
(IV)

Embodiment 16. The compound of embodiment 15, or a pharmaceutically acceptable salt thereof, wherein the compound is of Formula (IIIb):

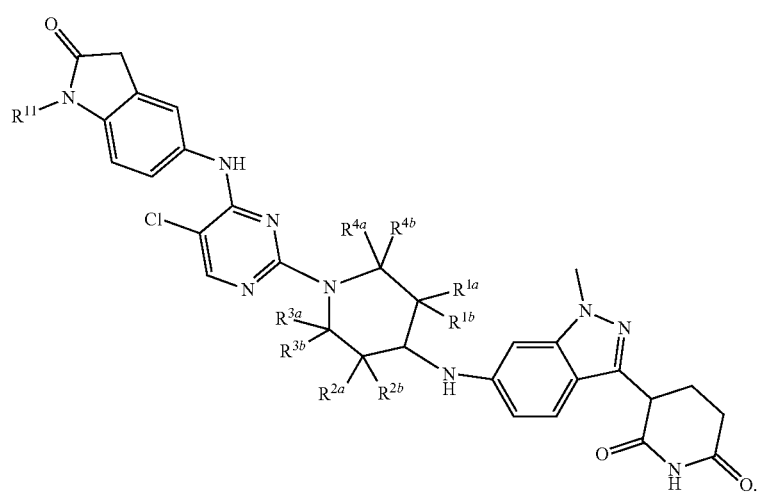

(IIIb)

Embodiment 17. A compound selected from the compounds of Table 1 and pharmaceutically acceptable salts thereof.

Embodiment 18. A pharmaceutical composition comprising the compound of any one of embodiments 1-17, or a pharmaceutically acceptable salt thereof, and a pharmaceutically acceptable excipient.

Embodiment 19. A method of degrading B-cell lymphoma 6 protein (BCL6) comprising contacting BCL6 with an effective amount of the compound of any one of embodiments 1-17, or a pharmaceutically acceptable salt thereof, or the pharmaceutical composition of embodiment 18.

Embodiment 20. A method of treating a cancer or an autoimmune disease in a subject in need thereof, comprising administering to the subject an effective amount of the compound of any one of embodiments 1-17, or a pharmaceutically acceptable salt thereof, or the pharmaceutical composition of embodiment 18.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean±20%, ±10%, ±5%, or ±1% of the indicated range, value, or structure, unless otherwise indicated.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkyl-OH" refers to an unbranched or branched alkyl group as defined above, wherein one or more hydrogen atoms are replaced by —OH. For example, "$C_1$-$C_6$ alkyl-OH" refers to a $C_1$-$C_6$ alkyl which is substituted by one or more —OH groups. An alkyl-OH may contain multiple hydroxy groups that are attached to the same carbon atom or to multiple carbon atoms.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "carbocyclyl". Examples of monocyclic carbocyclyls include, e.g., cyclopropyl, cyclobutyl, cyclopentyl, cyclohexyl, cycloheptyl, and cyclooctyl. An unsaturated carbocyclyl is also referred to as "cycloalkenyl". Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7 dimethyl bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbonyl" refers to a radical of the formula —C(O)$R^{10}R^{20}$, wherein $R^{10}$ and $R^{20}$ is independently selected from —OH, halo, cyano, nitro, oxo, thioxo, imino, oximo, trimethylsilanyl, —$R^a$, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Halo" or "halogen" refers to bromo, chloro, fluoro or iodo substituents.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl group has one to six carbon atoms and is substituted by one or more halo radicals ($C_1$-$C_6$ haloalkyl), or the haloalkyl group has one to five carbon atoms and is substituted by one or more halo radicals ($C_1$-$C_5$ haloalkyl), or the haloalkyl group has one to three carbon atoms and is substituted by one or more halo radicals ($C_1$-$C_3$ haloalkyl). The halo radicals may be all the same or the halo radicals may be different. Unless specifically stated otherwise, a haloalkyl group is optionally substituted.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3 to 18 membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$ heterocyclyl where $R^c$ is an alkylene chain as defined above. If the heterocyclyl is a nitrogen containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3 to 18 membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$ heteroaryl, where $R^c$ is an alkylene chain as defined above. If the heteroaryl is a nitrogen containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

Embodiments of the disclosure are meant to encompass pharmaceutically acceptable salts, tautomers, isotopologues, and stereoisomers of the compounds provided herein, such as the compounds of Formula (I).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences*, 18th eds., Mack Publishing, Easton PA (1990) or *Remington: The Science and Practice of Pharmacy*, 19th eds., Mack Publishing, Easton PA (1995).

As used herein and unless otherwise indicated, the term "stereoisomer" or "stereoisomerically pure" means one stereoisomer of a particular compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereoisomerically pure forms of the compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); Wilen, S. H., Tables of *Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

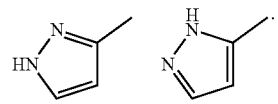

As readily understood by one skilled in the art, a wide variety of functional groups and other structures may exhibit tautomerism and all tautomers of compounds of Formula (I) are within the scope of the present disclosure.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan.

It should also be noted the compounds disclosed herein can contain unnatural proportions of atomic isotopes at one or more of the atoms. For example, the compounds may be radiolabeled with radioactive isotopes, such as for example tritium (H), iodine-125 ($^{125}$I), sulfur-35 ($^{35}$S), or carbon-14 ($^{14}$C), or may be isotopically enriched, such as with deuterium (2H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are deuterium, carbon-13, and/or nitrogen-15 enriched compounds. As used herein, "deuterated", means a compound wherein at least one hydrogen (H) has been replaced by deuterium (indicated by D or $^2$H), that is, the compound is enriched in deuterium in at least one position.

The disclosure also includes "deuterated analogs" of compounds described herein in which from 1 to n hydrogens attached to a carbon atom is/are replaced by deuterium, in which n is the number of hydrogens in the molecule. When multiple deuterium atoms are present in a compound, the deuterium atoms may be on the same portion of the molecule (for example, on a single alkyl group or on a single ring) or on different portions of the molecule (for example, on separate alkyl groups or separate rings). Such compounds may exhibit increased resistance to metabolism and thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

It is understood that, independently of stereoisomerical or isotopic composition, each compound disclosed herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof disclosed herein, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a cancer, as described herein, or symptoms thereof.

The term "effective amount" in connection with a compound disclosed herein means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having A BCL6 mediated disease, or a symptom thereof.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (IA):

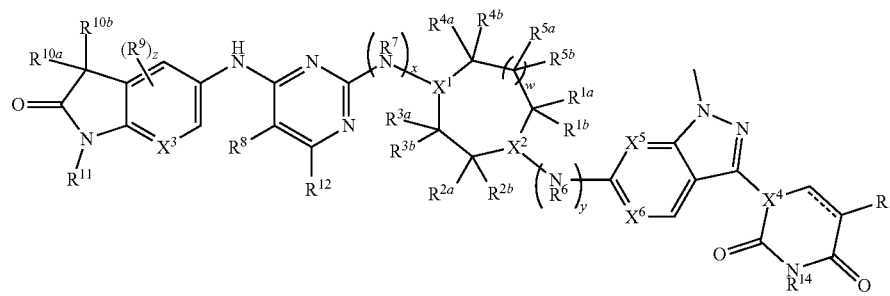

(IA)

or a pharmaceutically acceptable salt thereof, wherein:

$X^1$ and $X^2$ are each independently N or CH, provided that at least one of $X^1$ and $X^2$ is N;

$R^{1a}$ and $R^{1b}$ are each independently H, halo, or $C_1$-$C_6$ alkyl;

$R^{2a}$ and $R^{2b}$ are each independently H, $C_1$-$C_6$ alkyl, —O($C_1$-$C_6$ alkyl), —OH, halo, $C_1$-$C_6$ haloalkyl, or $C_1$-$C_6$ alkyl-OH, or $R^{2a}$ and $R^{2b}$ are taken together with the carbon atom to which they are attached to form a spiro $C_3$-$C_5$ cycloalkyl, or $R^{2a}$ and $R^{2b}$ are taken together to form oxo;

or $R^{1a}$ and $R^{2a}$ are taken together to form a bridging $C_2$-$C_3$ alkylene;

$R^{3a}$ and $R^{3b}$ are each independently H, halo, or $C_1$-$C_6$ alkyl;

$R^{4a}$ and $R^{4b}$ are each independently H, halo, or $C_1$-$C_6$ alkyl, or $R^{4a}$ and $R^{4b}$ are taken together with the carbon atom to which they are attached to form a spiro $C_3$-$C_5$ cycloalkyl;

$R^{5a}$ and $R^{5b}$ are each independently H, halo, or $C_1$-$C_6$ alkyl;

w is 0 or 1;

$R^6$ is H or $C_1$-$C_6$ alkyl;

$R^7$ is H or $C_1$-$C_6$ alkyl;

x and y are each independently 0 or 1, provided that x and y are not both 1;

$R^8$ is Cl or —CN;
$R^9$ is F;
$X^3$ is N or CH;
z is 0 or 1;
$R^{10a}$ and $R^{10b}$ are each independently H or halo;
$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;
$R^{12}$ is H, halo, or $C_1$-$C_6$ alkyl;
$R^{13}$ is H or halo;
$R^{14}$ is H or $C_1$-$C_6$ alkyl;
$X^4$ is N or $CR^{15}$;
$R^{15}$ is H or $C_1$-$C_6$ alkyl;
$X^5$ and $X^6$ are each independently N or CH; and
═══ is a single or double bond;
wherein one or more hydrogen atoms in the compound are optionally replaced by deuterium.

In a further aspect, provided herein is a compound of Formula (I):

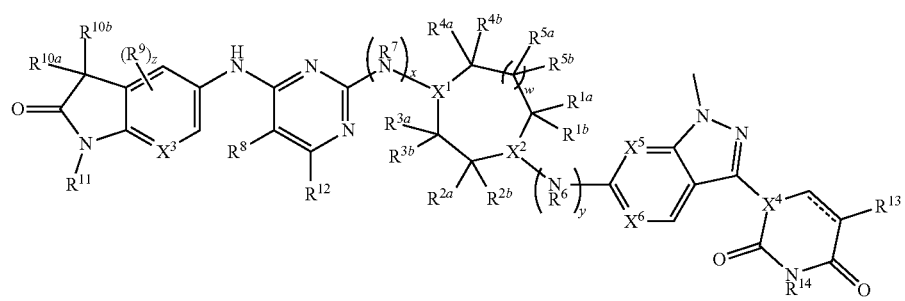

(I)

or a pharmaceutically acceptable salt thereof, wherein:
$X^1$ and $X^2$ are each independently N or CH, provided that at least one of $X^1$ and $X^2$ is N;
$R^{1a}$ and $R^{1b}$ are each independently H, halo, or $C_1$-$C_6$ alkyl;
$R^{2a}$ and $R^{2b}$ are each independently H, $C_1$-$C_6$ alkyl, —OH, halo, or $C_1$-$C_6$ alkyl-OH,
or $R^{2a}$ and $R^{2b}$ are taken together with the carbon atom to which they are attached to form a spiro $C_3$-$C_5$ cycloalkyl,
or $R^{2a}$ and $R^{2b}$ are taken together to form oxo;
or $R^{1a}$ and $R^{2a}$ are taken together to form a bridging $C_2$-$C_3$ alkylene;
$R^{3a}$ and $R^{3b}$ are each independently H, halo, or $C_1$-$C_6$ alkyl;
$R^{4a}$ and $R^{4b}$ are each independently H, halo, or $C_1$-$C_6$ alkyl,
or $R^{4a}$ and $R^{4b}$ are taken together with the carbon atom to which they are attached to form a spiro $C_3$-$C_5$ cycloalkyl;
$R^{5a}$ and $R^{5b}$ are each independently H, halo, or $C_1$-$C_6$ alkyl;
w is 0 or 1;
$R^6$ is H or $C_1$-$C_6$ alkyl;
$R^7$ is H or $C_1$-$C_6$ alkyl;
x and y are each independently 0 or 1, provided that x and y are not both 1;
$R^8$ is Cl or —CN;
$R^9$ is F;
$X^3$ is N or CH;
z is 0 or 1;
$R^{10a}$ and $R^{10b}$ are each independently H or halo;
$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;
$R^{12}$ is H, halo, or $C_1$-$C_6$ alkyl;
$R^{13}$ is H or halo;
$R^{14}$ is H or $C_1$-$C_6$ alkyl;
$X^4$ is N or $CR^{15}$;
$R^{15}$ is H or $C_1$-$C_6$ alkyl;
$X^5$ and $X^6$ are each independently N or CH; and
═══ is a single or double bond;
wherein one or more hydrogen atoms in the compound are optionally replaced by deuterium.

In some embodiments, $X^1$ is CH and $X^2$ is N. In some embodiments, $X^1$ is N and $X^2$ is CH. In some embodiments, $X^1$ and $X^2$ are both N.

In some embodiments, $R^{1a}$ is H, halo, or $C_1$-$C_6$ alkyl. In some embodiments, $R^{1a}$ is H, halo, or $C_1$-$C_3$ alkyl. In some embodiments, $R^{1a}$ is H, F, Cl, Br, I, or $C_1$-$C_3$ alkyl. In some embodiments, $R^{1a}$ is H, F, Cl, Br, I, methyl, ethyl, or propyl.

In some embodiments, $R^{1a}$ is H.

In some embodiments, $R^{1a}$ is halo. In some embodiments, $R^{1a}$ is F, Cl, Br, or I. In some embodiments, $R^{1a}$ is F.

In some embodiments, $R^{1a}$ is $C_1$-$C_6$ alkyl. In some embodiments, $R^{1a}$ is $C_1$-$C_3$ alkyl. In some embodiments, $R^{1a}$ is methyl, ethyl, or propyl. In some embodiments, $R^{1a}$ is methyl.

In some embodiments, $R^{1b}$ is H, halo, or $C_1$-$C_6$ alkyl. In some embodiments, $R^{1b}$ is H, halo, or $C_1$-$C_3$ alkyl. In some embodiments, $R^{1b}$ is H, F, Cl, Br, I, or $C_1$-$C_3$ alkyl. In some embodiments, $R^{1b}$ is H, F, Cl, Br, I, methyl, ethyl, or propyl.

In some embodiments, Rib is H.

In some embodiments, $R^{1b}$ is halo. In some embodiments, $R^{1b}$ is F, Cl, Br, or I. In some embodiments, $R^{1b}$ is F.

In some embodiments, $R^{1a}$ and $R^{1b}$ are each independently H, halo, or $C_1$-$C_3$ alkyl. In some embodiments, $R^{1a}$ and $R^{1b}$ are each independently H, F, Cl, Br, I, methyl, ethyl, or propyl. In some embodiments, $R^{1a}$ and $R^{1b}$ are each independently H or —$CH_3$.

In some embodiments, $R^{1b}$ is $C_1$-$C_6$ alkyl. In some embodiments, $R^{1b}$ is $C_1$-$C_3$ alkyl. In some embodiments, $R^{1b}$ is methyl, ethyl, or propyl. In some embodiments, $R^{1b}$ is methyl.

In some embodiments, $R^{2a}$ is H, $C_1$-$C_6$ alkyl, —O($C_1$-$C_6$ alkyl), —OH, halo, $C_1$-$C_6$ haloalkyl, or $C_1$-$C_6$ alkyl-OH. In some embodiments, $R^{2a}$ is H, $C_1$-$C_3$ alkyl, —O($C_1$-$C_3$ alkyl), —OH, F, Cl, Br, I, $C_1$-$C_3$ haloalkyl, or $C_1$-$C_3$ alkyl-OH. In some embodiments, $R^{2a}$ is H, methyl, ethyl, propyl, —OCH$_3$, —OH, F, Cl, Br, I, —CF$_3$, —CHF$_2$, —CCl$_3$, —CH$_2$OH, —(CH$_2$CH$_2$)OH, or —(CH$_2$CH$_2$CH$_2$)OH.

In some embodiments, R$^{2a}$ is H.

In some embodiments, R$^{2a}$ is C$_1$-C$_6$ alkyl. In some embodiments, R$^{2a}$ is C$_1$-C$_3$ alkyl. In some embodiments, R$^{2a}$ is methyl, ethyl, or propyl. In some embodiments, R$^{2a}$ is methyl.

In some embodiments, R$^{2a}$ is —O(C$_1$-C$_6$ alkyl). In some embodiments, R$^{2a}$ is —O(C$_1$-C$_3$ alkyl). In some embodiments, R$^{2a}$ is —OCH$_3$, —OCH$_2$CH$_3$, —OCH$_2$CH$_2$CH$_3$, or —OCH(CH$_3$)$_2$. In some embodiments, R$^{2a}$ is —OCH$_3$.

In some embodiments, R$^{2a}$ is —OH.

In some embodiments, R$^{2a}$ is halo. In some embodiments, R$^{2a}$ is F, Cl, Br, or I. In some embodiments, R$^{2a}$ is F.

In some embodiments, R$^{2a}$ is C$_1$-C$_6$ haloalkyl. In some embodiments, R$^{2a}$ is C$_1$-C$_6$ haloalkyl containing 1-13 halogen atoms. In some embodiments, R$^{2a}$ is C$_1$-C$_3$ haloalkyl. In some embodiments, R$^{2a}$ is C$_1$-C$_3$ haloalkyl containing 1-7 halogen atoms. In some embodiments, R$^{2a}$ is —CF$_3$, —CHF$_2$, —CH$_2$F, —CCl$_3$, —CHCl$_2$, —CH$_2$Cl, —CF$_2$Cl, —CFCl$_2$, —CH$_2$CF$_3$, —CH$_2$CHF$_2$, or —CH$_2$CCl$_3$. In some embodiments, R$^{2a}$ is —CF$_3$.

In some embodiments, R$^{2a}$ is C$_1$-C$_6$ alkyl-OH. In some embodiments, R$^{2a}$ is C$_1$-C$_3$ alkyl-OH. In some embodiments, R$^{2a}$ is —CH$_2$OH, —(CH$_2$CH$_2$)OH, or —(CH$_2$CH$_2$CH$_2$)OH. In some embodiments, R$^{2a}$ is —CH$_2$OH.

In some embodiments, R$^{2b}$ is H, C$_1$-C$_6$ alkyl, —OH, halo, or C$_1$-C$_6$ alkyl-OH. In some embodiments, R$^{2b}$ is H, C$_1$-C$_3$ alkyl, —OH, F, Cl, Br, I, or C$_1$-C$_3$ alkyl-OH. In some embodiments, R$^{2b}$ is H, methyl, ethyl, propyl, —OH, F, Cl, Br, I, —CH$_2$OH, —(CH$_2$CH$_2$)OH, or —(CH$_2$CH$_2$CH$_2$)OH.

In some embodiments, R$^{2b}$ is H.

In some embodiments, R$^{2b}$ is C$_1$-C$_6$ alkyl. In some embodiments, R$^{2b}$ is C$_1$-C$_3$ alkyl. In some embodiments, R$^{2b}$ is methyl, ethyl, or propyl. In some embodiments, R$^{2b}$ is methyl.

In some embodiments, R$^{2b}$ is —O(C$_1$-C$_6$ alkyl). In some embodiments, R$^{2b}$ is —O(C$_1$-C$_3$ alkyl). In some embodiments, R$^{2b}$ is —OCH$_3$, —OCH$_2$CH$_3$, —OCH$_2$CH$_2$CH$_3$, or —OCH(CH$_3$)$_2$. In some embodiments, R$^{2b}$ is —OCH$_3$.

In some embodiments, R$^{2b}$ is —OH.

In some embodiments, R$^{2b}$ is halo. In some embodiments, R$^{2b}$ is F, Cl, Br, or I. In some embodiments, R$^{2b}$ is F.

In some embodiments, R$^{2b}$ is C$_1$-C$_6$ haloalkyl. In some embodiments, R$^{2b}$ is C$_1$-C$_6$ haloalkyl containing 1-13 halogen atoms. In some embodiments, R$^{2b}$ is C$_1$-C$_3$ haloalkyl. In some embodiments, R$^{2b}$ is C$_1$-C$_3$ haloalkyl containing 1-7 halogen atoms. In some embodiments, R$^{2b}$ is —CF$_3$, —CHF$_2$, —CH$_2$F, —CCl$_3$, —CHCl$_2$, —CH$_2$Cl, —CF$_2$Cl, —CFCl$_2$, —CH$_2$CF$_3$, —CH$_2$CHF$_2$, or —CH$_2$CCl$_3$. In some embodiments, R$^{2b}$ is —CF$_3$.

In some embodiments, R$^{2b}$ is C$_1$-C$_6$ alkyl-OH. In some embodiments, R$^{2b}$ is C$_1$-C$_3$ alkyl-OH. In some embodiments, R$^{2b}$ is —CH$_2$OH, —(CH$_2$CH$_2$)OH, or —(CH$_2$CH$_2$CH$_2$)OH. In some embodiments, R$^{2b}$ is —CH$_2$OH.

In some embodiments, R$^{2a}$ and R$^{2b}$ are taken together with the carbon atom to which they are attached to form a spiro C$_3$-C$_5$ cycloalkyl. In some embodiments, R$^{2a}$ and R$^{2b}$ are taken together with the carbon atom to which they are attached to form a spiro C$_3$-C$_4$ cycloalkyl. In some embodiments, R$^{2a}$ and R$^{2b}$ are taken together with the carbon atom to which they are attached to form a spiro cyclobutyl.

In some embodiments, R$^{2a}$ and R$^{2b}$ are taken together to form oxo.

In some embodiments, R$^{1a}$ and R$^{1b}$ are both H, and at least one of R$^{2a}$ and R$^{2b}$ is other than H.

In some embodiments, R$^{1a}$ and R$^{2a}$ are taken together to form a bridging C$_2$-C$_3$ alkylene. In some embodiments, R$^{1a}$ and R$^{2a}$ are taken together to form a bridging ethylene.

In some embodiments, R$^{3a}$ is H, halo, or C$_1$-C$_6$ alkyl. In some embodiments, R$^{3a}$ is H, F, Cl, Br, I, or C$_1$-C$_3$ alkyl. In some embodiments, R$^{3a}$ is H, F, Cl, Br, I, methyl, ethyl, or propyl.

In some embodiments, R$^{3a}$ is H.

In some embodiments, R$^{3a}$ is halo. In some embodiments, R$^{3a}$ is F, Cl, Br, or I. In some embodiments, R$^{3a}$ is F.

In some embodiments, R$^{3a}$ is C$_1$-C$_6$ alkyl. In some embodiments, R$^{3a}$ is C$_1$-C$_3$ alkyl. In some embodiments, R$^{3a}$ is methyl, ethyl, or propyl. In some embodiments, R$^{3a}$ is methyl.

In some embodiments, R$^{3b}$ is H, halo, or C$_1$-C$_6$ alkyl. In some embodiments, R$^{3b}$ is H, F, Cl, Br, I, or C$_1$-C$_3$ alkyl. In some embodiments, R$^{3b}$ is H, F, Cl, Br, I, methyl, ethyl, or propyl.

In some embodiments, R$^{3b}$ is H.

In some embodiments, R$^{3b}$ is halo. In some embodiments, R$^{3b}$ is F, Cl, Br, or I. In some embodiments, R$^{3b}$ is F.

In some embodiments, R$^{3b}$ is C$_1$-C$_6$ alkyl. In some embodiments, R$^{3b}$ is C$_1$-C$_3$ alkyl. In some embodiments, R$^{3b}$ is methyl, ethyl, or propyl. In some embodiments, R$^{3b}$ is methyl.

In some embodiments, R$^{4a}$ is H, halo, or C$_1$-C$_6$ alkyl. In some embodiments, R$^{4a}$ is H, F, Cl, Br, I, or C$_1$-C$_3$ alkyl. In some embodiments, R$^{4a}$ is H, F, Cl, Br, I, methyl, ethyl, or propyl.

In some embodiments, R$^{4a}$ is H.

In some embodiments, R$^{4a}$ is halo. In some embodiments, R$^{4a}$ is F, Cl, Br, or I. In some embodiments, R$^{4a}$ is F.

In some embodiments, R$^{4a}$ is C$_1$-C$_6$ alkyl. In some embodiments, R$^{4a}$ is C$_1$-C$_3$ alkyl. In some embodiments, R$^{4a}$ is methyl, ethyl, or propyl. In some embodiments, R$^{4a}$ is methyl.

In some embodiments, R$^{4b}$ is H, halo, or C$_1$-C$_6$ alkyl. In some embodiments, R$^{4b}$ is H, F, Cl, Br, I, or C$_1$-C$_3$ alkyl. In some embodiments, R$^{4b}$ is H, F, Cl, Br, I, methyl, ethyl, or propyl.

In some embodiments, R$^{4b}$ is H.

In some embodiments, R$^{4b}$ is halo. In some embodiments, R$^{4b}$ is F, Cl, Br, or I. In some embodiments, R$^{4b}$ is F.

In some embodiments, R$^{4b}$ is C$_1$-C$_6$ alkyl. In some embodiments, R$^{4b}$ is C$_1$-C$_3$ alkyl. In some embodiments, R$^{4b}$ is methyl, ethyl, or propyl. In some embodiments, R$^{4b}$ is methyl.

In some embodiments, R$^{4a}$ and R$^{4b}$ are taken together with the carbon atom to which they are attached to form a spiro C$_3$-C$_5$ cycloalkyl. In some embodiments, R$^{4a}$ and R$^{4b}$ are taken together with the carbon atom to which they are attached to form a spiro C$_3$-C$_4$ cycloalkyl. In some embodiments, R$^{4a}$ and R$^{4b}$ are taken together with the carbon atom to which they are attached to form a spiro cyclobutyl.

In some embodiments, R$^{3a}$, R$^{3b}$, R$^{4a}$, and R$^{4b}$ are each H.

In some embodiments, at least one of R$^{3a}$ and R$^{3b}$ is other than H, and at least one of R$^{4a}$ and R$^{4b}$ is other than H.

In some embodiments, R$^{5a}$ is H, halo, or C$_1$-C$_6$ alkyl. In some embodiments, R$^{5a}$ is H, F, Cl, Br, I, or C$_1$-C$_3$ alkyl. In some embodiments, R$^{5a}$ is H, F, Cl, Br, I, methyl, ethyl, or propyl.

In some embodiments, R$^{5a}$ is H.

In some embodiments, $R^{5b}$ is H, halo, or $C_1$-$C_6$ alkyl. In some embodiments, $R^{5b}$ is H, F, Cl, Br, I, or $C_1$-$C_3$ alkyl. In some embodiments, $R^{5b}$ is H, F, Cl, Br, I, methyl, ethyl, or propyl.

In some embodiments, $R^{5b}$ is H.

In some embodiments, $R^{5a}$ and $R^{5b}$ are each H.

In some embodiments, at least one of $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ is other than H.

In some embodiments, one, two, or three of $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ is other than H.

In some embodiments, one or two of $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ is other than H.

In some embodiments, w is 0. In some embodiments, w is 1.

In some embodiments,

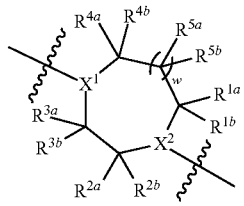

is:

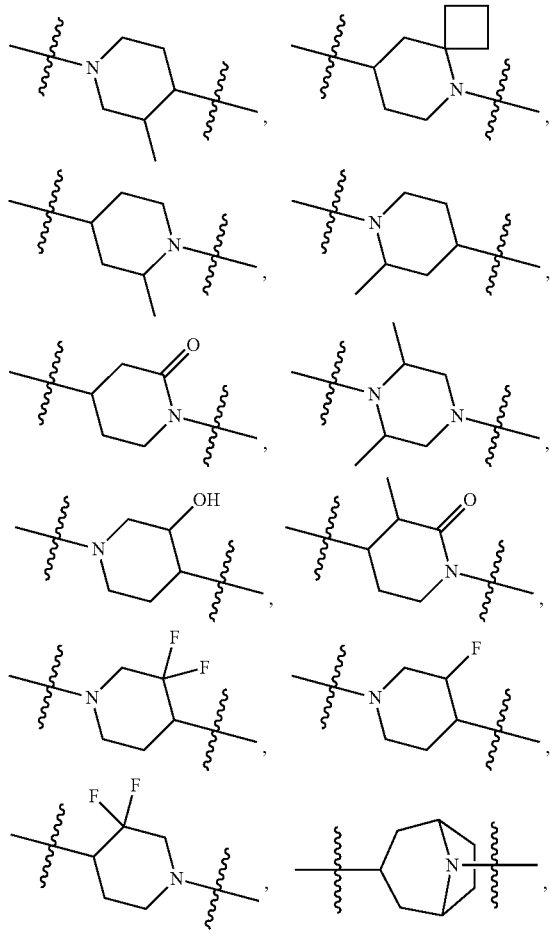

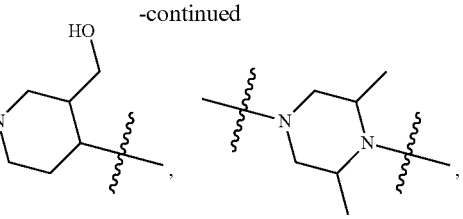

In some embodiments, x and y are each 0. In some embodiments, x is 0 and y is 1. In some embodiments, x is 1 and y is 0.

In some embodiments, $R^6$ is H or $C_1$-$C_6$ alkyl. In some embodiments, $R^6$ is H or $C_1$-$C_3$ alkyl. In some embodiments, $R^6$ is H, methyl, ethyl, or propyl.

In some embodiments, $R^6$ is H.

In some embodiments, $R^6$ is $C_1$-$C_6$ alkyl. In some embodiments, $R^6$ is $C_1$-$C_3$ alkyl. In some embodiments, $R^6$ is methyl, ethyl, or propyl. In some embodiments, $R^6$ is methyl.

In some embodiments, x is 0, y is 1, and $R^6$ is H.

In some embodiments, x is 0, y is 1, and $R^6$ is $C_1$-$C_6$ alkyl. In some embodiments, x is 0, y is 1, and $R^6$ is $C_1$-$C_3$ alkyl. In some embodiments, x is 0, y is 1, and $R^6$ is methyl.

In some embodiments, $R^7$ is H or $C_1$-$C_6$ alkyl. In some embodiments, $R^7$ is H or $C_1$-$C_3$ alkyl. In some embodiments, $R^7$ is H, methyl, ethyl, or propyl.

In some embodiments, $R^7$ is H.

In some embodiments, $R^7$ is $C_1$-$C_6$ alkyl. In some embodiments, $R^7$ is $C_1$-$C_3$ alkyl. In some embodiments, $R^7$ is methyl, ethyl, or propyl. In some embodiments, $R^7$ is methyl.

In some embodiments, x is 1, y is 0, and $R^7$ is H.

In some embodiments, x is 1, y is 0, and $R^7$ is $C_1$-$C_6$ alkyl. In some embodiments, x is 1, y is 0, and $R^7$ is $C_1$-$C_3$ alkyl.

In some embodiments, x is 1, y is 0, and $R^7$ is methyl.

In some embodiments, $R^8$ is Cl. In some embodiments, $R^8$ is —CN.

In some embodiments, $R^9$ is F.

In some embodiments, $X^3$ is N. In some embodiments, $X^3$ is CH.

In some embodiments, z is 0. In some embodiments, z is 1.

In some embodiments, $R^{10a}$ is H or halo. In some embodiments, $R^{10a}$ is H, F, Cl, Br, or I.

In some embodiments, $R^{10a}$ is H.

In some embodiments, $R^{10a}$ is halo. In some embodiments, $R^{10a}$ is H, F, Cl, Br, or I. In some embodiments, $R^{10a}$ is F.

In some embodiments, $R^{10b}$ is H or halo. In some embodiments, $R^{10b}$ is H, F, Cl, Br, or I.

In some embodiments, $R^{10b}$ is H.

In some embodiments, $R^{10b}$ is halo. In some embodiments, $R^{10b}$ is H, F, Cl, Br, or I. In some embodiments, $R^{10b}$ is F.

In some embodiments, $R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S. In some embodiments, $R^{11}$ is H, $C_1$-$C_3$ alkyl, —($C_1$-$C_3$ alkylene)-(5- to 6-membered heterocyclyl), —($C_1$-$C_3$ alkylene)-O($C_1$-$C_3$ alkyl), $C_1$-$C_5$ haloalkyl, $C_1$-$C_5$ alkyl-OH, or —($C_1$-$C_3$ alkylene)-NH($C_1$-$C_3$ alkyl), wherein the heterocyclyl contains 1-3 heteroatoms selected from N, O, and S. In some embodiments, $R^{11}$ is H, $C_1$-$C_3$ alkyl, —($C_1$-$C_3$ alkylene)-(5- to 6-membered heterocyclyl), —($C_1$-$C_3$ alkylene)-O($C_1$-$C_3$ alkyl), $C_1$-$C_5$ haloalkyl, $C_1$-$C_5$ alkyl-OH, or —($C_1$-$C_3$ alkylene)-NH($C_1$-$C_3$ alkyl), wherein the heterocyclyl contains 1-2 heteroatoms selected from N and O. In some embodiments, $R^{11}$ is H, methyl, ethyl, propyl, -CD$_3$, —(CH$_2$)—(5- to 6-membered heterocyclyl), —(CH$_2$CH$_2$)—(5- to 6-membered heterocyclyl), —(CH$_2$CH$_2$CH$_2$)—(5- to 6-membered heterocyclyl), —CH$_2$OCH$_3$, —CH$_2$OCH$_2$CH$_3$, —CH$_2$OCH$_2$CH$_2$CH$_3$, —CH$_2$CH$_2$OCH$_3$, —CH$_2$CH$_2$OCH$_2$CH$_3$, —CH$_2$CH$_2$OCH$_2$CH$_2$CH$_3$, —CH$_2$CH$_2$CH$_2$OCH$_3$, —CH$_2$CH$_2$CH$_2$OCH$_2$CH$_3$, —CH$_2$CH$_2$CH$_2$OCH$_2$CH$_2$CH$_3$, —(CH$_2$)$_3$CF$_3$, —(CH$_2$)$_3$CHF$_2$, —(CH$_2$)$_3$CH$_2$F, —CH$_2$CF$_2$CH$_3$, —CH$_2$CHFCH$_3$, —CH$_2$CF$_2$CH$_3$, —CH$_2$CH$_2$CF$_3$, —CH$_2$CH$_2$CF$_2$(CH$_3$), —CH$_2$CH$_2$CF(CH$_3$)$_2$, —CH$_2$OH, —CH$_2$CH$_2$OH, —CH$_2$CH$_2$CH$_2$OH, —CH$_2$CH$_2$CH(OH)(CH$_3$), —CH$_2$CH$_2$C(OH)(CH$_3$)$_2$, —CH$_2$—N(H)CH$_3$, —CH$_2$—N(H)CH$_2$CH$_3$, —CH$_2$—N(H)CH$_2$CH$_2$CH$_3$, —CH$_2$CH$_2$—N(H)CH$_3$, —CH$_2$CH$_2$—N(H)CH$_2$CH$_3$, —CH$_2$CH$_2$—N(H)CH$_2$CH$_2$CH$_3$, —CH$_2$CH$_2$CH$_2$—N(H)CH$_3$, —CH$_2$CH$_2$CH$_2$—N(H)CH$_2$CH$_3$, or —CH$_2$CH$_2$CH$_2$—N(H)CH$_2$CH$_2$CH$_3$, wherein the heterocyclyl contains 1-2 heteroatoms selected from N and O.

In some embodiments, $R^{11}$ is H.

In some embodiments, $R^{11}$ is $C_1$-$C_6$ alkyl. In some embodiments, $R^{11}$ is $C_1$-$C_3$ alkyl. In some embodiments, $R^{11}$ is methyl, ethyl, propyl, or -CD$_3$. In some embodiments, $R^{11}$ is —CH$_3$. In some embodiments, $R^{11}$ includes one or more deuterium atoms. In some embodiments, $R^{11}$ is -CD$_3$. In some embodiments, $R^{11}$ is —CH$_2$CH$_3$. In some embodiments, $R^{11}$ is —CH(CH$_3$)$_2$.

In some embodiments, $R^{11}$ is —($C_1$-$C_6$ alkylene)-(5- to 6-membered heterocyclyl), wherein the heterocyclyl contains 1-3 heteroatoms selected from N, O, and S. In some embodiments, $R^{11}$ is —($C_1$-$C_3$ alkylene)-(5- to 6-membered heterocyclyl), wherein the heterocyclyl contains 1-3 heteroatoms selected from N, O, and S. In some embodiments, $R^{11}$ is —($C_1$-$C_3$ alkylene)-(5- to 6-membered heterocyclyl), wherein the heterocyclyl contains 1-2 heteroatoms selected from N, and O. In some embodiments, $R^{11}$ is

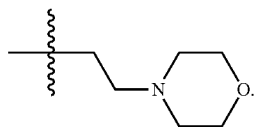

In some embodiments, $R^{11}$ is —($C_1$-$C_6$ alkylene)-O($C_1$-$C_6$ alkyl). In some embodiments, $R^{11}$ is —($C_1$-$C_3$ alkylene)-O($C_1$-$C_3$ alkyl). In some embodiments, $R^{11}$ is —CH$_2$OCH$_3$, —CH$_2$OCH$_2$CH$_3$, —CH$_2$OCH$_2$CH$_2$CH$_3$, —CH$_2$CH$_2$OCH$_3$, —CH$_2$CH$_2$OCH$_2$CH$_3$, —CH$_2$CH$_2$OCH$_2$CH$_2$CH$_3$, —CH$_2$CH$_2$CH$_2$OCH$_3$, —CH$_2$CH$_2$CH$_2$OCH$_2$CH$_3$, or —CH$_2$CH$_2$CH$_2$OCH$_2$CH$_2$CH$_3$. In some embodiments, $R^{11}$ is —CH$_2$CH$_2$OCH$_3$.

In some embodiments, $R^{11}$ is $C_1$-$C_6$ haloalkyl. In some embodiments, $R^{11}$ is $C_1$-$C_5$ haloalkyl. In some embodiments, $R^{11}$ is —CF$_3$, —CH$_2$CH$_2$F3, —(CH$_2$)$_2$CHF$_2$, —(CH$_2$)$_2$CF$_3$, —CH$_2$CF(CH$_3$)$_2$, —CH$_2$CF$_2$CH$_3$, —CH$_2$CF$_3$, —CH$_2$CH$_2$CF(CH$_3$)$_2$, —CH$_2$CH$_2$CF$_2$CH$_3$ or —CH$_2$CH$_2$CF$_3$. In some embodiments, $R^{11}$ is —(CH$_2$)$_3$CF$_3$, —CH$_2$CF$_2$CH$_3$, —CH$_2$CH$_2$CF(CH$_3$)$_2$, or —CH$_2$CF(CH$_3$)$_2$.

In some embodiments, $R^{11}$ is $C_1$-$C_6$ alkyl-OH. In some embodiments, $R^{11}$ is $C_1$-$C_5$ alkyl-OH. In some embodiments, $R^{11}$ is —CH$_2$OH, —CH$_2$CH$_2$OH, —CH$_2$CH$_2$CH$_2$OH, —CH$_2$CH$_2$CH(OH)(CH$_3$), or —CH$_2$CH$_2$C(OH)(CH$_3$)$_2$. In some embodiments, $R^{11}$ is —CH$_2$CH$_2$C(OH)(CH$_3$)$_2$.

In some embodiments, $R^{11}$ is —($C_1$-$C_6$ alkylene)-NH($C_1$-$C_6$ alkyl). In some embodiments, $R^{11}$ is —($C_1$-$C_3$ alkylene)-NH($C_1$-$C_3$ alkyl). In some embodiments, $R^{11}$ is —CH$_2$—N(H)CH$_3$, —CH$_2$—N(H)CH$_2$CH$_3$, —CH$_2$—N(H)CH$_2$CH$_2$CH$_3$, —CH$_2$CH$_2$—N(H)CH$_3$, —CH$_2$CH$_2$—N(H)CH$_2$CH$_3$, —CH$_2$CH$_2$—N(H)CH$_2$CH$_2$CH$_3$, —CH$_2$CH$_2$CH$_2$—N(H)CH$_3$, —CH$_2$CH$_2$CH$_2$—N(H)CH$_2$CH$_3$, or —CH$_2$CH$_2$CH$_2$—N(H)CH$_2$CH$_2$CH$_3$. In some embodiments, $R^{11}$ is —CH$_2$CH$_2$N(H)CH$_3$.

In some embodiments,

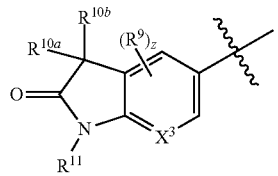

is:

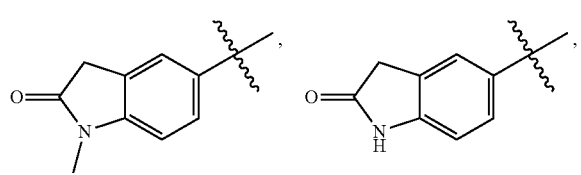

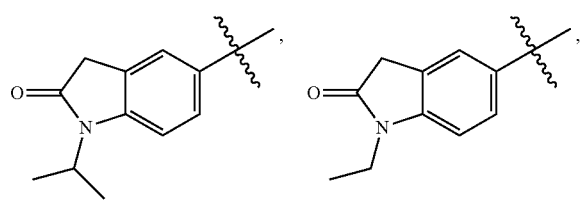

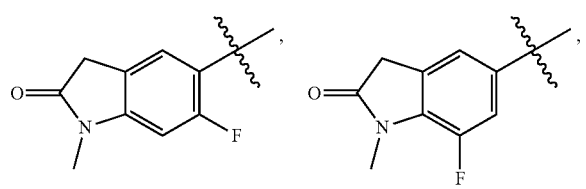

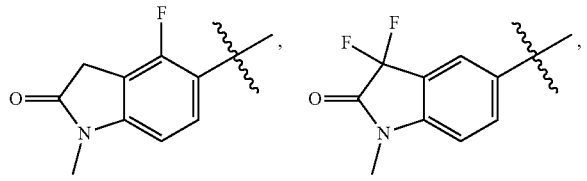

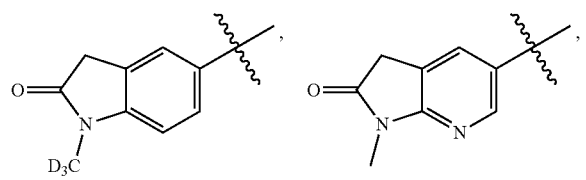

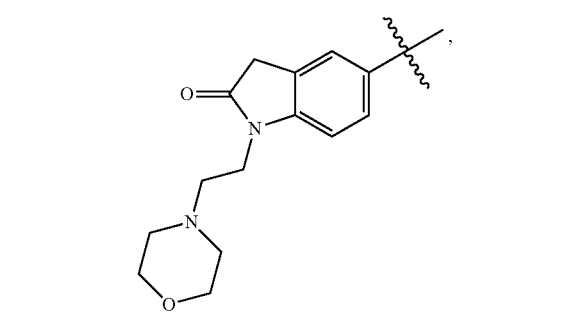

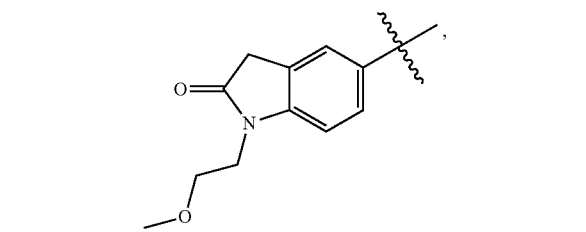

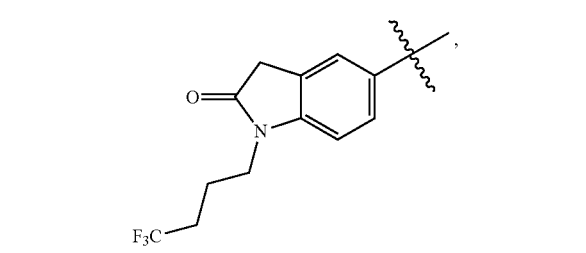

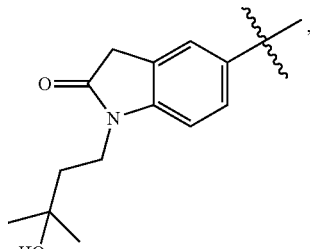

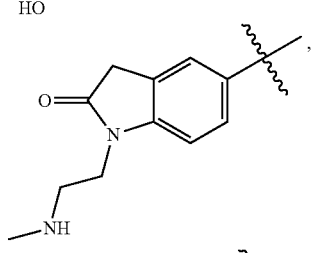

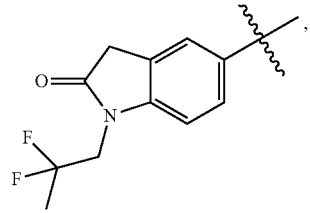

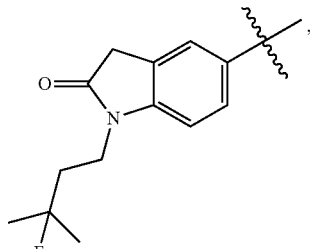

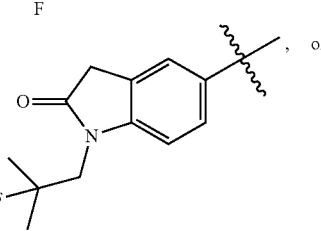

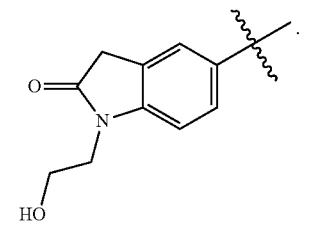

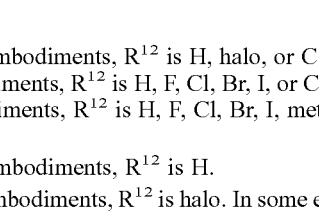

In some embodiments, $R^{12}$ is H, halo, or $C_1$-$C_6$ alkyl. In some embodiments, $R^{12}$ is H, F, Cl, Br, I, or $C_1$-$C_3$ alkyl. In some embodiments, $R^{12}$ is H, F, Cl, Br, I, methyl, ethyl, or propyl.

In some embodiments, $R^{12}$ is H.

In some embodiments, $R^{12}$ is halo. In some embodiments, $R^{12}$ is F, Cl, Br, or I. In some embodiments, $R^{12}$ is F.

In some embodiments, $R^{12}$ is $C_1$-$C_6$ alkyl. In some embodiments, $R^{12}$ is $C_1$-$C_3$ alkyl. In some embodiments, $R^{12}$ is methyl, ethyl, or propyl. In some embodiments, $R^{12}$ is methyl.

In some embodiments,

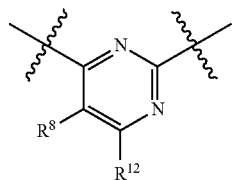

is:

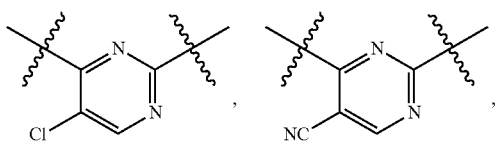

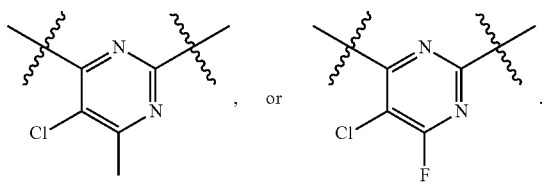

In some embodiments, $R^{13}$ is H or halo. In some embodiments, $R^{13}$ is H, F, Cl, Br, or I.

In some embodiments, $R^{13}$ is H.

In some embodiments, $R^{13}$ is halo. In some embodiments, $R^{13}$ is F, Cl, Br, or I. In some embodiments, $R^{13}$ is F.

In some embodiments, $R^{14}$ is H or $C_1$-$C_6$ alkyl. In some embodiments, $R^{14}$ is H or $C_1$-$C_3$ alkyl. In some embodiments, $R^{14}$ is H, methyl, ethyl, or propyl.

In some embodiments, $R^{14}$ is H.

In some embodiments, $R^{14}$ is $C_1$-$C_6$ alkyl. In some embodiments, $R^{14}$ is $C_1$-$C_3$ alkyl. In some embodiments, $R^{14}$ is methyl, ethyl, or propyl. In some embodiments, $R^{14}$ is methyl.

In some embodiments, $R^{14}$ is H. In some embodiments, $R^{14}$ is methyl.

In some embodiments, $X^4$ is N. In some embodiments, $X^4$ is $CR^{15}$.

In some embodiments, $R^{15}$ is H or $C_1$-$C_6$ alkyl. In some embodiments, $R^{15}$ is H or $C_1$-$C_3$ alkyl. In some embodiments, $R^{15}$ is H, methyl, ethyl, or propyl.

In some embodiments, $R^{15}$ is H.

In some embodiments, $R^{15}$ is $C_1$-$C_6$ alkyl. In some embodiments, $R^{15}$ is $C_1$-$C_3$ alkyl. In some embodiments, $R^{15}$ is methyl, ethyl, or propyl. In some embodiments, $R^{15}$ is methyl.

In some embodiments, $X^5$ is N. In some embodiments, $X^5$ is CH.

In some embodiments, $X^6$ is N. In some embodiments, $X^6$ is CH.

In some embodiments, ≡≡≡ is a single bond. In some embodiments, ≡≡≡ is a double bond.

In some embodiments,

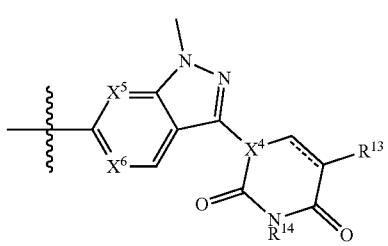

is:

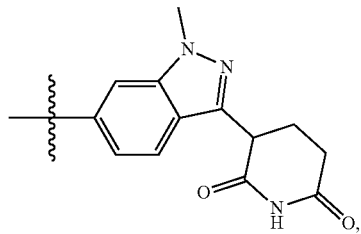

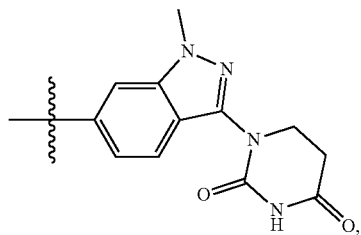

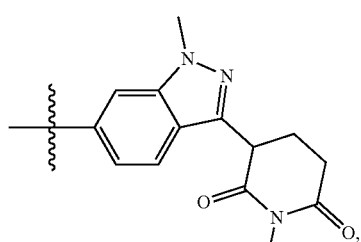

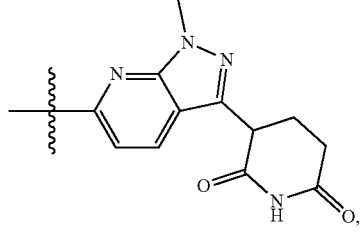

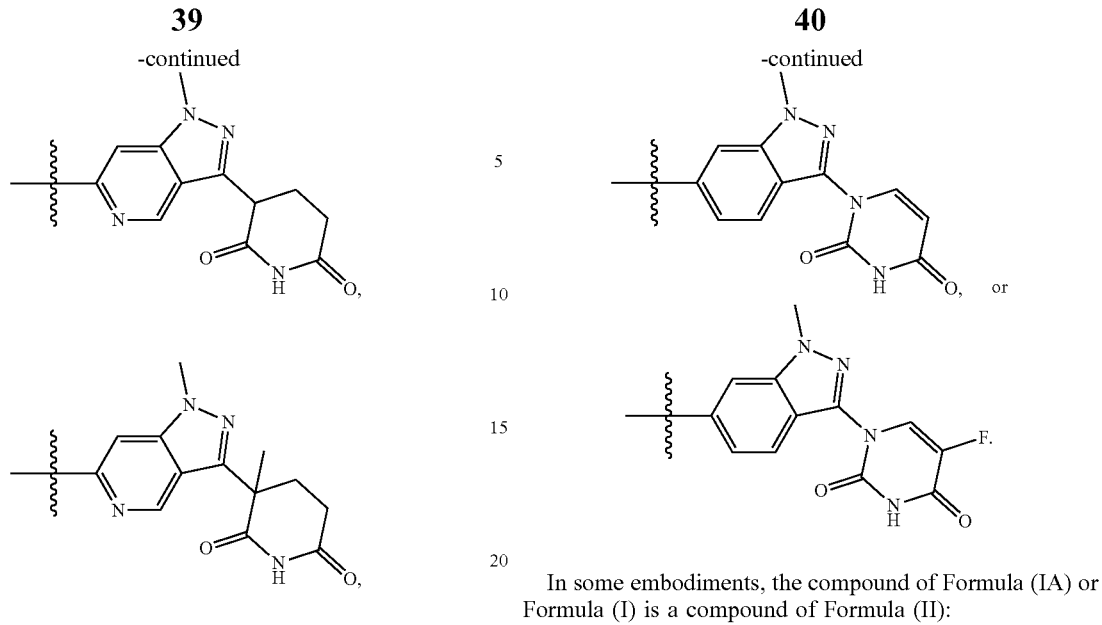

In some embodiments, the compound of Formula (IA) or Formula (I) is a compound of Formula (II):

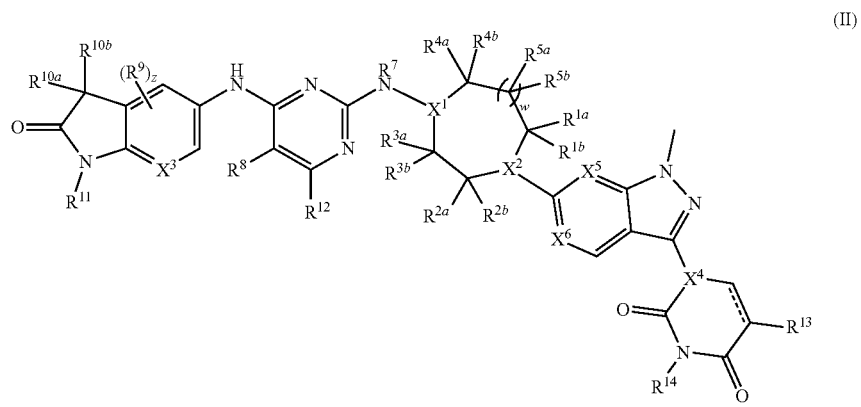

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{7}$, $R^{8}$, $R^{9}$, $R^{10a}$, $R^{10b}$, $R^{11}$, $R^{12}$, $R^{13}$, $R^{14}$, $R^{15}$, $X^{1}$, $X^{2}$, $X^{3}$, $X^{4}$, $X^{5}$, $X^{6}$, w, z, and ══ are as described for Formula (IA) or Formula (I).

In some embodiments, the compound of Formula (IA) or Formula (I) is a compound of Formula (IIa):

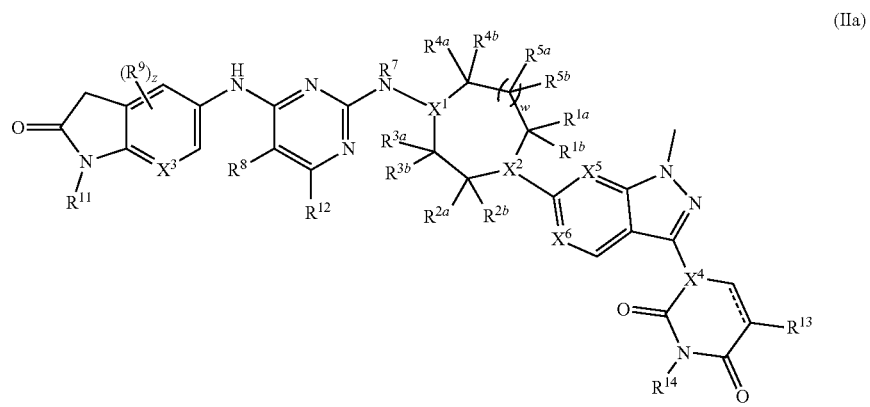

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^7$, $R^8$, $R^9$, $R^{11}$, $R^{12}$, $R^{13}$, $R^{14}$, $R^{15}$, $X^1$, $X^2$, $X^3$, $X^4$, $X^5$, $X^6$, w, z, and === are as described for Formula (IA) or Formula (I).

In some embodiments, the compound of Formula (IA) or Formula (I) is a compound of Formula (IIb):

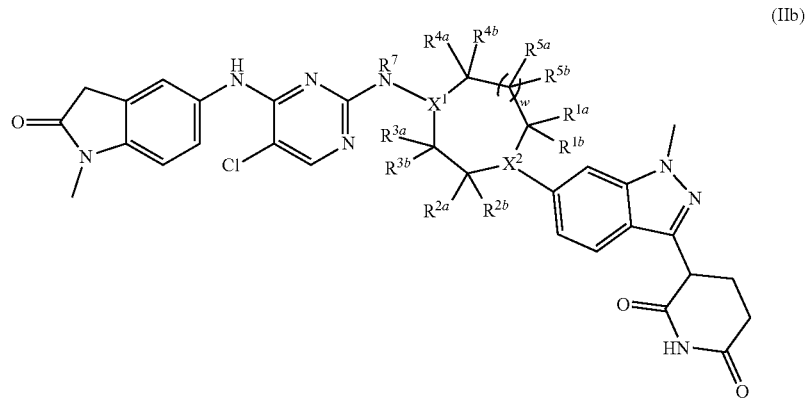

(IIb)

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^7$, $X^1$, $X^2$, and w are as described for Formula (IA) or Formula (I).

In some embodiments, the compound of Formula (IA) or Formula (I) is a compound of Formula (IIc):

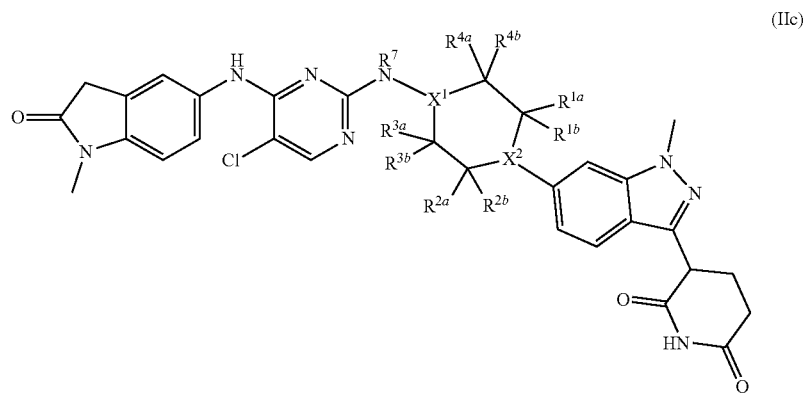

(IIc)

wherein $R^{1a}$, $R^{1b}$, $R^{2a}$, $R^{2b}$, $R^{3a}$, $R^{3b}$, $R^{4a}$, $R^{4b}$, $R^7$, $X^1$, and $X^2$ are as described for Formula Formula (IA) or (I).

In some embodiments, the compound of Formula (IA) or Formula (I) is a compound of Formula (III):

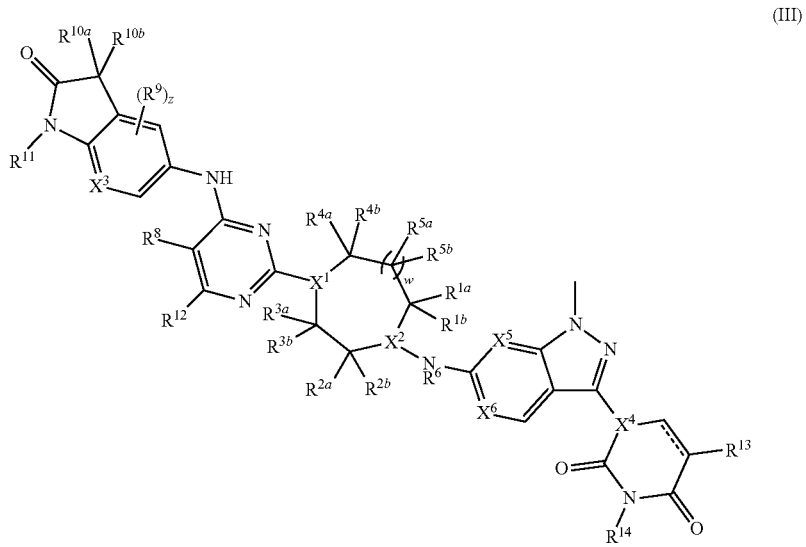

(III)

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^6$, $R^8$, $R^9$, $R^{10a}$, $R^{10b}$, $R^{11}$, $R^{12}$, $R^{13}$, $R^{14}$, $R^{15}$, $X^1$, $X^2$, $X^3$, $X^4$, $X^5$, $X^6$, w, z, and === are as described for Formula (IA) or Formula (I).

In some embodiments, the compound of Formula (IA) or Formula (I) is a compound of Formula (IIIa):

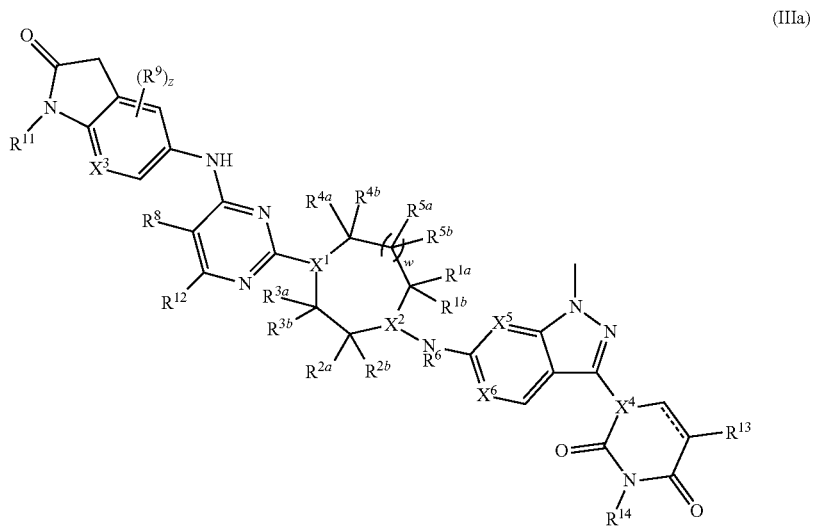

(IIIa)

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^6$, $R^8$, $R^9$, $R^{11}$, $R^{12}$, $R^{13}$, $R^{14}$, $R^{15}$, $X^1$, $X^2$, $X^3$, $X^4$, $X^5$, $X^6$, w, z, and === are as described for Formula (IA) or (I).

In some embodiments, the compound of Formula (IA) or Formula (I) is a compound of Formula (IIIb):

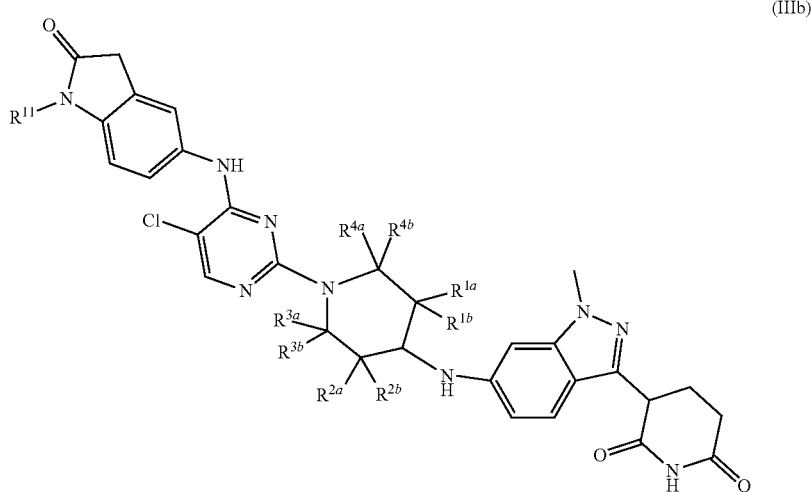

(IIIb)

wherein $R^{1a}$, $R^{1b}$, $R^{2a}$, $R^{2b}$, $R^{3a}$, $R^{3b}$, $R^{4a}$, $R^{4b}$, and $R^{11}$ are as described for Formula (IA) or Formula (I).

In some embodiments, the compound of Formula (IA) or Formula (I) is a compound of Formula (IV):

In some embodiments, the compound of Formula (IA) or Formula (I) is a compound of Formula (IVa):

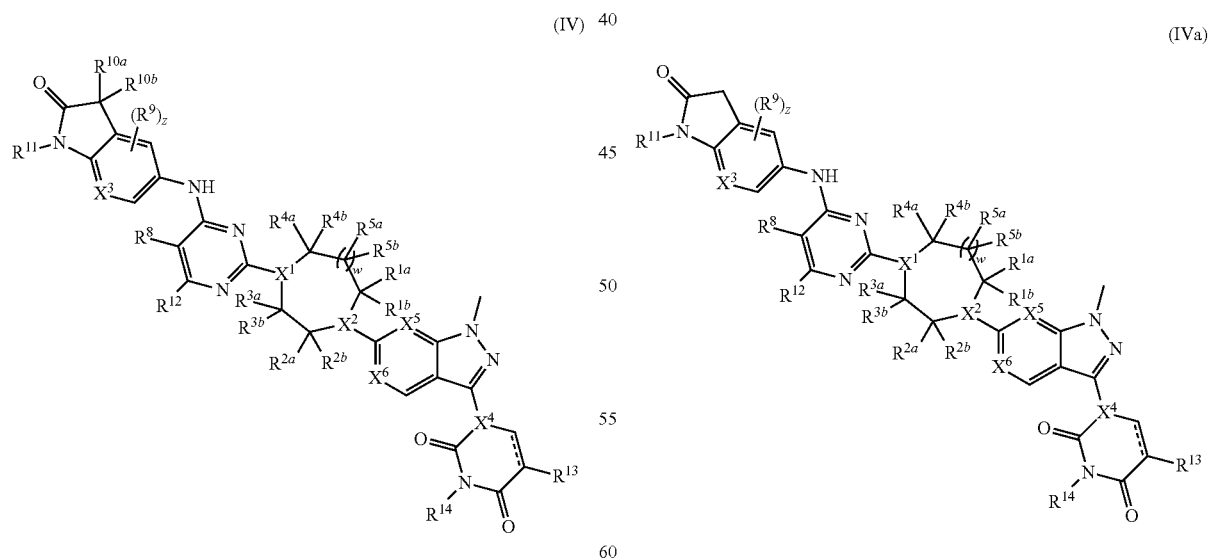

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{8}$, $R^{9}$, $R^{10a}$, $R^{10b}$, $R^{11}$, $R^{12}$, $R^{13}$, $R^{14}$, $R^{15}$, $X^{1}$, $X^{2}$, $X^{3}$, $X^{4}$, $X^{5}$, $X^{6}$, w, z, and === are as described for Formula (IA) or Formula (I).

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{8}$, $R^{9}$, $R^{11}$, $R^{12}$, $R^{13}$, $R^{14}$, $R^{15}$, $X^{1}$, $X^{2}$, $X^{3}$, $X^{4}$, $X^{5}$, $X^{6}$, w, z, and === are as described for Formula (IA) or Formula (I).

In some embodiments, the compound of Formula (IA) or Formula (I) is a compound of Formula (IVb):

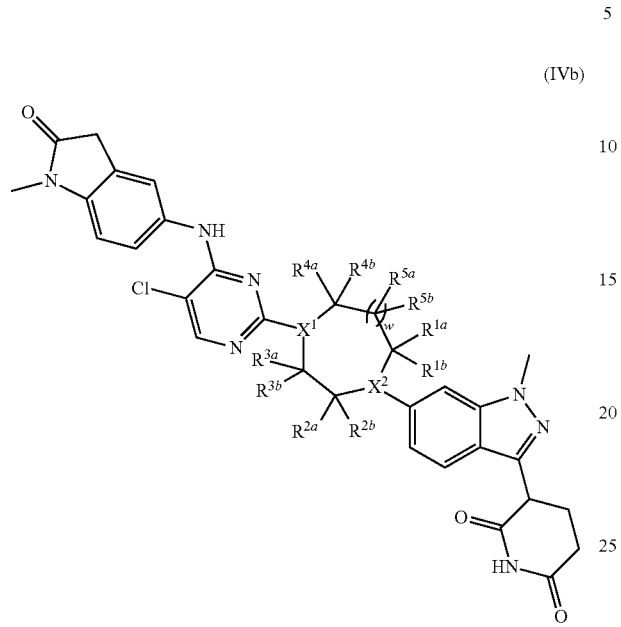

(IVb)

wherein $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $X^1$, $X^2$, and w are as described for Formula (IA) or Formula (I).

In some embodiments, the compound of Formula (IA) or Formula (I) is a compound of Formula (IVc):

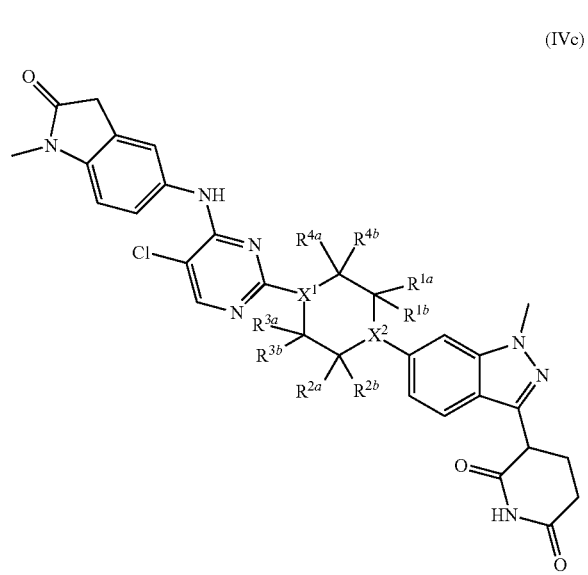

(IVc)

wherein $R^{1a}$, $R^{1b}$, $R^{2a}$, $R^{2b}$, $R^{3a}$, $R^{3b}$, $R^{4a}$, $R^{4b}$, $X^1$, and $X^2$ are as described for Formula (IA) or Formula (I).

In some embodiments, the compound of Formula (IA) or Formula (I) is a compound of Formula (IVd):

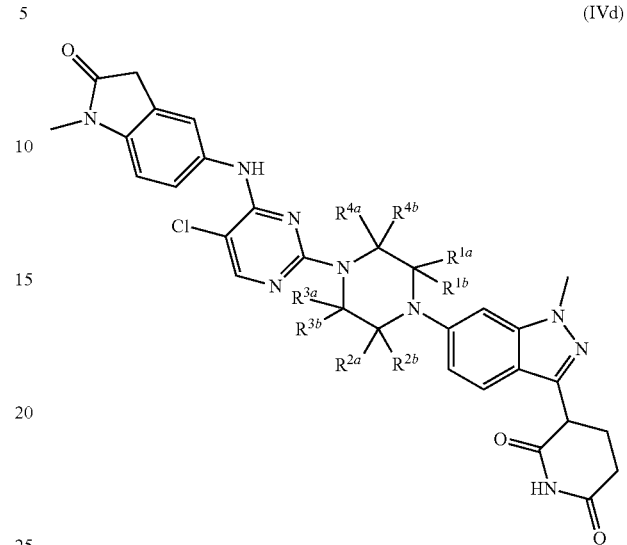

(IVd)

wherein $R^{1a}$, $R^{1b}$, $R^{2a}$, $R^{2b}$, $R^{3a}$, $R^{3b}$, $R^{4a}$, and $R^{4b}$ are as described for Formula (IA) or Formula (I).

It is understood that any of the compounds described herein can include replacement of one or more hydrogen atoms by deuterium. Any one or more of the substituents of Formula (IA) or Formula (I) can be deuterated, such as one or more of $X^1$, $X^2$, $X^3$, $X^5$, $X^6$, $R^{1a}$, $R^{1b}$, $R^{3a}$, $R^{3b}$, $R^{4a}$, $R^{4b}$, $R^{5a}$, $R^{5b}$, $R^6$, $R^7$, $R^{10a}$, $R^{10b}$, $R^{11}$, $R^{12}$, $R^{13}$, $R^{14}$, and $R^{15}$. For example, in some embodiments, $R^{11}$ is a deuterated group, such as -CD$_3$.

In the descriptions herein, it is understood that all descriptions, variations, embodiments, or aspects of Formula (IA) or Formula (I), where applicable, apply equally to other formulae detailed herein, and are equally described, the same as if each and every description, variation, embodiment, or aspect were separately and individually listed. It is also understood that all descriptions, variations, embodiments, or aspects of Formula (IA) or Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (IA) or Formula (I), where applicable, apply equally to any of the formulae as detailed herein, such as Formulae (II), (IIa), (IIb), (IIc), (III), (IIIa), (IIIb), (IV), (IVa), (IVb), (IVc), and (MV), and are equally described, the same as if each and every description, variation, embodiment, or aspect were separately and individually listed for all formulae.

In some embodiments, provided is a compound selected from the compounds in Table 1 or a pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

TABLE 1
| Compound No. | Structure |
|---|---|
| 1 | 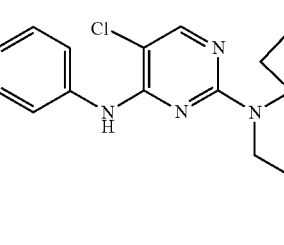 |
| 2 | 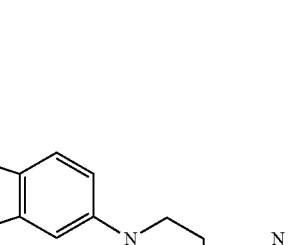 |
| 3 | 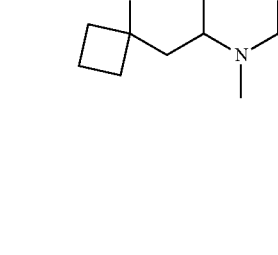 |
| 4 | 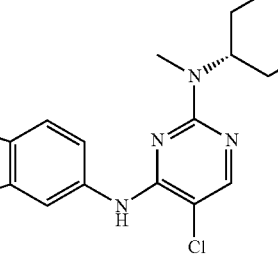 |

| Compound No. | Structure |
|---|---|
| 5 | 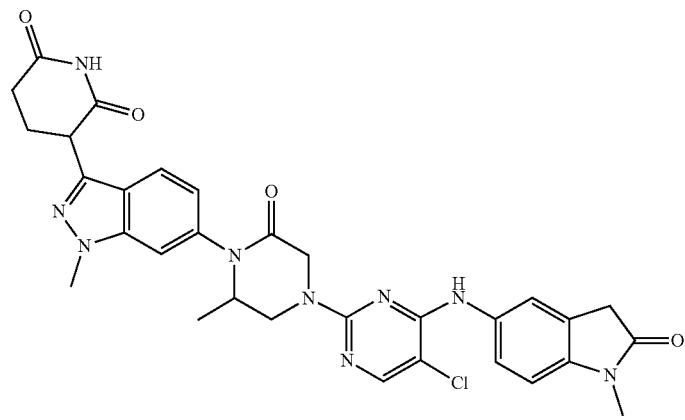 [SMILES: CC1CN(c2ncc(Cl)c(Nc3ccc4c(c3)CC(=O)N4C)n2)CC(=O)N1c1ccc2c(C3CCC(=O)NC3=O)nn(C)c2c1] |
| 6 | 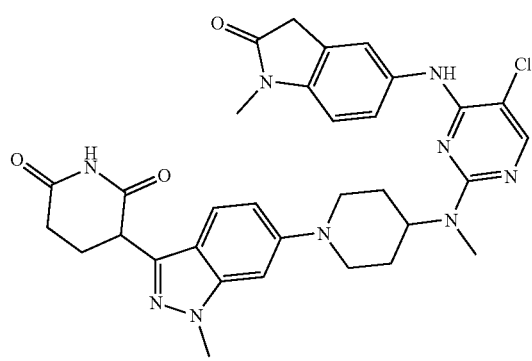 [SMILES: CN1C(=O)Cc2cc(Nc3nc(N(C)C4CCN(c5ccc6c(C7CCC(=O)NC7=O)nn(C)c6c5)CC4)ncc3Cl)ccc21] |
| 7 | 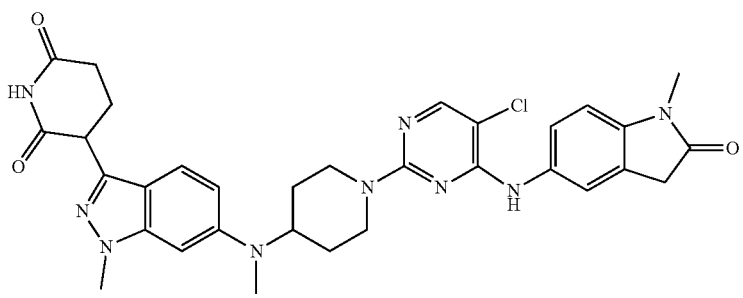 |
| 8 | 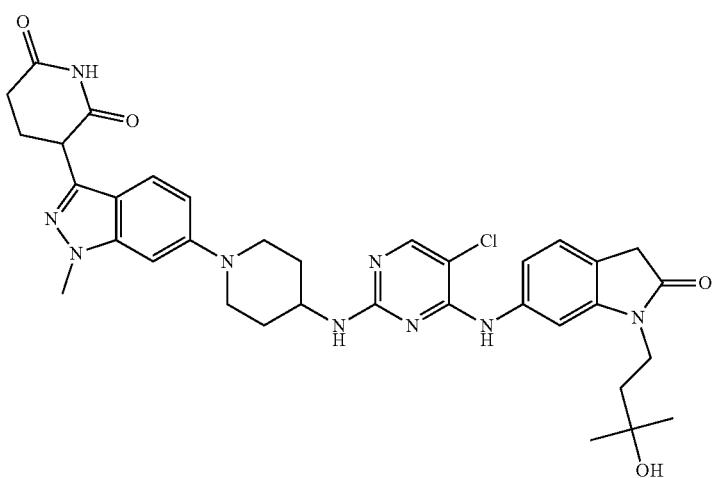 [SMILES: Cn1nc(C2CCC(=O)NC2=O)c2ccc(N3CCC(Nc4ncc(Cl)c(Nc5ccc6c(c5)N(CCC(C)(C)O)C(=O)C6)n4)CC3)cc21] |

TABLE 1-continued
| Compound No. | Structure |
|---|---|
| 9 | 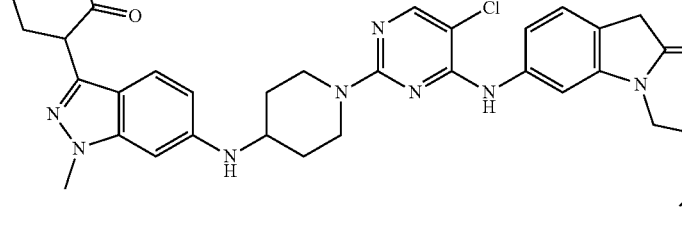 |
| 10 | 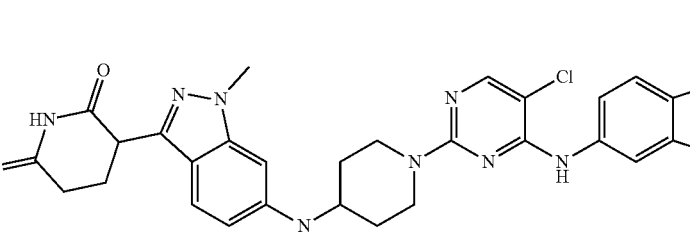 |
| 11 | 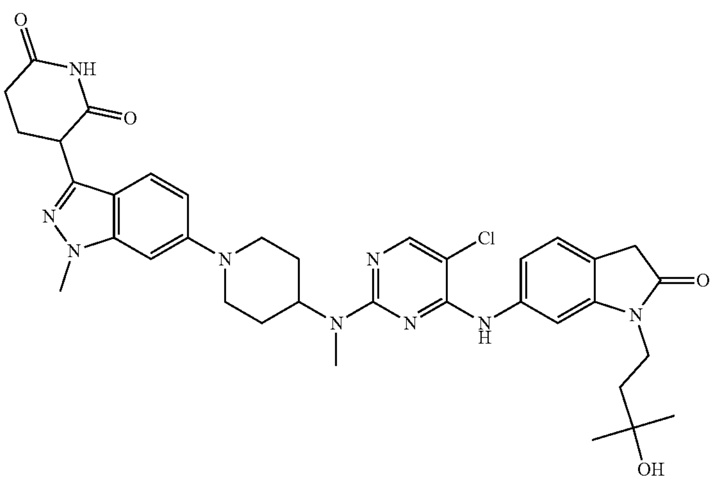 [SMILES: CN(c1ncc(Cl)c(Nc2ccc3c(c2)N(CCC(C)(C)O)C(=O)C3)n1)C1CCN(c2ccc3c(C4CCC(=O)NC4=O)nn(C)c3c2)CC1] |
| 12 | 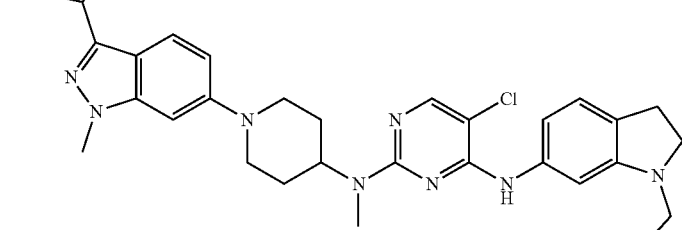 |

TABLE 1-continued
| Compound No. | Structure |
|---|---|
| 13 | 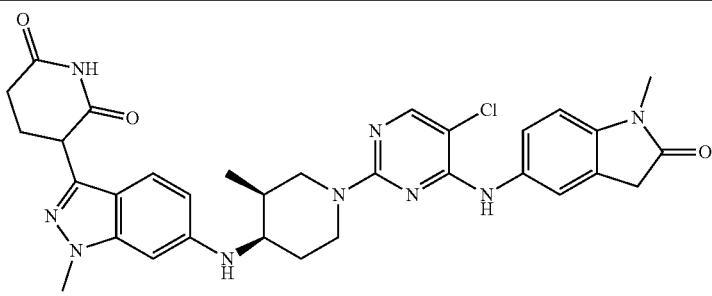 |
| 14 | 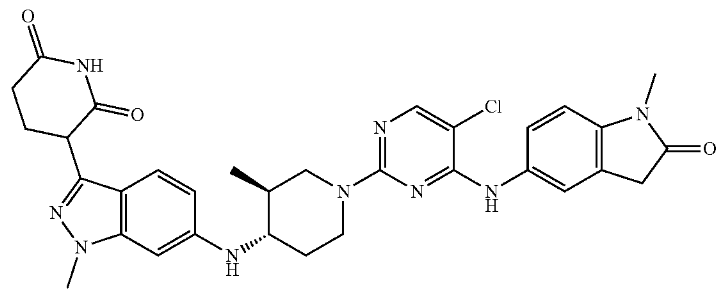 [SMILES: C[C@H]1CN(c2ncc(Cl)c(Nc3ccc4c(c3)CC(=O)N4C)n2)CC[C@@H]1Nc1ccc2c(C3CCC(=O)NC3=O)nn(C)c2c1] |
| 15 | 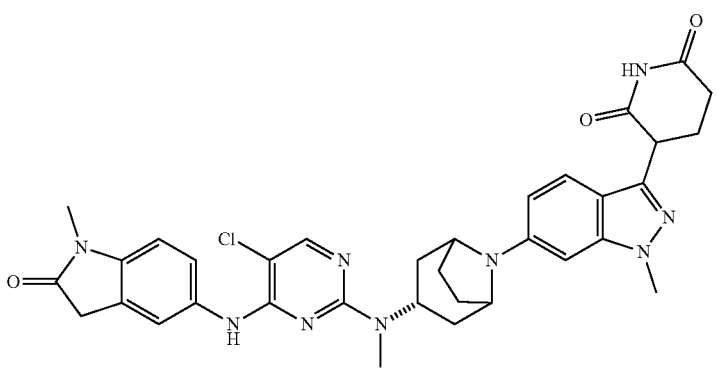 |
| 16 | 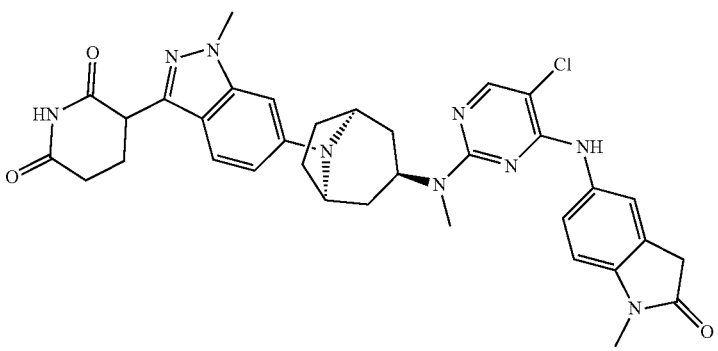 [SMILES: CN1C(=O)Cc2cc(Nc3nc(N(C)[C@H]4C[C@H]5CC[C@@H](C4)N5c4ccc5c(C6CCC(=O)NC6=O)nn(C)c5c4)ncc3Cl)ccc21] |
| 17 | 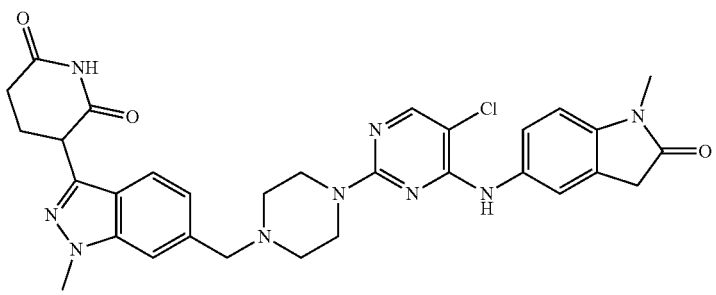 [SMILES: CN1C(=O)Cc2cc(Nc3nc(N4CCN(Cc5ccc6c(C7CCC(=O)NC7=O)nn(C)c6c5)CC4)ncc3Cl)ccc21] |

TABLE 1-continued

| Compound No. | Structure |
|---|---|
| 18 | 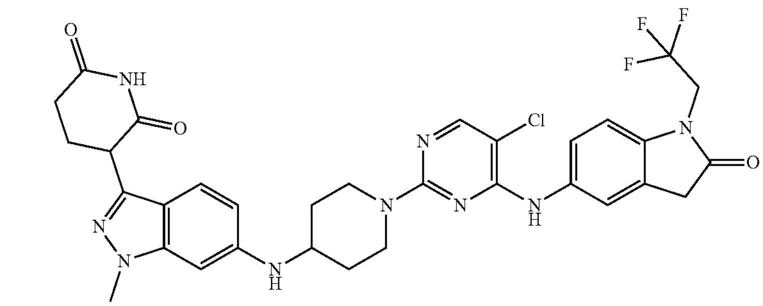 [SMILES: Cn1nc(C2CCC(=O)NC2=O)c2ccc(NC3CCN(c4ncc(Cl)c(Nc5ccc6c(c5)CC(=O)N6CC(F)(F)F)n4)CC3)cc21] |
| 19 | 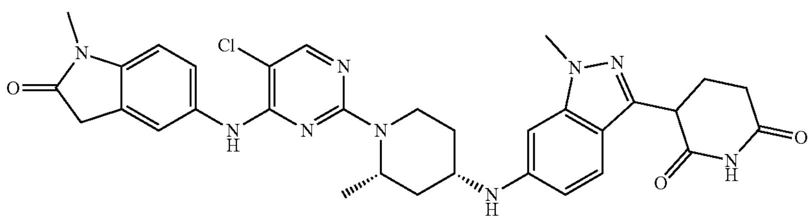 [SMILES: C[C@H]1C[C@@H](Nc2ccc3c(C4CCC(=O)NC4=O)nn(C)c3c2)CCN1c1ncc(Cl)c(Nc2ccc3c(c2)CC(=O)N3C)n1] |
| 20 | 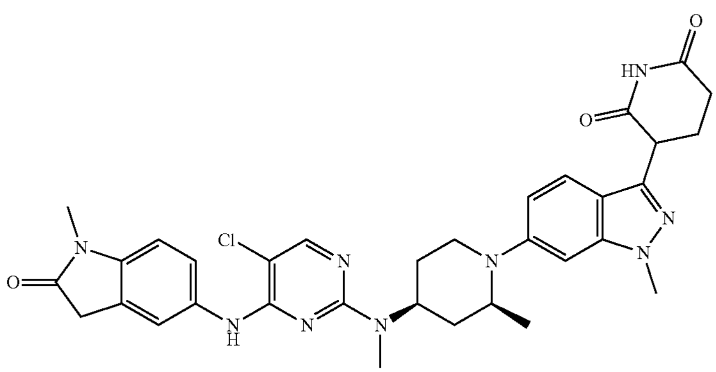 [SMILES: C[C@H]1C[C@@H](N(C)c2ncc(Cl)c(Nc3ccc4c(c3)CC(=O)N4C)n2)CCN1c1ccc2c(C3CCC(=O)NC3=O)nn(C)c2c1] |
| 21 | 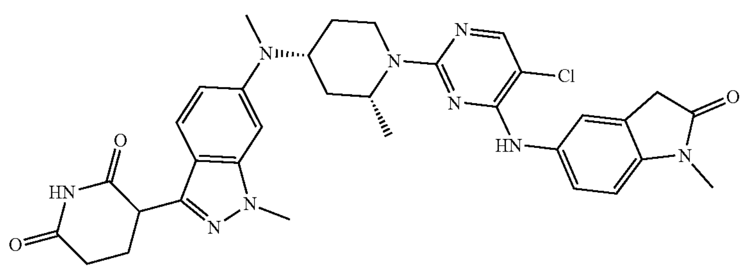 [SMILES: C[C@@H]1C[C@H](N(C)c2ccc3c(C4CCC(=O)NC4=O)nn(C)c3c2)CCN1c1ncc(Cl)c(Nc2ccc3c(c2)CC(=O)N3C)n1] |
| 22 | 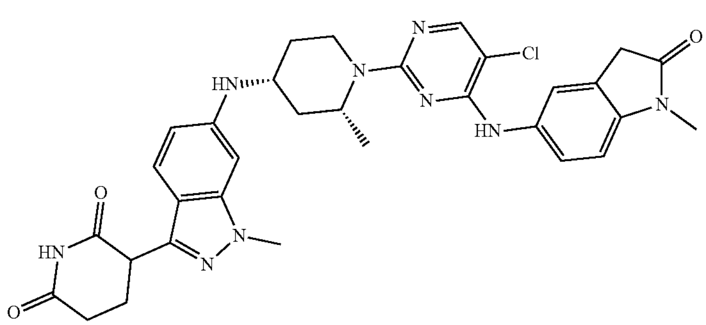 [SMILES: C[C@@H]1C[C@H](Nc2ccc3c(C4CCC(=O)NC4=O)nn(C)c3c2)CCN1c1ncc(Cl)c(Nc2ccc3c(c2)CC(=O)N3C)n1] |

TABLE 1-continued

| Compound No. | Structure |
|---|---|
| 23 | 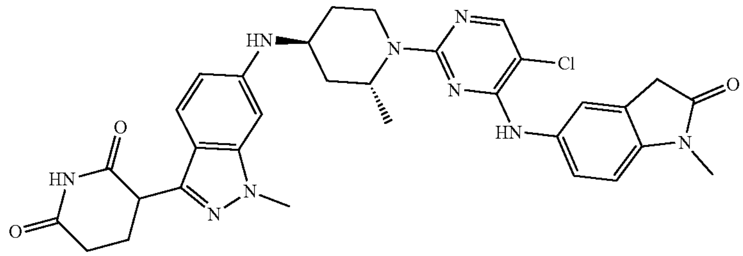 [SMILES: C[C@@H]1C[C@@H](Nc2ccc3c(C4CCC(=O)NC4=O)nn(C)c3c2)CCN1c1ncc(Cl)c(Nc2ccc3c(c2)CC(=O)N3C)n1] |
| 24 | 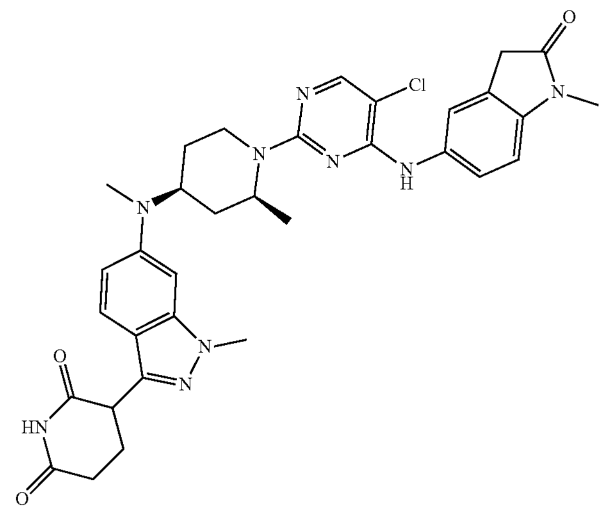 [SMILES: C[C@H]1C[C@@H](N(C)c2ccc3c(C4CCC(=O)NC4=O)nn(C)c3c2)CCN1c1ncc(Cl)c(Nc2ccc3c(c2)CC(=O)N3C)n1] |
| 25 | 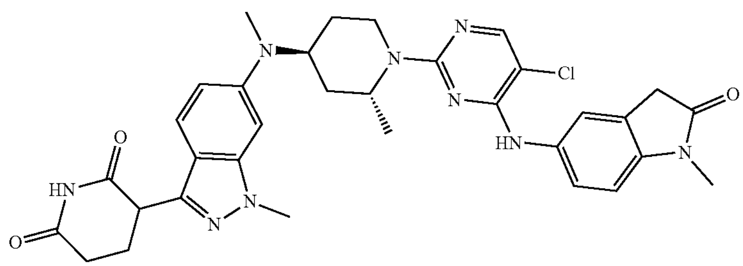 [SMILES: C[C@@H]1C[C@@H](N(C)c2ccc3c(C4CCC(=O)NC4=O)nn(C)c3c2)CCN1c1ncc(Cl)c(Nc2ccc3c(c2)CC(=O)N3C)n1] |
| 26 | 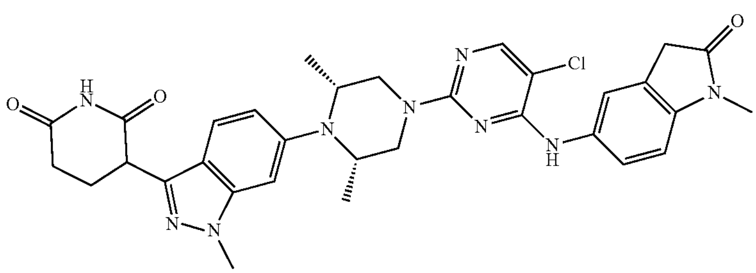 [SMILES: C[C@@H]1CN(c2ncc(Cl)c(Nc3ccc4c(c3)CC(=O)N4C)n2)C[C@H](C)N1c1ccc2c(C3CCC(=O)NC3=O)nn(C)c2c1] |
| 27 | 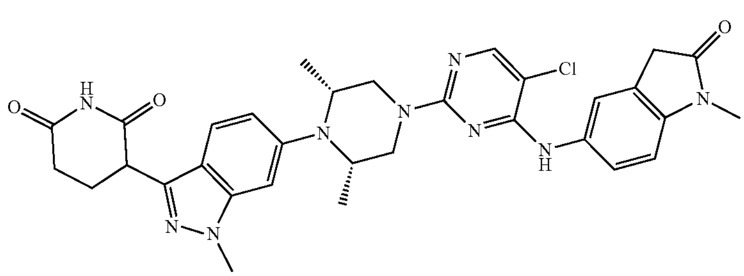 |

TABLE 1-continued
| Compound No. | Structure |
|---|---|
| 28 | 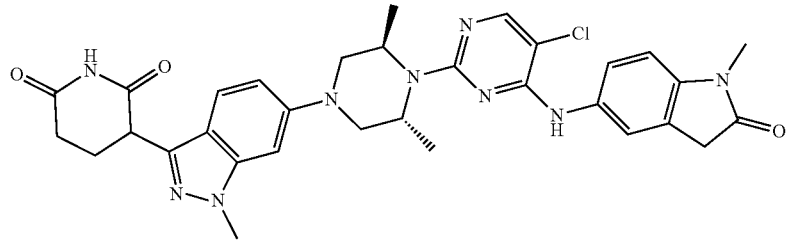 [SMILES: C[C@@H]1CN(c2ccc3c(C4CCC(=O)NC4=O)nn(C)c3c2)C[C@@H](C)N1c1ncc(Cl)c(Nc2ccc3c(c2)CC(=O)N3C)n1] |
| 29 | 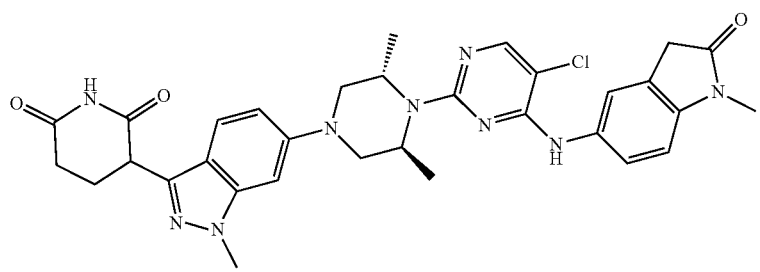 [SMILES: C[C@H]1CN(c2ccc3c(C4CCC(=O)NC4=O)nn(C)c3c2)C[C@H](C)N1c1ncc(Cl)c(Nc2ccc3c(c2)CC(=O)N3C)n1] |
| 30 | 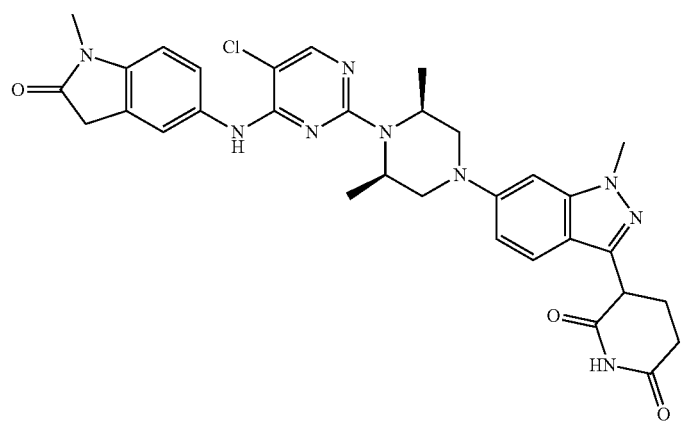 [SMILES: C[C@@H]1CN(c2ccc3c(C4CCC(=O)NC4=O)nn(C)c3c2)C[C@H](C)N1c1ncc(Cl)c(Nc2ccc3c(c2)CC(=O)N3C)n1] |
| 31 | 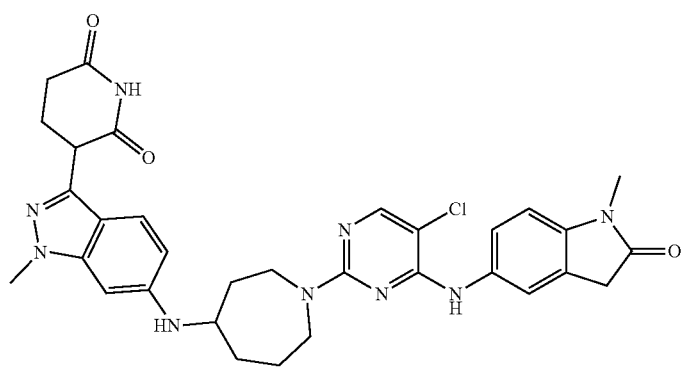 [SMILES: CN1C(=O)Cc2cc(Nc3nc(N4CCCC(Nc5ccc6c(C7CCC(=O)NC7=O)nn(C)c6c5)CC4)ncc3Cl)ccc21] |
| 32 | 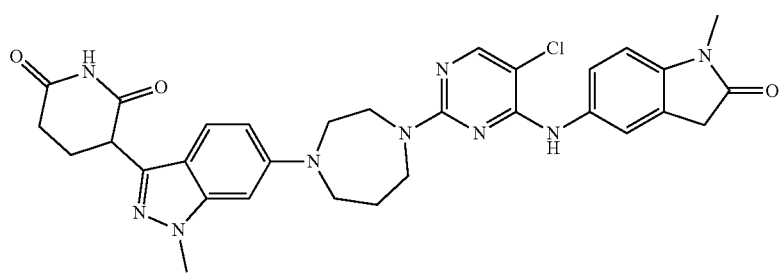 [SMILES: CN1C(=O)Cc2cc(Nc3nc(N4CCCN(c5ccc6c(C7CCC(=O)NC7=O)nn(C)c6c5)CC4)ncc3Cl)ccc21] |

TABLE 1-continued
| Compound No. | Structure |
|---|---|
| 33 | 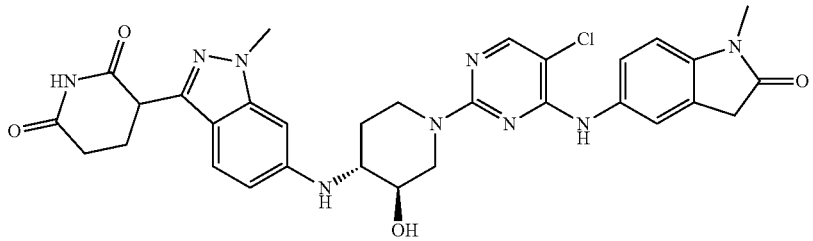 [SMILES: CN1C(=O)Cc2cc(Nc3nc(N4CC[C@@H](Nc5ccc6c(C7CCC(=O)NC7=O)nn(C)c6c5)[C@H](O)C4)ncc3Cl)ccc21] |
| 34 | 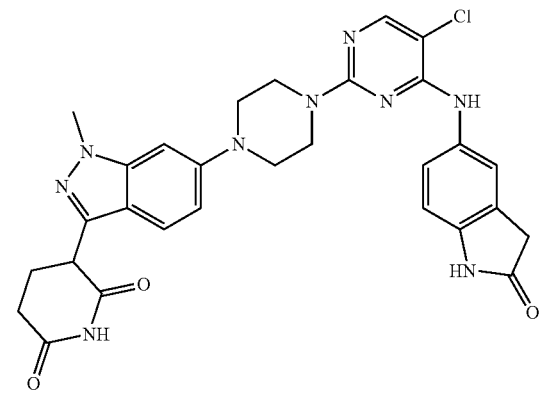 |
| 35 | 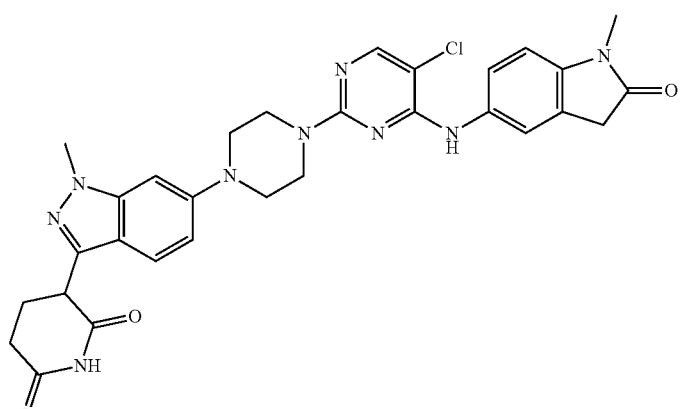 |

TABLE 1-continued
| Compound No. | Structure |
| --- | --- |
| 36 | 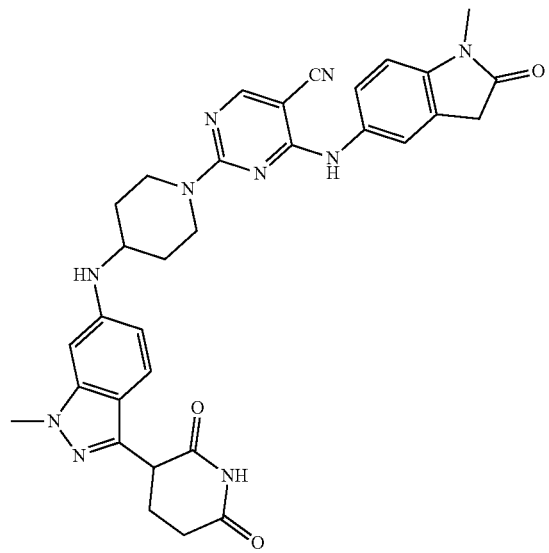 [SMILES: CN1C(=O)Cc2cc(Nc3nc(N4CCC(Nc5ccc6c(C7CCC(=O)NC7=O)nn(C)c6c5)CC4)ncc3C#N)ccc21] |
| 37 | 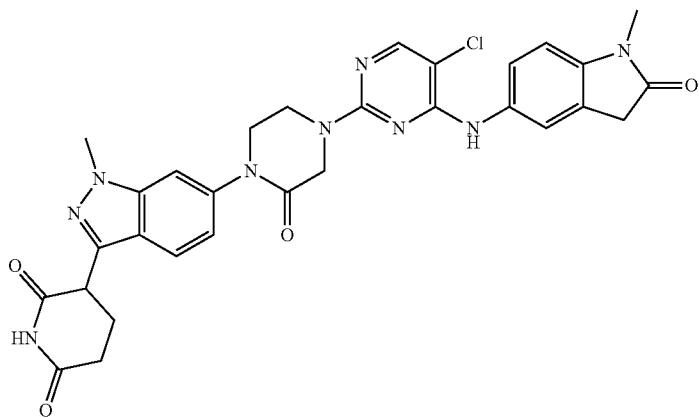 [SMILES: CN1C(=O)Cc2cc(Nc3nc(N4CCN(c5ccc6c(C7CCC(=O)NC7=O)nn(C)c6c5)C(=O)C4)ncc3Cl)ccc21] |
| 38 | 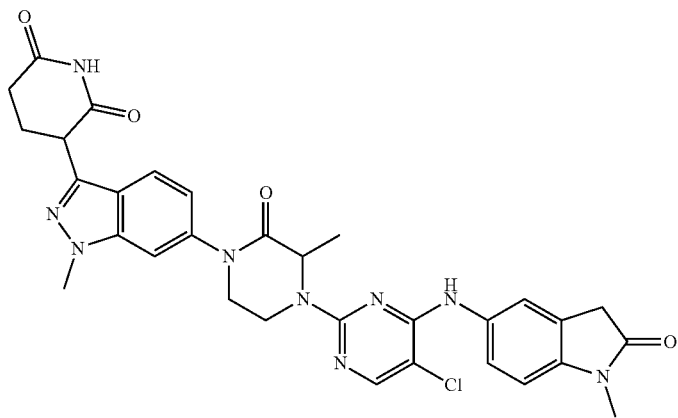 [SMILES: CC1C(=O)N(c2ccc3c(C4CCC(=O)NC4=O)nn(C)c3c2)CCN1c1ncc(Cl)c(Nc2ccc3c(c2)CC(=O)N3C)n1] |

TABLE 1-continued
| Compound No. | Structure |
|---|---|
| 39 | 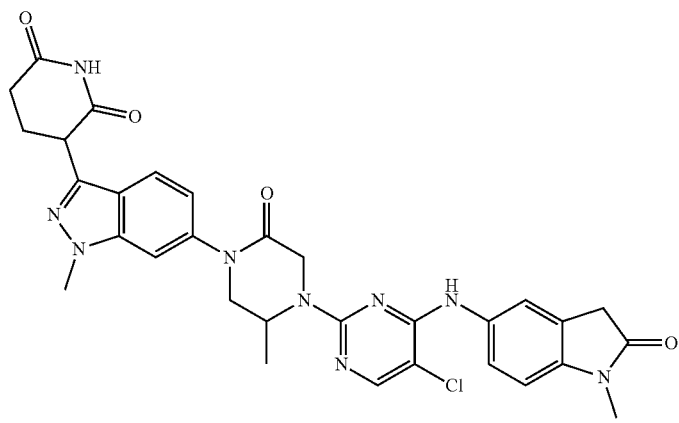 [SMILES: CC1CN(c2ccc3c(C4CCC(=O)NC4=O)nn(C)c3c2)C(=O)CN1c1ncc(Cl)c(Nc2ccc3c(c2)CC(=O)N3C)n1] |
| 40 | 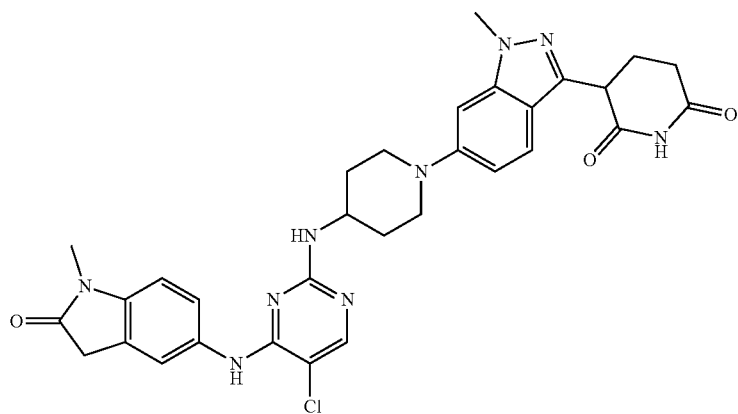 [SMILES: CN1C(=O)Cc2cc(Nc3nc(NC4CCN(c5ccc6c(C7CCC(=O)NC7=O)nn(C)c6c5)CC4)ncc3Cl)ccc21] |
| 41 | 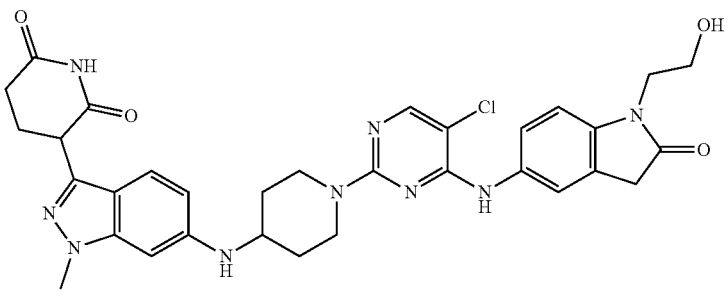 [SMILES: Cn1nc(C2CCC(=O)NC2=O)c2ccc(NC3CCN(c4ncc(Cl)c(Nc5ccc6c(c5)CC(=O)N6CCO)n4)CC3)cc21] |
| 42 | 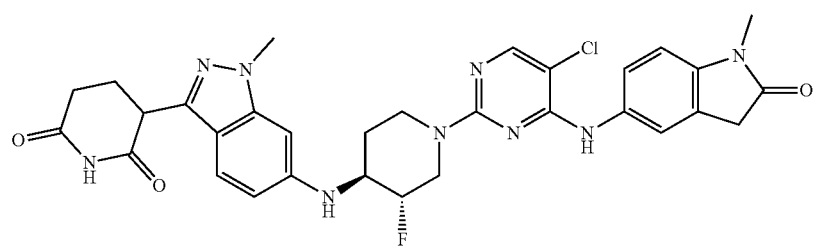 [SMILES: CN1C(=O)Cc2cc(Nc3nc(N4CC[C@H](Nc5ccc6c(C7CCC(=O)NC7=O)nn(C)c6c5)[C@@H](F)C4)ncc3Cl)ccc21] |

| Compound No. | Structure |
|---|---|
| 43 | 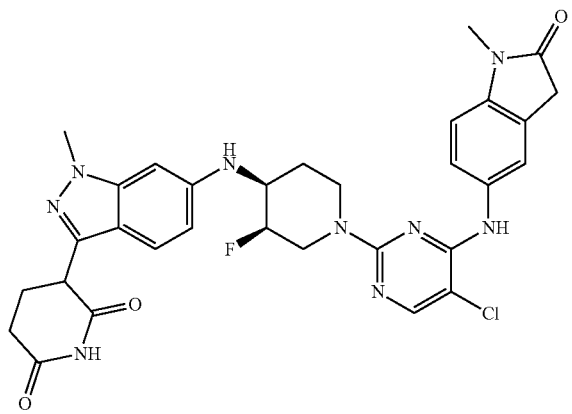 [SMILES: CN1C(=O)Cc2cc(Nc3nc(N4CC[C@H](Nc5ccc6c(C7CCC(=O)NC7=O)nn(C)c6c5)[C@H](F)C4)ncc3Cl)ccc21] |
| 44 | 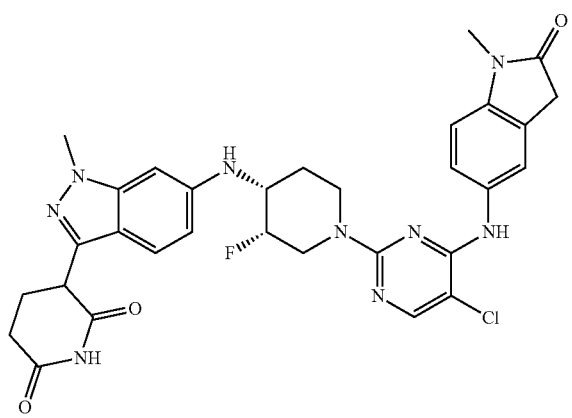 [SMILES: CN1C(=O)Cc2cc(Nc3nc(N4CC[C@@H](Nc5ccc6c(C7CCC(=O)NC7=O)nn(C)c6c5)[C@@H](F)C4)ncc3Cl)ccc21] |
| 45 | 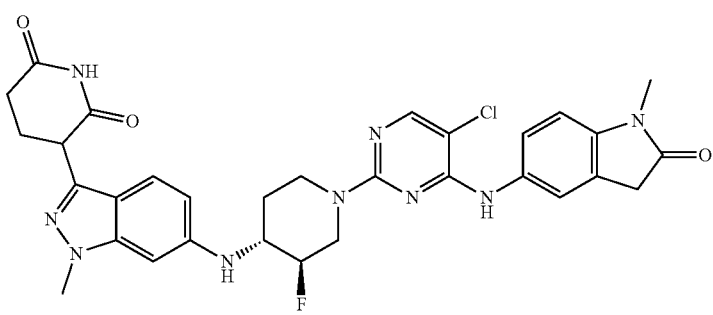 [SMILES: CN1C(=O)Cc2cc(Nc3nc(N4CC[C@@H](Nc5ccc6c(C7CCC(=O)NC7=O)nn(C)c6c5)[C@H](F)C4)ncc3Cl)ccc21] |
| 46 | 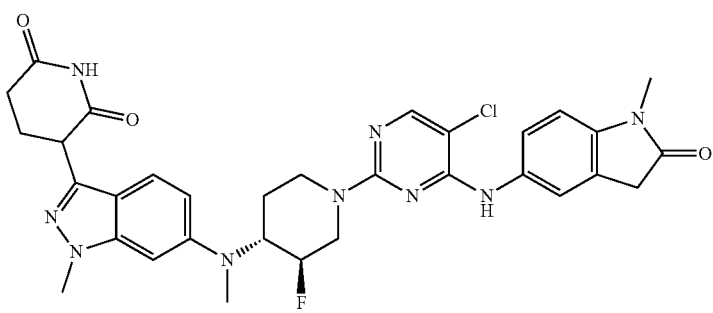 |

TABLE 1-continued
| Compound No. | Structure |
|---|---|
| 47 | 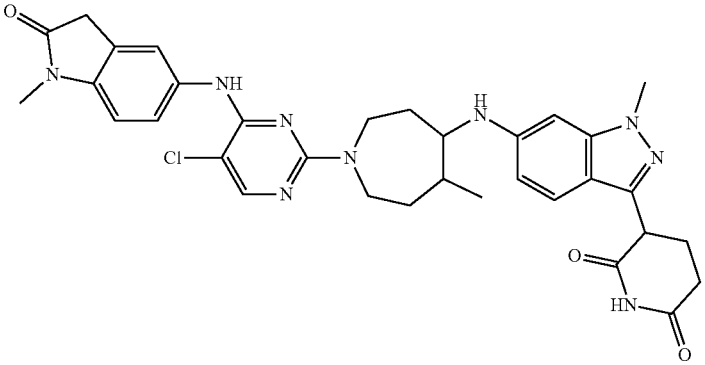 [SMILES: CC1CCN(c2ncc(Cl)c(Nc3ccc4c(c3)CC(=O)N4C)n2)CCC1Nc1ccc2c(C3CCC(=O)NC3=O)nn(C)c2c1] |
| 48 | 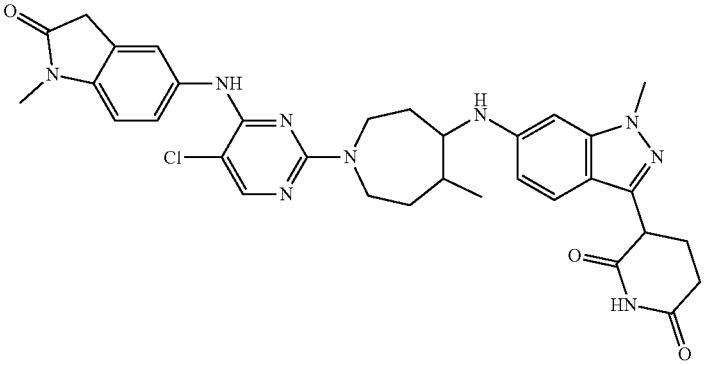 [SMILES: CC1CCN(c2ncc(Cl)c(Nc3ccc4c(c3)CC(=O)N4C)n2)CCC1Nc1ccc2c(C3CCC(=O)NC3=O)nn(C)c2c1] |
| 49 | 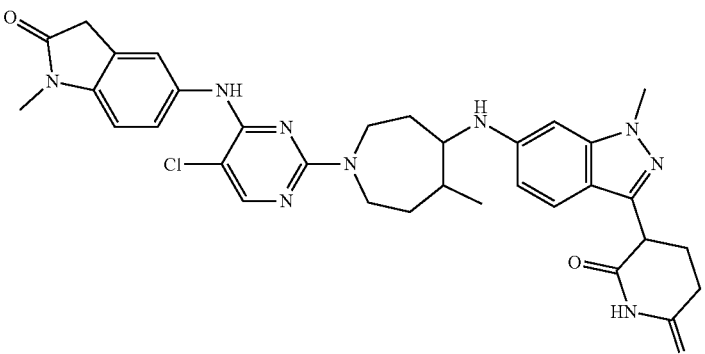 |
| 50 | 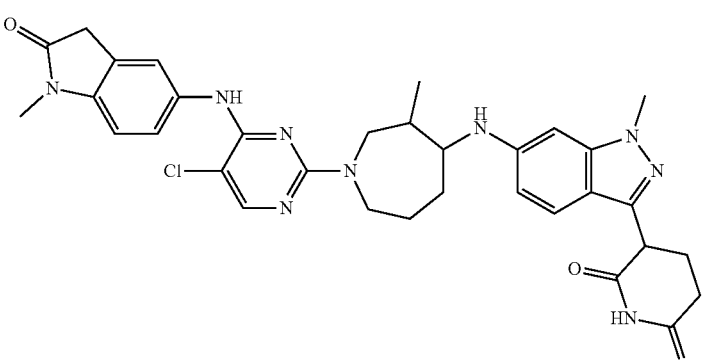 |

TABLE 1-continued
| Compound No. | Structure |
|---|---|
| 51 | 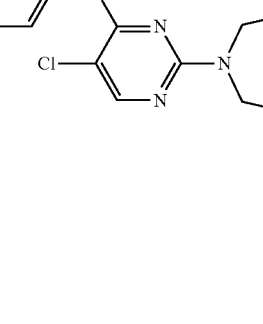 |
| 52 | 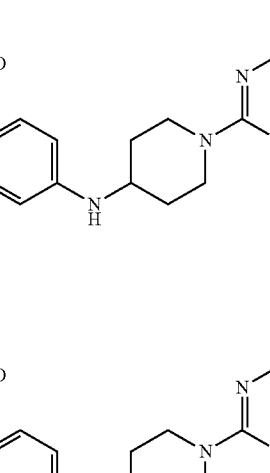 |
| 53 | 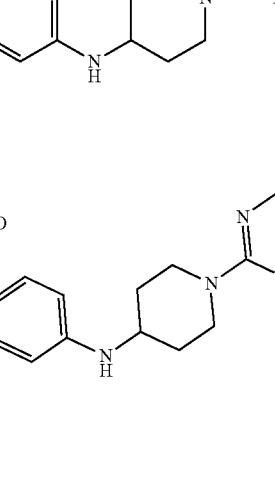 |
| 54 | 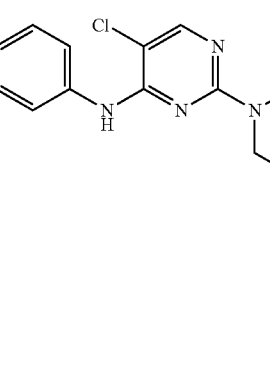 |
| 55 | 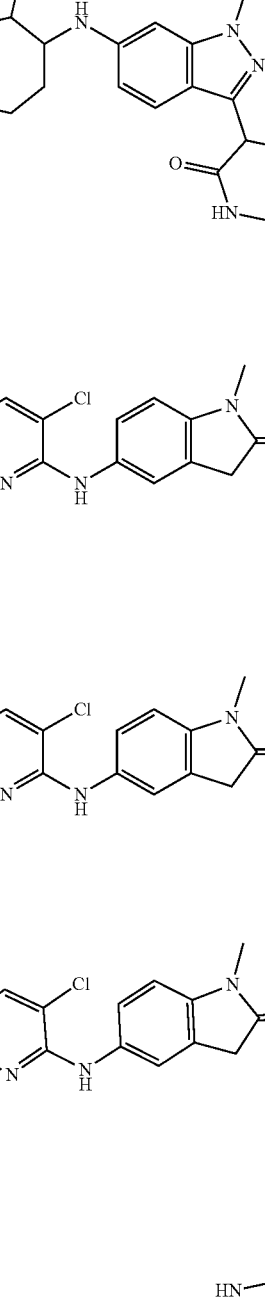 |

TABLE 1-continued
| Compound No. | Structure |
|---|---|
| 56 | 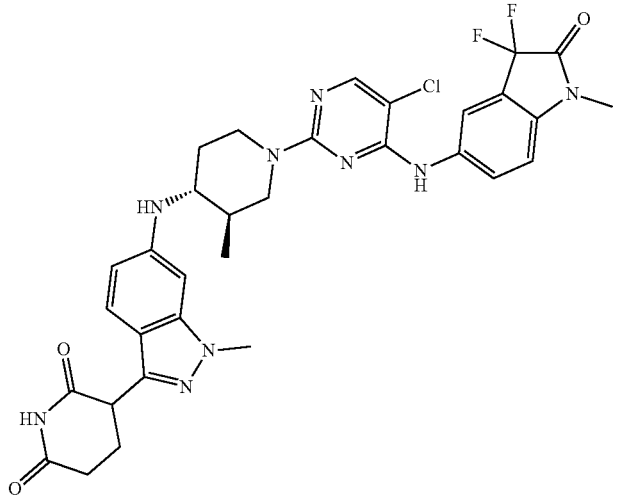 [SMILES: C[C@@H]1CN(c2ncc(Cl)c(Nc3ccc4c(c3)C(F)(F)C(=O)N4C)n2)CC[C@H]1Nc1ccc2c(C3CCC(=O)NC3=O)nn(C)c2c1] |
| 57 | 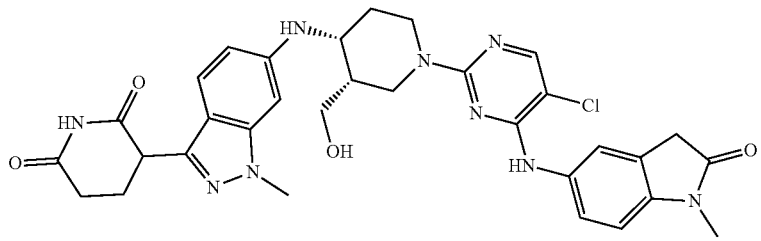 [SMILES: CN1C(=O)Cc2cc(Nc3nc(N4CC[C@@H](Nc5ccc6c(C7CCC(=O)NC7=O)nn(C)c6c5)[C@@H](CO)C4)ncc3Cl)ccc21] |
| 58 | 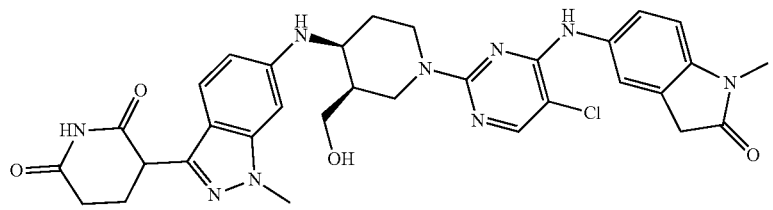 [SMILES: CN1C(=O)Cc2cc(Nc3nc(N4CC[C@H](Nc5ccc6c(C7CCC(=O)NC7=O)nn(C)c6c5)[C@H](CO)C4)ncc3Cl)ccc21] |
| 59 | 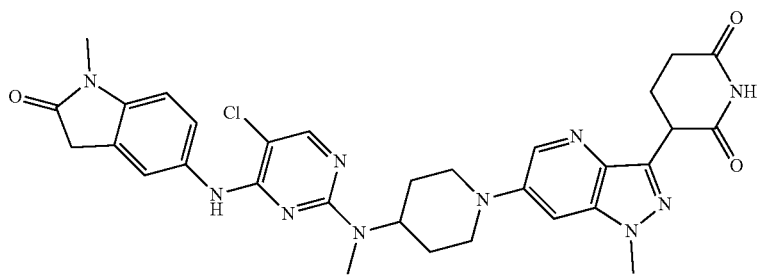 [SMILES: CN1C(=O)Cc2cc(Nc3nc(N(C)C4CCN(c5cnc6c(C7CCC(=O)NC7=O)nn(C)c6c5)CC4)ncc3Cl)ccc21] |
| 60 | 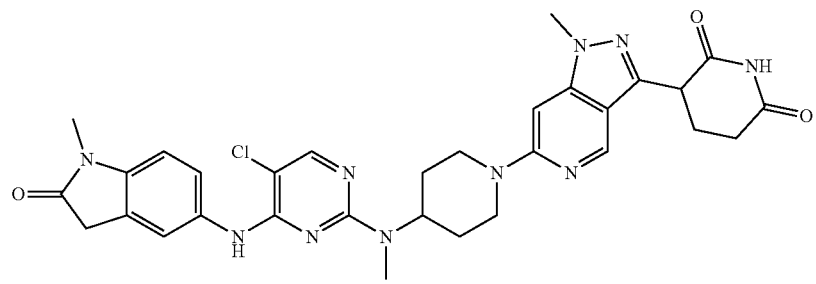 [SMILES: CN1C(=O)Cc2cc(Nc3nc(N(C)C4CCN(c5cc6c(cn5)c(C5CCC(=O)NC5=O)nn6C)CC4)ncc3Cl)ccc21] |

TABLE 1-continued
| Compound No. | Structure |
|---|---|
| 61 | 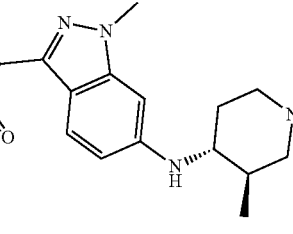 |
| 62 | 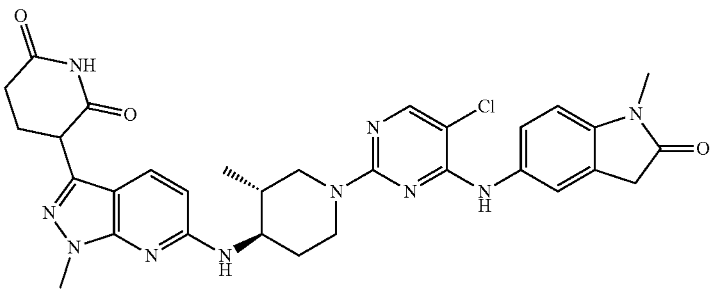 [SMILES: C[C@@H]1CN(c2ncc(Cl)c(Nc3ccc4c(c3)CC(=O)N4C)n2)CC[C@H]1Nc1ccc2c(C3CCC(=O)NC3=O)nn(C)c2n1] |
| 63 | 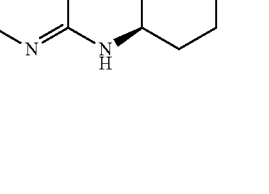 |
| 64 | 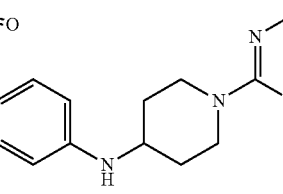 |
| 65 | 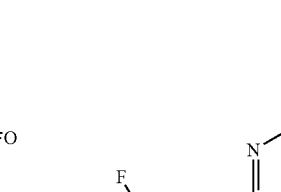 |

TABLE 1-continued

| Compound No. | Structure |
|---|---|
| 66 | 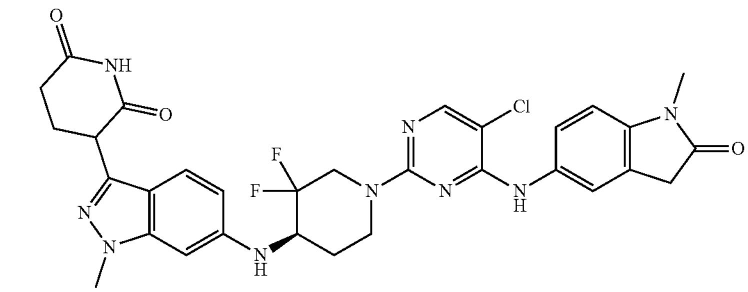 [SMILES: CN1C(=O)Cc2cc(Nc3nc(N4CC[C@@H](Nc5ccc6c(C7CCC(=O)NC7=O)nn(C)c6c5)C(F)(F)C4)ncc3Cl)ccc21] |
| 67 | 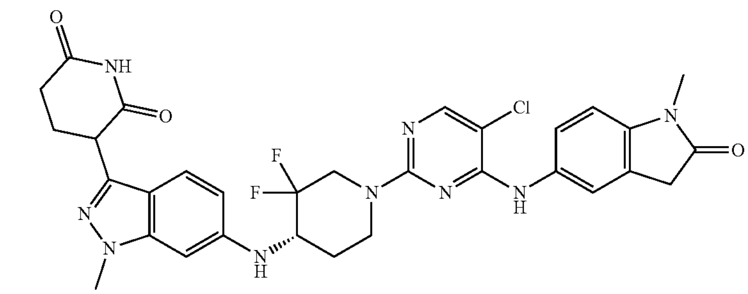 [SMILES: CN1C(=O)Cc2cc(Nc3nc(N4CC[C@H](Nc5ccc6c(C7CCC(=O)NC7=O)nn(C)c6c5)C(F)(F)C4)ncc3Cl)ccc21] |
| 68 | 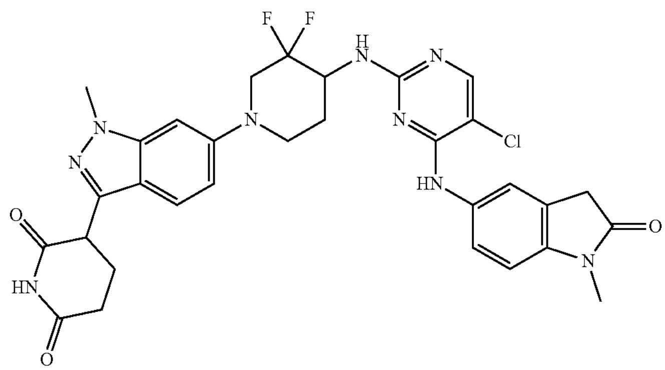 [SMILES: CN1C(=O)Cc2cc(Nc3nc(NC4CCN(c5ccc6c(C7CCC(=O)NC7=O)nn(C)c6c5)CC4(F)F)ncc3Cl)ccc21] |
| 69 | 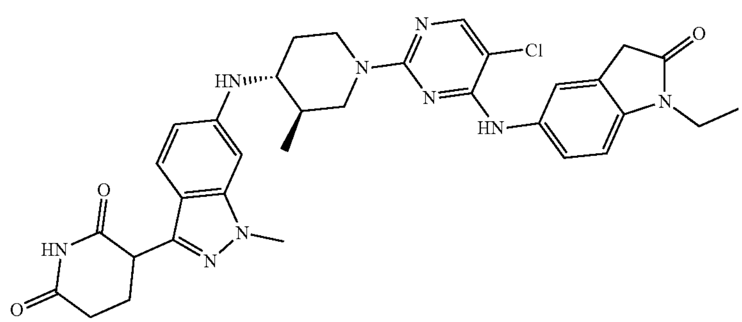 [SMILES: CCN1C(=O)Cc2cc(Nc3nc(N4CC[C@@H](Nc5ccc6c(C7CCC(=O)NC7=O)nn(C)c6c5)[C@H](C)C4)ncc3Cl)ccc21] |
| 70 | 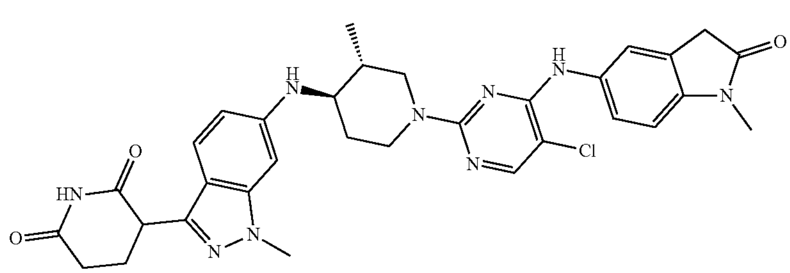 [SMILES: C[C@@H]1CN(c2ncc(Cl)c(Nc3ccc4c(c3)CC(=O)N4C)n2)CC[C@H]1Nc1ccc2c(C3CCC(=O)NC3=O)nn(C)c2c1] |

TABLE 1-continued
| Compound No. | Structure |
|---|---|
| 71 | 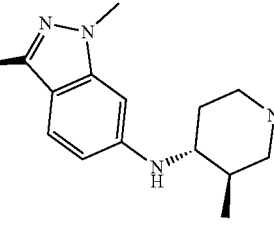 |
| 72 | 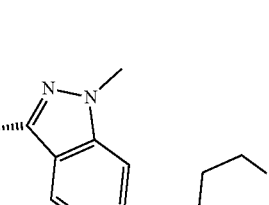 |
| 73 | 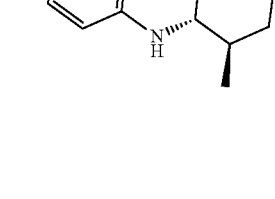 |
| 74 | 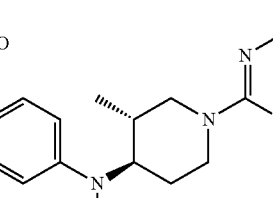 |
| 75 | 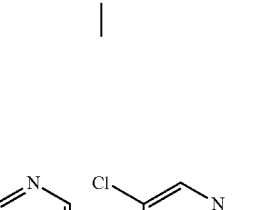 |

TABLE 1-continued

| Compound No. | Structure |
|---|---|
| 76 | 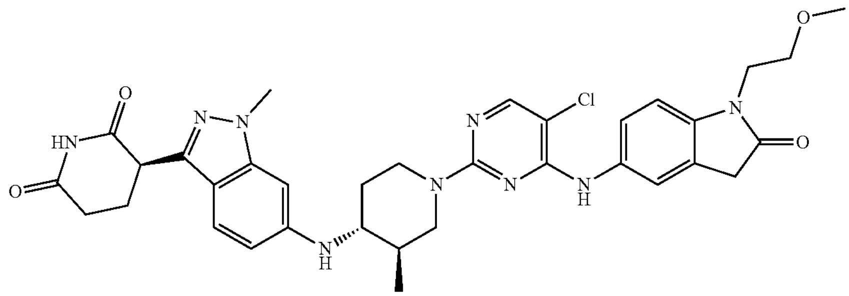 [SMILES: COCCN1C(=O)Cc2cc(Nc3nc(N4CC[C@@H](Nc5ccc6c([C@H]7CCC(=O)NC7=O)nn(C)c6c5)[C@H](C)C4)ncc3Cl)ccc21] |
| 77 | 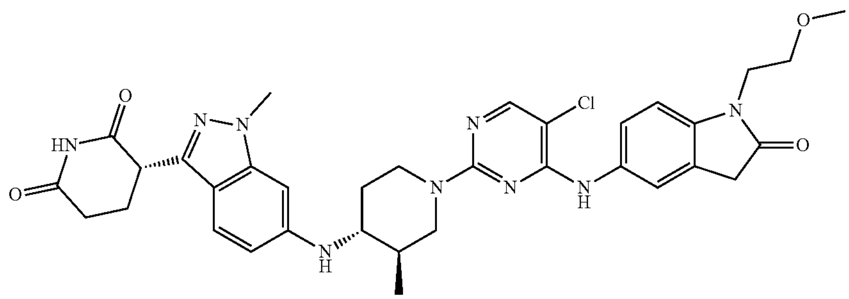 [SMILES: COCCN1C(=O)Cc2cc(Nc3nc(N4CC[C@@H](Nc5ccc6c([C@@H]7CCC(=O)NC7=O)nn(C)c6c5)[C@H](C)C4)ncc3Cl)ccc21] |
| 78 | 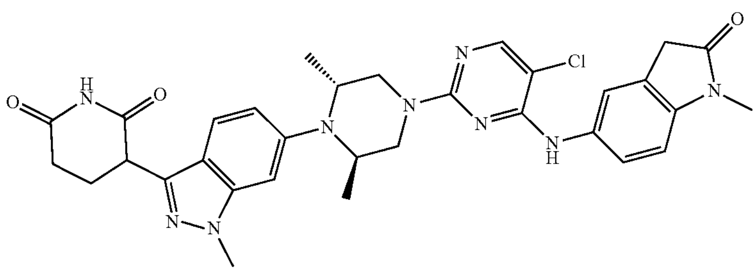 [SMILES: C[C@@H]1CN(c2ncc(Cl)c(Nc3ccc4c(c3)CC(=O)N4C)n2)C[C@@H](C)N1c1ccc2c(C3CCC(=O)NC3=O)nn(C)c2c1] |
| 79 | 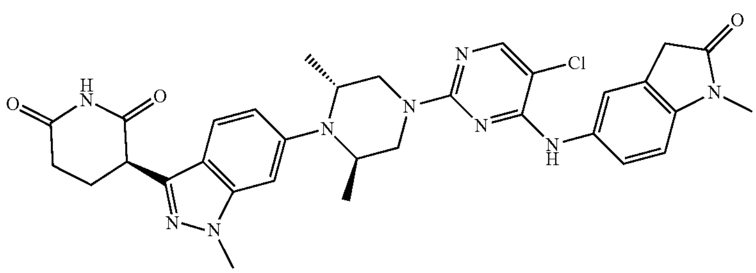 [SMILES: C[C@@H]1CN(c2ncc(Cl)c(Nc3ccc4c(c3)CC(=O)N4C)n2)C[C@@H](C)N1c1ccc2c([C@H]3CCC(=O)NC3=O)nn(C)c2c1] |
| 80 | 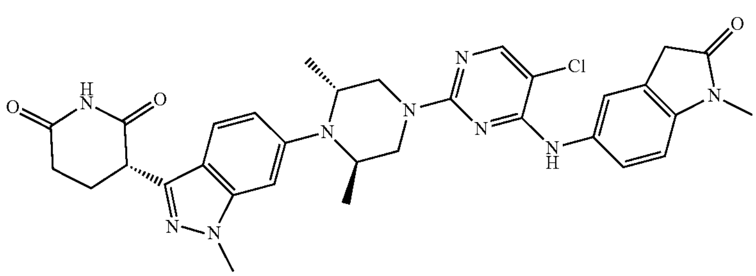 [SMILES: C[C@@H]1CN(c2ncc(Cl)c(Nc3ccc4c(c3)CC(=O)N4C)n2)C[C@@H](C)N1c1ccc2c([C@@H]3CCC(=O)NC3=O)nn(C)c2c1] |

TABLE 1-continued
| Compound No. | Structure |
|---|---|
| 81 | 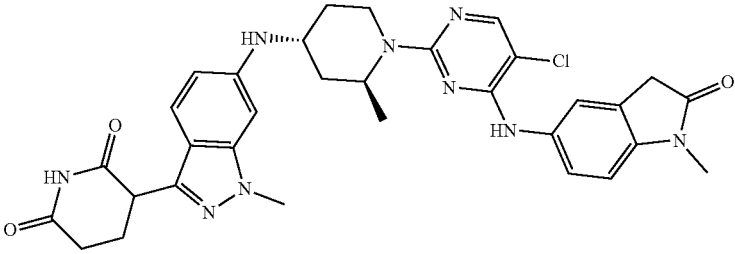 [SMILES: C[C@H]1C[C@H](Nc2ccc3c(C4CCC(=O)NC4=O)nn(C)c3c2)CCN1c1ncc(Cl)c(Nc2ccc3c(c2)CC(=O)N3C)n1] |
| 82 | 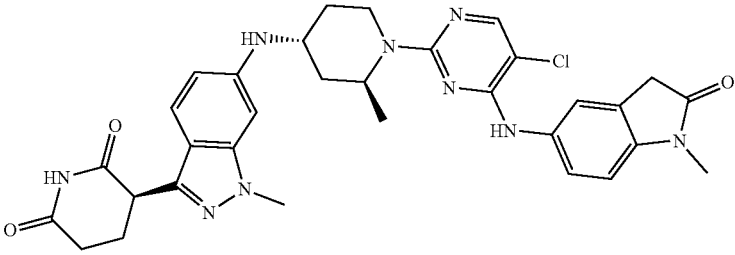 [SMILES: C[C@H]1C[C@H](Nc2ccc3c([C@H]4CCC(=O)NC4=O)nn(C)c3c2)CCN1c1ncc(Cl)c(Nc2ccc3c(c2)CC(=O)N3C)n1] |
| 83 | 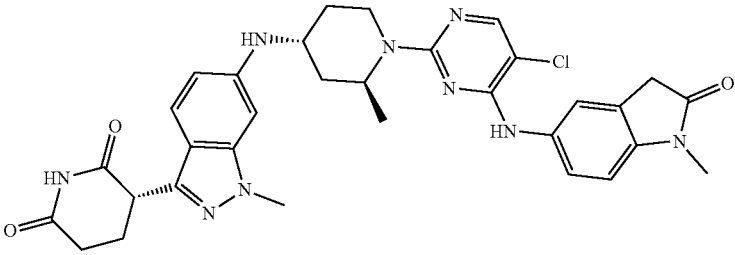 [SMILES: C[C@H]1C[C@H](Nc2ccc3c([C@@H]4CCC(=O)NC4=O)nn(C)c3c2)CCN1c1ncc(Cl)c(Nc2ccc3c(c2)CC(=O)N3C)n1] |
| 84 | 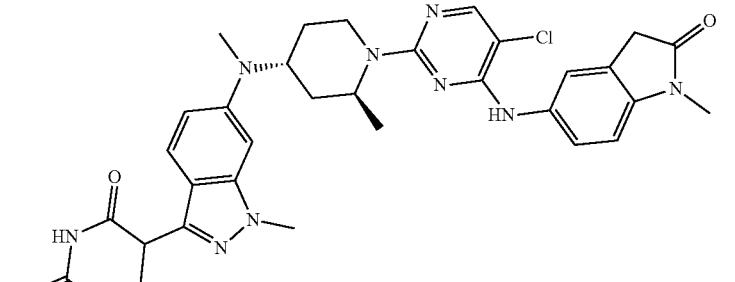 |
| 85 | 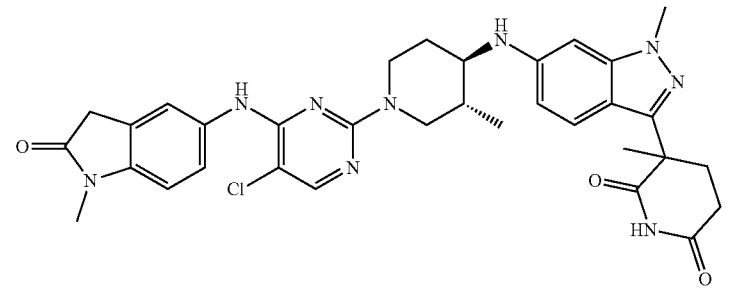 [SMILES: C[C@@H]1CN(c2ncc(Cl)c(Nc3ccc4c(c3)CC(=O)N4C)n2)CC[C@H]1Nc1ccc2c(C3(C)CCC(=O)NC3=O)nn(C)c2c1] |

TABLE 1-continued

| Compound No. | Structure |
|---|---|
| 86 | 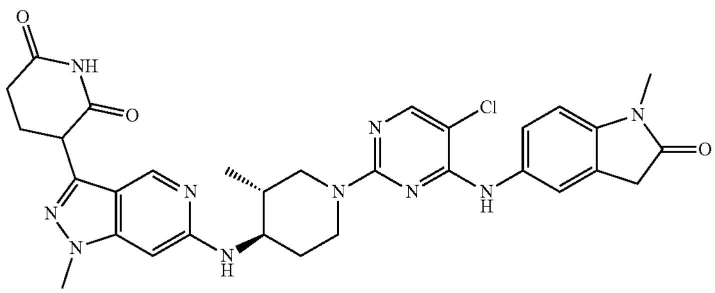 [SMILES: C[C@@H]1CN(c2ncc(Cl)c(Nc3ccc4c(c3)CC(=O)N4C)n2)CC[C@H]1Nc1cc2c(cn1)c(C1CCC(=O)NC1=O)nn2C] |
| 87 | 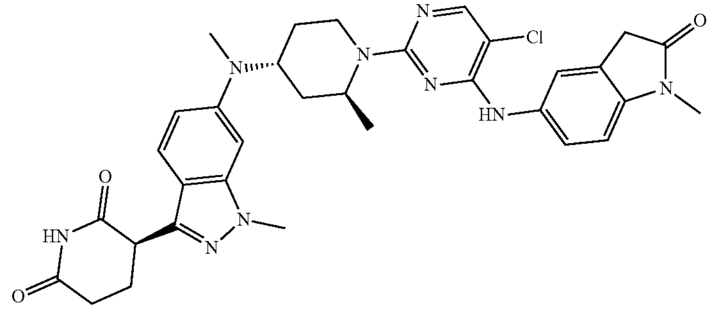 [SMILES: C[C@H]1C[C@H](N(C)c2ccc3c([C@H]4CCC(=O)NC4=O)nn(C)c3c2)CCN1c1ncc(Cl)c(Nc2ccc3c(c2)CC(=O)N3C)n1] |
| 88 | 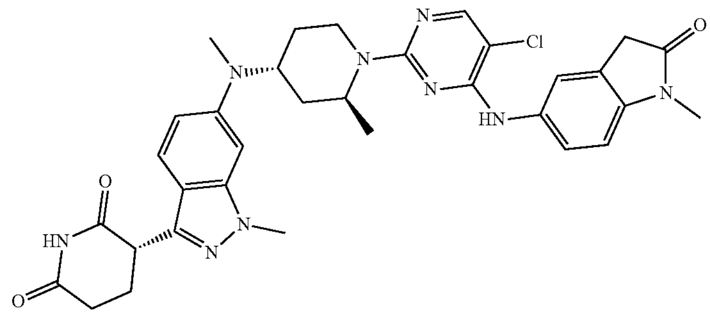 |
| 89 | 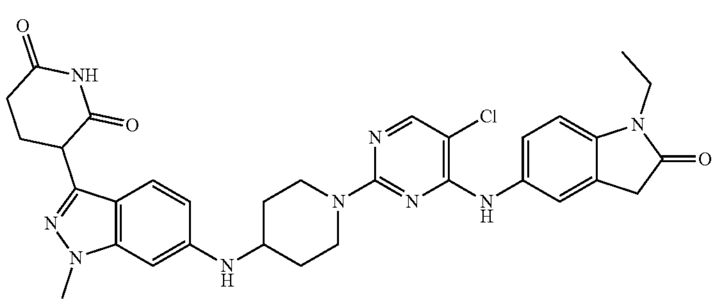 [SMILES: CCN1C(=O)Cc2cc(Nc3nc(N4CCC(Nc5ccc6c(C7CCC(=O)NC7=O)nn(C)c6c5)CC4)ncc3Cl)ccc21] |
| 90 | 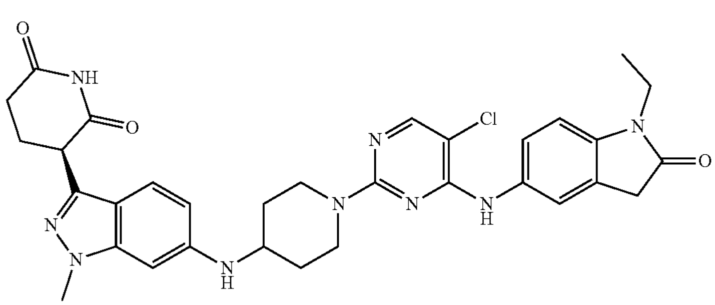 [SMILES: CCN1C(=O)Cc2cc(Nc3nc(N4CCC(Nc5ccc6c([C@H]7CCC(=O)NC7=O)nn(C)c6c5)CC4)ncc3Cl)ccc21] |

TABLE 1-continued

| Compound No. | Structure |
|---|---|
| 91 | 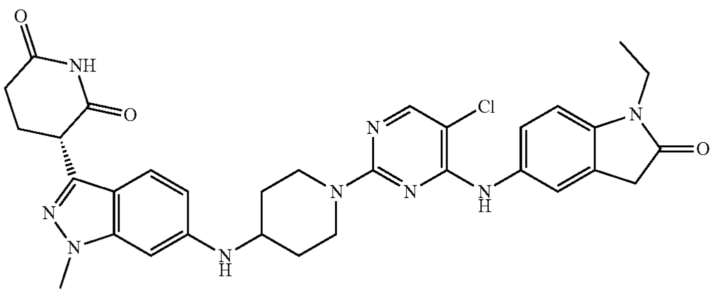 [SMILES: CCN1C(=O)Cc2cc(Nc3nc(N4CCC(Nc5ccc6c([C@@H]7CCC(=O)NC7=O)nn(C)c6c5)CC4)ncc3Cl)ccc21] |
| 92 | 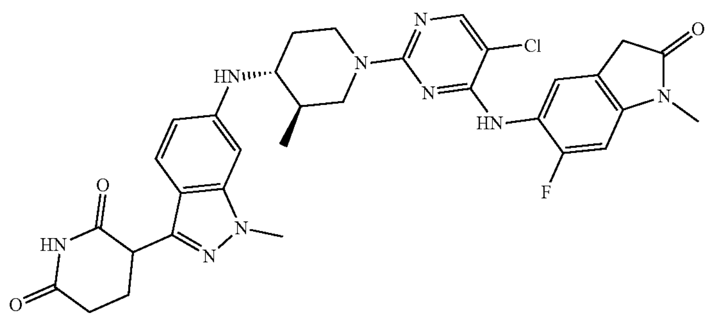 [SMILES: C[C@@H]1CN(c2ncc(Cl)c(Nc3cc4c(cc3F)N(C)C(=O)C4)n2)CC[C@H]1Nc1ccc2c(C3CCC(=O)NC3=O)nn(C)c2c1] |
| 93 | 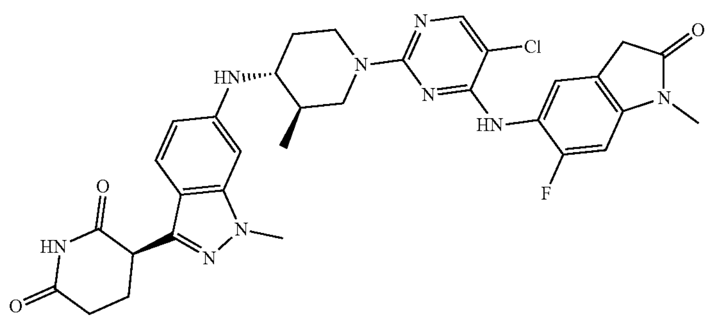 [SMILES: C[C@@H]1CN(c2ncc(Cl)c(Nc3cc4c(cc3F)N(C)C(=O)C4)n2)CC[C@H]1Nc1ccc2c([C@H]3CCC(=O)NC3=O)nn(C)c2c1] |
| 94 | 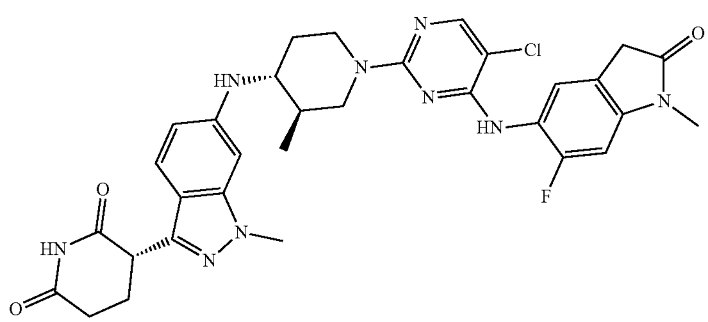 [SMILES: C[C@@H]1CN(c2ncc(Cl)c(Nc3cc4c(cc3F)N(C)C(=O)C4)n2)CC[C@H]1Nc1ccc2c([C@@H]3CCC(=O)NC3=O)nn(C)c2c1] |
| 95 | 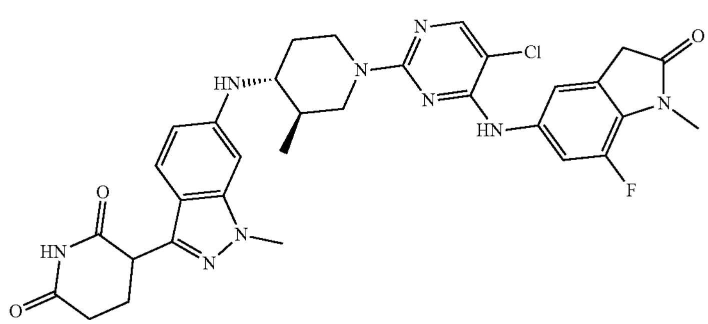 [SMILES: C[C@@H]1CN(c2ncc(Cl)c(Nc3cc(F)c4c(c3)CC(=O)N4C)n2)CC[C@H]1Nc1ccc2c(C3CCC(=O)NC3=O)nn(C)c2c1] |

TABLE 1-continued
| Compound No. | Structure |
|---|---|
| 96 | 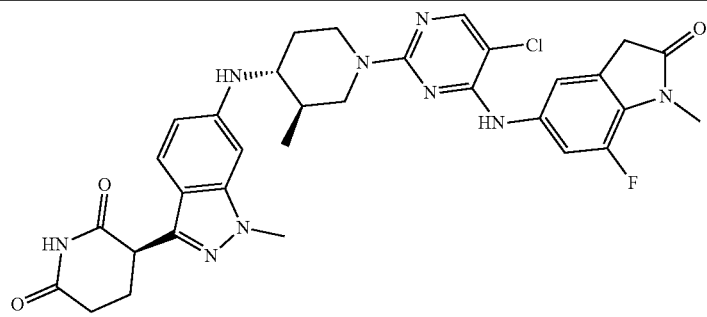 |
| 97 | 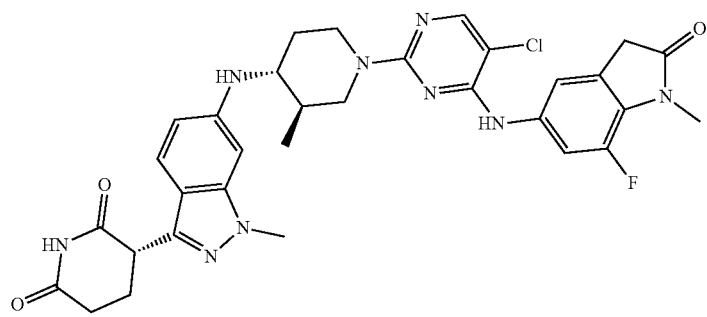 [SMILES: C[C@@H]1CN(c2ncc(Cl)c(Nc3cc(F)c4c(c3)CC(=O)N4C)n2)CC[C@H]1Nc1ccc2c([C@@H]3CCC(=O)NC3=O)nn(C)c2c1] |
| 98 | 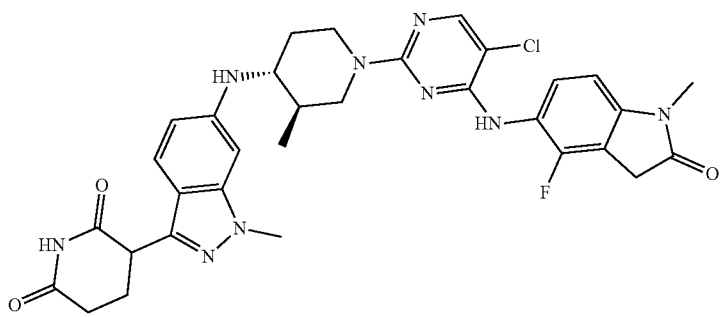 [SMILES: C[C@@H]1CN(c2ncc(Cl)c(Nc3ccc4c(c3F)CC(=O)N4C)n2)CC[C@H]1Nc1ccc2c(C3CCC(=O)NC3=O)nn(C)c2c1] |
| 99 | 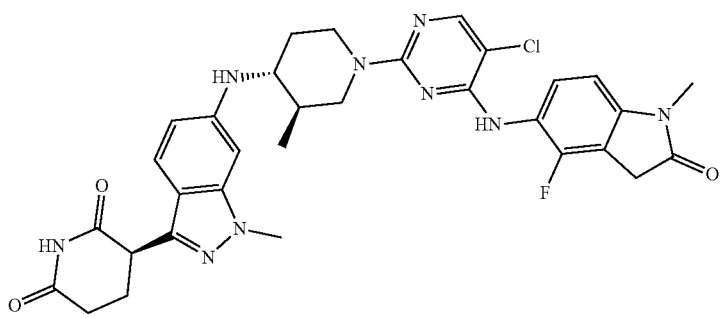 [SMILES: C[C@@H]1CN(c2ncc(Cl)c(Nc3ccc4c(c3F)CC(=O)N4C)n2)CC[C@H]1Nc1ccc2c([C@H]3CCC(=O)NC3=O)nn(C)c2c1] |
| 100 | 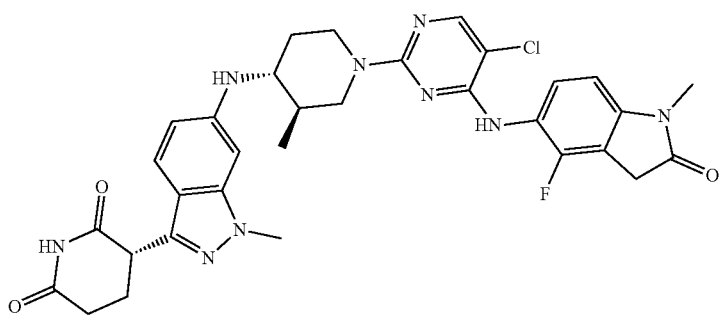 [SMILES: C[C@@H]1CN(c2ncc(Cl)c(Nc3ccc4c(c3F)CC(=O)N4C)n2)CC[C@H]1Nc1ccc2c([C@@H]3CCC(=O)NC3=O)nn(C)c2c1] |

TABLE 1-continued
| Compound No. | Structure |
| --- | --- |
| 101 | 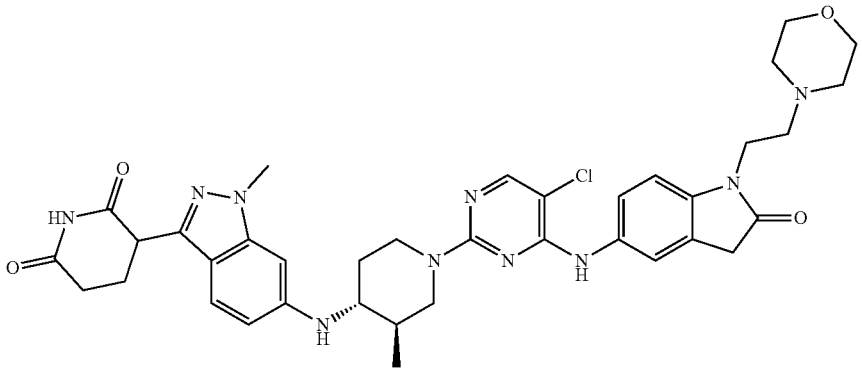 [SMILES: C[C@@H]1CN(c2ncc(Cl)c(Nc3ccc4c(c3)CC(=O)N4CCN3CCOCC3)n2)CC[C@H]1Nc1ccc2c(C3CCC(=O)NC3=O)nn(C)c2c1] |
| 102 | 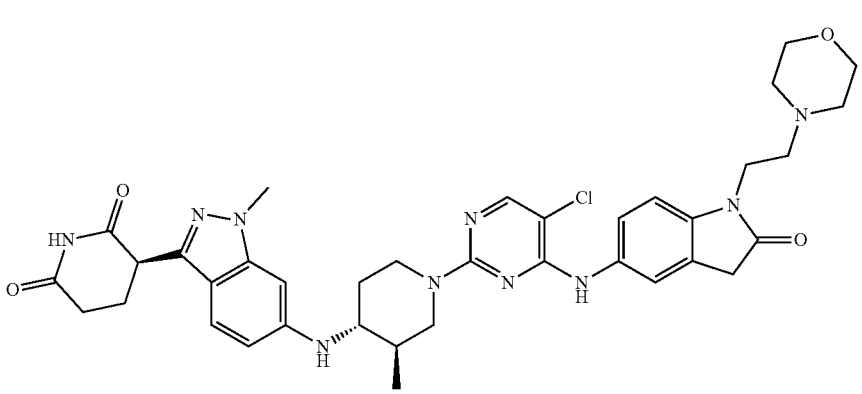 [SMILES: C[C@@H]1CN(c2ncc(Cl)c(Nc3ccc4c(c3)CC(=O)N4CCN3CCOCC3)n2)CC[C@H]1Nc1ccc2c([C@H]3CCC(=O)NC3=O)nn(C)c2c1] |
| 103 | 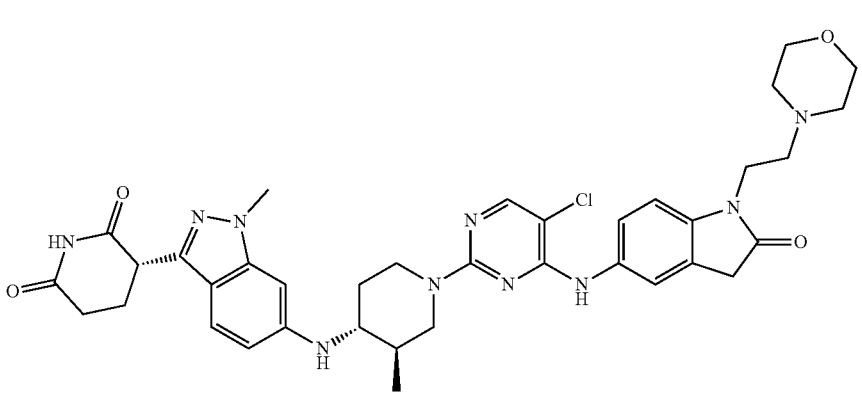 [SMILES: C[C@@H]1CN(c2ncc(Cl)c(Nc3ccc4c(c3)CC(=O)N4CCN3CCOCC3)n2)CC[C@H]1Nc1ccc2c([C@@H]3CCC(=O)NC3=O)nn(C)c2c1] |
| 104 | 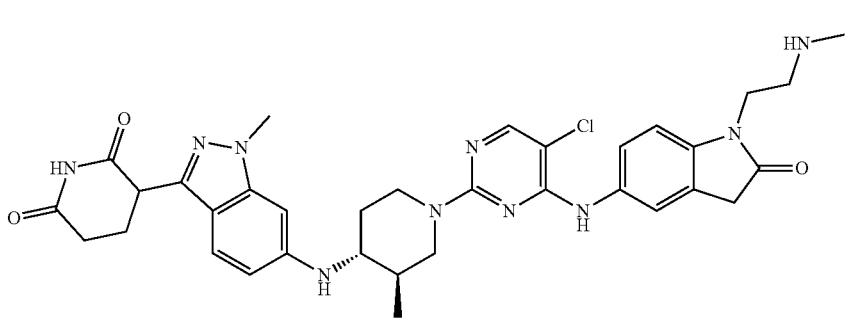 |

TABLE 1-continued
| Compound No. | Structure |
|---|---|
| 105 | 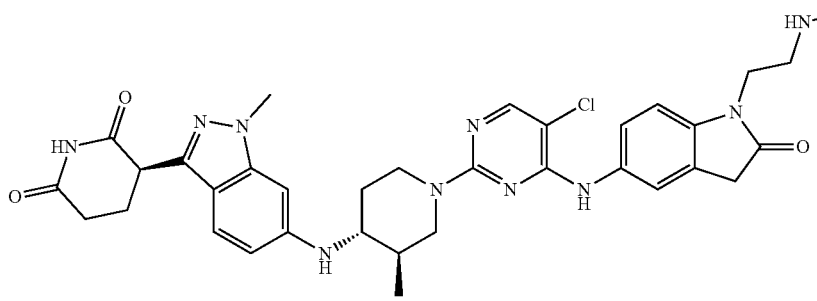 |
| 106 | 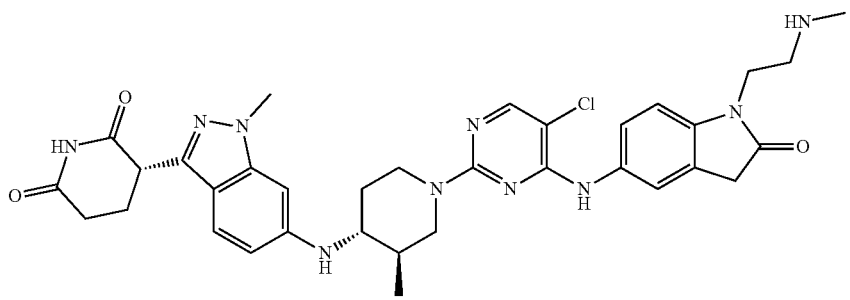 [SMILES: CNCCN1C(=O)Cc2cc(Nc3nc(N4CC[C@@H](Nc5ccc6c([C@@H]7CCC(=O)NC7=O)nn(C)c6c5)[C@H](C)C4)ncc3Cl)ccc21] |
| 107 | 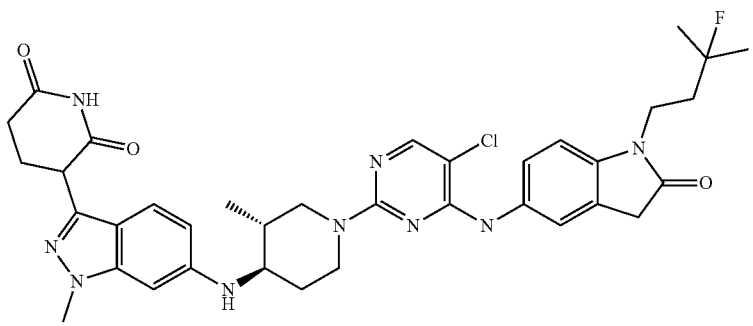 |
| 108 | 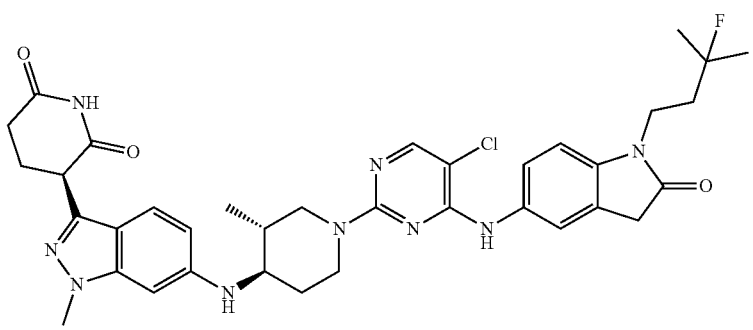 [SMILES: C[C@@H]1CN(c2ncc(Cl)c(Nc3ccc4c(c3)CC(=O)N4CCC(C)(C)F)n2)CC[C@H]1Nc1ccc2c([C@H]3CCC(=O)NC3=O)nn(C)c2c1] |
| 109 | 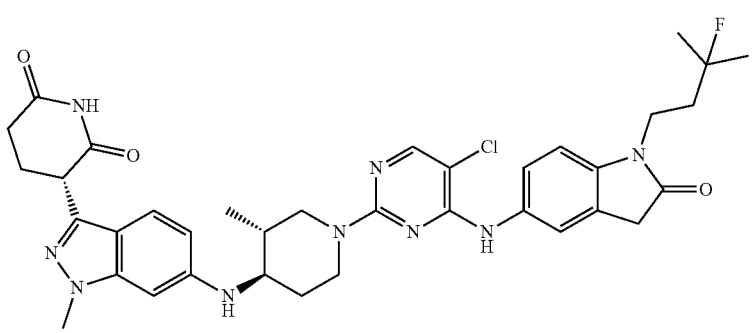 [SMILES: C[C@@H]1CN(c2ncc(Cl)c(Nc3ccc4c(c3)CC(=O)N4CCC(C)(C)F)n2)CC[C@H]1Nc1ccc2c([C@@H]3CCC(=O)NC3=O)nn(C)c2c1] |

TABLE 1-continued

| Compound No. | Structure |
|---|---|
| 110 | 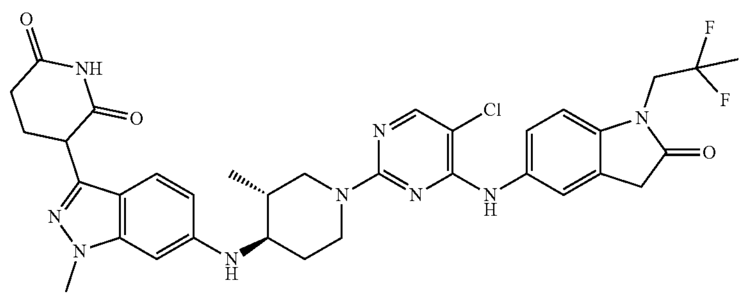 [SMILES: C[C@@H]1CN(c2ncc(Cl)c(Nc3ccc4c(c3)CC(=O)N4CC(C)(F)F)n2)CC[C@H]1Nc1ccc2c(C3CCC(=O)NC3=O)nn(C)c2c1] |
| 111 | 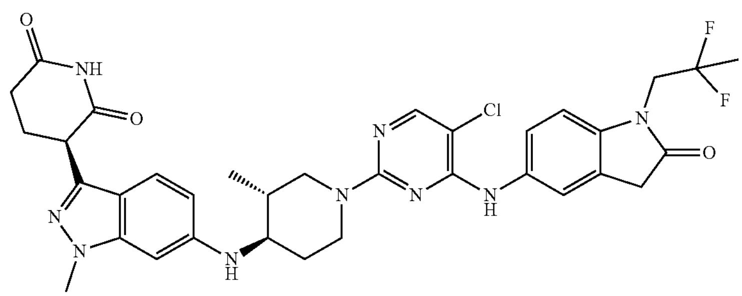 [SMILES: C[C@@H]1CN(c2ncc(Cl)c(Nc3ccc4c(c3)CC(=O)N4CC(C)(F)F)n2)CC[C@H]1Nc1ccc2c([C@H]3CCC(=O)NC3=O)nn(C)c2c1] |
| 112 | 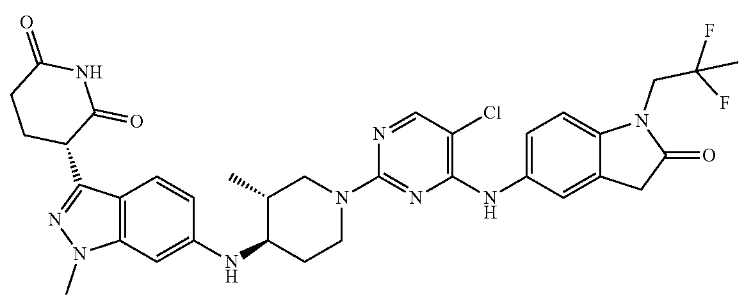 [SMILES: C[C@@H]1CN(c2ncc(Cl)c(Nc3ccc4c(c3)CC(=O)N4CC(C)(F)F)n2)CC[C@H]1Nc1ccc2c([C@@H]3CCC(=O)NC3=O)nn(C)c2c1] |
| 113 | 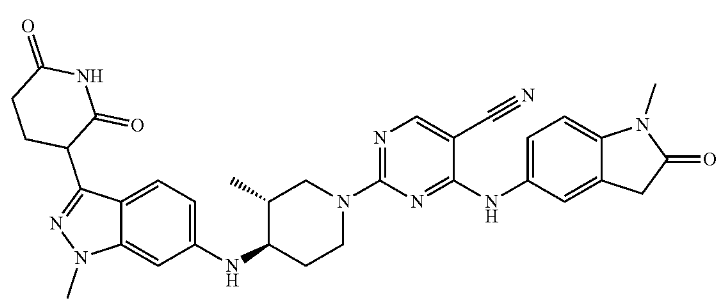 [SMILES: C[C@@H]1CN(c2ncc(C#N)c(Nc3ccc4c(c3)CC(=O)N4C)n2)CC[C@H]1Nc1ccc2c(C3CCC(=O)NC3=O)nn(C)c2c1] |
| 114 | 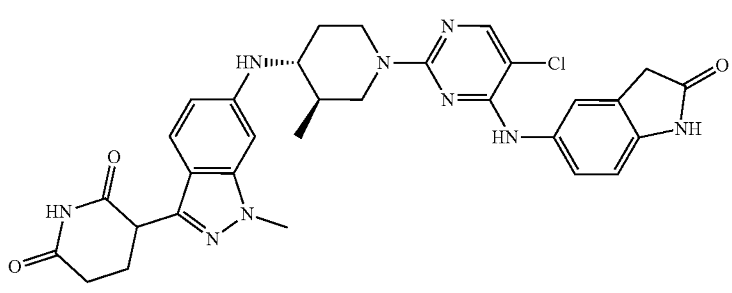 [SMILES: C[C@@H]1CN(c2ncc(Cl)c(Nc3ccc4c(c3)CC(=O)N4)n2)CC[C@H]1Nc1ccc2c(C3CCC(=O)NC3=O)nn(C)c2c1] |

TABLE 1-continued
| Compound No. | Structure |
|---|---|
| 115 | 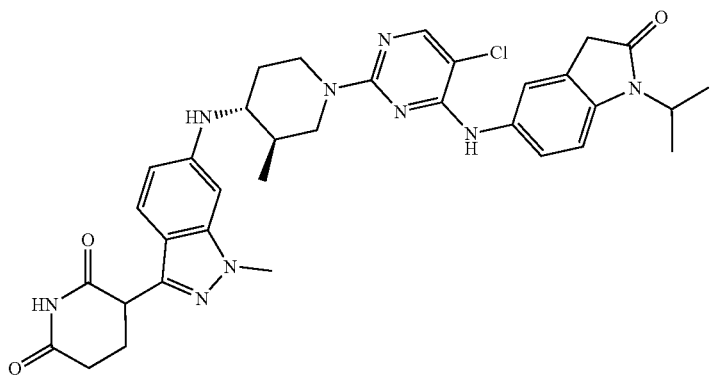 [SMILES: CC(C)N1C(=O)Cc2cc(Nc3nc(N4CC[C@@H](Nc5ccc6c(C7CCC(=O)NC7=O)nn(C)c6c5)[C@H](C)C4)ncc3Cl)ccc21] |
| 116 | 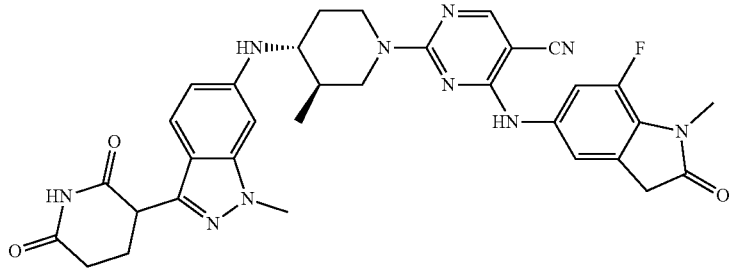 [SMILES: C[C@@H]1CN(c2ncc(C#N)c(Nc3cc(F)c4c(c3)CC(=O)N4C)n2)CC[C@H]1Nc1ccc2c(C3CCC(=O)NC3=O)nn(C)c2c1] |
| 117 | 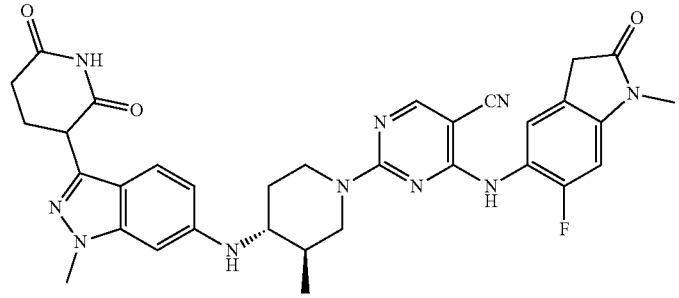 [SMILES: C[C@@H]1CN(c2ncc(C#N)c(Nc3cc4c(cc3F)N(C)C(=O)C4)n2)CC[C@H]1Nc1ccc2c(C3CCC(=O)NC3=O)nn(C)c2c1] |
| 118 | 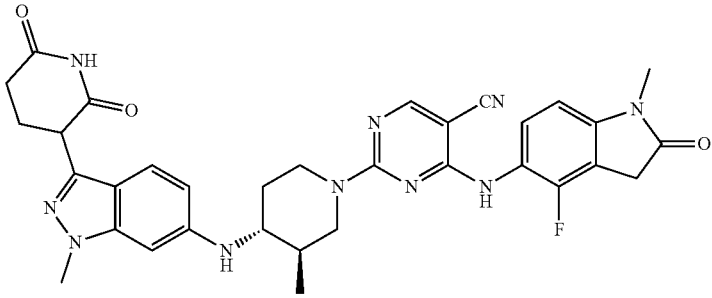 [SMILES: C[C@@H]1CN(c2ncc(C#N)c(Nc3ccc4c(c3F)CC(=O)N4C)n2)CC[C@H]1Nc1ccc2c(C3CCC(=O)NC3=O)nn(C)c2c1] |
| 119 | 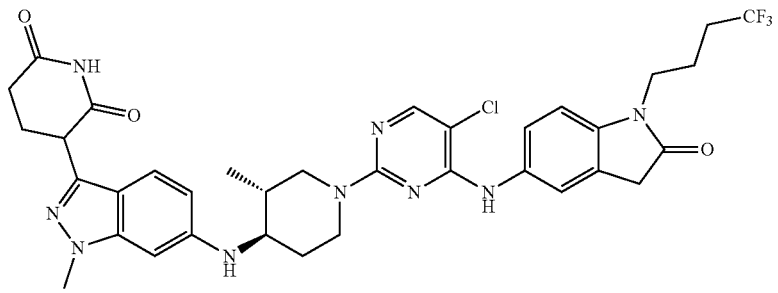 [SMILES: C[C@@H]1CN(c2ncc(Cl)c(Nc3ccc4c(c3)CC(=O)N4CCCC(F)(F)F)n2)CC[C@H]1Nc1ccc2c(C3CCC(=O)NC3=O)nn(C)c2c1] |

TABLE 1-continued

| Compound No. | Structure |
| --- | --- |
| 120 | 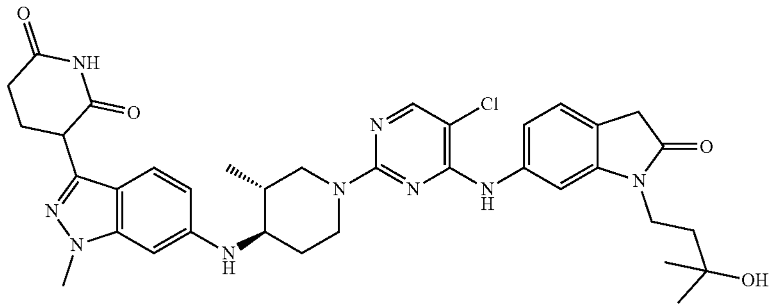 [SMILES: C[C@@H]1CN(c2ncc(Cl)c(Nc3ccc4c(c3)N(CCC(C)(C)O)C(=O)C4)n2)CC[C@H]1Nc1ccc2c(C3CCC(=O)NC3=O)nn(C)c2c1] |
| 121 | 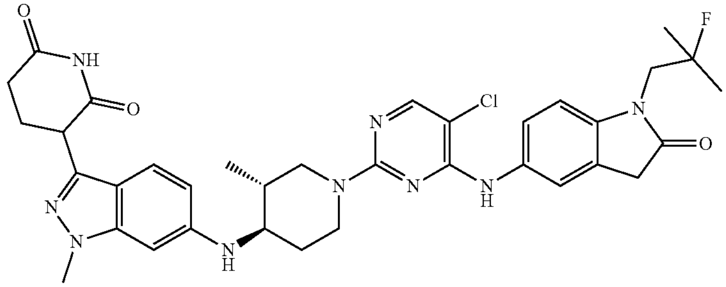 [SMILES: C[C@@H]1CN(c2ncc(Cl)c(Nc3ccc4c(c3)CC(=O)N4CC(C)(C)F)n2)CC[C@H]1Nc1ccc2c(C3CCC(=O)NC3=O)nn(C)c2c1] |
| 122 | 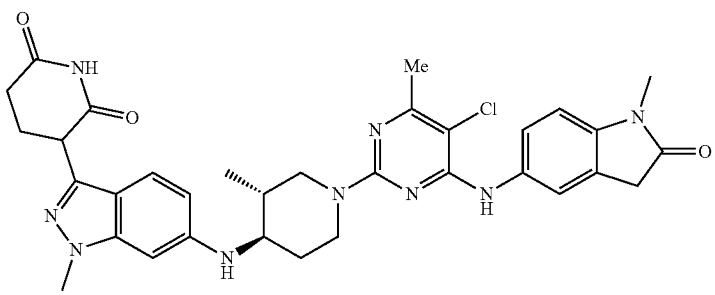 [SMILES: Cc1nc(N2CC[C@@H](Nc3ccc4c(C5CCC(=O)NC5=O)nn(C)c4c3)[C@H](C)C2)nc(Nc2ccc3c(c2)CC(=O)N3C)c1Cl] |
| 123 | 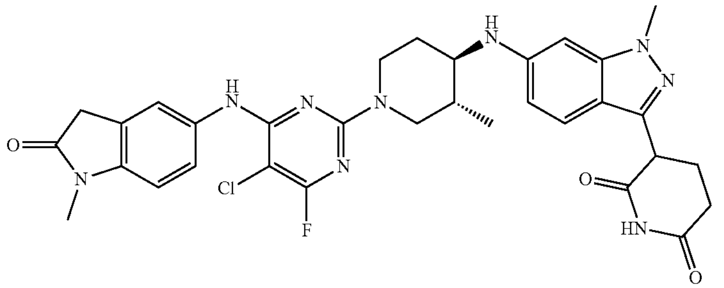 [SMILES: C[C@@H]1CN(c2nc(F)c(Cl)c(Nc3ccc4c(c3)CC(=O)N4C)n2)CC[C@H]1Nc1ccc2c(C3CCC(=O)NC3=O)nn(C)c2c1] |
| 124 | 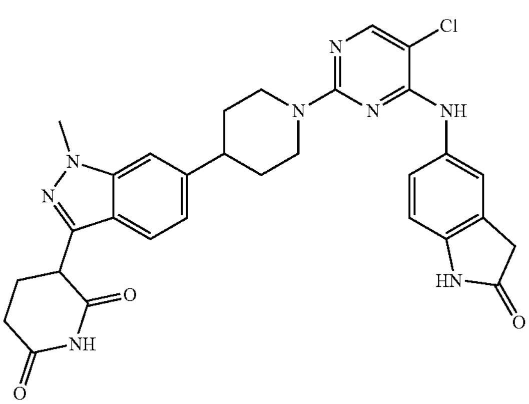 |

TABLE 1-continued
| Compound No. | Structure |
|---|---|
| 125 | 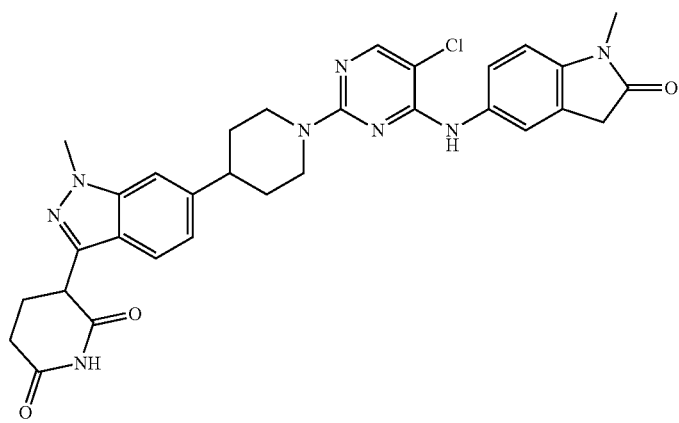 [SMILES: CN1C(=O)Cc2cc(Nc3nc(N4CCC(c5ccc6c(C7CCC(=O)NC7=O)nn(C)c6c5)CC4)ncc3Cl)ccc21] |
| 126 | 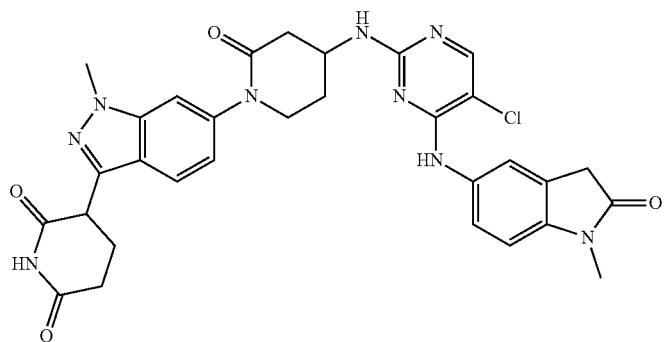 [SMILES: CN1C(=O)Cc2cc(Nc3nc(NC4CCN(c5ccc6c(C7CCC(=O)NC7=O)nn(C)c6c5)C(=O)C4)ncc3Cl)ccc21] |
| 127 | 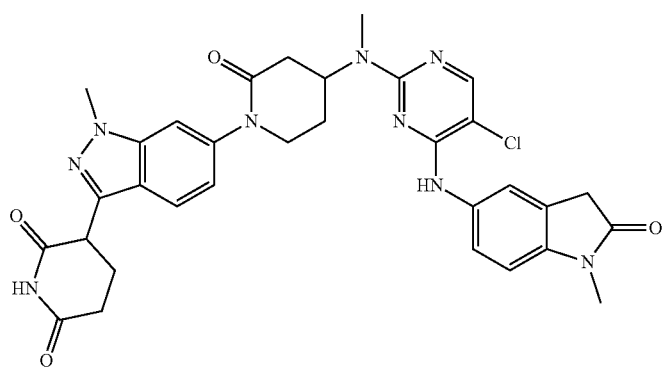 [SMILES: CN1C(=O)Cc2cc(Nc3nc(N(C)C4CCN(c5ccc6c(C7CCC(=O)NC7=O)nn(C)c6c5)C(=O)C4)ncc3Cl)ccc21] |
| 128 | 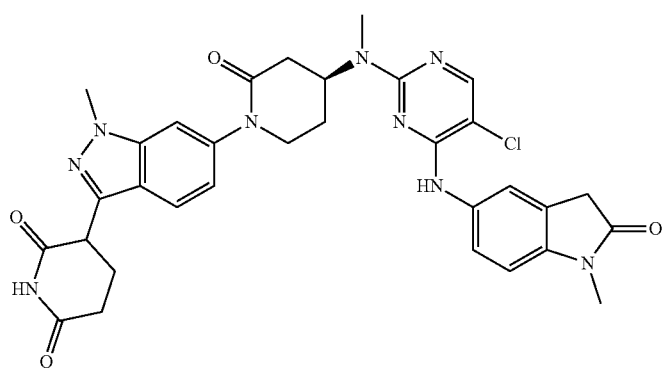 [SMILES: CN1C(=O)Cc2cc(Nc3nc(N(C)[C@H]4CCN(c5ccc6c(C7CCC(=O)NC7=O)nn(C)c6c5)C(=O)C4)ncc3Cl)ccc21] |

TABLE 1-continued

| Compound No. | Structure |
|---|---|
| 129 | 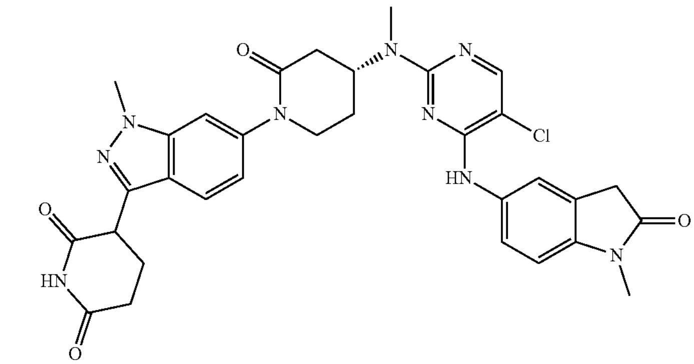 [SMILES: CN1C(=O)Cc2cc(Nc3nc(N(C)[C@@H]4CCN(c5ccc6c(C7CCC(=O)NC7=O)nn(C)c6c5)C(=O)C4)ncc3Cl)ccc21] |
| 130 | 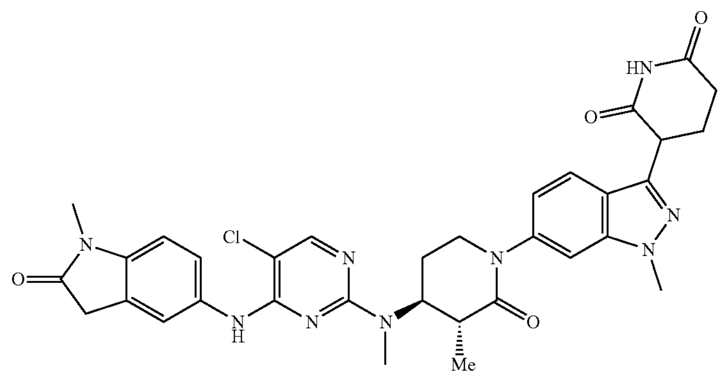 [SMILES: C[C@H]1C(=O)N(c2ccc3c(C4CCC(=O)NC4=O)nn(C)c3c2)CC[C@@H]1N(C)c1ncc(Cl)c(Nc2ccc3c(c2)CC(=O)N3C)n1] |
| 131 | 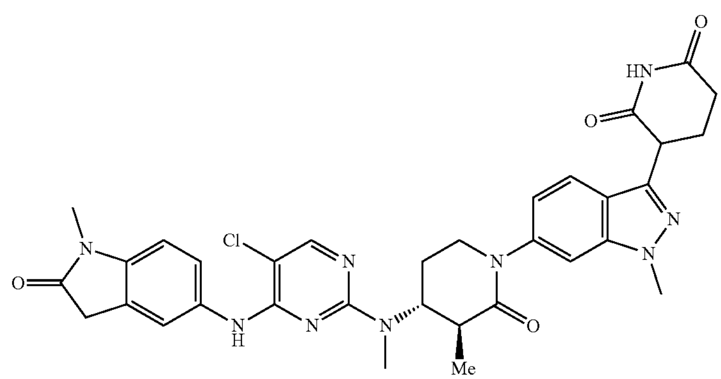 [SMILES: C[C@@H]1C(=O)N(c2ccc3c(C4CCC(=O)NC4=O)nn(C)c3c2)CC[C@H]1N(C)c1ncc(Cl)c(Nc2ccc3c(c2)CC(=O)N3C)n1] |
| 132 | 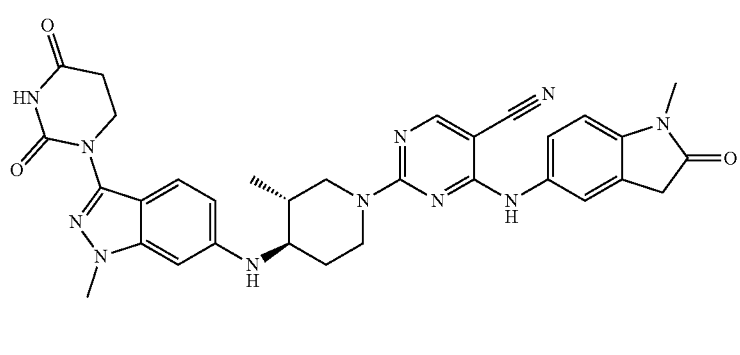 [SMILES: C[C@@H]1CN(c2ncc(C#N)c(Nc3ccc4c(c3)CC(=O)N4C)n2)CC[C@H]1Nc1ccc2c(N3CCC(=O)NC3=O)nn(C)c2c1] |

TABLE 1-continued
| Compound No. | Structure |
|---|---|
| 133 | 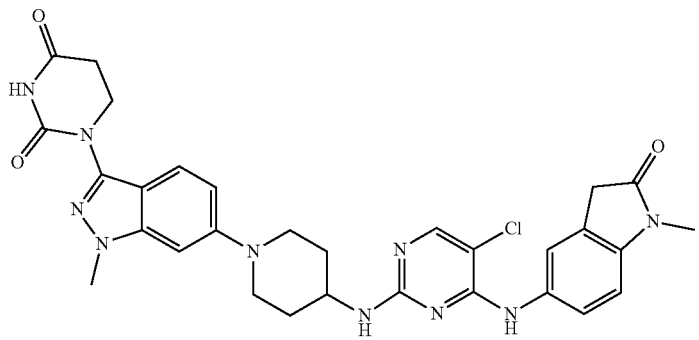 [SMILES: CN1C(=O)Cc2cc(Nc3nc(NC4CCN(c5ccc6c(N7CCC(=O)NC7=O)nn(C)c6c5)CC4)ncc3Cl)ccc21] |
| 134 | 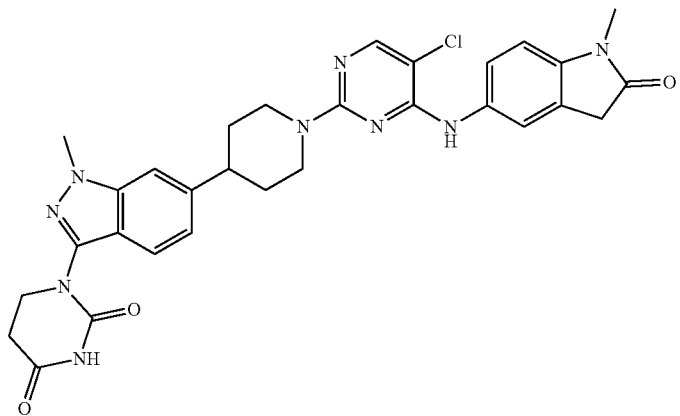 [SMILES: CN1C(=O)Cc2cc(Nc3nc(N4CCC(c5ccc6c(N7CCC(=O)NC7=O)nn(C)c6c5)CC4)ncc3Cl)ccc21] |
| 135 | 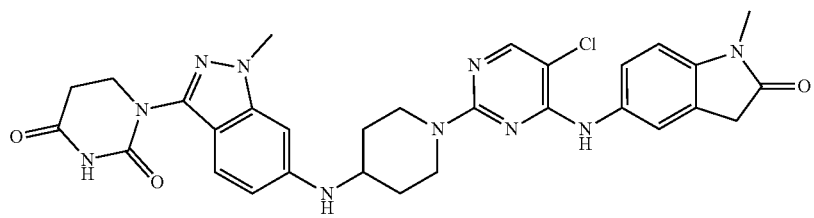 [SMILES: CN1C(=O)Cc2cc(Nc3nc(N4CCC(Nc5ccc6c(N7CCC(=O)NC7=O)nn(C)c6c5)CC4)ncc3Cl)ccc21] |
| 136 | 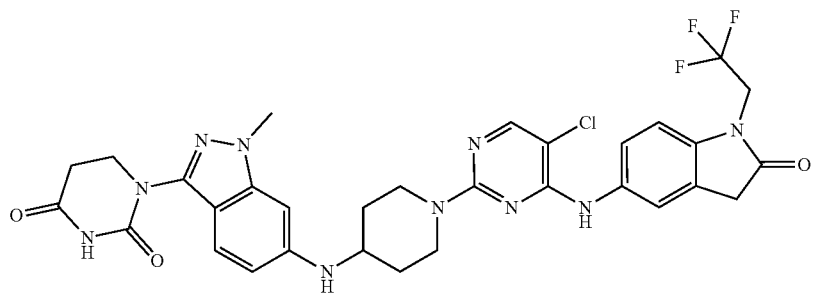 [SMILES: Cn1nc(N2CCC(=O)NC2=O)c2ccc(NC3CCN(c4ncc(Cl)c(Nc5ccc6c(c5)CC(=O)N6CC(F)(F)F)n4)CC3)cc21] |

TABLE 1-continued
| Compound No. | Structure |
|---|---|
| 137 | 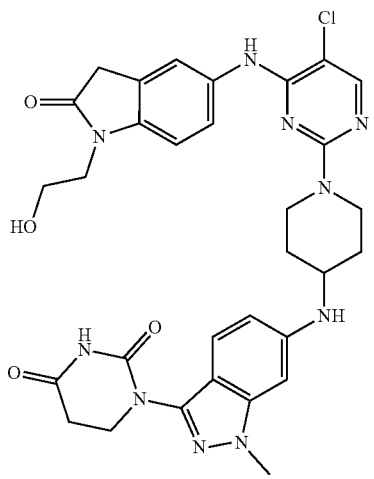 [SMILES: Cn1nc(N2CCC(=O)NC2=O)c2ccc(NC3CCN(c4ncc(Cl)c(Nc5ccc6c(c5)CC(=O)N6CCO)n4)CC3)cc21] |
| 138 | 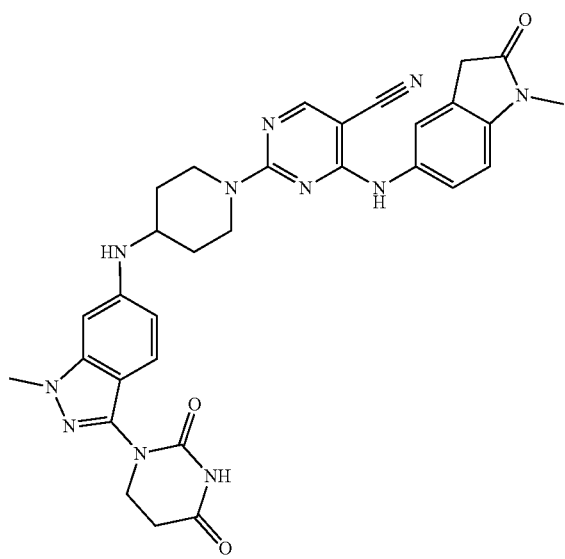 |
| 139 | 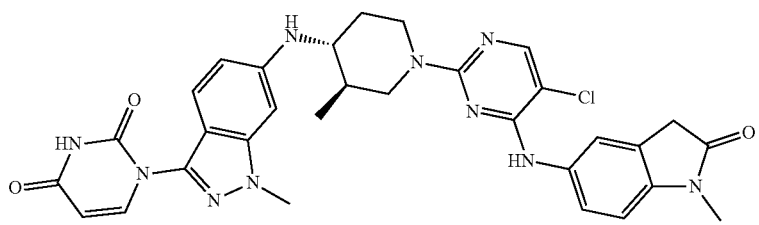 [SMILES: C[C@@H]1CN(c2ncc(Cl)c(Nc3ccc4c(c3)CC(=O)N4C)n2)CC[C@H]1Nc1ccc2c(-n3ccc(=O)[nH]c3=O)nn(C)c2c1] |
| 140 | 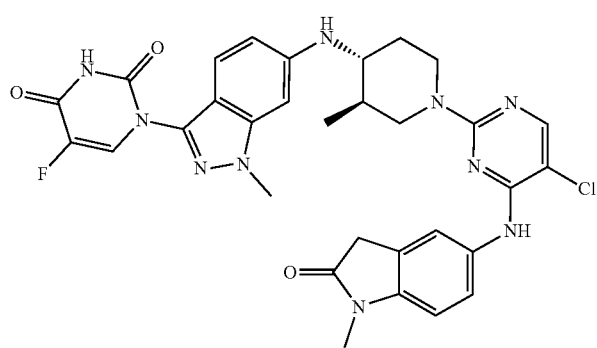 [SMILES: C[C@@H]1CN(c2ncc(Cl)c(Nc3ccc4c(c3)CC(=O)N4C)n2)CC[C@H]1Nc1ccc2c(-n3cc(F)c(=O)[nH]c3=O)nn(C)c2c1] |

TABLE 1-continued
| Compound No. | Structure |
|---|---|
| 141 | 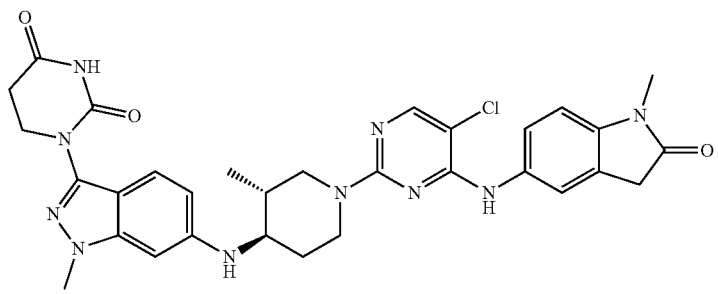 |
| 142 | 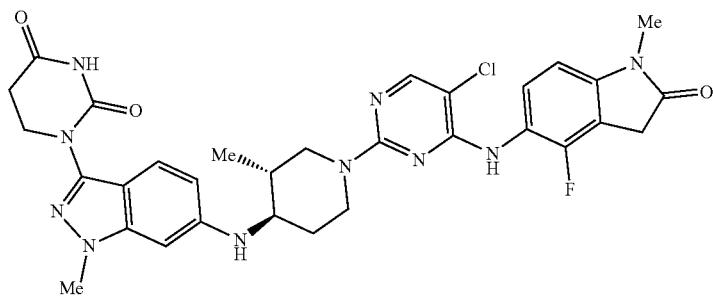 |
| 143 | 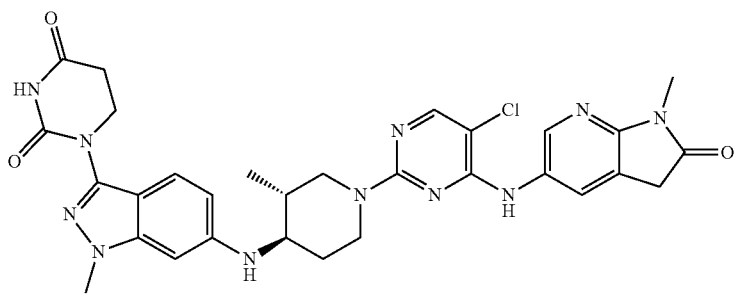 |
| 144 | 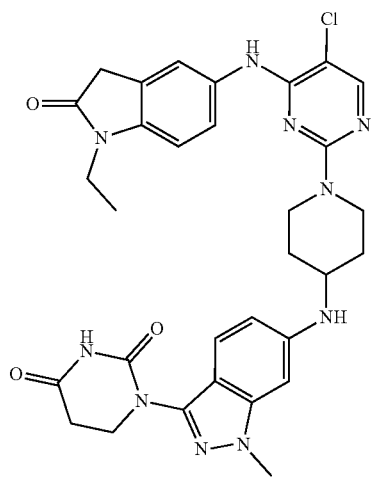 [SMILES: CCN1C(=O)Cc2cc(Nc3nc(N4CCC(Nc5ccc6c(N7CCC(=O)NC7=O)nn(C)c6c5)CC4)ncc3Cl)ccc21] |

TABLE 1-continued

| Compound No. | Structure |
|---|---|
| 145 | 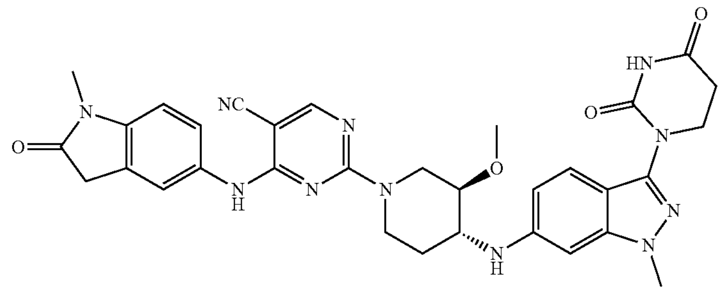 |
| 146 | 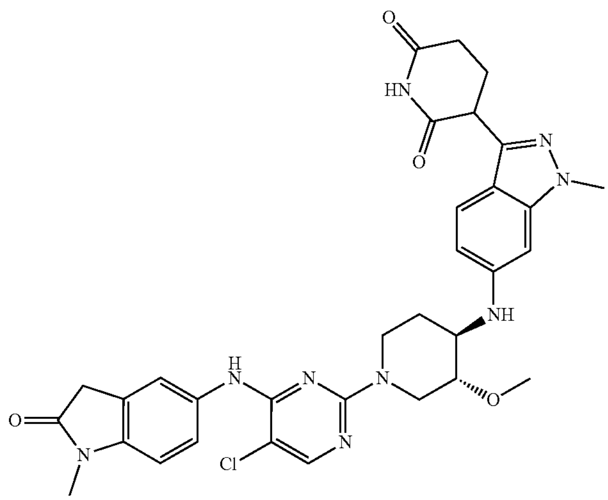 [SMILES: CO[C@@H]1CN(c2ncc(Cl)c(Nc3ccc4c(c3)CC(=O)N4C)n2)CC[C@H]1Nc1ccc2c(C3CCC(=O)NC3=O)nn(C)c2c1] |
| 147 | 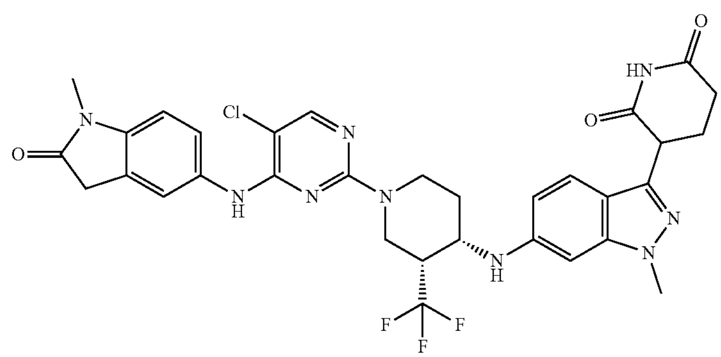 [SMILES: CN1C(=O)Cc2cc(Nc3nc(N4CC[C@H](Nc5ccc6c(C7CCC(=O)NC7=O)nn(C)c6c5)[C@H](C(F)(F)F)C4)ncc3Cl)ccc21] |
| 148 | 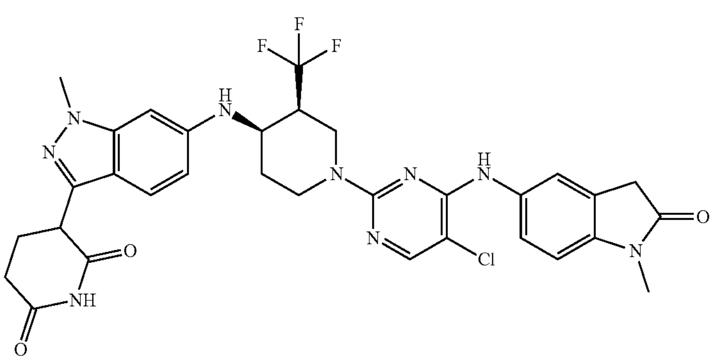 [SMILES: CN1C(=O)Cc2cc(Nc3nc(N4CC[C@@H](Nc5ccc6c(C7CCC(=O)NC7=O)nn(C)c6c5)[C@@H](C(F)(F)F)C4)ncc3Cl)ccc21] |

TABLE 1-continued

| Compound No. | Structure |
|---|---|
| 149 | 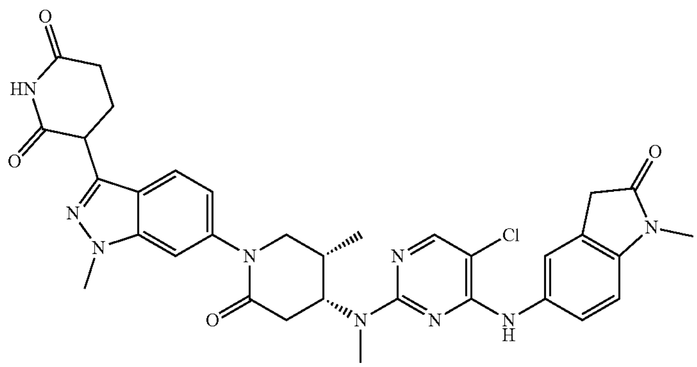 [SMILES: C[C@H]1CN(c2ccc3c(C4CCC(=O)NC4=O)nn(C)c3c2)C(=O)C[C@H]1N(C)c1ncc(Cl)c(Nc2ccc3c(c2)CC(=O)N3C)n1] |
| 150 | 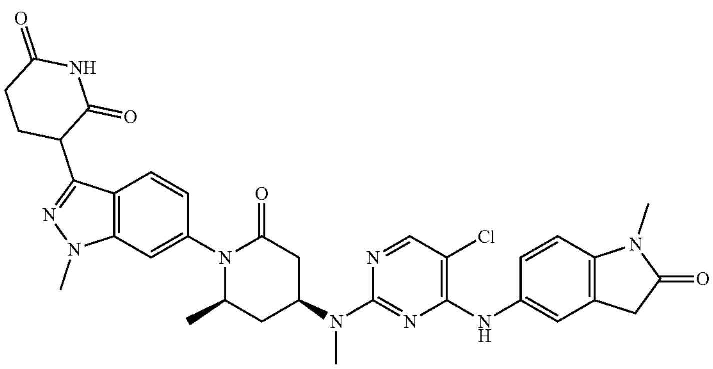 |
| 151 | 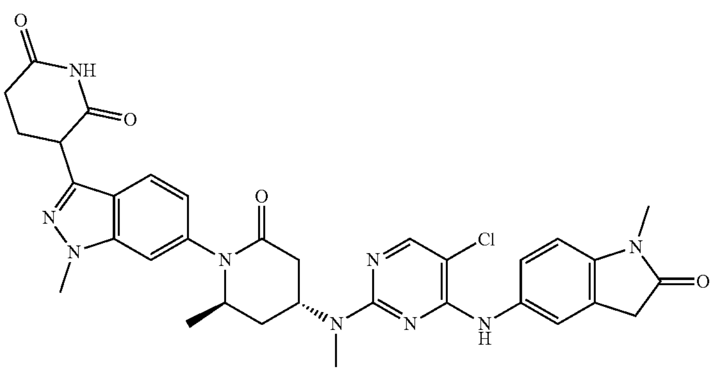 |
| 152 | 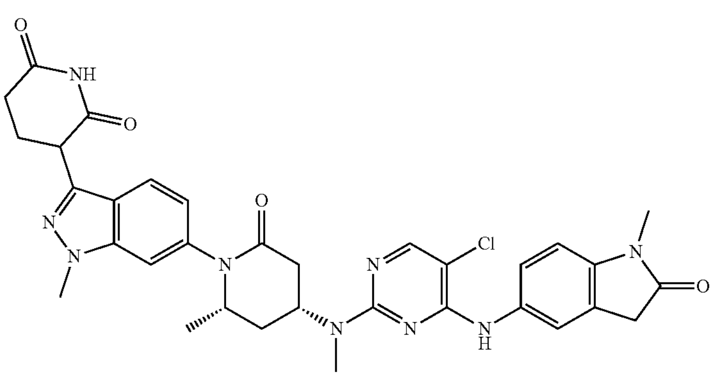 |

TABLE 1-continued

| Compound No. | Structure |
|---|---|
| 153 | 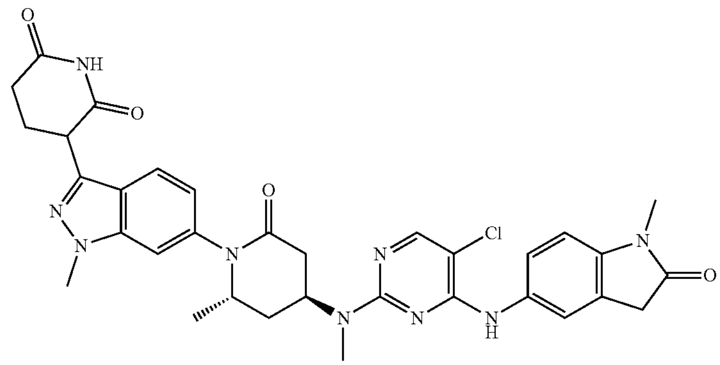 |
| 154 | 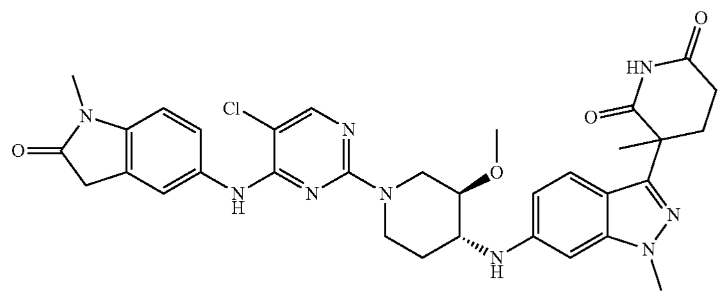 [SMILES: CO[C@@H]1CN(c2ncc(Cl)c(Nc3ccc4c(c3)CC(=O)N4C)n2)CC[C@H]1Nc1ccc2c(C3(C)CCC(=O)NC3=O)nn(C)c2c1] |
| 155 | 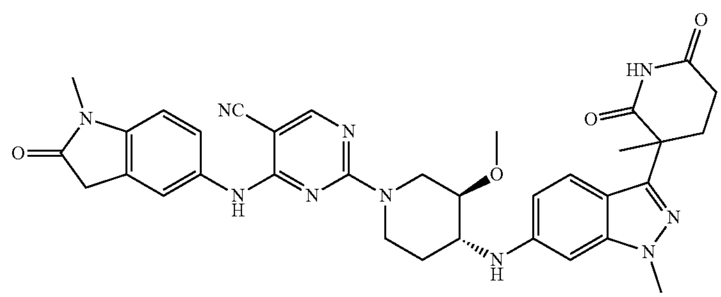 [SMILES: CO[C@@H]1CN(c2ncc(C#N)c(Nc3ccc4c(c3)CC(=O)N4C)n2)CC[C@H]1Nc1ccc2c(C3(C)CCC(=O)NC3=O)nn(C)c2c1] |
| 156 | 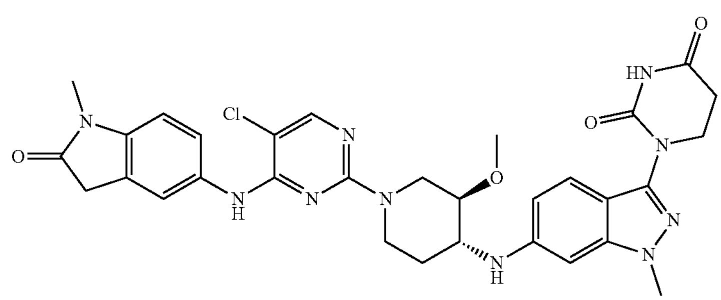 [SMILES: CO[C@@H]1CN(c2ncc(Cl)c(Nc3ccc4c(c3)CC(=O)N4C)n2)CC[C@H]1Nc1ccc2c(N3CCC(=O)NC3=O)nn(C)c2c1] |
| 157 | 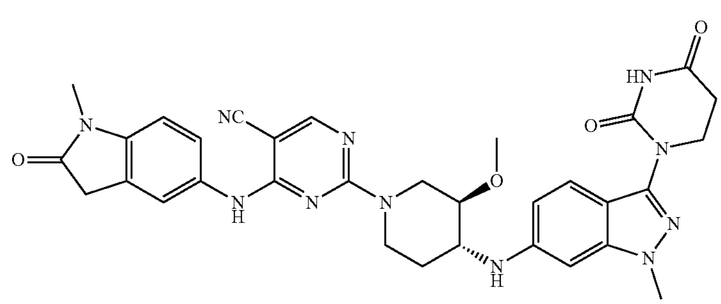 [SMILES: CO[C@@H]1CN(c2ncc(C#N)c(Nc3ccc4c(c3)CC(=O)N4C)n2)CC[C@H]1Nc1ccc2c(N3CCC(=O)NC3=O)nn(C)c2c1] |

TABLE 1-continued

| Compound No. | Structure |
|---|---|
| 158 | 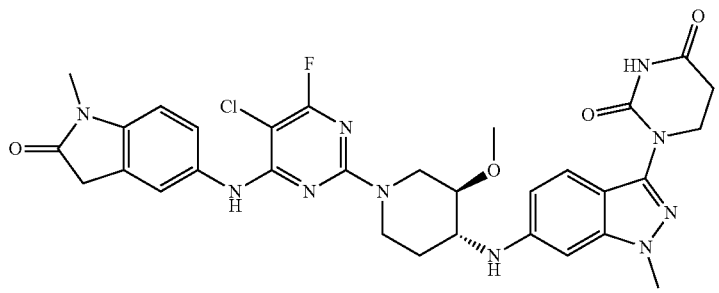 [SMILES: CO[C@@H]1CN(c2nc(F)c(Cl)c(Nc3ccc4c(c3)CC(=O)N4C)n2)CC[C@H]1Nc1ccc2c(N3CCC(=O)NC3=O)nn(C)c2c1] |
| 159 | 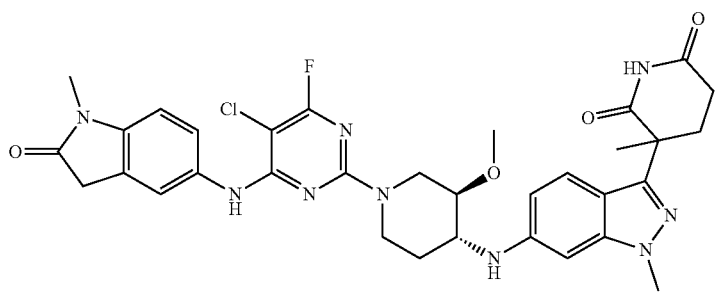 [SMILES: CO[C@@H]1CN(c2nc(F)c(Cl)c(Nc3ccc4c(c3)CC(=O)N4C)n2)CC[C@H]1Nc1ccc2c(C3(C)CCC(=O)NC3=O)nn(C)c2c1] | or a pharmaceutically acceptable salt thereof.

All compounds of Formula (IA) or Formula (I) that exist in free base or acid form can be converted to their pharmaceutically acceptable salts by treatment with the appropriate inorganic or organic base or acid by methods known to one skilled in the art. Salts of the compounds of Formula (IA) or Formula (I) can be converted to their free base or acid form by standard techniques.

Methods of Synthesis

The compounds described herein can be made using conventional organic syntheses and commercially available starting materials, or the methods provided herein. By way of example and not limitation, compounds of Formula (I-a) through Formula (I-h) can be prepared as outlined in Schemes 1-4, as well as in the Examples set forth herein. It should be noted that one skilled in the art would know how to modify the procedures set forth in the illustrative schemes and Examples to arrive at the desired products.

Scheme 1.

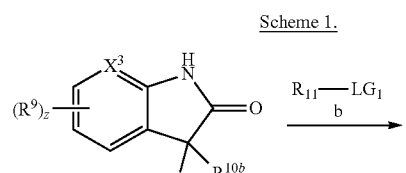

a

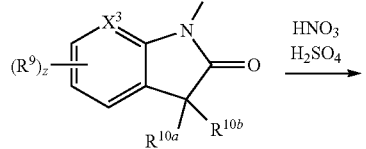

c

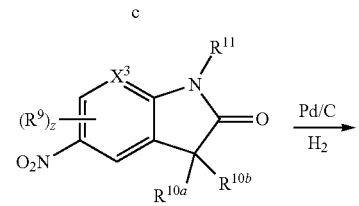

d

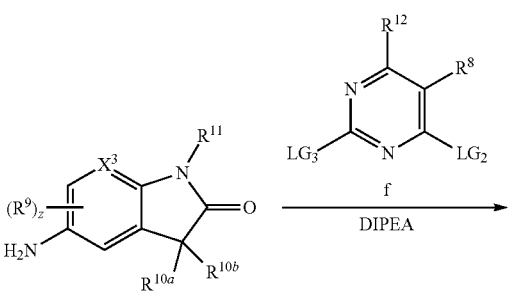

e f

-continued
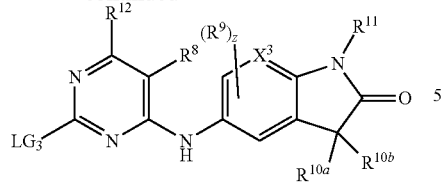
i-1
wherein $X^3$, $R^8$, $R^9$, $R^{10a}$, $R^{10b}$, $R^{11}$, $R^{12}$, and z are as defined for Formula (IA) or Formula (I); $LG_1$ is a leaving group, such as OTs, OMs, or I; and $LG_2$ and $LG_3$ are independently a leaving group, such as F or Cl.

Scheme 2.
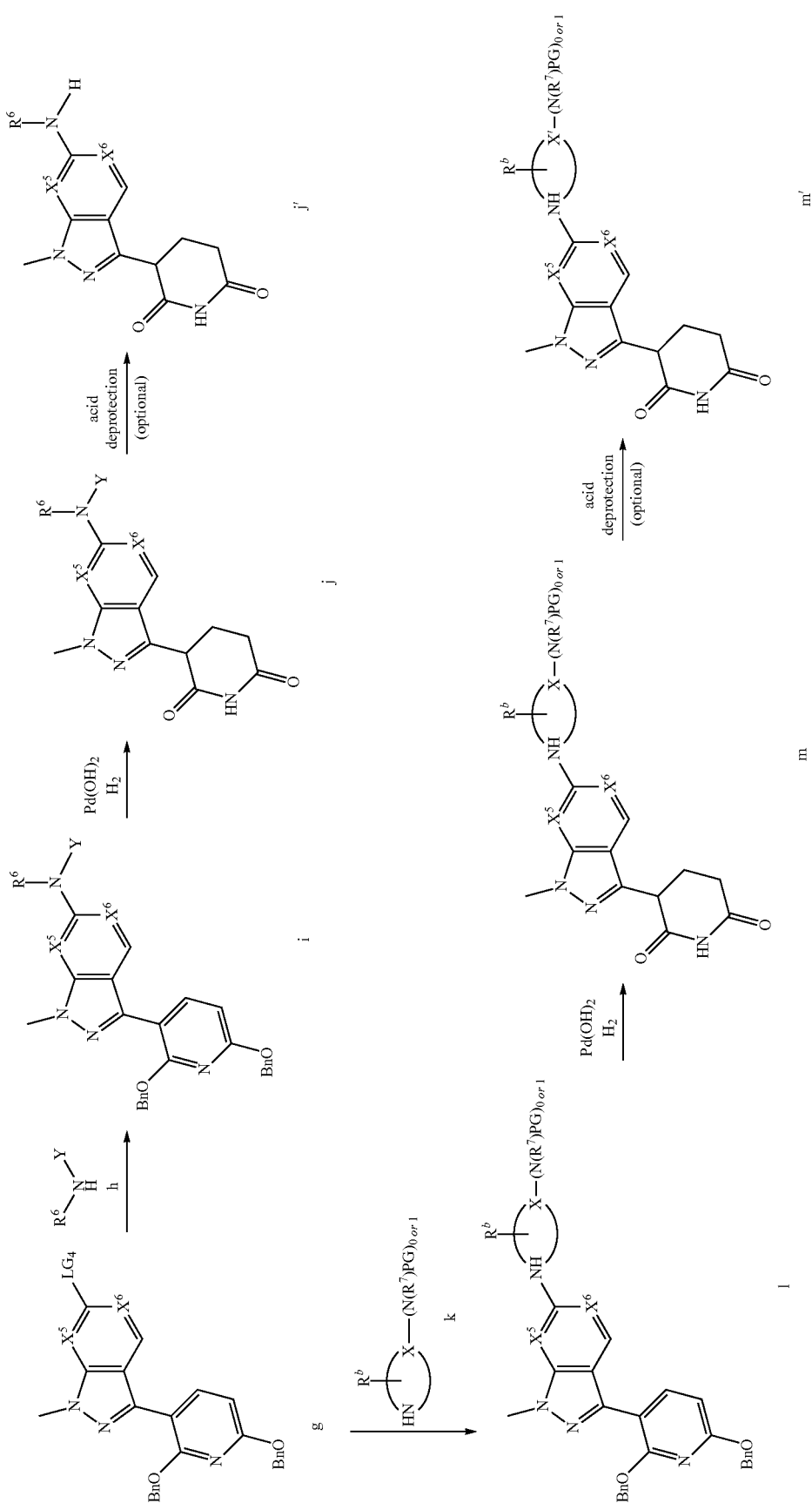

wherein X⁵, X⁶, R⁶, and R⁷ are as defined for Formula (IA) or Formula (I); LG₄ is a leaving group, such as Br or Cl; Y is H, $C_1$-$C_6$ alkyl, 6- or 7 membered heterocyclyl, or Boc, wherein the heterocyclyl contains 1-3 heteroatoms selected from N, O, and S; PG is a protecting group such as Boc; $R^b$ represents $R^{1a}$, $R^{2a}$, $R^{3a}$, $R^{4a}$, $R^{5a}$, $R^{2b}$, $R^{3b}$, $R^{4b}$, and $R^{5b}$, as defined for Formula (IA) or Formula (I); X is CH, CH₂, N, NH, or NBoc; X' is CH, CH₂, N, or NH;

is 6- or 7-membered heterocyclyl; and Bn is benzyl.

wherein PG is a protecting group, such as Fmoc or Boc; LG₄ is a leaving group, such as Br or Cl; R⁶ is as defined for Formula (IA) or Formula (I);

and Y is H, $C_1$-$C_6$ alkyl, 6- or 7 membered heterocyclyl, or Boc, wherein the heterocyclyl contains 1-3 heteroatoms selected from N, O, and S.

-continued
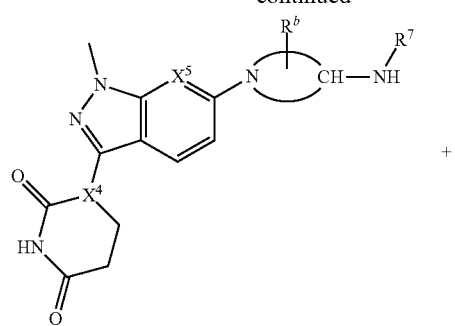
i-2b
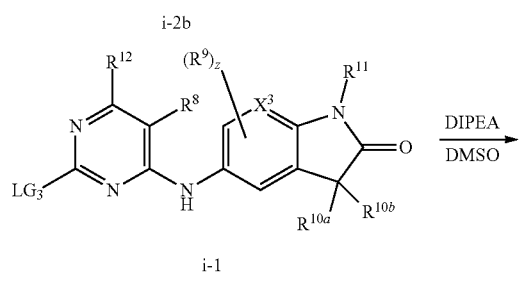
Formula (I-b)
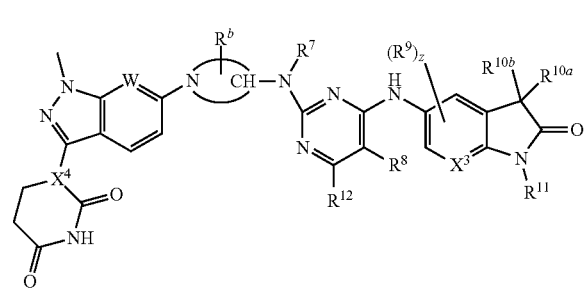
i-2c
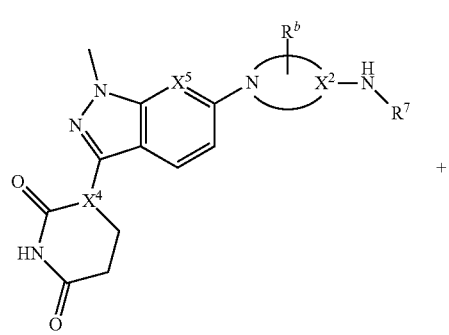
-continued
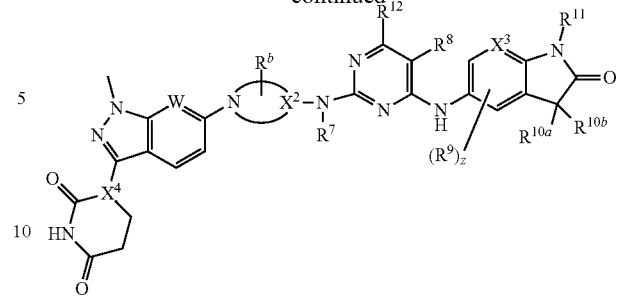
Formula (I-c)
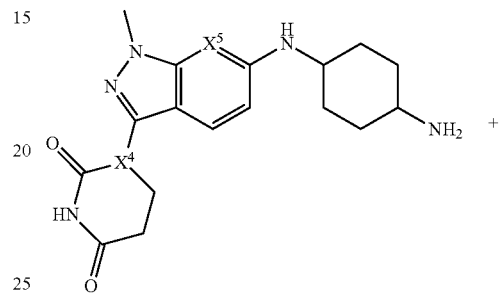
i-2d
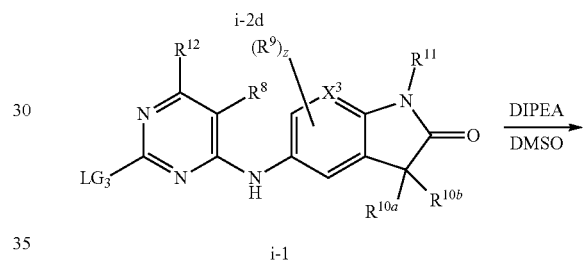
Formula (I-d)
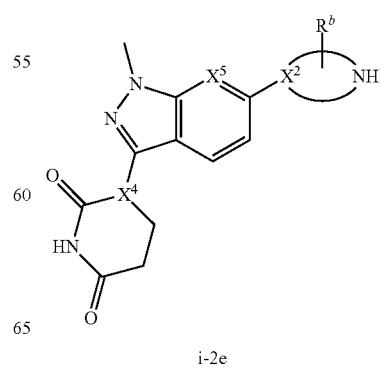
i-2e

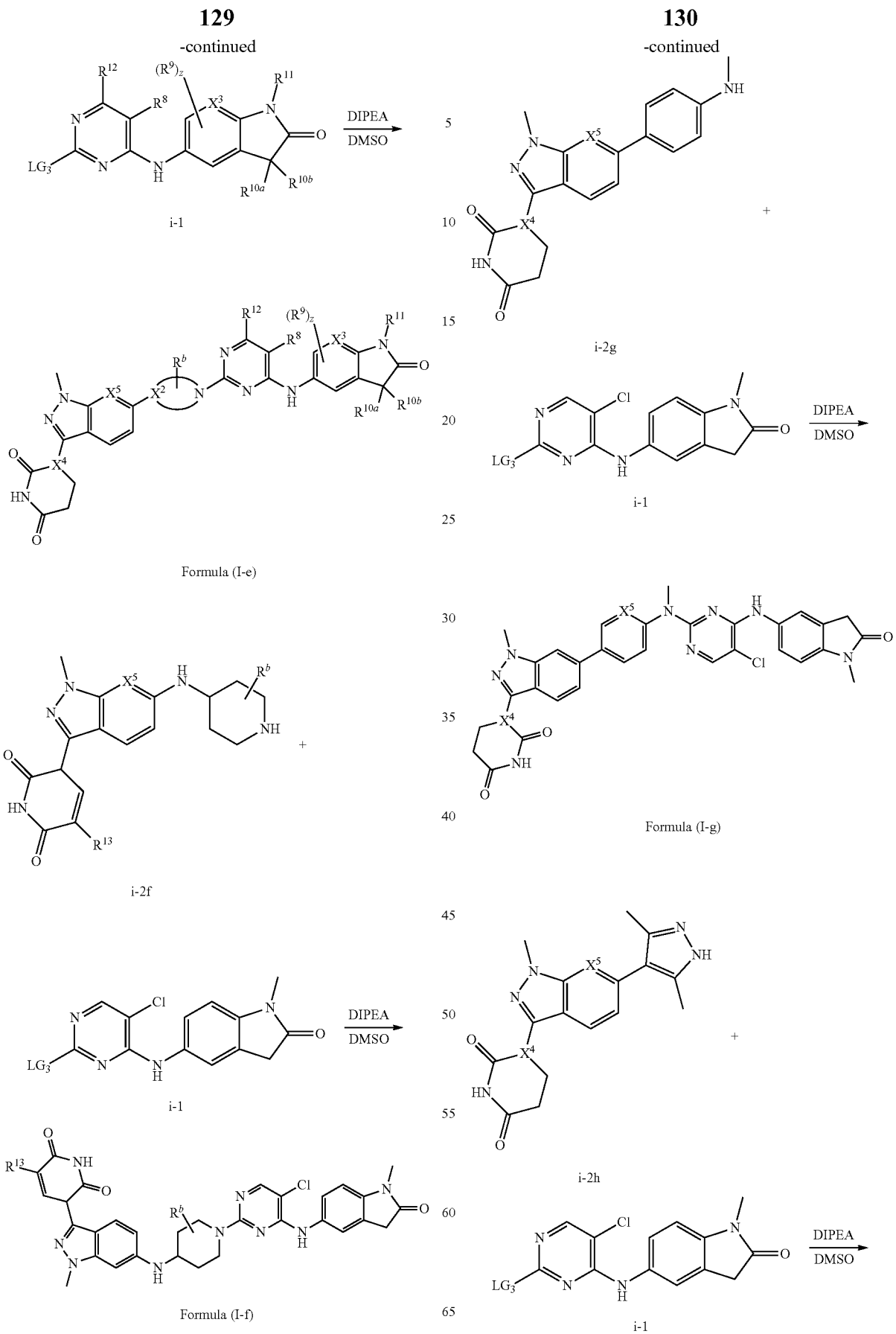

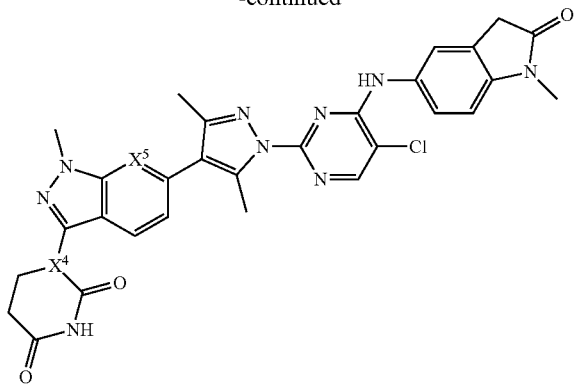

Formula (I-h)

wherein $X^3$, $X^4$, $R^6$, $R^8$, $R^9$, $R^{10a}$, $R^{10b}$, $R^{11}$, $R^{12}$, $R^{13}$, z are as defined for Formula (IA) or Formula (I); $LG_3$ is a leaving group, such as OTs, OMs, F, Cl, or I; $R^b$ represents $R^{1a}$, $R^{2a}$, $R^{3a}$, $R^{4a}$, $R^{5a}$, $R^{2b}$, $R^{3b}$, $R^{4b}$, or $R^{5b}$ as defined for Formula (IA) or Formula (I); and

is 6- or 7-membered heterocyclyl.

As outlined in Scheme 1, compounds of Formula (i-1) that contain an oxindole motif can be synthesized from coupling the indole derivatives a with intermediate compounds b to form intermediate compounds c, which are then nitrated to form intermediate compounds d. The nitro group is reduced to form intermediate compounds e, followed by coupling to intermediate f to form compounds of Formula (i-1).

Scheme 2 provides two routes for synthesizing compounds of Formula (i-2) that contain a glutarimide motif. Indazole derivatives g can be coupled to intermediate compounds h to afford intermediate compounds i. Deprotection and further reduction of intermediate compounds i forms intermediate compounds j, which are subjected to deprotection to form compounds of Formula (i-2). Alternatively, indazole derivatives g can be coupled to intermediate compounds k to afford intermediate compounds 1. Deprotection and further reduction of intermediate compounds 1 forms intermediate compounds i, which are subjected to deprotection of the amine to form compounds of Formula (i-2).

Scheme 3 provides the synthesis of compounds of Formula (i-2) that contain a dihydrouridine motif Indazole derivatives n can be coupled to intermediate compounds h to afford intermediate compounds o, which are deprotected to form intermediate compounds p and subsequently deprotected to form compounds of Formula (i-2).

Scheme 4 provides multiple routes for synthesizing various compounds of Formula (IA) or Formula (I). The compounds of Formula (i-1) can be coupled to various derivations of compounds of Formula (i-2) (denoted as Formula (i-2a) through Formula (i-2h)) to afford the compounds of Formula (I-a) through Formula (I-h).

Methods of Use

Embodiments of the present disclosure provide a method for modulating BCL6 in a subject in need thereof, the method comprising administering to the subject an effective amount of a compound of Formula (IA) or Formula (I). Modulation (e.g., inhibition or activation) of BCL6 can be assessed and demonstrated by a wide variety of ways known in the art. Kits and commercially available assays can be utilized for determining whether and to what degree BCL6 has been modulated (e.g., inhibited or activated).

In one aspect, provided herein is a method of modulating BCL6 comprising contacting BCL6 with an effective amount of a compound of Formula (IA) or Formula (I) or any embodiment or variation thereof. In some embodiments, the compound of Formula (IA) or Formula (I) inhibits BCL6. In some embodiments, the compound of Formula (IA) or Formula (I) causes degradation of BCL6.

In some embodiments, a compound of Formula (IA) or Formula (I) modulates the activity of BCL6 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of Formula (IA) or Formula (I) modulates the activity of BCL6 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

Also provided in certain embodiments of the present disclosure is a method for degrading BCL6 in a subject in need thereof, the method comprising administering to the subject an effective amount of a compound of Formula (IA) or Formula (I). Degradation of BCL6 can be assessed and demonstrated by a wide variety of ways known in the art. Kits and commercially available assays, including cell-based assays, can be utilized for determining whether and to what degree BCL6 has been degraded.

In one aspect, provided herein is a method of degrading BCL6 comprising contacting BCL6 with an effective amount of a compound of Formula (IA) or Formula (I) or any embodiment or variation thereof. In some embodiments, the compound of Formula (IA) or Formula (I) partially degrades BCL6. In some embodiments, the compound of Formula (IA) or Formula (I) fully degrades BCL6.

In some embodiments, a compound of Formula (IA) or Formula (I) degrades BCL6 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of Formula (IA) or Formula (I) degrades BCL6 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

In another aspect, provided herein is a method for treating a cancer in a subject in need thereof, comprising administering to the subject an effective amount of a compound of Formula (IA) or Formula (I). In some embodiments, provided herein is a method for preventing a cancer in a subject in need thereof, comprising administering to the subject an effective amount of a compound of Formula (IA) or Formula (I). Non-limiting examples of a cancer include squamous-cell carcinoma, basal cell carcinoma, adenocarcinoma, hepatocellular carcinomas, renal cell carcinomas, bladder cancer, bowel cancer, breast cancer, cervical cancer, colon cancer, esophageal cancer, cancer of the head, kidney cancer, liver cancer, lung cancer, neck cancer, ovarian cancer, pancreatic cancer, prostate cancer, stomach cancer, leukemia, benign lymphoma, malignant lymphoma, Burkitt's lymphoma, Non-Hodgkin's lymphoma (NHL), benign melanoma, malignant melanomas, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas, prostate cancer, uterine cancer, testicular cancer, thyroid cancer, astrocytoma, stomach cancer, melanoma, carcinosarcoma, Hodgkin's disease, Wilms' tumor, teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Diffuse Large B-cell Lymphoma, B-cell ALL, Philadelphia chromosome positive ALL, Philadelphia chromosome positive CML, follicular lymphoma, marginal zone lymphoma, mantle cell lymphoma, Waldenstroms Macroglobulinemia, Chronic Lymphocytic leukemia (CLL), Small Lymphocytic Lymphoma (SLL), intravascular large B-cell lymphoma, B-cell leukemia, chronic myeloid leukemia, and non-small cell lung cancer.

In some embodiments, administering a compound of Formula (IA) or Formula (I) to a subject in need thereof diminishes the extent of the cancer (such as tumor size, tumor growth rate, metastasis) in the subject. In some embodiments, administering a compound of Formula (IA) or Formula (I) to a subject in need thereof stabilizes the cancer (prevents or delays the worsening of the cancer). In some embodiments, administering a compound of Formula (IA) or Formula (I) to a subject in need thereof delays the occurrence or recurrence of the cancer. In some embodiments, administering a compound of Formula (IA) or Formula (I) to a subject in need thereof slows the progression of the cancer. In some embodiments, administering a compound of Formula (IA) or Formula (I) to a subject in need thereof provides a partial remission of the cancer. In some embodiments, administering a compound of Formula (IA) or Formula (I) to a subject in need thereof provides a total remission of the cancer. In some embodiments, administering a compound of Formula (IA) or Formula (I) to a subject in need thereof decreases the dose of one or more other medications required to treat the cancer. In some embodiments, administering a compound of Formula (IA) or Formula (I) to a subject in need thereof enhances the effect of another medication used to treat the cancer. In some embodiments, administering a compound of Formula (IA) or Formula (I) to a subject in need thereof delays the progression of the cancer. In some embodiments, administering a compound of Formula (IA) or Formula (I) to a subject in need thereof increases the quality of life of the subject having a cancer. In some embodiments, administering a compound of Formula (IA) or Formula (I) to a subject in need thereof prolongs survival of a subject having a cancer.

In some aspects, provided herein is a method of slowing progression of a cancer in a subject, the method comprising administering a compound of Formula (IA) or Formula (I) to the subject. In some embodiments, provided herein is a method of stabilizing a cancer in a subject, the method comprising administering a compound of Formula (IA) or Formula (I) to the subject. In some embodiments, the method prevents the progression of the cancer. In some embodiments, the method delays the progression of the cancer. In some embodiments, the method provides a partial or total remission of the cancer.

In another aspect, provided herein is a method of delaying the occurrence or recurrence of a cancer in a subject, the method comprising administering a compound of Formula (IA) or Formula (I) to the subject.

In further aspects, provided herein is a method of decreasing the dose of one or more other medications required to treat a cancer in a subject, the method comprising administering a compound of Formula (IA) or Formula (I) to the subject. In some embodiments, provided herein is a method of enhancing the effect of another medication used to treat a cancer in a subject, the method comprising administering a compound of Formula (IA) or Formula (I) to the subject.

Also provided here is a method of delaying the progression of a cancer in a subject, the method comprising administering a compound of Formula (IA) or Formula (I) to the subject. In some embodiments, the method increases the quality of life of the subject having a cancer. In some embodiments, the method prolongs survival of the subject having a cancer.

In a further aspect, provided herein is a method for treating an autoimmune disease in a subject in need thereof, comprising administering to the subject an effective amount of a compound of Formula (IA) or Formula (I). In some embodiments, provided herein is a method for preventing an autoimmune disease in a subject in need thereof, comprising administering to the subject an effective amount of a compound of Formula (IA) or Formula (I). Autoimmune diseases can be divided into two categories. Organ-specific autoimmune diseases occur when the immune system targets specific cells, tissues, or organs. Generalized autoimmune diseases occur when the immune system attacks the body without discriminating among different types of tissues or target cells. Exemplary organ-specific autoimmune diseases include atopic dermatitis, asthma, insulin dependent diabetes, Hashimoto's thyroiditis, Grave's disease, Pernicious anemia, Myasthenia gravis, Pemphigus vulgaris, and Crohn's disease. Exemplary generalized autoimmune diseases include Systemic lupus erythematosus (SLE), Rheumatoid arthritis, Scleroderma, Sarcoidosis, and Guillain-Barre Syndrome (GBS). The present disclosure encompasses treatment of all types of autoimmune disease, including organ-specific and general autoimmune diseases, including, but not limited to, lupus erythematosus, ankylosing spondylitis, Chagas disease, chronic obstructive pulmonary disease, Crohn's Disease, dermatomyositis, diabetes mellitus type 1, endometriosis, Goodpasture's syndrome, Graves' disease, Guillain-Barre syndrome (GBS), Hashimoto's disease, hidradenitis suppurativa, Kawasaki disease, IgA nephropathy, idiopathic thrombocytopenic purpura, interstitial cystitis, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, relapsing polychondritis, rheumatoid arthritis, sarcoidosis, schizophrenia, scleroderma, Sjögren's syndrome, stiff person syndrome, temporal arteritis, ulcerative colitis, vasculitis, vitiligo, and Wegener's granulomatosis.

In another aspect, provided herein is a method for treating a TH17-related condition, such as a TH17-related autoimmune condition, in a subject in need thereof, comprising administering to the subject an effective amount of a compound of Formula (IA) or Formula (I).

In some embodiments, administering a compound of Formula (IA) or Formula (I) to a subject in need thereof diminishes or reduces the symptoms of the autoimmune disease (such as inflammation, chronic fever, malaise, joint pains, myalgias, and fatigue) in the subject. In some embodiments, administering a compound of Formula (IA) or Formula (I) to a subject in need thereof shortens or reduces the duration of a symptom of the autoimmune disease. In some embodiments, administering a compound of Formula (IA) or Formula (I) to a subject in need thereof eliminates the symptoms of the autoimmune disease. In some embodiments, administering a compound of Formula (IA) or Formula (I) to a subject in need thereof delays the occurrence or recurrence of the autoimmune disease. In some embodiments, administering a compound of Formula (IA) or Formula (I) to a subject in need thereof slows the progression of the autoimmune disease. In some embodiments, administering a compound of Formula (IA) or Formula (I) to a subject in need thereof decreases the dose of one or more other medications required to treat the autoimmune disease. In some embodiments, administering a compound of Formula (IA) or Formula (I) to a subject in need thereof enhances the effect of another medication used to treat the autoimmune disease. In some embodiments, administering a compound of Formula (IA) or Formula (I) to a subject in need thereof delays the progression of the autoimmune disease. In some embodiments, administering a compound of Formula (IA) or Formula (I) to a subject in need thereof increases the quality of life of the subject having an autoimmune disease.

In some aspects, provided herein is a method of slowing progression of an autoimmune disease in a subject, the method comprising administering a compound of Formula (IA) or Formula (I) to the subject. In some embodiments, provided herein is a method of stabilizing an autoimmune disease in a subject, the method comprising administering a compound of Formula (IA) or Formula (I) to the subject. In some embodiments, the method prevents the progression of the autoimmune disease. In some embodiments, the method delays the progression of the autoimmune disease. In some embodiments, the method increases the quality of life of the subject having an autoimmune disease.

In further aspects, provided herein is a method of decreasing the dose of one or more other medications required to treat an autoimmune disease in a subject, the method comprising administering a compound of Formula (IA) or Formula (I) to the subject. In some embodiments, provided herein is a method of enhancing the effect of another medication used to treat an autoimmune disease in a subject, the method comprising administering a compound of Formula (IA) or Formula (I) to the subject.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds disclosed herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds of Formula (IA) or Formula (I) in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound of Formula (IA) or Formula (I) to be administered to a subject is rather widely variable and can be subject to the judgment of a health-care practitioner. In general, the compounds disclosed herein can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound of Formula (IA) or Formula (I) administered will depend on such factors as the solubility of the active component, the formulation used and the route of administration.

In some embodiments, a compound of Formula (IA) or Formula (I) is administered to a subject at a dose of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound of Formula (IA) or Formula (I).

In a particular embodiment, provided herein are unit dosage formulations comprising about 0.1 mg or 100 mg of a compound of Formula (IA) or Formula (I).

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound of Formula (IA) or Formula (I).

A compound of Formula (IA) or Formula (I) can be administered once, twice, three, four or more times daily. In a particular embodiment, doses of 100 mg or less are administered as a once daily dose and doses of more than 100 mg are administered twice daily in an amount equal to one half of the total daily dose.

A compound of Formula (IA) or Formula (I) can be administered orally for reasons of convenience. In one embodiment, when administered orally, a compound of Formula (IA) or Formula (I) is administered with a meal and water. In another embodiment, the compound of Formula (IA) or Formula (I) is dispersed in water or juice (e.g., apple juice or orange juice) or any other liquid and administered orally as a solution or a suspension.

The compounds disclosed herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound of Formula (IA) or Formula (I) without an additional carrier, excipient or vehicle.

In another embodiment, provided herein are compositions comprising an effective amount of a compound of Formula (IA) or Formula (I) and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound of Formula (IA) or Formula (I) with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound of Formula (IA) or Formula (I) as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound of Formula (IA) or Formula (I) can be delayed or prolonged by proper formulation. For example, a slowly soluble pellet of the compound of Formula (IA) or Formula (I) can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound of Formula (IA) or Formula (I) in oily or emulsified vehicles that allow it to disperse slowly in the serum.

It is understood that the pharmaceutical compositions described herein may include a mixture of compounds of Formula (IA) or Formula (I), including a racemic mixture of any of the compounds described herein.

Exemplary Embodiments

The present disclosure is further described by the following embodiments. The features of each of the embodiments are combinable with any of the other embodiments where appropriate and practical.

Embodiment P1. A compound of Formula (IA):

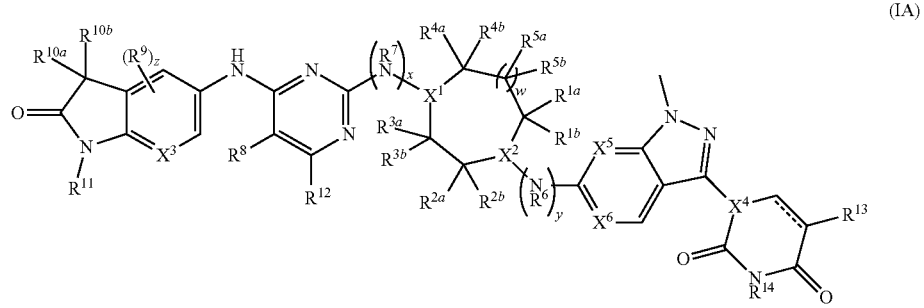

(IA)

or a pharmaceutically acceptable salt thereof, wherein:
$X^1$ and $X^2$ are each independently N or CH, provided that at least one of $X^1$ and $X^2$ is N;
$R^{1a}$ and $R^{1b}$ are each independently H, halo, or $C_1$-$C_6$ alkyl;
$R^{2a}$ and $R^{2b}$ are each independently H, $C_1$-$C_6$ alkyl, —O($C_1$-$C_6$ alkyl), —OH, halo, $C_1$-$C_6$ haloalkyl, or $C_1$-$C_6$ alkyl-OH,
or $R^{2a}$ and $R^{2b}$ are taken together with the carbon atom to which they are attached to form a spiro $C_3$-$C_5$ cycloalkyl,
or $R^{2a}$ and $R^{2b}$ are taken together to form oxo;
or $R^{1a}$ and $R^{2a}$ are taken together to form a bridging $C_2$-$C_3$ alkylene;
$R^{3a}$ and $R^{3b}$ are each independently H, halo, or $C_1$-$C_6$ alkyl;
$R^{4a}$ and $R^{4b}$ are each independently H, halo, or $C_1$-$C_6$ alkyl,
or $R^{4a}$ and $R^{4b}$ are taken together with the carbon atom to which they are attached to form a spiro $C_3$-$C_5$ cycloalkyl;
$R^{5a}$ and $R^{5b}$ are each independently H, halo, or $C_1$-$C_6$ alkyl;
w is 0 or 1;
$R^6$ is H or $C_1$-$C_6$ alkyl;
$R^7$ is H or $C_1$-$C_6$ alkyl;
x and y are each independently 0 or 1, provided that x and y are not both 1;
$R^8$ is Cl or —CN;
$R^9$ is F;
$X^3$ is N or CH;
z is 0 or 1;
$R^{10a}$ and $R^{10b}$ are each independently H or halo;
$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;
$R^{12}$ is H, halo, or $C_1$-$C_6$ alkyl;
$R^{13}$ is H or halo;
$R^{14}$ is H or $C_1$-$C_6$ alkyl;
$X^4$ is N or $CR^{15}$;
$R^{15}$ is H or $C_1$-$C_6$ alkyl;
$X^5$ and $X^6$ are each independently N or CH; and
=== is a single or double bond;
wherein one or more hydrogen atoms in the compound are optionally replaced by deuterium.

Embodiment P2. A compound of Formula (I):

or a pharmaceutically acceptable salt thereof, wherein:
$X^1$ and $X^2$ are each independently N or CH, provided that at least one of $X^1$ and $X^2$ is N;
$R^{1a}$ and $R^{1b}$ are each independently H, halo, or $C_1$-$C_6$ alkyl;
$R^{2a}$ and $R^{2b}$ are each independently H, $C_1$-$C_6$ alkyl, —OH, halo, or $C_1$-$C_6$ alkyl-OH,
or $R^{2a}$ and $R^{2b}$ are taken together with the carbon atom to which they are attached to form a spiro $C_3$-$C_5$ cycloalkyl,
or $R^{2a}$ and $R^{2b}$ are taken together to form oxo;
or $R^{1a}$ and $R^{2a}$ are taken together to form a bridging $C_2$-$C_3$ alkylene;
$R^{3a}$ and $R^{3b}$ are each independently H, halo, or $C_1$-$C_6$ alkyl;
$R^{4a}$ and $R^{4b}$ are each independently H, halo, or $C_1$-$C_6$ alkyl,
or $R^{4a}$ and $R^{4b}$ are taken together with the carbon atom to which they are attached to form a spiro $C_3$-$C_5$ cycloalkyl;
$R^{5a}$ and $R^{5b}$ are each independently H, halo, or $C_1$-$C_6$ alkyl;
w is 0 or 1;
$R^6$ is H or $C_1$-$C_6$ alkyl;
$R^7$ is H or $C_1$-$C_6$ alkyl;
x and y are each independently 0 or 1, provided that x and y are not both 1;
$R^8$ is Cl or —CN;
$R^9$ is F;
$X^3$ is N or CH;
z is 0 or 1;
$R^{10a}$ and $R^{10b}$ are each independently H or halo;
$R^{11}$ is H, $C_1$-$C_6$ alkyl, —($C_1$-$C_6$ alkylene)-(5- to 6-membered heterocyclyl), —($C_1$-$C_6$ alkylene)-O($C_1$-$C_6$ alkyl), $C_1$-$C_6$ haloalkyl, $C_1$-$C_6$ alkyl-OH, or —($C_1$-$C_6$ alkylene)-NH($C_1$-$C_6$ alkyl), wherein the heterocyclyl contains 1-3 heteroatoms selected from N, O, and S;
$R^{12}$ is H, halo, or $C_1$-$C_6$ alkyl;
$R^{13}$ is H or halo;
$R^{14}$ is H or $C_1$-$C_6$ alkyl;
$X^4$ is N or $CR^{15}$;
$R^{15}$ is H or $C_1$-$C_6$ alkyl;
$X^5$ and $X^6$ are each independently N or CH; and
=== is a single or double bond;
wherein one or more hydrogen atoms in the compound are optionally replaced by deuterium.

Embodiment P3. The compound of embodiment P1 or P2, or a pharmaceutically acceptable salt thereof, wherein:
$X^1$ is CH; and
$X^2$ is N.

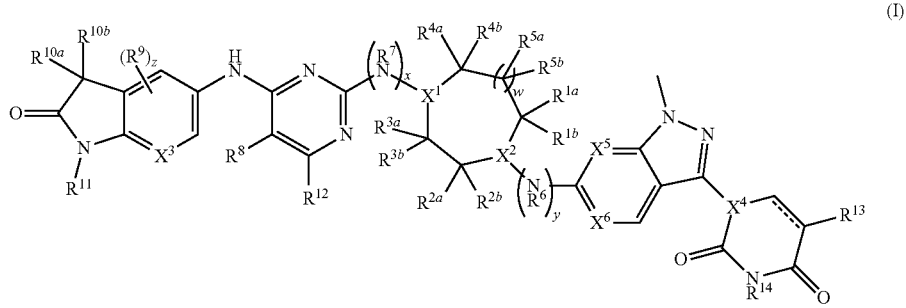

Embodiment P4. The compound of embodiment P1 or P2, or a pharmaceutically acceptable salt thereof, wherein:
$X^1$ is N; and
$X^2$ is CH.

Embodiment P5. The compound of embodiment P1 or P2, or a pharmaceutically acceptable salt thereof, wherein:
$X^1$ and $X^2$ are each N.

Embodiment P6. The compound of any one of embodiments P1-P5, or a pharmaceutically acceptable salt thereof, wherein:
$R^{1a}$ and $R^{1b}$ are each independently H, halo, or $C_1$-$C_3$ alkyl.

Embodiment P7. The compound of embodiment P6, or a pharmaceutically acceptable salt thereof, wherein:
$R^{1a}$ and $R^{1b}$ are each independently H or —$CH_3$.

Embodiment P8. The compound of any one of embodiments P1-P7, or a pharmaceutically acceptable salt thereof, wherein:
$R^{2a}$ and $R^{2b}$ are each independently H, $C_1$-$C_3$ alkyl, —O($C_1$-$C_3$ alkyl), —OH, halo, $C_1$-$C_3$ haloalkyl, or $C_1$-$C_3$ alkyl-OH,
or $R^{2a}$ and $R^{2b}$ are taken together with the carbon atom to which they are attached to form a spiro $C_3$-$C_4$ cycloalkyl,
or $R^{2a}$ and $R^{2b}$ are taken together to form oxo.

Embodiment P9. The compound of embodiment P8, or a pharmaceutically acceptable salt thereof, wherein:
$R^{2a}$ and $R^{2b}$ are each independently H, —$CH_3$, —$OCH_3$, —OH, F, —$CF_3$, or —$CH_2OH$,
or $R^{2a}$ and $R^{2b}$ are taken together with the carbon atom to which they are attached to form a spiro cyclobutyl,
or $R^{2a}$ and $R^{2b}$ are taken together to form oxo.

Embodiment P10. The compound of any one of embodiments P1-P9, or a pharmaceutically acceptable salt thereof, wherein $R^{1a}$ and $R^{1b}$ are each H, and at least one of $R^{2a}$ and $R^{2b}$ is other than H.

Embodiment P11. The compound of any one of embodiments P1-P9, or a pharmaceutically acceptable salt thereof, wherein:
$R^{1a}$ and $R^{2a}$ are taken together to form a bridging ethylene.

Embodiment P12. The compound of any one of embodiments P1-P11, or a pharmaceutically acceptable salt thereof, wherein:
$R^{3a}$ and $R^{3b}$ are each independently H, halo, or $C_1$-$C_3$ alkyl.

Embodiment P13. The compound of embodiment P12, or a pharmaceutically acceptable salt thereof, wherein:
$R^{3a}$ and $R^{3b}$ are each independently H, F, or —$CH_3$.

Embodiment P14. The compound of any one of embodiments P1-P13, or a pharmaceutically acceptable salt thereof, wherein:
$R^{4a}$ and $R^{4b}$ are each independently H, halo, or $C_1$-$C_3$ alkyl,
or $R^{4a}$ and $R^{4b}$ are taken together with the carbon atom to which they are attached to form a spiro $C_3$-$C_4$ cycloalkyl.

Embodiment P15. The compound of embodiment P14, or a pharmaceutically acceptable salt thereof, wherein:
$R^{4a}$ and $R^{4b}$ are each independently H, F, or —$CH_3$,
or $R^{4a}$ and $R^{4b}$ are taken together with the carbon atom to which they are attached to form a spiro cyclobutyl.

Embodiment P16. The compound of any one of embodiments P1-P15, or a pharmaceutically acceptable salt thereof, wherein $R^{3a}$, $R^{3b}$, $R^{4a}$, and $R^{4b}$ are each H.

Embodiment P17. The compound of any one of embodiments P1-P15, or a pharmaceutically acceptable salt thereof, wherein at least one of $R^{3a}$ and $R^{3b}$ is other than H, and at least one of $R^{4a}$ and $R^{4b}$ is other than H.

Embodiment P18. The compound of any one of embodiments P1-P17, or a pharmaceutically acceptable salt thereof, wherein:
w is 0.

Embodiment P19. The compound of any one of embodiments P1-P17, or a pharmaceutically acceptable salt thereof, wherein:
w is 1.

Embodiment P20. The compound of embodiment P19, or a pharmaceutically acceptable salt thereof, wherein:
$R^{5a}$ and $R^{5b}$ are each independently H, halo, or $C_1$-$C_3$ alkyl.

Embodiment P21. The compound of embodiment P20, or a pharmaceutically acceptable salt thereof, wherein:
$R^{5a}$ and $R^{5b}$ are each H.

Embodiment P22. The compound of any one of embodiments P1-P21, or a pharmaceutically acceptable salt thereof, wherein at least one of $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ is other than H.

Embodiment P23. The compound of embodiment P22, or a pharmaceutically acceptable salt thereof, wherein one or two of $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ is other than H.

Embodiment P24. The compound of any one of embodiments P1-P23, or a pharmaceutically acceptable salt thereof, wherein

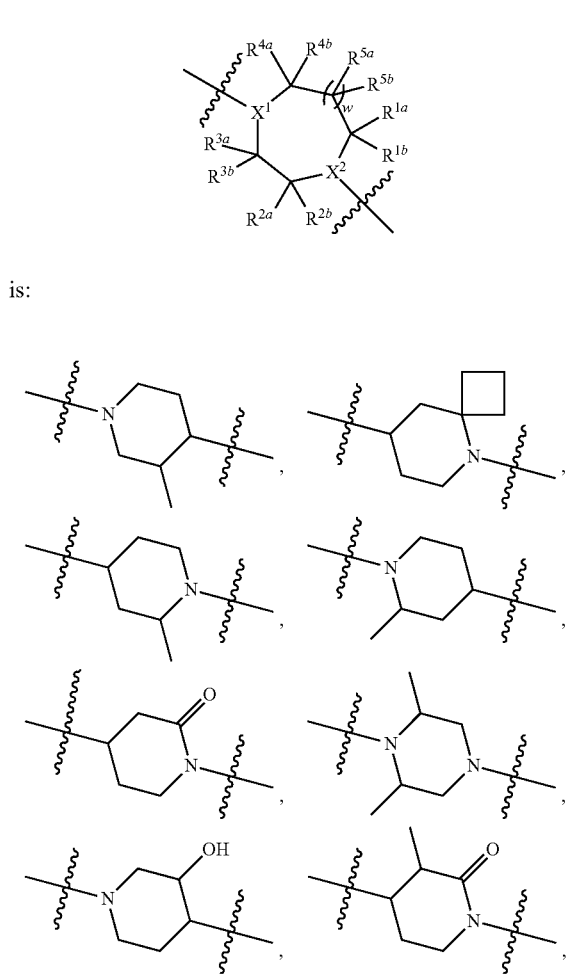

is:

-continued

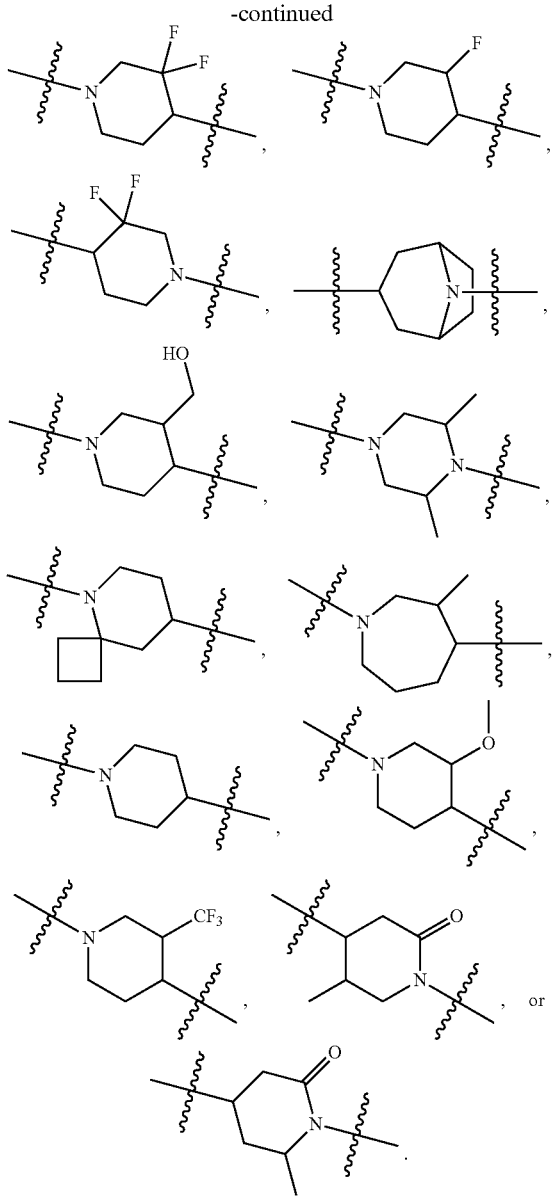

Embodiment P25. The compound of any one of embodiments P1-P24, or a pharmaceutically acceptable salt thereof, wherein:
x is 1;
y is 0; and
$R^7$ is H or $C_1$-$C_3$ alkyl.

Embodiment P26. The compound of embodiment P25, or a pharmaceutically acceptable salt thereof, wherein:
$R^7$ is H or —$CH_3$.

Embodiment P27. The compound of any one of embodiments P1-P24, or a pharmaceutically acceptable salt thereof, wherein:
x is 0;
y is 1; and
$R^6$ is H or $C_1$-$C_3$ alkyl.

Embodiment P28. The compound of embodiment P27, or a pharmaceutically acceptable salt thereof, wherein:
$R^6$ is H or —$CH_3$.

Embodiment P29. The compound of any one of embodiments P1-P24, or a pharmaceutically acceptable salt thereof, wherein:
x and y are each 0.

Embodiment P30. The compound of any one of embodiments P1-P29, or a pharmaceutically acceptable salt thereof, wherein:
$R^8$ is $C_1$.

Embodiment P31. The compound of any one of embodiments P1-P29, or a pharmaceutically acceptable salt thereof, wherein:
$R^8$ is —CN.

Embodiment P32. The compound of any one of embodiments P1-P31, or a pharmaceutically acceptable salt thereof, wherein:
$X^3$ is CH.

Embodiment P33. The compound of any one of embodiments P1-P31, or a pharmaceutically acceptable salt thereof, wherein:
$X^3$ is N.

Embodiment P34. The compound of any one of embodiments P1-P33, or a pharmaceutically acceptable salt thereof, wherein:
z is 0.

Embodiment P35. The compound of any one of embodiments P1-P33, or a pharmaceutically acceptable salt thereof, wherein:
z is 1.

Embodiment P36. The compound of any one of embodiments P1-P35, or a pharmaceutically acceptable salt thereof, wherein:
$R^{10a}$ and $R^{10b}$ are each independently H or F.

Embodiment P37. The compound of any one of embodiments P1-P36, or a pharmaceutically acceptable salt thereof, wherein:
$R^{11}$ is H, $C_1$-$C_3$ alkyl, —($C_1$-$C_3$ alkylene)-(6-membered heterocyclyl), —($C_1$-$C_3$ alkylene)-O($C_1$-$C_3$ alkyl), $C_1$-$C_5$ haloalkyl, $C_1$-$C_5$ alkyl-OH, or —($C_1$-$C_3$ alkylene)-NH($C_1$-$C_3$ alkyl), wherein the heterocyclyl contains 1-2 heteroatoms selected from N and O.

Embodiment P38. The compound of embodiment P37, or a pharmaceutically acceptable salt thereof, wherein:
$R^{11}$ is H, —$CH_3$, -$CD_3$, —$CH_2CH_3$, —$CH(CH_3)_2$, —$CH_2CH_2OCH_3$, —$CH_2CH_2OH$, —$CH_2CH_2C(OH)(CH_3)_2$, —$CH_2CH_2N(H)CH_3$, —$(CH_2)_3CF_3$, —$CH_2CF_2CH_3$, —$CH_2CH_2CF(CH_3)_2$, —$CH_2CF(CH_3)_2$, or

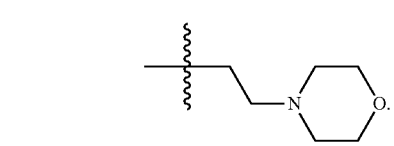 [SMILES: *CCN1CCOCC1]

Embodiment P39. The compound of any one of embodiments P1-P38, or a pharmaceutically acceptable salt thereof, wherein

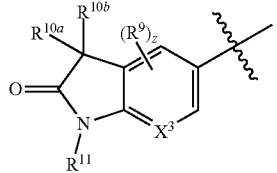

is:

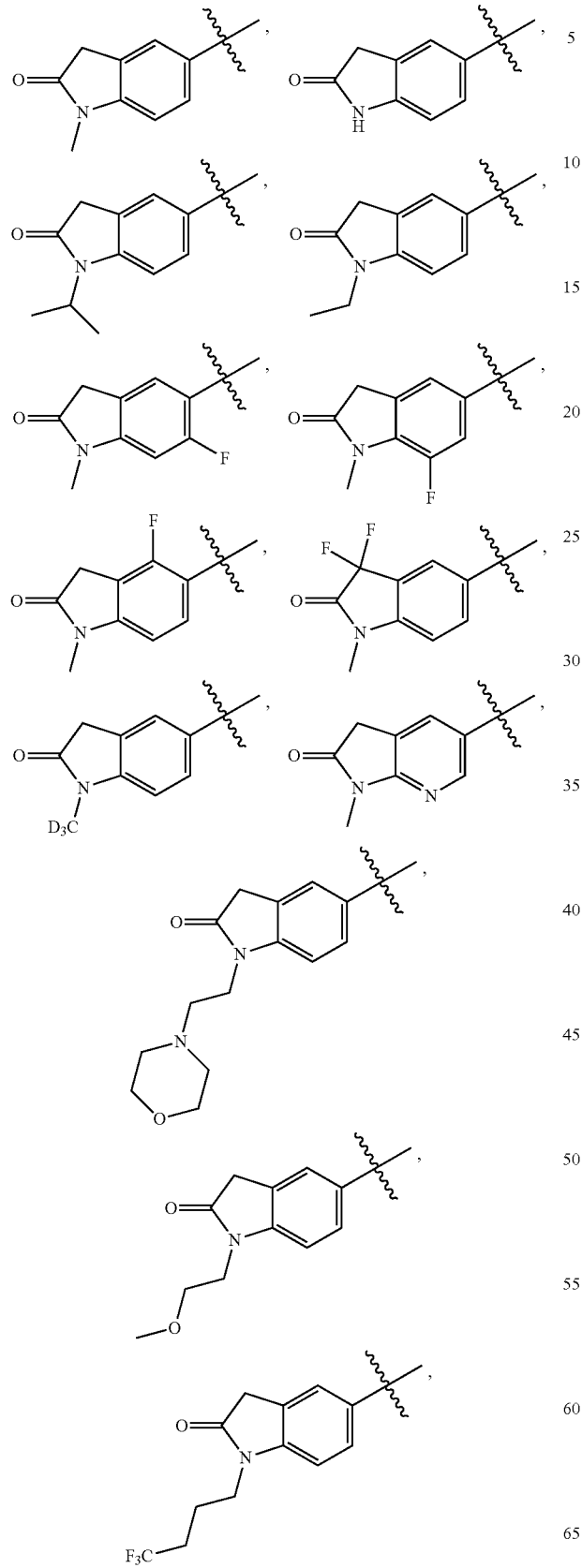

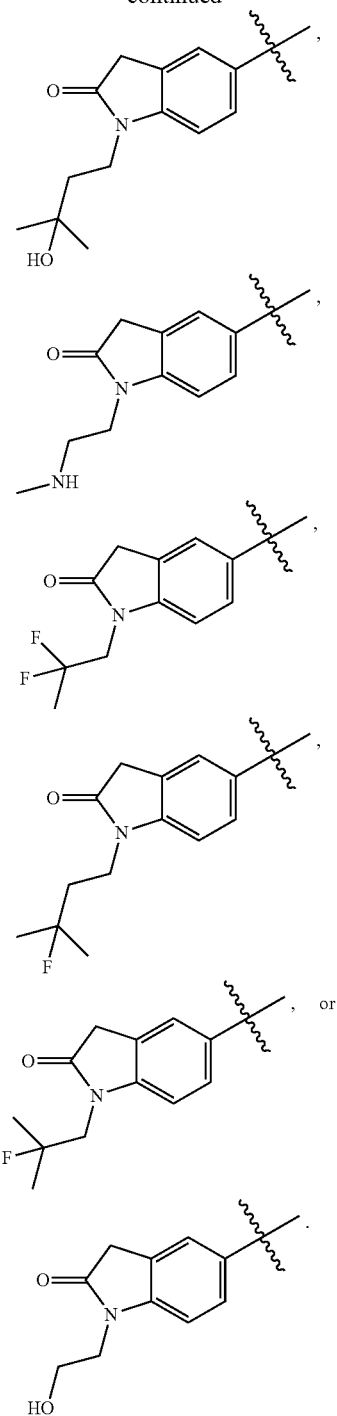

Embodiment P40. The compound of any one of embodiments P1-P39, or a pharmaceutically acceptable salt thereof, wherein:

$R^{12}$ is H, halo, or $C_1$-$C_3$ alkyl.

Embodiment P41. The compound of embodiment P40, or a pharmaceutically acceptable salt thereof, wherein:

$R^{12}$ is H, F, or —$CH_3$.

Embodiment P42. The compound of any one of embodiments P1-P41, or a pharmaceutically acceptable salt thereof, wherein is:

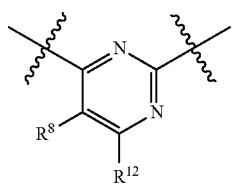

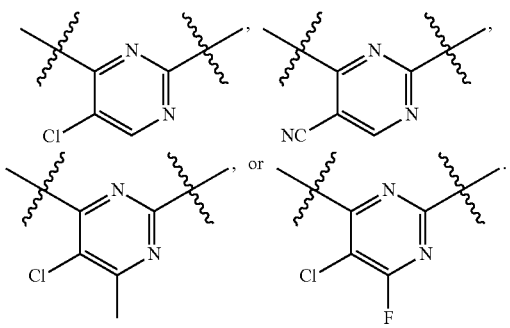

Embodiment P43. The compound of any one of embodiments P1-P42, or a pharmaceutically acceptable salt thereof, wherein:
$R^{13}$ is H or F.

Embodiment P44. The compound of any one of embodiments P1-P43, or a pharmaceutically acceptable salt thereof, wherein:
$R^{14}$ is H or $C_1$-$C_3$ alkyl.

Embodiment P45. The compound of embodiment P44, or a pharmaceutically acceptable salt thereof, wherein:
$R^{14}$ is H or —$CH_3$.

Embodiment P46. The compound of any one of embodiments P1-P45, or a pharmaceutically acceptable salt thereof, wherein:
$X^4$ is N.

Embodiment P47. The compound of any one of embodiments P1-P45, or a pharmaceutically acceptable salt thereof, wherein:
$X^4$ is $CR^{15}$; and
$R^{15}$ is H or $C_1$-$C_3$ alkyl.

Embodiment P48. The compound of embodiment P47, or a pharmaceutically acceptable salt thereof, wherein:
$X^4$ is $CR^{15}$; and
$R^{15}$ is H or —$CH_3$.

Embodiment P49. The compound of any one of embodiments P1-P48, or a pharmaceutically acceptable salt thereof, wherein:
$X^5$ is N.

Embodiment P50. The compound of any one of embodiments P1-P48, or a pharmaceutically acceptable salt thereof, wherein:
$X^5$ is CH.

Embodiment P51. The compound of any one of embodiments P1-P50, or a pharmaceutically acceptable salt thereof, wherein:
$X^6$ is N.

Embodiment P52. The compound of any one of embodiments P1-P50, or a pharmaceutically acceptable salt thereof, wherein:
$X^6$ is CH.

Embodiment P53. The compound of any one of embodiments P1-P52, or a pharmaceutically acceptable salt thereof, wherein:
═══ is a single bond.

Embodiment P54. The compound of any one of embodiments P1-P52, or a pharmaceutically acceptable salt thereof, wherein:
═══ is a double bond.

Embodiment P55. The compound of any one of embodiments P1-P54, or a pharmaceutically acceptable salt thereof, wherein

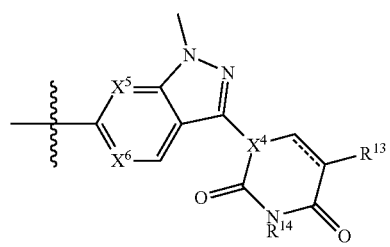

is:

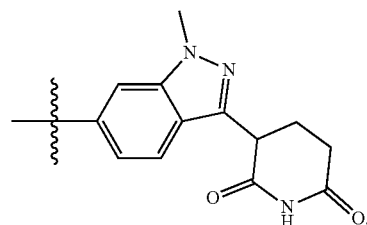

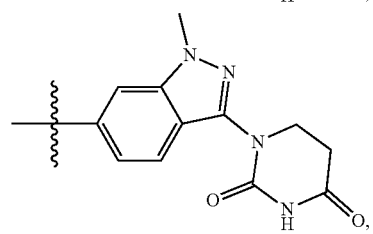

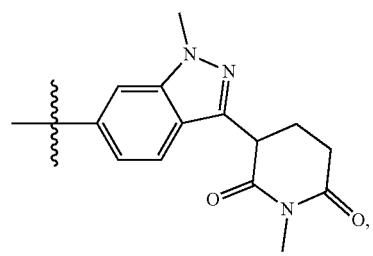

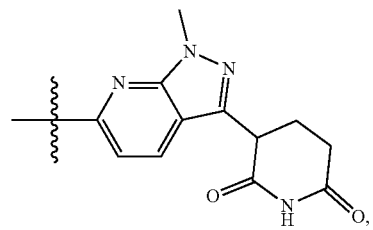

149
-continued
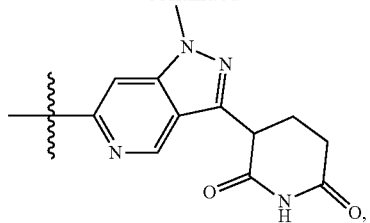
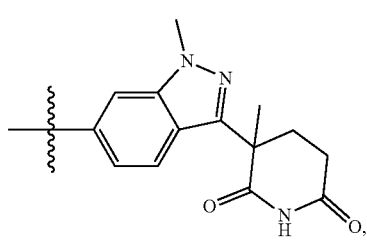
150
-continued
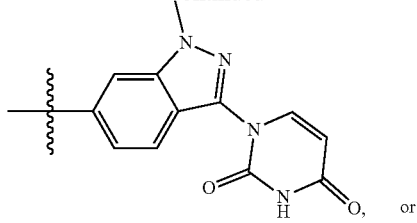
or
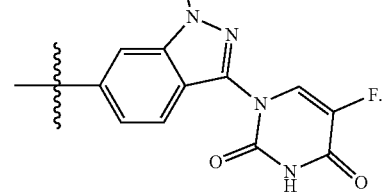
Embodiment P56. The compound of any one of embodiments P1-P55, or a pharmaceutically acceptable salt thereof, wherein the compound is of Formula (II), (III), or (IV):
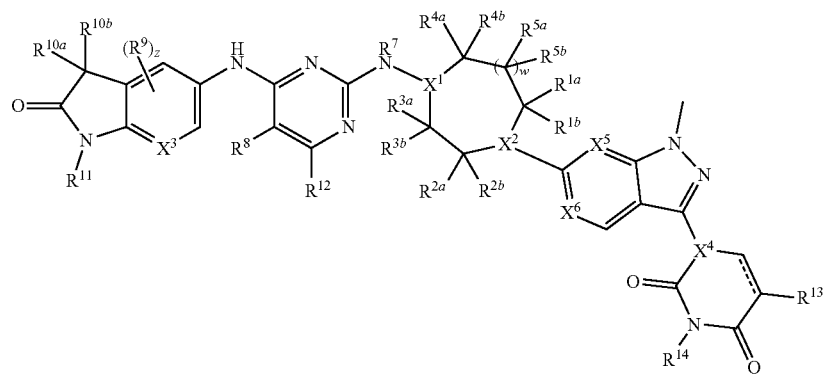
(II)
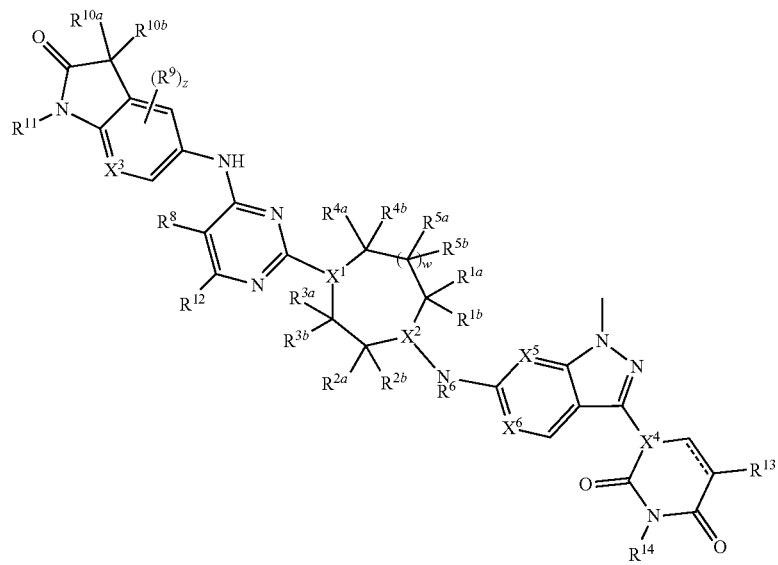
(III)

(IV)

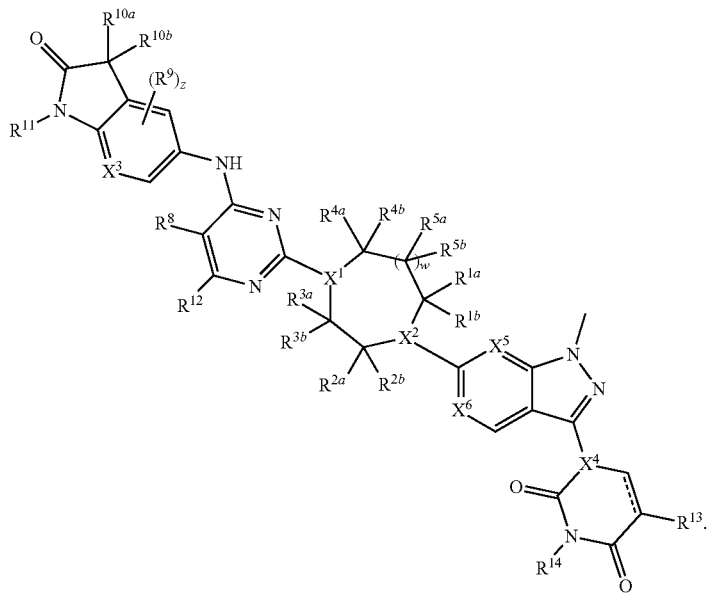

Embodiment P57. The compound of embodiment P56, or a pharmaceutically acceptable salt thereof, wherein the compound is of Formula (IIIb):

(IIIb)

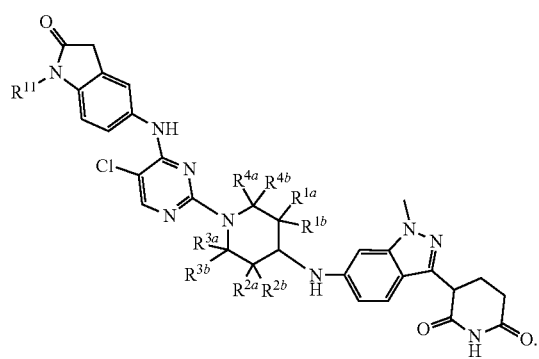

Embodiment P58. A compound selected from the compounds of Table 1 and pharmaceutically acceptable salts thereof.

Embodiment P59. A pharmaceutical composition comprising the compound of any one of embodiments P1-P58, or a pharmaceutically acceptable salt thereof, and a pharmaceutically acceptable excipient.

Embodiment P60. A method of degrading B-cell lymphoma 6 protein (BCL6) comprising contacting BCL6 with an effective amount of the compound of any one of embodiments P1-P58, or a pharmaceutically acceptable salt thereof, or the pharmaceutical composition of embodiment P59.

Embodiment P61. A method of treating a cancer in a subject in need thereof, comprising administering to the subject an effective amount of the compound of any one of embodiments P1-P58, or a pharmaceutically acceptable salt thereof, or the pharmaceutical composition of embodiment P59.

Embodiment P62. The method of embodiment P61, wherein the cancer is lymphoma.

Embodiment P63. The method of embodiment P62, wherein the lymphoma is Diffuse Large B-Cell Lymphoma.

Embodiment P64. A method of treating an autoimmune disease in a subject in need thereof, comprising administering to the subject an effective amount of the compound of any one of embodiments P1-P58, or a pharmaceutically acceptable salt thereof, or the pharmaceutical composition of embodiment P59.

Embodiment P65. The method of embodiment P64, wherein the autoimmune disease is selected from atopic dermatitis, asthma, lupus erythematosus, ankylosing spondylitis, Chagas disease, chronic obstructive pulmonary disease, Crohns Disease, dermatomyositis, diabetes mellitus type 1, endometriosis, Goodpasture's syndrome, Graves' disease, Guillain-Barre syndrome (GBS), Hashimoto's disease, hidradenitis suppurativa, Kawasaki disease, IgA nephropathy, idiopathic thrombocytopenic purpura, interstitial cystitis, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, relapsing polychondritis, rheumatoid arthritis, sarcoidosis, schizophrenia, scleroderma, Sjögren's syndrome, stiff person syndrome, temporal arteritis, ulcerative colitis, vasculitis, vitiligo, and Wegener's granulomatosis.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

The following abbreviations may be relevant for the application.

ABBREVIATIONS

ACN, MeCN acetonitrile
AcOH acetic acid
anh anhydrous
atm atmospheric pressure
$BF_3OEt_2$ boron trifluoride etherate
BINAP 2,2'-bis(diphenylphosphino)-1,1'-binaphthyl
BOC tert-butyloxycarbonyl
CBM Cereblon Binding Moiety
Cbz-Cl benzyl chloroformate
CDI 1,1'-carbonyldiimidazole
CPhos 2'-(dicyclohexylphosphanyl)-$N^2,N^2,N^6,N^6$-tetramethyl[1,1'-biphenyl]-2,6-diamine
DBU 1,8-diazabicyclo[5.4.0]undec-7-ene
DCE 1,2-dichloroethane
DCM dichloromethane
DIPEA N,N-diisopropylethylamine
DMA N,N-dimethylacetamide
DMAP 4-dimethylaminopyridine
DMEDA 1,2-dimethylethylenediamine
DMF dimethylformamide
DMSO dimethyl sulfoxide
EDC ethylene dichloride
eq or equiv equivalents
ESI electrospray ionization
$Et_3N$ triethylamine
$Et_2O$ diethyl ether
EtOAc or EA ethyl acetate
EtOH ethanol
FA formic acid
h or hrs hour
HATU N-[(Dimethylamino)-1H-1,2,3-triazolo-[4,5-b]pyridin-1-ylmethylene]-N-methylmethanaminium hexafluorophosphate N-oxide
hex hexanes
HPLC high pressure liquid chromatography
iPrOH isopropanol
Josiphos Pd G3 {(R)-1-[(Sp)-2-(dicyclohexylphosphino)ferrocenyl]ethyldi-tert-butylphosphine}[2-(2'-amino-1,1'-biphenyl)]palladium(II) methanesulfonate
LCMS liquid chromatography mass spectrometry
LHDMS lithium bis(trimethylsilyl)amide
M molarity
mCPBA meta-chloroperoxybenzoic acid
MeOH methanol
MeTHF 2-methyltetrahydrofuran
min minute
MS mass spectrometry
N normality
NaOtBu sodium tert-butoxide
NBS N-bromosuccinimide
NIS N-iodosuccinimide
NMP N-methyl-2-pyrrolidone
oMe mesylate
oTs tosylate
$Pd_2dba_3$ tris(dibenzylideneacetone)dipalladium(0)
Pd-Ruphos-G3 (2-dicyclohexylphosphino-2',6'-diisopropoxy-1,1'-biphenyl)(2-(2'-amino-1,1'-biphenyl))palladium(II) methanesulfonate
PE, pet ether petroleum ether
quant. quantitative
RBF round bottom flask
rt or RT room temperature
Rt retention time
SFC supercritical fluid chromatography
SM starting material
SNAr nucleophilic aromatic substitution
TBAB tetrabutylammonium bromide
tBuOH tert-butanol
TEA trimethylamine
TFA trifluoro acetic acid
THE tetrahydrofuran
TLC thin layer chromatography
xantphos
XPhos Pd G3

SYNTHETIC EXAMPLES

General Procedure 1: First SNAr onto Pyrimidine

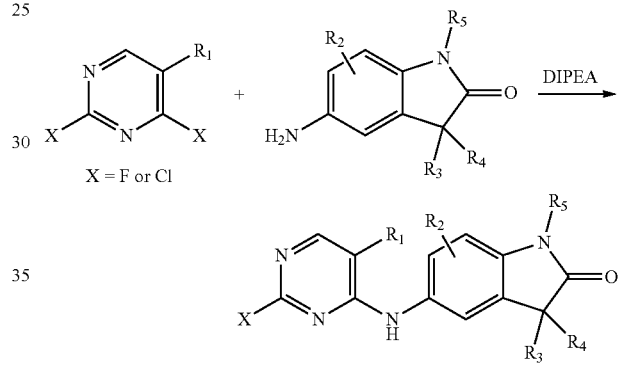

To a −40° C. mixture of 5-amino-1-methylindolin-2-one (1 eq) in dry tetrahydrofuran [0.4 M] was added DIPEA (1.1 eq). A solution of 5-chloro-2,4-difluoropyrimidine (1 eq) in dry tetrahydrofuran [1.5 M] was slowly added to the above mixture and allowed to slowly warm to rt. The reaction mixture was stirred at rt for 16 h. After this time, the reaction mixture was filtered and washed with acetonitrile. The solid was dried under vacuum to afford the title compound as a tan solid.

General Procedure 2: Buchwald Coupling of Amine to Indazole CBM

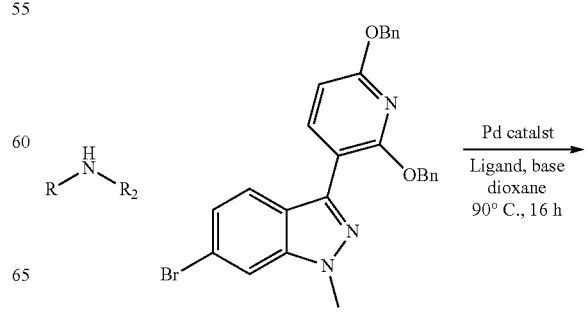

-continued

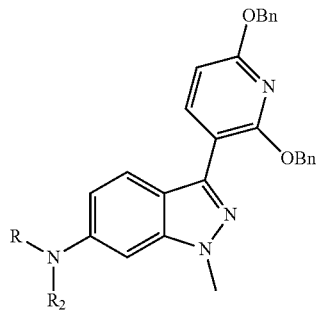

A mixture of 6-bromo-3-(2,6-dibenzyloxy-3-pyridyl)-1-methyl-indazole 1a (1.1 eq), amine (1.0 eq), Ruphos-Pd-G3 (0.20 equiv.) and NaOtBu (1.5 eq) in 1,4-dioxane [0.3 M] was heated to 90° C. for 16 h and then cooled to rt. The mixture was filtered on celite and the filter cake was washed with EtOAc. The filtrate was concentrated under reduced pressure and the residue was purified by column chromatography on silica gel using a gradient of 0-100% EtOAc in hexanes to afford the title compound.

General Procedure 3: Methylation of Amine

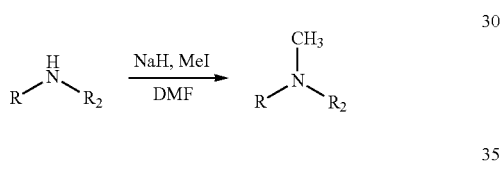

To a solution of amine (1.0 eq, 14.2 mmol) in DMF [0.15 M] was added NaH (4.4 eq), and stirred at 0° C. for 1 h. To the mixture was added iodomethane (2.8 eq) at 0° C. The resulting reaction mixture was stirred at room temperature for 16 hr. The reaction mixture was then quenched with water, and extracted with EA. The extracts were combined and washed with brine, dried over anhydrous sodium sulfate, filtered, and concentrated. The residue was purified by silica gel column chromatography eluting with PE/EA (15:1) to obtain the title compound.

General Procedure 4: Reduction of CBM with Hydrogen

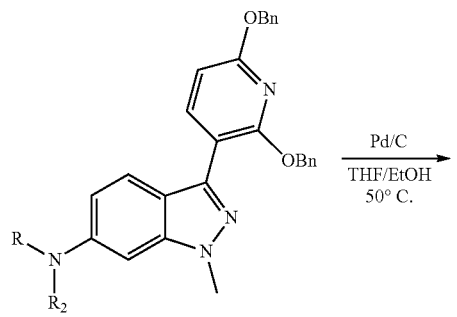

-continued

A mixture of indazole intermediate (1.0 equiv.) and Pd/C (10 wt. % palladium; 40% by weight) in EtOH:THF (1:1.5; [0.05 M]) was subjected to hydrogen (1 atm) at 50° C. for 4 h. The mixture was degassed with nitrogen and filtered through Celite. The filter cake was washed sequentially with EtOH and THF. The filtrate was concentrated under reduced pressure and the residue was purified by column chromatography on silica gel using a gradient of 0-100% EtOAc in hexanes to afford title compound.

General Procedure 5: BOC Deprotection with HCl or TFA

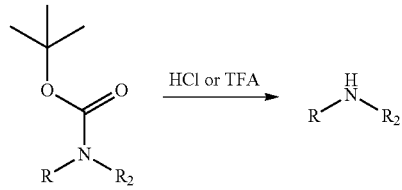

To a solution of BOC protected amine (1.0 eq) in 1,4-dioxane [0.3 M] was added 4N HCl in 1,4-dioxane (14 eq.), and the reaction mixture was stirred at rt for 12 h. The volatiles were evaporated under reduced pressure to afford title compound (quant.) as a solid, which was used in the next step without further purification.

General Procedure 6: SNAr of Decorated TBM with CBM

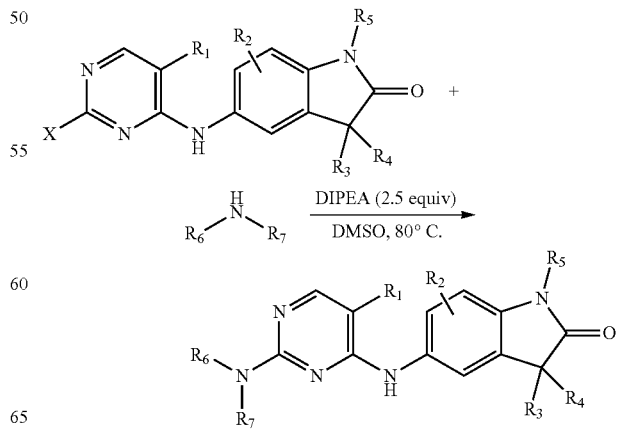

A solution of amine hydrochloride (1.0 eq), the chloro/fluoro pyrimidine (1.0 eq), N,N-diisopropylethylamine (3 to 5 eq) in DMSO [0.1-0.2 M] was stirred at 80° C. for 2 hr. The reaction mixture was filtered and purified by reverse-phased semi-preparative HPLC (10-100% acetonitrile+0.1% formic acid in water 0.1% formic acid, over 30 min). Fractions containing clean product were combined and lyophilized to afford the title compounds.

Example i-1. Synthesis of Intermediate 1: 3-(1-Methyl-6-(4-(methylamino)piperidin-1-yl)-1H-indazol-3-yl)piperidine-2,6-dione Hydrochloride

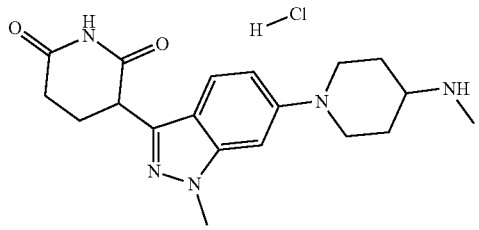

Step 1: Synthesis of tert-Butyl (1-(3-(2,6-bis(benzyloxy)pyridin-3-yl)-1-methyl-1H-indazol-6-yl)piperidin-4-yl)(methyl)carbamate. 6-bromo-3-(2,6-dibenzyloxy-3-pyridyl)-1-methyl-indazole (300 mg, 0.6000 mmol), tert-butyl N-methyl-N-(piperidin-4-yl)carbamate (192.72 mg, 0.9000 mmol), cesium carbonate (390.68 mg, 1.2 mmol), and RuPhos-Pd-G3 (50.14 mg, 0.0600 mmol) were added to a 1 dram vial and purged with nitrogen for 1 min. After which, 1,4-dioxane (0.8 mL) was added and the reaction mixture was stirred at 100° C. for overnight. Product was purified from crude mixture using column chromatography (10 g SNAP cartridge, 0-7% Methanol/DCM 25 CV, 7% methanol/DCM 10 CV) to give the title compound (106 mg, 0.1673 mmol, 27.8% yield) as a white solid. MS (ESI) m/z 634.0 [M+H]$^+$; $^1$H NMR (400 MHz, DMSO-d6) δ ppm 7.89 (d, J=8.19 Hz, 1H), 7.26-7.51 (m, 11H), 6.88 (d, J=1.59 Hz, 1H), 6.82 (dd, J=9.17, 1.96 Hz, 1H), 6.57 (d, J=8.19 Hz, 1H), 5.44 (d, J=13.57 Hz, 4H), 3.97 (s, 3H), 3.87 (br d, J=12.59 Hz, 2H), 2.77 (br t, J=11.55 Hz, 2H), 2.70 (s, 3H), 1.71-1.89 (m, 2H), 1.61-1.70 (m, 2H), 1.42 (s, 9H).

Step 2: Synthesis of tert-butyl (1-(3-(2,6-dioxopiperidin-3-yl)-1-methyl-1H-indazol-6-yl)piperidin-4-yl)(methyl)carbamate. Tert-butyl N-[1-[3-(2,6-dibenzyloxy-3-pyridyl)-1-methyl-indazol-6-yl]-4-piperidyl]-N-methyl-carbamate (106 mg, 0.1700 mmol) and ethanol (4.1813 mL) were dissolved in a 40 mL vial equipped with a sir bar. The mixture was purged with nitrogen and palladium on carbon (17.8 mg, 0.1700 mmol) was added. The mixture was purged again with nitrogen and then hydrogen. The reaction stirred under a balloon of hydrogen overnight. The slurry was filtered through celite and concentrated. The residue was loaded onto a SNAP25G column and purified with 0-50% EtOAC/hex with 2-5% MeOH additive to give the title compound (50 mg, 0.110 mmol, 65.6% yield) as yellow oil.

Step 3: Synthesis of 3-(1-Methyl-6-(4-(methylamino)piperidin-1-yl)-1H-indazol-3-yl)piperidine-2,6-dione hydrochloride. Tert-butyl N-[1-[3-(2,6-dioxo-3-piperidyl)-1-methyl-indazol-6-yl]-4-piperidyl]-N-methyl-carbamate (50 mg, 0.1100 mmol) was added to a vial equipped with a stir bar and dichloromethane (1 mL) was added. HCl 4N in 1,4-dioxane (0.4400 mmol) was then added to the mixture and stirred for 2 hours. The stir bar was removed and the solvent was removed in vacuo to give the title compound (42 mg, 0.107 mmol, 97.6% yield) as an off white solid.

Example i-2. Synthesis of Intermediate 2: 3-(1-methyl-6-(piperidin-4-ylamino)-1H-indazol-3-yl)piperidine-2,6-dione Hydrochloride

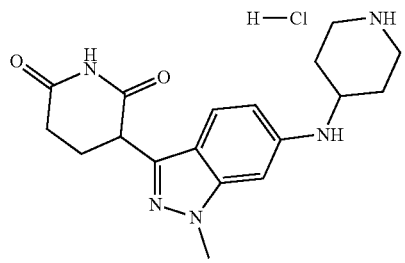

Step 1: Synthesis of 6-bromo-3-iodo-1-methyl-indazole. To a solution of 6-bromo-1-methyl-indazole (8.00 g, 37.9 mmol) in DMF (100 mL) was added NIS (25.58 g, 113.7 mmol). The reaction mixture was heated to 150° C. for on and then cooled to rt. The volatiles were evaporated under reduced pressure. The material was purified by column chromatography on silica gel using a gradient of 0-20% ethyl acetate in hexane to afford the title compound (4.95 g, 14.7 mmol, 39% yield) as a solid. MS (ESI) [M+H]$^+$ 336.90.

Step 2: Synthesis of 6-bromo-3-(2,6-dibenzyloxy-3-pyridyl)-1-methyl-indazole. To a solution of 6-bromo-3-iodo-1-methyl-indazole (2. g, 5.94 mmol) in 1,4-Dioxane (30 mL) and water (3 mL) was added (2,6-dibenzyloxy-3-pyridyl)boronic acid (1.99 g, 5.94 mmol), potassium phosphate (3.78 g, 17.81 mmol) and [1,1'-bis(diphenylphosphino)ferrocene]dichloropalladium(ii) (0.43 g, 0.5900 mmol) under N$_2$, then the mixture was stirred at 80° C. for 17 hrs under N$_2$. LCMS showed the reactant was consumed completely, and desired MS as main peak. The reaction was then cooled to room temperature and filtered. The filtrate was extracted with ethyl acetate (3×40 mL), washed with brine (2×40 mL), dried over anhydrous Na$_2$SO$_4$ and concentrated under reduced pressure. The crude was purified by column chromatography (silica, gradient: 0-30% Ethyl acetate in petroleum ether) to the title compound (2.1 g, 4.20 mmol, 71% yield) as a pale yellow solid. MS (ES) [M+H]$^+$ 500.3. $^1$H NMR (400 MHz, DMSO-d6) δ 7.96 (s, 1H), 7.91 (d, J=8.1 Hz, 1H), 7.62 (d, J=8.7 Hz, 1H), 7.50-7.24 (m, 10H), 7.12 (dd, J=8.7, 1.4 Hz, 1H), 6.60 (d, J=8.1 Hz, 1H), 5.45 (s, 2H), 5.43 (s, 2H), 4.05 (s, 3H).

Step 3: Synthesis of tert-butyl 4-[[3-(2,6-dibenzyloxy-3-pyridyl)-1-methyl-indazol-6-yl]amino]piperidine-1-carboxylate. A mixture of 6-bromo-3-(2,6-dibenzyloxy-3-pyridyl)-1-methyl-indazole (4.0 g, 7.99 mmol), tert-butyl 4-aminopiperidine-1-carboxylate (1.92 g, 9.59 mmol), XPhos-Pd-G3 (1.35 g, 1.6 mmol) and Cs$_2$CO$_3$ (5.2 g, 15.99 mmol) in 1,4-Dioxane (53.292 mL) was heated to 110° C. for 28 h and then cooled to rt. The mixture was filtered through Celite and washed with EtOAc (3×10 mL). The filtrate was concentrated under reduced pressure. The material was purified by column chromatography on silica gel using a gradient of 0-90% ethyl acetate in hexane to afford tert-butyl 4-[[3-(2,6-dibenzyloxy-3-pyridyl)-1-methyl-indazol-6-yl]amino]piperidine-1-carboxylate (2.81 g, 4.53 mmol, 57% yield) as a solid. MS (ESI) [M+H]$^+$: 620.4; $^1$H NMR (500 MHz, CDCl$_3$) δ 7.89 (d, J=8.1 Hz, 1H), 7.47 (d, J=8.7 Hz, 1H), 7.45-7.42 (m, 2H), 7.39-7.27 (m, 7H), 7.25-7.22 (m, 1H), 6.49 (d, J=8.1 Hz, 1H), 6.36 (dd, J=8.8, 1.9 Hz, 1H), 6.31 (d, J=1.7 Hz, 1H), 5.46 (s, 2H), 5.38 (s, 2H), 4.06 (br, 2H), 3.98 (s, 3H), 3.73 (br, 1H), 3.57-3.46 (m, 2H), 3.00 (t, J=11.9 Hz, 2H), 2.10 (dd, J=13.0, 2.8 Hz, 2H), 1.48 (s, 9H).

Step 4: Synthesis of tert-butyl 4-[[3-(2,6-dioxo-3-piperidyl)-1-methyl-indazol-6-yl]amino]piperidine-1-carboxylate. A mixture of tert-butyl 4-[[3-(2,6-dibenzyloxy-3-pyridyl)-1-methyl-indazol-6-yl]amino]piperidine-1-carboxylate (600 mg, 0.970 mmol) and Pearlman's Catalyst (167 mg, 0.240 mmol) in THF (5 mL) and Ethanol (3 mL) was subjected to hydrogenation at 1 atm and 50° C. for 4 h. At this time, only the alkene product was observed. Additional Pearlman's Catalyst (33.4 mg, 0.0500 mmol) was added and the mixture was subjected to hydrogenation at 1 atm and 50° C. for 24 h. The mixture was filtered through Celite and washed with MeOH:MeCN (1:1 ratio, 3×50.0 mL). The filtrate was concentrated under reduced pressure to afford tert-butyl 4-[[3-(2,6-dioxo-3-piperidyl)-1-methyl-indazol-6-yl]amino]piperidine-1-carboxylate (495 mg, 0.9496 mmol, 98.085% yield) as a solid. MS (ESI) [M+H]$^+$: 442.4; $^1$H NMR (400 MHz, DMSO-d6) δ 10.81 (s, 1H), 7.33 (d, J=8.7 Hz, 1H), 6.52 (dd, J=8.8, 1.8 Hz, 1H), 6.43 (s, 1H), 5.79 (d, J=8.2 Hz, 1H), 4.18 (dd, J=8.7, 5.2 Hz, 1H), 3.93-3.86 (m, 2H), 3.81 (s, 3H), 2.96 (br, 2H), 2.60 (t, J=7.0 Hz, 2H), 2.30-2.20 (m, 1H), 2.18-2.11 (m, 1H), 1.94 (d, J=11.0 Hz, 2H), 1.41 (s, 9H), 1.30-1.19 (m, 3H).

Step 5: Synthesis of 3-[1-Methyl-6-(4-piperidylamino) indazol-3-yl]piperidine-2,6-dione hydrochloride salt. To a solution of tert-butyl 4-[[3-(2,6-dioxo-3-piperidyl)-1-methyl-indazol-6-yl]amino]piperidine-1-carboxylate (1.22 g, 2.76 mmol) in 1,4-dioxane (20 mL) was added hydrogen chloride 4N in 1,4 dioxane (3.45 mL, 13.8 mmol). The reaction mixture was stirred at 80° C. for 2 hours. The solid was collected by filtration to give title compound (1.0 g, 2.65 mmol, 96% yield) as white solid. MS (ESI) m/z 342.2 [M+H]$^+$. $^1$H NMR (400 MHz, DMSO-d6) δ ppm 10.85 (s, 1H), 9.01 (br d, J=2.45 Hz, 1H), 8.76-8.95 (m, 1H), 7.48 (br s, 1H), 6.72 (br s, 3H), 4.21-4.30 (m, 1H), 3.87 (s, 3H), 3.63-3.75 (m, 1H), 3.32 (br d, J=12.59 Hz, 2H), 2.99 (br d, J=10.39 Hz, 2H), 2.55-2.69 (m, 2H), 2.22-2.34 (m, 1H), 2.07-2.22 (m, 3H), 1.72 (br s, 2H).

Example i-3. Synthesis of Intermediate 3: 3-(6-amino-1-methyl-1H-indazol-3-yl)piperidine-2,6-dione

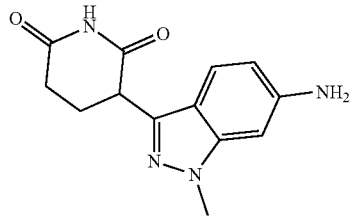 [SMILES: Cn1nc(C2CCC(=O)NC2=O)c2ccc(N)cc21]

Step 1: Synthesis of tert-butyl (3-(2,6-bis(benzyloxy) pyridin-3-yl)-1-methyl-1H-indazol-6-yl)carbamate. 3-(2,6-bis(benzyloxy)pyridin-3-yl)-6-bromo-1-methyl-1H-indazole (160 g, 320 mmol) was taken in 1,4-Dioxane (1600 mL) in a 3000 ml multineck RBF fitted with reflux condenser under N$_2$ atm with mechanical stirring. Next, tert-butyl carbamate (56.2 g, 480 mmol) was added, followed by K$_2$CO$_3$ (133 g, 959 mmol) and then purged for 5 minutes, followed by addition of XPhos Pd G2 (25.2 g, 32.0 mmol), purged again for 5 minutes and then refluxed at 110° C. for overnight. The reaction mixture was filtered through a celite bed, washing with ethyl acetate. The filtrate obtained was evaporated to give crude product which was purified using ISCO in silica gel with PE/EtOAc as eluant to give the title compound (148 g, 275 mmol, 86% yield) as white solid. MS (ESI) m/z 537.30 [M+H]$^+$. $^1$H NMR (400 MHz, DMSO-d6) δ ppm 9.5 (s, 1H), 7.89-7.91 (m, 1H), 7.28-7.54 (m, 12H), 6.94 (d, 1H), 6.58 (d, 1H), 5.41-5.45 (d, 4H), 3.96 (s, 3H), 1.50 (s, 9H), 1.37 (s, 1H).

Step 2: Synthesis of tert-butyl (3-(2,6-dioxopiperidin-3-yl)-1-methyl-1H-indazol-6-yl)carbamate. To a flask was added tert-butyl (3-(2,6-bis(benzyloxy)pyridin-3-yl)-1-methyl-1H-indazol-6-yl)carbamate (25 g, 46.6 mmol) and THF (500 mL). This mixture was purged with nitrogen for 5 min and then palladium on carbon (24.79 g, 23.29 mmol) was added and then stirred under H$_2$ atmosphere overnight at 55° C. After this time, the reaction mixture was filtered through celite washing with THF (2 L) and then the filtrate obtained was evaporated to give the title compound (15.69 g, 43.8 mmol, 94% yield) as white solid. MS (ESI) m/z 359.1 [M+H]$^+$; $^1$H NMR (400 MHz, DMSO-d6) δ ppm 10.90 (s, 1H), 9.54 (s, 1H), 7.82 (m, 1H), 7.55-7.57 (d, 1H), 7.04 (d, 1H), 4.30 (m, 1H), 3.90 (s, 3H), 2.30-2.70 (m, 2H) 2.13-2.37 (m, 2H), 1.36 (s, 9H).

Step 3: Synthesis of 3-(6-amino-1-methyl-1H-indazol-3-yl)piperidine-2,6-dione, HCl salt. tert-butyl (3-(2,6-dioxopiperidin-3-yl)-1-methyl-1H-indazol-6-yl)carbamate (25 g, 69.8 mmol) was dissolved in 1,4-Dioxane (250 mL) in a 2 L RBF under magnetic stirring. HCl (4 M in dioxane) (250 mL, 69.8 mmol) was added slowly and then the reaction was stirred at RT for 48 hours. After this time, the mixture was filtered and then the solids obtained were taken up in methanol and then stirred well for 20 minutes and then filtered again to give the title compound (18 g, 57.2 mmol, 82% yield) as pale yellow solid. MS (ESI) m/z 259.1 [M+H]$^+$. $^1$H NMR (400 MHz, DMSO-d6) δ ppm 7.80-7.82 (d, 1H), 7.53 (s, 1H), 7.08-7.11 (d 1H), 4.39-4.43 (m, 1H), 3.99 (s, 3H), 2.50-2.73 (m, 2H), 2.38-2.40 (m, 1H), 2.18-2.36 (m, 1H).

Example i-4. Synthesis of Intermediate 4: 3-(1-methyl-6-(methyl(piperidin-4-yl)amino)-1H-indazol-3-yl)piperidine-2,6-dione Hydrochloride

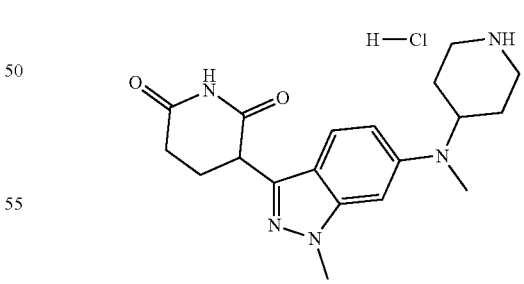

Step 1: Synthesis of tert-Butyl 4-[[3-(2,6-dibenzyloxy-3-pyridyl)-1-methyl-indazol-6-yl]amino]piperidine-1-carboxylate. A mixture of 6-bromo-3-(2,6-dibenzyloxy-3-pyridyl)-1-methyl-indazole (500 mg, 1 mmol), tert-butyl 4-aminopiperidine-1-carboxylate (240 mg, 1.2 mmol), RuPhos-Pd-G3 (83 mg, 0.1000 mmol) and Cs$_2$CO$_3$ (651 mg, 2 mmol) in 1,4-dioxane (5 mL) was heated to 90° C. for 18 h and then cooled to rt. The mixture was filtered through Celite and washed with EtOAc (3×10 mL). The filtrate was concentrated under reduced pressure. The material was purified by column chromatography on silica gel using a gradient of 0-100% EtOAc in hexanes to afford the title compound (550 mg, 89%) as a solid. ¹H NMR (500 MHz, CDCl₃) δ 7.89 (d, J=8.1 Hz, 1H), 7.47 (d, J=8.7 Hz, 1H), 7.45-7.41 (m, 2H), 7.39-7.24 (m, 8H), 6.49 (d, J=8.1 Hz, 1H), 6.36 (dd, J=8.7, 1.9 Hz, 1H), 6.31 (d, J=1.7 Hz, 1H), 5.46 (s, 2H), 5.38 (s, 2H), 4.13-4.03 (m, 2H), 3.98 (s, 3H), 3.73 (s, 1H), 3.57-3.50 (m, 1H), 3.00 (t, J=12.1 Hz, 2H), 2.10 (d, J=10.8 Hz, 2H), 1.48 (s, 9H), 1.43-1.35 (m, 2H). MS (ESI) [M+H]⁺ 620.5.

Step 2: Synthesis of tert-Butyl 4-[[3-(2,6-dibenzyloxy-3-pyridyl)-1-methyl-indazol-6-yl]-methyl-amino]piperidine-1-carboxylate. To a solution of tert-butyl 4-[[3-(2,6-dibenzyloxy-3-pyridyl)-1-methyl-indazol-6-yl]amino]piperidine-1-carboxylate (550 mg, 0.89 mmol) in DMSO (3.6 mL) and acetic acid (0.9 mL) were sequentially added aqueous solution of formaldehyde (0.13 mL, 1.8 mmol) and NaBH(OAc)₃ (282 mg, 1.3 mmol). The reaction mixture was stirred at rt for 1 h. Water (10 mL) and EtOAc (25 mL) were added and the layers were separated. The organic layer was washed with a saturated aqueous solution of NaHCO₃ (5 mL), water (3×5 mL), brine (5 mL), dried on Na₂SO₄, filtered and concentrated under reduced pressure. The material was purified by column chromatography on silica gel using a gradient of 0-100% EtOAc in hexanes to afford the title compound (467 mg, 83% yield) as a solid. ¹H NMR (400 MHz, CDCl₃) δ 7.91 (d, J=8.1 Hz, 1H), 7.56 (d, J=9.0 Hz, 1H), 7.46-7.40 (m, 2H), 7.40-7.30 (m, 5H), 7.29-7.23 (m, 3H), 6.72 (dd, J=9.3, 2.1 Hz, 1H), 6.50 (d, J=8.1 Hz, 1H), 6.48 (d, J=1.9 Hz, 1H), 5.47 (s, 2H), 5.38 (s, 2H), 4.25 (s, 2H), 4.01 (s, 3H), 3.80 (td, J=10.8, 5.3 Hz, 1H), 2.84 (s, 3H), 2.83-2.74 (m, 2H), 1.81-1.64 (m, 4H), 1.49 (s, 9H). MS (ESI) [M+H]⁺ 635.5.

Step 3: tert-Butyl 4-[[3-(2,6-dioxo-3-piperidyl)-1-methyl-indazol-6-yl]-methyl-amino]piperidine-1-carboxylate. A mixture of tert-butyl 4-[[3-(2,6-dibenzyloxy-3-pyridyl)-1-methyl-indazol-6-yl]-methyl-amino]piperidine-1-carboxylate (467 mg, 0.74 mmol) and 20% Pd(OH)₂/C (117 mg, 25 wt %) in THF (7 mL) and EtOH (7 mL) was subjected to hydrogenation at 1 atm and 50° C. for 2 h. The mixture was filtered through Celite, washed with a mixture of MeCN and MeOH (1:1, 3×10 mL), and the filtrate was concentrated under reduced pressure. The material was purified by column chromatography on silica gel using a gradient of 0-20% MeOH in DCM to afford the title compound (258 mg, 77%) as a solid. ¹H NMR (500 MHz, DMSO) δ 10.83 (s, 1H), 7.46 (d, J=9.0 Hz, 1H), 6.87 (dd, J=9.2, 2.0 Hz, 1H), 6.65 (d, J=1.9 Hz, 1H), 4.23 (dd, J=9.0, 5.1 Hz, 1H), 4.09-3.99 (m, 2H), 3.98-3.91 (m, 1H), 3.87 (s, 3H), 2.86 (br s, 2H), 2.76 (s, 3H), 2.64-2.56 (m, 2H), 2.33-2.25 (m, 1H), 2.21-2.13 (m, 1H), 1.67-1.54 (m, 4H), 1.41 (s, 9H). MS (ESI) [M+H]⁺ 456.3.

Step 4: Synthesis of 3-[1-Methyl-6-[methyl(4-piperidyl)amino]indazol-3-yl]piperidine-2,6-dione; hydrochloride. To a solution of tert-butyl 4-[[3-(2,6-dioxo-3-piperidyl)-1-methyl-indazol-6-yl]-methyl-amino]piperidine-1-carboxylate (258 mg, 0.57 mmol) in 1,4-dioxane (10 mL) was added 4 M HCl in 1,4-dioxane (1.42 mL, 5.66 mmol). The reaction mixture was heated to 100° C. for 3 h then cooled to rt. The volatiles were evaporated under reduced pressure. Et₂O (5×mL) was added and the resulting precipitate was collected by filtration, washed with 1,4-dioxane (3×1 mL) and Et₂O (10×2 mL) then dried under vacuum to afford the title compound (217 mg, 92%) as a solid. ¹H NMR (400 MHz, D₂O) δ 7.93 (d, J=8.3 Hz, 1H), 7.65 (s, 1H), 7.31 (d, J=8.0 Hz, 1H), 4.56 (dd, J=10.8, 4.2 Hz, 1H), 4.18-4.09 (m, 1H), 4.07 (s, 3H), 3.61 (d, J=12.6 Hz, 2H), 3.33 (s, 3H), 3.11 (t, J=12.9 Hz, 2H), 2.91-2.79 (m, 2H), 2.61-2.48 (m, 1H), 2.44-2.35 (m, 1H), 2.28 (d, J=12.0 Hz, 2H), 2.05-1.90 (m, 2H). Note: exchangeable protons not observed, contains <1 wt % 1,4-dioxane. MS (ESI) [M+H]⁺ 356.2.

Example i-5. Synthesis of Intermediate 5: 5-amino-1-(2-morpholinoethyl)indolin-2-one

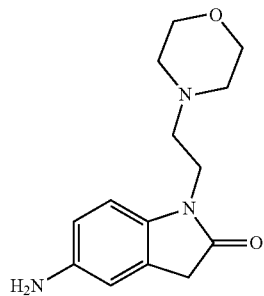 [SMILES: Nc1ccc2c(c1)CC(=O)N2CCN1CCOCC1]

Step 1: Synthesis of 1-(2-morpholinoethyl)-5-nitroindolin-2-one. To a stirred solution of triphenylphosphine (1.104 g, 4.21 mmol) in THF (20 mL) was added diisopropyl azodicarboxylate (1.091 mL, 5.61 mmol) dropwise at 0° C. under nitrogen and stirred for 20 min. Then 2-morpholinoethan-1-ol (736 mg, 5.61 mmol) was added and stirred for 15 min. Subsequently, 5-nitroindolin-2-one (500 mg, 2.81 mmol) was added and slowly warmed to 25° C. and stirred for 16 h. The reaction mixture was concentrated under reduced pressure to afford the crude product which was purified by flash column chromatography on silica gel with 60-80% ethyl acetate/pet ether to afford the title compound (273 mg, 0.937 mmol, 24% yield) as an off-white solid. MS (ESI) [M+H]⁺ 292.0.

Step 2: Synthesis of 5-amino-1-(2-morpholinoethyl)indolin-2-one. To a stirred suspension of 1-(2-morpholinoethyl)-5-nitroindolin-2-one (300 mg, 1.030 mmol) in ethanol (5.0 mL) and THF (5.0 mL) was added 10% Pd/C (150 mg) under nitrogen at 25° C. The reaction mixture was stirred under hydrogen atmosphere for 8 h. The reaction mixture was filtered through celite and the celite pad was washed with ethanol (2×50 mL). The filtrate was concentrated under reduced pressure to obtain the title compound (280 mg, 1.071 mmol, 45% yield) as a grey liquid. The crude product was used for the next step without further purification. MS (ESI) [M+H]⁺ 262.2.

Example i-6. Synthesis of Intermediate 6: 5-amino-1-(4,4,4-trifluorobutyl)indolin-2-one

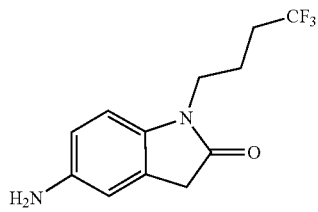 [SMILES: Nc1ccc2c(c1)CC(=O)N2CCCC(F)(F)F]

Step 1: Synthesis of 5-amino-1-(4,4,4-trifluorobutyl)indolin-2-one The synthesis of the title compound was accomplished analogously to Intermediate 5 and using 4,4,4-trifluorobutan-1-ol as the starting material.

Example i-7. Synthesis of Intermediate 7:
5-amino-6-fluoro-1-methylindolin-2-one

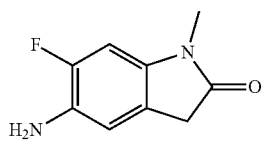

Step 1: Synthesis of 6-fluoro-1-methyl-5-nitroindolin-2-one. To a solution of 6-fluoro-1-methylindolin-2-one (100 mg, 0.605 mmol) in TFA (1 mL) was added to sodium nitrate (51.5 mg, 0.605 mmol) at 0° C., The reaction mixture was allow warm to room temperature and stirred for 3 hours. LCMS indicated the reaction was complete. The reaction mixture was then quenched with saturate sodium bicarbonate (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated. The crude was purified by silica gel column chromatography (0-100% ethyl acetate in hexane) to afford the title compound (100 mg, 0.476 mmol, 79% yield) as white solid; MS (ESI) m/z 211.0 [M+H]$^+$; $^1$H NMR (400 MHz, DMSO-d6) δ ppm 8.06 (br d, J=7.46 Hz, 1H), 6.95-7.10 (m, 1H), 3.63 (s, 2H), 3.28-3.33 (m, 43H), 3.24 (s, 3H).

Step 2: Synthesis of 5-amino-6-fluoro-1-methylindolin-2-one. A suspension of 6-fluoro-1-methyl-5-nitroindolin-2-one (100 mg, 0.476 mmol) in methanol (10 mL) was stirred with palladium on carbon (50.6 mg, 0.476 mmol) under hydrogen (1 atm) at room temperature for 2 h. The reaction mixture was filtered. Concentration of the filtrate under reduced pressure afforded the title compound (80 mg, 0.444 mmol, 93% yield) as off-white solid; MS (ESI) m/z 181.2 [M+H]$^+$.

Example i-8. Synthesis of Intermediate 8:
5-amino-7-fluoro-1-methylindolin-2-one

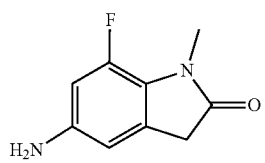

Step 1: Synthesis of 7-fluoro-1-methylindolin-2-one. To a suspension of 7-fluoroindolin-2-one (0.400 g, 2.65 mmol) in water (10 mL) was added sodium hydroxide 1N (3.97 mL, 3.97 mmol) and dimethyl sulfate (0.379 mL, 3.97 mmol), The reaction mixture was stirred at 120° C. for 40 min. LCMS indicated the reaction was incomplete with 20% SM remaining. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried (anhydrous sodium sulfate), filtered over celite, and concentrated. The crude was purified by silica gel column chromatography (0-50% ethyl acetate in hexane). Concentration of the desired fractions under reduced pressure afforded the title compound 7-fluoro-1-methylindolin-2-one (0.3 g, 1.82 mmol, 69% yield) as yellow solid; MS (ESI) m/z 331.2 [M+H]$^+$.

Step 2: Synthesis of 5-amino-7-fluoro-1-methylindolin-2-one. The synthesis of the title compound was accomplished analogously to Intermediate 7 using 7-fluoro-1-methylindolin-2-one as the starting material.

Example i-9. Synthesis of Intermediate 9:
5-amino-4-fluoro-1-methylindolin-2-one

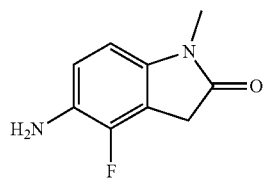

Step 1: Synthesis of 4-fluoro-1-methylindolin-2-one. To a suspension of 4-fluoroindolin-2-one (1.0 g, 6.62 mmol) in water (18 mL) was added sodium hydroxide 1N (9.92 mL, 9.92 mmol) and dimethyl sulfate (0.695 mL, 7.28 mmol), The reaction mixture was stirred at 120° C. for 40 min. LCMS indicated the reaction was incomplete with 20% SM remaining. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried (anhydrous magnesium sulfate), filtered over celite, and concentrated. The crude was purified by silica gel column chromatography (0-50% ethyl acetate in hexane). Concentration of the desired fractions under reduced pressure afforded the title compound (1.48 g, 100%) as white solid; MS (ESI) m/z 166.2 [M+H]$^+$.

Step 2: Synthesis of 4-fluoro-1-methyl-5-nitroindolin-2-one. To a −30° C. solution of 4-fluoro-1-methylindolin-2-one (0.68 g, 4.12 mmol) in sulfuric acid (10 mL) was added nitric acid 90% (0.195 mL, 4.53 mmol) in sulfuric acid 98 (1 mL) slowly. The reaction mixture was stirred at −30° C. and allowed warm to 0° C. over 30 min. The reaction mixture was poured onto 100 g ice, then extracted with ethyl acetate (3×25 mL). The combined organic phases were washed with saturated aqueous sodium chloride (1×25 mL). The organic layer was dried over anhydrous sodium sulfate, filtered over celite, and concentrated. The crude was purified by silica gel column chromatography (0-100% ethyl acetate in hexane) to afford the title compound 4-fluoro-1-methyl-5-nitroindolin-2-one (0.260 g, 1.24 mmol, 30.0% yield) as yellow solid; MS (ESI) m/z 211.2 [M+H]$^+$.

Step 3: Synthesis of 5-amino-4-fluoro-1-methylindolin-2-one. The suspension of 4-fluoro-1-methyl-5-nitroindolin-2-one (60 mg, 0.285 mmol) in methanol (10 mL) was stirred with palladium on carbon (30.4 mg, 0.285 mmol) under hydrogen (1 atm) at room temperature for 2 h. The reaction mixture was filtered. Concentration of the elute under reduced pressure afforded the title compound (44 mg, 0.244 mmol, 86% yield) as white solid; MS (ESI) m/z 181.2

[M+H]⁺; ¹H NMR (400 MHz, DMSO-d6) δ ppm 6.68 (t, J=8.56 Hz, 1H), 6.54 (d, J=8.07 Hz, 1H), 4.76 (s, 2H), 3.52 (s, 2H), 3.04 (s, 3H).

Example i-10. Synthesis of Intermediate 10:
5-amino-1-isopropylindolin-2-one

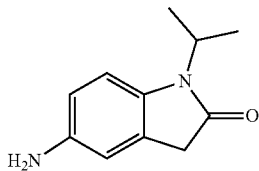

Step 1: Synthesis of 1-isopropyl-5-nitroindolin-2-one A solution of 2-(2-fluoro-5-nitrophenyl)acetic acid (0.5 g, 2.51 mmol), propan-2-amine (0.445 g, 7.53 mmol) in DMSO (4 mL) was stirred at 60° C. for 15 h. The reaction mixture was quenched with saturated aqueous ammonium chloride (25 mL) and then extracted with ethyl acetate (3×25 mL). The organic phase was combined and washed with saturated aqueous sodium chloride (1×25 mL). The organic layer was dried (anhydrous sodium sulfate), filtered, and concentrated. The crude was purified by silica gel column chromatography (0-100% ethyl acetate in hexane in hexane). Concentration of the desired fractions under reduced pressure afforded the 2-(2-(isopropylamino)-5-nitrophenyl)acetic acid (0.528 g, 87%) as yellow solid. The solid 2-(2-(isopropylamino)-5-nitrophenyl)acetic acid (0.528 g) was then stirred with 2N HCl 10 mL at room temperature for 15 hours. The resulting solid was collected by filtration to give the title compound (0.45 g, 2.043 mmol, 81% yield) as yellow solid; MS (ESI) m/z 221.2 [M+H]⁺.

Step 2: Synthesis of 5-amino-1-isopropylindolin-2-one The suspension of 1-isopropyl-5-nitroindolin-2-one (450 mg, 2.043 mmol) in methanol (10 mL) was stirred with palladium on carbon (217 mg, 2.043 mmol) under hydrogen (1 atm) at room temperature for 15 h. The reaction mixture was filtered. Concentration of the elute under reduced pressure afforded the title compound 5-amino-1-isopropylindolin-2-one (350 mg, 1.840 mmol, 90% yield) as off-white solid; MS (ESI) m/z 191.2 [M+H]⁺; ¹H NMR (400 MHz, DMSO-d6) δ ppm 6.80 (d, J=8.31 Hz, 1H), 6.55 (d, J=1.96 Hz, 1H), 6.43 (dd, J=8.31, 2.32 Hz, 1H), 4.72 (br s, 2H), 4.45 (spt, J=6.99 Hz, 1H), 3.35 (s, 2H), 1.34 (d, J=7.09 Hz, 6H).

Example i-11. Synthesis of Intermediate 11:
5-amino-1-ethylindolin-2-one

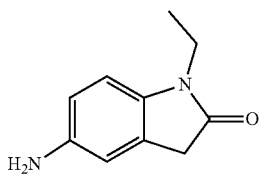

Step 1: Synthesis of 5-amino-1-ethylindolin-2-one The synthesis of the title compound was accomplished analogously to Intermediate 10 and using ethanamine hydrochloride as the starting material.

Example i-12. Synthesis of Intermediate 12:
5-amino-1-(2-hydroxyethyl)indolin-2-one

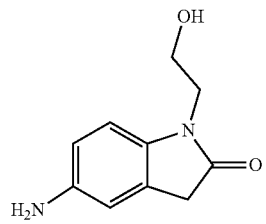 [SMILES: Nc1ccc2c(c1)CC(=O)N2CCO]

Step 1: Synthesis of 5-amino-1-(2-hydroxyethyl)indolin-2-one The synthesis of the title compound was accomplished analogously to Intermediate 10 and using 2-aminoethanol as the starting material.

Example i-13. Synthesis of Intermediate 13:
5-amino-1-(2-methoxyethyl)indolin-2-one

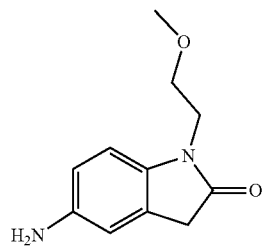

Step 1: Synthesis of 2-(2-((2-methoxyethyl)amino)-5-nitrophenyl)acetic acid. To a solution of 2-(2-fluoro-5-nitrophenyl) acetic acid (1, 500 mg, 2.51 mmol) in THF (5.0 mL) was added 2-methoxyethan-1-amine (2, 377 mg, 5.02 mmol) and DIPEA (0.877 mL, 5.02 mmol) under nitrogen at 25° C. The reaction mixture was heated to 60° C. and stirred for 16 h. The reaction mixture was concentrated under reduced pressure to give the title compound (550 mg, 0.543 mmol, 21% yield) as yellow solid.

Step 2: Synthesis of 1-(2-methoxyethyl)-5-nitroindolin-2-one. To a solution of 2-(2-((2-methoxyethyl)amino)-5-nitrophenyl)acetic acid (550 mg, 2.16 mmol) in water (2.0 mL) was added 1.5N HCl (3.0 mL). The reaction mixture was heated to 60° C. and stirred for 16 h. The reaction mixture was slowly poured in sodium bicarbonate solution at 0° C. and extracted with ethyl acetate. The combine organic layer was dried over sodium sulphate, filtered, and concentrated under reduced pressure to afford the title compound (240 mg, 0.95 mmol, 44% yield) as a light brown solid.

Step 3: Synthesis of 5-amino-1-(2-methoxyethyl) indolin-2-one. To a stirred solution of 1-(2-methoxyethyl)-5-nitroindolin-2-one (240 mg, 0.945 mmol) in ethanol (10 mL) was added 10% Pd/C (101 mg) under nitrogen at 25° C. The reaction mixture was stirred under hydrogen atmosphere for 8 h. The reaction mixture was filtered through celite and the celite pad was washed with ethanol (3×10 mL). The filtrate was concentrated under reduced pressure to obtain the title compound (200 mg, 0.563 mmol, 59% yield). The product was used for the next step without further purification. MS (ESI) m/z 207.2 [M+H]⁺.

Example i-14. Synthesis of Intermediate 14: 5-amino-1-methyl-1,3-dihydro-2H-pyrrolo[2,3-b]pyridin-2-one

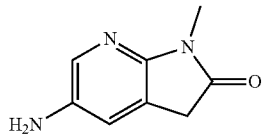

Step 1: Synthesis of 3,3-dibromo-1-methyl-5-nitro-1,3-dihydro-2H-pyrrolo[2,3-b]pyridin-2-one. To a stirred solution of 1-methyl-5-nitro-1H-pyrrolo[2,3-b]pyridine (800 mg, 3.66 mmol) in t-Butanol (1 mL) and water (1 mL). was added NBS (1.37 g, 7.68 mmol) at 0° C. the reaction mixture was stirred at 25° C. for 2 h. The reaction mixture was monitored by TLC and LCMS. When the reaction was complete, the reaction mixture was diluted with water (100 mL) and extracted with EtOAc (3×100 ml). The combined organic layers were evaporated to obtain crude title compound that was used without further purification.

Step 2: Synthesis of 5-amino-1-methyl-1,3-dihydro-2H-pyrrolo[2,3-b]pyridin-2-one To a stirred solution of 3,3-dibromo-1-methyl-5-nitro-1,3-dihydro-2H-pyrrolo[2,3-b]pyridin-2-one (1.4 g, 3.99 mmol) in AcOH (20 mL) was added zinc dust (1.30 g, 20.0 mmol) and the reaction mixture was stirred at 25° C. for 6 h. The reaction mixture was monitored by TLC and LCMS. After this time, the reaction mixture was evaporated. The resulting reside was basified by using NaOH solution (100 ml) and extracted with 10% MeOH in DCM. The organic fraction was evaporated to obtained the title compound which was used without further purification. MS (ESI) m/z 164.1 [M+H]$^+$.

Example i-15. Synthesis of Intermediate 15: 6-amino-1-(3-hydroxy-3-methylbutyl)indolin-2-one

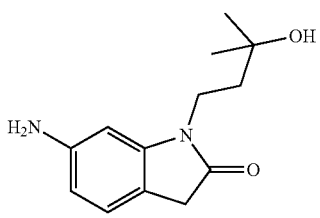 [SMILES: CC(C)(O)CCN1C(=O)Cc2ccc(N)cc21]

Step 1: Synthesis of 2-methyl-4-(6-nitro-1H-indol-1-yl)butan-2-ol To a stirred solution of 6-nitro-1H-indole (1, 1.0 g, 6.17 mmol) in DMF (10 mL) was added compound 3-hydroxy-3-methylbutyl 4-methylbenzenesulfonate (2, 2.30 g, 8.02 mmol) and cesium carbonate (3.01 g, 9.25 mmol) at 25° C. The reaction mixture was heated to 120° C. for 16 h. The reaction mixture was then cooled to room temperature and treated with water and extracted with ethyl acetate (3×50 mL). The combined organic layers were dried over anhydrous sodium sulfate, filtered, and concentrated under reduced pressure to afford the crude compound which was purified by flash column chromatography on silica with 20-30% ethyl acetate/pet ether to afford the title compound (1.4 g, 5.44 mmol, 88% yield) as a brown semi solid. MS (ESI) m/z 249.1 [M+H]$^+$.

Step 2: Synthesis of 3,3-dibromo-1-(3-hydroxy-3-methylbutyl)-6-nitroindolin-2-one. To a stirred solution of 2-methyl-4-(6-nitro-1H-indol-1-yl)butan-2-ol (100 mg, 0.380 mmol) in t-BuOH (1 mL) and water (1.0 mL) was added NBS (142 mg, 0.797 mmol) at 0° C. The reaction mixture was slowly warmed to 25° C. and stirred for 2 h. The reaction mixture was treated with water (30 mL) and extracted with ethyl acetate (2×50 mL). The combined organic layers were dried over anhydrous sodium sulphate, filtered, and concentrated under reduced pressure to afford the title compound (150 mg, 94% yield). The crude product was used for the next step without further purification.

Step 3: Synthesis of 6-amino-1-(3-hydroxy-3-methylbutyl)indolin-2-one. To a stirred solution of 3,3-dibromo-1-(3-hydroxy-3-methylbutyl)-6-nitroindolin-2-one (150 mg) in AcOH (3.0 mL) was added zinc dust (116 mg, 1.78 mmol) at 0° C. The reaction mixture was slowly warmed to 25° C. and stirred for 8 h. The reaction mixture was concentrated under reduced pressure to afford the crude compound. The crude was purified by flash column chromatography on silica with 6% methanol/DCM to afford the title compound (100 mg, 0.333 mmol, 87% yield) as a brown gummy solid. MS (ESI) m/z 235.2 [M+H]$^+$.

Example i-16. Synthesis of Intermediate 16: 6-amino-1-(3-hydroxy-3-methylbutyl)-3,3-dimethyl-indolin-2-one

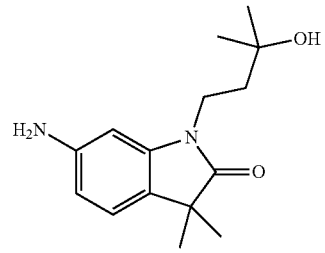 [SMILES: CC(C)(O)CCN1C(=O)C(C)(C)c2ccc(N)cc21]

Step 1: Synthesis of N-(2-Bromo-5-nitro-phenyl)-2-methyl-prop-2-enamide. To a solution of 2-bromo-5-nitro-aniline (1.00 g, 4.61 mmol) in DMA (20 mL) was added 2-methylprop-2-enoyl chloride (0.45 mL, 4.61 mmol) and the reaction mixture was stirred at rt for 12 h. Water (5.0 mL) was added and the resulting precipitate was collected by filtration, washed with water (20 mL), then dried under vacuum to afford the title compound (950 mg, 72%) as a solid. $^1$H NMR (400 MHz, DMSO d6): δ 9.69 (s, 1H), 8.44 (s, 1H), 8.00 (d, J=1.2 Hz, 2H), 5.97 (s, 1H), 5.63 (s, 1H), 2.00 (s, 3H). MS (ESI) [M+H]$^+$ 285.1.

Step 2: Synthesis of 3,3-Dimethyl-6-nitro-indolin-2-one. To a solution of N-(2-bromo-5-nitro-phenyl)-2-methyl-prop-2-enamide (950 mg, 3.33 mmol) in DMF (33 mL) were added sequentially triethylamine (1.16 mL, 8.33 mmol), TBAB (1.07 g, 3.33 mmol) and Pd(OAc)$_2$ (15.0 mg, 0.07 mmol) under nitrogen, and the reaction mixture was stirred at 80° C. for 1 h. HCOONa (227 mg, 3.33 mmol) was added and the reaction mixture was stirred at 80° C. for 12 h. Water (5 mL) and ethyl acetate (15 mL) were added and the layers were separated. The organic layer was washed with brine (3×10 mL), dried on Na$_2$SO$_4$, filtered and concentrated under reduced pressure. Et$_2$O (5 mL) was added and the resulting precipitate was collected by filtration and dried under vacuum to afford the title compound (180 mg, 26%) as a solid. $^1$H NMR (400 MHz, DMSO d6): δ 10.75 (s, 1H), 7.90 (dd, J=8.2, 2.1 Hz, 1H), 7.60 (d, J=8.2 Hz, 1H), 7.57 (d, J=2.1 Hz, 1H), 1.30 (s, 6H). MS (ESI) [M+H]+ 207.0.

Step 3: Synthesis of 1-(3-Hydroxy-3-methyl-butyl)-3,3-dimethyl-6-nitro-indolin-2-one. To a solution of 3,3-dimethyl-6-nitro-indolin-2-one (180 mg, 0.87 mmol) in DMF (3 mL) were added sequentially (3-hydroxy-3-methyl-butyl) 4-methylbenzenesulfonate (271 mg, 1.05 mmol) and $K_2CO_3$ (362 mg, 2.62 mmol), and the reaction mixture was stirred at 80° C. for 12 h. Water (10 mL) and ethyl acetate (60 mL) were added and the layers were separated. The organic layer was washed with brine (10 mL), dried on $Na_2SO_4$, filtered and concentrated under reduced pressure. The residue was purified by column chromatography on silica gel using a gradient of 0-100% EtOAc in hexanes to afford the title compound (145 mg, 57%) as a solid. $^1$H NMR (500 MHz, DMSO d6): δ 7.96 (dd, J=8.1, 2.1 Hz, 1H), 7.77 (d, J=2.1 Hz, 1H), 7.66 (d, J=8.1 Hz, 1H), 4.50 (s, 1H), 3.86-3.78 (m, 2H), 1.69-1.62 (m, 2H), 1.31 (s, 6H), 1.17 (s, 6H). MS (ESI) [M+H]+ 275.2.

Step 4: Synthesis of 6-Amino-1-(3-hydroxy-3-methyl-butyl)-3,3-dimethyl-indolin-2-one. A mixture of 1-(3-hydroxy-3-methyl-butyl)-3,3-dimethyl-6-nitro-indolin-2-one (145 mg, 0.50 mmol) and $Pd(OH)_2$/C (70.0 mg, 0.10 mmol) in iPrOH (3 mL) was subjected to hydrogenation (1 atm) at rt for overnight. The mixture was filtered through Celite and washed with MeOH (10 mL). The filtrate was concentrated under reduced pressure to afford the title compound (125 mg, 96%) as a solid which was used directly in the next step without further purification. MS (ESI) [M+H]+ 263.2.

Example i-17. Synthesis of Intermediate 17: tert-butyl (2-(5-amino-2-oxoindolin-1-yl)ethyl)(methyl) carbamate

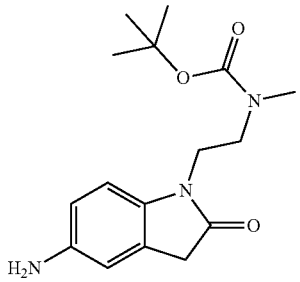 [SMILES: CN(CCN1C(=O)Cc2cc(N)ccc21)C(=O)OC(C)(C)C]

Step 1: Synthesis of 1-(2-(methylamino)ethyl)-5-nitroindolin-2-one To a stirred solution of 2-(2-fluoro-5-nitrophenyl)acetic acid (1, 1.0 g, 5.02 mmol) in THF (30 mL) was added tert-butyl (2-aminoethyl)(methyl)carbamate (2, 1.750 g, 10.04 mmol) and DIPEA (1.754 mL, 10.04 mmol) under nitrogen at 25° C. The reaction mixture was heated to 65° C. and stirred for 16 h. The reaction mixture was concentrated under reduced pressure to afford the crude as brown liquid. The crude was dissolved in water (20 mL) and 6.0N HCl (6 ml, 36.0 mmol) was added dropwise at 25° C. The reaction mixture was heated to 65° C. and stirred for 16 h. The reaction mixture was cooled to room temperature and neutralized with sodium bicarbonate and extracted with ethyl acetate (3×100 mL). The combined organic layers were dried over anhydrous sodium sulfate, filtered, and concentrated under reduced pressure to afford the title compound (400 mg, 0.909 mmol, 18% yield) that was used in the next step without further purification.

Step 2: Synthesis of tert-butyl methyl(2-(5-nitro-2-oxoindolin-1-yl)ethyl)carbamate. To a stirred solution of 1-(2-(methylamino)ethyl)-5-nitroindolin-2-one (400 mg, 0.909 mmol) in DCM (10 mL) was added DIPEA (0.397 mL, 2.272 mmol) and Boc-anhydride (0.422 mL, 1.818 mmol) dropwise at 0° C. under nitrogen. The reaction mixture was slowly warmed to 25° C. and stirred for 16 h. The reaction mixture was treated with water (50 mL) and extracted with ethyl acetate (3×100 mL). The combined organic layers were dried over anhydrous sodium sulphate, filtered, and concentrated under reduced pressure to afford the crude compound which was purified by flash column chromatography on silica gel with 20-40% ethyl acetate/pet ether to afford the title compound (240 mg, 0.697 mmol, 77% yield).

Step 3: Synthesis of tert-butyl (2-(5-amino-2-oxoindolin-1-yl)ethyl)(methyl)carbamate. To a stirred solution of tert-butyl methyl(2-(5-nitro-2-oxoindolin-1-yl)ethyl)carbamate (240 mg, 0.716 mmol) in ethanol (2.5 mL) and THF (2.5 mL) was added 10% Pd/C (120 mg) under nitrogen at 25° C. The reaction mixture was stirred under hydrogen atmosphere for 6 h. The reaction mixture was filtered through celite and the celite pad was washed with ethanol (2×50 mL). The filtrate was concentrated under reduced pressure to obtain compound 5 (200 mg, 0.504 mmol, 70% yield) as a dark brown liquid. The crude product was used for the next step without further purification.

Example i-18. Synthesis of Intermediate 18: 5-amino-1-(2,2-difluoropropyl)indolin-2-one

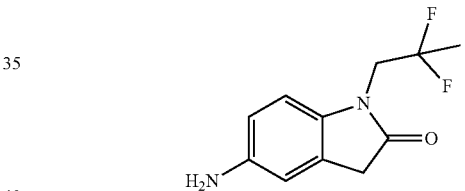

Step 1: Synthesis of 2,2-difluoropropyl 4-methylbenzenesulfonate. To a solution of 2,2-difluoropropan-1-ol (1, 1.0 g, 10.4 mmol) in DCM (10 mL) was added triethylamine (2.18 mL, 15.61 mmol) at 25° C. The mixture was cooled to 0° C. and 4-dimethylaminopyridine (0.127 g, 1.041 mmol) followed by 4-methylbenzenesulfonyl chloride (2.381 g, 12.49 mmol) were added. The reaction mixture was slowly warmed up to 25° C. and stirred for 16 h. The resulting reaction mixture was added to water (25 mL) and was extracted with DCM (3×50 mL). The combined organic layers were washed with brine (20 mL), dried over sodium sulphate, filtered, and concentrated under reduced pressure to afford the title compound (2.0 g, 7.95 mmol, 76% yield) as an off white solid. The crude product was used for the next step without further purification. MS (ESI) m/z 268.0 [M+$H_2O$].

Step 2: Synthesis of 1-(2,2-difluoropropyl)-5-nitro-1H-indole. To a solution of 2,2-difluoropropyl 4-methylbenzenesulfonate (931 mg, 3.70 mmol) in DMF (5 mL) at 25° C. was added cesium carbonate (1507 mg, 4.63 mmol) and 5-nitro-1H-indole (3, 500.0 mg, 3.08 mmol). The mixture was heated to 120° C. and stirred for 16 h. The reaction mixture was quenched by the addition of water (15 mL) and extracted with ethyl acetate (3×30 mL). The combined organic layers were washed with brine (15 mL), dried over anhydrous sodium sulphate, filtered, and concentrated under reduced pressure to give crude product. The crude was purified by flash column chromatography on silica with 35-40% ethyl acetate/pet ether to afford the title compound (250.0 mg, 0.997 mmol, 32% yield) as a pale-yellow solid. MS (ESI) m/z 240.9 [M+H]$^+$.

Step 3: Synthesis of 3,3-dibromo-1-(2,2-difluoropropyl)-5-nitroindolin-2-one. To a solution of 1-(2,2-difluoropropyl)-5-nitro-1H-indole (250.0 mg, 0.997 mmol) in tert-butanol (2.5 mL, 26.1 mmol) and water (2.5 mL) at 0° C., NBS (373 mg, 2.094 mmol) was added in portion wise. The reaction mixture was slowly warmed to 25° C. and stirred for 6 h. The reaction mixture was quenched with water (15 mL) and extracted with ethyl acetate (3×30 mL). The combined organic layer was washed with brine (15 mL), dried over anhydrous sodium sulfate, filtered, and concentrated under reduced pressure to afford the title compound (350.0 mg, 0.619 mmol, 62% yield) as a pale-yellow solid. MS (ESI) m/z 415.0 [M+H]$^+$.

Step 4: Synthesis of 5-amino-1-(2,2-difluoropropyl)indolin-2-one. To a stirred solution of 3,3-dibromo-1-(2,2-difluoropropyl)-5-nitroindolin-2-one (350.0 mg, 0.619 mmol) in acetic acid (5.0 mL), zinc dust (202 mg, 3.10 mmol) was slowly added at 25° C. and stirring was continued for 6 h. The reaction mixture was concentrated under reduced pressure and diluted by the addition of water (15 mL). The resulting residue was extracted with ethyl acetate (3×30 mL). The combined organic layers were washed with brine (10 mL), dried over anhydrous sodium sulphate, filtered, and concentrated under reduced pressure to afford the title compound (150.0 mg, 0.299 mmol, 48% yield) as a brown solid. The crude product was used for the next step without further purification. MS (ESI) m/z 227.0 [M+H]$^+$.

Example i-19. Synthesis of Intermediate 19:
5-amino-1-(3-fluoro-3-methylbutyl)indolin-2-one

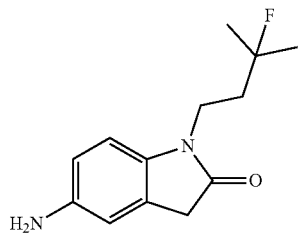 [SMILES: CC(C)(F)CCN1C(=O)Cc2cc(N)ccc21]

Step 1: Synthesis of 5-amino-1-(3-fluoro-3-methylbutyl)indolin-2-one. The title compound was synthesized analogously to Intermediate 18 using 3-fluoro-3-methylbutan-1-ol as starting material.

Example i-20. Synthesis of Intermediate 20:
5-amino-1-(2-fluoro-2-methylpropyl)indolin-2-one

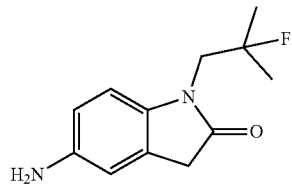 [SMILES: CC(C)(F)CN1C(=O)Cc2cc(N)ccc21]

Step 1: Synthesis of 2-fluoro-2-methylpropyl trifluoromethanesulfonate. To a stirred mixture of trifluoromethanesulfonic anhydride (2.75 mL, 16.28 mmol) in DCM (10 mL) was added 2,6-dimethylpyridine (2.26 mL, 19.5 mmol) at −10° C. slowly and then a solution of 2-fluoro-2-methylpropan-1-ol (1.50 g, 16.3 mmol) in DCM (35 mL) was added dropwise. The reaction mixture was stirred for 4 h at 0° C. The reaction mixture was concentrated under reduced pressure to obtain residue. The residue was dissolved in DCM and washed with 1.0N HCl solution, followed by saturated bicarbonate solution and then washed with brine. The organic phase dried over sodium sulphate, filtered, and concentrated to afford the title compound (2.5 g, 11.2 mmol, 68% yield) as a brown liquid. The crude product was used in the next step without purification.

Step 2: Synthesis of 1-(2-fluoro-2-methylpropyl)-5-nitro-1H-indole. To a stirred solution of 5-nitro-1H-indole (700 mg, 4.32 mmol) in DMF (10 mL) was added compound 2-fluoro-2-methylpropyl trifluoromethanesulfonate (2419 mg 10.79 mmol). The reaction mixture was heated to 100° C. and stirred for 4 h. The reaction mixture was poured in ice cold water extracted with ethyl acetate (3×50 mL). The combined organic layer was dried over sodium sulfate, filtered, and concentrated to afford the title compound (600 mg, 2.41 mmol, 56% yield). The crude product was used for the next step without purification. MS (ESI) m/z 237.1 [M+H]$^+$.

Synthesis of 5-amino-1-(2-fluoro-2-methylpropyl)indolin-2-one. To a stirred solution 1-(2-fluoro-2-methylpropyl)-5-nitro-1H-indole (100 mg, 0.423 mmol) in t-butanol (2.0 mL) was added bromine (0.218 mL, 4.23 mmol) at 0° C. and the reaction mixture was stirred for 5 min. Then water (2 mL) was added slowly and warmed to 25° C. and stirred for 4 h. The reaction mixture was treated with water and extracted with ethyl acetate (3×10 mL). The combined organic layers were dried over anhydrous sodium sulphate, filtered, and concentrated under reduced pressure to afford 110 mg of the crude material. This residue was dissolved in acetic acid (3.5 mL) and zinc powder (88 mg, 1.34 mmol) was added and stirred for 1 h at 25° C. The reaction mixture was concentrated under reduced pressure to get crude product. The crude was dissolved in ethyl acetate and treated with sodium bicarbonate solution. The organic layer was dried over sodium sulfate, filtered, and concentrated to afford the title compound compound (55 mg, 0.132 mmol, 49% yield). The crude product was used for the next step without purification.

Example i-21. Synthesis of Intermediate 21:
5-amino-1-(2,2,2-trifluoroethyl)indolin-2-one

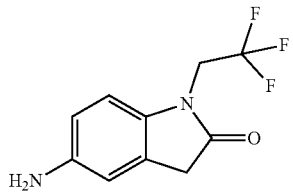 [SMILES: Nc1ccc2c(c1)CC(=O)N2CC(F)(F)F]

Step 1: Synthesis of 5-nitro-1-(2,2,2-trifluoroethyl)indoline-2,3-dione. To a solution of 5-nitroindoline-2,3-dione (0.96 g, 5.00 mmol) in DMF (35.0 mL) cooled to 0° C. was added NaH (60% dispersion in mineral oil, 220.0 mg, 5.50 mmol). After stirring for 45 min at 0° C., 2,2,2-trifluoroethyl trifluoromethanesulfonate (1.28 g, 5.50 mmol) was added. The reaction mixture was warmed to rt for 1 h. A saturated aqueous solution of NH$_4$Cl (300.0 mL) and EtOAc were added and the layers were separated. The aqueous layer was extracted with EtOAc and the combined organic layers were washed with water, brine, dried (Na$_2$SO$_4$), filtered and concentrated under reduced pressure. The material was purified by column chromatography on silica gel using a gradient of 20-70% ethyl acetate in hexane to afford the title compound (910.0 mg, 66%) as a solid. $^1$H NMR (500 MHz, DMSO) δ 8.60 (dd, J=8.8, 2.5 Hz, 1H), 8.30 (d, J=2.4 Hz, 1H), 7.55 (d, J=8.8 Hz, 1H), 4.77 (q, J=9.3 Hz, 2H).

Step 2: Synthesis of 5-amino-1-(2,2,2-trifluoroethyl)indoline-2,3-dione. A mixture of 5-nitro-1-(2,2,2-trifluoroethyl)indoline-2,3-dione (548.0 mg, 2.00 mmol) and 10% Pd/C (106.0 mg, 0.10 mmol) in methanol (25.0 mL) was shaken in a Parr flask at 50 psi hydrogen atmosphere at rt for 1 h. The mixture was filtered through Celite and washed with MeOH. The filtrate was concentrated under reduced pressure to afford the title compound (450.0 mg, 92%) as a solid, which was used in next step without further purification. MS (ESI) [M+H]$^+$ 247.1.

Step 3: Synthesis of 5-amino-1-(2,2,2-trifluoroethyl)indolin-2-one. A mixture of 5-amino-1-(2,2,2-trifluoroethyl)indoline-2,3-dione (450.0 mg, 1.84 mmol) and hydrazine hydrate (65%, 10.0 mL, 133.0 mmol) was heated to 115° C. for 1 h and then cooled to rt. The volatiles were evaporated under reduced pressure. The material was purified by reverse phase chromatography (C18), using a gradient of 10-70% acetonitrile and water (ammonium formate buffer pH4) to afford the title compound (150.0 mg, 35%) as a solid. $^1$H NMR (500 MHz, DMSO) δ 6.79 (d, J=8.3 Hz, 1H), 6.57 (s, 1H), 6.47 (dd, J=8.3, 2.1 Hz, 1H), 4.81 (s, 2H), 4.47 (q, J=9.5 Hz, 2H), 3.54 (s, 2H). MS (ESI) [M+H]$^+$ 231.1.

Example i-22. Synthesis of Intermediate 22: benzyl 4-amino-5-methylcycloheptane-1-carboxylate

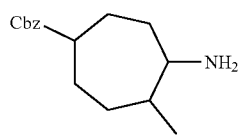

Step 1: Synthesis of 1-benzyl 4-ethyl 5-oxoazepane-1,4-dicarboxylate To a stirred solution of benzyl 4-oxopiperidine-1-carboxylate (2.5 g, 10.72 mmol) and ethyl 2-diazoacetate (9.78 g, 12.86 mmol) in THF (50 mL) was added BF$_3$OEt$_2$ (1.358 mL, 10.72 mmol) at −25° C. The reaction mixture stirred at 25° C. for 4 h. After, the reaction mixture was basified with sodium bicarbonate solution (100 ml) and the organics were extracted with EtOAc (3×100 ml). The combined organic fractions were dried and concentrated to give the crude material. This was purified by Combi-flash Column chromatography with product eluting at 15% EA in PE. Fractions containing product were combined and concentrated to give 1-benzyl 4-ethyl 5-oxoazepane-1,4-dicarboxylate (3.5 g, 3.40 mmol, 31.7% yield) as an colourless liquid. (ESI) [M+H]$^+$ 320.0, RT=2.15.

Step 2: Synthesis of 1-benzyl 4-ethyl 4-methyl-5-oxoazepane-1,4-dicarboxylate To a stirred solution of 1-benzyl 4-ethyl 5-oxoazepane-1,4-dicarboxylate (3.5 g, 10.96 mmol) in DMF (8 mL). was added Cs$_2$CO$_3$ (7.14 g, 21.92 mmol) and MeI (1.371 mL, 21.92 mmol) at 0° C. The reaction mixture warmed to room temperature and stirred at 25° C. for 6 h. The reaction mixture was evaporated to obtained the crude material which was purified by combi-flash column chromatography. The product eluted at 25-30% EA in PE and fractions containing product were combined and concentrating giving 1-benzyl 4-ethyl 4-methyl-5-oxoazepane-1,4-dicarboxylate (2.5 g, 76%) as a colorless liquid. $^1$H NMR (400 MHz, DMSO) δ 7.35 (br m, 5H), 5.07 (br m, 2H), 4.15 (br m, 2H), 3.68 (m, 2H), 3.40 (br m, 1H), 2.81 (br m, 2H), 2.15 (br m, 1H), 1.59 (br m, 1H), 1.19-1.24 (br m, 6H). MS (ESI) [M+H]$^+$ 334.1

Step 3: Synthesis of benzyl 4-methyl-5-oxoazepane-1-carboxylate To a stirred solution of 1-benzyl 4-ethyl 4-methyl-5-oxoazepane-1,4-dicarboxylate (2.5 g, 5.70 mmol) in MeOH (20 mL) and water (20 mL). was added KOH (0.959 g, 17.10 mmol) at 25° C. The reaction mixture stirred at 60° C. for 4 h. After, the reaction mixture was diluted with water (50 ml) and extracted with DCM (2×100 ml). This was purified via reverse phase prep HPLC with a gradient of 2-98% MeCN in 5 mm Ammonium formate pH 3.3. Fractions containing the desired product were combined and concentrated giving benzyl 4-methyl-5-oxoazepane-1-carboxylate (1.50 g, 80%) as a yellow oil. $^1$H NMR (400 MHz, DMSO) δ 7.31-7.39 (m, 5H), 5.07 (s, 2H), 3.82-3.98 (m, 2H), 3.46 (m, 1H), 3.34 (m, 1H), 3.19 (m, 1H), 3.01 (m, 1H). 2.59 (m, 1H), 1.66 (m, 1H), 1.30 (m, 1H), 0.95 (d, 2H). MS (ESI) [M+H]$^+$ 262.2

Step 4: Synthesis of benzyl 4-amino-5-methylazepane-1-carboxylate To a stirred solution of benzyl 4-methyl-5-oxoazepane-1-carboxylate (1.0 g, 3.02 mmol) in 2-propanol (20 mL) was added ammonium acetate (4.66 g, 60.5 mmol) and NaCNBH$_4$ (1.140 g, 18.14 mmol) at 25° C. The reaction mixture was stirred at 50° C. for 3 h and was monitored by TLC and LCMS. After, the reaction mixture was diluted with water (80 ml) and extracted with DCM (3×80 ml). The organic fractions were concentrated to give benzyl 4-amino-5-methylazepane-1-carboxylate (700 mg, 65%) as a yellow solid. MS (ESI) [M+H]$^+$ 263.2, RT=0.78

Example i-23. Synthesis of Intermediate 23: benzyl 4-amino-3-methylazepane-1-carboxylate

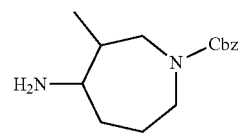 [SMILES: CC1CN(C(=O)OCc2ccccc2)CCCC1N]

Step 1: Synthesis of 1-benzyl 3-ethyl 4-oxoazepane-1,3-dicarboxylate To a stirred solution of benzyl 3-oxopiperidine-1-carboxylate (5.0 g, 21.43 mmol) and ethyl 2-diazoacetate (21.20 g, 27.9 mmol) in THF (50 mL), was added BF$_3$OEt$_2$ (2.72 mL, 21.43 mmol) at −78° C. The reaction mixture warmed to room temperature and stirred at 25° C. for 4 h. After, the reaction mixture was basified with sodium bicarbonate solution (100 ml) and the organics were extracted with EtOAc (3×100 ml). The combined organic fractions were dried and concentrated to give the crude material. This was purified by Combi-flash Column chromatography with product eluting at 20-30% EA in PE. Fractions containing product were combined and concentrated to give 1-benzyl 3-ethyl 4-oxoazepane-1,3-dicarboxylate (4.5 g, 10.00 mmol, 46.7% yield) as a colourless liquid. (ESI) [M+H]$^+$320.1, RT=2.11

Step 2: Synthesis of 1-benzyl 3-ethyl 3-methyl-4-oxoazepane-1,3-dicarboxylate To a stirred solution of 1-benzyl 3-ethyl 4-oxoazepane-1,3-dicarboxylate (4.0 g, 10.02 mmol) in DMF (1 mL). was $Cs_2CO_3$ (6.53 g, 20.04 mmol) and MeI (1.253 mL, 20.04 mmol) at 0° C. and the reaction mixture was stirred at 25° C. for 16 h. The reaction mixture warmed to room temperature and stirred at 25° C. for 6 h. The reaction mixture was evaporated to obtained the crude material which was purified by combi-flash column chromatography. The product eluted at 20% EtOAc in PE and fractions containing product were combined and concentrating to obtain 1-benzyl 3-ethyl 3-methyl-4-oxoazepane-1,3-dicarboxylate (2.2 g, 5.61 mmol, 56.0% yield) as an colourless liquid. $^1$H NMR (400 MHz, DMSO) δ 7.32-7.40 (m, 5H), 5.08 (s, 2H), 3.34-4.04 (m, 6H), 2.71 (m, 2H), 1.64-1.78 (m, 3H). 1.10-1.24 (m, 5H). MS (ESI) $[M+H]^+$ 334.2

Step 3: Synthesis of benzyl 3-methyl-4-oxoazepane-1-carboxylate To a stirred solution of 1-benzyl 3-ethyl 3-methyl-4-oxoazepane-1,3-dicarboxylate (1.0 g, 2.55 mmol) in MeOH (7.5 mL) and $H_2O$ (7.5 mL) was added KOH (0.429 g, 7.65 mmol) and the reaction mixture was stirred at 60° C. for 2 h. the reaction mixture was monitored by TLC and LCMS. The reaction mixture stirred at 60° C. for 4 h. After, the reaction mixture was diluted with water (50 ml) and extracted with DCM (2×100 ml). This was purified via reverse phase prep HPLC with a gradient of 2-98% MeCN in 5 mm Ammonium formate pH 3.3. Fractions containing the desired product were combined and concentrated giving benzyl 3-methyl-4-oxoazepane-1-carboxylate (550 mg, 76%) as a yellow oil. $^1$H NMR (400 MHz, DMSO) δ 7.29-7.37 (m, 5H), 5.08 (s, 2H), 3.33-4.04 (m, 6H), 2.51 (m, 2H), 1.99 (m, 1H), 1.76 (m, 1H), 1.64 (m, 1H). 1.09-1.23 (m, 6H). MS (ESI) $[M+H]^+$ 262.1

Step 4: Synthesis of benzyl 4-amino-3-methylazepane-1-carboxylate To a stirred solution of benzyl 3-methyl-4-oxoazepane-1-carboxylate (100 mg, 0.352 mmol) in 2-Propanol (4 mL), was added ammonium acetate (543 mg, 7.04 mmol) and $NaCNBH_4$ (133 mg, 2.112 mmol) at 25° C. The reaction mixture stirred at 50° C. for 3 h. After, the reaction mixture was diluted with water and extracted with EtOAC. The organic fractions were concentrated to give benzyl 4-amino-3-methylazepane-1-carboxylate (100 mg, 40%) as a yellow solid. MS (ESI) $[M+H]^+$ 263.2, RT=1.35.

Example S1. Synthesis of 3-(6-((5-(5-chloro-4-((1-methyl-2-oxoindolin-5-yl)amino)pyrimidin-2-yl)-5-azaspiro[3.5]nonan-8-yl)amino)-1-methyl-1H-indazol-3-yl)piperidine-2,6-dione (1)

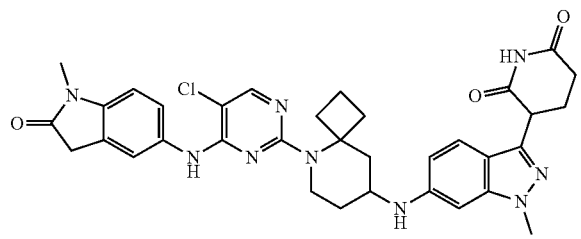 [SMILES: CN1C(=O)Cc2cc(Nc3nc(N4CCC(Nc5ccc6c(C7CCC(=O)NC7=O)nn(C)c6c5)CC45CCC5)ncc3Cl)ccc21]

Step 1: Synthesis of 5-((5-chloro-2-fluoropyrimidin-4-yl)amino)-1-methylindolin-2-one. To a solution of 5-amino-1-methylindolin-2-one (2.0 g, 12.3 mmol) in tetrahydrofuran (32 mL) was added DIPEA (2.37 ml, 13.6 mmol) at −40° C. A solution of 5-chloro-2,4-difluoropyrimidine (1.86 g, 12.3 mmol) in dry tetrahydrofuran (8 mL) was slowly added to the above mixture and allowed to slowly warm to rt. The reaction mixture was stirred at rt for 16 h. After this time, the reaction mixture was filtered and washed with acetonitrile (~50 mL). The solid was dried under vacuum to afford the title compound as a tan solid. MS (ESI) $[M+H]^+$ 293.1.

Step 2: Synthesis of tert-Butyl 8-[[3-(2,6-dioxo-3-piperidyl)-1-methyl-indazol-6-yl]amino]-5-azaspiro[3.5]nonane-5-carboxylate. To a solution of 3-(6-amino-1-methyl-indazol-3-yl)piperidine-2,6-dione hydrochloride (200 mg, 0.68 mmol), tert-butyl 8-oxo-5-azaspiro[3.5]nonane-5-carboxylate (201 mg, 0.81 mmol), and AcOH (1 mL) in DMSO (5 mL), was added decaborane (38 mg, 0.34 mmol). The reaction mixture was stirred for 5 h at rt and the volatiles were evaporated under reduced pressure. The residue was purified by reverse phase chromatography (C18) using a gradient of 0-80% MeCN and 10 mM ammonium formate in water to afford title compound (325 mg, 76%) as a solid. MS (ESI) $[M+H]^+$ 482.3. $^1$H NMR (400 MHz, DMSO-d6) δ 10.82 (s, 1H), 7.32 (d, J=8.7 Hz, 1H), 6.52-6.40 (m, 1H), 6.48 (br s, 1H), 5.78 (d, J=8.7 Hz, 1H), 4.18 (dd, J=8.8, 5.2 Hz, 1H), 3.82 (s, 3H), 3.73-3.68 (m, 2H), 2.75-2.68 (m, 1H), 2.62-2.59 (m, 2H), 2.30-2.13 (m, 4H), 1.98-1.86 (m, 4H), 1.72-1.60 (m, 3H), 1.40 (s, 9H), 1.06-0.98 (m, 1H).

Step 3: Synthesis of 3-[6-(5-Azaspiro[3.5]nonan-8-ylamino)-1-methyl-indazol-3-yl]piperidine-2,6-dione 2,2,2-trifluoroacetic acid. To a solution of tert-butyl 8-[[3-(2,6-dioxo-3-piperidyl)-1-methyl-indazol-6-yl]amino]-5-azaspiro[3.5]nonane-5-carboxylate (325 mg, 0.67 mmol) in DCM (5 mL) was added trifluoroacetic acid (0.31 mL, 4.1 mmol), and the reaction mixture was stirred for 18 h at rt. The volatiles were evaporated under reduced pressure to afford title compound as a solid, which was used in the next step without further purification. MS (ESI) $[M+H]^+$ 382.3. $^1$H NMR (500 MHz, DMSO-d6) δ 10.82 (s, 1H), 8.98 (d, J=8.5 Hz, 1H), 8.75-8.71 (m, 1H), 7.37 (d, J=8.7 Hz, 1H), 6.55 (dd, J=8.7, 1.8 Hz, 1H), 6.51 (br s, 1H), 4.19 (dd, J=8.9, 5.1 Hz, 1H), 3.83 (s, 3H), 3.63-3.57 (m, 1H), 3.30-3.27 (m, 1H), 3.02-2.96 (m, 1H), 2.63-2.60 (m, 2H), 2.36 (d, J=12.9 Hz, 1H), 2.30-2.23 (m, 4H), 2.17-2.12 (m, 2H), 2.01-1.97 (m, 1H), 1.95-1.87 (m, 2H), 1.63-1.58 (m, 1H), 1.40-1.32 (m, 1H).

Step 4: Synthesis of 3-[6-[[5-[5-Chloro-4-[(1-methyl-2-oxo-indolin-5-yl)amino]pyrimidin-2-yl]-5-azaspiro[3.5]nonan-8-yl]amino]-1-methyl-indazol-3-yl]piperidine-2,6-dione. To a solution of 3-[6-(5-azaspiro[3.5]nonan-8-ylamino)-1-methyl-indazol-3-yl]piperidine-2,6-dione 2,2,2-trifluoroacetic acid (20 mg, 40 µmol) in NMP (0.7 mL) was added 5-((5-chloro-2-fluoropyrimidin-4-yl)amino)-1-methylindolin-2-one5-((5-chloro-2-fluoropyrimidin-4-yl)amino)-1-methylindolin-2-one (11 mg, 40 µmol) under $N_2$ (1 atm). The reaction mixture was heated to 160° C. for 18 h and then cooled to rt. The crude reaction mixture was purified by reverse phase chromatography (C18) using a gradient of 0-100% MeCN and water (containing 0.1% formic acid) to afford title compound (13 mg, 44%) as a solid. LCMS: $C_{34}H_{36}ClN_9O_3$ requires 653.3, found 654.3 $[M+H]^+$; $^1$H NMR (500 MHz, DMSO-d6) δ 10.80 (s, 1H), 8.62 (s, 1H), 8.01 (s, 1H), 7.39 (s, 1H), 7.38-7.36 (m, 1H), 7.30 (d, J=8.8 Hz, 1H), 6.92 (d, J=8.3 Hz, 1H), 6.48-6.45 (m, 2H), 5.65 (d, J=8.8 Hz, 1H), 4.25 (d, J=12.1 Hz, 1H), 4.17 (dd, J=8.9, 5.1 Hz, 1H), 3.83-3.80 (m, 1H), 3.81 (s, 3H) 3.51-3.50 (m, 2H), 3.09 (s, 3H), 2.88 (t, J=10.0 Hz, 1H), 2.62-2.59 (m, 2H), 2.38-2.34 (m, 2H), 2.26-2.24 (m, 1H), 2.19-2.12 (m, 2H), 1.96-1.88 (m, 3H), 1.67-1.56 (m, 3H), 1.07-0.99 (m, 1H).

Example S2. Synthesis of 3-(6-(8-((5-chloro-4-((1-methyl-2-oxoindolin-5-yl)amino)pyrimidin-2-yl)(methyl)amino)-5-azaspiro[3.5]nonan-5-yl)-1-methyl-1H-indazol-3-yl)piperidine-2,6-dione (2)

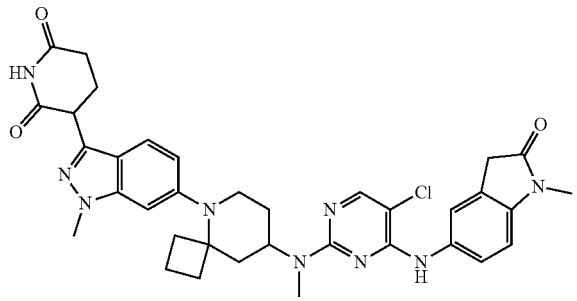 [SMILES: CN1C(=O)Cc2cc(Nc3nc(N(C)C4CCN(c5ccc6c(C7CCC(=O)NC7=O)nn(C)c6c5)C5(CCC5)C4)ncc3Cl)ccc21]

Step 1: Synthesis of 2-[2-bis-[3,5-bis-(Trifluoromethyl)phenyl]phosphanyl-3,6-dimethoxy-phenyl]-N1,N1,N3,N3-tetramethyl-benzene-1,3-diamine[2-[2-(methylamino)phenyl]phenyl]-methylsulfonyloxy-palladium. A mixture of (2'-methylamino-1,1'-biphenyl-2-yl)methanesulfonatopalladium(II) dimer (406 mg, 0.53 mmol) and 2-[2-bis-[3,5-bis-(trifluoromethyl)phenyl]phosphanyl-3,6-dimethoxy-phenyl]-N1,N1,N3,N3-tetramethyl-benzene-1,3-diamine (800 mg, 1.06 mmol) was evacuated and backfilled with argon. DCM (5 mL) was added via syringe and the mixture was stirred at rt for 2 h. The reaction mixture was diluted with Et$_2$O (5 mL) and filtered. The filtrate was concentrated, and pentane (5 mL) was added to the residue and the mixture was concentrated under reduced pressure to afford the title compound (1.08 g, 90%) as a yellow solid. $^1$H NMR (500 MHz, MeOD-d$_4$) δ 8.38 (s, 1H), 8.13 (s, 1H), 8.00 (t, J=8.1 Hz, 1H), 7.74 (d, J=11.2 Hz, 2H), 7.62 (d, J=11.4 Hz, 2H), 7.59-7.55 (m, 1H), 7.51 (d, J=9.0 Hz, 1H), 7.42 (dd, J=7.5, 1.4 Hz, 1H), 7.34-7.28 (m, 3H), 7.25 (t, J=7.3 Hz, 1H), 7.21 (d, J=8.1 Hz, 1H), 7.16-7.13 (m, 1H), 7.03 (d, J=8.1 Hz, 1H), 6.84 (t, J=7.7 Hz, 1H), 6.33-6.29 (m, 1H), 3.71 (s, 3H), 3.42 (s, 3H), 2.78 (s, 6H), 2.69 (s, 3H), 2.61-2.54 (m, 1H), 2.15 (dd, J=5.9, 2.9 Hz, 3H), 2.09 (s, 6H). $^{19}$F NMR (471 MHz, MeOD-d$_4$) δ −64.20, −64.42. $^{31}$P NMR (203 MHz, MeOD-d$_4$) δ 33.80.

Step 2: Synthesis of tert-Butyl N-[5-[3-(2,6-dibenzyloxy-3-pyridyl)-1-methyl-indazol-6-yl]-5-azaspiro[3.5]nonan-8-yl]carbamate. A mixture of 6-bromo-3-(2,6-dibenzyloxy-3-pyridyl)-1-methyl-indazole (600 mg, 1.20 mmol), tert-butyl N-(5-azaspiro[3.5]nonan-8-yl)carbamate (375 mg, 1.56 mmol), NaOtBu (288 mg, 3.0 mmol), 2-[2-bis-[3,5-bis-(Trifluoromethyl)phenyl]phosphanyl-3,6-dimethoxy-phenyl]-N1,N1,N3,N3-tetramethyl-benzene-1,3-diamine[2-[2-(methylamino)phenyl]phenyl]-methylsulfonyloxy-palladium (137 mg, 0.12 mmol) in cyclopentyl methyl ether (12 mL) was heated to 85° C. for 4 h and then cooled to rt. The mixture was filtered through celite and washed with EtOAc (3×15 mL). The filtrate was concentrated under reduced pressure and the residue was purified by column chromatography on silica gel using a gradient of 0-60% EtOAc in hexanes to afford the title compound (600 mg, 76%) as a solid. MS (ESI) [M+H]$^+$ 660.2. $^1$H NMR (400 MHz, DMSO-d6) δ 7.88 (d, J=8.1 Hz, 1H), 7.50-7.43 (m, 3H), 7.42-7.32 (m, 5H), 7.32-7.25 (m, 3H), 6.79 (d, J=7.5 Hz, 1H), 6.73 (d, J=1.5 Hz, 1H), 6.62 (dd, J=9.0, 1.8 Hz, 1H), 6.57 (d, J=8.1 Hz, 1H), 5.44 (s, 2H), 5.42 (s, 2H), 3.95 (s, 3H), 3.69-3.57 (m, 1H), 3.51-3.43 (m, 1H), 3.12-3.00 (m, 1H), 2.17-2.04 (m, 4H), 1.98-1.89 (m, 1H), 1.80-1.68 (m, 2H), 1.59-1.48 (m, 2H), 1.38 (s, 9H), 1.27-1.16 (m, 1H).

Step 3: Synthesis of tert-Butyl N-[5-[3-(2,6-dibenzyloxy-3-pyridyl)-1-methyl-indazol-6-yl]-5-azaspiro[3.5]nonan-8-yl]-N-methyl-carbamate. To an ice-cold solution of tert-butyl N-[5-[3-(2,6-dibenzyloxy-3-pyridyl)-1-methyl-indazol-6-yl]-5-azaspiro[3.5]nonan-8-yl]carbamate (1.05 g, 1.59 mmol) and NaH (159 mg, 3.98 mmol, 60% dispersion in mineral oil) in DMF (6 mL) was added iodomethane (198 μL, 3.18 mmol), and the mixture was stirred at rt for 2 h. Another batch was prepared using the same procedure. Water (50 mL) was added and the combined mixture was extracted with EtOAc (3×75 mL). The organic fractions were washed with brine, dried over Na$_2$SO$_4$, filtered and concentrated. The residue was purified by reverse phase chromatography (C18) using a gradient of 20-100% MeCN and 10 mM ammonium formate in water to afford the title compound (700 mg, 65% combined yield) as a solid. MS (ESI) [M+H]$^+$ 674.4.

Step 4: Synthesis of tert-Butyl N-[5-[3-(2,6-dioxo-3-piperidyl)-1-methyl-indazol-6-yl]-5-azaspiro[3.5]nonan-8-yl]-N-methyl-carbamate. A mixture of tert-butyl N-[5-[3-(2,6-dibenzyloxy-3-pyridyl)-1-methyl-indazol-6-yl]-5-azaspiro[3.5]nonan-8-yl]-N-methyl-carbamate (700 mg, 1.04 mmol) and Pearlman's catalyst (365 mg, 0.26 mmol) in EtOH (15 mL) and THF (15 mL) was stirred under a hydrogen atmosphere (1 atm) at 50° C. for 2 h. The mixture was filtered through celite, washing with MeOH (3×15 mL) and the filtrate was concentrated to afford the title compound (425 mg, 83%) as a solid, which was used in the next step without further purification. MS (ESI) [M+H]$^+$ 496.2. $^1$H NMR (400 MHz, DMSO-d6) δ 10.86 (s, 1H), 7.48 (d, J=8.7 Hz, 1H), 6.77 (s, 1H), 6.77-6.73 (m, 1H), 4.30-4.22 (m, 1H), 3.89 (s, 3H), 3.62-3.53 (m, 1H), 3.16-3.05 (m, 1H), 2.70-2.57 (m, 5H), 2.38-2.25 (m, 1H), 2.19-2.07 (m, 4H), 2.06-1.93 (m, 2H), 1.93-1.81 (m, 1H), 1.78-1.67 (m, 1H), 1.62-1.31 (m, 4H), 1.41 (s, 9H).

Step 5: Synthesis of 3-[1-Methyl-6-[8-(methylamino)-5-azaspiro[3.5]nonan-5-yl]indazol-3-yl]piperidine-2,6-dione hydrochloride. To a solution of tert-butyl N-[5-[3-(2,6-dioxo-3-piperidyl)-1-methyl-indazol-6-yl]-5-azaspiro[3.5]nonan-8-yl]-N-methyl-carbamate (425 mg, 0.86 mmol) in DCM (4 mL) was added 4N HCl in 1,4-dioxane (4 mL, 16 mmol), and the mixture was stirred for 4 h at rt. The resulting precipitate was collected by filtration, washed with Et$_2$O (2×5 mL), and dried under vacuum to afford the title compound (340 mg, 92%) as a solid, which was used in the next step without further purification. MS (ESI) [M+H]$^+$ 396.3. $^1$H NMR (500 MHz, DMSO-d6) δ 10.49 (s, 1H), 9.08 (br s, 2H), 7.56 (d, J=8.8 Hz, 1H), 6.95 (s, 1H), 6.87 (dd, J=8.8, 1.4 Hz, 1H), 4.27 (dd, J=8.8, 5.2 Hz, 1H), 3.92 (s, 3H), 3.60 (dt, J=13.6, 3.2 Hz, 1H), 3.43-3.32 (m, 1H), 3.25-3.16 (m, 1H), 2.68-2.63 (m, 2H), 2.56 (t, J=5.3 Hz, 3H), 2.49-2.43 (m, 1H), 2.39-2.29 (m, 1H), 2.27-2.20 (m, 2H), 2.20-2.13 (m, 2H), 2.13-2.04 (m, 2H), 1.96-1.89 (m, 1H), 1.82-1.70 (m, 1H), 1.64-1.53 (m, 2H).

Step 6: Synthesis of 3-[6-[8-[[5-Chloro-4-[(1-methyl-2-oxo-indolin-5-yl)amino]pyrimidin-2-yl]-methyl-amino]-5-azaspiro[3.5]nonan-5-yl]-1-methyl-indazol-3-yl]piperidine-2,6-dione. To a mixture of 3-[1-methyl-6-[8-(methylamino)-5-azaspiro[3.5]nonan-5-yl]indazol-3-yl]piperidine-2,6-dione hydrochloride (46.5 mg, 0.11 mmol) and DIPEA (110 μL, 0.61 mmol) in DMSO (1 mL) at rt was added 5-((5-chloro-2-fluoropyrimidin-4-yl)amino)-1-methylindolin-2-one (30 mg, 0.10 mmol), and the reaction mixture was heated to 80° C. for 16 h. The crude reaction mixture was purified by preparative HPLC (BEH column, C18), using a gradient of 48-58% MeCN and 10 mM ammonium formate in water to afford the title compound (14.9 mg, 22%) as a solid. LCMS: $C_{34}H_{36}ClN_9O_3$ requires 667.3, found 668.3 $[M+H]^+$; $^1H$ NMR (500 MHz, DMSO-d6) δ 10.49 (br s, 1H), 8.29 (s, 1H), 8.00 (s, 1H), 7.56 (s, 1H), 7.54-7.49 (m, 2H), 6.93 (d, J=8.3 Hz, 1H), 6.80-6.76 (m, 2H), 4.89-4.80 (m, 1H), 4.26 (dd, J=8.6, 5.2 Hz, 1H), 3.91 (s, 3H), 3.57 (d, J=13.3 Hz, 1H), 3.54 (s, 2H), 3.15 (s, 3H), 2.89 (s, 3H), 2.74-2.60 (m, 2H), 2.40-2.30 (m, 1H), 2.27-2.16 (m, 2H), 2.13-2.05 (m, 2H), 2.01-1.88 (m, 3H), 1.69-1.55 (m, 2H), 1.55-1.41 (m, 2H). Note: one CH obscured by water signal.

Example S3. Synthesis of 3-(6-(((trans)-4-((5-chloro-4-((1-methyl-2-oxoindolin-5-yl)amino)pyrimidin-2-yl)(methyl)amino)cyclohexyl)amino)-1-methyl-1H-indazol-3-yl)piperidine-2,6-dione (3)

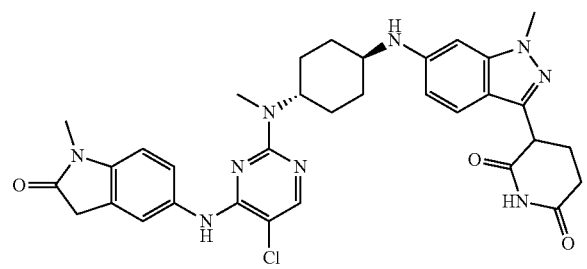 [SMILES: CN1C(=O)Cc2cc(Nc3nc(N(C)[C@H]4CC[C@H](Nc5ccc6c(C7CCC(=O)NC7=O)nn(C)c6c5)CC4)ncc3Cl)ccc21]

The title compound was synthesized analogously to Example S2 using trans-tert-butyl N-(4-aminocyclohexyl)carbamate as the starting material. Isolated title compound as an off-white solid (36.7 mg, 0.05 mmol, 20.6% yield). LCMS: $C_{33}H_{36}ClN_9O_3$ requires 641, found 642 $[M+H]^+$; $^1H$ NMR (400 MHz, DMSO-d6) δ 10.83 (s, 1H), 8.14 (s, 1H), 7.60 (s, 1H), 7.54 (d, J=8.2 Hz, 1H), 7.42 (d, J=8.7 Hz, 1H), 7.00 (d, J=8.4 Hz, 1H), 6.60 (d, J=8.9 Hz, 1H), 6.55 (s, 1H), 4.30 (s, 1H), 4.22 (dd, J=9.0, 5.1 Hz, 1H), 3.86 (s, 3H), 3.59 (s, 2H), 3.36 (s, 1H), 3.15 (s, 3H), 2.95 (s, 3H), 2.62 (s, 2H), 2.28 (s, 1H), 2.20-2.09 (m, 3H), 1.76 (d, J=11.8 Hz, 1H), 1.70 (s, 3H), 1.25 (s, 2H).

Example S4. Synthesis of 3-(6-((2R,4R)-4-((5-chloro-4-((1-methyl-2-oxoindolin-5-yl)amino)pyrimidin-2-yl)(methyl)amino)-2-methylpiperidin-1-yl)-1-methyl-1H-indazol-3-yl)piperidine-2,6-dione (4)

carbamate. The title compound was synthesized according to General Procedure 2 using tert-butyl N-[(2R,4R)-2-methyl-4-piperidyl]carbamate as the reactant in toluene at 110° C. for 18 h. The title compound was isolated by reverse phase chromatography (C18) using a gradient of 30-100% MeCN and 10 mM ammonium formate in water (700 mg, 86%) as a solid. LCMS: $C_{38}H_{43}N_5O_4$ requires 633.3, found 635.9 $[M+H]^+$.

Step 2: Synthesis of tert-Butyl N-[(2R,4R)-1-[3-(2,6-Dibenzyloxy-3-pyridyl)-1-methyl-indazol-6-yl]-2-methyl-4-piperidyl]-N-methyl-carbamate. To a solution of tert-butyl N-[(2R,4R)-1-[3-(2,6-dibenzyloxy-3-pyridyl)-1-methyl-indazol-6-yl]-2-methyl-4-piperidyl]carbamate (800 mg, 1.26 mmol) in DMF (13 mL) cooled to 0° C. was added NaH (151 mg, 3.8 mmol), and the reaction mixture was stirred at 0° C. for 15 min. Iodomethane (0.24 mL, 3.79 mmol) was added, the reaction mixture was warmed to rt and stirred for 1 h. The reaction was diluted by the dropwise addition of water (5 mL). Water (50 mL) and EtOAc (100 mL) were added and the layers were separated. The organic layer was washed with water (5×20 mL), brine (50 mL), dried (MgSO4), filtered and concentrated under reduced pressure. The residue was purified by reverse phase chromatography (C18) using a gradient of 30-100% MeCN and 10 mM ammonium formate in water to afford title compound (700 mg, 86%) as a solid. LCMS: $C_{39}H_{45}N_5O_4$ requires 647.4, found 648.4 $[M+H]^+$.

Step 3: Synthesis of 3-(6-((2R,4R)-4-((5-chloro-4-((1-methyl-2-oxoindolin-5-yl)amino)pyrimidin-2-yl)(methyl)amino)-2-methylpiperidin-1-yl)-1-methyl-1H-indazol-3-yl)piperidine-2,6-dione. The synthesis of the title compound was accomplished using General Procedures 4, 5, and 6 with tert-Butyl N-[(2R,4R)-1-[3-(2,6-Dibenzyloxy-3-pyridyl)-1-methyl-indazol-6-yl]-2-methyl-4-piperidyl]-N-methyl-carbamate as the starting material. The crude residue was purified by reverse phase chromatography (C18) using a gradient of 10-70% MeCN and 10 mM ammonium formate in water to afford title compound (19 mg, 25%) as a solid. LCMS $C_{33}H_{36}ClN_9O_3$ requires 641.3, found 642.3 $[M+H]^+$; $^1H$ NMR (500 MHz, DMSO-d6) δ 10.88 (s, 1H), 8.60 (s, 1H), 8.02 (s, 1H), 7.70 (s, 1H), 7.60 (d, J=8.7 Hz, 1H), 7.54 (s, 1H), 7.29 (s, 1H), 6.98-6.89 (m, 2H), 4.59 (br s, 1H), 4.33 (dd, J=9.5, 4.9 Hz, 1H), 3.97 (s, 3H), 3.59 (s, 2H), 3.28-3.21 (m, 2H), 3.10 (s, 3H), 2.96 (s, 3H), 2.81 (br s, 1H), 2.68-2.59 (m, 2H), 2.38-2.31 (m, 1H), 2.22-2.13 (m, 1H), 1.95-1.86 (m, 1H), 1.76 (d, J=10.6 Hz, 1H), 1.70-1.58 (m, 2H), 0.93 (d, J=5.7 Hz, 3H).

Example S5. Synthesis of 3-(6-(4-(5-chloro-4-((1-methyl-2-oxoindolin-5-yl)amino)pyrimidin-2-yl)-2-methyl-6-oxopiperazin-1-yl)-1-methyl-1H-indazol-3-yl)piperidine-2,6-dione (5)

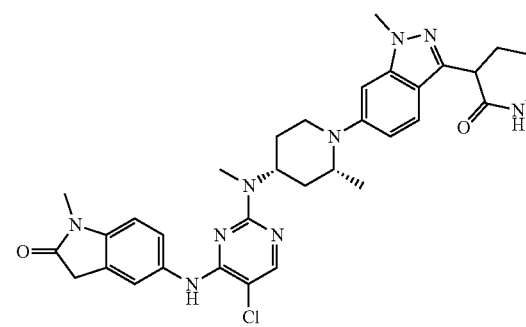

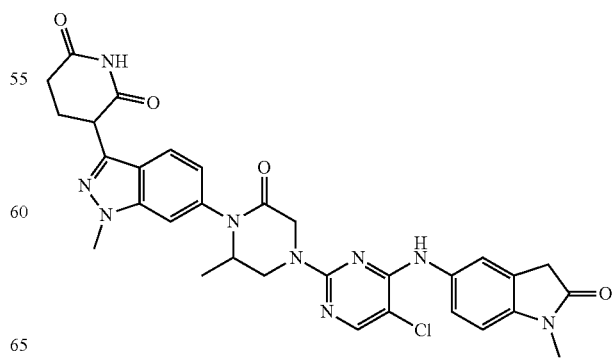

Step 1: Synthesis of N-[(2R,4R)-1-[3-(2,6-Dibenzyloxy-3-pyridyl)-1-methyl-indazol-6-yl]-2-methyl-4-piperidyl]

Step 1: Synthesis of 6-methylpiperazin-2-one. To a stirred solution of 6-methylpiperazin-2-one (1.0 g, 8.76 mmol) and triethylamine (1.83 mL, 13.14 mmol) in $CH_2Cl_2$ (20 mL) was added Boc-anhydride (2.24 mL, 9.64 mmol) under nitrogen at 0° C. The reaction mixture was slowly warmed to 25° C. and stirred for 3 h. The reaction mixture was treated with 0.5N HCl (2.0 mL), water (50 mL) and extracted with DCM (2×50 mL). The combined organic layers were dried over anhydrous sodium sulfate, filtered, and concentrated under reduced pressure to afford the title compound (1.81 g, 8.43 mmol, 96% yield) as an off-white solid. The crude product was used for the next step without further purification.

Step 2: Synthesis of tert-butyl 4-(3-(2,6-bis(benzyloxy)pyridin-3-yl)-1-methyl-1H-indazol-6-yl)-3-methyl-5-oxopiperazine-1-carboxylate. A stirred solution of 6-methylpiperazin-2-one (750 mg, 3.49 mmol) and 3-(2,6-bis(benzyloxy)pyridin-3-yl)-6-bromo-1-methyl-1H-indazole (1.50 g, 3.00 mmol) in DMF (10 mL) was degassed with nitrogen for 5 min. Then copper(I)iodide (571 mg, 3.00 mmol), $K_2CO_3$ (621 mg, 4.50 mmol) and $N_1,N_2$-dimethylethane-1,2-diamine (264 mg, 3.00 mmol) were added and degassed for 10 min. The reaction mixture was heated to 100° C. and stirred for 16 h. The reaction mixture was cooled to room temperature and treated with water (30 mL) and extracted with ethyl acetate (2×50 mL). The combined organic layers were dried over anhydrous sodium sulphate, filtered, and concentrated under reduced pressure to afford the crude compound. The crude was purified by flash column chromatography on silica with 80-100% ethyl acetate/pet ether to afford the title compound (650 mg, 0.779 mmol, 26% yield) as an off-white solid. MS (ESI) m/z 634.8 $[M+H]^+$.

Step 3: Synthesis of 3-(6-(4-(5-chloro-4-((1-methyl-2-oxoindolin-5-yl)amino)pyrimidin-2-yl)-2-methyl-6-oxopiperazin-1-yl)-1-methyl-1H-indazol-3-yl)piperidine-2,6-dione The synthesis of the title compound was accomplished using General Procedures 4, 5, and 6 beginning with tert-butyl 4-(3-(2,6-bis(benzyloxy)pyridin-3-yl)-1-methyl-1H-indazol-6-yl)-3-methyl-5-oxopiperazine-1-carboxylate as starting material. LCMS $C_{31}H_{30}ClN_9O_4$ requires 627.2, found 628.2$[M+H]^+$; $^1H$ NMR (400 MHz, DMSO-d6): δ 10.92 (s, 1H), 8.83 (s, 1H), 8.10 (s, 1H), 7.73 (d, J=8.5 Hz, 1H), 7.59 (s, 1H), 7.55-7.53 (m, 2H), 7.01-6.96 (m, 2H), 4.58-4.50 (m, 1H), 4.39 (dd, J=5.1 Hz and 10.2 Hz, 1H), 4.24-4.16 (m, 2H), 4.25-4.07 (m, 1H), 3.98 (s, 3H), 3.90-3.83 (m, 1H), 3.55 (s, 2H), 3.12 (s, 3H), 2.73-2.66 (m, 2H), 2.66-2.61 (m, 1H), 2.43-2.36 (m, 1H), 1.07 (d, J=6.3 Hz, 3H).

Examples in Table 2 below have been made according to the general procedures outlined in the table beginning with their respective commercial starting materials and intermediates found within this document.

TABLE 2

| Compound | General Procedure No. | MS Data | NMR Data |
|---|---|---|---|
| 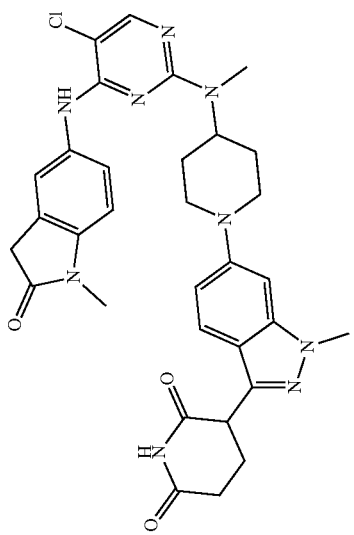 Example S6 3-(6-(4-((5-Chloro-4-((1-methyl-2-oxoindolin-5-yl)amino)pyrimidin-2-yl)(methyl)amino)piperidin-1-yl)-1-methyl-1H-indazol-3-yl)piperidine-2,6-dione (6) | 1, 6 | Required 627.3, Found 628.3 [M + H]$^+$ | $^1$H NMR (DMSO-d$_6$, 400 MHz) δ 10.86 (s, 1H), 8.6-8.7 (m, 1H), 8.0-8.1 (m, 1H), 7.6-7.7 (m, 1H), 7.5-7.6 (m, 1H), 7.4-7.5 (m, 1H), 6.9-7.0 (m, 3H), 4.4-4.6 (m, 1H), 4.2-4.4 (m, 1H), 3.91 (s, 5H), 3.56 (s, 2H), 3.09 (s, 3H), 2.9-3.0 (m, 2H), 2.7-2.8 (m, 1H), 2.6-2.7 (m, 1H), 2.3-2.3 (m, 1H), 2.1-2.2 (m, 1H), 1.92 (s, 2H), 1.7-1.7 (m, 2H) |
| 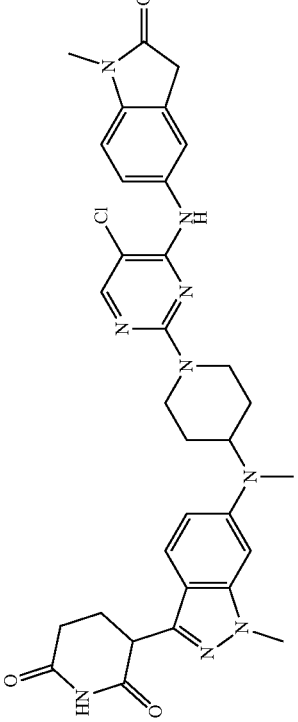 Example S7 3-(6-((1-(5-chloro-4-((1-methyl-2-oxoindolin-5-yl)amino)pyrimidin-2-yl)piperidin-4-yl)(methyl)amino)-1-methyl-1H-indazol-3-yl)piperidine-2,6-dione (7) | 1, 6 | Required 627.3, Found 628.4 [M + H]$^+$ | $^1$H NMR (500 MHz, DMSO) δ 10.83 (s, 1H), 8.65 (s, 1H), 8.01 (s, 1H), 7.54 (s, 1H), 7.52 (d, J = 8.5 Hz, 1H), 7.47 (d, J = 9.0 Hz, 1H), 6.93 (d, J = 8.3 Hz, 1H), 6.89 (d, J = 9.1 Hz, 1H), 6.66 (s, 1H), 4.64-4.59 (m, 2H), 4.24 (dd, J = 9.2, 5.1 Hz, 1H), 4.10-3.99 (m, 1H), 3.87 (s, 3H), 3.54 (s, 2H), 3.10 (s, 3H), 2.94 (t, J = 11.6 Hz, 2H), 2.74 (s, 3H), 2.64-2.59 (m, 2H), 2.31-2.25 (m, 1H), 2.19-2.13 (m, 1H), 1.70-1.59 (m, 4H) |

TABLE 2-continued

| Compound | General Procedure No. | MS Data | NMR Data |
|---|---|---|---|
| 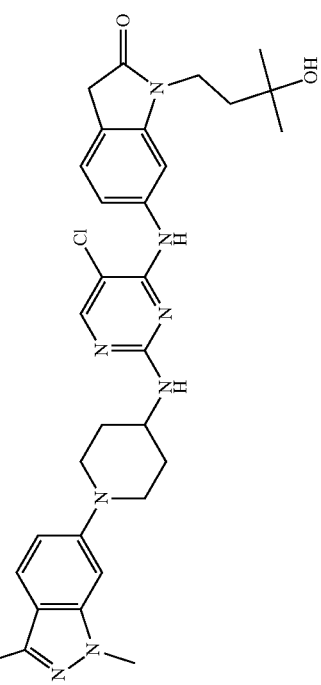<br>Example S8<br>3-(6-(4-((5-chloro-4-((1-(3-hydroxy-3-methylbutyl)-2-oxoindolin-6-yl)amino)pyrimidin-2-yl)amino)piperidin-1-yl)-1-methyl-1H-indazol-3-yl)piperidine-2,6-dione (8) | 1, 2,‡ 4, 5, 6<br>‡ 10 mol %<br>RuPhos-<br>Pd-G3<br>Cs₂CO₃<br>(1.3 equiv),<br>1,4-dioxane,<br>90° C. | Required 685.3, Found 686.3 [M + H]⁺ | ¹H NMR (400 MHz, acetic acid) δ 8.13 (s, 1H), 7.67 (d, J = 9.0 Hz, 1H), 7.57 (d, J = 7.8 Hz, 1H), 7.38 (d, J = 8.0 Hz, 1H), 7.29 (s, 1H), 7.17 (d, J = 8.3 Hz, 2H), 4.48 (dd, J = 10.6, 5.1 Hz, 1H), 4.08-4.00 (m, 4H), 3.99-3.89 (m, 2H), 3.88-3.77 (m, 2H), 3.65 (s, 2H), 3.17 (t, J = 10.5 Hz, 2H), 2.96-2.75 (m, 2H), 2.60-2.51 (m, 1H), 2.44-2.32 (m, 1H), 2.31-2.21 (m, 2H), 2.01-1.95 (m, 2H), 1.93-1.85 (m, 2H), 1.34 (s, 6H) |
| 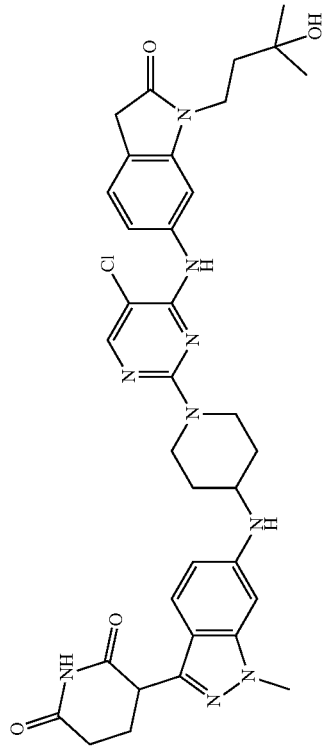<br>Example S9<br>3-[6-[[1-[5-Chloro-4-[[1-(3-hydroxy-3-methyl-butyl)-2-oxo-indolin-6-yl]amino]pyrimidin-2-yl]-4-piperidyl]amino]-1-methyl-indazol-3-yl]piperidine-2,6-dione (9) | 1, 6 | Required 685.3, Found 686.4 [M + H]⁺ | ¹H NMR (400 MHz, DMSO) δ 8.73 (s, 1H), 8.06 (s, 1H), 7.32 (d, J = 8.7 Hz, 1H), 7.30-7.24 (m, 2H), 7.19 (d, J = 8.0 Hz, 1H), 6.51 (dd, J = 8.8, 1.6 Hz, 1H), 6.44 (d, J = 1.2 Hz, 1H), 5.76 (d, J = 8.0 Hz, 1H), 4.41 (d, J = 12.9 Hz, 2H), 4.18 (dd, J = 8.8, 5.2 Hz, 1H), 3.82 (s, 3H), 3.75-3.65 (m, 2H), 3.64-3.56 (m, 1H), 3.48 (s, 2H), 3.13 (t, J = 11.4 Hz, 2H), 2.60 (t, J = 7.1 Hz, 2H), 2.30-2.20 (m, 1H), 2.19-2.10 (m, 1H), 2.05-1.95 (m, 2H), 1.70-1.56 (m, 2H), 1.40-1.25 (m, 2H), 1.16 (s, 6H) |

TABLE 2-continued

| Compound | General Procedure No. | MS Data | NMR Data |
|---|---|---|---|
| 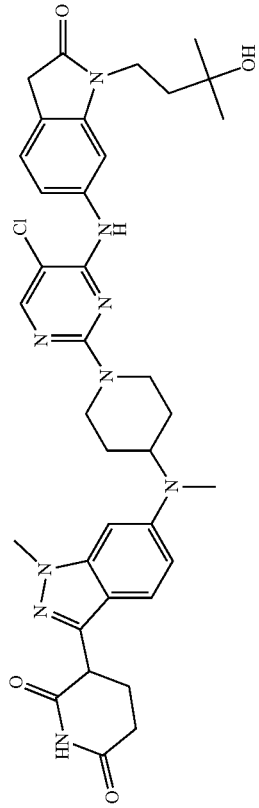<br>Example S10<br>3-(6-((1-(5-chloro-4-((1-(3-hydroxy-3-methylbutyl)-2-oxoindolin-6-yl)amino)pyrimidin-2-yl)piperidin-4-yl)(methyl)amino)-1-methyl-1H-indazol-3-yl)piperidine-2,6-dione (10) | 1, 6 | Required 699.3, Found 699.5 [M − H]− | $^1$H NMR (500 MHz, DMSO-d$_6$) δ 10.83 (s, 1H), 8.73 (s, 1H), 8.05 (s, 1H), 7.46 (d, J = 9.0 Hz, 1H), 7.28 (s, 1H), 7.26 (dd, J = 8.0, 1.7 Hz, 1H), 7.19 (d, J = 8.0 Hz, 1H), 6.88 (dd, J = 9.2, 1.9 Hz, 1H), 6.65 (d, J = 1.7 Hz, 1H), 4.66 (d, J = 11.9 Hz, 2H), 4.40 (s, 1H), 4.24 (dd, J = 8.9, 5.1 Hz, 1H), 4.13-3.96 (m, 1H), 3.87 (s, 3H), 3.73-3.61 (m, 2H), 3.48 (s, 2H), 3.03-2.90 (m, 2H), 2.74 (s, 3H), 2.62 (dt, J = 10.3, 3.7 Hz, 2H), 2.32-2.26 (m, 1H), 2.20-2.13 (m, 1H), 1.73-1.58 (m, 6H), 1.16 (s, 6H). |
| 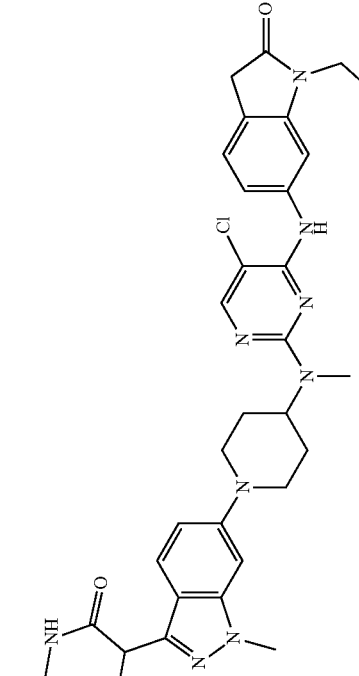<br>Example S11<br>3-(6-(4-((5-chloro-4-((1-(3-hydroxy-3-methylbutyl)-2-oxoindolin-6-yl)amino)pyrimidin-2-yl)(methyl)amino)piperidin-1-yl)-1-methyl-1H-indazol-3-yl)piperidine-2,6-dione (11) | 1, 6 | Required 699.3, Found 699.5 [M − H]− | $^1$H NMR (500 MHz, DMSO-d$_6$) δ 10.83 (s, 1H), 8.73 (s, 1H), 8.05 (s, 1H), 7.46 (d, J = 9.0 Hz, 1H), 7.28 (s, 1H), 7.26 (dd, J = 8.0, 1.7 Hz, 1H), 7.19 (d, J = 8.0 Hz, 1H), 6.88 (dd, J = 9.2, 1.9 Hz, 1H), 6.65 (d, J = 1.7 Hz, 1H), 4.66 (d, J = 11.9 Hz, 2H), 4.40 (s, 1H), 4.24 (dd, J = 8.9, 5.1 Hz, 1H), 4.13-3.96 (m, 1H), 3.87 (s, 3H), 3.73-3.61 (m, 2H), 3.48 (s, 2H), 3.03-2.90 (m, 2H), 2.74 (s, 3H), 2.62 (dt, J = 10.3, 3.7 Hz, 2H), 2.32-2.26 (m, 1H), 2.20-2.13 (m, 1H), 1.73-1.58 (m, 6H), 1.16 (s, 6H) |

TABLE 2-continued

| Compound | General Procedure No. | MS Data | NMR Data |
|---|---|---|---|
| 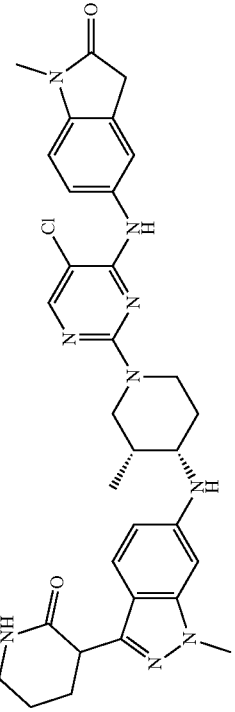<br>Example S12<br>3-(6-{[(3R,4S)-1-{5-chloro-4-[(1-methyl-2-oxo-2,3-dihydro-1H-indol-5-yl)amino]pyrimidin-2-yl}-3-methylpiperidin-4-yl]amino}-1-methyl-1H-indazol-3-yl)piperidine-2,6-dione (12) | 2,‡ 4, 5, 6<br>‡ 10 mol %<br>XPhos-Pd-G3<br>Cs₂CO₃ (2.0 equiv),<br>1,4-dioxane, 90° C. | Required 627.3, Found 628.3 [M + H]⁺ | ¹H NMR (500 MHz, DMSO) δ 10.81 (s, 1H), 8.61 (s, 1H), 7.99 (s, 1H), 7.58-7.48 (m, 2H), 7.33 (d, J = 8.8 Hz, 1H), 6.93 (d, J = 7.8 Hz, 1H), 6.65 (d, J = 8.5 Hz, 1H), 6.46 (s, 1H), 5.79 (d, J = 7.9 Hz, 1H), 4.22-4.13 (m, 1H), 4.05-3.94 (m, 1H), 3.94-3.86 (m, 1H), 3.81 (s, 3H), 3.79-3.70 (m, 1H), 3.53 (s, 2H), 3.58-3.51 (m, 1H), 3.50-3.42 (m, 1H), 3.10 (s, 3H), 2.66-2.56 (m, 2H), 2.31-2.23 (m, 1H), 2.23-2.12 (m, 2H), 1.77-1.55 (m, 2H), 0.83 (d, J = 6.7 Hz, 3H) |
| 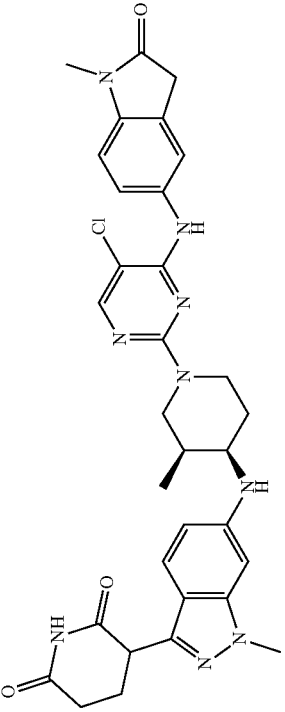<br>Example S13<br>3-(6-(((3S,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione (13) | 2,‡ 4, 5, 6<br>‡ 10 mol %<br>XPhos-Pd-G3<br>Cs₂CO₃ (2.0 equiv),<br>1,4-dioxane, 90° C. | Required 627.3, Found 628.3 [M + H]⁺ | ¹H NMR (400 MHz, DMSO-d₆) δ 10.81 (s, 1H), 8.61 (s, 1H), 7.99 (s, 1H), 7.56-7.48 (m, J = 9.2 Hz, 2H), 7.33 (d, J = 8.7 Hz, 1H), 6.94 (d, J = 8.1 Hz, 1H), 6.65 (dd, J = 8.9, 1.0 Hz, 1H), 6.46 (s, 1H), 5.79 (d, J = 8.3 Hz, 1H), 4.18 (dd, J = 8.7, 5.2 Hz, 1H), 4.04-3.94 (m, 1H), 3.95-3.87 (m, 1H), 3.81 (s, 3H), 3.79-3.70 (m, 1H), 3.59-3.54 (m, 1H), 3.53 (s, 2H), 3.51-3.42 (m, 1H), 3.10 (s, 3H), 2.64-2.55 (m, 2H), 2.30-2.10 (m, 3H), 1.76-1.57 (m, 2H), 0.82 (d, J = 6.7 Hz, 3H) |

TABLE 2-continued

| Compound | General Procedure No. | MS Data | NMR Data |
|---|---|---|---|
| 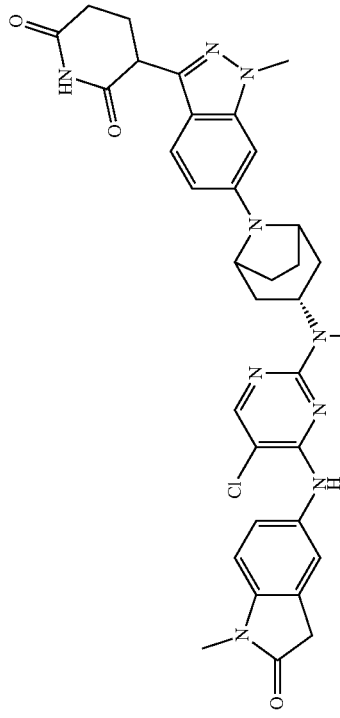<br>Example S14<br>3-(6-(((3S,4S)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione (14) | 2,‡ 4, 5, 6<br>‡ 25 mol %<br>RuPhos-Pd-G3<br>Cs₂CO₃<br>(1.2 equiv),<br>1,4-dioxane,<br>90° C. | Required 627.3,<br>Found 628.3<br>[M + H]⁺ | ¹H NMR (400 MHz, DMSO) δ 10.81 (s, 1H), 8.65 (s, 1H), 8.02 (d, J = 2.2 Hz, 1H), 7.57 (s, 1H), 7.53 (d, J = 8.0 Hz, 1H), 7.31 (dd, J = 8.5, 1.6 Hz, 1H), 6.93 (d, J = 6.8 Hz, 1H), 6.51 (d, J = 8.0 Hz, 1H), 6.44 (s, 1H), 5.69 (d, J = 8.5 Hz, 1H), 4.52-4.41 (m, 2H), 4.21-4.12 (m, 1H), 3.81 (s, 3H), 3.53 (s, 2H), 3.10 (s, 3H), 3.07-2.95 (m, 1H), 2.76-2.64 (m, 1H), 2.64-2.57 (m, 2H), 2.31-2.20 (m, 1H), 2.20-2.12 (m, 1H), 2.12-2.00 (m, 2H), 1.64-1.53 (m, 1H), 1.25-1.11 (m, 1H), 0.97 (d, J = 3.3 Hz, 3H) |
| 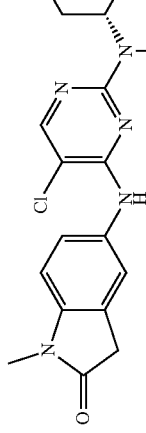<br>Example S15<br>3-(6-(((1R,3s,5S)-3-((5-chloro-4-((1-methyl-2-oxoindolin-5-yl)amino)pyrimidin-2-yl)(methyl)amino)-8-azabicyclo[3.2.1]octan-8-yl)-1-methyl-1H-indazol-3-yl)piperidine-2,6-dione (15) | 2,‡ 3, 4, 5, 6<br>‡ 15 mol %<br>RuPhos-Pd-G3<br>Cs₂CO₃<br>(2.5 equiv),<br>1,4-dioxane,<br>90° C. | Required 653.3,<br>Found 654.3<br>[M + H]⁺ | ¹H NMR (500 MHz, DMSO-d₆) δ 10.85 (br s, 1H), 8.48 (s, 1H), 7.84 (s, 1H), 7.64 (br d, J = 7.7 Hz, 1H), 7.50 (br s, 1H), 7.45 (d, J = 9.3 Hz, 1H), 6.87-6.82 (m, 2H), 6.70 (br s, 1H), 4.75-4.64 (m, 1H), 4.49-4.40 (m, 2H), 4.24 (dd, J = 8.9, 5.1 Hz, 1H), 3.86 (s, 3H), 3.46 (s, 2H), 2.94-2.79 (m, 3H), 2.85 (s, 3H), 2.66-2.59 (m, 2H), 2.42-2.33 (m, 2H), 2.33-2.25 (m, 1H), 2.22-2.13 (m, 1H), 2.02-1.94 (m, 2H), 1.78-1.70 (m, 2H), 1.54-1.44 (m, 2H) |

TABLE 2-continued

| Compound | General Procedure No. | MS Data | NMR Data |
|---|---|---|---|
| Example S16<br>3-(6-((1R,3r,5S)-3-((5-chloro-4-((1-methyl-2-oxoindolin-5-yl)amino)pyrimidin-2-yl)(methyl)amino)-8-azabicyclo[3.2.1]octan-8-yl)-1-methyl-1H-indazol-3-yl)piperidine-2,6-dione (16) | 2‡ 3, 4, 5, 6<br>‡ 15 mol %<br>RuPhos-Pd-G3<br>Cs₂CO₃<br>(2.0 equiv),<br>1,4-dioxane,<br>90° C. | Required 653.3,<br>Found 654.3<br>[M + H]⁺ | ¹H NMR (500 MHz, DMSO-d₆) δ 10.46 (br s, 1H), 8.26 (br s, 1H), 7.96 (s, 1H), 7.54-7.46 (m, 3H), 6.91 (d, J = 8.2 Hz, 1H), 6.80 (dd, J = 9.0, 1.8 Hz, 1H), 6.71 (d, J = 1.4 Hz, 1H), 5.18-5.08 (m, 1H), 4.42 (br s, 2H), 4.22 (dd, J = 8.2, 5.2 Hz, 1H), 3.86 (s, 3H), 3.52 (s, 2H), 3.13 (s, 3H), 2.72-2.62 (m, 2H), 2.61 (s, J = 2.7 Hz, 3H), 2.36-2.27 (m, 1H), 2.27-2.19 (m, 1H), 2.02-1.93 (m, 4H), 1.72-1.65 (m, 2H), 1.47-1.39 (m, 2H) |
| Example S17<br>3-(6-(((4-(5-chloro-4-((1-methyl-2-oxoindolin-5-yl)amino)pyrimidin-2-yl)piperazin-1-yl)methyl)-1-methyl-1H-indazol-3-yl)piperidine-2,6-dione (17) | 1, 6 | Required 613.2,<br>Found 614.3<br>[M + H]⁺ | ¹H NMR (500 MHz, DMSO-d₆) δ 10.88 (br s, 1H), 8.64 (s, 1H), 7.99 (s, 1H), 7.65 (d, J = 8.4 Hz, 1H), 7.52-7.46 (m, 3H), 7.13 (dd, J = 8.4, 0.9 Hz, 1H), 6.93-6.89 (m, 1H), 4.35 (dd, J = 9.8, 5.1 Hz, 1H), 3.98 (s, 3H), 3.65-3.56 (m, 6H), 3.53 (s, 2H), 3.09 (s, 3H), 2.72-2.57 (m, 2H), 2.44-2.39 (m, 4H), 2.39-2.32 (m, 1H), 2.21-2.14 (m, 1H). |

TABLE 2-continued

| Compound | General Procedure No. | MS Data | NMR Data |
|---|---|---|---|
| 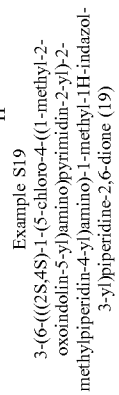 Example S18 3-(6-((1-(5-chloro-4-((2-oxo-1-(2,2,2-trifluoroethyl)indolin-5-yl)amino)pyrimidin-2-yl)piperidin-4-yl)amino)-1-methyl-1H-indazol-3-yl)piperidine-2,6-dione (18) | 2, 4, 5, 6 | Required 681.2, Found 682.3 [M + H]+ | 1H NMR (500 MHz, DMSO) δ 10.79 (br, 1H), 8.68 (s, 1H), 8.03 (s, 1H), 7.59 (s, 1H), 7.54 (dd, J = 8.5, 2.1 Hz, 1H), 7.33 (d, J = 8.8 Hz, 1H), 7.11 (d, J = 8.5 Hz, 1H), 6.52 (dd, J = 8.8, 1.7 Hz, 1H), 6.46 (d, J = 1.2 Hz, 1H), 5.77 (d, J = 8.4 Hz, 1H), 4.58 (q, J = 9.4 Hz, 2H), 4.42-4.33 (m, 2H), 4.18 (dd, J = 8.8, 5.1 Hz, 1H), 3.82 (s, 3H), 3.70 (s, 2H), 3.64 (br, 1H), 3.12 (t, J = 11.2 Hz, 2H), 2.64-2.56 (m, 2H), 2.30-2.21 (m, 1H), 2.18-2.10 (m, 1H), 2.05-1.95 (m, 2H), 1.37-1.26 (m, 2H). MS (ESI) [M + H]+ 682.3. |
| 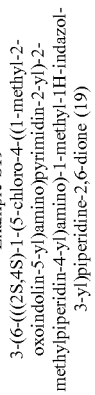 Example S19 3-(6-(((2S,4S)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (19) | 2, 3, 4, 5, 6 | Required 627.3, Found 628.3 [M + H]+ | 1H NMR (400 MHz, DMSO-d6) δ 10.81 (s, 1H), 8.59 (s, 1H), 8.00 (s, 1H), 7.58 (s, 1H), 7.53 (dd, J = 8.4, 1.9 Hz, 1H), 7.33 (d, J = 8.8 Hz, 1H), 6.92 (d, J = 8.4 Hz, 1H), 6.60 (dd, J = 8.8, 1.7 Hz, 1H), 6.37 (d, J = 1.3 Hz, 1H), 5.87 (d, J = 6.5 Hz, 1H), 4.52 (dd, J = 12.1, 5.7 Hz, 1H), 4.35-4.27 (m, 1H), 4.18 (dd, J = 8.8, 5.1 Hz, 1H), 3.80 (s, 3H), 3.70-3.61 (m, 1H), 3.53 (s, 2H), 3.10 (s, 3H), 2.64-2.57 (m, 2H), 2.34-2.23 (m, 1H), 2.22-2.04 (m, 2H), 2.04-1.94 (m, 1H), 1.91-1.81 (m, 2H), 1.69 (d, J = 13.0 Hz, 1H), 1.18 (d, J = 6.7 Hz, 3H) |

TABLE 2-continued

| Compound | General Procedure No. | MS Data | NMR Data |
|---|---|---|---|
| Example S20<br>3-(6-(((2S,4S)-4-((5-chloro-4-((1-methyl-2-oxoindolin-5-yl)amino)pyrimidin-2-yl)(methyl)amino)-2-methylpiperidin-1-yl)-1-methyl-1H-indazol-3-yl)piperidine-2,6-dione (20) | 2, 3, 4, 5, 6 | Required 641.3, Found 642.4 [M + H]⁺ | ¹H NMR (500 MHz, DMSO-d₆) δ 10.87 (s, 1H), 8.59 (s, 1H), 8.02 (s, 1H), 7.70 (br s, 1H), 7.61-7.58 (m, 2H), 7.55 (br s, 1H), 7.28 (s, 1H), 6.94 (t, J = 8.0 Hz, 2H), 4.55 (br s, 1H), 4.33 (dd, J = 9.7, 5.2 Hz, 1H), 3.96 (s, 3H), 3.69-3.48 (m, 2H), 3.25 (d, J = 12.6 Hz, 1H), 3.10 (s, 4H), 2.96 (s, 3H), 2.82 (br s, 1H), 2.72-2.57 (m, 2H), 2.39-2.29 (m, 1H), 2.23-2.13 (m, 1H), 1.91 (qd, J = 12.0, 4.1 Hz, 1H), 1.80-1.72 (m, 1H), 1.71-1.56 (m, 2H), 0.93 (d, J = 5.9 Hz, 3H). |
| Example S21<br>3-(6-(((2R,4R)-4-((5-chloro-4-((1-methyl-2-oxoindolin-5-yl)amino)pyrimidin-2-yl)(methyl)amino)-2-methylpiperidin-4-yl)(methyl)amino)-1-methyl-1H-indazol-3-yl)piperidine-2,6-dione (21) | 2, 4, 5, 6 | Required 641.3, Found 642.3 [M + H]⁺ | ¹H NMR (500 MHz, DMSO-d₆) δ 10.82 (s, 1H), 8.57 (s, 1H), 8.00 (s, 1H), 7.63 (s, 1H), 7.55 (dd, J = 8.4, 1.9 Hz, 1H), 7.41 (d, J = 9.0 Hz, 1H), 6.92 (d, J = 8.5 Hz, 1H), 6.81 (dd, J = 9.2, 2.0 Hz, 1H), 6.65 (d, J = 1.8 Hz, 1H), 4.35 (dd, J = 13.6, 7.5 Hz, 1H), 4.27-4.18 (m, 2H), 4.01-3.91 (m, 1H), 3.85 (s, 3H), 3.52 (s, 2H), 3.28-3.23 (m, 1H), 3.10 (s, 3H), 2.81 (s, 3H), 2.63-2.55 (m, 2H), 2.31-2.22 (m, 1H), 2.17-2.11 (m, 1H), 2.03-1.97 (m, 1H), 1.93-1.85 (m, 1H), 1.83-1.77 (m, 1H), 1.70-1.62 (m, 1H), 1.19 (d, J = 6.1 Hz, 3H). |

TABLE 2-continued

| Compound | General Procedure No. | MS Data | NMR Data |
|---|---|---|---|
| 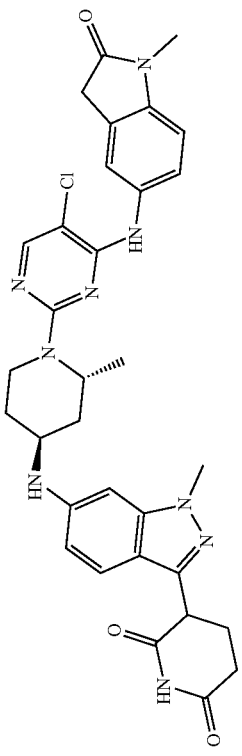 Example S22<br>3-(6-(((2R,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (22) | 2, 4, 5, 6 | Required 627.3, Found 628.3 [M + H]+ | 1H NMR (500 MHz, DMSO-d6) δ 10.80 (s, 1H), 8.60 (s, 1H), 8.00 (s, 1H), 7.58 (s, 1H), 7.53 (d, J = 8.0 Hz, 1H), 7.33 (d, J = 8.8 Hz, 1H), 6.92 (d, J = 8.4 Hz, 1H), 6.60 (d, J = 7.7 Hz, 1H), 6.37 (s, 1H), 5.88 (d, J = 6.1 Hz, 1H), 4.54-4.51 (m 1H), 4.33-4.29 (m, 1H), 4.18 (dd, J = 8.7, 5.1 Hz, 1H), 3.80 (s, 3H), 3.72-3.63 (m, 1H), 3.53 (s, 2H), 3.37-3.33 (m, 1H), 3.10 (s, 3H), 2.63-2.58 (m, 2H), 2.31-2.22 (m, 1H), 2.17-2.11 (m, 1H), 2.03-1.96 (m, 1H), 1.90-1.83 (m, 2H), 1.72-1.66 (m, 1H), 1.18 (d, J = 6.7 Hz, 3H). |
| Example S23<br>3-(6-(((2R,4S)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (23) | 2, 3, 4, 5, 6 | Required 627.3, Found 628.3 [M + H]+ | 1H NMR (500 MHz, DMSO-d6) δ 8.63 (s, 1H), 8.37 (s, 1H), 8.01 (s, 1H), 7.55 (s, 1H), 7.51 (d, J = 8.4 Hz, 1H), 7.33 (d, J = 8.7 Hz, 1H), 6.93 (d, J = 8.5 Hz, 1H), 6.52 (dd, J = 8.8, 1.7 Hz, 1H), 6.47 (s, 1H), 5.67 (d, J = 7.9 Hz, 1H), 4.90 (s, 1H), 4.47 (s, 1H), 4.18 (dd, J = 8.8, 5.1 Hz, 1H), 3.83 (s, 3H), 3.78 (s, 1H), 3.54 (s, 2H), 3.11 (s, 3H), 3.06 (t, J = 12.2 Hz, 1H), 2.65-2.56 (m, 2H), 2.30-2.22 (m, 1H), 2.14 (dt, J = 16.8, 8.7 Hz, 2H), 1.92 (d, J = 12.6 Hz, 1H), 1.47 (td, J = 12.0, 5.0 Hz, 1H), 1.26 (d, J = 6.9 Hz, 3H), 1.15 (m, 1H). |

TABLE 2-continued

| Compound | General Procedure No. | MS Data | NMR Data |
|---|---|---|---|
| Example S24<br>3-(6-(((2S,4S)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione (24) | 2, 3, 4, 5, 6 | Required 641.3, Found 642.3 [M + H]+. | $^1$H NMR (500 MHz, DMSO-d$_6$) δ 10.81 (s, 1H), 8.57 (s, 1H), 8.32 (s, 1H), 7.99 (s, 1H), 7.62 (s, 1H), 7.54 (d, J = 8.5 Hz, 1H), 7.41 (d, J = 9.0 Hz, 1H), 6.91 (d, J = 8.4 Hz, 1H), 6.80 (d, J = 7.9 Hz, 1H), 6.64 (s, 1H), 4.34 (dd, J = 13.8, 7.5 Hz, 1H), 4.27-4.16 (m, 2H), 3.99-3.91 (m, 1H), 3.84 (s, 3H), 3.52 (s, 2H), 3.09 (s, 3H), 2.80 (s, 3H), 2.67-2.61 (m, 1H), 2.61-2.54 (m, 2H), 2.30-2.21 (m, 1H), 2.17-2.09 (m, 1H), 2.03-1.95 (m, 1H), 1.93-1.85 (m, 1H), 1.82-1.75 (m, 1H), 1.69-1.61 (m, 1H), 1.18 (d, J = 6.0 Hz, 3H). |
| Example S25<br>3-(6-(((2R,4S)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione (25) | 2,‡ 4, 5, 6<br>‡ 5 mol % CPhos-Pd-G3 NaOtBu (1.5 equiv), PhMe, 100° C. | Required 641.3, Found 642.4 [M + H]+. | $^1$H NMR (500 MHz, DMSO-d$_6$) δ 10.83 (s, 1H), 8.63 (s, 1H), 8.01 (s, 1H), 7.56 (s, 1H), 7.52-7.45 (m, 2H), 6.97-6.86 (m, 2H), 6.65 (s, 1H), 5.12-4.83 (m, 1H), 4.67-4.39 (m, 1H), 4.27-4.17 (m, 2H), 3.87 (s, 3H), 3.54 (s, 2H), 3.11-3.09 (m, 1H), 3.15-3.01 (m, 4H), 2.75 (s, 3H), 2.66-2.56 (m, 2H), 2.33-2.24 (m, 1H), 2.22-2.12 (m, 1H), 1.86-1.77 (m, 1H), 1.74 (d, J = 10.8 Hz, 1H), 1.69-1.61 (m, 1H), 1.58 (d, J = 11.6 Hz, 1H), 1.25 (d, J = 6.7 Hz, 3H). |

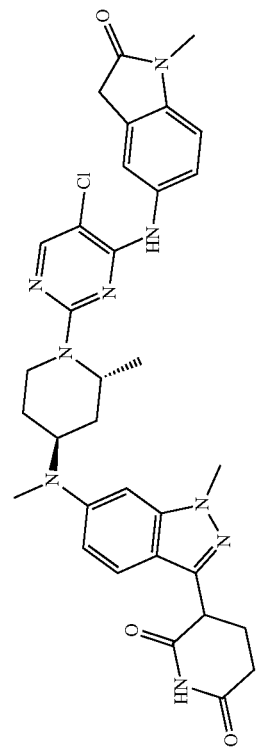

TABLE 2-continued

| Compound | General Procedure No. | MS Data | NMR Data |
|---|---|---|---|
| Example S26 3-(6-((2S,6R)-3-chloro-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione (26) | 2,‡ 4, 5, 6 ‡ 5 mol % CPhos-Pd-G3 NaO^tBu (1.5 equiv), PhMe, 100° C. | Required 627.3, Found 628.2 [M + H]+ | 1H NMR (400 MHz, DMSO-d6): δ 10.87 (s, 1H), 8.72 (s, 1H), 8.06 (s, 1H), 7.62-7.58 (m, 2H), 7.53 (dd, J = 2.0 Hz and 8.4 Hz, 1H), 7.25 (d, J = 1.2 Hz, 1H), 6.97-6.94 (m, 2H), 4.34-4.31 (m, 1H), 4.15-4.12 (m, 2H), 3.94 (s, 3H), 3.54 (s, 2H), 3.45-3.35 (m, 2H), 3.27-3.27 (m, 2H), 3.12 (s, 3H), 2.68-2.62 (m, 2H), 2.35-2.30 (m, 1H), 2.20-2.19 (m, 1H), 0.83 (d, J = 6.0 Hz, 6H). |
| Example S27 3-(6-((2S,6S)-3-chloro-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione (27) | 2,‡ 4, 5, 6 ‡ 5 mol % CPhos-Pd-G3 NaO^tBu (1.5 equiv), PhMe, 110° C. | Required 627.3, Found 628.2 [M + H]+ | 1H NMR (400 MHz, DMSO-d6): δ 10.88 (s, 1H), 8.90 (s, 1H), 8.08 (s, 1H), 7.59 (d, J = 7.6 Hz, 2H), 7.52 (d, J = 8.4 Hz, 1H), 7.06 (s, 1H), 6.96 (d, J = 7.2 Hz, 1H), 6.90 (d, J = 3.6 Hz, 1H), 4.32-4.28 (dd, J = 5.2, 9.6 Hz, 1H), 3.93 (s, 3H), 3.72-3.69 (m, 2H), 3.57 (s, 2H), 3.12 (s, 3H), 2.68-2.63 (m, 2H), 2.34-2.28 (m, 1H), 2.19-2.15 (m, 1H), 0.97 (d, J = 6.0 Hz, 6H). |

TABLE 2-continued

| Compound | General Procedure No. | MS Data | NMR Data |
|---|---|---|---|
| Example S28<br>3-(6-((3R,5R)-4-(5-chloro-4-((1-methyl-2-oxoindolin-5-yl)amino)pyrimidin-2-yl)-3,5-dimethylpiperazin-1-yl)-1-methyl-1H-indazol-3-yl)piperidine-2,6-dione (28) | 2,‡ 4, 5, 6<br>‡ 5 mol % CPhos-Pd-G3<br>NaO$^t$Bu (1.5 equiv), PhMe, 100° C. | Required 627.3, Found 628.2 [M + H]$^+$ | $^1$H NMR (400 MHz, DMSO-d$_6$): δ 10.84 (s, 1H), 8.66 (s, 1H), 8.07 (s, 1H), 7.67 (s, 1H), 7.55-7.50 (m, 2H), 6.95 (d, J = 8.40 Hz, 1H), 6.71 (dd, J = 2.00 Hz and 9.2 Hz, 1H), 6.54 (d, J = 1.6 Hz, 1H), 4.55-4.48 (m, 2H), 4.28-4.22 (m, 1H), 3.87 (s, 3H), 3.84-3.78 (m, 2H), 3.59-3.55 (m, 4H), 3.13 (s, 3H), 2.63-2.60 (m, 2H), 2.33-2.28 (m, 1H), 2.21-2.15 (m, 1H), 1.22 (d, J = 6.40 Hz, 6H). |
| Example S29<br>3-(6-((3S,5S)-4-(5-chloro-4-((1-methyl-2-oxoindolin-5-yl)amino)pyrimidin-2-yl)-3,5-dimethylpiperazin-1-yl)-1-methyl-1H-indazol-3-yl)piperidine-2,6-dione (29) | 2,‡ 4, 5, 6<br>‡ 5 mol % CPhos-Pd-G3<br>NaO$^t$Bu (1.5 equiv), PhMe, 110° C. | Required 627.3, Found 628.2 [M + H]$^+$ | $^1$H NMR (400 MHz, DMSO-d$_6$): δ 10.85 (s, 1H), 8.67 (s, 1H), 8.07 (s, 1H), 7.67 (s, 1H), 7.54-7.50 (m, 2H), 6.94 (d, J = 8.8 Hz, 1H), 6.71 (dd, J = 2.0, 9.2 Hz, 1H), 6.54 (s, 1H), 4.56-4.48 (m, 2H), 4.26-4.23 (m, 1H), 3.86 (s, 3H), 3.82-3.74 (m, 2H), 3.62-3.55 (m, 4H), 3.12 (s, 3H), 2.68-2.56 (m, 3H), 2.35-2.26 (m, 1H), 2.19-2.14 (m, 1H), 1.22 (d, J = 6.4 Hz, 6H). |

TABLE 2-continued

| Compound | General Procedure No. | MS Data | NMR Data |
|---|---|---|---|
| 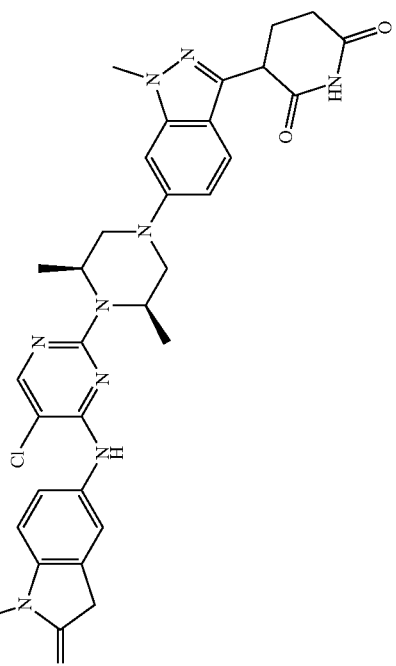<br>Example S30<br>3-(6-((3R,5S)-4-(5-chloro-4-((1-methyl-2-oxoindolin-5-yl)amino)pyrimidin-2-yl)-3,5-dimethylpiperazin-1-yl)-1-methyl-1H-indazol-3-yl)piperidine-2,6-dione (30) | 2,‡ 4, 5, 6<br>‡ 5 mol % CPhos-Pd-G3 NaO'Bu (1.5 equiv), PhMe, 100° C. | Required 627.3, Found 628.2 [M + H]+ | ¹H NMR (400 MHz, DMSO-d₆): δ 10.85 (brs, 1H), 8.71 (s, 1H), 8.41 (s, 1H), 7.66 (s, 1H), 7.55-7.50 (m, 2H), 6.96-6.92 (m, 3H), 4.65-4.61 (m, 2H), 4.30-4.26 (m, 1H), 3.91 (s, 3H), 3.73-3.70 (m, 2H), 3.60 (s, 3H), 3.14 (s, 3H), 2.88-2.85 (m, 2H), 2.62-2.59 (m, 1H), 2.31-2.28 (m, 1H), 2.19-2.14 (m, 1H), 1.32 (d, J = 6.40 Hz, 6H) |
| 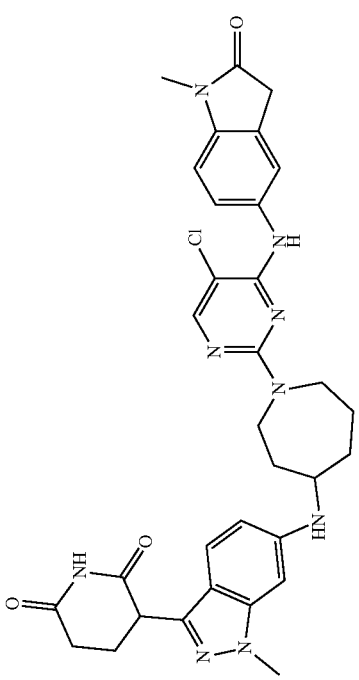<br>Example S31<br>3-(6-((1-(5-chloro-4-((1-methyl-2-oxoindolin-5-yl)amino)pyrimidin-2-yl)azepan-4-yl)amino)-1-methyl-1H-indazol-3-yl)piperidine-2,6-dione (31) | 2,‡ 4, 5, 6<br>‡ 10 mol % CPhos-Pd-G3 NaO'Bu (4.0 equiv), PhMe, 100° C. | Required 627.3, Found 628.2 [M + H]+ | ¹H NMR (400 MHz, DMSO-d₆): δ 10.83 (s, 1H), 8.60 (s, 1H), 8.01 (s, 1H), 7.62 (s, 1H), 7.58 (d, J = 8.40 Hz, 1H), 7.31 (d, J = 8.40 Hz, 1H), 6.93-6.89 (m, 1H), 6.49 (d, J = 8.80 Hz, 1H), 6.27 (s, 1H), 5.80 (d, J = 7.60 Hz, 1H), 4.19-4.15 (m, 1H), 3.78 (s, 3H), 3.82-3.72 (m, 4H), 3.09 (s, 3H), 2.59-2.85 (m, 2H), 2.26-2.22 (m, 1H), 2.16-2.10 (m, 2H), 1.91-1.88 (m, 2H), 1.76-1.65 (m, 2H), 1.45-1.41 (m, 1H) |

TABLE 2-continued

| Compound | General Procedure No. | MS Data | NMR Data |
|---|---|---|---|
| 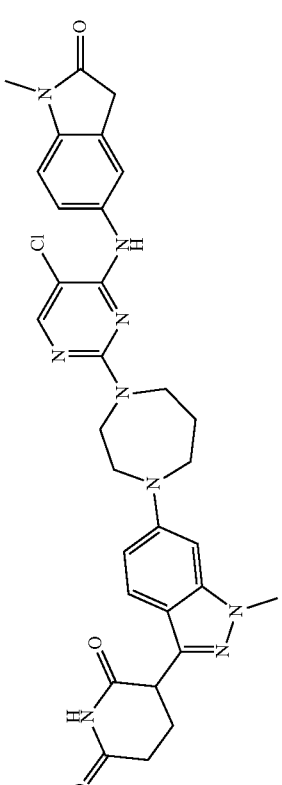<br>Example S32<br>3-(6-(4-(5-chloro-4-((1-methyl-2-oxoindolin-5-yl)amino)pyrimidin-2-yl)-1,4-diazepan-1-yl)-1-methyl-1H-indazol-3-yl)piperidine-2,6-dione (32) | 2,‡ 4, 5, 6<br>‡ 10 mol %<br>RuPhos-<br>Pd-G3<br>Cs₂CO₃<br>(2.0 equiv),<br>1,4-dioxane,<br>100° C. | Required 613.2,<br>Found 614.2<br>[M + H]⁺ | ¹H NMR (DMSO-d6, 400 MHz) δ 10.84 (s, 1H), 8.7-9.0 (m, 1H), 8.0-8.1 (m, 1H), 7.5-7.6 (m, 1H), 7.45 (d, 2H, J = 9.0 Hz), 7.2-7.3 (m, 1H), 7.08 (s, 1H), 6.7-6.9 (m, 1H), 6.62 (d, 1H, J = 1.1 Hz), 4.2-4.3 (m, 1H), 3.4-3.6 (m, 12H), 3.1-3.2 (m, 3H), 2.6-2.6 (m, 1H), 2.1-2.3 (m, 3H), 1.9-2.0 (m, 2H) |
| 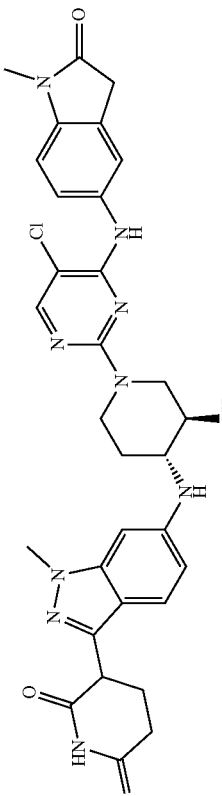<br>Example S33<br>3-(6-(((3R,4R)-1-(5-chloro-4-((1-methyl-2-oxoindolin-5-yl)amino)pyrimidin-4-yl)amino)-3-hydroxypiperidin-4-yl)amino)-1-methyl-1H-indazol-3-yl)piperidine-2,6-dione (33) | 2,‡ 4, 5, 6<br>‡ 10 mol %<br>RuPhos-<br>Pd-G3<br>Cs₂CO₃<br>(2.0 equiv),<br>1,4-dioxane,<br>100° C. | Required 629.2,<br>Found 630.2<br>[M + H]⁺ | ¹H NMR (400 MHz, DMSO-d₆) δ ppm 10.82 (s, 1H), 8.87 (br s, 1H), 8.05 (s, 1H), 7.53 (s, 1H), 7.45-7.52 (m, 1H), 7.33 (d, J = 8.80 Hz, 1H), 6.95 (d, J = 8.31 Hz, 1H), 6.56 (br d, J = 9.05 Hz, 1H), 6.50 (s, 1H), 5.81 (br s, 1H), 4.29-4.38 (m, 2H), 4.18 (br dd, J = 8.74, 5.07 Hz, 2H), 3.82 (s, 3H), 3.55 (s, 2H), 3.40-3.47 (m, 2H), 3.14-3.23 (m, 1H), 3.11 (s, 3H), 2.98-3.07 (m, 1H), 2.58-2.64 (m, 3H), 2.20-2.31 (m, 1H), 2.06-2.19 (m, 2H), 1.18-1.34 (m, 1H) |

TABLE 2-continued

| Compound | General Procedure No. | MS Data | NMR Data |
|---|---|---|---|
| Example S34<br>3-(6-(4-(5-chloro-4-((2-oxoindolin-5-yl)amino)pyrimidin-2-yl)piperazin-1-yl)-1-methyl-1H-indazol-3-yl)piperidine-2,6-dione (34) | 1, 6<br>‡ 25 mol % RuPhos-Pd-G3<br>$Cs_2CO_3$ (1.2 equiv),<br>1,4-dioxane,<br>90° C. | Required 585.2,<br>Found 586.3<br>$[M + H]^+$ | $^1$H NMR (400 MHz, DMSO) δ 10.84 (s, 1H), 10.36 (s, 1H), 8.67 (s, 1H), 8.03 (s, 1H), 7.52 (d, J = 8.8 Hz, 1H), 7.46 (s, 1H), 7.38 (dd, J = 8.6, 1.6 Hz, 1H), 6.96 (dd, J = 9.1, 1.5 Hz, 1H), 6.90 (d, J = 1.1 Hz, 1H), 6.79 (d, J = 8.4 Hz, 1H), 4.26 (dd, J = 9.2, 5.0 Hz, 1H), 3.89 (s, 3H), 3.81-3.72 (m, 4H), 3.52 (s, 2H), 3.26-3.22 (m, 4H, masked with H$_2$O signal in DMSO), 2.65-2.59 (m, 2H), 2.34-2.27 (m, 1H), 2.19-2.13 (m, 1H) |
| Example S35<br>3-[6-[4-[5-chloro-4-[(1-methyl-2-oxo-indolin-5-yl)amino]pyrimidin-2-yl]piperazin-1-yl]-1-methyl-indazol-3-yl]piperidine-2,6-dione (35) | 1, 6<br>‡ 25 mol % RuPhos-Pd-G3<br>$Cs_2CO_3$ (1.2 equiv),<br>1,4-dioxane,<br>90° C. | Required 599.2,<br>Found 600.0<br>$[M + H]^+$ | $^1$H NMR (400 MHz, DMSO-d6) δ ppm 10.78 (s, 1H), 8.66 (s, 1H), 7.98 (s, 1H), 7.41-7.51 (m, 3H), 6.90 (d, J = 8.44 Hz, 2H), 6.83 (s, 1H), 4.20 (dd, J = 9.17, 5.14 Hz, 1H), 3.83 (s, 3H), 3.71 (br s, 4H), 3.49-3.58 (m, 2H), 3.14-3.22 (m, 4H), 3.07 (s, 3H), 2.47-2.63 (m, 2H), 2.03-2.30 (m, 1H), 2.00-2.16 (m, 2H) |

TABLE 2-continued
| Compound | General Procedure No. | MS Data | NMR Data |
|---|---|---|---|
| 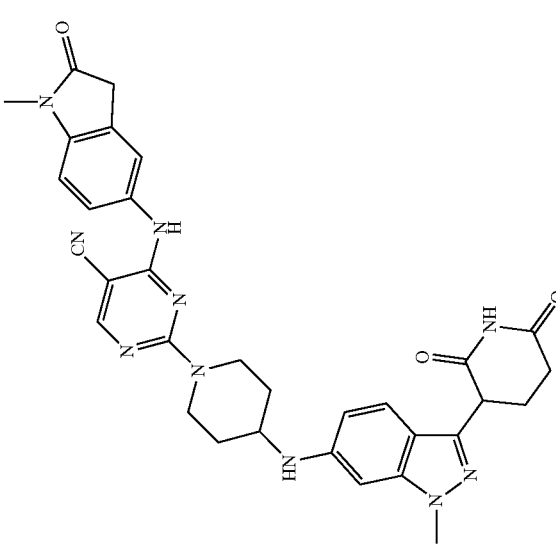<br>Example S36<br>2-(4-((3-(2-(2,6-dioxopiperidin-3-yl)-1-methyl-1H-indazol-6-yl)amino)piperidin-1-yl)-4-((1-methyl-2-oxoindolin-5-yl)amino)pyrimidine-5-carbonitrile (36) | 1, 2, 4, 5, 6 | Required 604.3, Found 605.4 [M + H]⁺ | ¹H NMR (400 MHz, DMSO) δ 10.81 (s, 1H), 9.27 (s, 1H), 8.40 (s, 1H), 7.46-7.44 (m, 1H), 7.44-7.42 (m, 1H), 7.33 (d, J = 8.7 Hz, 1H), 6.93 (d, J = 9.0 Hz, 1H), 6.52 (dd, J = 8.8, 1.7 Hz, 1H), 6.46 (d, J = 1.4 Hz, 1H), 5.79 (d, J = 8.0 Hz, 1H), 4.57 (s, 1H), 4.34 (s, 1H), 4.18 (dd, J = 8.8, 5.2 Hz, 1H), 3.82 (s, 3H), 3.71-3.61 (m, 3H), 3.54 (s, 2H), 3.10 (s, 3H), 2.60 (t, J = 6.1 Hz, 2H), 2.29-2.20 (m, 1H), 2.19-2.11 (m, 1H), 2.06-1.99 (m, 2H), 1.38-1.30 (m, 2H) |

TABLE 2-continued

| Compound | General Procedure No. | MS Data | NMR Data |
|---|---|---|---|
| Example S37 3-(6-(4-(5-chloro-4-(((1-methyl-2-oxoindolin-5-yl)amino)pyrimidin-2-yl)-2-oxopiperazin-1-yl)-1-methyl-1H-indazol-3-yl)piperidine-2,6-dione (37) | 2,‡ 4, 5, 6 ‡ 10 mol % Pd₂(dba)₃, 20 mol % Xantphos, Cs₂CO₃ (1.5 equiv), 1,4-dioxane, 100° C. | Required 613.2, found 614.1 [M + H]⁺ | ¹H-NMR (400 MHz, DMSO-d6): δ 10.90 (s, 1H), 9.01 (s, 1H), 8.14 (s, 1H), 7.71 (d, J = 8.8 Hz, 1H), 7.62 (d, J = 1.1 Hz, 1H), 7.54 (s, 2H), 7.10 (dd, J = 1.6, 8.6 Hz, 1H), 6.97 (d, J = 8.3 Hz, 1H), 4.36-4.33 (m, 3H), 4.03-3.99 (m, 5H), 3.80-3.75 (m, 2H), 3.55 (s, 2H), 3.12 (s, 3H), 2.70-2.52 (m, 2H), 2.43-2.34 (m, 1H), 2.23-2.13 (m, 1H). |
| Example S38 3-(6-(4-(5-chloro-4-(((1-methyl-2-oxoindolin-5-yl)amino)pyrimidin-2-yl)-3-methyl-2-oxopiperazin-1-yl)-1-methyl-1H-indazol-3-yl)piperidine-2,6-dione (38) | 2,‡ 4, 5, 6 ‡ 10 mol % Pd₂(dba)₃, 20 mol % Xantphos, Cs₂CO₃ (2.0 equiv), 1,4-dioxane, 100° C. | Required 627.2, Found 628.2 [M + H]⁺ | ¹H NMR (400 MHz, DMSO-d₆): δ 10.91 (s, 1H), 8.85 (s, 1H), 8.10 (s, 1H), 7.71 (d, J = 8.4 Hz, 1H), 7.61 (d, J = 1.0 Hz, 1H), 7.55 (s, 1H), 7.51 (dd, J = 2.0 Hz and 8.4 Hz, 1H), 7.10-7.06 (m, 1H), 6.96 (d, J = 8.1 Hz, 1H), 5.02-4.95 (m, 1H), 4.53-4.44 (m, 1H), 4.41-4.35 (m, 1H), 3.97 (s, 3H), 3.93-3.85 (m, 1H), 3.78-3.71 (m, 1H), 3.67-3.59 (m, 1H), 3.57-3.54 (m, 2H), 3.12 (s, 3H), 2.74-2.59 (m, 2H), 2.44-2.36 (m, 1H), 2.20-2.13 (m, 1H), 1.48 (d, J = 8.0 Hz, 3H) |

TABLE 2-continued

| Compound | General Procedure No. | MS Data | NMR Data |
|---|---|---|---|
| Example S39<br>3-(6-(4-(5-chloro-4-((1-methyl-2-oxoindolin-5-yl)amino)pyrimidin-2-yl)-5-methyl-2-oxopiperazin-1-yl)-1-methyl-1H-indazol-3-yl)piperidine-2,6-dione (39) | 2,‡ 4, 5, 6<br>‡ 10 mol % Pd$_2$(dba)$_3$, 20 mol % Xantphos, Cs$_2$CO$_3$ (1.5 equiv), 1,4-dioxane, 100° C. | Required 627.2, Found 628.2 [M + H]$^+$ | $^1$H NMR (400 MHz, DMSO-d$_6$): δ 10.92 (s, 1H), 8.83 (s, 1H), 8.12 (s, 1H), 7.72 (d, J = 8.8 Hz, 1H), 7.60-7.58 (m, 2H), 7.53-7.50 (m, 1H), 7.10 (d, J = 8.8 Hz, 1H), 6.96 (d, J = 8.4 Hz, 1H), 4.76-4.72 (m, 1H), 4.56-4.48 (m, 1H), 4.43-4.35 (m, 1H), 4.20-4.13 (m, 1H), 4.06-3.99 (m, 1H), 3.98 (s, 3H), 3.67-3.64 (m, 1H), 3.56 (s, 2H), 3.12 (s, 3H), 2.72-2.61 (m, 1H), 2.41-2.29 (m, 1H), 2.20-2.15 (m, 1H), 1.33 (d, J = 6.4 Hz, 3H). |
| Example S40<br>3-(6-(4-((5-Chloro-4-((1-methyl-2-oxoindolin-5-yl)amino)pyrimidin-2-yl)amino)piperidin-1-yl)-1-methyl-1H-indazol-3-yl)piperidine-2,6-dione (40) | 2,‡ 4, 5, 6<br>‡ 10 mol % RuPhos-Pd-G3 Cs$_2$CO$_3$ (2.0 equiv), 1,4-dioxane, 100° C. | Required 613.2, Found 614.0 [M + H]$^+$ | $^1$H NMR (DMSO-d$_6$, 400 MHz) δ 10.7-10.9 (m, 1H), 8.0-8.2 (m, 1H), 7.5-7.7 (m, 3H), 7.23 (s, 2H), 7.10 (s, 2H), 6.97 (s, 5H), 4.2-4.3 (m, 1H), 3.90 (s, 3H), 3.8-3.8 (m, 2H), 3.12 (s, 3H), 2.7-2.9 (m, 2H), 2.62 (s, 2H), 2.3-2.3 (m, 1H), 2.1-2.2 (m, 1H), 1.9-2.0 (m, 2H), 1.6-1.7 (m, 2H) |

TABLE 2-continued

| Compound | General Procedure No. | MS Data | NMR Data |
|---|---|---|---|
| 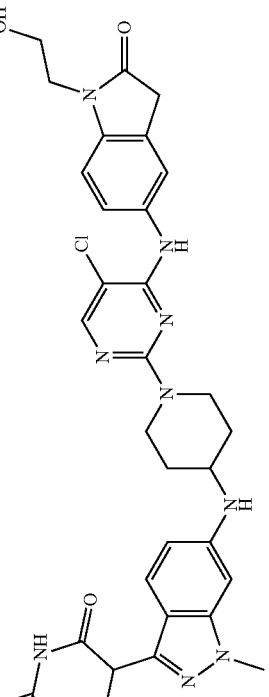<br>Example S41<br>3-[6-[[1-[5-chloro-4-[[1-(2-hydroxyethyl)-2-oxo-indolin-5-yl]amino]pyrimidin-2-yl]-4-piperidyl]amino]-1-methyl-indazol-3-yl]piperidine-2,6-dione (41) | 2,‡ 4, 5, 6<br>‡ 10 mol %<br>RuPhos-Pd-G3<br>$Cs_2CO_3$<br>(2.0 equiv),<br>1,4-dioxane,<br>100° C. | Required 643.2, Found 644.3 $[M + H]^+$ | $^1$H NMR (500 MHz, DMSO) δ 10.81 (s, 1H), 8.63 (s, 1H), 8.01 (s, 1H), 7.53 (s, 1H), 7.49 (d, J = 8.5 Hz, 1H), 7.32 (d, J = 8.7 Hz, 1H), 6.99 (d, J = 8.4 Hz, 1H), 6.51 (d, J = 8.7 Hz, 1H), 6.46 (s, 1H), 5.77 (d, J = 8.0 Hz, 1H), 4.80 (br, 1H), 4.44-4.31 (m, 2H), 4.18 (dd, J = 8.6, 5.1 Hz, 1H), 3.82 (s, 3H), 3.70 (t, J = 5.8 Hz, 2H), 3.66-3.60 (m, 1H), 3.57 (t, J = 5.7 Hz, 2H), 3.53 (s, 2H), 3.11 (t, J = 11.8 Hz, 2H), 2.65-2.56 (m, 2H), 2.30-2.21 (m, 1H), 2.19-2.10 (m, 1H), 2.04-1.95 (m, 2H), 1.38-1.26 (m, 2H) |
| 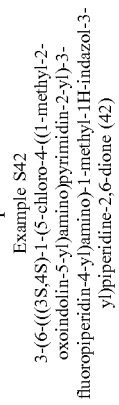<br>Example S42<br>3-(6-(((3S,4S)-1-(5-chloro-4-((1-methyl-2-oxoindolin-5-yl)amino)pyrimidin-2-yl)-3-fluoropiperidin-4-yl)amino)-1-methyl-1H-indazol-3-yl)piperidine-2,6-dione (42) | 2,‡ 4, 5, 6<br>‡ 10 mol %<br>XPhos-Pd-G3<br>$Cs_2CO_3$<br>(2.0 equiv),<br>1,4-dioxane,<br>100° C. | Requires 631.2, found 632.2 $[M + H]^+$ | $^1$H NMR (DMSO-$d_6$, 400 MHz) δ 10.8-10.9 (m, 1H), 8.7-9.0 (m, 1H), 8.08 (s, 1H), 7.4-7.6 (m, 2H), 7.3-7.4 (m, 1H), 6.8-7.0 (m, 1H), 6.5-6.6 (m, 2H), 4.5-4.6 (m, 1H), 4.4-4.5 (m, 1H), 4.3-4.3 (m, 2H), 4.2-4.2 (m, 1H), 4.1-4.1 (m, 1H), 3.9-3.9 (m, 1H), 3.83 (s, 3H), 3.5-3.6 (m, 3H), 3.3-3.5 (m, 1H), 3.11 (s, 3H), 2.6-2.6 (m, 1H), 2.2-2.3 (m, 1H), 2.1-2.2 (m, 2H), 1.4-1.5 (m, 1H) |

TABLE 2-continued

| Compound | General Procedure No. | MS Data | NMR Data |
|---|---|---|---|
| Example S43 3-(6-(((3R,4S)-1-(5-Chloro-4-((1-methyl-2-oxoindolin-5-yl)amino)pyrimidin-2-yl)-3-fluoropiperidin-4-yl)amino)-1-methyl-1H-indazol-3-yl)piperidine-2,6-dione (43) | 2,‡ 4, 5, 6 ‡ 10 mol % XPhos-Pd-G3 Cs₂CO₃ (2.0 equiv), 1,4-dioxane, 100° C. | Requires 631.2, found 632.2 [M + H]⁺ | ¹H NMR (DMSO-d₆, 400 MHz) δ 10.7-10.9 (m, 1H), 8.6-8.7 (m, 1H), 8.02 (s, 1H), 7.5-7.6 (m, 2H), 7.3-7.4 (m, 1H), 6.9-7.0 (m, 1H), 6.5-6.7 (m, 2H), 5.8-5.9 (m, 1H), 4.8-5.0 (m, 2H), 4.5-4.7 (m, 1H), 4.1-4.3 (m, 1H), 3.84 (s, 4H), 3.5-3.6 (m, 2H), 3.1-3.2 (m, 1H), 3.1-3.1 (m, 3H), 3.0-3.1 (m, 1H), 2.6-2.6 (m, 1H), 2.1-2.3 (m, 3H), 1.8-1.8 (m, 1H), 1.6-1.7 (m, 1H) |
| Example S44 3-(6-(((3S,4R)-1-(5-chloro-4-((1-methyl-2-oxoindolin-5-yl)amino)pyrimidin-2-yl)-3-fluoropiperidin-4-yl)amino)-1-methyl-1H-indazol-3-yl)piperidine-2,6-dione (44) | 2,‡ 4, 5, 6 ‡ 10 mol % XPhos-Pd-G3 Cs₂CO₃ (2.0 equiv), 1,4-dioxane, 100° C. | Requires 631.2, found 632.2 [M + H]⁺ | ¹H NMR (400 MHz, DMSO-d6) δ ppm 10.83 (s, 1H), 8.69 (s, 1H), 8.01 (s, 1H), 7.47-7.55 (m, 2H), 7.35 (br d, J = 8.80 Hz, 1H), 6.88-7.04 (m, 2H), 6.51-6.67 (m, 2H), 5.86 (br d, J = 8.93 Hz, 1H), 4.79-5.07 (m, 2H), 4.57 (br s, 1H), 4.19 (br dd, J = 8.50, 5.07 Hz, 1H), 3.83 (s, 3H), 3.53-3.60 (m, 3H), 3.11 (s, 3H), 3.02 (br t, J = 12.72 Hz, 1H), 2.60 (br s, 2H), 2.09-2.29 (m, 2H), 1.76-1.87 (m, 1H), 1.56-1.76 (m, 1H) |

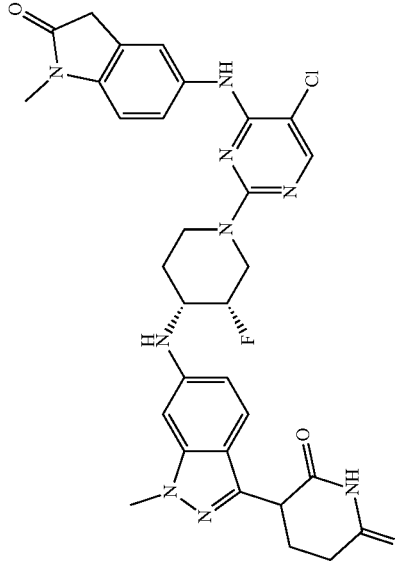

TABLE 2-continued

| Compound | General Procedure No. | MS Data | NMR Data |
|---|---|---|---|
| Example S45<br>3-(6-(((3R,4R)-1-(5-chloro-4-((1-methyl-2-oxoindolin-5-yl)amino)pyrimidin-2-yl)-3-fluoropiperidin-4-yl)amino)-1-methyl-1H-indazol-3-yl)piperidine-2,6-dione (45) | 2,‡ 4, 5, 6<br>‡ 20 mol %<br>RuPhos-Pd-G3<br>Cs$_2$CO$_3$<br>(2.0 equiv),<br>1,4-dioxane,<br>90° C. | Requires 631.2, found 632.3 [M + H]$^+$ | $^1$H NMR (500 MHz, DMSO-d$_6$) δ 10.82 (s, 1H), 8.75 (s, 1H), 8.04 (s, 1H), 7.52 (s, 1H), 7.49 (d, J = 8.7 Hz, 1H), 7.35 (d, J = 8.9 Hz, 1H), 6.94 (d, J = 8.1 Hz, 1H), 6.56 (d, J = 9.3 Hz, 1H), 6.53 (s, 1H), 5.97 (d, J = 7.4 Hz, 1H), 4.57-4.41 (m, 1H), 4.39-4.27 (m, 1H), 4.23-4.16 (m, 1H), 4.12-4.04 (m, 1H), 3.92-3.84 (m, 1H), 3.82 (s, 3H), 3.53 (s, 2H), 3.51-3.46 (m, 2H), 3.10 (s, 3H), 2.65-2.57 (m, 2H), 2.31-2.21 (m, 1H), 2.19-2.11 (m, 1H), 2.11-2.03 (m, 1H), 1.48-1.37 (m, 1H) |
| Example S46<br>3-[6-[[(3R,4R)-1-[5-Chloro-4-[(1-methyl-2-oxo-indolin-5-yl)amino]pyrimidin-2-yl]-3-fluoro-4-piperidyl]-methyl-amino]-1-methyl-indazol-3-yl]piperidine-2,6-dione (46) | 2,‡ 3, 4, 5, 6<br>‡ 20 mol %<br>RuPhos-Pd-G3<br>Cs$_2$CO$_3$<br>(2.0 equiv),<br>1,4-dioxane,<br>90° C. | Requires 645.2, found 646.3 [M + H]$^+$ | $^1$H NMR (400 MHz, Acetic acid-d$_4$) δ 8.25 (s, 1H), 7.76 (s, 1H), 7.73 (d, J = 8.5 Hz, 1H), 7.64 (dd, J = 9.1, 3.0 Hz, 1H), 7.15-7.08 (m, 2H), 6.81 (s, 1H), 5.03-4.93 (m, 1H), 4.91-4.80 (m, 1H), 4.64 (d, J = 13.0 Hz, 1H), 4.57 (dd, J = 10.0, 5.4 Hz, 1H), 4.39-4.24 (m, 1H), 4.07 (s, 3H), 3.80 (s, 2H), 3.37 (s, 3H), 3.34-3.23 (m, 2H), 3.06 (s, 3H), 3.00-2.90 (m, 2H), 2.69-2.58 (m, 1H), 2.51-2.43 (m, 1H), 2.11-1.99 (m, 2H).<br>Note:<br>exchangeable protons and one aromatic proton not visible. |

TABLE 2-continued

| Compound | General Procedure No. | MS Data | NMR Data |
|---|---|---|---|
| Example S47<br>3-(6-((1-(5-chloro-4-((1-methyl-2-oxoindolin-5-yl)amino)pyrimidin-2-yl)-5-methylazepan-4-yl)amino)-1-methyl-1H-indazol-3-yl)piperidine-2,6-dione (47) | 2,‡ 4, 6‡‡<br>‡ 10 mol % RuPhos-Pd-G3<br>NaO^tBu (3.0 equiv), PhMe, 100° C.<br>‡‡ Diasteromeric separation | Requires 642.3, found 642.2 [M + H]+ | 1H-NMR (400 MHz, DMSO-d6): δ 10.81 (s, 1H), 8.17 (d, J = 8.00 Hz, 1H), 7.54-7.61 (m, 1H), 7.33 (t, J = 4.00 Hz, 2H), 6.65 (d, J = 8.00 Hz, 2H), 6.42 (s, 1H), 4.17 (s, 1H), 3.82 (s, 5H), 3.73 (d, J = 16.00 Hz, 3H), 3.49-3.64 (m, 4H), 3.13 (d, J = 16.00 Hz, 2H), 3.00 (s, 1H), 2.59 (s, 1H), 2.11-2.34 (m, 4H), δ 1.82 (s, 2H), 0.94 (d, J = 8.00 Hz, 3H). |
| Example S48<br>3-(6-((1-(5-chloro-4-((1-methyl-2-oxoindolin-5-yl)amino)pyrimidin-2-yl)-5-methylazepan-4-yl)amino)-1-methyl-1H-indazol-3-yl)piperidine-2,6-dione (Isomer 2) (48) | 2,‡ 4, 6‡‡<br>‡ 10 mol % RuPhos-Pd-G3<br>NaO^tBu (3.0 equiv), PhMe, 100° C.<br>‡‡ Diasteromeric separation | Requires 642.3, found 642.2 [M + H]+ | 1H-NMR (400 MHz, DMSO-d6): δ 10.83 (s, 1H), 8.58 (s, 1H), 8.02 (s, 1H), 7.53-7.65 (m, 2H), 7.30 (d, J = 8.40 Hz, 1H), 6.92 (d, J = 20.40 Hz, 1H), 6.76 (s, 1H), 6.58 (t, J = 4.80 Hz, 1H), 6.35 (s, 1H), 5.57 (q, J = 4.40 Hz, 1H), 4.17 (q, J = 5.60 Hz, 1H), 3.79 (s, 3H), 3.66-3.68 (m, 1H), 3.56 (t, J = 2.80 Hz, 3H), δ 3.48 (s, 5H), 3.05-3.12 (m, 4H), 2.61 (s, 4H), 1.13 (d, J = 806.80 Hz, 2H), 1.86-1.90 (m, 4H), 0.89 (d, J = 5.60 Hz, 3H). |

TABLE 2-continued

| Compound | General Procedure No. | MS Data | NMR Data |
|---|---|---|---|
| 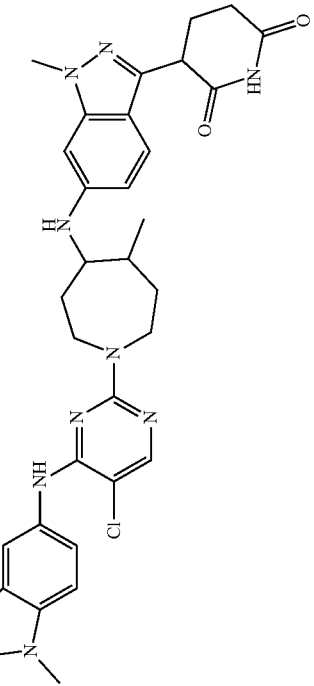<br>Example S49<br>3-(6-((1-(5-chloro-4-((1-methyl-2-oxoindolin-5-yl)amino)pyrimidin-2-yl)-5-methylazepan-4-yl)amino)-1-methyl-1H-indazol-3-yl)piperidine-2,6-dione (Isomer 1) (49) | 2,‡ 4, 6‡‡<br>‡ 10 mol % RuPhos-Pd-G3 NaO$^t$Bu (3.0 equiv), PhMe, 100° C.<br>‡‡ Diasteromeric separation | Requires 642.3, found 642.2 [M + H]$^+$ | $^1$H-NMR (400 MHz, DMSO-d$_6$): δ 10.83 (s, 1H), 8.60 (s, 1H), 8.02 (s, 1H), 7.59 (t, J = 8.80 Hz, 2H), 7.30 (d, J = 8.40 Hz, 1H), 6.86-6.95 (m, 1H), 6.51-6.56 (m, 1H), 6.30 (s, 1H), 3.30 (d, J = 2008.40 Hz, 1H), 4.17 (q, J = 5.20 Hz, 1H), 3.90 (t, J = 3.20 Hz, 1H), 3.78 (s, 1H), 3.50 (s, 6H), 3.07 (d, J = 3.60 Hz, 4H), 8 2.61 (d, J = 2.00 Hz, 4H), 2.25 (q, J = 6.00 Hz, 1H), 2.15 (q, J = 7.20 Hz, 1H), 2.08 (s, 1H), 1.92-1.96 (m, 2H), 1.59-1.77 (m, 1H), 0.99 (d, J = 6.80 Hz, 3H |
| 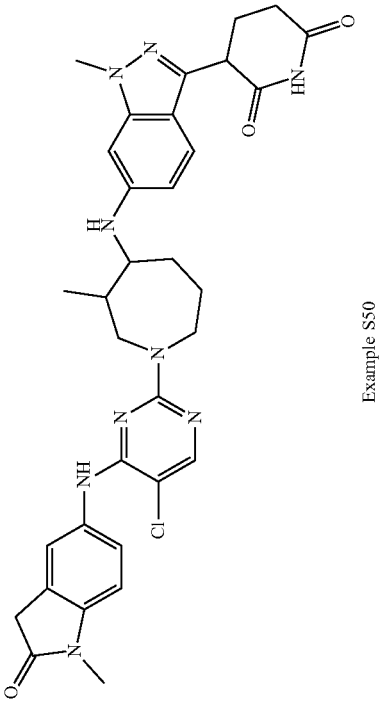<br>Example S50<br>3-(6-((1-(5-chloro-4-((1-methyl-2-oxoindolin-5-yl)amino)pyrimidin-2-yl)-3-methylazepan-4-yl)amino)-1-methyl-1H-indazol-3-yl)piperidine-2,6-dione (Isomer 1) (50) | 2,‡ 4, 6‡‡<br>‡ 10 mol % CPhos-Pd-G3 NaO$^t$Bu (3.0 equiv), PhMe, 100° C.<br>‡‡ Diasteromeric separation | Requires 642.3, found 642.3 [M + H]$^+$ | $^1$H-NMR (400 MHz, DMSO-d$_6$): δ 10.83 (s, 1H), 8.61 (s, 1H), 8.03 (s, 1H), 7.65 (s, 1H), 7.58 (d, J = 8.40 Hz, 1H), 7.31 (d, J = 8.80 Hz, 1H), 6.91 (s, 1H), 6.61 (q, J = 4.40 Hz, 2H), 6.26 (s, 1H), 5.68 (d, J = 7.20 Hz, 1H), 4.15-4.18 (m, 2H), 3.89 (d, J = 11.20 Hz, 2H), 3.75 (d, J = 15.60 Hz, 2H), 3.09 (s, 4H), 8 2.51 (d, J = 2.00 Hz, 2H), 2.25 (q, J = 4.80 Hz, 2H), 2.08-2.16 (m, 1H), 1.95 (s, 1H), 1.76 (s, 3H), 1.47 (s, 1H), 0.85 (s, 3H). |

TABLE 2-continued

| Compound | General Procedure No. | MS Data | NMR Data |
|---|---|---|---|
| 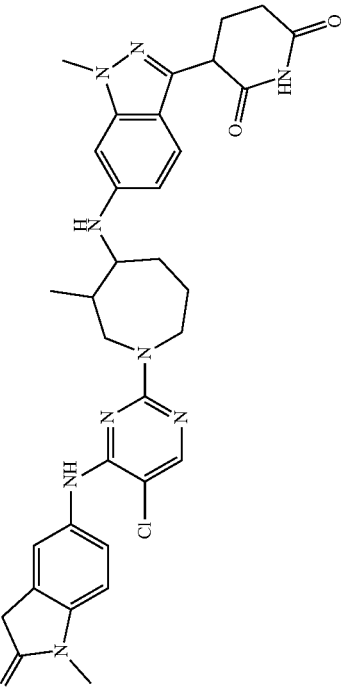<br>Example S51<br>3-(6-((1-(5-chloro-4-((1-methyl-2-oxoindolin-5-yl)amino)pyrimidin-2-yl)-3-methylazepan-4-yl)amino)-1-methyl-1H-indazol-3-yl)piperidine-2,6-dione (Isomer 2) (51) | 2,‡ 4, 6‡‡<br>‡ 10 mol % CPhos-Pd-G3 NaO$^t$Bu (3.0 equiv), PhMe, 100° C.<br>‡‡ Diasteromeric separation | Requires 642.3, found 642.2 [M + H]$^+$ | $^1$H-NMR (400 MHz, DMSO-d6): δ 10.83 (s, 1H), 8.57 (s, 1H), 7.95 (s, 1H), 7.60 (s, 1H), 7.29 (d, J = 8.80 Hz, 2H), 6.94 (s, 1H), 6.50 (s, 1H), 6.28 (s, 1H), 5.40 (d, J = 8.40 Hz, 2H), 4.03 (d, J = 7.20 Hz, 2H), 3.80 (s, 4H), 3.11 (s, 4H), 2.34 (s, 1H), 2.09 (s, 1H), δ 1.93 (s, 4H), 1.80 (s, 4H), 0.90 (s, 5H). |

Example S52. Synthesis of 3-(6-((1-(5-chloro-4-((1-methyl-2-oxoindolin-5-yl)amino)pyrimidin-2-yl)piperidin-4-yl)amino)-1-methyl-1H-indazol-3-yl)piperidine-2,6-dione (52)

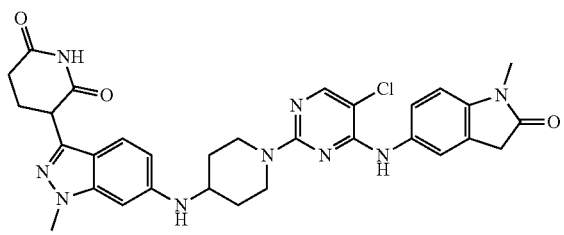

Step 1: Synthesis of 3-(6-((1-(5-Chloro-4-((1-methyl-2-oxoindolin-5-yl)amino)pyrimidin-2-yl)piperidin-4-yl)amino)-1-methyl-1H-indazol-3-yl)piperidine-2,6-dione. 3-[1-methyl-6-(4-piperidylamino)indazol-3-yl]piperidine-2,6-dione (40.3 mg, 0.120 mmol), 5-((5-chloro-2-fluoropyrimidin-4-yl)amino)-1-methylindolin-2-one (28.8 mg, 0.100 mmol), N,N-diisopropylethylamine (0.03 mL, 0.2000 mmol) and DMSO (0.1969 mL) were added to a 1 dram vial equipped with a stir bar and heated to 80° C. for overnight. The reaction mixture was filtered and purified by reverse-phased semi-preparative HPLC (10-100% acetonitrile+0.1% formic acid in water 0.1% formic acid, over 30 min). Fraction containing clean product were combined and lyophilized to give the title compound (3.0 mg, 0.0049 mmol, 4.9% yield) as an off white solid. LCMS $C_{31}H_{32}ClN_9O_3$ requires 613.2, found 614.2 [M+H]+; $^1$H NMR (DMSO-d6, 400 MHz) δ 10.7-10.8 (m, 1H), 8.5-8.6 (m, 1H), 7.95 (s, 1H), 7.45 (s, 2H), 7.2-7.3 (m, 1H), 6.8-6.9 (m, 1H), 6.4-6.5 (m, 3H), 5.7-5.7 (m, 1H), 4.2-4.4 (m, 2H), 4.0-4.1 (m, 1H), 3.75 (s, 3H), 3.5-3.6 (m, 1H), 3.4-3.5 (m, 2H), 3.03 (s, 5H), 2.5-2.6 (m, 1H), 2.0-2.2 (m, 3H), 1.9-2.0 (m, 2H), 1.2-1.3 (m, 2H).

Example S53. Synthesis of rel-(R)-3-(6-((1-(5-chloro-4-((1-methyl-2-oxoindolin-5-yl)amino)pyrimidin-2-yl)piperidin-4-yl)amino)-1-methyl-1H-indazol-3-yl)piperidine-2,6-dione (Single Isomer, Stereochemistry not Determined) (53)

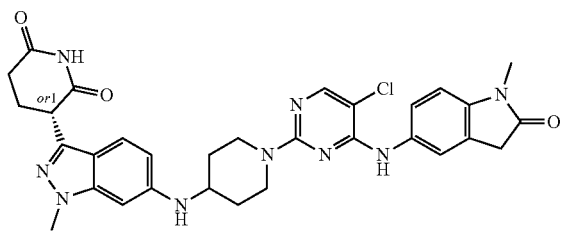 [SMILES: CN1C(=O)Cc2cc(Nc3nc(N4CCC(Nc5ccc6c([C@@H]7CCC(=O)NC7=O)nn(C)c6c5)CC4)ncc3Cl)ccc21]

Step 1: Synthesis of rel-(R)-3-(6-((1-(5-chloro-4-((1-methyl-2-oxoindolin-5-yl)amino)pyrimidin-2-yl)piperidin-4-yl)amino)-1-methyl-1H-indazol-3-yl)piperidine-2,6-dione. The product of Example S52 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=11.0 min. LCMS $C_{31}H_{32}ClN_9O_3$ requires 614.2, found 614.2 [M+H]+; $^1$H NMR (DMSO-d6, 400 MHz) δ 10.7-10.8 (m, 1H), 8.5-8.6 (m, 1H), 7.95 (s, 1H), 7.45 (s, 2H), 7.2-7.3 (m, 1H), 6.8-6.9 (m, 1H), 6.4-6.5 (m, 3H), 5.7-5.7 (m, 1H), 4.2-4.4 (m, 2H), 4.0-4.1 (m, 1H), 3.75 (s, 3H), 3.5-3.6 (m, 1H), 3.4-3.5 (m, 2H), 3.03 (s, 5H), 2.5-2.6 (m, 1H), 2.0-2.2 (m, 3H), 1.9-2.0 (m, 2H), 1.2-1.3 (m, 2H).

Example S54. Synthesis of rel-(S)-3-(6-((1-(5-chloro-4-((1-methyl-2-oxoindolin-5-yl)amino)pyrimidin-2-yl)piperidin-4-yl)amino)-1-methyl-1H-indazol-3-yl)piperidine-2,6-dione (Single Isomer, Stereochemistry not Determined) (54)

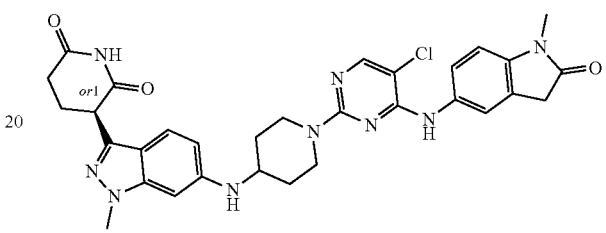

Step 1: Synthesis of rel-(S)-3-(6-((1-(5-chloro-4-((1-methyl-2-oxoindolin-5-yl)amino)pyrimidin-2-yl)piperidin-4-yl)amino)-1-methyl-1H-indazol-3-yl)piperidine-2,6-dione. The product of Example S52 was then separated using preparatory HPLC with a Regis Whelk-O1 SS, 21×250 mm, 5 column, 1 mL/min flow rate in 100% MeCN (no additives) isocratic elution at 22° C. The title compound was isolated as the first eluting peak, Rt=18.9 min. LCMS $C_{31}H_{32}ClN_9O_3$ requires 614.2, found 614.2 [M+H]+; $^1$H NMR (DMSO-d6, 400 MHz) δ 10.7-10.8 (m, 1H), 8.5-8.6 (m, 1H), 7.95 (s, 1H), 7.45 (s, 2H), 7.2-7.3 (m, 1H), 6.8-6.9 (m, 1H), 6.4-6.5 (m, 3H), 5.7-5.7 (m, 1H), 4.2-4.4 (m, 2H), 4.0-4.1 (m, 1H), 3.75 (s, 3H), 3.5-3.6 (m, 1H), 3.4-3.5 (m, 2H), 3.03 (s, 5H), 2.5-2.6 (m, 1H), 2.0-2.2 (m, 3H), 1.9-2.0 (m, 2H), 1.2-1.3 (m, 2H).

Example S55. Synthesis of 3-(6-(((3R,4R)-1-(5-chloro-4-((1-methyl-2-oxoindolin-5-yl)amino)pyrimidin-2-yl)-3-hydroxypiperidin-4-yl)amino)-1-methyl-1H-pyrazolo[3,4-b]pyridin-3-yl)piperidine-2,6-dione (55)

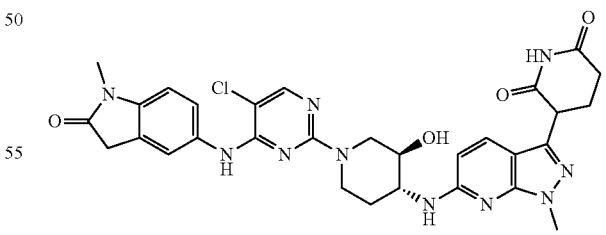

Step 1: Synthesis of 6-chloro-3-iodo-1-methyl-1H-pyrazolo[3,4-b]pyridine. To a 0° C. solution of 6-chloro-3-iodo-1H-pyrazolo[3,4-b]pyridine (1 g, 3.58 mmol) in DMF (20 mL) was added sodium hydride (0.150 g, 3.76 mmol), The reaction mixture was stirred for 30 min. Then sodium hydride (0.150 g, 3.76 mmol) was added dropwise. The reaction mixture was allowed to warm to room temperature and stirred and stirred for another hour. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered over celite, and concentrated. The crude was purified by silica gel column chromatography (0-100% ethyl acetate in hexane). Concentration of the desired fractions under reduced pressure afforded the title compound (0.75 g, 2.56 mmol, 71% yield) as white solid; MS (ESI) m/z 293.8 [M+H]+; 1H NMR (400 MHz, DMSO-d6) δ ppm 8.59 (s, 1H), 7.92 (s, 1H), 4.06 (d, J=0.98 Hz, 3H).

Step 2: Synthesis of 3-(2,6-bis(benzyloxy)pyridin-3-yl)-6-chloro-1-methyl-1H-pyrazolo[3,4-b]pyridine. The solution of 6-chloro-3-iodo-1-methyl-1H-pyrazolo[3,4-b]pyridine (500 mg, 1.704 mmol), (2,6-bis(benzyloxy)pyridin-3-yl)boronic acid (628 mg, 1.874 mmol) and sodium carbonate (379 mg, 3.58 mmol) in 1,4-dioxane (6 mL) and water (2 mL) was stirred with tetrakis(triphenylphosphine)palladium (0) (197 mg, 0.170 mmol) at 100° C. for 15 h. After this tie, the reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered over celite, and concentrated. The crude was purified by silica gel column chromatography (0-50% ethyl acetate in hexane). Concentration of the desired fractions under reduced pressure afforded the title compound (520 mg, 1.14 mmol, 67% yield) as white solid; MS (ESI) m/z 456.8 [M+H]+; 1H NMR (400 MHz, DMSO-d6) δ ppm 8.25 (d, J=8.44 Hz, 1H), 8.02 (d, J=8.07 Hz, 1H), 7.45-7.51 (m, 2H), 7.28-7.44 (m, 8H), 7.11 (d, J=8.44 Hz, 1H), 6.62 (d, J=8.19 Hz, 1H), 5.49 (s, 2H), 5.44 (s, 2H), 4.04 (s, 3H).

Step 3: Synthesis of tert-butyl (3R,4R)-4-((3-(2,6-bis(benzyloxy)pyridin-3-yl)-1-methyl-1H-pyrazolo[3,4-b]pyridin-6-yl)amino)-3-hydroxypiperidine-1-carboxylate. To a solution of 3-(2,6-bis(benzyloxy)pyridin-3-yl)-6-chloro-1-methyl-1H-pyrazolo[3,4-b]pyridine (500 mg, 1.094 mmol), RuPhos Pd G3 (92 mg, 0.109 mmol) and tert-butyl (3R,4R)-4-amino-3-hydroxypiperidine-1-carboxylate (237 mg, 1.094 mmol) in 1,4-dioxane (5 mL) was added cesium carbonate (713 mg, 2.189 mmol). The reaction mixture was degassed with argon for 1 min and then stirred at 100° C. for 15 h. LCMS indicated the reaction was complete. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered over celite, and concentrated. The crude was purified by silica gel column chromatography (0-100% ethyl acetate in hexane). Concentration of the desired fractions under reduced pressure afforded the crude. The crude was further purified by reveres-phased semi-preparative HPLC (10-100% acetonitrile+0.1% TFA in water 0.1% TFA, over 30 min). Fraction containing clean product were combined and lyophilized to give the title compound (120 mg, 0.188 mmol, 17% yield) as white solid; MS (ESI) m/z 636.8 [M+H]+; 1H NMR (400 MHz, DMSO-d6) δ ppm 7.95 (d, J=8.07 Hz, 1H), 7.65 (d, J=8.93 Hz, 1H), 7.43-7.50 (m, 2H), 7.28-7.43 (m, 8H), 6.97 (d, J=7.09 Hz, 1H), 6.56 (d, J=8.07 Hz, 1H), 6.24 (d, J=8.93 Hz, 1H), 5.46 (s, 2H), 5.39-5.44 (m, 2H), 5.18 (d, J=4.65 Hz, 1H), 3.71-3.98 (m, 6H), 3.40 (tt, J=9.00, 4.63 Hz, 1H), 2.94 (br d, J=1.47 Hz, 1H), 2.69-2.85 (m, 1H), 1.99-2.15 (m, 1H), 1.41 (s, 9H), 1.24-1.34 (m, 1H).

Step 4: Synthesis of 3-(6-(((3R,4R)-3-hydroxypiperidin-4-yl)amino)-1-methyl-1H-pyrazolo[3,4-b]pyridin-3-yl)piperidine-2,6-dione. The solution of tert-butyl (3R,4R)-4-((3-(2,6-bis(benzyloxy)pyridin-3-yl)-1-methyl-1H-pyrazolo[3,4-b]pyridin-6-yl)amino)-3-hydroxypiperidine-1-carboxylate (0.120 g, 0.188 mmol) in ethanol (10 mL) was stirred with palladium on carbon 10% w/w (0.020 g, 0.019 mmol) under hydrogen (1 atm) at 50° C. for 15 h. The reaction mixture was filtered through celite, the filtrate was concentrated and the residue was then stirrer with 1 mL TFA in DCM (1 mL) for 30 min at room temperature. The volatiles were removed under reduced pressure to give the desired product (67 mg, 0.187 mmol, 99% yield) as TFA salt which was used without further purification.

Step 5: Synthesis of 3-(6-(((3R,4R)-1-(5-chloro-4-((1-methyl-2-oxoindolin-5-yl)amino)pyrimidin-2-yl)-3-hydroxypiperidin-4-yl)amino)-1-methyl-1H-pyrazolo[3,4-b]pyridin-3-yl)piperidine-2,6-dione. A solution of 3-(6-(((3R,4R)-3-hydroxypiperidin-4-yl)amino)-1-methyl-1H-pyrazolo[3,4-b]pyridin-3-yl)piperidine-2,6-dione (68 mg, 0.190 mmol) and 5-((5-chloro-2-fluoropyrimidin-4-yl)amino)-1-methylindolin-2-one (55.5 mg, 0.190 mmol) in DMSO (3 mL) was added DIPEA (0.10 mL, 0.57 mmol). The reaction mixture was stirred at 80° C. for 16 hours. The reaction mixture was filtered and purified by reveres-phased semi-preparative HPLC (10-100% acetonitrile+0.1% formic acid in water 0.1% formic acid, over 30 min). Fraction containing clean product were combined and lyophilized to give the title compound (3.7 mg, 5.86 μmol, 3.09% yield) as white solid; MS (ESI) m/z 630.8 [M+H]+; 1H NMR (400 MHz, DMSO-d6) δ ppm 10.83 (s, 1H), 8.68 (s, 1H), 8.02 (s, 1H), 7.65 (d, J=8.68 Hz, 1H), 7.54 (s, 1H), 7.50 (dd, J=8.44, 2.20 Hz, 1H), 6.99 (br d, J=7.21 Hz, 1H), 6.94 (d, J=8.44 Hz, 1H), 6.37 (d, J=8.80 Hz, 1H), 5.16 (dd, J=5.07, 1.77 Hz, 1H), 4.39-4.53 (m, 1H), 4.24-4.38 (m, 1H), 4.14 (dd, J=9.35, 5.07 Hz, 1H), 3.89-4.02 (m, 1H), 3.77 (s, 3H), 3.54 (s, 2H), 3.44 (tt, J=9.25, 4.88 Hz, 1H), 3.29 (s, 1H), 3.11 (s, 3H), 3.05 (br t, J=11.19 Hz, 1H), 2.88 (dd, J=12.78, 9.60 Hz, 1H), 2.55-2.64 (m, 2H), 2.21-2.31 (m, 1H), 2.06-2.20 (m, 2H), 1.26-1.42 (m, 1H).

Example S56. Synthesis of 3-(6-(((3R,4R)-1-(5-chloro-4-((3,3-difluoro-1-methyl-2-oxoindolin-5-yl)amino)pyrimidin-2-yl)-3-methylpiperidin-4-yl)amino)-1-methyl-1H-indazol-3-yl)piperidine-2,6-dione (56)

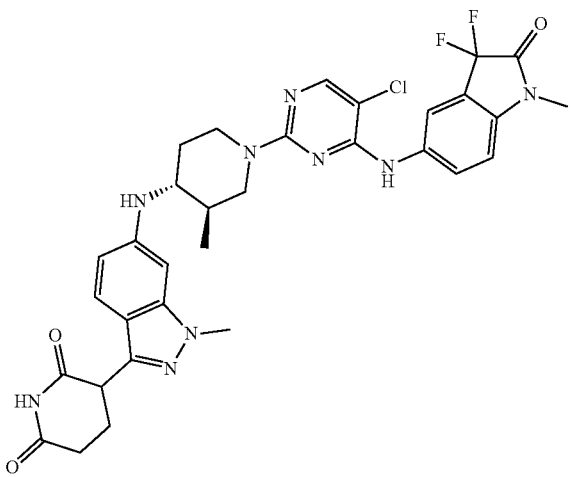 [SMILES: C[C@@H]1CN(c2ncc(Cl)c(Nc3ccc4c(c3)C(F)(F)C(=O)N4C)n2)CC[C@H]1Nc1ccc2c(C3CCC(=O)NC3=O)nn(C)c2c1]

Step 1: Synthesis of 3,3-difluoro-5-nitroindolin-2-one. To a −78° C. suspension of 5-nitroindoline-2,3-dione (2.2 g, 11.5 mmol) in dichloromethane (50 mL) was added diethylaminosulfur trifluoride (4.06 g, 25.2 mmol) dropwise. The reaction mixture was allowed warm up to room temperature and stirred for 2 days. LCMS indicated the reaction was complete. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried (anhydrous magnesium sulfate), filtered over celite, and concentrated. The crude was purified by silica gel column chromatography (0-75% ethyl acetate in hexane). Concentration of the desired fractions under reduced pressure afforded the title compound 3,3-difluoro-5-nitroindolin-2-one (1.52 g, 7.10 mmol, 62.0% yield) as yellow solid; MS (ESI) m/z 215.2 [M+H]$^+$; $^1$H NMR (400 MHz, DMSO-d6) δ ppm 11.89 (br s, 1H), 8.56-8.60 (m, 1H), 8.43 (d, J=8.78 Hz, 1H), 7.20 (d, J=8.68 Hz, 1H).

Step 2: Synthesis of 3,3-difluoro-1-methyl-5-nitroindolin-2-one. To a solution of 3,3-difluoro-5-nitroindolin-2-one (0.53 g, 2.475 mmol) in DMF (1 mL) as added DBU (0.485 mL, 3.22 mmol) followed by iodomethane (0.185 mL, 2.97 mmol). The reaction mixture was stirred at room temperature for 15 hours. The reaction mixture was quenched with saturated aqueous sodium chloride (25 mL) and then extracted with ethyl acetate (3×50 mL). The organic phase was combined and washed with saturated aqueous sodium chloride (1×25 mL). The organic layer was dried (anhydrous magnesium sulfate), filtered over celite, and concentrated. The crude was purified by silica gel column chromatography (0-80% ethyl acetate in hexane). Concentration of the desired fractions under reduced pressure afforded the title compound (0.339 g, 1.485 mmol, 60% yield) as yellow solid; MS (ESI) m/z 229.2 [M+H]$^+$; $^1$H NMR (400 MHz, DMSO-d6) δ ppm 8.61 (d, J=1.96 Hz, 1H), 8.54 (d, J=8.91 Hz, 1H), 7.46 (d, J=8.80 Hz, 1H), 3.25 (s, 3H).

Step 3: Synthesis of 5-amino-3,3-difluoro-1-methylindolin-2-one. A suspension of 3,3-difluoro-1-methyl-5-nitroindolin-2-one (360 mg, 1.578 mmol) in ethanol (15 mL) was stirred under hydrogen (45 psi) at room temperature for 15 h. To the reaction mixture was filtered over celite. Concentration of the filtrate under reduced pressure afforded the title compound (300 mg, 1.514 mmol, 96% yield) as yellow solid; MS (ESI) m/z 199.2 [M+H]$^+$; $^1$H NMR (400 MHz, DMSO-d6) δ ppm 6.90 (d, J=8.44 Hz, 1H), 6.87 (d, J=1.96 Hz, 1H), 6.75 (d, J=7.91 Hz, 1H), 5.22 (s, 2H), 3.09 (s, 3H).

Step 4: Synthesis of 3-(6-(((3R,4R)-1-(5-chloro-4-((3,3-difluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The synthesis of the title compound was accomplished using General Procedures 1 and 6 using 5-amino-3,3-difluoro-1-methylindolin-2-one and 3-(1-methyl-6-(((3R,4R)-3-methylpiperidin-4-yl)amino)-1H-indazol-3-yl)piperidine-2,6-dione hydrochloride as staring materials. The reaction mixture was filtered and purified by reveres-phased semi-preparative HPLC (10-100% acetonitrile+0.1% formic acid in water 0.1% formic acid, over 30 min). Fraction containing clean product were combined and lyophilized to give the title compound (8 mg, 0.012 mmol, 23.46% yield) as yellow solid; MS (ESI) m/z 664.2 [M+H]$^+$; $^1$H NMR (400 MHz, DMSO-d6) δ ppm 10.81 (s, 1H), 8.94 (s, 1H), 8.03-8.14 (m, 2H), 7.77 (br d, J=8.56 Hz, 1H), 7.31 (d, J=8.80 Hz, 1H), 7.21 (d, J=8.44 Hz, 1H), 6.51 (br d, J=8.80 Hz, 1H), 6.44 (s, 1H), 5.70 (br d, J=8.80 Hz, 1H), 4.47 (br s, 2H), 4.17 (dd, J=8.62, 5.07 Hz, 1H), 3.81 (s, 3H), 3.17 (s, 3H), 3.04 (br t, J=12.10 Hz, 1H), 2.65-2.76 (m, 1H), 2.56-2.63 (m, 2H), 2.19-2.31 (m, 1H), 2.11-2.19 (m, 1H), 2.06 (br d, J=10.64 Hz, 1H), 1.46-1.66 (m, 1H), 1.07-1.28 (m, 2H), 0.96 (d, J=6.36 Hz, 3H).

Example S57. Synthesis of 3-[6-[[(3S,4R)-1-[5-Chloro-4-[(1-methyl-2-oxo-indolin-5-yl)amino]pyrimidin-2-yl]-3-(hydroxymethyl)-4-piperidyl]amino]-1-methyl-indazol-3-yl]piperidine-2,6-dione (57)

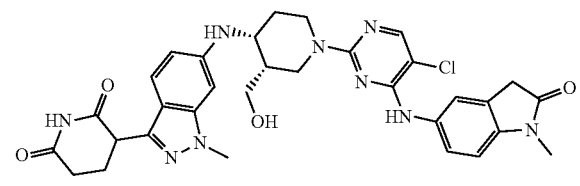 [SMILES: CN1C(=O)Cc2cc(Nc3nc(N4CC[C@@H](Nc5ccc6c(C7CCC(=O)NC7=O)nn(C)c6c5)[C@@H](CO)C4)ncc3Cl)ccc21]

Step 1: Synthesis of tert-Butyl 05-ethyl 4-[[(1R)-1-phenylethyl]amino]-3,6-dihydro-2H-pyridine-1,5-dicarboxylate. To a solution of 01-tert-butyl O3-ethyl 4-oxopiperidine-1,3-dicarboxylate (22 g, 81 mmol) and (1R)-1-phenylethanamine (12.5 mL, 97.2 mmol) in toluene (400 mL) was added PTSA (1.39 g, 8.1 mmol) and the mixture was heated to reflux with a Dean-Stark trap for 18 h. The mixture was cooled to rt, washed with a saturated aqueous solution of NaHCO$_3$ (2×200 mL) and brine (2×200 mL). The combined organic fractions were dried over MgSO$_4$, filtered and concentrated. The residue was filtered on a pad of silica, rinsed with DCM (2×100 mL) and concentrated to afford the title compound (30.2 g, 99%) as an oil, which was used in the next step without further purification. MS (ESI) [M+H]$^+$ 375.2. $^1$H NMR (400 MHz, CDCl$_3$) δ 9.25 (d, J=7.5 Hz, 1H), 7.36-7.28 (m, 2H), 7.26-7.18 (m, 3H), 4.66-4.54 (m, 1H), 4.24-4.14 (m, 2H), 4.07 (br s, 2H), 3.48-3.35 (m, 1H), 3.35-3.24 (m, 1H), 2.39 (dd, J=13.0, 6.2 Hz, 1H), 2.09-2.00 (m, 1H), 1.50 (d, J=6.8 Hz, 3H), 1.43 (s, 9H), 1.29 (t, J=7.0 Hz, 3H).

Step 2: Synthesis of tert-butyl O3-ethyl (3S,4R)-4-[[(1R)-1-phenylethyl]amino]piperidine-1,3-dicarboxylate and tert-butyl O3-ethyl (3R,4S)-4-[[(1R)-1-phenylethyl]amino]piperidine-1,3-dicarboxylate To a solution of tert-butyl 05-ethyl 4-[[(1R)-1-phenylethyl]amino]-3,6-dihydro-2H-pyridine-1,5-dicarboxylate (15 g, 40.1 mmol) in MeCN (200 mL) and AcOH (100 mL) cooled to 0° C. was added portion-wise sodium triacetoxyborohydride (34 g, 160 mmol) over 2 h, and the reaction mixture was stirred at 0° C. for 2 h. The mixture was then cooled to −10° C. and slowly treated with a 1 M aqueous solution of NaOH (100 mL), a 4 M aqueous solution of NaOH (100 mL), a 6 M aqueous solution of NaOH (100 mL), followed by a 50% aqueous solution of NaOH (50 mL). The mixture was warmed to rt and the layers were separated. The aqueous layer was extracted with DCM (3×80 mL). The combined organic layers were dried over MgSO$_4$, filtered, and concentrated under reduced pressure. The residue was purified by column chromatography on silica gel using a gradient of 0-50% EtOAc in hexanes to afford a 4:1 mixture of title compounds (14.8 g, 98%) as an oil. A portion (7 g) of the 4:1 mixture of title compounds was separated by SFC to afford tert-butyl O3-ethyl (3S,4R)-4-[[(1R)-1-phenylethyl]amino]piperidine-1,3-dicarboxylate (3.7 g) as an oil and title compound tert-butyl O3-ethyl (3R,4S)-4-[[(1R)-1-phenylethyl]amino]piperidine-1,3-dicarboxylate (1.1 g) as an oil.

Step 3: Synthesis of tert-butyl (3S,4R)-3-(hydroxymethyl)-4-[[(1R)-1-phenylethyl]amino]piperidine-1-carboxylate. To a solution of tert-butyl O3-ethyl (3S,4R)-4-[[(1R)-1-phenylethyl]amino]piperidine-1,3-dicarboxylate (500 mg, 1.33 mmol) in THF (3 mL) was added LiBH$_4$ (1.33 mL, 2.66 mmol), and the mixture was heated to reflux for 2 h, then cooled to rt. Ice-water (10 mL) was added and the mixture was concentrated under reduced pressure. The residue was extracted with EtOAc (3×30 mL). The combined organic fractions were dried over Na$_2$SO$_4$, filtered, and concentrated to afford the title compound (404 mg, 91%) as an oil, which was used in the next step without further purification. MS (ESI) [M+H]$^+$ 335.3.

Step 4: Synthesis of tert-Butyl (3S,4R)-3-[[tert-butyl (dimethyl)silyl]oxymethyl]-4-[[(1R)-1-phenylethyl]amino]piperidine-1-carboxylate. To a solution of tert-butyl (3S,4R)-3-(hydroxymethyl)-4-[[(1R)-1-phenylethyl]amino]piperidine-1-carboxylate (404 mg, 1.21 mmol) in DCM (5 mL) was added sequentially tert-butylchlorodimethylsilane (218 mg, 1.45 mmol) and imidazole (123 mg, 1.81 mmol), and the reaction mixture was stirred at rt for 3 h. Water (15 mL) and Et$_2$O (20 mL) were added and the layers were separated. The aqueous layer was washed with Et$_2$O (3×10 mL) and the combined organic fractions were dried over Na$_2$SO$_4$, filtered, and concentrated to afford the title compound (540 mg, 99%) as an oil, which was used in the next step without further purification. Note: SFC analysis confirmed the presence of only one diastereomer. MS (ESI) [M+H]$^+$ 449.4. $^1$H NMR (400 MHz, DMSO-d6) δ 7.35-7.26 (m, 4H), 7.23-7.16 (m, 1H), 3.86-3.68 (m, 3H), 3.68-3.54 (m, 1H), 3.48 (t, J=9.6 Hz, 1H), 2.89-2.68 (m, 1H), 2.81 (dd, J=13.1, 3.2 Hz, 1H), 2.59-2.52 (m, 1H), 1.82-1.72 (m, 1H), 1.36 (s, 9H), 1.34-1.27 (m, 1H), 1.26-1.18 (m, 1H), 1.22 (d, J=6.7 Hz, 3H), 0.90 (s, 9H), 0.07 (d, J=3.1 Hz, 6H).

Step 5: Synthesis of tert-butyl (3S,4R)-4-amino-3-[[tert-butyl(dimethyl)silyl]oxymethyl]piperidine-1-carboxylate. A mixture of tert-butyl (3S,4R)-3-[[tert-butyl(dimethyl)silyl]oxymethyl]-4-[[(1R)-1-phenylethyl]amino]piperidine-1-carboxylate (530 mg, 1.18 mmol), ammonium formate (596 mg, 9.45 mmol) and Pd/C (126 mg, 0.12 mmol) in EtOH (15 mL) was heated to 65° C. for 2 h. The mixture was filtered through celite and washed with MeOH (3×15 mL). The filtrate was concentrated under reduced pressure to afford the title compound (320 mg, 79%) as a solid, which was used in the next step without further purification. MS (ESI) [M+H]$^+$ 345.3. $^1$H NMR (400 MHz, DMSO-d6) δ 3.61 (dd, J=10.2, 4.9 Hz, 1H), 3.49-3.41 (m, 2H), 3.39-3.24 (m, 3H), 3.23-3.08 (m, 1H), 3.06-2.98 (m, 1H), 1.71-1.55 (m, 2H), 1.55-1.44 (m, 1H), 1.40-1.33 (m, 1H), 1.38 (s, 9H), 0.89-0.84 (m, 9H), 0.06-0.01 (m, 6H).

Step 6: Synthesis of tert-butyl (3S,4R)-3-[[tert-butyl(dimethyl) silyl]oxymethyl]-4-[[3-(2,6-dibenzyloxy-3-pyridyl)-1-methyl-indazol-6-yl]amino]piperidine-1-carboxylate. A mixture of 6-bromo-3-(2,6-dibenzyloxy-3-pyridyl)-1-methyl-indazole (471 mg, 0.94 mmol), tert-butyl (3S,4R)-4-amino-3-[[tert-butyl(dimethyl)silyl]oxymethyl] piperidine-1-carboxylate (270 mg, 0.78 mmol), Cs$_2$CO$_3$ (638 mg, 1.96 mmol) and RuPhos Pd G3 (98.3 mg, 0.12 mmol) in 1,4-dioxane (7 mL) was heated to 90° C. for 16 h and then cooled to rt. The residue was purified by column chromatography on silica gel using a gradient of 0-50% EtOAC in hexanes to afford the title compound (458 mg, 67%) as a solid. Note: the reaction was repeated and the crude residue combined before purification. MS (ESI) [M+H]$^+$ 764.4. $^1$H NMR (400 MHz, DMSO-d6) δ 7.87 (d, J=8.1 Hz, 1H), 7.50-7.44 (m, 2H), 7.42-7.26 (m, 9H), 6.55 (d, J=7.9 Hz, 1H), 6.52 (dd, J=9.0, 1.9 Hz, 1H), 6.45 (d, J=1.3 Hz, 1H), 5.78 (d, J=8.6 Hz, 1H), 5.44 (s, 2H), 5.41 (s, 2H), 3.88 (s, 3H), 3.85-3.77 (m, 1H), 3.67-3.61 (m, 1H), 3.60-3.41 (m, 4H), 3.39-3.32 (m, 1H), 2.10-2.00 (m, 1H), 1.67-1.53 (m, 2H), 1.41 (s, 9H), 0.82 (s, 9H), −0.05 (d, J=15.0 Hz, 6H).

Step 7: Synthesis of tert-Butyl (3S,4R)-3-[[tert-butyl(dimethyl)silyl]oxymethyl]-4-[[3-(2,6-dioxo-3-piperidyl)-1-methyl-indazol-6-yl]amino]piperidine-1-carboxylate. A mixture of tert-butyl (3S,4R)-3-[[tert-butyl(dimethyl)silyl] oxymethyl]-4-[[3-(2,6-dibenzyloxy-3-pyridyl)-1-methyl-indazol-6-yl]amino]piperidine-1-carboxylate (458 mg, 0.60 mmol) and Pearlman's catalyst (210 mg, 0.15 mmol) in EtOH (10 mL) and THF (10 mL) was subjected to hydrogenation (1 atm) at 50° C. for 2 h. The mixture was filtered through celite and washed with MeOH (3×15 mL). The filtrate was concentrated under reduced pressure to afford the title compound (350 mg, quant.) as a solid, which was used in the next step without further purification. MS (ESI) [M+H]$^+$ 586.4.

Step 8: Synthesis of 3-[6-[[(3S,4R)-3-(Hydroxymethyl)-4-piperidyl]amino]-1-methyl-indazol-3-yl]piperidine-2,6-dione dihydrochloride. To a solution of tert-butyl (3S,4R)-3-[[tert-butyl(dimethyl)silyl]oxymethyl]-4-[[3-(2,6-dioxo-3-piperidyl)-1-methyl-indazol-6-yl]amino]piperidine-1-carboxylate (350 mg, 0.60 mmol) in DCM (2.5 mL) was added 4N HCl in 1,4-dioxane (1.5 mL, 6.0 mmol) and the mixture was stirred for 2 h at rt. The resulting precipitate was collected by filtration, washed with Et$_2$O (3×5 mL) and dried under vacuum to afford the title compound (250 mg, 77%) as a solid, which was used in the next step without further purification. MS (ESI) [M+H]$^+$ 372.2. $^1$H NMR (500 MHz, DMSO-d6) δ 10.82 (s, 1H), 8.89-8.68 (m, 2H), 7.35 (d, J=8.8 Hz, 1H), 6.66 (dd, J=8.8, 1.7 Hz, 1H), 6.51 (s, 1H), 4.18 (dd, J=9.0, 5.1 Hz, 1H), 3.99-3.92 (m, 1H), 3.82 (s, 3H), 3.51-3.41 (m, 2H), 3.27-3.15 (m, 2H), 3.15-3.04 (m, 2H), 2.67-2.54 (m, 2H), 2.32-2.21 (m, 2H), 2.18-2.10 (m, 1H), 1.98-1.89 (m, 1H), 1.87-1.78 (m, 1H).

Step 9: Synthesis of 3-[6-[[(3S,4R)-1-[5-Chloro-4-[(1-methyl-2-oxo-indolin-5-yl)amino]pyrimidin-2-yl]-3-(hydroxymethyl)-4-piperidyl]amino]-1-methyl-indazol-3-yl]piperidine-2,6-dione. To a mixture of 5-[(5-chloro-2-fluoropyrimidin-4-yl)amino]-1-methyl-indolin-2-one (35 mg, 0.12 mmol) and DIPEA (0.10 mL, 0.60 mmol) in DMF (2 mL) at rt was added 3-[6-[[(3S,4R)-3-(hydroxymethyl)-4-piperidyl]amino]-1-methyl-indazol-3-yl]piperidine-2,6-dione dihydrochloride (77.8 mg, 0.14 mmol), and the reaction mixture was heated to 80° C. for 2 h. The volatiles were removed under reduced pressure and the residue was purified by preparative HPLC (BEH column, C18) using a gradient of 31-41% MeCN and 10 mM ammonium formate in water to afford the title compound (22.1 mg, 28%) as a solid. LCMS C$_{32}$H$_{34}$ClN$_9$O$_4$ requires 643.2, found 644.4

[M+H]⁺; ¹H NMR (500 MHz, DMSO-d₆) δ 10.81 (s, 1H), 8.61 (s, 1H), 8.00 (s, 1H), 7.75-7.57 (m, 1H), 7.52 (d, J=7.9 Hz, 1H), 7.33 (d, J=8.7 Hz, 1H), 6.90 (d, J=8.4 Hz, 1H), 6.65 (d, J=8.9 Hz, 1H), 6.48 (s, 1H), 5.85 (d, J=8.5 Hz, 1H), 4.46 (s, 1H), 4.18 (dd, J=8.4, 5.1 Hz, 1H), 3.96-3.85 (m, 2H), 3.81 (s, 3H), 3.80-3.75 (m, 1H), 3.75-3.63 (m, 2H), 3.52 (s, 2H), 3.51-3.46 (m, 1H), 3.09 (s, 3H), 2.66-2.55 (m, 2H), 2.31-2.21 (m, 1H), 2.20-2.11 (m, 1H), 2.11-2.02 (m, 1H), 1.79-1.69 (m, 1H), 1.67-1.56 (m, 1H).

Example S58. Synthesis of 3-(6-(((3R,4S)-1-(5-chloro-4-((1-methyl-2-oxoindolin-5-yl)amino)pyrimidin-2-yl)-3-(hydroxymethyl)piperidin-4-yl)amino)-1-methyl-1H-indazol-3-yl)piperidine-2,6-dione (58)

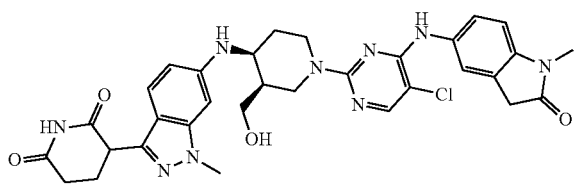 [SMILES: CN1C(=O)Cc2cc(Nc3nc(N4CC[C@H](Nc5ccc6c(C7CCC(=O)NC7=O)nn(C)c6c5)[C@H](CO)C4)ncc3Cl)ccc21]

Step 1: Synthesis of 3-(6-(((3R,4S)-1-(5-chloro-4-((1-methyl-2-oxoindolin-5-yl)amino)pyrimidin-2-yl)-3-(hydroxymethyl)piperidin-4-yl)amino)-1-methyl-1H-indazol-3-yl)piperidine-2,6-dione. The title compound was synthesized analogously to Example S57 beginning with the other diastereomer isolated from Example S57, Step 2. The crude reaction mixture was purified by preparative HPLC (BEH column, C18) using a gradient of 44-54% MeCN and 10 mM ammonium formate in water to afford title compound (5.5 mg, 14%) as a solid. LCMS C₃₂H₃₄ClN₉O₄ requires 643.2, found 644.3 [M+H]⁺; ¹H NMR (400 MHz, DMSO-d6) δ 8.61 (s, 1H), 8.00 (s, 1H), 7.66 (br s, 1H), 7.53 (d, J=8.5 Hz, 1H), 7.33 (d, J=8.8 Hz, 1H), 6.90 (d, J=8.4 Hz, 1H), 6.65 (dd, J=8.8, 1.7 Hz, 1H), 6.48 (s, 1H), 5.85 (d, J=8.5 Hz, 1H), 4.18 (dd, J=8.8, 5.1 Hz, 1H), 3.92-3.84 (m, 2H), 3.81 (s, 3H), 3.80-3.74 (m, 1H), 3.52 (s, 2H), 3.51-3.46 (m, 2H), 3.39-3.29 (m, 2H), 3.09 (s, 3H), 2.63-2.57 (m, 2H), 2.30-2.19 (m, 1H), 2.19-2.11 (m, 1H), 2.11-2.01 (m, 1H), 1.78-1.69 (m, 1H), 1.67-1.52 (m, 1H).

Example S59. Synthesis of 3-(6-(4-((5-chloro-4-((1-methyl-2-oxoindolin-5-yl)amino)pyrimidin-2-yl)(methyl)amino)piperidin-1-yl)-1-methyl-1H-pyrazolo[4,3-b]pyridin-3-yl)piperidine-2,6-dione (59)

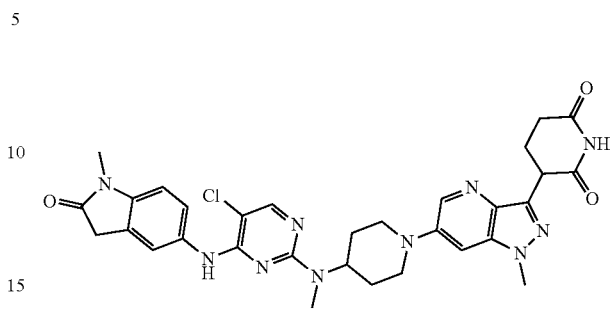

Step 1: Synthesis of 6-Bromo-3-iodo-1H-pyrazolo[4,3-b]pyridine. To a solution of 6-bromo-1H-pyrazolo[4,3-b]pyridine (3.75 g, 18.9 mmol) in MeCN (90 mL) was added NIS (5.11 g, 22.7 mmol). The reaction mixture was heated to 85° C. for 18 h and then cooled to rt. The volatiles were evaporated under reduced pressure and the residue was purified by column chromatography on silica gel using a gradient of 0-15% EtOAc in hexanes to afford title compound (6.05 g, 98%) as a solid. MS (ESI) [M+H]⁺ 324.0.

Step 2: Synthesis of 6-Bromo-3-iodo-1-methyl-pyrazolo[4,3-b]pyridine. The title compound was synthesized analogously to General Procedure 3 using 6-Bromo-3-iodo-1H-pyrazolo[4,3-b]pyridine as the starting material.

Step 3: Synthesis of 6-Bromo-3-(2,6-dibenzyloxy-3-pyridyl)-1-methyl-pyrazolo[4,3-b]pyridine. A mixture of 6-bromo-3-iodo-1-methyl-pyrazolo[4,3-b]pyridine (900 mg, 2.66 mmol), (2,6-dibenzyloxy-3-pyridyl)boronic acid (5.36 g, 7.99 mmol, intermediate provided by Celgene), Pd(PPh₃)₂Cl₂ (374 mg, 0.53 mmol) and a 2 M aqueous solution of Na₂CO₃ (2.66 mL, 5.33 mmol) in 1,4-dioxane (18 mL) was heated to 80° C. for 16 h and then cooled to rt. The volatiles were evaporated under reduced pressure and the residue was purified by column chromatography on silica gel using a gradient of 0-20% EtOAc in hexanes to afford title compound (835 mg, 62%) as a solid. MS (ESI) [M+H]⁺ 502.2.

Step 4: Synthesis of tert-Butyl N-[1-[3-(2,6-dibenzyloxy-3-pyridyl)-1-methyl-pyrazolo[4,3-b]pyridin-6-yl]-4-piperidyl]-N-methyl-carbamate. The title compound was synthesized according to General Procedure 2 using 6-Bromo-3-(2,6-dibenzyloxy-3-pyridyl)-1-methyl-pyrazolo[4,3-b]pyridine and tert-butyl N-methyl-N-(4-piperidyl)carbamate as starting materials in toluene.

Step 5: Synthesis of 3-(6-(4-((5-chloro-4-((1-methyl-2-oxoindolin-5-yl)amino)pyrimidin-2-yl)(methyl)amino)piperidin-1-yl)-1-methyl-1H-pyrazolo[4,3-b]pyridin-3-yl)piperidine-2,6-dione. The synthesis of the title compound was accomplished using General Procedures 4, 5, and 6 using tert-Butyl N-[1-[3-(2,6-dibenzyloxy-3-pyridyl)-1-methyl-pyrazolo[4,3-b]pyridin-6-yl]-4-piperidyl]-N-methyl-carbamate as the starting material. The crude reaction mixture was purified by preparative HPLC (BEH column, C18) using a gradient of 44-54% MeCN and 10 mM ammonium formate in water to afford title compound (5.4 mg, 12%) as a solid. LCMS C₃₁H₃₃ClN₁₀O₃ requires 628.2, found 629.3 [M+H]⁺; ¹H NMR (500 MHz, DMSO-d6) δ 10.89-10.82 (m, 1H), 8.59 (s, 1H), 8.41 (d, J=2.3 Hz, 1H), 8.03 (s, 1H), 7.65 (s, 1H), 7.57 (d, J=7.9 Hz, 1H), 7.37 (d, J=2.3 Hz, 1H), 6.95 (d, J=8.6 Hz, 1H), 4.28 (dd, J=9.8, 5.2 Hz, 1H), 3.97-3.91 (m, 5H), 3.55 (s, 2H), 3.28 (s, 2H), 3.08 (s, 3H), 2.92 (s, 3H), 2.87-2.72 (m, 2H), 2.72-2.64 (m, 1H), 2.62-2.55 (m, 1H), 2.22-2.10 (m, 1H), 1.97-1.84 (m, 2H), 1.76-1.66 (m, 2H).

Example S60. Synthesis of 3-(6-(4-((5-chloro-4-((1-methyl-2-oxoindolin-5-yl)amino)pyrimidin-2-yl)(methyl)amino)piperidin-1-yl)-1-methyl-1H-pyrazolo[4,3-c]pyridin-3-yl)piperidine-2,6-dione (60)

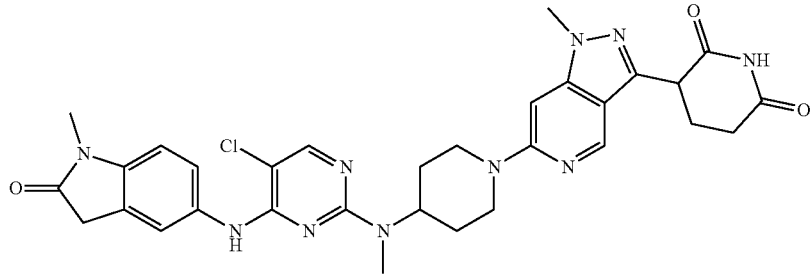 [SMILES: CN1C(=O)Cc2cc(Nc3nc(N(C)C4CCN(c5cc6c(cn5)c(C5CCC(=O)NC5=O)nn6C)CC4)ncc3Cl)ccc21]

Step 1: 6-Bromo-3-iodo-1H-pyrazolo[4,3-c]pyridine To a solution of 6-bromo-1H-pyrazolo[4,3-c]pyridine (3.5 g, 17.7 mmol) in MeCN (177 mL) was added NIS (7.95 g, 35.4 mmol). The reaction mixture was heated to 85° C. for 18 h and then cooled to rt. Water (50 mL) was added and the resulting precipitate was collected by filtration, washed with water (50 mL), DCM (50 mL), and dried under vacuum to afford the title compound (6.21 g, quant.) as a solid. MS (ESI) [M+H]$^+$ 325.8. $^1$H NMR (400 MHz, DMSO-d6) δ 8.44 (s, 1H), 7.57 (s, 1H).

Step 2: 6-Bromo-3-iodo-1-methyl-pyrazolo[4,3-c]pyridine. To a mixture of 6-bromo-3-iodo-1H-pyrazolo[4,3-c]pyridine (100 mg, 0.31 mmol) in DMF (2 mL) at 0° C. was added NaH (60% dispersion in mineral oil, 31 mg, 0.77 mmol), and the reaction mixture was stirred at 0° C. for 15 min. A solution of iodomethane (50 µL, 0.77 mmol) in DMF (1 mL) was added and the reaction was warmed to rt and stirred for 2 h. Water (20 mL) and DCM (20 mL) were added, and the layers were separated. The aqueous layer was extracted with DCM (2×20 mL). The combined organic fractions were washed with brine (40 mL), dried over MgSO$_4$, filtered, concentrated under reduced pressure. The residue was purified by column chromatography on silica gel using a gradient of 10-35% EtOAc in hexanes to afford the title compound (46 mg, 44%) as a solid. $^1$H NMR (400 MHz, DMSO-d$_6$) δ 8.58 (d, J=1.0 Hz, 1H), 8.09 (d, J=1.0 Hz, 1H), 4.05 (s, 3H).

Step 3: 6-Bromo-3-(2,6-dibenzyloxy-3-pyridyl)-1-methyl-pyrazolo[4,3-c]pyridine. A mixture of 6-bromo-3-iodo-1-methyl-pyrazolo[4,3-c]pyridine (100 mg, 0.30 mmol), (2,6-dibenzyloxy-3-pyridyl)boronic acid (595 mg, 0.89 mmol), Pd(PPh$_3$)$_2$Cl$_2$ (41.5 mg, 60 µmol) and a 2 M aqueous solution of Na$_2$CO$_3$ (300 µL, 0.59 mmol) in 1,4-dioxane (1.5 mL) was heated to 80° C. for 16 h and then cooled to rt. Water (40 mL) and EtOAc (40 mL) were added and the layers were separated. The aqueous layer was extracted with EtOAc (2×20 mL). The combined organic fractions were washed with brine (40 mL), dried (MgSO$_4$), filtered, and concentrated under reduced pressure. The residue was purified by column chromatography on silica gel using a gradient of 0-15% EtOAc in hexanes to afford the title compound (99.0 mg, 67%) as a solid. $^1$H NMR (400 MHz, DMSO-d$_6$) δ 8.87 (d, J=1.0 Hz, 1H), 8.09-7.96 (m, 2H), 7.49-7.44 (m, 2H), 7.43-7.39 (m, 2H), 7.38-7.33 (m, 3H), 7.33-7.24 (m, 3H), 6.63 (d, J=8.2 Hz, 1H), 5.52 (s, 2H), 5.44 (s, 2H), 4.06 (s, 3H).

Step 4: tert-Butyl N-[1-[3-(2,6-dibenzyloxy-3-pyridyl)-1-methyl-pyrazolo[4,3-c]pyridin-6-yl]-4-piperidyl]-N-methyl-carbamate. A mixture of 6-bromo-3-(2,6-dibenzyloxy-3-pyridyl)-1-methyl-pyrazolo[4,3-c]pyridine (1.44 g, 2.87 mmol), tert-butyl N-methyl-N-(4-piperidyl)carbamate (677 mg, 3.16 mmol), RuPhos-Pd-G3 (480 mg, 0.57 mmol) and NaOtBu (552 mg, 5.74 mmol) in 1,4-dioxane (58 mL) was heated to 90° C. for 16 h and then cooled to rt. The volatiles were evaporated under reduced pressure and the residue was purified by column chromatography on silica gel using a gradient of 0-40% EtOAc in hexanes to afford the title compound (1.08 g, 59%) as a solid. $^1$H NMR (400 MHz, DMSO-d$_6$) δ 8.71 (d, J=1.0 Hz, 1H), 7.97 (d, J=8.1 Hz, 1H), 7.51-7.43 (m, 2H), 7.43-7.33 (m, 5H), 7.33-7.23 (m, 3H), 6.72 (d, J=1.1 Hz, 1H), 6.58 (d, J=8.1 Hz, 1H), 5.51 (s, 2H), 5.40 (s, 2H), 4.47 (d, J=12.6 Hz, 2H), 3.93 (s, 3H), 2.82 (t, J=12.5 Hz, 2H), 2.72-2.66 (m, 1H), 2.64 (s, 3H), 1.80-1.52 (m, 4H), 1.40 (s, 9H).

Step 5: tert-Butyl N-[1-[3-(2,6-dioxo-3-piperidyl)-1-methyl-pyrazolo[4,3-c]pyridin-6-yl]-4-piperidyl]-N-methyl-carbamate. A mixture of tert-butyl N-[1-[3-(2,6-dibenzyloxy-3-pyridyl)-1-methyl-pyrazolo[4,3-c]pyridin-6-yl]-4-piperidyl]-N-methyl-carbamate (1.59 g, 1.88 mmol) and Pd(OH)$_2$/C (200 mg, 0.38 mmol) in THF (12.5 mL) and EtOH (12.5 mL) was subjected to hydrogenation (1 atm) at rt for 2 h. The mixture was filtered through celite and washed with DMF (60 mL). The filtrate was concentrated under reduced pressure and the residue was purified by column chromatography on silica gel using a gradient of 0-100% EtOAc in hexanes to afford the title compound (927 mg, quant.) as a solid. MS (ESI) [M+H]$^+$457.4.

Step 6: 3-[1-Methyl-6-[4-(methylamino)-1-piperidyl]pyrazolo[4,3-c]pyridin-3-yl]piperidine-2,6-dione hydrochloride. To a solution of tert-butyl N-[1-[3-(2,6-dioxo-3-piperidyl)-1-methyl-pyrazolo[4,3-c]pyridin-6-yl]-4-piperidyl]-N-methyl-carbamate (927 mg, 2.03 mmol) in DCM (40.6 mL) was added 4N HCl in 1,4-dioxane (5.08 mL, 20.3 mmol), and the reaction mixture was stirred at rt for 16 h. The reaction was diluted with Et$_2$O (20 mL), filtered and rinsed with Et$_2$O (2×10 mL) to afford the title compound (688 mg, 86%) as a solid, which was used in the next step without further purification. MS (ESI) [M+H]$^+$ 357.3. $^1$H NMR (400 MHz, DMSO-d$_6$) δ 10.99 (s, 1H), 9.06 (s, 2H), 8.91 (s, 1H), 7.17 (s, 1H), 4.51 (dd, J=10.9, 4.9 Hz, 1H), 4.33 (d, J=13.3 Hz, 2H), 3.97 (s, 3H), 3.36-3.17 (m, 1H), 3.07 (t, J=12.6 Hz, 2H), 2.77-2.60 (m, 2H), 2.56 (t, J=5.4 Hz, 3H), 2.48-2.38 (m, 1H), 2.25-2.15 (m, 1H), 2.14 (d, J=13.4 Hz, 2H), 1.75-1.57 (m, 2H).

Step 7: 3-[6-[4-[[5-Chloro-4-[(1-methyl-2-oxo-indolin-5-yl)amino]pyrimidin-2-yl]-methyl-amino]-1-piperidyl]-1-methyl-pyrazolo[4,3-c]pyridin-3-yl]piperidine-2,6-dione To a solution of 3-[1-methyl-6-[4-(methylamino)-1-piperidyl]pyrazolo[4,3-c]pyridin-3-yl]piperidine-2,6-dione hydrochloride (50 mg, 0.13 mmol) in DMSO (1.6 mL) were added sequentially 5-((5-chloro-2-fluoropyrimidin-4-yl)amino)-1-methylindolin-2-one (34 mg, 0.12 mmol) and DIPEA (0.2 mL, 1.16 mmol). The reaction mixture was heated to 100° C. for 18 h and then cooled to rt. The crude reaction mixture was purified by preparative HPLC (BEH column, C18) using a gradient of 44-54% MeCN and 10 mM ammonium formate in water to afford the title compound (18.6 mg, 25%) as a solid. LCMS $C_{31}H_{33}ClN_{10}O_3$ requires 628.2, found 629.3 [M+H]$^+$; $^1$H NMR (400 MHz, DMSO-d$_6$) δ 10.90 (s, 1H), 8.64 (s, 1H), 8.59 (s, 1H), 8.11-7.84 (m, 1H), 7.64 (s, 1H), 7.58 (d, J=8.4 Hz, 1H), 6.94 (d, J=8.3 Hz, 1H), 6.74 (s, 1H), 4.53 (d, J=12.9 Hz, 2H), 4.35-4.25 (m, 1H), 3.98-3.82 (m, 3H), 3.54 (s, 1H), 3.30-3.26 (m, 3H), 3.09 (s, 2H), 2.91-2.73 (m, 4H), 2.73-2.54 (m, 3H), 2.41-2.29 (m, 1H), 2.23-2.13 (m, 1H), 1.82-1.59 (m, 4H).

Example S61. Synthesis of 3-(6-(((3R,4R)-1-(5-chloro-4-((1-methyl-2-oxoindolin-6-yl)amino)pyrimidin-2-yl)-3-methylpiperidin-4-yl)amino)-1-methyl-1H-indazol-3-yl)piperidine-2,6-dione (61)

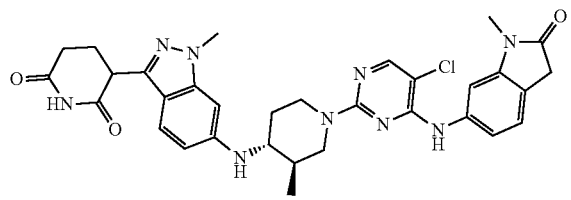 [SMILES: C[C@@H]1CN(c2ncc(Cl)c(Nc3ccc4c(c3)N(C)C(=O)C4)n2)CC[C@H]1Nc1ccc2c(C3CCC(=O)NC3=O)nn(C)c2c1]

Step 1: Synthesis of 1-methyl-6-nitroindoline-2,3-dione. To a stirred solution of 6-nitroindoline-2,3-dione (1.0 g, 5.20 mmol) in DMF (20 mL) was added sodium hydride (0.312 g, 7.81 mmol) at 0° C. under nitrogen and stirred for 10 min. Methyl iodide (0.651 mL, 10.41 mmol) was added to the reaction mixture and slowly warmed to 25° C. The reaction mixture was stirred for 1 h, treated with saturated NH$_4$Cl solution (100 mL) and extracted with ethyl acetate (3×100 mL). The combined organic layers were dried over anhydrous sodium sulfate, filtered, and concentrated under reduced pressure to afford the crude compound which was purified by flash column chromatography on silica gel with 40-50% ethyl acetate/pet ether to afford the title compound (320 mg, 1.531 mmol, 29% yield) as an off-white solid.

Step 2: Synthesis of 1-methyl-6-nitroindolin-2-one. To a stirred solution of 1-methyl-6-nitroindoline-2,3-dione (200 mg, 0.957 mmol) in n-butanol (5.0 mL) was added hydrazine hydrate (144 mg, 2.87 mmol) at 25° C. The reaction was heated 80° C. and stirred for 4 h. Then the reaction mixture was cooled to 25° C. and added triethylamine (0.533 mL, 3.83 mmol) and stirred at 80° C. for 14 h. The reaction mixture was cooled to room temperature and concentrated under reduced pressure to obtain crude compound which was purified by flash column chromatography on silica gel with 35-45% ethyl acetate/pet ether to afford the title compound (40 mg, 0.171 mmol, 18% yield) as an off-white solid. LCMS found 193.2 [M+H]$^+$, Rt 1.686 min Step 3: Synthesis of 6-amino-1-methylindolin-2-one. To a stirred solution of 1-methyl-6-nitroindolin-2-one (40 mg, 0.171 mmol) in ethanol (2.5 mL) and THF (2.5 mL) was added 10% Pd/C (20 mg) under nitrogen at 25° C. The reaction mixture was stirred under hydrogen atmosphere for 6 h. The reaction mixture was filtered through celite and the celite pad was washed with ethanol (2×20 mL). The filtrate was concentrated under reduced pressure to obtain the title compound (35 mg, crude) which was used for the next step without further purification. $^1$H NMR (400 MHz, CDCl$_3$): δ 6.86 (d, J=8.4 Hz, 1H), 6.20-6.18 (m, 2H), 5.11 (brs, 2H), 3.32 (s, 2H), 3.02 (s, 3H).

Step 4: Synthesis of 3-(6-(((3R,4R)-1-(5-chloro-4-((1-methyl-2-oxoindolin-6-yl)amino)pyrimidin-2-yl)-3-methylpiperidin-4-yl)amino)-1-methyl-1H-indazol-3-yl)piperidine-2,6-dione. The synthesis of the title compound was accomplished using General Procedures 1 and 6 using 6-amino-1-methylindolin-2-one and 3-(1-methyl-6-(((3R,4R)-3-methylpiperidin-4-yl)amino)-1H-indazol-3-yl)piperidine-2,6-dione as starting materials. The crude material was purified by preparative HPLC to afford the title compound (18 mg, 0.028 mmol, 17% yield) as an off-white solid. LCMS $C_{32}H_{34}ClN_9O_3$ requires 627.3, found 628.3 [M+H]$^+$; $^1$H NMR (400 MHz, DMSO-d$_6$): δ 10.84 (s, 1H), 8.99 (s, 1H), 8.12 (s, 1H), 7.42 (s, 1H), 7.32 (d, J=8.80 Hz, 1H), 7.26 (d, J=9.20 Hz, 1H), 7.21 (d, J=8.00 Hz, 1H), 6.52 (dd, J=8.80, 1.60 Hz, 1H), 6.45 (s, 1H), 5.79 (brs, 1H), 4.55-4.47 (m, 2H), 4.19-4.16 (m, 1H), 3.81 (s, 3H), 3.12-3.06 (m, 4H), 2.75-2.70 (m, 1H), 2.66-2.58 (m, 3H), 2.28-2.19 (m, 1H), 2.16-2.08 (m, 2H), 1.62-1.53 (m, 1H), 1.25-1.18 (m, 1H), 0.97 (d, J=6.4 Hz, 3H).

Example S62. Synthesis of 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-pyrazolo[3,4-b]pyridin-3-yl)piperidine-2,6-dione (62)

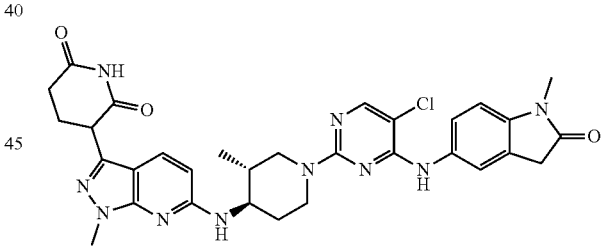

Step 1. 6-chloro-3-iodo-1-methyl-1H-pyrazolo[3,4-b]pyridine To a 0° C. solution of 6-chloro-3-iodo-1H-pyrazolo[3,4-b]pyridine (2 g, 7.16 mmol) in DMF (20 mL) was added sodium hydride (0.301 g, 7.51 mmol), The reaction mixture was stirred for 30 min and then sodium hydride (0.301 g, 7.51 mmol) was added dropwise. The reaction mixture was allowed to warm to rt and stirred for 1 h. The reaction mixture was treated with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated under reduced pressure. The crude material was purified by silica gel column chromatography (0-100% ethyl acetate in hexane). Concentration of the desired fractions under reduced pressure afforded the title compound 6-chloro-3-iodo-1-methyl-1H-pyrazolo

[3,4-b]pyridine (1.7 g, 5.79 mmol, 81% yield) as white solid; MS (ESI) m/z 293.8 [M+H]⁺; ¹H NMR (400 MHz, DMSO-d₆) δ ppm 7.99 (d, J=8.31 Hz, 1H), 7.32 (d, J=8.31 Hz, 1H), 4.03 (s, 3H).

Step 2. tert-butyl (3R,4R)-4-((3-iodo-1-methyl-1H-pyrazolo[3,4-b]pyridin-6-yl)amino)-3-methylpiperidine-1-carboxylate The solution of 6-chloro-3-iodo-1-methyl-1H-pyrazolo[3,4-b]pyridine (500 mg, 1.704 mmol) and N-ethyl-N-isopropylpropan-2-amine (0.607 mL, 3.41 mmol) in DMSO (1 mL) was added tert-butyl (3R,4R)-4-amino-3-methylpiperidine-1-carboxylate (365 mg, 1.704 mmol). The reaction mixture stirred at 120° C. for 48 h. The reaction mixture was filtered and purified by reveres-phased semi-preparative HPLC (10-100% acetonitrile+0.1% formic acid in water 0.1% formic acid, over 30 min). Fractions containing clean product were combined and lyophilized to give the title compound (250 mg, 0.530 mmol, 31.1% yield) as white solid. MS (ESI) m/z 472.2 [M+H]⁺; ¹H NMR (400 MHz, DMSO-d₆) δ ppm 7.33 (dd, J=8.68, 1.71 Hz, 1H), 7.18 (br d, J=7.83 Hz, 1H), 6.33-6.46 (m, 1H), 3.86-4.05 (m, 2H), 3.81 (d, J=1.83 Hz, 4H), 2.79-2.99 (m, 1H), 2.56-2.64 (m, 1H), 1.98 (br d, J=12.35 Hz, 1H), 1.47-1.63 (m, 1H), 1.41 (d, J=1.71 Hz, 9H), 1.17-1.32 (m, 1H), 0.88 (br d, J=4.89 Hz, 3H).

Step 3. tert-butyl (3R,4R)-4-((3-(2,6-bis(benzyloxy)pyridin-3-yl)-1-methyl-1H-pyrazolo[3,4-b]pyridin-6-yl)amino)-3-methylpiperidine-1-carboxylate. The solution of tert-butyl (3R,4R)-4-((3-iodo-1-methyl-1H-pyrazolo[3,4-b]pyridin-6-yl)amino)-3-methylpiperidine-1-carboxylate (250 mg, 0.530 mmol), 2,6-bis(benzyloxy)-3-(4,4,5,5-tetramethyl-1,3,2-dioxaborolan-2-yl)pyridine (243 mg, 0.583 mmol) and sodium bicarbonate (98 mg, 1.167 mmol) in mixed solvent of 1,4-dioxane (10 mL) and water (2 mL) was stirred with tetrakis(triphenylphosphine)palladium(0) (61.3 mg, 0.053 mmol) at 80° C. for 15 h. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated under reduced pressure. The crude was purified by silica gel column chromatography (0-100% ethyl acetate in hexane). Concentration of the desired fractions under reduced pressure afforded the crude product, which further purified by reveres-phased semi-preparative HPLC (10-100% acetonitrile+0.1% formic acid in water 0.1% formic acid, over 30 min). Fraction containing clean product were combined and lyophilized to give the title compound as a white solid (110 mg, 0.173 mmol, 32.7% yield). MS (ESI) m/z 372.0 [M+H]⁺; ¹H NMR (400 MHz, DMSO-d₆) δ ppm 7.94 (d, J=8.07 Hz, 1H), 7.64 (d, J=8.80 Hz, 1H), 7.43-7.51 (m, 2H), 7.36-7.42 (m, 4H), 7.26-7.36 (m, 4H), 6.92 (d, J=8.19 Hz, 1H), 6.55 (d, J=8.19 Hz, 1H), 6.19 (d, J=8.93 Hz, 1H), 5.46 (s, 2H), 5.41 (s, 2H), 3.86-3.99 (m, 2H), 3.81-3.85 (m, 3H), 3.69-3.81 (m, 1H), 2.75-3.07 (m, 1H), 1.91-2.07 (m, 1H), 1.45-1.64 (m, 1H), 1.41 (s, 9H), 1.24-1.32 (m, 2H), 0.88 (d, J=6.60 Hz, 3H).

Step 4. 3-(1-methyl-6-(((3R,4R)-3-methylpiperidin-4-yl)amino)-1H-pyrazolo[3,4-b]pyridin-3-yl)piperidine-2,6-dione. The solution of tert-butyl (3R,4R)-4-((3-(2,6-bis(benzyloxy)pyridin-3-yl)-1-methyl-1H-pyrazolo[3,4-b]pyridin-6-yl)amino)-3-methylpiperidine-1-carboxylate (0.105 g, 0.165 mmol) in ethanol (10 mL) was stirred with palladium on carbon 10% w/w (0.018 g, 0.017 mmol) under hydrogen (1 atm) at 50° C. for 15 h. The reaction mixture was filter over celite, the elute was concentrated and the residue was then stirred at rt with 1 mL TFA in DCM (1 mL) for 30 min. The TFA and solvent were removed under reduced pressure to give the desired product 3-(1-methyl-6-(((3R,4R)-3-methylpiperidin-4-yl)amino)-1H-pyrazolo[3,4-b]pyridin-3-yl)piperidine-2,6-dione (60 mg, 0.168 mmol, quant yield) as TFA salt which was use without further purification.

Step 5. 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-pyrazolo[3,4-b]pyridin-3-yl)piperidine-2,6-dione The synthesis of the title compound was accomplished using General Procedures 6 using 3-(1-methyl-6-(((3R,4R)-3-methylpiperidin-4-yl)amino)-1H-pyrazolo[3,4-b]pyridin-3-yl)piperidine-2,6-dione hydrochloride (40 mg, 0.102 mmol) and 5-((5-chloro-2-fluoropyrimidin-4-yl)amino)-1-methylindolin-2-one (29.8 mg, 0.102 mmol). The reaction mixture was filtered and purified by reveres-phased semi-preparative HPLC (10-100% acetonitrile+0.1% formic acid in water 0.1% formic acid, over 30 min). Fraction containing clean product were combined and lyophilized to give the title compound as a white solid (13 mg, 0.02 mmol, 19.4%). MS (ESI) m/z 628.8 [M+H]⁺; ¹H NMR (400 MHz, DMSO-d₆) δ ppm 10.83 (s, 1H), 8.66 (s, 1H), 8.02 (s, 1H), 7.63 (d, J=8.80 Hz, 1H), 7.57 (s, 1H), 7.52 (dd, J=8.44, 2.08 Hz, 1H), 6.87-6.98 (m, 2H), 6.31 (d, J=8.80 Hz, 1H), 4.48 (br s, 2H), 4.13 (dd, J=9.35, 5.07 Hz, 1H), 3.82-3.95 (m, 1H), 3.77 (s, 3H), 3.53 (s, 2H), 3.06-3.15 (m, 3H), 2.92-3.03 (m, 1H), 2.64-2.73 (m, 1H), 2.52-2.64 (m, 2H), 2.21-2.31 (m, 1H), 2.09-2.19 (m, 1H), 2.02 (br d, J=9.29 Hz, 1H), 1.54-1.67 (m, 1H), 1.21-1.37 (m, 1H), 0.93 (d, J=6.48 Hz, 3H).

Example S63. Synthesis of 3-(6-((1-(5-chloro-4-((2-oxoindolin-5-yl)amino)pyrimidin-2-yl)piperidin-4-yl)amino)-1-methyl-1H-indazol-3-yl)piperidine-2,6-dione (63)

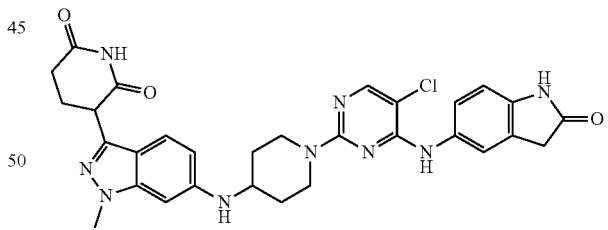

Step 1: Synthesis of 3-(6-((1-(5-chloro-4-((2-oxoindolin-5-yl)amino)pyrimidin-2-yl)piperidin-4-yl)amino)-1-methyl-1H-indazol-3-yl)piperidine-2,6-dione. The title compound was synthesized analogously to Example S62 above using 3-[1-methyl-6-(4-piperidylamino)indazol-3-yl]piperidine-2,6-dione and 5-aminoindolin-2-one as starting materials. LCMS C₃₀H₃₀ClN₉O₃ requires 599.2, found 600.0 [M+H]⁺; ¹H NMR (DMSO-d₆, 400 MHz) δ 10.8-10.9 (m, 1H), 10.3-10.4 (m, 1H), 8.0-8.1 (m, 1H), 7.4-7.5 (m, 1H), 7.3-7.4 (m, 2H), 6.8-6.8 (m, 1H), 6.4-6.6 (m, 2H), 4.2-4.4 (m, 2H), 4.1-4.2 (m, 1H), 3.9-4.0 (m, 2H), 3.84 (s, 3H), 3.6-3.7 (m, 1H), 3.49 (s, 2H), 3.1-3.2 (m, 2H), 2.6-2.6 (m, 2H), 2.2-2.3 (m, 1H), 2.1-2.2 (m, 1H), 2.0-2.1 (m, 2H), 1.3-1.4 (m, 2H).

Example S64. Synthesis of 3-(6-((1-(5-Chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione (64)

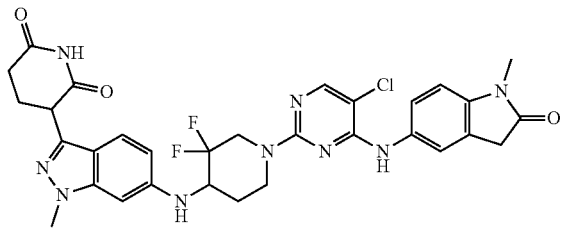 [SMILES: CN1C(=O)Cc2cc(Nc3nc(N4CCC(Nc5ccc6c(C7CCC(=O)NC7=O)nn(C)c6c5)C(F)(F)C4)ncc3Cl)ccc21]

Step 1: Synthesis of 3-(6-((3,3-Difluoropiperidin-4-yl)amino)-1-methyl-1H-indazol-3-yl)piperidine-2,6-dione hydrochloride. A mixture of 3-(6-amino-1-methyl-indazol-3-yl)piperidine-2,6-dione (500 mg, 1.94 mmol), tert-butyl 3,3-difluoro-4-oxopiperidine-1-carboxylate hydrate (500.9 mg, 2.13 mmol) and decaborane (14) (108.54 mg, 0.9700 mmol) was stirred in DMSO (5 mL) and acetic acid (0.22 mL, 3.87 mmol) at ambient temperature. After 2 hours, the reaction was complete according to LCMS. The reaction was diluted with methanol (1 mL) which resulted in bubbling. After 10 min, the bubbling subsided and the solution was diluted with ethyl acetate, washed with water and then brine, dried (sodium sulfate), filtered and concentrated. The resulting solid was triturated with diethyl ether. The resulting solid was then purified using silica gel chromatography using 4% methanol and a gradient of 0-50% ethyl acetate in hexanes. The resulting intermediate tert-butyl 4-[[3-(2,6-dioxo-3-piperidyl)-1-methyl-indazol-6-yl]amino]-3,3-difluoro-piperidine-1-carboxylate (230 mg, 0.4817 mmol, 24.8% yield) was isolated and treated with 2 mL 4N HCL in 1,4-dioxane and stirred for 3 h. After this time, the reaction mixture was concentrated to give the title compound (270 mg, 0.6524 mmol, 33.7% yield) as a light yellow powder.

Step 2: Synthesis of 3-(6-((1-(5-Chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione 3-{6-[(3,3-difluoropiperidin-4-yl)amino]-1-methyl-1H-indazol-3-yl}piperidine-2,6-dione hydrochloride (278 mg, 0.650 mmol), 5-((5-chloro-2-fluoropyrimidin-4-yl)amino)-1-methylindolin-2-one (172 mg, 0.590 mmol), N,N-diisopropylethylamine (0.2 mL, 1.17 mmol) and DMSO (1.17 mL) were added to a 1 dram vial equipped with a stir bar and heated to 80° C. for 15 hours. The reaction mixture was filtered and purified by reverse-phased semi-preparative HPLC (10-100% acetonitrile+0.1% formic acid in water 0.1% formic acid, over 30 min). Fraction containing clean product were combined and lyophilized to give the title compound (12 mg, 0.0184 mmol, 3.14% yield). $^1$H NMR (DMSO-$d_6$, 400 MHz) δ 10.8-10.9 (m, 1H), 8.8-8.9 (m, 1H), 8.2-8.2 (m, 1H), 8.0-8.1 (m, 1H), 7.4-7.5 (m, 2H), 7.3-7.4 (m, 1H), 6.9-7.0 (m, 1H), 6.6-6.7 (m, 2H), 5.9-6.1 (m, 1H), 4.6-4.8 (m, 1H), 4.4-4.5 (m, 1H), 4.2-4.3 (m, 2H), 3.8-3.9 (m, 3H), 3.4-3.6 (m, 3H), 3.2-3.3 (m, 1H), 3.1-3.1 (m, 3H), 2.6-2.7 (m, 2H), 2.5-2.6 (m, 4H), 2.2-2.3 (m, 1H), 2.1-2.2 (m, 1H), 1.9-2.0 (m, 1H), 1.5-1.7 (m, 1H).

Example S65. Synthesis of 1-(6-((1-(5-chloro-4-((1-methyl-2-oxoindolin-5-yl)amino)pyrimidin-2-yl)-3,3-difluoropiperidin-4-yl)amino)-1-methyl-1H-indazol-3-yl)dihydropyrimidine-2,4(1H,3H)-dione (65)

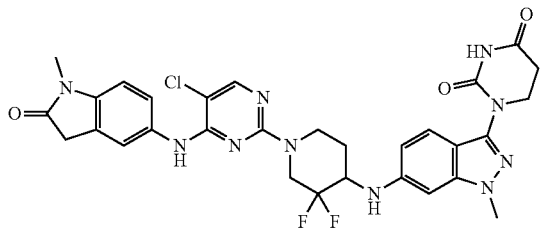 [SMILES: CN1C(=O)Cc2cc(Nc3nc(N4CCC(Nc5ccc6c(N7CCC(=O)NC7=O)nn(C)c6c5)C(F)(F)C4)ncc3Cl)ccc21]

Step 1: Synthesis of tert-butyl 4-[[3-(2,4-dioxohexahydropyrimidin-1-yl)-1-methyl-indazol-6-yl]amino]-3,3-difluoro-piperidine-1-carboxylate. To a solution of 1-(6-amino-1-methyl-indazol-3-yl) hexahydropyrimidine-2,4-dione (900 mg, 3.47 mmol), tert-butyl 3,3-difluoro-4-oxo-piperidine-1-carboxylate (980 mg, 4.17 mmol) in acetic acid (5 mL) and DMSO (25 mL) was added Decaborane (14) (195 mg, 1.74 mmol) and the mixture was stirred for 6 h at rt. Volatiles were removed and the residue was purified by reverse phase chromatography (C18) with a gradient of 20-100% MeCN and 10 mM ammonium formate in water to afford the title compound (450 mg, 27%) as a solid. MS (ESI) [M−H]⁻ 477.3.

Step 2: Synthesis of 1-(6-((1-(5-chloro-4-((1-methyl-2-oxoindolin-5-yl)amino)pyrimidin-2-yl)-3,3-difluoropiperidin-4-yl)amino)-1-methyl-1H-indazol-3-yl)dihydropyrimidine-2,4(1H,3H)-dione. The title compound was synthesized according to General Procedures 5 and 6 using tert-butyl 4-[[3-(2,4-dioxohexahydropyrimidin-1-yl)-1-methyl-indazol-6-yl]amino]-3,3-difluoro-piperidine-1-carboxylate as the starting material. LCMS $C_{30}H_{29}ClF_2N_{10}O_3$ requires 650.2, found 651.3 [M+H]⁺; $^1$H NMR (400 MHz, DMSO-$d_6$) δ 10.47 (s, 1H), 8.82 (s, 1H), 8.06 (s, 1H), 7.51 (d, J=2.1 Hz, 1H), 7.47 (dd, J=8.4, 2.2 Hz, 1H), 7.31 (d, J=8.8 Hz, 1H), 6.95 (d, J=8.4 Hz, 1H), 6.65 (dd, J=8.9, 1.9 Hz, 1H), 6.61 (d, J=1.8 Hz, 1H), 6.05 (d, J=9.2 Hz, 1H), 4.77-4.63 (m, 1H), 4.49-4.36 (m, 1H), 4.33-4.17 (m, 1H), 3.87 (t, J=6.7 Hz, 2H), 3.81 (s, 3H), 3.55-3.51 (m, 2H), 3.58-3.44 (m, 1H), 3.28-3.18 (m, 1H), 3.11 (s, 3H), 2.72 (t, J=6.7 Hz, 2H), 2.03-1.95 (m, 1H), 1.70-1.57 (m, 1H).

Example S66. Synthesis of 3-(6-(((R)-1-(5-chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione (66)

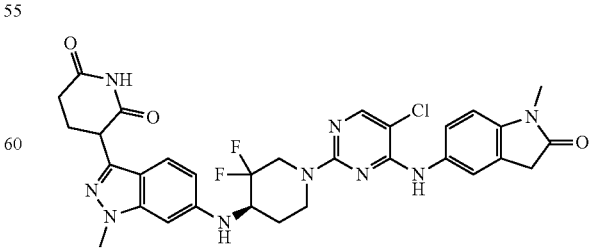

Step 1: Synthesis of tert-butyl 3,3-difluoro-4-(((R)-1-phenylethyl)amino)piperidine-1-carboxylate. A mixture of tert-butyl 3,3-difluoro-4-oxo-piperidine-1-carboxylate (3.53 g, 15.0 mmol) and (1R)-1-phenylethanamine (2.18 g, 18.0 mmol) in toluene (35 mL) was heated to reflux with a Dean-Stark trap for 18 h. The mixture was cooled to rt and the volatiles were removed under reduced pressure. DCM (35 mL) was added, followed by sodium triacetoxyborohydride (7.15 g, 33.7 mmol) portion wise over 1 h. The mixture was heated to 50° C. for 18 h. Another batch of sodium triacetoxyborohydride (3.56 g, 16.8 mmol) was added and the reaction mixture was heated to 50° C. for another 6 h. The mixture was cooled to rt and the volatiles were removed under reduced pressure. A 2 M solution of $Na_2CO_3$ (50 mL) was added and the mixture was stirred for 1 h at rt, followed by the addition of EtOAc (50 mL). The phases were separated and the aqueous phase was extracted with EtOAc (3×50 mL). The combined organic fractions were washed with brine (50 mL), dried over $Na_2SO_4$, filtered and concentrated under reduced pressure. The residue was purified by column chromatography on silica gel using 0-3% MeOH in DCM to afford the title compound (4.21 g, 82%) as an oil. $^1$H NMR (500 MHz, Methanol-d4) δ 7.29-7.35 (m, 4H), 7.20-7.25 (m, 1H), 5.48 (s, 1H), 4.08 (q, J=6.7 Hz, 1H), 4.04 (br s, 1H), 3.73-3.79 (m, 1H), 3.17 (br s, 1H), 2.91 (br s, 1H), 2.70-2.80 (m, 1H), 1.65-1.72 (m, 1H), 1.45-1.50 (m, 1H), 1.44 (s, 9H), 1.31 (d, J=6.62 Hz, 3H).

Step 2: Synthesis of tert-Butyl (4R)-3,3-difluoro-4-[[(1R)-1-phenylethyl]amino]piperidine-1-carboxylate 4-methyl benzenesulfonic acid salt. To a solution of tert-butyl 3,3-difluoro-4-[[(1R)-1-phenylethyl]amino]piperidine-1-carboxylate (4.21 g, 12.4 mmol) in EtOH (50 mL) at rt was added 4-methylbenzenesulfonic acid hydrate (2.35 g, 12.4 mmol), and the mixture was heated to 60° C. for 1 h. The volatiles were removed under reduced pressure to afford a mixture of diastereomers as solids. The crude mixture of intermediates (6.07 g) was dissolved in a 10:1 mixture of acetone:EtOH (68.5 mL) and the mixture was heated to reflux. The flask was removed from the oil bath and left to stand overnight. The precipitated solid was filtered, rinsed with cold acetone (2×1 mL) and dried to afford the first crop of the title compound which was carried forward.

Step 3: Synthesis of tert-Butyl (4R)-3,3-difluoro-4-[[(1R)-1-phenylethyl]amino]piperidine-1-carboxylate. The compound tert-Butyl (4R)-3,3-difluoro-4-[[(1R)-1-phenylethyl]amino]piperidine-1-carboxylate 4-methyl benzenesulfonic acid salt (1.99 g, 3.88 mmol) was partitioned between EtOAc (50 mL) and a saturated aqueous solution of $NaHCO_3$ (50 mL). The organic layer was separated, and the aqueous phase was extracted with EtOAc (3×40 mL). The combined organic layers were dried ($MgSO_4$), filtered and concentrated under reduced pressure to afford the title compound (1.30 g, 98%) as an oil. MS (ESI) [M+H]$^+$ 341.3. $^1$H NMR (400 MHz, DMSO-d$_6$) δ 7.36-7.27 (m, 4H), 7.26-7.15 (m, 1H), 4.01-3.95 (m, 1H), 3.94-3.80 (m, 1H), 3.66-3.54 (m, 1H), 3.29-3.20 (m, 1H), 3.04-2.91 (m, 1H), 2.71-2.64 (m, 1H), 2.37 (t, J=7.2 Hz, 1H), 1.64-1.58 (m, 1H), 1.38 (s, 9H), 1.22 (d, J=6.6 Hz, 3H).

Step 4: Synthesis of tert-Butyl (4R)-4-amino-3,3-difluoro-piperidine-1-carboxylate. A mixture of tert-butyl (4R)-3,3-difluoro-4-[[(1SR)-1-phenylethyl]amino]piperidine-1-carboxylate (1.29 g, 3.79 mmol) and 10% Pd/C (202 mg, 0.19 mmol) in EtOH (41 mL) was shaken in a Parr flask under hydrogen atmosphere (50 psi) at rt for 18 h. The mixture was filtered on Celite and washed with MeOH (3×50 mL). The filtrate was concentrated under reduced pressure to afford title compound (845 mg, 94%) as an oil, which was used in the next step without further purification. MS (ESI) [M-butene]+181.0. [α]D+0.19° (c=0.142, EtOH). $^1$H NMR (400 MHz, Methanol-d4) δ 4.22-4.12 (m, 1H), 3.96 (dt, J=13.7, 4.0 Hz, 1H), 3.25-3.15 (m, 1H), 3.14-3.00 (m, 2H), 1.93-1.82 (m, 1H), 1.59-1.48 (m, 1H), 1.46 (s, 9H).

Step 5: Synthesis of tert-Butyl (4R)-4-[[3-(2,6-dibenzyloxy-3-pyridyl)-1-methyl-indazol-6-yl]amino]-3,3-difluoro-piperidine-1-carboxylate. To a degassed mixture of 6-bromo-3-(2,6-dibenzyloxy-3-pyridyl)-1-methyl-indazole (200 mg, 0.40 mmol), tert-butyl (4R)-4-amino-3,3-difluoro-piperidine-1-carboxylate (123 mg, 0.520 mmol) and tBuONa (57.7 mg, 0.60 mmol) in THF (2 mL) at rt was added tBuXPhos-Pd-G3 (33.9 mg, 40 μmol). The reaction vessel was sealed and the reaction mixture was heated to 80° C. for 18 h and cooled to rt. DCM (10 mL) was added and the mixture was filtered on Celite and rinsed with DCM (3×10 mL). The volatiles were concentrated under reduced pressure and the residue was purified by column chromatography on silica gel using a gradient of 0-60% of EtOAc in hexanes to afford the title compound (200 mg, 76%) as a solid. MS (ESI) [M+H]$^+$ 657.6. $^1$H NMR (400 MHz, DMSO-d$_6$) δ 7.86 (d, J=8.1 Hz, 1H), 7.50-7.43 (m, 2H), 7.42-7.23 (m, 9H), 6.59 (s, 1H), 6.58-6.52 (m, 2H), 6.00 (d, J=9.1 Hz, 1H), 5.44 (s, 2H), 5.41 (s, 2H), 4.25-4.08 (m, 2H), 3.97-3.92 (m, 1H), 3.89 (s, 3H), 3.50-3.36 (m, 1H), 3.19-3.00 (m, 1H), 1.97-1.87 (m, 1H), 1.65-1.52 (m, 1H), 1.42 (s, 9H).

Step 6: Synthesis of 3-(6-(((R)-1-(5-chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione. The title compound was synthesized according to General Procedures 4, 5, and 6 using tert-Butyl (4R)-4-[[3-(2,6-dibenzyloxy-3-pyridyl)-1-methyl-indazol-6-yl]amino]-3,3-difluoro-piperidine-1-carboxylate as the starting material. LCMS $C_{31}H_{30}ClF_2N_9O_3$ requires 649.2, found 650.2 [M+H]$^+$; $^1$H NMR (400 MHz, DMSO-d$_6$) δ 8.82 (s, 1H), 8.41 (s, 1H), 8.06 (s, 1H), 7.51 (s, 1H), 7.47 (dd, J=8.4, 2.1 Hz, 1H), 7.35 (d, J=8.7 Hz, 1H), 6.95 (d, J=8.4 Hz, 1H), 6.66 (dd, J=8.8, 1.8 Hz, 1H), 6.62 (s, 1H), 6.00 (d, J=8.9 Hz, 1H), 4.75-4.64 (m, 1H), 4.41 (d, J=11.6 Hz, 1H), 4.26-4.13 (m, 2H), 3.82 (s, 3H), 3.60-3.42 (m, 3H), 3.23 (t, J=11.7 Hz, 1H), 3.11 (s, 3H), 2.65-2.55 (m, 2H), 2.30-2.22 (m, 1H), 2.20-2.11 (m, 1H), 2.04-1.94 (m, 1H), 1.70-1.52 (m, 1H).

Example S67. Synthesis of 3-(6-(((S)-1-(5-chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione (67)

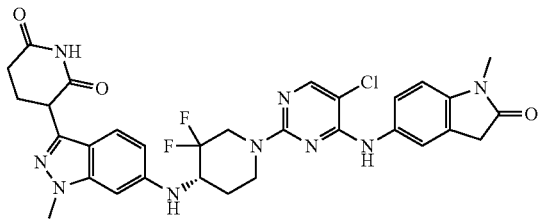

Step 1: Synthesis of 3-(6-(((S)-1-(5-chloro-4-((1-methyl-2-oxoindolin-5-yl)amino)pyrimidin-2-yl)-3,3-difluoropiperidin-4-yl)amino)-1-methyl-1H-indazol-3-yl)piperidine-2,6-dione The title compound was synthesized analogously to Example S66 starting using (1S)-1-phenylethanamine in Step 1. LCMS $C_{31}H_{30}ClF_2N_9O_3$ requires 649.2, found 650.3 [M+H]$^+$; $^1$H NMR (500 MHz, DMSO-d$_6$) δ 10.81 (s, 1H), 8.82 (s, 1H), 8.06 (s, 1H), 7.51 (s, 1H), 7.48 (d, J=8.3 Hz, 1H), 7.35 (d, J=8.7 Hz, 1H), 6.95 (d, J=8.4 Hz, 1H), 6.66 (d, J=8.4 Hz, 1H), 6.62 (s, 1H), 6.00 (d, J=9.0 Hz, 1H), 4.78-4.63 (m, 1H), 4.47-4.33 (m, 1H), 4.30-4.18 (m, 2H), 3.82 (s, 3H), 3.60-3.45 (m, 3H), 3.26-3.19 (m, 1H), 3.11 (s, 3H), 2.69-2.57 (m, 2H), 2.31-2.23 (m, 1H), 2.15 (dd, J=12.8, 5.9 Hz, 1H), 2.05-1.92 (m, 1H), 1.70-1.56 (m, 1H).

Example S68. Synthesis of 3-(6-(4-((5-chloro-4-((1-methyl-2-oxoindolin-5-yl)amino)pyrimidin-2-yl)amino)-3,3-difluoropiperidin-1-yl)-1-methyl-1H-indazol-3-yl)piperidine-2,6-dione (68)

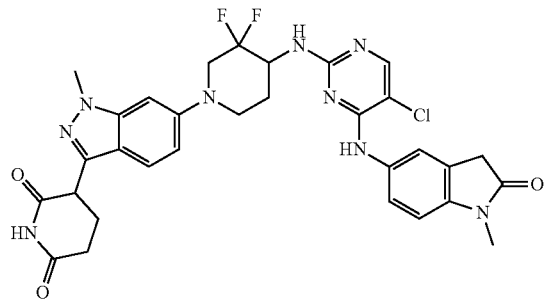 [SMILES: CN1C(=O)Cc2cc(Nc3nc(NC4CCN(c5ccc6c(C7CCC(=O)NC7=O)nn(C)c6c5)CC4(F)F)ncc3Cl)ccc21]

Step 1: Synthesis of 3-(6-(4-((5-chloro-4-((1-methyl-2-oxoindolin-5-yl)amino)pyrimidin-2-yl)amino)-3,3-difluoropiperidin-1-yl)-1-methyl-1H-indazol-3-yl)piperidine-2,6-dione. The title compound was synthesized according to General Procedures 2, 4, 5, and 6 using tert-butyl (3,3-difluoropiperidin-4-yl)carbamate as starting material. LCMS $C_{31}H_{30}ClF_2N_9O_3$ requires 649, found 650 [M+H]$^+$; $^1$H NMR (DMSO-d$_6$, 400 MHz) δ 10.8-10.9 (m, 1H), 8.5-8.7 (m, 1H), 7.9-8.1 (m, 1H), 7.6-7.8 (m, 1H), 7.4-7.6 (m, 2H), 7.2-7.4 (m, 1H), 6.9-7.0 (m, 3H), 4.2-4.4 (m, 1H), 4.0-4.2 (m, 1H), 3.92 (s, 4H), 3.56 (s, 2H), 3.3-3.3 (m, 1H), 3.1-3.2 (m, 3H), 3.0-3.1 (m, 1H), 2.9-2.9 (m, 1H), 2.7-2.7 (m, 1H), 2.6-2.7 (m, 1H), 2.2-2.3 (m, 1H), 2.1-2.2 (m, 1H), 1.9-2.0 (m, 2H).

Example S69. Synthesis of 3-(6-(((3R,4R)-1-(5-chloro-4-((1-ethyl-2-oxoindolin-5-yl)amino)pyrimidin-2-yl)-3-methylpiperidin-4-yl)amino)-1-methyl-1H-indazol-3-yl)piperidine-2,6-dione (69)

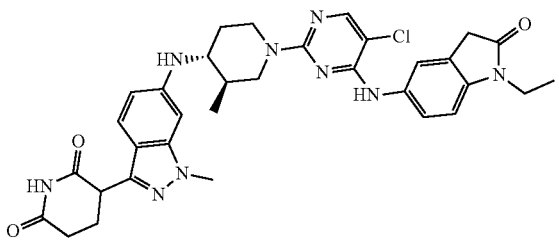 [SMILES: CCN1C(=O)Cc2cc(Nc3nc(N4CC[C@@H](Nc5ccc6c(C7CCC(=O)NC7=O)nn(C)c6c5)[C@H](C)C4)ncc3Cl)ccc21]

Step 1: Synthesis of 3-(6-(((3R,4R)-1-(5-chloro-4-((1-ethyl-2-oxoindolin-5-yl)amino)pyrimidin-2-yl)-3-methylpiperidin-4-yl)amino)-1-methyl-1H-indazol-3-yl)piperidine-2,6-dione. The title compound was synthesized according to General Procedures 1 and 6 using 5-amino-1-ethylindolin-2-one and 3-(1-methyl-6-(((3R,4R)-3-methylpiperidin-4-yl)amino)-1H-indazol-3-yl)piperidine-2,6-dione as starting materials. LCMS $C_{33}H_{36}ClN_9O_3$ requires 641.3, found 642.4 [M+H]$^+$; $^1$H NMR (400 MHz, DMSO-d$_6$) δ ppm 10.82 (s, 1H), 9.03 (br s, 1H), 8.09 (s, 1H), 7.55 (s, 1H), 7.50 (dd, J=8.50, 1.90 Hz, 1H), 7.31 (d, J=8.68 Hz, 1H), 7.01 (d, J=8.44 Hz, 1H), 6.51 (dd, J=8.68, 1.59 Hz, 1H), 6.45 (s, 1H), 5.54-6.00 (m, 1H), 4.39 (br d, J=7.70 Hz, 2H), 4.17 (dd, J=8.68, 5.14 Hz, 1H), 3.81 (s, 3H), 3.68 (q, J=7.09 Hz, 2H), 3.54 (s, 2H), 3.25-3.37 (m, 1H), 3.08 (br t, J=12.10 Hz, 1H), 2.75 (br t, J=12.41 Hz, 1H), 2.54-2.64 (m, 2H), 2.20-2.31 (m, 1H), 2.04-2.19 (m, 2H), 1.52-1.69 (m, 1H), 1.16-1.27 (m, 1H), 1.13 (t, J=7.09 Hz, 3H), 0.97 (d, J=6.48 Hz, 3H).

Example S70. Synthesis of 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione (70)

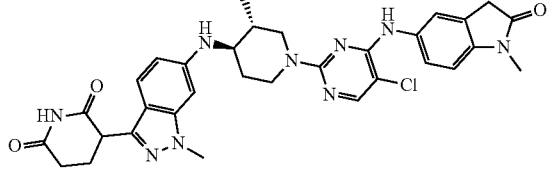

Step 1: Synthesis of tert-Butyl (3R,4R)-4-[[3-(2,6-dibenzyloxy-3-pyridyl)-1-methyl-indazol-6-yl]amino]-3-methyl-piperidine-1-carboxylate (Intermediate 24). A mixture of 6-bromo-3-(2,6-dibenzyloxy-3-pyridyl)-1-methyl-indazole (1.92 g, 3.84 mmol), tert-butyl (3R,4R)-4-amino-3-methyl-piperidine-1-carboxylate (685 mg, 3.20 mmol), RuPhos Pd G3 (668.6 mg, 0.80 mmol) and Cs$_2$CO$_3$ (1.25 g, 3.84 mmol) in 1,4-dioxane (15 mL) was heated to 90° C. for 20 h. The mixture was cooled to rt, filtered through celite and washed with EtOAc (4×30 mL). The filtrate was concentrated under reduced pressure and the residue was purified by column chromatography on silica gel using a gradient of 0-40% EtOAc in hexanes to afford title compound (1.37 g, 68%) as a solid. MS (ESI) [M+H]$^+$ 634.1. $^1$H NMR (400 MHz, DMSO-d$_6$) δ 7.86 (d, J=8.1 Hz, 1H), 7.50-7.46 (m, 1H), 7.46-7.25 (m, 10H), 6.54 (d, J=8.1 Hz, 1H), 6.43 (d, J=1.8 Hz, 1H), 6.41 (d, J=2.2 Hz, 1H), 5.70 (d, J=8.9 Hz, 1H), 5.44 (s, 2H), 5.40 (s, 2H), 3.97-3.89 (m, 2H), 3.88 (s, 3H), 3.24-3.14 (m, 1H), 2.99-2.87 (m, 1H), 2.05-2.01 (m, 1H), 2.01-1.98 (m, 1H), 1.57-1.47 (m, 1H), 1.41 (s, 9H), 1.17-1.08 (m, 1H), 0.93 (d, J=6.5 Hz, 3H).

Step 2: Synthesis of tert-Butyl (3R,4R)-4-[[3-(2,6-dioxo-3-piperidyl)-1-methyl-indazol-6-yl]amino]-3-methyl-piperidine-1-carboxylate. A mixture of tert-butyl (3R,4R)-4-[[3-(2,6-dibenzyloxy-3-pyridyl)-1-methyl-indazol-6-yl]amino]-3-methyl-piperidine-1-carboxylate (1.40 g, 2.21 mmol) and Pd(OH)$_2$/C (1.18 g, 1.10 mmol) in MeOH (25 mL) and THF (75 mL) was hydrogenated under H$_2$ (1 atm) at 50° C. for 9 h. The mixture was filtered through celite and washed with MeOH (2×50 mL) and THF (2×100 mL). The filtrate was concentrated under reduced pressure and the residue was purified by column chromatography on silica gel using a gradient of 0-5% MeOH in DCM to afford title compound (695 mg, 69%) as a solid. MS (ESI) [M+H]$^+$ 456.3. $^1$H NMR (400 MHz, DMSO-d$_6$) δ 10.81 (s, 1H), 7.31 (d, J=8.8 Hz, 1H), 6.51 (dd, J=8.8, 1.7 Hz, 1H), 6.40 (s, 1H), 5.72 (d, J=8.9 Hz, 1H), 4.17 (dd, J=8.7, 5.2 Hz, 1H), 3.98-3.88 (m, 2H), 3.80 (s, 3H), 3.26-3.14 (m, 1H), 3.00-2.86 (m, 1H), 2.65-2.56 (m, 3H), 2.34-2.20 (m, 1H), 2.18-2.09 (m, 1H), 2.05-1.94 (m, 1H), 1.60-1.46 (m, 1H), 1.41 (s, 9H), 1.22-1.05 (m, 1H), 0.92 (d, J=6.5 Hz, 3H).

Step 3: Synthesis of 3-(1-methyl-6-(((3R,4R)-3-methylpiperidin-4-yl)amino)-1H-indazol-3-yl)piperidine-2,6-dione hydrochloride. To a solution of tert-butyl (3R,4R)-4-[[3-(2,6-dioxo-3-piperidyl)-1-methyl-indazol-6-yl]amino]-3-methyl-piperidine-1-carboxylate (8 g, 17.6 mmol) in ethyl acetate (35 mL) was added 4 M HCl in ethyl acetate (35 mL) at 25° C. After addition, the reaction mixture was stirred at 25° C. for 16 hrs. The reaction mixture was filtered to offer the title compound (8 g, 100% yield) as an off-white solid.

MS (ESI) [M+H]⁺356.2. 400 MHz MeOD δ: 8.04 (s, 1H), 7.81 (d, J=8.8 Hz, 1H), 7.11 (d, J=8.8 Hz, 1H), 4.59-4.55 (m, 1H), 4.11 (s, 3H), 3.75-7.71 (m, 1H), 3.49-3.46 (m, 2H), 3.20-3.15 (m, 1H), 3.03 (s, 2H), 2.93-2.89 (m, 1H), 2.83-2.81 (m, 2H), 2.52-2.48 (m, 1H), 2.40-2.35 (m, 1H), 2.30-2.26 (m, 1H), 2.20-2.15 (m, 1H), 2.02 (s, 1H), 1.80-1.75 (m, 1H), 1.24-1.22 (m, 3H).

Step 4: Synthesis of 3-[6-[[(3R,4R)-1-[5-Chloro-4-[(1-methyl-2-oxo-indolin-5-yl)amino]pyrimidin-2-yl]-3-methyl-4-piperidyl]amino]-1-methyl-indazol-3-yl]piperidine-2,6-dione. To a solution of 3-(1-methyl-6-(((3R,4R)-3-methylpiperidin-4-yl)amino)-1H-indazol-3-yl)piperidine-2,6-dione hydrochloride (50.0 mg, 0.130 mmol) in DMSO (0.50 mL) was added sequentially 5-((5-chloro-2-fluoropyrimidin-4-yl)amino)-1-methylindolin-2-one (41.1 mg, 0.140 mmol) and DIPEA (90 µL, 0.510 mmol), and was heated to 80° C. for 2 h. The reaction mixture was cooled to rt and was purified directly by preparative HPLC (BEH column, C18) using a gradient of 44-54% MeCN and 10 mM ammonium formate in water to afford the title compound (13.5 mg, 16%) as a solid. LCMS C₃₂H₃₄ClN₉O₃ requires 627.3, found 628.4 [M+H]⁺; ¹H NMR (500 MHz, DMSO-d₆) δ 10.81 (s, 1H), 8.65 (s, 1H), 8.02 (s, 1H), 7.57 (s, 1H), 7.52 (d, J=8.4 Hz, 1H), 7.30 (d, J=8.8 Hz, 1H), 6.93 (d, J=8.4 Hz, 1H), 6.50 (d, J=8.8 Hz, 1H), 6.43 (s, 1H), 5.68 (d, J=9.1 Hz, 1H), 4.53-4.39 (m, 2H), 4.17 (dd, J=8.7, 5.2 Hz, 1H), 3.81 (s, 3H), 3.53 (s, 2H), 3.27-3.21 (m, 1H), 3.10 (s, 3H), 3.02 (t, J=12.2 Hz, 1H), 2.76-2.65 (m, 1H), 2.64-2.56 (m, 2H), 2.32-2.19 (m, 1H), 2.18-2.09 (m, 1H), 2.10-2.02 (m, 1H), 1.65-1.51 (m, 1H), 1.21-1.11 (m, 1H), 0.97 (d, J=6.5 Hz, 3H).

Example S71. Synthesis of (R)-3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione (71)

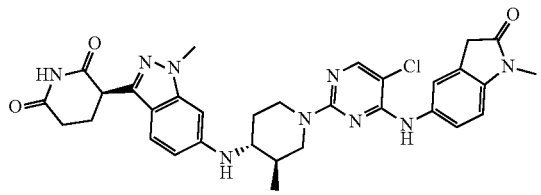 [SMILES: C[C@@H]1CN(c2ncc(Cl)c(Nc3ccc4c(c3)CC(=O)N4C)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S70 was then separated using preparatory HPLC with a Regis Whelk-O1 RR or SS column, 1 mL/min flow rate in 100% ACN (no additives) isocratic elution at 22° C. The title compound elutes as the first peak, Rt=10.01 min. LCMS C₃₂H₃₄ClN₉O₃ requires 627.3, found 628.4 [M+H]⁺; ¹H NMR (DMSO-d₆, 400 MHz) δ 10.7-10.9 (m, 1H), 8.5-8.8 (m, 1H), 7.9-8.1 (m, 1H), 7.5-7.7 (m, 2H), 7.2-7.4 (m, 1H), 6.9-7.1 (m, 1H), 6.4-6.7 (m, 2H), 5.6-5.7 (m, 1H), 4.4-4.7 (m, 2H), 4.0-4.3 (m, 1H), 3.8-3.9 (m, 3H), 3.4-3.6 (m, 2H), 2.9-3.2 (m, 4H), 2.7-2.8 (m, 2H), 2.0-2.3 (m, 5H), 1.5-1.6 (m, 1H), 1.1-1.3 (m, 1H), 0.8-1.1 (m, 3H).

Example S72. Synthesis of (S)-3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione (72)

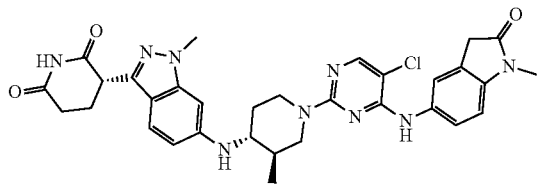 [SMILES: C[C@@H]1CN(c2ncc(Cl)c(Nc3ccc4c(c3)CC(=O)N4C)n2)CC[C@H]1Nc1ccc2c([C@@H]3CCC(=O)NC3=O)nn(C)c2c1]

Step 1: Synthesis of (S)-3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)piperidine-2,6-dione The product of Example S70 was then separated using preparatory HPLC with a Regis Whelk-O1 RR or SS column, 1 mL/min flow rate in 100% ACN (no additives) isocratic elution at 22° C. The title compound elutes as the second peak, Rt=14.87 min. LCMS C₃₂H₃₄ClN₉O₃ requires 627.3, found 628.4 [M+H]⁺; ¹H NMR (DMSO-d₆, 400 MHz) δ 10.7-10.9 (m, 1H), 8.6-8.8 (m, 1H), 7.9-8.1 (m, 1H), 7.5-7.7 (m, 2H), 7.2-7.4 (m, 1H), 6.9-7.0 (m, 1H), 6.3-6.6 (m, 2H), 5.6-5.9 (m, 1H), 4.4-4.6 (m, 2H), 4.1-4.4 (m, 1H), 3.8-3.9 (m, 3H), 3.5-3.6 (m, 2H), 2.9-3.2 (m, 4H), 2.7-2.8 (m, 2H), 2.0-2.3 (m, 5H), 1.5-1.7 (m, 1H), 1.1-1.3 (m, 1H), 0.9-1.0 (m, 3H)

Example S73. Synthesis of 3-(6-(((3R,4R)-1-(5-chloro-4-((1-methyl-2-oxoindolin-5-yl)amino)pyrimidin-2-yl)-3-methylpiperidin-4-yl)(methyl)amino)-1-methyl-1H-indazol-3-yl)piperidine-2,6-dione (73)

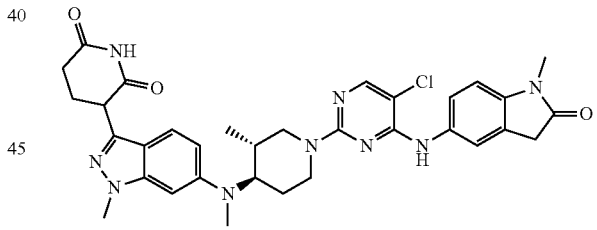

Step 1: Synthesis of tert-butyl (3R,4R)-4-[[3-(2,6-dibenzyloxy-3-pyridyl)-1-methyl-indazol-6-yl]-methyl-amino]-3-methyl-piperidine-1-carboxylate. To an ice-cold solution of tert-butyl (3R,4R)-4-[[3-(2,6-dibenzyloxy-3-pyridyl)-1-methyl-indazol-6-yl]amino]-3-methyl-piperidine-1-carboxylate (1.55 g, 2.45 mmol) and 60% NaH dispersion in mineral oil (245 mg, 6.11 mmol) in DMF (20 mL) was added iodomethane (305 µL, 4.89 mmol), and the mixture was stirred at rt for 48 h. Another batch was prepared using the same procedure. Water (50 mL) was added to the combined mixtures and the layers separated. The aqueous layer was extracted with EtOAc (3×75 mL). The combined organic fractions were washed with brine (20 mL), dried over MgSO₄, filtered and concentrated. The residue was purified by reverse phase chromatography (C18) using a gradient of 20-100% MeCN and 10 mM ammonium formate in water to afford the title compound (700 mg, 44%) as a solid. MS (ESI) [M+H]⁺ 649.34. ¹H NMR (400 MHz, DMSO-d₆) δ 7.88 (d, J=8.1 Hz, 1H), 7.47 (dd, J=8.7, 7.1 Hz, 3H), 7.43-7.23 (m, 8H), 6.78 (dd, J=9.4, 2.0 Hz, 1H), 6.61 (d, J=1.9 Hz, 1H), 6.56 (d, J=8.1 Hz, 1H), 5.44 (s, 2H), 5.40 (s, 2H), 4.05-3.99 (m, 2H), 3.94 (s, 3H), 3.65-3.59 (m, 1H), 2.92-2.85 (m, 1H), 2.75 (s, 3H), 2.60-2.54 (m, 1H), 1.72-1.77 (m, 1H), 1.60-1.54 (m, 2H), 1.42 (s, 9H), 0.75 (d, J=6.5 Hz, 3H).

Step 2: Synthesis of 3-(6-(((3R,4R)-1-(5-chloro-4-((1-methyl-2-oxoindolin-5-yl)amino)pyrimidin-2-yl)-3-methylpiperidin-4-yl)(methyl)amino)-1-methyl-1H-indazol-3-yl)piperidine-2,6-dione. The title compound was synthesized according to General Procedures 4, 5, and 6 using tert-butyl (3R,4R)-4-[[3-(2,6-dibenzyloxy-3-pyridyl)-1-methyl-indazol-6-yl]-methyl-amino]-3-methyl-piperidine-1-carboxylate as the starting material. LCMS $C_{32}H_{34}ClN_9O_3$ requires 641.3, found 642.4 [M+H]$^+$; $^1$H NMR (400 MHz, DMSO-d$_6$) δ 10.80 (s, 1H), 8.62 (s, 1H), 7.98 (s, 1H), 7.55 (s, 1H), 7.49 (d, J=8.4 Hz, 1H), 7.41 (d, J=9.1 Hz, 1H), 6.90 (d, J=8.5 Hz, 1H), 6.85 (d, J=7.4 Hz, 1H), 6.59 (s, 1H), 4.58-4.51 (m, 2H), 4.19 (dd, J=8.9, 5.2 Hz, 1H), 3.83 (s, 3H), 3.74-3.65 (m, 1H), 3.49 (s, 2H), 3.07 (s, 3H), 2.97-2.90 (m, 1H), 2.69 (s, 3H), 2.63-2.57 (m, 3H), 2.30-2.23 (m, 1H), 2.16-2.09 (m, 1H), 1.86-1.76 (m, 1H), 1.60-1.53 (m, 2H), 0.77 (d, J=6.5 Hz, 3H).

Example S74. Synthesis of 3-(6-(((3R,4R)-1-(5-chloro-4-((1-methyl-2-oxo-2,3-dihydro-1H-pyrrolo[2,3-b]pyridin-5-yl)amino)pyrimidin-2-yl)-3-methylpiperidin-4-yl)amino)-1-methyl-1H-indazol-3-yl)piperidine-2,6-dione (74)

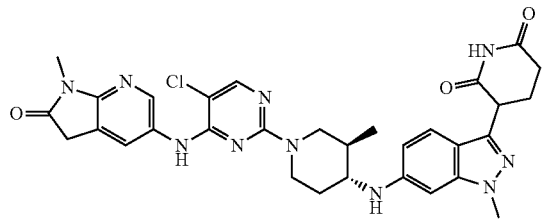 [SMILES: C[C@@H]1CN(c2ncc(Cl)c(Nc3cnc4c(c3)CC(=O)N4C)n2)CC[C@H]1Nc1ccc2c(C3CCC(=O)NC3=O)nn(C)c2c1]

Step 1: Synthesis of 5-((5-chloro-2-fluoropyrimidin-4-yl)amino)-1-methyl-1,3-dihydro-2H-pyrrolo[2,3-b]pyridin-2-one. To a stirred solution of 5-amino-1-methyl-1,3-dihydro-2H-pyrrolo[2,3-b]pyridin-2-one (1.2 g, 1.18 mmol) in EtOH (30 mL) was added DIPEA (0.617 mL, 3.53 mmol) and 5-chloro-2,4-difluoropyrimidine (0.266 g, 1.765 mmol) at −25° C. The reaction was allowed to slowly warm to rt after 1 hr and then the reaction was stirred at 25° C. for 16 h. After this time, the reaction mixture was evaporated. The crude residue was purified by silica gel chromatography using 50-100% EtOAc in PE to obtain the title compound (190 mg, 0.252 mmol, 21.44% yield) as an pale yellow solid. MS (ESI) m/z 294.0 [M+H]$^+$.

Step 2: Synthesis of 3-(6-(((3R,4R)-1-(5-chloro-4-((1-methyl-2-oxo-2,3-dihydro-1H-pyrrolo[2,3-b]pyridin-5-yl)amino)pyrimidin-2-yl)-3-methylpiperidin-4-yl)amino)-1-methyl-1H-indazol-3-yl)piperidine-2,6-dione. To a stirred solution of 5-((5-chloro-2-fluoropyrimidin-4-yl)amino)-1-methyl-1,3-dihydro-2H-pyrrolo[2,3-b]pyridin-2-one (80 mg, 0.104 mmol) and 3-(1-methyl-6-(((3R,4R)-3-methylpiperidin-4-yl)amino)-1H-indazol-3-yl)piperidine-2,6-dione (49.1 mg, 0.104 mmol) in DMSO (1 mL) was added DIPEA (0.054 mL, 0.311 mmol) and the reaction mixture was stirred at 90° C. for 4 h. The reaction mixture was purified by preparatory HPLC to obtain the title compound (30 mg, 0.047 mmol, 45.8% yield) as an off white solid. LCMS $C_{31}H_{33}ClN_{10}O_3$ requires 628.2, found 629.2 [M+H]$^+$; $^1$H NMR (400 MHz, DMSO-d$_6$): δ 10.82 (s, 1H), 8.85 (s, 1H), 8.36 (d, J=2.00 Hz, 1H), 8.06 (s, 1H), 7.86 (s, 1H), 7.31 (d, J=8.80 Hz, 1H), 6.44-6.52 (m, 2H), 5.69 (d, J=8.80 Hz, 1H), 4.44 (d, J=9.20 Hz, 2H), 4.17 (q, J=5.20 Hz, 1H), 3.82 (s, 3H), 3.61 (s, 2H), 3.13 (s, 3H), δ 3.02 (t, J=Hz, 1H), 2.53-2.68 (m, 3H), 2.33 (t, J=1.60 Hz, 1H), 2.25 (t, J=6.00 Hz, 1H), 2.06-2.17 (m, 2H), 1.58 (d, J=4.80 Hz, 1H), 1.15-1.17 (m, 1H), 0.96 (d, J=6.40 Hz, 3H).

Example S75. Synthesis of 3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione (75)

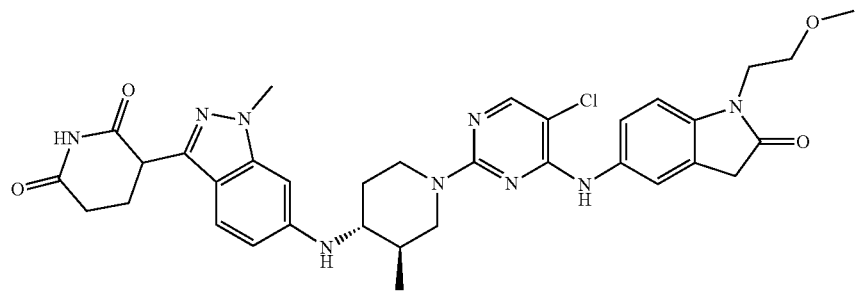 [SMILES: COCCN1C(=O)Cc2cc(Nc3nc(N4CC[C@@H](Nc5ccc6c(C7CCC(=O)NC7=O)nn(C)c6c5)[C@H](C)C4)ncc3Cl)ccc21]

Step 1: Synthesis of 5-((5-chloro-2-fluoropyrimidin-4-yl)amino)-1-(2-methoxyethyl) indolin-2-one. To a stirred solution of 5-amino-1-(2-methoxyethyl) indolin-2-one (200 mg, 0.97 mmol) in THF (5 mL) was added DIPEA (0.254 mL, 1.46 mmol) and 5-chloro-2,4-difluoropyrimidine (219 mg, 1.46 mmol) under nitrogen atmosphere at −45° C. The reaction mixture was slowly warmed to 25° C. and stirred for 12 h. The reaction mixture was concentrated under reduced pressure to obtain crude. The crude product was purified by flash column chromatography on silica gel with 30% ethyl acetate/pet ether to afford the title compound (80 mg, 0.210 mmol, 21% yield) as an off-white solid. MS: 337.0 [M+H]+.

Step 2: Synthesis of 3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione. To a stirred solution 3-(1-methyl-6-(((3R,4R)-3-methylpiperidin-4-yl)amino)-1H-indazol-3-yl)piperidine-2,6-dione (117 mg, 0.238 mmol) in DMSO (2.0 mL) was added 5-((5-chloro-2-fluoropyrimidin-4-yl)amino)-1-(2-methoxyethyl) indolin-2-one (80 mg, 0.238 mmol) and DIPEA (0.166 mL, 0.95 mmol) at 25° C. The reaction mixture was heated to 80° C. stirred for 4 h. The crude was purified by Prep-HPLC to afford the title compound (24 mg, 0.028 mmol, 25% yield). LCMS $C_{34}H_{38}ClN_9O_4$ requires 671.3, found 672.3 [M+H]+; 1H NMR (400 MHz, DMSO-$d_6$): δ 10.83 (s, 1H), 8.67 (s, 1H), 8.02 (s, 1H), 7.56 (s, 1H), 7.50 (d, J=8.40 Hz, 1H), 7.31 (d, J=8.80 Hz, 1H), 7.01 (d, J=8.40 Hz, 1H), 6.51 (dd, J=1.6 Hz and 8.8 Hz, 1H), 6.44 (s, 1H), 5.71 (d, J=9.20 Hz, 1H), 4.51-4.44 (m, 2H), 4.18 (dd, J=5.2 Hz and 8.4 Hz, 1H), 3.84-3.82 (m, 2H), 3.82 (s, 3H), 3.56-3.52 (m, 4H), 3.22 (s, 3H), 3.05-2.99 (m, 1H), 2.68-2.65 (m, 1H), 2.62-2.58 (m, 2H), 2.28-2.23 (m, 1H), 2.17-2.06 (m, 2H), 1.60-1.57 (m, 1H), 1.18-1.16 (m, 1H), 0.97 (d, J=6.40 Hz, 3H).

Example S76. Synthesis of (R)-3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione (76)

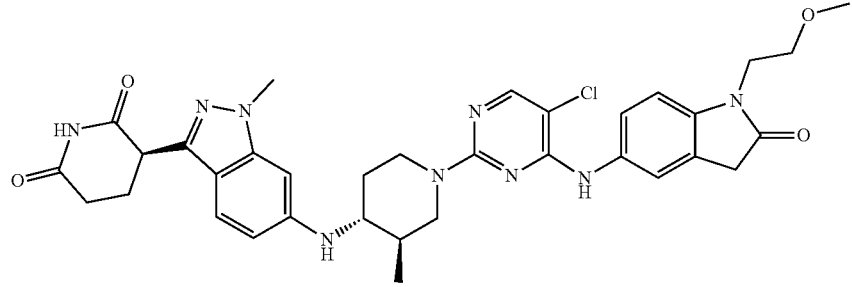 [SMILES: COCCN1C(=O)Cc2cc(Nc3nc(N4CC[C@@H](Nc5ccc6c([C@H]7CCC(=O)NC7=O)nn(C)c6c5)[C@H](C)C4)ncc3Cl)ccc21]

Step 1: Synthesis of (R)-3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione The product of Example S75 was then separated using preparatory HPLC with a Regis Whelk-O1 SS, 21×250 mm, 5 u column, 1 mL/min flow rate in 100% ACN (no additives) isocratic elution at 22° C., isolated as the first eluting peak, Rt=9.85 min. LCMS $C_{34}H_{38}ClN_9O_4$ requires 671.3, found 672.3 [M+H]+; 1H NMR (400 MHz, DMSO-d6) δ (ppm)=10.81 (s, 1H), 8.65 (s, 1H), 8.02 (s, 1H), 7.56 (s, 1H), 7.49 (dd, J=2.0, 8.5 Hz, 1H), 7.30 (d, J=8.8 Hz, 1H), 7.00 (d, J=8.6 Hz, 1H), 6.50 (dd, J=1.7, 8.8 Hz, 1H), 6.43 (d, J=1.1 Hz, 1H), 5.69 (d, J=8.9 Hz, 1H), 4.53-4.40 (m, 2H), 4.17 (dd, J=5.2, 8.7 Hz, 1H), 3.86-3.79 (m, 5H), 3.58-3.48 (m, 4H), 3.21 (s, 3H), 3.06-2.96 (m, 1H), 2.73-2.56 (m, 3H), 2.35-2.01 (m, 4H), 1.63-1.50 (m, 1H), 1.23-1.10 (m, 1H), 0.96 (d, J=6.6 Hz, 3H).

Example S77. Synthesis of (S)-3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione (77)

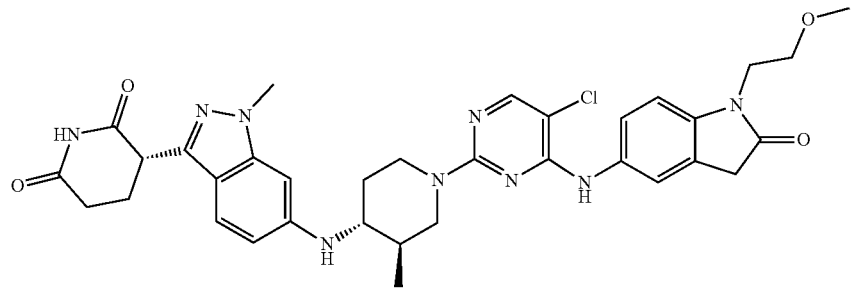 [SMILES: COCCN1C(=O)Cc2cc(Nc3nc(N4CC[C@@H](Nc5ccc6c([C@@H]7CCC(=O)NC7=O)nn(C)c6c5)[C@H](C)C4)ncc3Cl)ccc21]

Step 1: Synthesis of (S)-3-(6-(((3R,4R)-1-(5-chloro-4-((1-(2-methoxyethyl)-2-oxoindolin-5-yl)amino)pyrimidin-2-yl)-3-methylpiperidin-4-yl)amino)-1-methyl-1H-indazol-3-yl)piperidine-2,6-dione The product of Example S75 was then separated using preparatory HPLC with a Regis Whelk-O1 SS, 21×250 mm, 5 u column, 1 mL/min flow rate in 100% ACN (no additives) isocratic elution at 22° C. isolated as the second eluting peak, Rt=13.85 min. LCMS $C_{34}H_{38}ClN_9O_4$ requires 671.3, found 672.3 [M+H]$^+$; $^1$H NMR (400 MHz, DMSO-d$_6$) δ (ppm)=10.81 (s, 1H), 8.65 (s, 1H), 8.02 (s, 1H), 7.56 (s, 1H), 7.49 (dd, J=2.1, 8.4 Hz, 1H), 7.30 (d, J=8.7 Hz, 1H), 7.00 (d, J=8.6 Hz, 1H), 6.50 (dd, J=1.7, 8.8 Hz, 1H), 6.43 (d, J=1.2 Hz, 1H), 5.69 (d, J=9.2 Hz, 1H), 4.52-4.41 (m, 2H), 4.17 (dd, J=5.2, 8.7 Hz, 1H), 3.86-3.79 (m, 5H), 3.58-3.48 (m, 4H), 3.21 (s, 3H), 3.07-2.96 (m, 1H), 2.73-2.56 (m, 3H), 2.34-2.02 (m, 4H), 1.63-1.53 (m, 1H), 1.22-1.10 (m, 1H), 0.97 (d, J=6.5 Hz, 3H).

Example S78. Synthesis of 3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione (78)

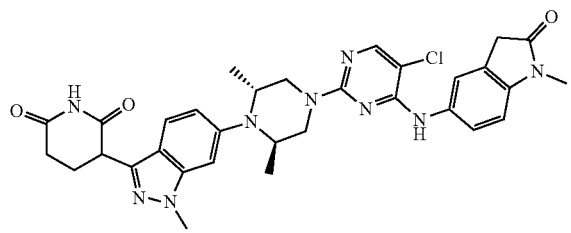 [SMILES: C[C@@H]1CN(c2ncc(Cl)c(Nc3ccc4c(c3)CC(=O)N4C)n2)C[C@@H](C)N1c1ccc2c(C3CCC(=O)NC3=O)nn(C)c2c1]

Step 1: Synthesis of tert-butyl (3R,5R)-4-(3-(2,6-bis(benzyloxy)pyridin-3-yl)-1-methyl-1H-indazol-6-yl)-3,5-dimethylpiperazine-1-carboxylate. A stirred solution of 3-(2,6-bis(benzyloxy)pyridin-3-yl)-6-bromo-1-methyl-1H-indazole (2.335 g, 4.67 mmol) and tert-butyl (3R,5R)-3,5-dimethylpiperazine-1-carboxylate (1.0 g, 4.67 mmol) in toluene (25 ml) was degassed with nitrogen for 15 min. Then sodium tert-butoxide (0.673 g, 7.00 mmol) and CPhos-Pd-G3 (0.188 g, 0.233 mmol) were added. The reaction mixture was heated to 100° C. and stirred for 8 h. The reaction mixture was cooled to room temperature and treated with water (150 mL) and extracted with ethyl acetate (3×100 ml). The combined organic layers were dried over anhydrous sodium sulphate, filtered, and concentrated under reduced pressure to afford the crude compound. The crude was purified by flash column chromatography on silica with 35-40% ethyl acetate/pet ether to afford the title compound (950 mg, 1.364 mmol, 29% yield) as an off-white solid. MS (ESI) m/z 634.8 [M+H]$^+$.

Step 2: Synthesis of tert-butyl (3R,5R)-4-(3-(2,6-dioxopiperidin-3-yl)-1-methyl-1H-indazol-6-yl)-3,5-dimethylpiperazine-1-carboxylate. To a stirred solution of tert-butyl (3R,5R)-4-(3-(2,6-bis(benzyloxy)pyridin-3-yl)-1-methyl-1H-indazol-6-yl)-3,5-dimethylpiperazine-1-carboxylate (950 mg, 1.364 mmol) in ethanol (20 mL) and THF (20 mL) was added 20% palladium hydroxide on carbon (192 mg) under nitrogen. The reaction mixture was stirred under hydrogenation pressure at 25° C. for 8 h. The reaction mixture was filtered through celite pad and the celite pad was washed with 1:1 mixture of acetonitrile and methanol (3×25 mL). The filtrate was concentrated under reduced pressure to afford the crude compound. The crude was purified by flash column chromatography on silica with 5% MeOH/DCM to afford the title compound (330 mg, 0.719 mmol, 52.7% yield) as an off-white solid. MS (ESI) m/z 456.2 [M+H]$^+$.

Step 3: Synthesis of 3-(6-((2R,6R)-2,6-dimethylpiperazin-1-yl)-1-methyl-1H-indazol-3-yl)piperidine-2,6-dione, TFA salt. To a stirred solution of tert-butyl (3R,5R)-4-(3-(2,6-dioxopiperidin-3-yl)-1-methyl-1H-indazol-6-yl)-3,5-dimethylpiperazine-1-carboxylate (250 mg, 0.450 mmol) in DCM (5 mL) was added TFA (0.34 mL) at 0° C. The reaction mixture was slowly warmed to 25° C. and stirred for 4 h. The reaction mixture was concentrated under reduced pressure to afford the crude compound. The crude compound was triturated with diethyl ether and dried under reduced pressure to afford the title compound (220 mg, 0.410 mmol, 91% yield) as an off-white solid. The crude product was used for the next step without further purification. MS (ESI) m/z 356.0 [M+H]$^+$.

Step 4: Synthesis of 3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione. To a stirred solution of 3-(6-((2R,6R)-2,6-dimethylpiperazin-1-yl)-1-methyl-1H-indazol-3-yl)piperidine-2,6-dione, TFA salt (70 mg, 0.137 mmol) and 5-((5-chloro-2-fluoropyrimidin-4-yl)amino)-1-methylindolin-2-one (40.2 mg, 0.137 mmol) in DMSO (1 mL) was added DIPEA (0.096 mL, 0.549 mmol) at 25° C. The reaction mixture was heated to 80° C. and stirred for 6 h. The reaction mixture was cooled to room temperature and purified by Prep-HPLC to afford the title compound (26 mg, 0.040 mmol, 29% yield) as an off-white solid. LCMS $C_{32}H_{34}ClN_9O_3$ requires 627.3, found 628.2 [M+H]$^+$; $^1$H NMR (400 MHz, DMSO-d$_6$): δ 10.88 (s, 1H), 8.72 (s, 1H), 8.04 (s, 1H), 7.60 (s, 1H), 7.57-7.52 (m, 2H), 7.01 (s, 1H), 6.96 (d, J=8.40 Hz, 1H), 6.87 (d, J=8.80 Hz, 1H), 4.31-4.27 (m, 1H), 3.92 (s, 3H), 3.93-3.90 (m, 2H), 3.81-3.77 (m, 2H), 3.69-3.65 (m, 2H), 3.57 (s, 2H), 3.12 (s, 3H), 2.67-2.64 (m, 2H), 2.33-2.30 (m, 1H), 2.19-2.15 (m, 1H), 0.96 (d, J=6.4 Hz, 6H).

Example S79. Synthesis of (R)-3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione (79)

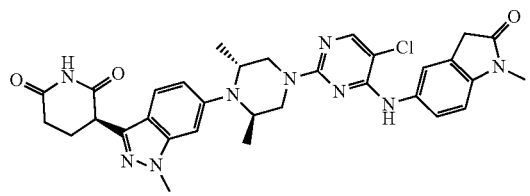 [SMILES: C[C@@H]1CN(c2ncc(Cl)c(Nc3ccc4c(c3)CC(=O)N4C)n2)C[C@@H](C)N1c1ccc2c([C@H]3CCC(=O)NC3=O)nn(C)c2c1]

Step 1: Synthesis of (R)-3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione The product of Example S78 was then separated using preparatory HPLC with a Regis Whelk-O1 SS, 21×250 mm, 5 u column, 1 mL/min flow rate in 100% ACN (no additives) isocratic elution at 22° C. The title compound was isolated as the first eluting peak, Rt=10.08 min. LCMS $C_{32}H_{34}ClN_9O_3$ requires 627.3, found 628.2 [M+H]$^+$; $^1$H NMR (400 MHz, DMSO-d$_6$) δ (ppm)=10.86 (s, 1H), 8.69 (s, 1H), 8.03 (s, 1H), 7.60 (d, J=1.7 Hz, 1H), 7.57-7.50 (m, 2H), 7.00 (d, J=1.2 Hz, 1H), 6.95 (d, J=8.4 Hz, 1H), 6.86 (dd, J=1.6, 8.9 Hz, 1H), 4.28 (dd, J=5.1, 9.5 Hz, 1H), 3.91 (s, 5H), 3.82-3.73 (m, 2H), 3.67 (dd, J=5.3, 12.8 Hz, 2H), 3.56 (s, 2H), 3.12 (s, 3H), 2.69-2.58 (m, 2H), 2.38-2.26 (m, 1H), 2.21-2.10 (m, 1H), 0.95 (d, J=6.2 Hz, 6H).

Example S80. Synthesis of (S)-3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione (80)

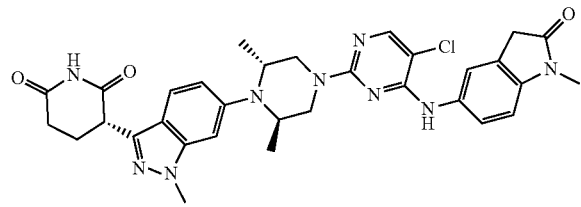 [SMILES: C[C@@H]1CN(c2ncc(Cl)c(Nc3ccc4c(c3)CC(=O)N4C)n2)C[C@@H](C)N1c1ccc2c([C@@H]3CCC(=O)NC3=O)nn(C)c2c1]

Step 1: Synthesis of (S)-3-(6-((2R,6R)-4-(5-chloro-4-((1-methyl-2-oxoindolin-5-yl)amino)pyrimidin-2-yl)-2,6-dimethylpiperazin-1-yl)-1-methyl-1H-indazol-3-yl)piperidine-2,6-dione The product of Example S78 was then separated using preparatory HPLC with a Regis Whelk-O1 SS, 21×250 mm, 5 u column, 1 mL/min flow rate in 100% ACN (no additives) isocratic elution at 22° C. The title compound was isolated as the second eluting peak, Rt=13.90 min. LCMS $C_{32}H_{34}ClN_9O_3$ requires 627.3, found 628.2 [M+H]$^+$; $^1$H NMR (400 MHz, DMSO-d$_6$) δ (ppm)=10.86 (s, 1H), 8.69 (s, 1H), 8.03 (s, 1H), 7.60 (d, J=1.7 Hz, 1H), 7.57-7.50 (m, 2H), 7.00 (d, J=1.3 Hz, 1H), 6.95 (d, J=8.3 Hz, 1H), 6.86 (dd, J=1.6, 8.9 Hz, 1H), 4.28 (dd, J=5.2, 9.4 Hz, 1H), 3.91 (s, 5H), 3.82-3.74 (m, 2H), 3.67 (dd, J=5.3, 12.7 Hz, 2H), 3.56 (s, 2H), 3.12 (s, 3H), 2.70-2.56 (m, 2H), 2.37-2.29 (m, 2H), 2.22-2.12 (m, 1H), 0.95 (d, J=6.1 Hz, 6H).

Example S81. Synthesis of 3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (81)

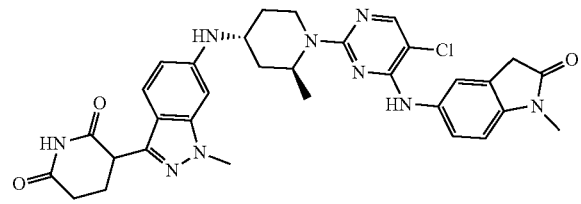 [SMILES: C[C@H]1C[C@H](Nc2ccc3c([C@@H]4CCC(=O)NC4=O)nn(C)c3c2)CCN1c1ncc(Cl)c(Nc2ccc3c(c2)CC(=O)N3C)n1]

Step 1: Synthesis of tert-butyl (2S,4R)-4-[[3-(2,6-dibenzyloxy-3-pyridyl)-1-methyl-indazol-6-yl]amino]-2-methyl-piperidine-1-carboxylate. A mixture of 6-bromo-3-(2,6-dibenzyloxy-3-pyridyl)-1-methyl-indazole (1.9 g, 3.80 mmol), tert-butyl (2S,4R)-4-amino-2-methyl-piperidine-1-carboxylate hydrochloride (1.05 g, 4.18 mmol) and tBuXPhos-Pd-G3 (302 mg, 0.380 mmol) and NaOtBu (912 mg, 9.49 mmol) in MeTHF (38 mL) was evacuated and refilled with nitrogen for 3 cycles. The mixture was heated to 85° C. for 1.5 h and cooled to rt. DCM (30 mL) was added and the mixture was filtered on a Celite pad and rinsed with DCM (3×30 mL). The volatiles were concentrated under reduced pressure and the residue was purified by column chromatography on silica gel using a gradient of 0-60% of EtOAc in hexanes to afford the title compound (2.01 g, 84%) as a solid. MS (ESI) [M+H]$^+$ 634.1. $^1$H NMR (400 MHz, DMSO-d$_6$) δ 7.87 (d, J=8.1 Hz, 1H), 7.46 (d, J=6.9 Hz, 2H), 7.42-7.21 (m, 9H), 6.55 (d, J=8.1 Hz, 1H), 6.47-6.36 (m, 2H), 5.66 (d, J=8.3 Hz, 1H), 5.44 (s, 2H), 5.41 (s, 2H), 4.45-4.33 (m, 1H), 3.89 (s, 3H), 3.88-3.86 (m, 1H), 3.76-3.62 (m, 1H), 3.01 (t, J=13.9 Hz, 1H), 2.05 (d, J=11.5 Hz, 1H), 1.87-1.83 (m, 1H), 1.48-1.43 (m, 1H), 1.41 (s, 9H), 1.23 (d, J=7.0 Hz, 3H), 1.16-1.05 (m, 1H).

Step 2: Synthesis of 3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione. The title compound was synthesized according to General Procedures 4, 5, and 6 using tert-butyl (2S,4R)-4-[[3-(2,6-dibenzyloxy-3-pyridyl)-1-methyl-indazol-6-yl]amino]-2-methyl-piperidine-1-carboxylate as the starting material. LCMS $C_{32}H_{34}ClN_9O_3$ requires 627.3, found 628.3 [M+H]$^+$; $^1$H NMR (500 MHz, DMSO-d$_6$) δ 10.81 (s, 1H), 8.63 (s, 1H), 8.01 (s, 1H), 7.55 (s, 1H), 7.54-7.46 (m, 1H), 7.33 (d, J=8.7 Hz, 1H), 6.93 (d, J=8.4 Hz, 1H), 6.52 (dd, J=8.8, 1.7 Hz, 1H), 6.47 (s, 1H), 5.67 (d, J=8.3 Hz, 1H), 4.91 (br s, 1H), 4.48 (br s, 1H), 4.18 (dd, J=8.8, 5.1 Hz, 1H), 3.83 (s, 3H), 3.81-3.74 (m, 1H), 3.54 (s, 2H), 3.11 (s, 3H), 3.06 (td, J=13.1, 1.7 Hz, 1H), 2.66-2.56 (m, 2H), 2.31-2.22 (m, 1H), 2.17-2.08 (m, 2H), 1.92 (d, J=11.3 Hz, 1H), 1.47 (td, J=13.0, 5.7 Hz, 1H), 1.26 (d, J=6.9 Hz, 3H), 1.15 (td, J=13.9, 5.3 Hz, 1H).

Example S82. Synthesis of (R)-3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (82)

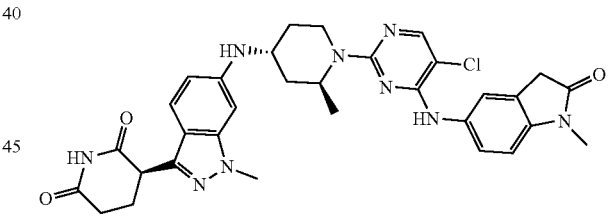

Step 1: Synthesis of (R)-3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione. The product of Example S81 was then separated using preparatory HPLC with a Regis Whelk-O1 SS, 21×250 mm, 5 u column, 1 mL/min flow rate in 100% ACN (no additives) isocratic elution at 22° C. The title compound was isolated as the first eluting peak, Rt=11.30 min. LCMS $C_{32}H_{34}ClN_9O_3$ requires 627.3, found 628.3 [M+H]$^+$; $^1$H NMR (400 MHz, DMSO-d$_6$) δ (ppm) 10.81 (s, 1H), 8.62 (s, 1H), 8.01 (s, 1H), 7.61-7.42 (m, 2H), 7.33 (d, J=8.7 Hz, 1H), 6.93 (d, J=8.3 Hz, 1H), 6.62-6.40 (m, 2H), 5.67 (br d, J=8.5 Hz, 1H), 5.09-4.32 (m, 2H), 4.18 (dd, J=5.1, 8.8 Hz, 1H), 3.91-3.69 (m, 4H), 3.54 (s, 2H), 3.11 (s, 4H), 2.31-2.06 (m, 3H), 1.91 (br d, J=10.5 Hz, 1H), 1.46 (dt, J=5.2, 11.9 Hz, 1H), 1.26 (br d, J=6.7 Hz, 3H), 1.20-1.09 (m, 1H).

Example S83. Synthesis of (S)-3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione (83)

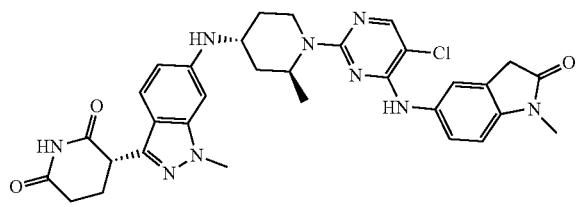

Step 2: Synthesis of (S)-3-(6-(((2S,4R)-1-(5-chloro-4-((1-methyl-2-oxoindolin-5-yl)amino)pyrimidin-2-yl)-2-methylpiperidin-4-yl)amino)-1-methyl-1H-indazol-3-yl)piperidine-2,6-dione. The product of Example S81 was then separated using preparatory HPLC with a Regis Whelk-O1 SS, 21×250 mm, 5 u column, 1 mL/min flow rate in 100% ACN (no additives) isocratic elution at 22° C. The title compound was isolated as the second eluting peak, Rt=19.77 min. LCMS $C_{32}H_{34}ClN_9O_3$ requires 627.3, found 628.3 [M+H]$^+$; $^1$H NMR (400 MHz, DMSO-d$_6$) δ (ppm) 10.81 (br s, 1H), 8.62 (br s, 1H), 8.01 (br s, 1H), 7.65-7.44 (m, 2H), 7.33 (br d, J=8.8 Hz, 1H), 6.93 (br d, J=8.1 Hz, 1H), 6.58-6.39 (m, 2H), 5.67 (br d, J=8.5 Hz, 1H), 5.13-4.32 (m, 2H), 4.31-4.10 (m, 1H), 3.97-3.71 (m, 4H), 3.54 (br s, 2H), 3.11 (br s, 4H), 2.33-2.08 (m, 3H), 1.97-1.86 (m, 1H), 1.55-1.41 (m, 1H), 1.26 (br d, J=6.6 Hz, 3H), 1.20-1.07 (m, 1H).

Example S84. Synthesis of 3-(6-(((2S,4R)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione (84)

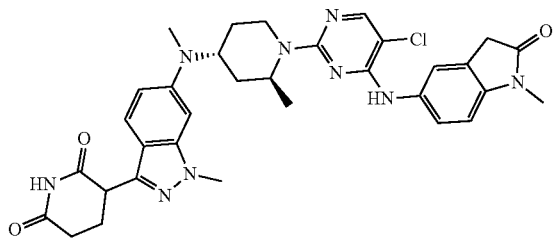

Step 1: Synthesis of tert-Butyl (2S,4R)-4-[[3-(2,6-dibenzyloxy-3-pyridyl)-1-methyl-indazol-6-yl]amino]-2-methyl-piperidine-1-carboxylate. A mixture of 6-bromo-3-(2,6-dibenzyloxy-3-pyridyl)-1-methyl-indazole (1.9 g, 3.80 mmol, intermediate provided by Celgene), tert-butyl (2S,4R)-4-amino-2-methyl-piperidine-1-carboxylate hydrochloride (1.05 g, 4.18 mmol) and tBuXPhos-Pd-G3 (302 mg, 0.380 mmol) and NaOtBu (912 mg, 9.49 mmol) in MeTHF (38 mL) was evacuated and refilled with nitrogen for 3 cycles. The mixture was heated to 85° C. for 1.5 h and cooled to rt. DCM (30 mL) was added and the mixture was filtered on a Celite pad and rinsed with DCM (3×30 mL). The volatiles were concentrated under reduced pressure and the residue was purified by column chromatography on silica gel using a gradient of 0-60% of EtOAc in hexanes to afford the title compound (2.01 g, 84%) as a solid. MS (ESI) [M+H]$^+$ 634.1. $^1$H NMR (400 MHz, DMSO-d$_6$) δ 7.87 (d, J=8.1 Hz, 1H), 7.46 (d, J=6.9 Hz, 2H), 7.42-7.21 (m, 9H), 6.55 (d, J=8.1 Hz, 1H), 6.47-6.36 (m, 2H), 5.66 (d, J=8.3 Hz, 1H), 5.44 (s, 2H), 5.41 (s, 2H), 4.45-4.33 (m, 1H), 3.89 (s, 3H), 3.88-3.86 (m, 1H), 3.76-3.62 (m, 1H), 3.01 (t, J=13.9 Hz, 1H), 2.05 (d, J=11.5 Hz, 1H), 1.87-1.83 (m, 1H), 1.48-1.43 (m, 1H), 1.41 (s, 9H), 1.23 (d, J=7.0 Hz, 3H), 1.16-1.05 (m, 1H).

Step 2: Synthesis of tert-Butyl (2S,4R)-4-[[3-(2,6-dibenzyloxy-3-pyridyl)-1-methyl-indazol-6-yl]-methyl-amino]-2-methyl-piperidine-1-carboxylate. To a solution of tert-butyl (2S,4R)-4-[[3-(2,6-dibenzyloxy-3-pyridyl)-1-methyl-indazol-6-yl]amino]-2-methyl-piperidine-1-carboxylate (525 mg, 0.83 mmol) in DMSO (6.5 mL) was added sequentially a formaldehyde solution (0.53 mL, 7.09 mmol, 37%) and decaborane (152 mg, 1.24 mmol). The mixture was stirred at rt for 2 h. Water (25 mL) was added, and the precipitated solid was collected by filtration. The residue was purified by column chromatography on silica gel using a gradient of 0-50% EtOAc in hexanes to afford the title compound (449 mg, 84%) as a solid. MS (ESI) [M+H]$^+$ 648.7; $^1$H NMR (500 MHz, DMSO-d$_6$) δ 7.89 (d, J=8.1 Hz, 1H), 7.51-7.44 (m, 3H), 7.42-7.36 (m, 4H), 7.36-7.24 (m, 4H), 6.77 (dd, J=9.3, 2.0 Hz, 1H), 6.63 (d, J=1.8 Hz, 1H), 6.56 (d, J=8.1 Hz, 1H), 5.48-5.41 (m, 2H), 5.41 (s, 2H), 4.51-4.36 (m, 1H), 4.10 (t, J=11.9 Hz, 1H), 4.00-3.86 (m, 4H), 3.17-2.96 (m, 1H), 2.75 (s, 3H), 1.83-1.72 (m, 1H), 1.70-1.55 (m, 2H), 1.48 (d, J=13.3 Hz, 1H), 1.41 (s, 9H), 1.25-1.19 (m, 3H).

Step 3: Synthesis of tert-Butyl (2S,4R)-4-[[3-(2,6-dioxo-3-piperidyl)-1-methyl-indazol-6-yl]-methyl-amino]-2-methyl-piperidine-1-carboxylate. A mixture of tert-butyl (2S,4R)-4-[[3-(2,6-dibenzyloxy-3-pyridyl)-1-methyl-indazol-6-yl]-methyl-amino]-2-methyl-piperidine-1-carboxylate (446 mg, 0.69 mmol) and Pearlman's catalyst (96.7 mg, 0.340 mmol) in THF (9 mL) and EtOH (9 mL) was stirred under a hydrogen atmosphere (1 atm) at 50° C. for 6 h and cooled to rt. The mixture was filtered on a pad of Celite and rinsed with THF (3×30 mL). The volatiles were concentrated under reduced pressure and the residue was purified by column chromatography on silica gel using a gradient of 10-100% of EtOAc in hexanes to afford the title compound (303 mg, 94%) as a solid. MS (ESI) [M+H]$^+$ 470.3. $^1$H NMR (400 MHz, DMSO-d$_6$) δ 10.83 (s, 1H), 7.48 (d, J=9.0 Hz, 1H), 6.88 (dd, J=9.2, 1.9 Hz, 1H), 6.64 (d, J=1.7 Hz, 1H), 4.49-4.36 (m, 1H), 4.24 (dd, J=8.9, 5.1 Hz, 1H), 4.18-4.08 (m, 1H), 3.99-3.91 (m, 1H), 3.86 (s, 3H), 3.15-2.97 (m, 1H), 2.75 (s, 3H), 2.68-2.55 (m, 2H), 2.33-2.23 (m, 1H), 2.22-2.12 (m, 1H), 1.84-1.71 (m, 1H), 1.71-1.55 (m, 2H), 1.49 (d, J=12.1 Hz, 1H), 1.41 (s, 9H), 1.25-1.17 (m, 3H).

Step 4: Synthesis of 3-[1-Methyl-6-[methyl-[(2S,4R)-2-methyl-4-piperidyl]amino]indazol-3-yl]piperidine-2,6-dione hydrochloride. To a solution of tert-butyl (2S,4R)-4-[[3-(2,6-dioxo-3-piperidyl)-1-methyl-indazol-6-yl]-methyl-amino]-2-methyl-piperidine-1-carboxylate (400 mg, 0.85 mmol) in 1,4-dioxane (5 mL) was added 4N HCl in 1,4-dioxane (2.13 mL, 8.52 mmol), and the mixture was stirred at rt for 15 h. The volatiles were evaporated under reduced pressure and the residue was triturated in Et$_2$O (10 mL) to afford title compound (295 mg, 85%) as a solid, which was used in the next step without further purification. MS (ESI) [M+H]$^+$ 370.3. $^1$H NMR (500 MHz, DMSO-d$_6$) δ 10.88 (s, 1H), 9.12 (br s, 1H), 9.05-8.83 (m, 1H), 7.71 (br s, 1H), 7.21 (br s, 1H), 4.40-4.30 (m, 1H), 4.27-3.98 (m, 6H), 3.95 (s, 3H), 3.89-3.73 (m, 1H), 3.34-3.24 (m, 1H), 3.22-3.11 (m, 1H), 3.07-2.85 (m, 2H), 2.75-2.55 (m, 2H), 2.42-2.29 (m, 1H), 2.19-2.11 (m, 1H), 1.35 (d, J=5.4 Hz, 3H).

Step 5: Synthesis of 3-[6-[[(2S,4R)-1-[5-Chloro-4-[(1-methyl-2-oxo-indolin-5-yl)amino]pyrimidin-2-yl]-2-methyl-4-piperidyl]-methyl-amino]-1-methyl-indazol-3-yl] piperidine-2,6-dione. To a solution of 3-[1-methyl-6-[methyl-[(2S,4R)-2-methyl-4-piperidyl]amino]indazol-3-yl]piperidine-2,6-dione hydrochloride (64.1 mg, 0.16 mmol) in DMF (2 mL) and DMSO (0.5 mL) added was sequentially 5-[(5-chloro-2-fluoro-pyrimidin-4-yl)amino]-1-methyl-indolin-2-one (42 mg, 0.14 mmol) and DIPEA (0.2 mL, 1.15 mmol). The mixture was heated to 100° C. for 18 h and then cooled to rt. The volatiles were removed under reduced pressure and the residue was purified by using a gradient of 20-75% MeCN and 10 mM ammonium formate in water to afford the title compound (47 mg, 48%) as a solid. LCMS $C_{33}H_{36}ClN_9O_3$ requires 641.3, found 642.3 [M+H]$^+$; $^1$H NMR (500 MHz, DMSO-d$_6$) δ 10.83 (s, 1H), 8.63 (s, 1H), 8.01 (s, 1H), 7.56 (br s, 1H), 7.52-7.43 (m, 2H), 6.96-6.85 (m, 2H), 6.65 (d, J=1.6 Hz, 1H), 5.17-4.78 (m, 1H), 4.72-4.36 (m, 1H), 4.29-4.16 (m, 2H), 3.87 (s, 3H), 3.54 (s, 2H), 3.15-3.03 (m, 4H), 2.75 (s, 3H), 2.68-2.54 (m, 2H), 2.34-2.26 (m, 1H), 2.17 (td, J=11.9, 6.0 Hz, 1H), 1.86-1.71 (m, 2H), 1.71-1.52 (m, 2H), 1.25 (d, J=6.8 Hz, 3H).

Example S85. Synthesis of 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)-3-methylpiperidine-2,6-dione (85)

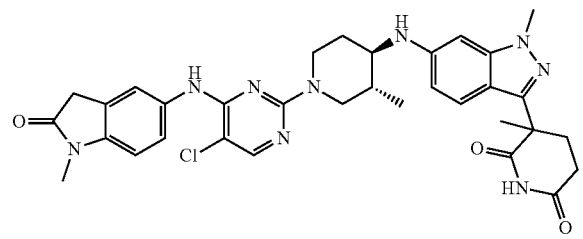 [SMILES: C[C@@H]1CN(c2ncc(Cl)c(Nc3ccc4c(c3)CC(=O)N4C)n2)CC[C@H]1Nc1ccc2c(C3(C)CCC(=O)NC3=O)nn(C)c2c1]

Step 1: Synthesis of 6-bromo-1-methyl-indazole-3-carbaldehyde To a solution of 6-bromo-1H-indazole-3-carbaldehyde (5.000 g, 22.22 mmol, 1.00 eq) in Dimethyl Formamide (50 mL) was added cesium carbonate (14.480 g, 44.44 mmol, 2.00 eq) and iodomethane (3.780 g, 26.66 mmol, 1.7 mL, 1.20 eq) the mixture was stirred at 50° C. for 12 h. The reaction mixture was cooled to room temperature. The mixture was filtered and the filtrate was added ethyl acetate (100 mL) and water (50 mL) and organic layers were separated. The aqueous phase was extracted with ethyl acetate (50 mL×2). Combined extracts were washed with sat brine (50 mL), dried over magnesium sulfate, filtered and the filtrate were concentrated to give the product. The residue was purified by silica gel column (5~10% ethyl acetate in petroleum ether). The title compound (3.500 g, 14.64 mmol, 65.9% yield) was obtained as a white solid. LCMS: 240.9[M+H]$^+$ Step 2: Synthesis of (6-bromo-1-methyl-indazol-3-yl) methanol To a solution of 6-bromo-1-methyl-indazole-3-carbaldehyde (2.800 g, 11.71 mmol, 1.00 eq) in ethyl alcohol (40 mL) was added sodium borohydride (0.886 g, 23.42 mmol, 2.00 eq) at 0° C. The mixture was stirred at 20° C. for 1 h. 6-bromo-1-methyl-indazole-3-carbaldehyde was consumed and desired mass was detected by LCMS. The mixture was filtered and the filtrate under pressure was added ethyl acetate (50 mL) and water (50 mL) and organic layers were separated. The aqueous phase was extracted with ethyl acetate (50 mL×2). Combined extracts were washed with sat brine (50 mL), dried over magnesium sulfate, filtered and the filtrate were concentrated to give the title compound (3.000 g, crude) as a white solid. LCMS: 242.0 [M+H]$^+$ Step 3: Synthesis of 6-bromo-3-(chloromethyl)-1-methyl-1H-indazole To a solution of (6-bromo-1-methyl-indazol-3-yl) methanol (3.000 g, 12.44 mmol, 1.00 eq) in dichloromethane (50 mL) was added thionyl chloride (2.960 g, 24.89 mmol, 1.8 mL, 2.00 eq) at 0° C. The mixture was stirred at 20° C. for 2 h. (6-bromo-1-methyl-indazol-3-yl) methanol was consumed and desired mass was detected by LCMS. The mixture was concentrated under pressure. The mixture was filtered and the filtrate was concentrated. The residue was purified by silica gel column (5~20% ethyl acetate in petroleum ether. The title compound (1.600 g, 6.16 mmol, 49.5% yield) was obtained as a yellow solid. LCMS: 260.9[M+1]+. $^1$H NMR (400 MHz, chloroform-d) δ, 7.69 (d, J=8.8 Hz, 1H), 7.59 (s, 1H), 7.31 (m, J=1.2, 8.4 Hz, 1H), 4.93 (s, 2H), 4.02 (s, 3H)

Step 4: Synthesis of 2-(6-bromo-1-methyl-1H-indazol-3-yl)acetonitrile To a solution of 6-bromo-3-(chloromethyl)-1-methyl-1H-indazole (1.95 g, 7.51 mmol) in DMF (25.05 ml) was added sodium cyanide (0.479 g, 9.77 mmol) the mixture was stirred at 60° C. for 3 h. The reaction mixture was cooled to room temperature, and ethyl acetate (100 mL) and water (50 mL) were added. The aqueous phase was extracted with ethyl acetate (50 mL×2). Combined extracts were washed with sat brine (50 mL), dried over magnesium sulfate, filtered and concentrated to give the (1.867 g, 7.47 mmol, 99% yield)) as a yellow solid. Used as is in the following step. LCMS: 249.8 [M+H]$^+$.

Step 5: Synthesis of 2-(6-bromo-1-methyl-1H-indazol-3-yl)propanenitrile To a solution of 2-(6-bromo-1-methyl-1H-indazol-3-yl)acetonitrile (1.867 g, 7.47 mmol) in Tetrahydrofuran (46.7 ml) was added potassium tert-butoxide (1.005 g, 8.96 mmol) at −20° C., After the mixture was stirred at −20° C. for 30 min, a solution of iodomethane (0.467 ml, 7.47 mmol) was added dropwise. The mixture stirred overnight while warming to room temperature. The mixture was filtered and the filtrate was concentrated. The residue was purified with 20% EtOAc in hexanes and the title compound (0.5885 g, 2.228 mmol, 29.8% yield) was obtained as a yellow oil. LCMS: 265.1 [M+H]$^+$. $^1$H NMR (chloroform-d, 400 MHz) δ 7.6-7.8 (m, 1H), 7.5-7.6 (m, 1H), 7.3-7.5 (m, 1H), 4.3-4.4 (m, 1H), 4.39 (s, 1H), 3.9-4.1 (m, 5H), 1.6-1.9 (m, 3H)

Step 6: Synthesis of tert-butyl 4-(6-bromo-1-methyl-1H-indazol-3-yl)-4-cyanopentanoate To a solution of 2-(6-bromo-1-methyl-1H-indazol-3-yl)propanenitrile (0.300 g, 1.136 mmol) and tert-butyl acrylate (0.333 ml, 2.272 mmol) in toluene (4.54 ml) was added potassium carbonate (0.314 g, 2.272 mmol)) and N-benzyl-N,N-diethylethanaminium chloride (0.026 g, 0.114 mmol). The mixture was stirred for 12 h at 65° C. After cooling, the mixture was filtered and the filtrate was concentrated. The residue was further purified by prep-TLC (20% ethyl acetate in hexanes). (0.212 g, 0.540 mmol, 47.6% yield) was obtained as a yellow oil. LCMS: 336.1 (M-$^t$Bu+H)$^+$. $^1$H NMR (chloroform-d, 400 MHz) δ 7.84 (s, 1H), 7.8-7.9 (m, 1H), 7.57 (s, 1H), 7.5-7.7 (m, 1H), 7.30 (s, 1H), 7.3-7.3 (m, 1H), 4.00 (s, 3H), 2.3-2.6 (m, 4H), 1.87 (s, 3H), 1.41 (s, 9H)

Step 7: Synthesis of tert-butyl (3R,4R)-4-((3-(5-(tert-butoxy)-2-cyano-5-oxopentan-2-yl)-1-methyl-1H-indazol- 6-yl)amino)-3-methylpiperidine-1-carboxylate A 0.5-2 mL microwave vial was charged with tert-butyl 4-(6-bromo-1-methyl-1H-indazol-3-yl)-4-cyanopentanoate (25 mg, 0.064 mmol), bis(dibenzylideneacetone)palladium(0) (0.366 mg, 0.637 µmol), sodium tert-butoxide (12.25 mg, 0.127 mmol), 2,2'-Bis(diphenylphosphino)-1,1'-binaphthalene (1.190 mg, 1.912 µmol), tert-butyl (3R,4R)-4-amino-3-methylpiperidine-1-carboxylate (20.49 mg, 0.096 mmol) and PhMe (319 µL). This was sparged with $N_2$ for five minutes then heated overnight at 80° C. overnight. This was filtered through a celite plug, rinsing with EtOAc and DCM to give the crude product. This was purified via normal phase chromatography with MeOH in DCM. This title compound was obtained as a yellow solid. LCMS: 470.0 [M+H]+. 1H NMR (chloroform-d, 400 MHz) δ 7.5-7.8 (m, 1H), 6.1-6.6 (m, 2H), 4.0-4.2 (m, 3H), 3.7-3.9 (m, 3H), 3.0-3.2 (m, 2H), 2.8-3.0 (m, 3H), 2.3-2.7 (br m, 2H), 2.0-2.2 (m, 3H), 1.6-1.8 (m, 3H), 1.47 (s, 11H), 1.2-1.3 (m, 8H), 0.9-1.1 (m, 3H), 0.8-0.9 (m, 2H), 0.8-0.9 (m, 2H)

Step 8: Synthesis of 5-amino-4-(6-(((3R,4R)-1-(tert-butoxycarbonyl)-3-methylpiperidin-4-yl)amino)-1-methyl-1H-indazol-3-yl)-4-methyl-5-oxopentanoic acid To a mixture of tert-butyl (3R,4R)-4-((3-(5-(tert-butoxy)-2-cyano-5-oxopentan-2-yl)-1-methyl-1H-indazol-6-yl)amino)-3-methylpiperidine-1-carboxylate (32.3 mg, 0.061 mmol) in DMSO (307 µL) and Ethanol (307 µL) was added sodium hydroxide (123 µL, 0.123 mmol) and hydrogen peroxide (126 µL, 1.229 mmol) at 0° C. The reaction mixture was stirred at 20° C. for 12 hrs. tert-Butyl 4-(6-bromo-1-methyl-1H-indazol-3-yl)-4-cyanopentanoate was consumed and desired mass was detected by LCMS. The mixture was quenched with saturated ammonium chloride aqueous solution. The pH was adjusted to 5 with 1 M hydrochloric acid, and the mixture was extracted with ethyl acetate (30 mL×2), Then the organic layers was dried over anhydrous sodium sulfate and filtered. The filtrate was concentrated under reduced pressure The title compound (30 mg, 0.062 mmol, 100% yield)) was obtained as a white solid. LCMS: 488.20 [M+H]+. 1H NMR (chloroform-d, 400 MHz) δ 7.4-7.5 (m, 1H), 6.4-6.5 (m, 1H), 6.2-6.3 (m, 1H), 5.9-6.0 (m, 1H), 4.6-4.9 (m, 2H), 3.9-4.0 (m, 3H), 3.1-3.2 (m, 2H), 2.7-2.9 (m, 3H), 2.2-2.5 (m, 2H), 2.1-2.2 (m, 1H), 2.0-2.1 (m, 1H), 1.5-1.6 (m, 2H), 1.47 (s, 9H), 1.2-1.4 (m, 7H), 1.0-1.1 (m, 3H)

Step 9: Synthesis of tert-butyl (3R,4R)-3-methyl-4-((1-methyl-3-(3-methyl-2,6-dioxopiperidin-3-yl)-1H-indazol-6-yl)amino)piperidine-1-carboxylate To a solution of 5-amino-4-(6-(((3R,4R)-1-(tert-butoxycarbonyl)-3-methylpiperidin-4-yl)amino)-1-methyl-1H-indazol-3-yl)-4-methyl-5-oxopentanoic acid (30 mg, 0.062 mmol) in THF (615 µL) was added CDI (29.9 mg, 0.185 mmol) and DMAP (0.752 mg, 6.15 µmol) and the mixture was stirred for 12 h at 70° C. The mixture was filtered and the filtrate was concentrated. This was purified via reverse phase (accq prep) with a gradient of 0-100% acetonitrile in water. The fractions were concentrated to give the title compound (21.89 mg, 0.047 mmol, 76% yield) as a white solid. LCMS: 470.0 [M+H]+. 1H NMR (chloroform-d, 400 MHz) δ 7.86 (s, 1H), 7.8-8.1 (m, 1H), 7.5-7.7 (m, 1H), 6.4-6.6 (m, 1H), 6.2-6.3 (m, 1H), 4.0-4.2 (m, 2H), 3.87 (s, 3H), 3.0-3.2 (m, 1H), 2.5-3.0 (m, 5H), 2.0-2.3 (m, 2H), 2.01 (s, 3H), 1.6-1.7 (m, 2H), 1.47 (s, 9H), 1.2-1.3 (m, 2H), 1.0-1.1 (m, 3H)

Step 10: Synthesis of 3-methyl-3-(1-methyl-6-(((3R,4R)-3-methylpiperidin-4-yl)amino)-1H-indazol-3-yl)piperidine-2,6-dione A 2 dram vial charged with tert-butyl (3R,4R)-3-methyl-4-((1-methyl-3-(3-methyl-2,6-dioxopiperidin-3-yl)-1H-indazol-6-yl)amino)piperidine-1-carboxylate (21.89 mg, 0.047 mmol) in DCM (466 µL) and hydrochloric acid (4 M in dioxane) (58.3 µL, 0.233 mmol) was added dropwise. This stirred at room temperature for 1 hour. After, the solution was concentrated to give the title compound (17.22 mg, 0.047 mmol, 100% yield) as a white solid. Used as is in the next step. LCMS: 370.5 [M+H]+.

Step 11: Synthesis of 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)-3-methylpiperidine-2,6-dione A solution of 3-methyl-3-(1-methyl-6-(((3R,4R)-3-methylpiperidin-4-yl)amino)-1H-indazol-3-yl)piperidine-2,6-dione (17 mg, 0.046 mmol), 5-((5-chloro-2-fluoropyrimidin-4-yl)amino)-1-methylindolin-2-one (13.47 mg, 0.046 mmol), DIPEA (0.020 mL, 0.115 mmol) in DMSO (0.5 mL) was stirred at 80° C. for 2 hours. After, the reaction was quenched with 10% formic acid in DMSO and filtered through a syringe filter. The crude material was purified by preparative HPLC to afford the title compound (30 mg, 0.045 mmol, 23% yield) as an off-white solid. LCMS $C_{31}H_{30}ClFN_{10}O_3$ requires 642.2, found 642.8 [M+H]+; 1H NMR (chloroform-d, 400 MHz) δ 7.98 (s, 1H), 7.76 (s, 1H), 7.7-7.8 (m, 1H), 7.5-7.6 (m, 2H), 7.4-7.5 (m, 1H), 6.9-7.1 (m, 1H), 6.7-6.8 (m, 1H), 6.4-6.6 (m, 1H), 6.2-6.3 (m, 1H), 4.5-4.7 (m, 2H), 3.88 (s, 3H), 3.6-3.8 (m, 1H), 3.4-3.6 (m, 2H), 3.21 (s, 3H), 3.0-3.1 (m, 1H), 2.8-2.9 (m, 1H), 2.7-2.8 (m, 2H), 2.5-2.7 (m, 1H), 2.2-2.3 (m, 1H), 2.0-2.1 (m, 1H), 1.75 (s, 3H), 1.6-1.7 (m, 1H), 1.2-1.4 (m, 1H), 1.0-1.1 (m, 3H)

Example S86. Synthesis of 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-pyrazolo[4,3-c]pyridin-3-yl)piperidine-2,6-dione (86)

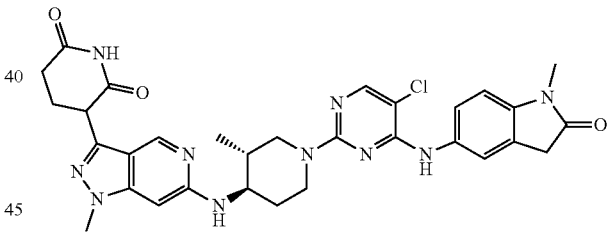

Step 1. 6-chloro-3-iodo-1-methyl-1H-pyrazolo[4,3-c]pyridine To a 0° C. solution of 6-chloro-3-iodo-1H-pyrazolo[4,3-c]pyridine (1 g, 3.58 mmol) in DMF (20 mL) was added sodium hydride (0.150 g, 3.76 mmol), The reaction mixture was stirred for 30 min. Then sodium hydride (0.150 g, 3.76 mmol) was added dropwise. The reaction mixture was allowed to warm to rt and stirred for another 1 h. The reaction mixture was quenched with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated under reduced pressure. The crude was purified by silica gel column chromatography (0-100% ethyl acetate in hexane). Concentration of the desired fractions under reduced pressure afforded the title compound as a white solid (0.75 g, 2.56 mmol, 71.4% yield). MS (ESI) m/z 293.8 [M+H]+; 1H NMR (400 MHz, DMSO-$d_6$) δ ppm 8.59 (s, 1H), 7.92 (s, 1H), 4.06 (d, J=0.98 Hz, 3H).

Step 2. 3-(2,6-bis(benzyloxy)pyridin-3-yl)-6-chloro-1-methyl-1H-pyrazolo[4,3-c]pyridine The solution of 6-chloro-3-iodo-1-methyl-1H-pyrazolo[4,3-c]pyridine (415 mg, 1.414 mmol), (2,6-bis(benzyloxy)pyridin-3-yl)boronic acid (521 mg, 1.555 mmol) and sodium bicarbonate (261 mg, 3.11 mmol) in mixed solvent of DME (10 mL) and water (2 mL) was stirred with tetrakis(triphenylphosphine)palladium(0) (163 mg, 0.141 mmol) at 100° C. for 15 h. The reaction mixture was treated with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated under reduced pressure. The crude was purified by silica gel column chromatography (0-100% ethyl acetate in hexane). Concentration of the desired fractions under reduced pressure afforded the title compound as a white solid (300 mg, 0.657 mmol, 46.4% yield). MS (ESI) m/z 457.2 [M+H]$^+$; $^1$H NMR (400 MHz, DMSO-d$_6$) δ ppm 8.89 (d, J=0.98 Hz, 1H), 8.02 (d, J=8.19 Hz, 1H), 7.86 (d, J=0.98 Hz, 1H), 7.26-7.49 (m, 10H), 6.63 (d, J=8.19 Hz, 1H), 5.52 (s, 2H), 5.44 (s, 2H), 4.02-4.08 (m, 3H).

Step 3. tert-butyl (3R,4R)-4-((3-(2,6-bis(benzyloxy)pyridin-3-yl)-1-methyl-1H-pyrazolo[4,3-c]pyridin-6-yl)amino)-3-methylpiperidine-1-carboxylate To a solution of 3-(2,6-bis(benzyloxy)pyridin-3-yl)-6-chloro-1-methyl-1H-pyrazolo[4,3-c]pyridine (400 mg, 0.875 mmol), RuPhos Pd G3 (73.2 mg, 0.088 mmol) and tert-butyl (3R,4R)-4-amino-3-methylpiperidine-1-carboxylate (188 mg, 0.875 mmol) in 1,4-dioxane (5 mL) was added cesium carbonate (570 mg, 1.751 mmol). The reaction mixture was purged with argon for 1 min and them stirred at 100° C. for 15 h. LCMS indicated the reaction was complete. The reaction mixture was treated with saturated aqueous sodium chloride (25 mL) and then extracted with ethyl acetate (3×25 mL). The organic phase was combined and washed with saturated aqueous sodium chloride (1×25 mL). The organic layer was dried over anhydrous magnesium sulfate, filtered through celite, and concentrated under reduced pressure. The crude was purified by silica gel column chromatography (0-100% ethyl acetate in hexane). Concentration of the desired fractions under reduced pressure afforded a solid that was further purified by reveres-phased semi-preparative HPLC (10-100% acetonitrile+0.1% TFA in water 0.1% TFA, over 30 min). Fraction containing clean product were combined and lyophilized to give the title compound as a white solid (95 mg, 0.150 mmol, 17.1% yield). MS (ESI) m/z 635.0 [M+H]$^+$; $^1$H NMR (400 MHz, DMSO-d$_6$) δ ppm 8.60 (br s, 1H), 7.96 (d, J=8.07 Hz, 1H), 7.23-7.51 (m, 10H), 6.59 (d, J=8.07 Hz, 1H), 6.34 (br s, 1H), 5.49 (s, 2H), 5.41 (s, 2H), 3.93 (br s, 2H), 3.87 (s, 3H), 3.44-3.56 (m, 1H), 2.88 (br s, 1H), 2.51-2.62 (m, 1H), 1.92 (br d, J=9.66 Hz, 1H), 1.52-1.63 (m, 1H), 1.41 (s, 9H), 1.16-1.29 (m, 1H), 0.89 (d, J=6.48 Hz, 3H).

Step 4. 3-(1-methyl-6-(((3R,4R)-3-methylpiperidin-4-yl)amino)-1H-pyrazolo[4,3-c]pyridin-3-yl)piperidine-2,6-dione A solution of tert-butyl (3R,4R)-4-((3-(2,6-bis(benzyloxy)pyridin-3-yl)-1-methyl-1H-pyrazolo[4,3-c]pyridin-6-yl)amino)-3-methylpiperidine-1-carboxylate (0.095 g, 0.150 mmol) in ethanol (10 mL) was stirred with palladium on carbon 10% w/w (0.016 g, 0.015 mmol) under hydrogen (1 atm) at 80° C. for 15 h. The reaction mixture was filtered through celite, the elute was concentrated and the residue was then stirred at rt with 1 mL TFA in DCM (1 mL) for 30 min. The TFA and solvent was removed under reduced pressure to give the desired product as TFA salt which was use without further purification (53 mg, 0.149 mmol, 99% yield).

Step 5. 3-(6-(((3R,4R)-1-(5-chloro-4-((1-methyl-2-oxoindolin-5-yl)amino)pyrimidin-2-yl)-3-methylpiperidin-4-yl)amino)-1-methyl-1H-pyrazolo[4,3-c]pyridin-3-yl)piperidine-2,6-dione The synthesis of the title compound was accomplished using General Procedures 6 using 3-(1-methyl-6-(((3R,4R)-3-methylpiperidin-4-yl)amino)-1H-pyrazolo[4,3-c]pyridin-3-yl)piperidine-2,6-dione (53 mg, 0.149 mmol) and 5-((5-chloro-2-fluoropyrimidin-4-yl)amino)-1-methylindolin-2-one (43.5 mg, 0.149 mmol). The reaction mixture was filtered and purified by reverse-phased semi-preparative HPLC (10-100% acetonitrile+0.1% formic acid in water 0.1% formic acid, over 30 min). Fraction containing clean product were combined and lyophilized to give the title compound as white solid (7.7 mg, 0.012 mmol, 8.23% yield). MS (ESI) m/z 628.8 [M+H]$^+$; $^1$H NMR (400 MHz, DMSO-d$_6$) δ ppm 10.89 (s, 1H), 8.65 (s, 1H), 8.49 (d, J=0.86 Hz, 1H), 8.01 (s, 1H), 7.57 (s, 1H), 7.52 (dd, J=8.50, 1.90 Hz, 1H), 6.94 (d, J=8.44 Hz, 1H), 6.23-6.31 (m, 2H), 4.42-4.59 (m, 2H), 4.28 (dd, J=9.84, 5.07 Hz, 1H), 3.78 (s, 3H), 3.55-3.66 (m, 1H), 3.53 (s, 2H), 3.10 (s, 3H), 2.89-3.04 (m, 1H), 2.54-2.65 (m, 2H), 2.35-2.41 (m, 1H), 2.09-2.23 (m, 1H), 1.98 (br d, J=10.39 Hz, 1H), 1.54-1.72 (m, 1H), 1.16-1.37 (m, 1H), 0.93 (d, J=6.36 Hz, 3H).

Example S87. Synthesis of (R)-3-(6-(((2S,4R)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione (87)

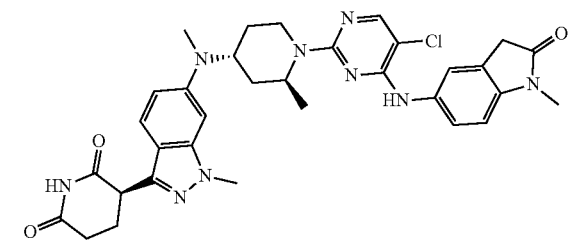 [SMILES: C[C@H]1C[C@H](N(C)c2ccc3c([C@H]4CCC(=O)NC4=O)nn(C)c3c2)CCN1c1ncc(Cl)c(Nc2ccc3c(c2)CC(=O)N3C)n1]

Step 1: Synthesis of (R)-3-(6-(((2S,4R)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione. The product of Example S84 was then separated using preparatory HPLC with a Regis Whelk-O1 SS, 21×250 mm, 5 u column, 1 mL/min flow rate in 100% ACN (no additives) isocratic elution at 22° C. The title compound was isolated as the first eluting peak, Rt=13.41 min. LCMS C$_{33}$H$_{36}$ClN$_9$O$_3$ requires 641.3, found 642.3 [M+H]$^+$; $^1$H NMR (400 MHz, DMSO-d$_6$) δ (ppm) 10.84 (s, 1H), 8.64 (s, 1H), 8.01 (s, 1H), 7.56 (br s, 1H), 7.52-7.45 (m, 2H), 6.96-6.88 (m, 2H), 6.65 (d, J=1.6 Hz, 1H), 4.24 (dd, J=8.9, 5.1 Hz, 2H), 3.87 (s, 3H), 3.54 (s, 2H), 3.15-3.04 (m, 4H), 2.75 (s, 3H), 2.69-2.58 (m, 2H), 2.37-2.06 (m, 2H), 1.86-1.52 (m, 4H), 1.25 (br d, J=6.8 Hz, 3H).

Example S88. Synthesis of (S)-3-(6-(((2S,4R)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione (88)

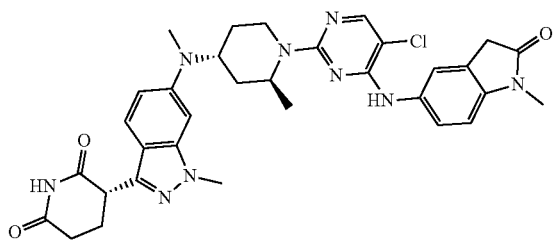

Step 1: Synthesis of (S)-3-(6-(((2S,4R)-1-(5-chloro-4-((1-methyl-2-oxoindolin-5-yl)amino)pyrimidin-2-yl)-2-methylpiperidin-4-yl)(methyl)amino)-1-methyl-1H-indazol-3-yl)piperidine-2,6-dione. The product of Example S84 was then separated using preparatory HPLC with a Regis Whelk-O1 SS, 21×250 mm, 5 u column, 1 mL/min flow rate in 100% MECN (no additives) isocratic elution at 22° C. The title compound was isolated as the second eluting peak, Rt=23.26 min. LCMS $C_{33}H_{36}ClN_9O_3$ requires 641.3, found 642.3 [M+H]$^+$; $^1$H NMR (400 MHz, CD$_3$SOCD$_3$, 298 K) δ (ppm)= 10.84 (s, 1H), 8.64 (s, 1H), 8.01 (s, 1H), 7.56 (br s, 1H), 7.53-7.44 (m, 2H), 6.96-6.87 (m, 2H), 6.65 (d, J=1.6 Hz, 1H), 4.24 (dd, J=9.1, 5.1 Hz, 2H), 3.87 (s, 3H), 3.54 (s, 2H), 3.15-3.04 (m, 4H), 2.75 (s, 3H), 2.68-2.58 (m, 2H), 2.36-2.09 (m, 2H), 1.88-1.51 (m, 4H), 1.24 (br d, J=7.0 Hz, 3H).

Example S89. Synthesis of 3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione (89)

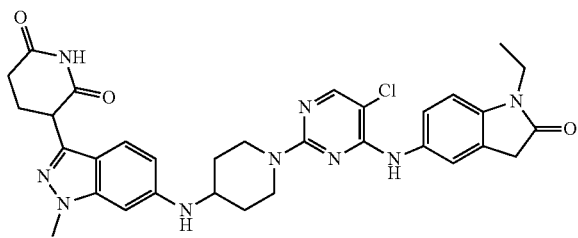 [SMILES: CCN1C(=O)Cc2cc(Nc3nc(N4CCC(Nc5ccc6c(C7CCC(=O)NC7=O)nn(C)c6c5)CC4)ncc3Cl)ccc21]

Step 1: Synthesis of 3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione. The title compound was synthesized according to General Procedures 1 and 6 using 5-amino-1-ethylindolin-2-one and 3-(1-methyl-6-(piperidin-4-ylamino)-1H-indazol-3-yl)piperidine-2,6-dione as starting materials. LCMS $C_{32}H_{34}ClN_9O_3$ requires 627.3, found 628.4 [M+H]$^+$; $^1$H NMR (500 MHz, DMSO) δ 8.64 (s, 1H), 8.44 (br, 1H), 8.01 (s, 1H), 7.54 (s, 1H), 7.54-7.49 (m, 1H), 7.32 (d, J=8.7 Hz, 1H), 6.98 (d, J=8.4 Hz, 1H), 6.52 (dd, J=8.8, 1.7 Hz, 1H), 6.46 (s, 1H), 5.82-5.73 (m, 1H), 4.42-4.35 (m, 2H), 4.18 (dd, J=8.8, 5.1 Hz, 1H), 3.82 (s, 3H), 3.67 (q, J=7.2 Hz, 2H), 3.53 (s, 2H), 3.11 (t, J=11.3 Hz, 2H), 2.64-2.56 (m, 2H), 2.30-2.21 (m, 1H), 2.18-2.10 (m, 1H), 2.04-1.94 (m, 2H), 1.36-1.26 (m, 2H), 1.13 (t, J=7.1 Hz, 3H).

Example S90. Synthesis of (R)-3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione (90)

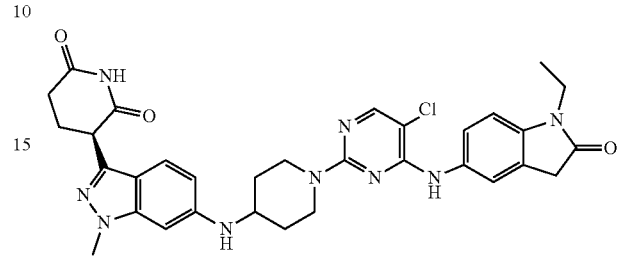

Step 1: Synthesis of (R)-3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione. The product of Example S89 was then separated using preparatory HPLC with a Regis Whelk-O1 SS, 21×250 mm, 5 u column, 1 mL/min flow rate in 100% MECN (no additives) isocratic elution at 22° C. The title compound was isolated as the first eluting peak, Rt=11.16 min. LCMS $C_{32}H_{34}ClN_9O_3$ requires 627.3, found 628.4 [M+H]$^+$; $^1$H NMR (500 MHz, DMSO) δ 10.81 (s, 1H), 8.63 (s, 1H), 8.01 (s, 1H), 7.60-7.47 (m, 2H), 7.32 (d, J=8.8 Hz, 1H), 6.98 (d, J=8.5 Hz, 1H), 6.52 (dd, J=1.5, 8.8 Hz, 1H), 6.46 (s, 1H), 5.76 (d, J=8.2 Hz, 1H), 4.38 (br d, J=13.4 Hz, 2H), 4.18 (dd, J=5.1, 8.8 Hz, 1H), 3.82 (s, 3H), 3.71-3.59 (m, 3H), 3.53 (s, 2H), 3.11 (br t, J=11.0 Hz, 2H), 2.62-2.58 (m, 2H), 2.30-2.21 (m, 1H), 2.19-2.09 (m, 1H), 2.00 (br d, J=9.4 Hz, 2H), 1.38-1.26 (m, 2H), 1.13 (t, J=7.2 Hz, 3H)

Example S91. Synthesis of (S)-3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione (91)

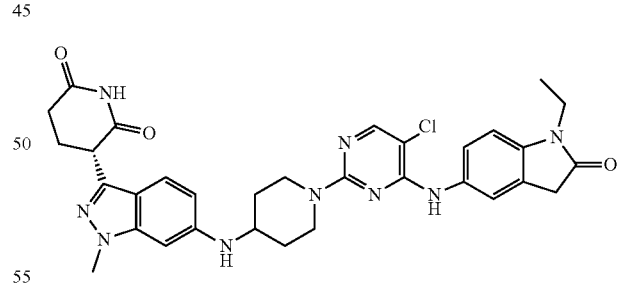

Step 1: Synthesis of (S)-3-(6-((1-(5-chloro-4-((1-ethyl-2-oxoindolin-5-yl)amino)pyrimidin-2-yl)piperidin-4-yl)amino)-1-methyl-1H-indazol-3-yl)piperidine-2,6-dione. The product of Example S89 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=18.20 min. LCMS $C_{32}H_{34}ClN_9O_3$ requires 627.3, found 628.4 [M+H]$^+$; $^1$H NMR (500 MHz, DMSO) δ 10.81 (s, 1H), 8.63 (s, 1H), 8.02 (s, 1H), 7.58-7.50 (m, 2H), 7.32 (d, J=8.8 Hz, 1H), 6.98 (d, J=8.3 Hz, 1H), 6.55-6.49 (m, 1H), 6.46 (s, 1H), 5.76 (d, J=8.3 Hz, 1H), 4.43-4.35 (m, 2H), 4.18 (dd, J=5.2, 8.9 Hz, 1H), 3.82 (s, 3H), 3.71-3.59 (m, 3H), 3.53 (s, 2H), 3.11 (br t, J=11.2 Hz, 2H), 2.62-2.58 (m, 2H), 2.32-2.20 (m, 1H), 2.19-2.11 (m, 1H), 2.00 (br d, J=8.6 Hz, 2H), 1.37-1.27 (m, 2H), 1.13 (t, J=7.2 Hz, 3H).

Example S92. Synthesis of 3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (92)

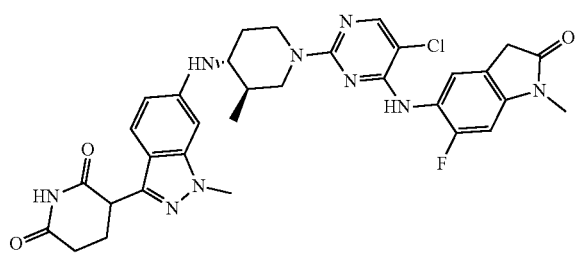 [SMILES: C[C@@H]1CN(c2ncc(Cl)c(Nc3cc4c(cc3F)N(C)C(=O)C4)n2)CC[C@H]1Nc1ccc2c(C3CCC(=O)NC3=O)nn(C)c2c1]

Step 1: Synthesis of 3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The title compound was synthesized according to General Procedures 1 and 6 using 5-amino-6-fluoro-1-methylindolin-2-one and 3-(1-methyl-6-(((3R,4R)-3-methylpiperidin-4-yl)amino)-1H-indazol-3-yl)piperidine-2,6-dione as starting materials. LCMS $C_{32}H_{33}ClFN_9O_3$ requires 645.2, found 646.4 [M+H]$^+$; $^1$H NMR (500 MHz, DMSO) δ ppm 10.81 (s, 1H), 8.58 (s, 1H), 8.00 (s, 1H), 7.27-7.33 (m, 2H), 7.02 (d, J=10.64 Hz, 1H), 6.49 (dd, J=8.80, 1.59 Hz, 1H), 6.40 (s, 1H), 5.67 (d, J=9.05 Hz, 1H), 4.33 (br s, 2H), 4.16 (dd, J=8.74, 5.32 Hz, 1H), 3.80 (s, 3H), 3.53 (s, 2H), 3.23 (br d, J=5.38 Hz, H), 3.10 (s, 3H), 2.91 (br t, J=11.74 Hz, 1H), 2.54-2.64 (m, 3H), 2.19-2.30 (m, 1H), 2.09-2.19 (m, 1H), 1.99 (br d, J=10.15 Hz, 1H), 1.45-1.56 (m, 1H), 1.10 (br d, J=13.33 Hz, 1H), 0.90 (br d, J=6.48 Hz, 3H).

Example S93. Synthesis of (R)-3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (93)

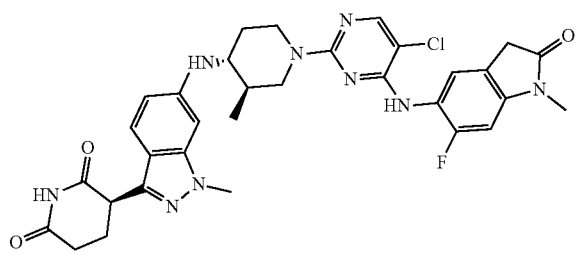 [SMILES: C[C@@H]1CN(c2ncc(Cl)c(Nc3cc4c(cc3F)N(C)C(=O)C4)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S92 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=8.86 min. LCMS $C_{32}H_{33}ClFN_9O_3$ requires 645.2, found 646.4 [M+H]$^+$; $^1$H NMR (500 MHz, DMSO) δ ppm 10.80 (s, 1H), 8.57 (s, 1H), 8.00 (s, 1H), 7.36-7.27 (m, 2H), 7.02 (d, J=10.6 Hz, 1H), 6.49 (dd, J=1.5, 8.8 Hz, 1H), 6.40 (s, 1H), 5.66 (d, J=9.1 Hz, 1H), 4.42-4.25 (m, 2H), 4.16 (dd, J=5.1, 8.8 Hz, 1H), 3.80 (s, 3H), 3.53 (s, 2H), 3.23 (dq, J=3.9, 9.7 Hz, 1H), 3.10 (s, 3H), 2.96-2.87 (m, 1H), 2.64-2.57 (m, 3H), 2.31-2.19 (m, 1H), 2.18-2.09 (m, 1H), 1.99 (br d, J=10.0 Hz, 1H), 1.58-1.43 (m, 1H), 1.17-1.04 (m, 1H), 0.90 (br d, J=6.3 Hz, 3H).

Example S94. Synthesis of (S)-3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (94)

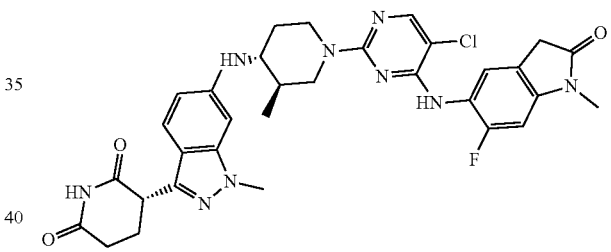

Step 1: Synthesis of (s)-3-(6-(((3R,4R)-1-(5-chloro-4-((6-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S92 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=12.57 min. LCMS $C_{32}H_{33}ClFN_9O_3$ requires 645.2, found 646.4 [M+H]$^+$; $^1$H NMR (500 MHz, DMSO) δ ppm 10.80 (s, 1H), 8.57 (s, 1H), 8.00 (s, 1H), 7.35-7.27 (m, 2H), 7.02 (d, J=10.6 Hz, 1H), 6.49 (dd, J=1.7, 8.8 Hz, 1H), 6.40 (s, 1H), 5.66 (d, J=9.1 Hz, 1H), 4.45-4.23 (m, 2H), 4.16 (dd, J=5.2, 8.8 Hz, 1H), 3.80 (s, 3H), 3.53 (s, 2H), 3.27-3.17 (m, 1H), 3.10 (s, 3H), 2.97-2.86 (m, 1H), 2.61-2.57 (m, 3H), 2.29-2.19 (m, 1H), 2.18-2.09 (m, 1H), 1.99 (br d, J=9.9 Hz, 1H), 1.55-1.47 (m, 1H), 1.17-1.04 (m, 1H), 0.90 (br d, J=6.3 Hz, 3H).

Example S95. Synthesis of 3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (95)

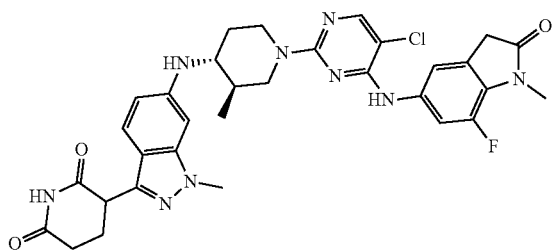 [SMILES: C[C@@H]1CN(c2ncc(Cl)c(Nc3cc(F)c4c(c3)CC(=O)N4C)n2)CC[C@H]1Nc1ccc2c(C3CCC(=O)NC3=O)nn(C)c2c1]

Step 1: Synthesis of 3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione The title compound was synthesized according to General Procedures 1 and 6 using 5-amino-7-fluoro-1-methylindolin-2-one and 3-(1-methyl-6-(((3R,4R)-3-methylpiperidin-4-yl)amino)-1H-indazol-3-yl)piperidine-2,6-dione as starting materials. LCMS $C_{32}H_{33}ClFN_9O_3$ requires 645.2, found 646.4 [M+H]$^+$; $^1$H NMR (500 MHz, DMSO) δ ppm 10.81 (s, 1H), 8.79 (s, 1H), 8.06 (s, 1H), 7.61 (br d, J=13.57 Hz, 1H), 7.43 (s, 1H), 7.31 (d, J=8.80 Hz, 1H), 6.41-6.61 (m, 2H), 5.70 (d, J=8.93 Hz, 1H), 4.40-4.59 (m, 2H), 4.17 (dd, J=8.68, 5.26 Hz, 1H), 3.81 (s, 3H), 3.61 (s, 2H), 3.26 (d, J=2.45 Hz, H), 3.01-3.11 (m, 1H), 2.69-2.78 (m, 1H), 2.56-2.64 (m, 2H), 2.19-2.30 (m, 1H), 2.04-2.18 (m, 2H), 1.53-1.67 (m, 1H), 1.11-1.26 (m, 1H), 0.99 (d, J=6.48 Hz, 3H).

Example S96. Synthesis of (R)-3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (96)

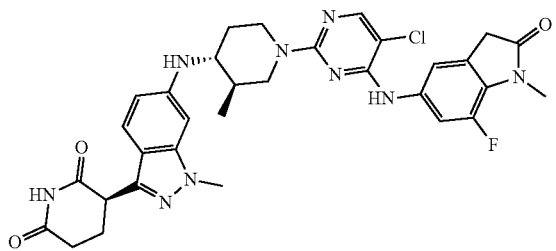 [SMILES: C[C@@H]1CN(c2ncc(Cl)c(Nc3cc(F)c4c(c3)CC(=O)N4C)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S95 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=10.48 min. LCMS $C_{32}H_{33}ClFN_9O_3$ requires 645.2, found 646.4 [M+H]$^+$; $^1$H NMR (500 MHz, DMSO) δ ppm 10.81 (s, 1H), 8.79 (s, 1H), 8.06 (s, 1H), 7.62 (br d, J=13.1 Hz, 1H), 7.44 (br s, 1H), 7.31 (br d, J=8.6 Hz, 1H), 6.51 (br d, J=8.8 Hz, 1H), 6.45 (s, 1H), 5.70 (br d, J=8.0 Hz, 1H), 4.58-4.41 (m, 2H), 4.25-4.12 (m, 1H), 3.82 (br s, 3H), 3.62 (br s, 2H), 3.27 (br s, 3H), 3.14-3.02 (m, 1H), 2.83-2.69 (m, 1H), 2.64-2.59 (m, 1H), 2.33-2.04 (m, 3H), 1.69-1.55 (m, 1H), 1.31-1.13 (m, 1H), 0.99 (br d, J=5.6 Hz, 3H)

Example S97. Synthesis of (S)-3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (97)

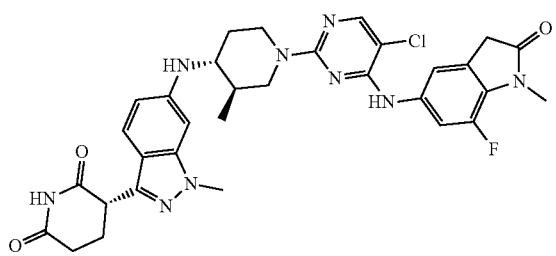 [SMILES: C[C@@H]1CN(c2ncc(Cl)c(Nc3cc(F)c4c(c3)CC(=O)N4C)n2)CC[C@H]1Nc1ccc2c([C@@H]3CCC(=O)NC3=O)nn(C)c2c1]

Step 1: Synthesis of (S)-3-(6-(((3R,4R)-1-(5-chloro-4-((7-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione The product of Example S95 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=15.07 min. LCMS $C_{32}H_{33}ClFN_9O_3$ requires 645.2, found 646.4 [M+H]$^+$; $^1$H NMR (500 MHz, DMSO) δ ppm 10.81 (s, 1H), 8.79 (s, 1H), 8.07 (s, 1H), 7.62 (br d, J=14.2 Hz, 1H), 7.44 (br s, 1H), 7.32 (br d, J=8.7 Hz, 1H), 6.52 (br d, J=8.9 Hz, 1H), 6.45 (s, 1H), 5.70 (br d, J=8.7 Hz, 1H), 4.49 (br t, J=13.4 Hz, 2H), 4.18 (dd, J=5.3, 8.4 Hz, 1H), 3.82 (s, 3H), 3.62 (s, 2H), 3.27 (br s, 3H), 3.07 (t, J=12.2 Hz, 1H), 2.82-2.69 (m, 1H), 2.66-2.57 (m, 2H), 2.31-2.08 (m, 3H), 1.66-1.57 (m, 1H), 1.29-1.13 (m, 1H), 1.00 (d, J=6.3 Hz, 3H).

Example S98. Synthesis of 3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (98)

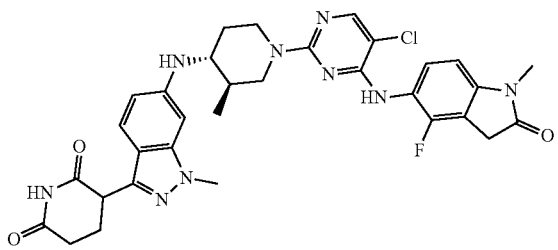 [SMILES: C[C@@H]1CN(c2ncc(Cl)c(Nc3ccc4c(c3F)CC(=O)N4C)n2)CC[C@H]1Nc1ccc2c(C3CCC(=O)NC3=O)nn(C)c2c1]

Step 1: Synthesis of 3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The title compound was synthesized according to General Procedures 1 and 6 using 5-amino-4-fluoro-1-methylindolin-2-one and 3-(1-methyl-6-(((3R,4R)-3-methylpiperidin-4-yl)amino)-1H-indazol-3-yl)piperidine- 2,6-dione as starting materials. LCMS $C_{32}H_{33}ClFN_9O_3$ requires 645.2, found 646.4 [M+H]$^+$; $^1$H NMR (400 MHz, DMSO-d$_6$) δ ppm 10.81 (s, 1H), 8.64 (s, 1H), 8.01 (s, 1H), 7.35 (t, J=7.95 Hz, 1H), 7.29 (d, J=8.80 Hz, 1H), 6.84 (d, J=8.31 Hz, 1H), 6.49 (dd, J=8.86, 1.53 Hz, 1H), 6.40 (s, 1H), 5.67 (d, J=8.93 Hz, 1H), 4.21-4.48 (m, 2H), 4.12-4.21 (m, 1H), 3.79 (s, 3H), 3.53-3.70 (m, 2H), 3.23 (qd, J=9.78, 3.79 Hz, 1H), 3.13 (s, 3H), 2.86-2.98 (m, 1H), 2.52-2.63 (m, 3H), 2.19-2.31 (m, 1H), 2.08-2.19 (m, 1H), 1.93-2.05 (m, 1H), 1.43-1.60 (m, 1H), 0.99-1.17 (m, 1H), 0.79-0.96 (m, 3H).

Example S99. Synthesis of (R)-3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (99)

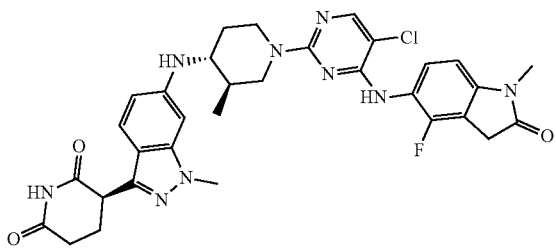 [SMILES: C[C@@H]1CN(c2ncc(Cl)c(Nc3ccc4c(c3F)CC(=O)N4C)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S98 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=8.56 min. LCMS $C_{32}H_{33}ClFN_9O_3$ requires 645.2, found 646.4 [M+H]$^+$; H NMR (400 MHz, DMSO-d$_6$) δ ppm 10.80 (br s, 1H), 9.99-9.96 (m, 1H), 8.63 (br s, 1H), 8.00 (s, 1H), 7.39-7.26 (m, 2H), 6.84 (br d, J=8.1 Hz, 1H), 6.49 (br d, J=8.5 Hz, 1H), 6.40 (br s, 1H), 5.66 (br d, J=8.8 Hz, 1H), 4.45-4.22 (m, 2H), 4.16 (br dd, J=4.9, 8.5 Hz, 1H), 3.79 (s, 3H), 3.70-3.51 (m, 2H), 3.26-3.18 (m, 1H), 3.12 (s, 3H), 2.96-2.87 (m, 1H), 2.67-2.55 (m, 3H), 2.29-2.19 (m, 1H), 2.18-2.10 (m, 1H), 1.99 (br d, J=10.1 Hz, 1H), 1.54-1.43 (m, 1H), 1.15-1.04 (m, 1H), 0.89 (br s, 3H).

Example S100. Synthesis of (S)-3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione (100)

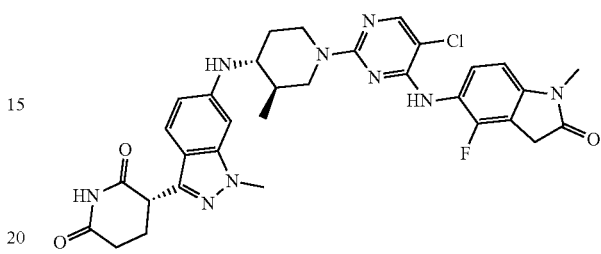

Step 1: Synthesis of(S)-3-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)piperidine-2,6-dione. The product of Example S98 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=12.25 min. LCMS $C_{32}H_{33}ClFN_9O_3$ requires 645.2, found 646.4 [M+H]$^+$; $^1$H NMR (400 MHz, DMSO-d$_6$) δ ppm 10.80 (s, 1H), 8.63 (br s, 1H), 8.00 (s, 1H), 7.46-7.20 (m, 2H), 6.84 (br d, J=8.2 Hz, 1H), 6.49 (br d, J=8.8 Hz, 1H), 6.40 (br s, 1H), 5.66 (br d, J=8.7 Hz, 1H), 4.42-4.21 (m, 2H), 4.16 (br dd, J=5.0, 8.3 Hz, 1H), 3.79 (s, 3H), 3.72-3.52 (m, 2H), 3.27-3.19 (m, 1H), 3.12 (s, 3H), 2.97-2.87 (m, 1H), 2.59 (br d, J=4.5 Hz, 3H), 2.29-2.19 (m, 1H), 2.18-2.07 (m, 1H), 1.99 (br d, J=10.8 Hz, 1H), 1.57-1.42 (m, 1H), 1.18-1.02 (m, 1H), 0.89 (br s, 3H).

Example S101. Synthesis of 3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione (101)

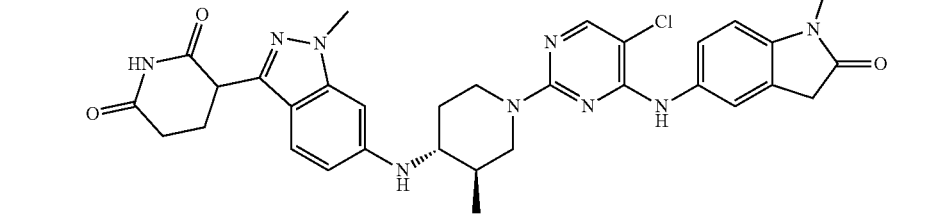

Step 1: Synthesis of 3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione. The title compound was synthesized according to General Procedures 1 and 6 using 5-amino-1-(2-morpholinoethyl)indolin-2-one and 3-(1-methyl-6-(((3R,4R)-3-methylpiperidin-4-yl)amino)-1H-indazol-3-yl)piperidine-2,6-dione as starting materials. LCMS $C_{37}H_{43}ClN_{10}O_4$ requires 726.3, found 727.2 [M+H]$^+$; $^1$H NMR (400 MHz, DMSO-d$_6$) δ 10.84 (s, 1H), 8.70 (s, 1H), 8.04 (s, 1H), 7.64-7.53 (m, 2H), 7.31 (d, J=8.80 Hz, 1H), 7.13-7.00 (m, 1H), 6.50 (d, J=8.80 Hz, 1H), 6.45 (s, 1H), 5.70 (d, J=8.40 Hz, 1H), 4.52-4.45 (m, 2H), 4.19-4.16 (m, 1H), 4.08-3.90 (m, 2H), 3.81 (s, 3H), 3.65-3.45 (m, 6H), 3.40-3.35 (m, 1H), 3.19-3.11 (s, 1H), 3.05-2.95 (m, 1H), 2.71-2.60 (m, 1H), 2.59-2.54 (m, 2H), 2.46-2.42 (m, 1H), 2.31-2.22 (m, 1H), 2.19-2.08 (m, 2H), 1.62-1.55 (m, 1H), 1.21-1.15 (m, 1H), 0.98 (d, J=6.0 Hz, 3H).

Example S102. Synthesis of (R)-3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione (102)

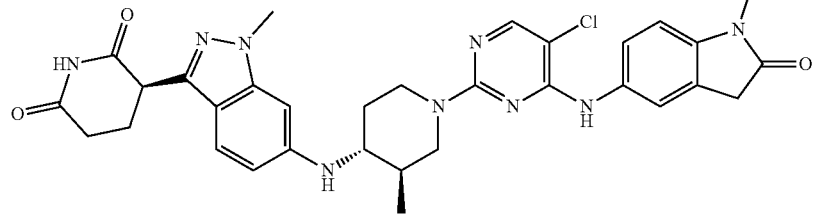

Step 1: Synthesis of (R)-3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione. The product of Example S101 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak. LCMS $C_{37}H_{43}ClN_{10}O_4$ requires 726.3, found 727.2 [M+H]$^+$; $^1$H NMR (500 MHz, DMSO-d$_6$) δ 10.80 (s, 1H), 8.64 (s, 1H), 8.02 (s, 1H), 7.56 (br s, 1H), 7.50 (br d, J=8.3 Hz, 1H), 7.30 (d, J=8.8 Hz, 1H), 6.99 (d, J=8.3 Hz, 1H), 6.50 (dd, J=1.5, 8.9 Hz, 1H), 6.43 (s, 1H), 5.68 (d, J=8.9 Hz, 1H), 4.51-4.41 (m, 2H), 4.17 (dd, J=5.2, 8.6 Hz, 1H), 3.81 (s, 3H), 3.76 (br t, J=6.5 Hz, 2H), 3.56-3.48 (m, 5H), 3.02 (br t, J=12.3 Hz, 1H), 2.73-2.57 (m, 4H), 2.42 (br s, 3H), 2.30-2.01 (m, 4H), 1.64-1.51 (m, 1H), 1.23-1.11 (m, 1H), 0.96 (br d, J=6.4 Hz, 3H).

Example S103. Synthesis of (S)-3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione (103)

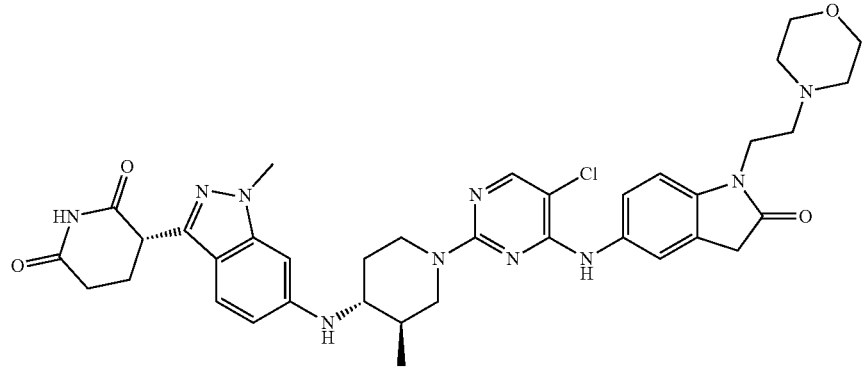

Step 1: Synthesis of (S)-3-(6-(((3R,4R)-1-(5-chloro-4-((1-(2-morpholinoethyl)-2-oxoindolin-5-yl)amino)pyrimidin-2-yl)-3-methylpiperidin-4-yl)amino)-1-methyl-1H-indazol-3-yl)piperidine-2,6-dione. The product of Example S101 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak. LCMS $C_{37}H_{43}ClN_{10}O_4$ requires 726.3, found 727.2 [M+H]$^+$; $^1$H NMR (500 MHz, DMSO-d$_6$) δ 10.80 (s, 1H), 8.65 (s, 1H), 8.02 (s, 1H), 7.56 (s, 1H), 7.50 (br d, J=8.5 Hz, 1H), 7.30 (d, J=8.8 Hz, 1H), 6.99 (br d, J=8.5 Hz, 1H), 6.50 (dd, J=1.5, 8.8 Hz, 1H), 6.43 (s, 1H), 5.68 (d, J=9.1 Hz, 1H), 4.46 (br s, 2H), 4.17 (dd, J=5.2, 8.8 Hz, 1H), 3.81 (s, 3H), 3.76 (br t, J=6.2 Hz, 2H), 3.52 (br d, J=16.2 Hz, 6H), 3.02 (br t, J=12.6 Hz, 1H), 2.74-2.56 (m, 4H), 2.42 (br s, 3H), 2.31-2.03 (m, 3H), 1.63-1.53 (m, 1H), 1.22-1.12 (m, 1H), 0.97 (br d, J=6.3 Hz, 3H).

Example S104. Synthesis of 3-(6-(((3R,4R)-1-(5-chloro-4-((1-(2-(methylamino)ethyl)-2-oxoindolin-5-yl)amino)pyrimidin-2-yl)-3-methylpiperidin-4-yl)amino)-1-methyl-1H-indazol-3-yl)piperidine-2,6-dione (104)

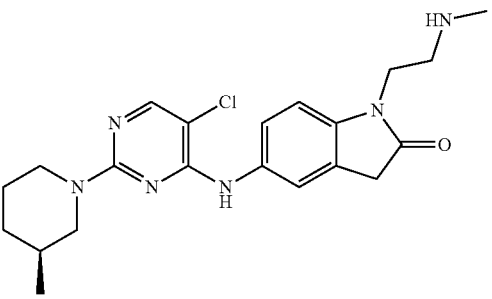

Step 1: Synthesis of 3-(6-(((3R,4R)-1-(5-chloro-4-((1-(2-(methylamino)ethyl)-2-oxoindolin-5-yl)amino)pyrimidin-2-yl)-3-methylpiperidin-4-yl)amino)-1-methyl-1H-indazol-3-yl)piperidine-2,6-dione. The title compound was synthesized according to General Procedures 1, 6, and 5 using tert-butyl (2-(5-amino-2-oxoindolin-1-yl)ethyl)(methyl)carbamate and 3-(1-methyl-6-(((3R,4R)-3-methylpiperidin-4-yl)amino)-1H-indazol-3-yl)piperidine-2,6-dione as starting materials. LCMS $C_{34}H_{39}ClN_{10}O_3$ requires 670.3, found 672.2 [M+H]$^+$; $^1$H NMR (400 MHz, DMSO-d$_6$): δ 10.84 (s, 1H), 8.67 (s, 1H), 8.03 (s, 1H), 7.59 (s, 1H), 7.51 (d, J=8.40, 1.60 Hz, 1H), 7.32 (d, J=8.40 Hz, 1H), 7.01 (d, J=8.40 Hz, 1H), 6.50 (dd, J=8.80, 1.60 Hz, 1H), 6.45 (s, 1H), 5.69-5.58 (m, 1H), 4.55-4.47 (m, 2H), 4.19-4.16 (m, 1H), 3.81 (s, 3H), 3.80-3.75 (m, 2H), 3.53 (s, 2H), 3.05-2.96 (s, 1H), 2.85-2.75 (m, 2H), 2.72-2.65 (m, 1H), 2.62-2.55 (m, 2H), 2.36 (s, 3H), 2.28-2.20 (m, 2H), 2.19-2.05 (m, 1H), 1.62-1.53 (m, 1H), 1.25-1.18 (m, 1H), 0.97 (d, J=6.4 Hz, 3H).

Example S105. Synthesis of (R)-3-(6-(((3R,4R)-1-(5-chloro-4-((1-(2-(methylamino)ethyl)-2-oxoindolin-5-yl)amino)pyrimidin-2-yl)-3-methylpiperidin-4-yl)amino)-1-methyl-1H-indazol-3-yl)piperidine-2,6-dione (105)

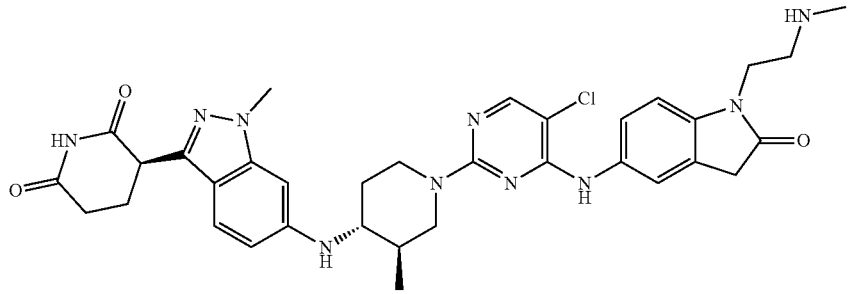 [SMILES: CNCCN1C(=O)Cc2cc(Nc3nc(N4CC[C@@H](Nc5ccc6c([C@H]7CCC(=O)NC7=O)nn(C)c6c5)[C@H](C)C4)ncc3Cl)ccc21]

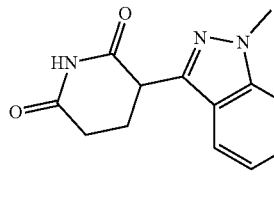

The product of Example S104 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=18.13 min. LCMS $C_{34}H_{39}ClN_{10}O_3$ requires 670.3, found 672.2 [M+H]$^+$; $^1$H NMR (400 MHz, DMSO-d$_6$): δ 10.80 (s, 1H), 8.64 (s, 1H), 8.02 (s, 1H), 7.56 (s, 1H), 7.50 (dd, J=1.8, 8.5 Hz, 1H), 7.30 (d, J=8.8 Hz, 1H), 6.99 (d, J=8.5 Hz, 1H), 6.50 (dd, J=1.7, 8.8 Hz, 1H), 6.44 (s, 1H), 5.68 (d, J=9.1 Hz, 1H), 4.53-4.41 (m, 2H), 4.17 (dd, J=5.1, 8.8 Hz, 1H), 3.81 (s, 3H), 3.71 (t, J=6.4 Hz, 2H), 3.52 (s, 2H), 3.07-2.96 (m, 1H), 2.73-2.57 (m, 7H), 2.32-2.20 (m, 5H), 2.19-2.02 (m, 3H), 1.64-1.54 (m, 1H), 1.20-1.11 (m, 1H), 0.97 (d, J=6.4 Hz, 3H).

Example S106. Synthesis of (S)-3-(6-(((3R,4R)-1-(5-chloro-4-((1-(2-(methylamino)ethyl)-2-oxoindolin-5-yl)amino)pyrimidin-2-yl)-3-methylpiperidin-4-yl)amino)-1-methyl-1H-indazol-3-yl)piperidine-2,6-dione (106)

Example S107. Synthesis of 3-(6-(((3R,4R)-1-(5-chloro-4-((1-(3-fluoro-3-methylbutyl)-2-oxoindolin-5-yl)amino)pyrimidin-2-yl)-3-methylpiperidin-4-yl)amino)-1-methyl-1H-indazol-3-yl)piperidine-2,6-dione (107)

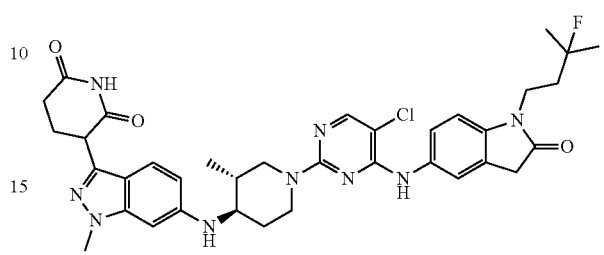

Step 1: Synthesis of 3-(6-(((3R,4R)-1-(5-chloro-4-((1-(3-fluoro-3-methylbutyl)-2-oxoindolin-5-yl)amino)pyrimidin-

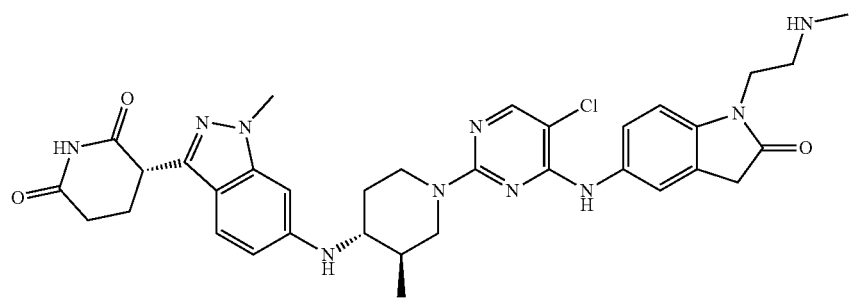

The product of Example S104 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=40.27 min. LCMS $C_{34}H_{39}ClN_{10}O_3$ requires 670.3, found 672.2 [M+H]$^+$; $^1$H NMR (400 MHz, DMSO-d$_6$): δ 10.80 (s, 1H), 8.64 (s, 1H), 8.01 (s, 1H), 7.56 (s, 1H), 7.50 (dd, J=1.7, 8.4 Hz, 1H), 7.30 (d, J=8.7 Hz, 1H), 6.99 (d, J=8.6 Hz, 1H), 6.50 (dd, J=1.5, 8.8 Hz, 1H), 6.44 (s, 1H), 5.68 (d, J=9.1 Hz, 1H), 4.53-4.39 (m, 2H), 4.17 (dd, J=5.1, 8.7 Hz, 1H), 3.81 (s, 3H), 3.70 (t, J=6.5 Hz, 2H), 3.52 (s, 2H), 3.02 (br t, J=11.7 Hz, 1H), 2.74-2.58 (m, 7H), 2.31-2.20 (m, 4H), 2.19-2.03 (m, 2H), 1.58 (br dd, J=4.5, 5.8 Hz, 1H), 1.22-1.12 (m, 1H), 0.97 (d, J=6.4 Hz, 3H).

2-yl)-3-methylpiperidin-4-yl)amino)-1-methyl-1H-indazol-3-yl)piperidine-2,6-dione. The title compound was synthesized according to General Procedures 1 and 6 using 5-amino-1-(3-fluoro-3-methylbutyl)indolin-2-one and 3-(1-methyl-6-(((3R,4R)-3-methylpiperidin-4-yl)amino)-1H-indazol-3-yl)piperidine-2,6-dione as starting materials. LCMS $C_{36}H_{41}ClFN_9O_3$ requires 701.3, found 702.2 [M+H]$^+$; $^1$H NMR (400 MHz, DMSO-d$_6$): δ 10.82 (s, 1H), 9.62 (s, 1H), 8.15 (s, 1H), 7.51 (s, 1H), 7.46 (d, J=8.40 Hz, 1H), 7.33 (d, J=8.80 Hz, 1H), 6.97 (d, J=8.40 Hz, 1H), 6.53 (d, J=8.80 Hz, 1H), 6.47 (s, 1H), 4.27-4.25 (m, 2H), 4.19-4.16 (m, 1H), 3.81 (s, 3H), 3.54 (s, 2H), 3.36-3.31 (m, 1H), 3.18-3.12 (m, 1H), 2.88-2.82 (m, 1H), 2.63-2.58 (m, 2H), 2.26-2.23 (m, 1H), 2.16-2.09 (m, 2H), 1.92-1.83 (m, 2H), 1.65-1.63 (m, 1H), 1.36 (d, J=21.60 Hz, 6H), 1.24-1.22 (m, 1H), 0.96 (d, J=6.40 Hz, 3H).

Example S108. Synthesis of (R)-3-(6-(((3R,4R)-1-(5-chloro-4-((1-(3-fluoro-3-methylbutyl)-2-oxoindolin-5-yl)amino)pyrimidin-2-yl)-3-methylpiperidin-4-yl)amino)-1-methyl-1H-indazol-3-yl)piperidine-2,6-dione (108)

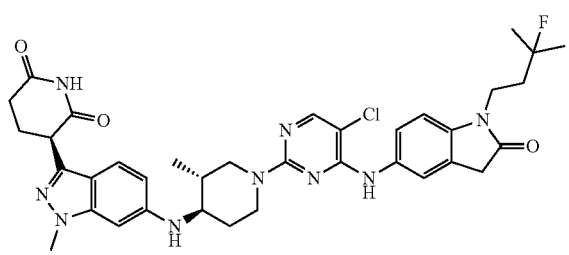 [SMILES: C[C@@H]1CN(c2ncc(Cl)c(Nc3ccc4c(c3)CC(=O)N4CCC(C)(C)F)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((1-(3-fluoro-3-methylbutyl)-2-oxoindolin-5-yl)amino)pyrimidin-2-yl)-3-methylpiperidin-4-yl)amino)-1-methyl-1H-indazol-3-yl)piperidine-2,6-dione. The product of Example S107 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=7.46 min. LCMS $C_{36}H_{41}ClFN_9O_3$ requires 701.3, found 702.2 [M+H]$^+$; $^1$H NMR (500 MHz, DMSO-d$_6$) δ 10.80 (s, 1H), 8.70 (br s, 1H), 8.03 (s, 1H), 7.59 (s, 1H), 7.51 (dd, J=1.8, 8.5 Hz, 1H), 7.30 (d, J=8.7 Hz, 1H), 6.93 (d, J=8.5 Hz, 1H), 6.50 (dd, J=1.4, 8.8 Hz, 1H), 6.43 (s, 1H), 5.68 (br d, J=8.9 Hz, 1H), 4.52-4.39 (m, 2H), 4.17 (dd, J=5.1, 8.7 Hz, 1H), 3.81 (s, 3H), 3.78-3.72 (m, 2H), 3.54 (s, 2H), 3.02 (br t, J=12.2 Hz, 1H), 2.73-2.56 (m, 4H), 2.31-2.04 (m, 4H), 1.96-1.84 (m, 2H), 1.64-1.52 (m, 1H), 1.40 (s, 3H), 1.35 (s, 3H), 1.26-1.10 (m, 2H), 0.96 (d, J=6.4 Hz, 3H).

Example S109. Synthesis of (S)-3-(6-(((3R,4R)-1-(5-chloro-4-((1-(3-fluoro-3-methylbutyl)-2-oxoindolin-5-yl)amino)pyrimidin-2-yl)-3-methylpiperidin-4-yl)amino)-1-methyl-1H-indazol-3-yl)piperidine-2,6-dione (109)

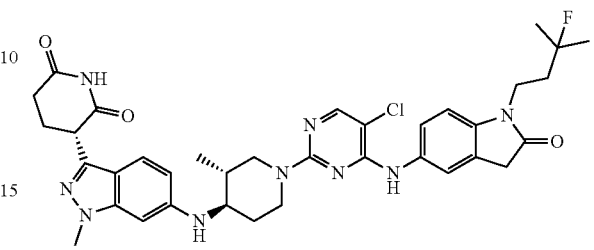

Step 1: Synthesis of (S)-3-(6-(((3R,4R)-1-(5-chloro-4-((1-(3-fluoro-3-methylbutyl)-2-oxoindolin-5-yl)amino)pyrimidin-2-yl)-3-methylpiperidin-4-yl)amino)-1-methyl-1H-indazol-3-yl)piperidine-2,6-dione. The product of Example S107 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=10.56 min. LCMS $C_{36}H_{41}ClFN_9O_3$ requires 701.3, found 702.2 [M+H]$^+$; $^1$H NMR (500 MHz, DMSO-d$_6$) δ 10.80 (s, 1H), 8.68 (br s, 1H), 8.02 (s, 1H), 7.59 (s, 1H), 7.51 (dd, J=1.8, 8.5 Hz, 1H), 7.30 (d, J=8.7 Hz, 1H), 6.92 (d, J=8.5 Hz, 1H), 6.51 (dd, J=1.4, 8.8 Hz, 1H), 6.43 (s, 1H), 5.68 (br d, J=9.1 Hz, 1H), 4.53-4.39 (m, 2H), 4.17 (dd, J=5.2, 8.9 Hz, 1H), 3.81 (s, 3H), 3.77-3.70 (m, 2H), 3.53 (s, 2H), 3.02 (br t, J=12.3 Hz, 1H), 2.72-2.58 (m, 4H), 2.30-2.03 (m, 4H), 1.94-1.83 (m, 2H), 1.63-1.53 (m, 1H), 1.40 (s, 3H), 1.35 (s, 3H), 1.28-1.12 (m, 2H), 0.96 (d, J=6.4 Hz, 3H).

Example S110. Synthesis of 3-(6-(((3R,4R)-1-(5-chloro-4-((1-(2,2-difluoropropyl)-2-oxoindolin-5-yl)amino)pyrimidin-2-yl)-3-methylpiperidin-4-yl)amino)-1-methyl-1H-indazol-3-yl)piperidine-2,6-dione (110)

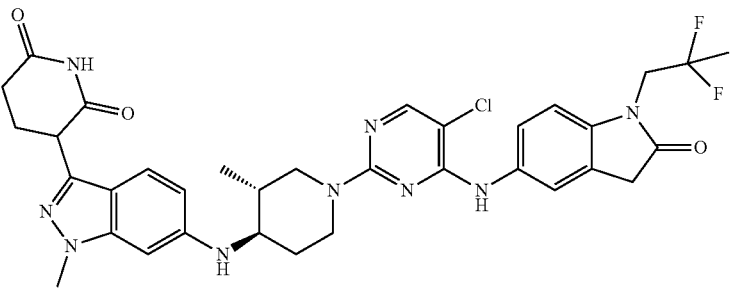

The title compound was synthesized according to General Procedures 1 and 6 using 5-amino-1-(2,2-difluoropropyl)indolin-2-one and 3-(1-methyl-6-(((3R,4R)-3-methylpiperidin-4-yl)amino)-1H-indazol-3-yl)piperidine-2,6-dione as starting materials. LCMS $C_{34}H_{36}ClF_2N_9O_3$ requires 691.3, found 692.2 [M+H]$^+$; $^1$H NMR (400 MHz, DMSO-d$_6$): δ 10.98 (s, 1H), 8.69 (s, 1H), 8.03 (s, 1H), 7.59 (s, 1H), 7.52 (dd, J=2.00 Hz and 8.4 Hz, 1H), 7.31 (d, J=8.80 Hz, 1H), 7.03 (d, J=8.80 Hz, 1H), 6.51 (dd, J=1.60 Hz and 8.8 Hz, 1H), 6.45 (s, 1H), 5.70 (d, J=8.80 Hz, 1H), 4.54-4.46 (m, 2H), 4.19-4.10 (m, 3H), 3.82 (s, 3H), 3.65 (s, 2H), 3.02 (t, J=12.80 Hz, 1H), 2.69-2.65 (m, 2H), 2.29-2.22 (m, 1H), 2.18-2.12 (m, 1H), 2.09-2.06 (m, 1H), 1.67 (t, J=19.2 Hz, 3H), 1.62-1.58 (m, 2H), 1.18-1.13 (m, 1H), 0.97 (d, J=6.80 Hz, 4H).

Example S111. Synthesis of (R)-3-(6-(((3R,4R)-1-(5-chloro-4-((1-(2,2-difluoropropyl)-2-oxoindolin-5-yl)amino)pyrimidin-2-yl)-3-methylpiperidin-4-yl)amino)-1-methyl-1H-indazol-3-yl)piperidine-2,6-dione (111)

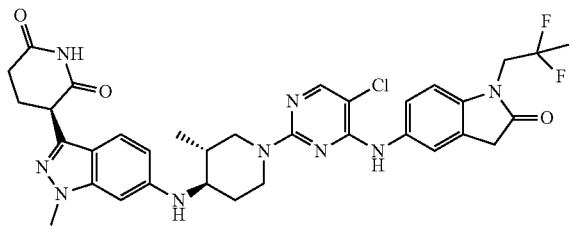 [SMILES: C[C@@H]1CN(c2ncc(Cl)c(Nc3ccc4c(c3)CC(=O)N4CC(C)(F)F)n2)CC[C@H]1Nc1ccc2c([C@H]3CCC(=O)NC3=O)nn(C)c2c1]

Step 1: Synthesis of (R)-3-(6-(((3R,4R)-1-(5-chloro-4-((1-(2,2-difluoropropyl)-2-oxoindolin-5-yl)amino)pyrimidin-2-yl)-3-methylpiperidin-4-yl)amino)-1-methyl-1H-indazol-3-yl)piperidine-2,6-dione. The product of Example 5110 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the first eluting peak, Rt=6.18 min. LCMS $C_{34}H_{36}ClF_2N_9O_3$ requires 691.3, found 692.2 [M+H]$^+$; $^1$H NMR (400 MHz, DMSO-d$_6$): δ 10.80 (s, 1H), 8.68 (s, 1H), 8.02 (s, 1H), 7.58 (s, 1H), 7.51 (dd, J=1.9, 8.6 Hz, 1H), 7.30 (d, J=8.7 Hz, 1H), 7.02 (d, J=8.3 Hz, 1H), 6.50 (dd, J=1.6, 8.8 Hz, 1H), 6.44 (s, 1H), 5.68 (br d, J=9.1 Hz, 1H), 4.54-4.39 (m, 2H), 4.26-4.06 (m, 3H), 3.81 (s, 3H), 3.64 (s, 2H), 3.02 (br t, J=11.8 Hz, 1H), 2.74-2.56 (m, 4H), 2.38-2.34 (m, 1H), 2.30-2.03 (m, 4H), 1.66 (t, J=19.1 Hz, 3H), 1.60-1.53 (m, 1H), 1.22-1.13 (m, 1H), 0.96 (d, J=6.4 Hz, 3H).

Example S112. Synthesis of (S)-3-(6-(((3R,4R)-1-(5-chloro-4-((1-(2,2-difluoropropyl)-2-oxoindolin-5-yl)amino)pyrimidin-2-yl)-3-methylpiperidin-4-yl)amino)-1-methyl-1H-indazol-3-yl)piperidine-2,6-dione (112)

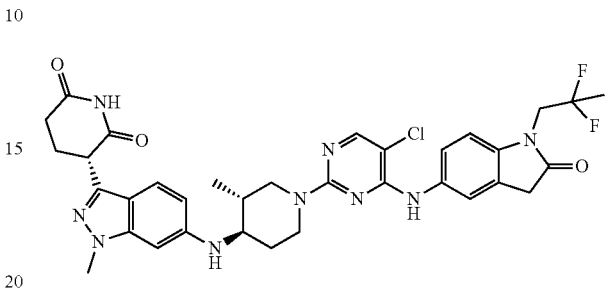

The product of Example S110 was then separated using preparatory HPLC with a Regis Whelk-O1 SS, 21×250 mm, 5 u column, 1 mL/min flow rate in 100% MeCN (no additives) isocratic elution at 22° C. The title compound was isolated as the second eluting peak, Rt=8.48 min. LCMS $C_{34}H_{36}ClF_2N_9O_3$ requires 691.3, found 692.2 [M+H]$^+$; $^1$H NMR (400 MHz, DMSO-d$_6$): δ 10.80 (s, 1H), 8.66 (s, 1H), 8.02 (s, 1H), 7.58 (s, 1H), 7.54-7.48 (m, 1H), 7.30 (d, J=8.7 Hz, 1H), 7.02 (d, J=8.7 Hz, 1H), 6.53-6.48 (m, 1H), 6.44 (s, 1H), 5.68 (d, J=9.1 Hz, 1H), 4.52-4.40 (m, 2H), 4.20-4.08 (m, 3H), 3.81 (s, 3H), 3.64 (s, 2H), 3.07-2.96 (m, 1H), 2.73-2.58 (m, 6H), 2.38-2.34 (m, 1H), 2.31-2.03 (m, 3H), 1.66 (t, J=19.1 Hz, 3H), 1.60-1.53 (m, 1H), 1.23-1.12 (m, 1H), 0.96 (d, J=6.4 Hz, 3H).

Examples in Table 3 below have been made according to the general procedures outlined in the table beginning with their respective commercial starting materials and intermediates found within this document.

TABLE 3

| Compound | General Procedure No. | MS Data | NMR Data |
|---|---|---|---|
| Example S113<br>2-((3R,4R)-4-((3-(2,6-dioxopiperidin-3-yl)-1-methyl-1H-indazol-6-yl)amino)-3-methylpiperidin-1-yl)-4-((1-methyl-2-oxoindolin-5-yl)amino)pyrimidine-5-carbonitrile (113) | 1, 6 | Requires 618.3, found 619.4 [M + H]$^+$ | $^1$H NMR (400 MHz, DMSO-d$_6$) δ ppm 0.85-0.97 (m, 3 H), 1.04-1.26 (m, 1 H) 1.52 (br s, 1 H) 2.00-2.25 (m, 3 H) 2.46-2.58 (m, 2 H) 2.72 (br d, J = 11.98 Hz, 1 H) 2.92-3.16 (m, 4 H) 3.27 (br s, 2 H) 3.38-3.54 (m, 5 H) 3.73-3.81 (m, 7 H) 3.92 (br s, 1 H) 4.11 (dd, J = 8.80, 5.14 Hz, 2 H) 4.36 (br s, 1 H) 4.58 (br s, 1 H) 6.37-6.48 (m, 2 H) 6.86 (br s, 1 H) 7.25 (d, J = 8.68 Hz, 1 H) 7.36 (br s, 1 H) 7.46 (br s, 1 H) 8.34 (s, 1 H) 9.23 (br s, 1 H) 10.75 (s, 1 H) |

TABLE 3-continued

| Compound | General Procedure No. | MS Data | NMR Data |
|---|---|---|---|
| Example S114<br>3-(6-(((3R,4R)-1-(5-chloro-4-((2-oxoindolin-5-yl)amino)pyrimidin-2-yl)-3-methylpiperidin-4-yl)amino)-1-methyl-1H-indazol-3-yl)piperidine-2,6-dione (114) | 1, 6 | Requires 613.2, found 614.2 [M + H]⁺ | ¹H NMR (400 MHz, DMSO-d₆) δ ppm 10.82 (s, 1H), 10.37 (s, 1H), 9.16 (br s, 1H), 8.11 (s, 1H), 7.46 (s, 1H), 7.37 (br d, J = 8.07 Hz, 1H), 7.32 (d, J = 8.80 Hz, 1H), 6.79 (d, J = 8.31 Hz, 1H), 6.52 (br d, J = 8.93 Hz, 1H), 6.44 (s, 1H), 4.34 (br d, J = 8.44 Hz, 2H), 4.17 (dd, J = 8.80, 5.26 Hz, 1H), 3.81 (s, 3H), 3.27-3.35 (m, 1H), 3.09 (br t, J = 11.98 Hz, 1H), 2.71-2.82 (m, 1H), 2.56-2.65 (m, 2H), 2.20-2.31 (m, 1H), 2.05-2.19 (m, 2H), 1.61 (br s, 1H), 1.20 (br d, J = 10.27 Hz, 1H), 0.96 (d, J = 6.60 Hz, 3H). 3 exchangeable protons not observed. |
| Example S115<br>3-(6-(((3R,4R)-1-(5-chloro-4-((1-isopropyl-2-oxoindolin-5-yl)amino)pyrimidin-2-yl)-3-methylpiperidin-4-yl)amino)-1-methyl-1H-indazol-3-yl)piperidine-2,6-dione (115) | 1, 6 | Requires 655.3, found 656.4 [M + H]⁺. | ¹H NMR (400 MHz, DMSO-d6) δ ppm 10.81 (s, 1 H), 8.65 (s, 1 H), 8.02 (s, 1 H), 7.59 (s, 1 H), 7.48 (dd, J = 8.62, 2.02 Hz, 1 H), 7.30 (d, J = 8.68 Hz, 1 H), 7.10 (d, J = 8.56 Hz, 1 H), 6.50 (dd, J = 8.86, 1.53 Hz, 1 H), 6.44 (s, 1 H), 5.69 (d, J = 9.05 Hz, 1 H), 4.39-4.59 (m, 3 H), 4.17 (dd, J = 8.68, 5.14 Hz, 1 H), 3.81 (s, 3 H), 3.50 (s, 2 H), 3.21-3.30 (m, 1 H), 3.02 (br t, J = 11.74 Hz, 1 H), 2.64-2.73 (m, 1 H), 2.56-2.63 (m, 2 H), 2.05-2.30 (m, 3 H), 1.50-1.64 (m, 1 H), 1.38 (d, J = 6.97 (Hz, 6 H), 1.09-1.26 (m, 1 H), 0.97 (d, J = 6.48 Hz, 3 H) |
| Example S116<br>2-((3R,4R)-4-((3-(2,6-dioxopiperidin-3-yl)-1-methyl-1H-indazol-6-yl)amino)-3-methylpiperidin-1-yl)-4-((7-fluoro-1-methyl-2-oxoindolin-5-yl)amino)pyrimidine-5-carbonitrile (116) | 1, 6 | Requires 636.3, found 637.4 [M + H]⁺. | ¹H NMR (400 MHz, DMSO-d6) δ ppm 0.92-1.06 (m, 3 H) 1.26 (d, J = 6.11 Hz, 6 H) 1.98-2.37 (m, 6 H) 2.57-2.73 (m, 1 H) 3.09-3.21 (m, 2 H) 3.23-3.34 (m, 5 H) 3.77-3.88 (m, 5 H) 4.15-4.23 (m, 1 H) 4.36-4.54 (m, 1 H) 4.54-4.73 (m, 1 H) 6.42-6.59 (m, 2 H) 6.92-7.25 (m, 1 H) 7.28-7.40 (m, 1 H) 7.28-7.29 (m, 1 H) 8.43-8.48 (m, 1 H) 10.80-10.86 (m, 1 H) |

TABLE 3-continued

| Compound | General Procedure No. | MS Data | NMR Data |
|---|---|---|---|
| 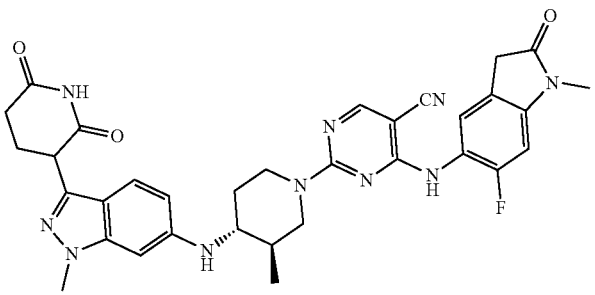 [SMILES: C[C@@H]1CN(c2ncc(C#N)c(Nc3cc4c(cc3F)N(C)C(=O)C4)n2)CC[C@H]1Nc1ccc2c(C3CCC(=O)NC3=O)nn(C)c2c1]

Example S117

2-((3R,4R)-4-((3-(2,6-dioxopiperidin-3-yl)-1-methyl-1H-indazol-6-yl)amino)-3-methylpiperidin-1-yl)-4-((6-fluoro-1-methyl-2-oxoindolin-5-yl)amino)pyrimidine-5-carbonitrile (117) | 1, 6 | Requires 636.3, found 637.2 [M + H]$^+$. | $^1$H NMR (400 MHz, DMSO-d6) δ ppm 0.83-1.01 (m, 3 H) 1.47-1.60 (m, 1 H) 1.98-2.36 (m, 6 H) 2.61-2.74 (m, 1 H) 3.04-3.18 (m, 3 H) 3.46-3.58 (m, 2 H) 3.80 (s, 3 H) 4.10-4.31 (m, 2 H) 4.13-4.31 (m, 2 H) 4.53-4.69 (m, 1 H) 5.64-5.73 (m, 1 H) 6.39-6.47 (m, 1 H) 6.47-6.57 (m, 1H) 6.96-7.10 (m, 1 H) 7.18-7.34 (m, 2 H) 8.31-8.46 (m, 1 H) 9.14-9.29 (m, 1 H) 10.71-10.90 (m, 1 H). |
| 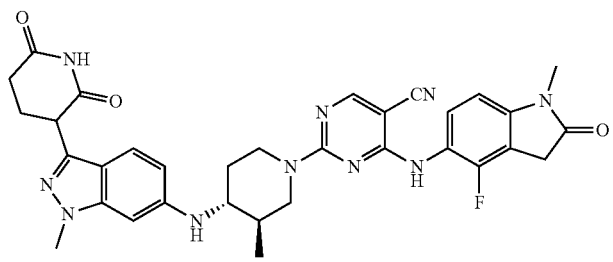 [SMILES: C[C@@H]1CN(c2ncc(C#N)c(Nc3ccc4c(c3F)CC(=O)N4C)n2)CC[C@H]1Nc1ccc2c(C3CCC(=O)NC3=O)nn(C)c2c1]

Example S118

2-((3R,4R)-4-((3-(2,6-dioxopiperidin-3-yl)-1-methyl-1H-indazol-6-yl)amino)-3-methylpiperidin-1-yl)-4-((4-fluoro-1-methyl-2-oxoindolin-5-yl)amino)pyrimidine-5-carbonitrile (118) | 1, 6 | Requires 636.3, found 637.2 [M + H]$^+$. | $^1$H NMR (DMSO-d6, 400 MHz) δ 10.7-10.8 (m, 1H), 9.1-9.3 (m, 1H), 8.3-8.4 (m, 1H), 7.2-7.3 (m, 2H), 6.7-6.9 (m, 1H), 6.4-6.5 (m, 1H), 6.3-6.4 (m, 1H), 5.6-5.7 (m, 1H), 4.5-4.6 (m, 1H), 4.1-4.2 (m, 3H), 3.73 (s, 4H), 3.4-3.7 (m, 3H), 3.0-3.1 (m, 5H), 2.8-2.9 (m, 1H), 2.6-2.7 (m, 1H), 2.5-2.6 (m, 5H), 2.2-2.3 (m, 1H), 1.9-2.2 (m, 4H), 1.4-1.5 (m, 1H), 1.0-1.2 (m, 1H), 0.7-0.9 (m, 3H) |
| 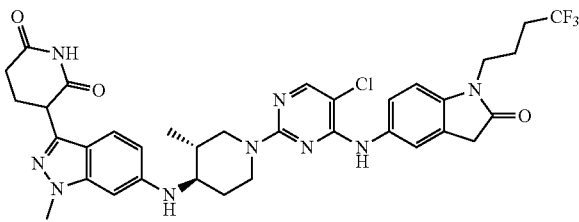 [SMILES: C[C@@H]1CN(c2ncc(Cl)c(Nc3ccc4c(c3)CC(=O)N4CCCC(F)(F)F)n2)CC[C@H]1Nc1ccc2c(C3CCC(=O)NC3=O)nn(C)c2c1]

Example S119

3-(6-(((3R,4R)-1-(5-chloro-4-((2-oxo-1-(4,4,4-trifluorobutyl)indolin-5-yl)amino)pyrimidin-2-yl)-3-methylpiperidin-4-yl)amino)-1-methyl-1H-indazol-3-yl)piperidine-2,6-dione (119) | 1, 6 | Requires 723.3, found 724.3 [M + H]$^+$. | $^1$H NMR (400 MHz, DMSO-d$_6$): δ 10.83 (s, 1H), 8.67 (s, 1H), 8.03 (s, 1H), 7.59 (s, 1H), 7.54-7.51 (m, 1H), 7.31 (d, J = 8.80 Hz, 1H), 7.04 (d, J = 8.40 Hz, 1H), 6.52-6.50 (m, 1H), 6.44 (s, 1H), 5.70 (d, J = 9.20 Hz, 1H), 4.52-4.45 (m, 2H), 4.18 (dd, J = 1.2 Hz, and 8.8 Hz, 1H), 3.82 (s, 3H), 3.75-3.72 (m, 2H), 3.57 (s, 2H), 3.05-2.99 (m, 1H), 2.51-2.50 (m, 1H), 2.30-2.23 (m, 2H), 2.18-2.06 (m, 2H), 1.82-1.74 (m, 2H), 1.61-1.57 (m, 1H), 1.25-1.10 (m, 1H), 1.21 (d, J = 14.4 Hz, 3H) |

TABLE 3-continued

| Compound | General Procedure No. | MS Data | NMR Data |
|---|---|---|---|
| 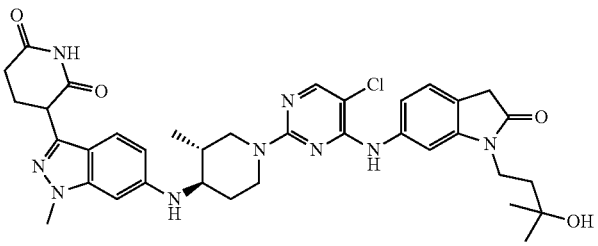 [SMILES: C[C@@H]1CN(c2ncc(Cl)c(Nc3ccc4c(c3)N(CCC(C)(C)O)C(=O)C4)n2)CC[C@H]1Nc1ccc2c(C3CCC(=O)NC3=O)nn(C)c2c1]<br>Example S120<br>3-(6-(((3R,4R)-1-(5-chloro-4-((1-(3-hydroxy-3-methylbutyl)-2-oxoindolin-6-yl)amino)pyrimidin-2-yl)-3-methylpiperidin-4-yl)amino)-1-methyl-1H-indazol-3-yl)piperidine-2,6-dione (120) | 1, 6 | Requires 699.3, found 724.3 [M + H]+. | $^1$H NMR (400 MHz, DMSO-d$_6$): δ 10.82 (s, 1H), 8.84 (s, 1H), 8.09 (s, 1H), 7.33-7.30 (m, 2H), 7.23-7.19 (m, 2H), 6.51 (dd, J = 1.60 Hz, and 8.8 Hz, 1H), 6.43 (s, 1H), 5.70 (s, 1H), 4.51-4.47 (m, 2H), 4.17 (dd, J = 5.2 Hz, and 8.8 Hz, 1H), 3.82 (s, 3H), 3.72-3.68 (m, 2H), 3.29-3.26 (m, 1H), 3.06 (t, J = 11.60 Hz, 1H), 2.72-2.70 (m, 1H), 2.69-2.67 (m, 2H), 2.29-2.23 (m, 1H), 2.17-2.07 (m, 2H), 1.67-1.60 (m, 3H), 1.19-1.17 (m, 1H), 1.17 (s, 6H), 0.96 (d, J = 6.40 Hz, 3H) |
| 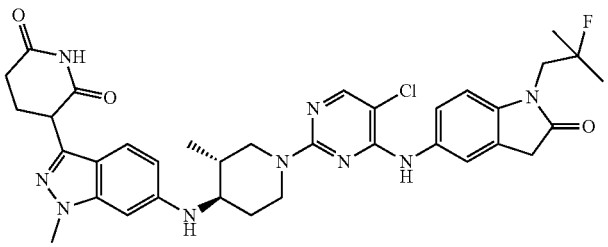 [SMILES: C[C@@H]1CN(c2ncc(Cl)c(Nc3ccc4c(c3)CC(=O)N4CC(C)(C)F)n2)CC[C@H]1Nc1ccc2c(C3CCC(=O)NC3=O)nn(C)c2c1]<br>Example S121<br>3-(6-(((3R,4R)-1-(5-chloro-4-((1-(2-fluoro-2-methylpropyl)-2-oxoindolin-5-yl)amino)pyrimidin-2-yl)-3-methylpiperidin-4-yl)amino)-1-methyl-1H-indazol-3-yl)piperidine-2,6-dione (121) | 1, 6 | Requires 687.3, found 688.2 [M + H]+. | $^1$H NMR (400 MHz, DMSO-d$_6$): δ 10.83 (s, 1H), 8.67 (s, 1H), 8.02 (s, 1H), 7.57 (s, 1H), 7.50-7.48 (m, 1H), 7.31 (d, J = 8.0 Hz, 1H), 7.00-6.97 (m, 1H), 6.52-6.50 (m, 1H), 6.44 (s, 1H), 5.70 (d, J = 8.8 Hz, 1H), 4.52-4.46 (m, 2H), 4.19-4.16 (m, 1H), 3.85-3.80 (m, 4H), 3.63 (s, 2H), 3.06-3.00 (m, 1H), 2.72-2.62 (m, 2H), 2.63-2.60 (m, 3H), 2.34-2.23 (m, 1H), 2.17-2.06 (m, 2H), 1.62-1.58 (m, 1H), 1.35 (d, J = 21.2 Hz, 6H), 1.20-1.10 (m, 1H), 0.96 (d, J = 6.4 Hz, 3H) |
| 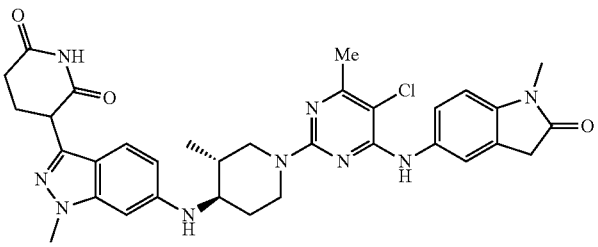 [SMILES: Cc1nc(N2CC[C@@H](Nc3ccc4c(C5CCC(=O)NC5=O)nn(C)c4c3)[C@H](C)C2)nc(Nc2ccc3c(c2)CC(=O)N3C)c1Cl]<br>Example S122<br>3-(6-(((3R,4R)-1-(5-chloro-4-methyl-6-((1-methyl-2-oxoindolin-5-yl)amino)pyrimidin-2-yl)-3-methylpiperidin-4-yl)amino)-1-methyl-1H-indazol-3-yl)piperidine-2,6-dione (122) | 1, 6 | Requires 641,3 found 641.8 [M + H]+. | $^1$H NMR (400 MHz, DMSO-d$_6$) δ ppm 10.81 (s, 1 H), 8.44-8.65 (m, 1 H), 7.56 (s, 1 H), 7.51 (dd, J = 8.44, 1.96 Hz, 1 H), 7.30 (d, J = 8.80 Hz, 1 H), 6.92 (d, J = 8.44 Hz, 1 H), 6.51 (dd, J = 8.80, 1.71 Hz, 1 H), 6.43 (s, 1 H), 5.69 (br d, J = 8.93 Hz, 1 H), 4.38-4.58 (m, 2 H), 4.17 (dd, J = 8.74, 5.20 Hz, 1 H), 3.81 (s, 3 H), 3.53 (s, 3 H), 3.27-3.30 (m, 1 H), 3.10 (s, 3 H), 2.94-3.05 (m, 1 H), 2.55-2.64 (m, 2 H), 2.30 (s, 3 H), 2.20-2.28 (m, 1 H), 2.10-2.19 (m, 1 H), 2.01-2.10 (m, 1 H), 1.51-1.67 (m, 1 H), 1.09-1.21 (m, 1 H), 0.97 (d, J = 6.48 Hz, 3 H) |

TABLE 3-continued

| Compound | General Procedure No. | MS Data | NMR Data |
|---|---|---|---|
| ![compound 123 structure]<br>Example S123<br>3-(6-(((3R,4R)-1-(5-chloro-4-fluoro-6-((1-methyl-2-oxoindolin-5-yl)amino)pyrimidin-2-yl)-3-methylpiperidin-4-yl)amino)-1-methyl-1H-indazol-3-yl)piperidine-2,6-dione (123) | 1, 6 | Requires 645.2, found 646.2 [M + H]+ | $^1$H NMR (400 MHz, DMSO-d$_6$): δ 10.83 (s, 1H), 9.00 (s, 1H), 7.49-7.47 (m, 2H), 7.32 (d, J = 8.80 Hz, 1H), 6.95 (d, J = 8.40 Hz, 1H), 6.53-6.51 (m, 1H), 6.45 (s, 1H), 4.36 (d, J = 10.80 Hz, 2H), 4.19-4.16 (m, 1H), 3.82 (s, 5H), 3.54 (s, 2H), 3.35-3.20 (m, 1H), 3.11 (s, 3H), 2.76-2.60 (m, 1H), 2.29-2.24 (m, 1H), 2.18-2.07 (m, 2H), 1.60 (s, 1H), 1.19-1.16 (m, 1H), 0.98 (d, J = 6.40 Hz, 3H), |

Example S124. Synthesis of 3-[6-[1-[5-chloro-4-[(2-oxoindolin-5-yl)amino]pyrimidin-2-yl]-4-piperidyl]-1-methyl-indazol-3-yl]piperidine-2,6-dione (124)

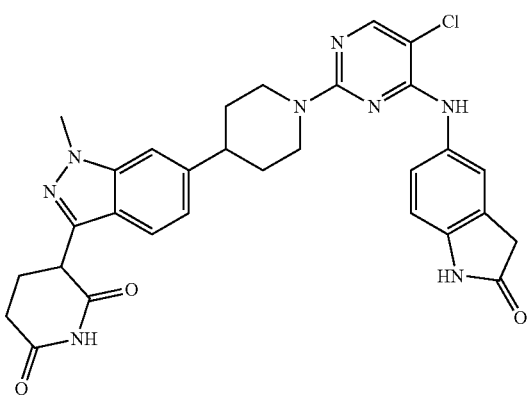 [SMILES: Cn1nc(C2CCC(=O)NC2=O)c2ccc(C3CCN(c4ncc(Cl)c(Nc5ccc6c(c5)CC(=O)N6)n4)CC3)cc21]

Step 1: Synthesis of tert-butyl 4-[3-(2,6-dibenzyloxy-3-pyridyl)-1-methyl-indazol-6-yl]piperidine-1-carboxylate.
To a reaction vial was added 3-[6-benzyloxy-2-(phenoxymethyl)-3-pyridyl]-6-bromo-1-methyl-indazole (300 mg, 0.60 mmol), tert-butyl 4-bromopiperidine-1-carboxylate (250 mg, 0.95 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (6.73 mg, 0.0100 mmol), tris(trimethylsilyl)silane (149.08 mg, 0.6000 mmol), and lithium hydroxide (28.72 mg, 1.2 mmol) to a vial equipped with a stir bar. Seal and purge with nitrogen before adding 1,4-dioxane (2 mL). A precatalyst solution was separately made. Add nickel (II) chloride ethylene glycol dimethyl ether complex (6.59 mg, 0.030 mmol) and 4,4'-di-tert-butyl-2,2'-bipyridyl (8.05 mg, 0.030 mmol) to a vial equipped with a stir bar. Seal and purge with nitrogen. Add 1,4-dioxane (2 mL) and stir/sonicate for 10 min. Add 0.2 mL of the pre-catalyst solution to the initial reaction vial. After which, purge with argon and stir for 10 minutes. Seal with parafilm and irradiate with 34 W Blue LED light overnight at room temperature. LCMS indicated the reaction was complete. The mixture was concentrated and purified with silica gel chromatography using 0-40% EA/hexanes to give the title compound (208 mg, 0.336 mmol, 56.0% yield) as a pale yellow oil.

Step 2: Synthesis of 3-[6-[1-[5-chloro-4-[(2-oxoindolin-5-yl)amino]pyrimidin-2-yl]-4-piperidyl]-1-methyl-indazol-3-yl]piperidine-2,6-dione The title compound was synthesized according to General Procedures 4, 5, and 6 using tert-butyl 4-[3-(2,6-dibenzyloxy-3-pyridyl)-1-methyl-indazol-6-yl]piperidine-1-carboxylate as the starting material. LCMS C$_{30}$H$_{29}$ClN$_8$O$_3$ requires 584.2, found 585.3 [M+H]+; $^1$H NMR (500 MHz, DMSO) δ 10.84 (s, 1H), 10.30 (s, 1H), 8.59 (s, 1H), 8.01 (s, 1H), 7.60 (d, J=8.4 Hz, 1H), 7.48 (s, 1H), 7.43 (s, 1H), 7.40 (dd, J=8.4, 2.0 Hz, 1H), 7.04 (d, J=7.9 Hz, 1H), 6.76 (d, J=8.3 Hz, 1H), 4.72-4.62 (m, 2H), 4.32 (dd, J=9.7, 5.1 Hz, 1H), 3.95 (s, 3H), 3.46 (s, 2H), 2.97-2.87 (m, 3H), 2.69-2.55 (m, 2H), 2.38-2.29 (m, 1H), 2.21-2.12 (m, 1H), 1.86 (d, J=11.9 Hz, 2H), 1.70-1.58 (m, 2H).

Example S125. Synthesis of 3-(6-(1-(5-Chloro-4-((1-methyl-2-oxoindolin-5-yl)amino)pyrimidin-2-yl)piperidin-4-yl)-1-methyl-1H-indazol-3-yl)piperidine-2,6-dione (125)

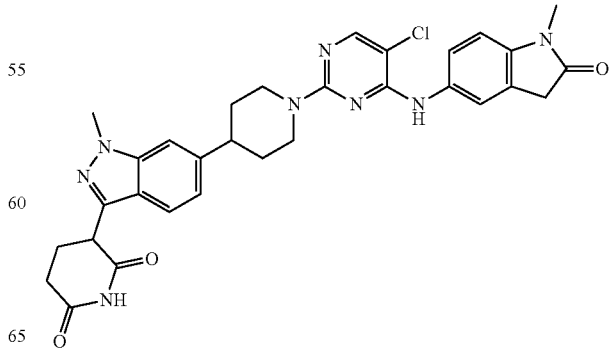

Step 1: Synthesis of 3-(6-(1-(5-Chloro-4-((1-methyl-2-oxoindolin-5-yl)amino)pyrimidin-2-yl)piperidin-4-yl)-1-methyl-1H-indazol-3-yl)piperidine-2,6-dione The title compound was synthesized according to General Procedures 4, 5, and 6 using tert-butyl 4-[3-(2,6-dibenzyloxy-3-pyridyl)-1-methyl-indazol-6-yl]piperidine-1-carboxylate as the starting material. LCMS $C_{30}H_{29}ClN_8O_3$ requires 598.2, found 599.3 [M+H]$^+$; $^1$H NMR (DMSO-d$_6$, 400 MHz) δ 10.8-10.9 (m, 1H), 8.6-8.7 (m, 1H), 8.03 (s, 1H), 7.6-7.6 (m, 1H), 7.5-7.6 (m, 2H), 7.4-7.5 (m, 1H), 7.0-7.1 (m, 1H), 6.9-7.0 (m, 1H), 4.6-4.7 (m, 2H), 4.3-4.4 (m, 1H), 3.9-4.0 (m, 3H), 3.5-3.6 (m, 2H), 3.1-3.1 (m, 3H), 2.9-3.0 (m, 3H), 2.5-2.7 (m, 2H), 2.3-2.4 (m, 1H), 2.1-2.2 (m, 1H), 1.8-1.9 (m, 2H), 1.6-1.7 (m, 2H).

Example S126. Synthesis of 3-(6-(4-((5-chloro-4-((1-methyl-2-oxoindolin-5-yl)amino)pyrimidin-2-yl)amino)-2-oxopiperidin-1-yl)-1-methyl-1H-indazol-3-yl)piperidine-2,6-dione (126)

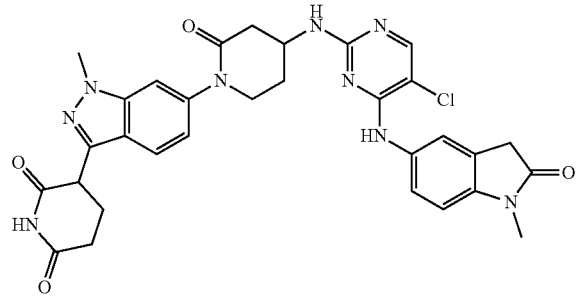 [SMILES: CN1C(=O)Cc2cc(Nc3nc(NC4CCN(c5ccc6c(C7CCC(=O)NC7=O)nn(C)c6c5)C(=O)C4)ncc3Cl)ccc21]

Step 1: Synthesis of tert-Butyl N-[1-[3-(2,6-dibenzyloxy-3-pyridyl)-1-methyl-indazol-6-yl]-2-oxo-4-piperidyl]carbamate. A mixture of tert-butyl N-(2-oxo-4-piperidyl)carbamate (1.3 g, 6.06 mmol), 6-bromo-3-(2,6-dibenzyloxy-3-pyridyl)-1-methyl-indazole (3.33 g, 6.66 mmol), Pd$_2$(dba)$_3$ (277 mg, 0.30 mmol), Me$_4$tBuXphos (291 mg, 0.61 mmol) and K$_3$PO$_4$ (3.21 g, 15.2 mmol) in tBuOH (60 mL) was heated to 100° C. for 24 h and then cooled to rt. The mixture was filtered on Celite and washed with DCM (15 mL). The filtrate was concentrated under reduced pressure and the residue was purified by column chromatography on silica gel using a gradient of 0-10% MeOH in DCM. The fractions were concentrated and the residue was further purified by reverse phase chromatography (C18) using a gradient of 0-100% MeCN and 10 mM ammonium formate in water to afford title compound (2.64 g, 69%) as a solid. MS (ESI) [M+H]$^+$ 634.7. $^1$H NMR (500 MHz, DMSO-d$_6$) δ 7.91 (d, J=8.1 Hz, 1H), 7.66 (d, J=8.7 Hz, 1H), 7.56 (d, J=1.1 Hz, 1H), 7.50-7.45 (m, 2H), 7.44-7.25 (m, 8H), 7.18 (s, 1H), 6.97 (dd, J=8.7, 1.7 Hz, 1H), 6.60 (d, J=8.1 Hz, 1H), 5.48 (s, 2H), 5.43 (s, 2H), 4.05 (s, 3H), 3.91 (s, 3H), 3.77-3.57 (m, 2H), 2.78-2.60 (m, 1H), 2.40-2.30 (m, 1H), 2.09 (d, J=6.0 Hz, 1H), 1.93-1.75 (m, 1H), 1.43 (s, 9H).

Step 2: Synthesis of 3-(6-(4-((5-chloro-4-((1-methyl-2-oxoindolin-5-yl)amino)pyrimidin-2-yl)amino)-2-oxopiperidin-1-yl)-1-methyl-1H-indazol-3-yl)piperidine-2,6-dione. The synthesis of the title compound was accomplished using General Procedures 4, 5, and 6 using tert-Butyl N-[1-[3-(2,6-dibenzyloxy-3-pyridyl)-1-methyl-indazol-6-yl]-2-oxo-4-piperidyl]carbamate as the starting material. The crude residue was purified by reverse phase chromatography (C18) using a gradient of 0-100% MeCN and 10 mM ammonium formate in water. The fractions were concentrated under reduced pressure and the residue was further purified by preparative HPLC (BEH column, C18) using a gradient of 25-35% MeCN and 10 mM ammonium formate in water to afford title compound (8.6 mg, 5%) as a solid. LCMS $C_{31}H_{30}ClN_9O_4$ requires 627.2, found 628.2 [M+H]$^+$. $^1$H NMR (500 MHz, DMSO-d$_6$) δ 10.91 (s, 1H), 8.60 (s, 1H), 7.98 (s, 1H), 7.70 (d, J=8.6 Hz, 2H), 7.55 (s, 1H), 7.51 (d, J=8.1 Hz, 1H), 7.20 (s, 1H), 7.03 (d, J=8.7 Hz, 1H), 6.95 (d, J=8.4 Hz, 1H), 4.38 (dd, J=10.1, 5.0 Hz, 1H), 3.98 (s, 3H), 3.69 (s, 2H), 3.57 (s, 2H), 3.12 (s, 3H), 2.78-2.58 (m, 4H), 2.47-2.33 (m, 2H), 2.23-2.15 (m, 2H), 1.96-1.88 (m, 1H).

Example S127. Synthesis of 3-(6-(4-((5-chloro-4-((1-methyl-2-oxoindolin-5-yl)amino)pyrimidin-2-yl)(methyl)amino)-2-oxopiperidin-1-yl)-1-methyl-1H-indazol-3-yl)piperidine-2,6-dione (127)

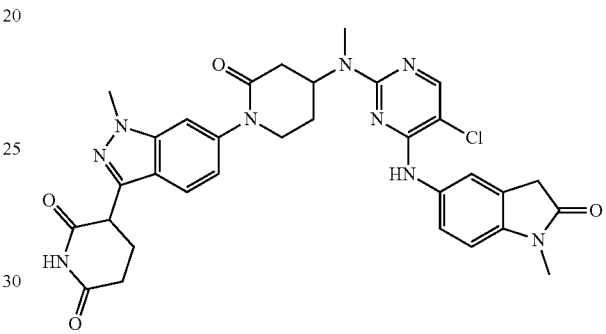

Step 1: Synthesis of 4-[Benzyl(methyl)amino]piperidin-2-one To a solution of piperidine-2,4-dione (1.0 g, 8.8 mmol) in DCE (25 mL) were added sequentially N-methyl-1-phenyl-methanamine (1.1 mL, 8.8 mmol) and AcOH (0.5 mL, 8.8 mmol), and the mixture was stirred for 2 h at rt. At this time, NaBH$_3$CN (833 mg, 13.3 mmol) was added to the reaction mixture and stirring was continued for 36 h. A saturated aqueous solution of NaHCO$_3$ (100 mL) and DCM (100 mL) were added, and the layers were separated. The organic layer was washed with water (100 mL), brine (20 mL), dried (Na$_2$SO$_4$), filtered and concentrated under reduced pressure. The residue was purified by column chromatography on silica gel using a gradient of 0-100% EtOAc in hexanes to afford the title compound (790 mg, 41%) as a semi-solid. MS (ESI) [M+H]$^+$ 219.2. $^1$H NMR (400 MHz, DMSO-d$_6$) δ 7.45 (br s, 1H), 7.35-7.28 (m, 4H), 7.27-7.19 (m, 1H), 3.54 (q, J=13.5 Hz, 2H), 3.22-3.16 (m, 1H), 3.08-2.99 (m, 1H), 2.89-2.80 (m, 1H), 2.31-2.20 (m, 2H), 2.09 (s, 3H), 1.97-1.87 (m, 1H), 1.68-1.54 (m, 1H).

Step 2: Synthesis of 4-[Benzyl(methyl)amino]-1-[3-(2,6-dibenzyloxy-3-pyridyl)-1-methyl-indazol-6-yl]piperidin-2-one To a solution of 4-[benzyl(methyl)amino]piperidin-2-one (300 mg, 1.24 mmol), 6-bromo-3-(2,6-dibenzyloxy-3-pyridyl)-1-methyl-indazole (681 mg, 1.36 mmol, intermediate provided by Celgene), Pd$_2$(dba)$_3$ (226 mg, 0.25 mmol) and XantPhos (358 mg, 0.62 mmol) in 1,4-dioxane (6.2 mL) was added Cs$_2$CO$_3$ (564 mg, 1.73 mmol) at rt. The reaction mixture was heated to 100° C. for 18 h and then cooled to rt. The mixture was diluted with DCM (100 mL), filtered over a pad of celite, and the filtrate concentrated under reduced pressure. The residue was purified by silica gel chromatography using a gradient of 0-20% MeOH in DCM to afford title compound (300 mg, 38%) as a solid. MS (ESI) [M+H]$^+$ 639.3.

Step 3: Synthesis of 3-[6-[4-[[5-Chloro-4-[(1-methyl-2-oxo-indolin-5-yl)amino]pyrimidin-2-yl]-methyl-amino]-2-oxo-1-piperidyl]-1-methyl-indazol-3-yl]piperidine-2,6-dione The synthesis of the title compound was accomplished using General Procedures 4 and 6 using 4-[Benzyl(methyl)amino]-1-[3-(2,6-dibenzyloxy-3-pyridyl)-1-methyl-indazol-6-yl]piperidin-2-one as the starting material. The final reaction was heated to 100° C. for 18 h. before purification by preparative HPLC (BEH column, C18) using a gradient of 26-36% MeCN and 10 mM ammonium formate in water to afford title compound (13.6 mg, 12%) as a solid. LCMS $C_{32}H_{32}ClN_9O_4$ requires 641.1, found 642.2 [M+H]$^+$; $^1$H NMR (400 MHz, DMSO-d$_6$) δ 10.90 (br s, 1H), 8.68 (s, 1H), 8.04 (s, 1H), 7.69 (d, J=8.5 Hz, 1H), 7.63 (s, 1H), 7.56-7.47 (m, 2H), 6.98 (d, J=8.2 Hz, 1H), 6.94 (d, J=8.6 Hz, 1H), 4.38 (dd, J=10.1, 5.0 Hz, 1H), 3.98 (s, 3H), 3.83-3.72 (m, 1H), 3.71-3.59 (m, 1H), 3.54 (d, J=4.9 Hz, 2H), 3.29 (s, 1H), 3.09 (s, 3H), 3.00 (s, 3H), 2.76-2.60 (m, 4H), 2.44-2.31 (m, 1H), 2.28-2.14 (m, 2H), 2.06-1.96 (m, 1H).

Example S128. Synthesis of 3-(6-((S)-4-((5-chloro-4-((1-methyl-2-oxoindolin-5-yl)amino)pyrimidin-2-yl)(methyl)amino)-2-oxopiperidin-1-yl)-1-methyl-1H-indazol-3-yl)piperidine-2,6-dione (128)

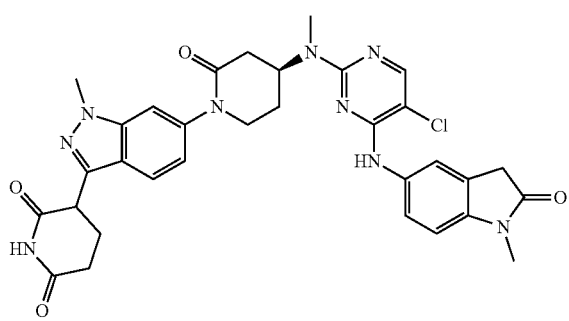 [SMILES: CN1C(=O)Cc2cc(Nc3nc(N(C)[C@H]4CCN(c5ccc6c(C7CCC(=O)NC7=O)nn(C)c6c5)C(=O)C4)ncc3Cl)ccc21]

Step 1: Synthesis of 3-(6-((S)-4-((5-chloro-4-((1-methyl-2-oxoindolin-5-yl)amino)pyrimidin-2-yl)(methyl)amino)-2-oxopiperidin-1-yl)-1-methyl-1H-indazol-3-yl)piperidine-2,6-dione. The title compound was synthesized using the product of Example S128 using chiral SFC and using the first eluting isomer in General Procedures 4, 5, and 6. Rt 6.63 min, SFC column: Lux C4; mobile phase: 55:45 (A:B), A=liquid CO$_2$, B=0.5% isopropyl amine in methanol; Flow Rate: 5.0 mL/min; MS (ESI) 642.2 [M+H]$^+$; $^1$H NMR (400 MHz, DMSO-d$_6$): δ 10.93 (s, 1H), 8.71 (s, 1H), 8.06 (s, 1H), 7.70 (d, J=8.40 Hz, 1H), 7.64 (s, 1H), 7.54-7.52 (m, 2H), 6.99-6.94 (m, 2H), 4.94 (brs, 1H), 4.41-4.37 (m, 1H), 3.99 (s, 3H), 3.82-3.75 (m, 1H), 3.67-3.62 (m, 1H), 3.55-3.54 (m, 2H), 3.10 (s, 3H), 3.00 (s, 3H), 2.68-2.59 (m, 2H), 2.46-2.38 (m, 1H), 2.25-2.15 (m, 2H), 2.05-1.95 (m, 1H).

Example S129. Synthesis of 3-(6-((R)-4-((5-chloro-4-((1-methyl-2-oxoindolin-5-yl)amino)pyrimidin-2-yl)(methyl)amino)-2-oxopiperidin-1-yl)-1-methyl-1H-indazol-3-yl)piperidine-2,6-dione (129)

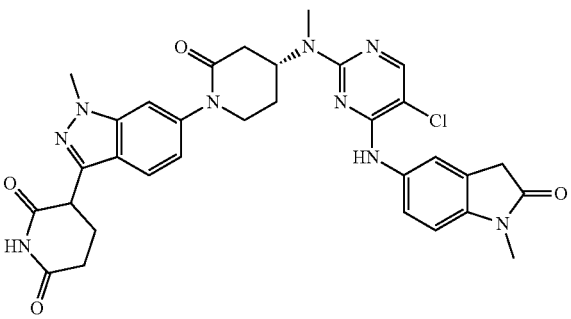 [SMILES: CN1C(=O)Cc2cc(Nc3nc(N(C)[C@@H]4CCN(c5ccc6c(C7CCC(=O)NC7=O)nn(C)c6c5)C(=O)C4)ncc3Cl)ccc21]

Step 1: Synthesis of 3-(6-((R)-4-((5-chloro-4-((1-methyl-2-oxoindolin-5-yl)amino)pyrimidin-2-yl)(methyl)amino)-2-oxopiperidin-1-yl)-1-methyl-1H-indazol-3-yl)piperidine-2,6-dione. The title compound was synthesized using the product of Example S128 using chiral SFC and using the second eluting isomer in General Procedures 4, 5, and 6. Rt 7.46 min, SFC column: Lux C4; mobile phase: 55:45 (A:B), A=liquid CO$_2$, B=0.5% isopropyl amine in methanol; Flow Rate: 5.0 mL/min. MS (ESI) 642.2 [M+H]$^+$; $^1$H NMR (400 MHz, DMSO-d$_6$): δ 10.92 (s, 1H), 8.70 (s, 1H), 8.05 (s, 1H), 7.70 (d, J=8.40 Hz, 1H), 7.64 (s, 1H), 7.53-7.51 (m, 2H), 6.99-6.94 (m, 2H), 4.95 (brs, 1H), 4.41-4.37 (m, 1H), 3.99 (s, 3H), 3.81-3.76 (m, 1H), 3.67-3.64 (m, 1H), 3.55-3.54 (m, 2H), 3.10 (s, 3H), 3.00 (s, 3H), 2.72-2.64 (m, 2H), 2.46-2.39 (m, 1H), 2.23-2.18 (m, 2H), 2.03-1.98 (s, 1H).

Example S130. Synthesis of 3-(6-((3R,4S)-4-((5-chloro-4-((1-methyl-2-oxoindolin-5-yl)amino)pyrimidin-2-yl)(methyl)amino)-3-methyl-2-oxopiperidin-1-yl)-1-methyl-1H-indazol-3-yl)piperidine-2,6-dione (130)

Step 1: Synthesis of (S)-4-(benzyl(methyl)amino)-1-(3-(2,6-bis(benzyloxy)pyridin-3-yl)-1-methyl-1H-indazol-6-yl)piperidin-2-one (Isomer 2) A stirred solution of 4-[Benzyl(methyl)amino]piperidin-2-one (3.66 g, 16.8 mmol) and 3-(2,6-bis(benzyloxy)pyridin-3-yl)-6-bromo-1-methyl-1H-indazole (7.0 g, 14.0 mmol) in 1,4-dioxane (150 mL) was degassed with nitrogen for 5 min. Then Pd$_2$(dba)$_3$ (1.28 g, 1.40 mmol), Xantphos (1.619 g, 2.80 mmol) and Cs$_2$CO$_3$ (6.84 g, 20.98 mmol) were added. The reaction mixture was heated to 100° C. and stirred for 16 h. The reaction mixture was treated with water (200 mL) and extracted with ethyl acetate (3×200 mL). The combined organic layer was dried over anhydrous sodium sulfate and concentrated under reduced pressure. The crude product was purified by flash column chromatography on silica gel with 10% methanol/dichloromethane to afford racemate (3.50 g) as an off-white solid. The racemate was separated by chiral preparative HPLC to afford isomer 1 (Rt 8.73 min) and the title compound as the second eluting isomer (Isomer-2, 1.55 g, 2.408 mmol, 17% yield) as off-white solids. Chiral-HPLC method: Column: Chiralpak IJ (250×4.6 mm), 5.0 μm; 0.2% ammonia in methanol/Isopropanol; Flow Rate: 3.0 mL/min: Rt 9.87 min. MS (ESI) [M+H]$^+$ 638.3.

Step 2: Synthesis of (3R,4S)-4-(benzyl(methyl)amino)-1-(3-(2,6-bis(benzyloxy)pyridin-3-yl)-1-methyl-1H-indazol-6-yl)-3-methylpiperidin-2-one. To a stirred solution of compound (S)-4-(benzyl(methyl)amino)-1-(3-(2,6-bis(benzyloxy)pyridin-3-yl)-1-methyl-1H-indazol-6-yl)piperidin-2-one (250 mg, 0.392 mmol) in THF (8.0 mL) was added 1.0 M LHMDS in Hexane (0.784 mL, 0.784 mmol) dropwise at −78° C. under nitrogen and stirred for 45 min. Then methyl iodide (0.049 mL, 0.784 mmol) was added and slowly warmed to 25° C., stirred for 1 h. The reaction mixture was treated with saturated NH$_4$Cl solution (30 mL) and extracted with ethyl acetate (3×50 mL). The combined organic layer was dried over anhydrous sodium sulphate and concentrated under reduced pressure to afford crude. The crude product was purified by flash column chromatography on silica gel with 50-70% ethyl acetate/pet ether to afford the title compound (180 mg, 0.271 mmol, 69% yield) as an off-white solid. MS (ESI) [M+H]$^+$ 652.3; $^1$H NMR (400 MHz, DMSO-d$_6$): δ 7.91 (d, J=8.8 Hz, 1H), 7.64 (d, J=8.8 Hz, 1H), 7.53 (s, 1H), 7.49-7.46 (m, 2H), 7.41-7.24 (m, 12H), 6.93 (dd, J=1.6 Hz and 8.8 Hz, 1H), 6.59 (d, J=8.0 Hz, 1H), 5.47 (s, 2H), 5.42 (s, 2H), 4.04 (s, 3H), 3.78 (d, J=13.6 Hz, 1H), 3.68-3.66 (m, 2H), 3.52 (d, J=13.6 Hz, 1H), 2.80-2.76 (m, 1H), 2.68-2.63 (m, 1H), 2.19 (s, 3H), 2.18-2.13 (m, 1H), 1.96-1.91 (m, 1H), 1.28 (d, J=6.8 Hz, 1H).

Step 3: Synthesis of 3-(1-methyl-6-((3R,4S)-3-methyl-4-(methylamino)-2-oxopiperidin-1-yl)-1H-indazol-3-yl)piperidine-2,6-dione. To a stirred solution of (3R,4S)-4-(benzyl(methyl)amino)-1-(3-(2,6-bis(benzyloxy)pyridin-3-yl)-1-methyl-1H-indazol-6-yl)-3-methylpiperidin-2-one (120 mg, 0.180 mmol) in ethanol (2.5 mL) and THF (2.5 mL) was added TFA (0.014 L, 0.180 mmol) and 20% palladium hydroxide on carbon (60 mg) under nitrogen. The reaction mixture was stirred under hydrogenation pressure (5 atm) at 50° C. for 16 h. The reaction mixture was filtered through celite pad and the celite pad was washed with 1:1 mixture of THF and ethanol (30 mL). The filtrate was concentrated under reduced pressure to afford the title compound (70 mg, 0.172 mmol, 96% yield) as crude. The crude product was used for the next step without further purification. MS (ESI) 384.2 [M+H]$^+$.

Step 4: Synthesis of 3-(6-((3R,4S)-4-((5-chloro-4-((1-methyl-2-oxoindolin-5-yl)amino)pyrimidin-2-yl)(methyl)amino)-3-methyl-2-oxopiperidin-1-yl)-1-methyl-1H-indazol-3-yl)piperidine-2,6-dione. To a stirred solution of compound 3-(1-methyl-6-((3R,4S)-3-methyl-4-(methylamino)-2-oxopiperidin-1-yl)-1H-indazol-3-yl)piperidine-2,6-dione (50 mg, 0.121 mmol) and 5-((5-chloro-2-fluoropyrimidin-4-yl)amino)-1-methylindolin-2-one (36.2 mg, 0.121 mmol) in DMSO (1.0 mL) was added DIPEA (0.064 mL, 0.364 mmol) at 25° C. The reaction mixture was heated to 80° C. and stirred for 5 h. The reaction mixture was cooled to room temperature and purified by preparative HPLC to afford the title compound (8 mg, 0.012 mmol, 10% yield) as an off-white solid. LCMS C$_{33}$H$_{34}$ClN$_9$O$_4$ requires 655.2, found 656.3 [M+H]$^+$; $^1$H NMR (400 MHz, DMSO-d$_6$): δ 10.93 (s, 1H), 8.93 (brs, 1H), 8.07 (s, 1H), 7.69 (d, J=8.8 Hz, 1H), 7.63-7.48 (m, 3H), 6.99-6.96 (m, 2H), 4.81 (brs, 1H), 4.41-4.37 (m, 1H), 3.99 (s, 3H), 3.69-3.62 (m, 2H), 3.54 (s, 2H), 3.11 (s, 3H), 2.97 (s, 3H), 2.21-2.18 (m, 2H), 1.99-1.90 (m, 1H), 1.02 (d, J=6.8 Hz, 3H).

Example S131. Synthesis of 3-(6-((3S,4R)-4-((5-chloro-4-((1-methyl-2-oxoindolin-5-yl)amino)pyrimidin-2-yl)(methyl)amino)-3-methyl-2-oxopiperidin-1-yl)-1-methyl-1H-indazol-3-yl)piperidine-2,6-dione (131)

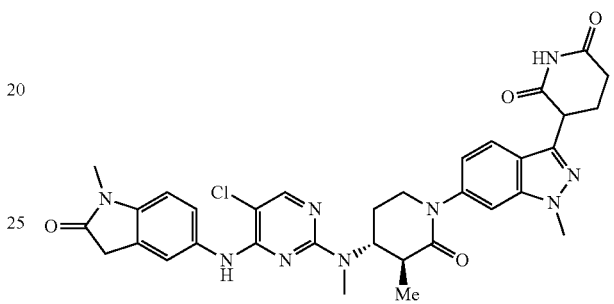

Step 1: Synthesis of 3-(6-((3S,4R)-4-((5-chloro-4-((1-methyl-2-oxoindolin-5-yl)amino)pyrimidin-2-yl)(methyl)amino)-3-methyl-2-oxopiperidin-1-yl)-1-methyl-1H-indazol-3-yl)piperidine-2,6-dione. The synthesis of the title compound was accomplished through the procedures outlined for Example S131 and using the first eluting isomer from Example S131, Step 1. LCMS C$_{33}$H$_{34}$ClN$_9$O$_4$ requires 655.2, found 656.2 [M+H]$^+$; $^1$H NMR (400 MHz, DMSO-d$_6$): δ 10.62-10.53 (m, 1H), 8.42 (s, 1H), 8.03 (s, 1H), 7.69 (d, J=8.5 Hz, 1H), 7.61 (s, 1H), 7.52 (br d, J=8.8 Hz, 1H), 7.45 (s, 1H), 6.97 (dd, J=1.4, 8.6 Hz, 1H), 6.94 (d, J=8.4 Hz, 1H), 4.87-4.77 (m, 1H), 4.36 (dd, J=5.3, 9.3 Hz, 1H), 3.99 (s, 3H), 3.76-3.66 (m, 2H), 3.53 (s, 2H), 3.16-3.12 (m, 3H), 3.01-3.00 (m, 3H), 2.71-2.66 (m, 2H), 2.44-2.33 (m, 2H), 2.29-2.19 (m, 2H), 2.05-1.96 (m, 1H), 1.07 (d, J=7.0 Hz, 3H).

Example S132. Synthesis of 2-((3R,4R)-4-((3-(2,4-dioxotetrahydropyrimidin-1(2H)-yl)-1-methyl-1H-indazol-6-yl)amino)-3-methylpiperidin-1-yl)-4-((1-methyl-2-oxoindolin-5-yl)amino)pyrimidine-5-carbonitrile (132)

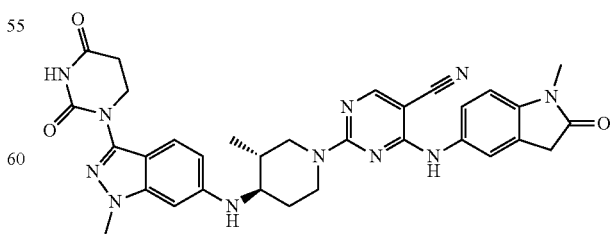

Step 1: Synthesis of 1-(1-methyl-6-nitro-indazol-3-yl)hexahydropyrimidine-2,4-dione. A mixture of 3-bromo-1-methyl-6-nitro-indazole (3.00 g, 11.7 mmol), hexahydropyrimidine-2,4-dione (1.60 g, 14.1 mmol), potassium phosphate tribasic (6.22 g, 29.3 mmol), tetramethyl tBuXPhos (281 mg, 0.58 mmol) and $Pd_2(dba)_3$ (268 mg, 0.29 mmol) in tert-butanol (125 mL) was degassed with nitrogen 3 times. The reaction mixture was heated to 100° C. for 24 h with stirring and then cooled to rt. Additional $Pd_2(dba)_3$ (268 mg, 0.29 mmol) and tetramethyl tBuXPhos (281 mg, 0.58 mmol) were added. The reaction mixture was heated to 100° C. for an additional 16 h and then cooled to rt. The volatiles were evaporated under reduced pressure. Water (200 mL) was added and the resulting precipitate was collected by filtration on a Buchner funnel. The solid was then washed with water (3×50 mL) and dried under vacuum. The material was triturated in diethyl ether (100 mL) and collected by filtration to afford title compound (2.64 g, 78%) as a solid, which was used in next step without further purification. LCMS $C_{12}H_{11}N_5O_4$ requires 289.1, found 290.2 $[M+H]^+$; $^1H$ NMR (500 MHz, DMSO) δ 10.67 (s, 1H), 8.70 (dd, J=1.7, 0.7 Hz, 1H), 7.95-7.84 (m, 2H), 4.14 (s, 3H), 3.97 (t, J=6.7 Hz, 2H), 2.77 (t, J=6.7 Hz, 2H).

Step 2: Synthesis of 1-(6-amino-1-methyl-indazol-3-yl)hexahydropyrimidine-2,4-dione. A mixture of 1-(1-methyl-6-nitro-indazol-3-yl)hexahydropyrimidine-2,4-dione (2.64 g, 9.13 mmol) and 10% Pd/C (0.97 g, 0.91 mmol) in methanol (250 mL) was hydrogenated under hydrogen atmosphere (1 atm) at rt for 6.5 h. The mixture was filtered through celite and washed with MeOH (5×45 mL). The filtrate was concentrated under reduced pressure, the material was triturated in diethyl ether and collected by filtration to afford title (1.92 g, 81%) as a solid.

Step 3: Synthesis of 1-(6-Iodo-1-methyl-indazol-3-yl)hexahydropyrimidine-2,4-dione. To a solution of 1-(6-amino-1-methyl-indazol-3-yl)hexahydropyrimidine-2,4-dione (2.1 g, 8.1 mmol) in acetic acid (21 mL) cooled to 0° C. was added sequentially a solution of $H_2SO_4$ (1.11 mL, 20.3 mmol) in water (5 mL) followed by a solution of sodium nitrite (838 mg, 12.15 mmol) in water (5 mL). The reaction mixture was stirred at 0° C. for 2 h. At this time, a solution of KI (4.0 g, 24 mmol) in water (5 mL) was added and the mixture was stirred at 0° C. for 2 h then warmed to rt. A 50% aqueous solution of $NaHSO_3$ (50 mL) was added to the mixture and stirred for 18 h. The resulting precipitate was collected by filtration, washed with water (3×10 mL) and $Et_2O$ (3×10 mL) then dried under vacuum to afford title compound (1.98 g, 66%) as a solid, which was used in the next step without further purification. LCMS $C_{12}H_{11}IN_4O_2$ requires 370.0, found 371.3 $[M+H]^+$; $^1H$ NMR (400 MHz, DMSO-$d_6$) δ 10.58 (s, 1H), 8.12 (d, J=0.6 Hz, 1H), 7.47 (d, J=8.6 Hz, 1H), 7.39 (dd, J=8.6, 1.3 Hz, 1H), 3.97 (s, 3H), 3.92 (t, J=6.7 Hz, 2H), 2.75 (t, J=6.7 Hz, 2H).

Step 4: Synthesis of 1-[1-Methyl-6-(4,4,5,5-tetramethyl-1,3,2-dioxaborolan-2-yl)indazol-3-yl]hexahydropyrimidine-2,4-dione. A mixture of 1-(6-iodo-1-methyl-indazol-3-yl)hexahydropyrimidine-2,4-dione (500 mg, 1.35 mmol), $B_2pin_2$ (412 mg, 1.62 mmol), $Pd(OAc)_2$ (30 mg, 0.14 mmol) and KOAc (398 mg, 4.05 mmol) in DMF (14 mL) was heated to 80° C. for 18 h and then cooled to rt. The mixture was filtered through celite and washed with EtOAc (5×15 mL). Water (50 mL) was added to the filtrate and the layers were separated. The organic layer was washed with water (5×25 mL), brine (25 mL), dried over $Na_2SO_4$, filtered, and concentrated under reduced pressure. The residue was purified by column chromatography on silica gel using a gradient of 50-100% EtOAc in hexanes to afford title compound (335 mg, 67%) as a solid. LCMS $C_{18}H_{23}BN_4O_4$ requires 372.2, found 371.2 $[M+H]^+$.

Step 5: Synthesis of [3-(2,4-Dioxohexahydropyrimidin-1-yl)-1-methyl-indazol-6-yl]boronic acid. To a solution of 1-[1-methyl-6-(4,4,5,5-tetramethyl-1,3,2-dioxaborolan-2-yl)indazol-3-yl]hexahydropyrimidine-2,4-dione (403 mg, 1.09 mmol) in THF (5 mL) and water (5 mL) were added sequentially $NaIO_4$ (698 mg, 3.27 mmol) and 1 M aqueous HCl (2.2 mL, 2.2 mmol). The reaction mixture was stirred at rt for 18 h. The volatiles were evaporated under reduced pressure and the resulting precipitate was collected by filtration, washed with water (3×2 mL), and $Et_2O$ (3×1 mL), then dried under vacuum to afford the title compound (240 mg, 76%) as a solid, which was used in the next step without further purification. LCMS $C_{12}H_{13}BN_4O_4$ requires 288.1, found 289.1$[M+H]^+$; $^1H$ NMR (400 MHz, DMSO-$d_6$) δ 10.54 (s, 1H), 8.16 (s, 2H), 8.01 (s, 1H), 7.59 (d, J=8.2 Hz, 1H), 7.52 (d, J=8.3 Hz, 1H), 4.00 (s, 3H), 3.92 (t, J=6.7 Hz, 2H), 2.76 (t, J=6.6 Hz, 2H).

Step 6: Synthesis of tert-Butyl (3R,4R)-4-[[3-(2,4-dioxohexahydropyrimidin-1-yl)-1-methyl-indazol-6-yl]amino]-3-methyl-piperidine-1-carboxylate. A mixture of [3-(2,4-dioxohexahydropyrimidin-1-yl)-1-methyl-indazol-6-yl] boronic acid (200 mg, 0.69 mmol), tert-butyl (3R,4R)-4-amino-3-methyl-piperidine-1-carboxylate (228 mg, 1.04 mmol), $Cu(OAc)_2$ (152 mg, 0.76 mmol), $Et_3N$ (190 µL, 1.39 mmol) and 3 Å MS (100 mg) in DCE (12.6 mL) under $O_2$ (1 atm) was heated to 50° C. for 18 h. The mixture was filtered through celite and washed with a 1:1 mixture of MeCN and MeOH (3×10 mL). The filtrate was concentrated under reduced pressure and the residue was purified by preparative HPLC (BEH column, C18) using a gradient of 10-80% MeCN and 10 mM ammonium formate in water to afford the title compound (76 mg, 24%) as a solid. LCMS $C_{23}H_{32}N_6O_4$ requires 456.3, found 457.3 $[M+H]^+$.

Step 7: Synthesis of 2-Chloro-4-[(1-methyl-2-oxo-indolin-5-yl)amino]pyrimidine-5-carbonitrile.

The title compound was synthesize according to General Procedure 1 using 2,4-dichloropyrimidine-5-carbonitrile as the starting material.

Step 8: Synthesis of 2-((3R,4R)-4-((3-(2,4-dioxotetrahydropyrimidin-1(2H)-yl)-1-methyl-1H-indazol-6-yl)amino)-3-methylpiperidin-1-yl)-4-((1-methyl-2-oxoindolin-5-yl)amino)pyrimidine-5-carbonitrile. The synthesis of the title compound was accomplished using General Procedures 4 and 5 using tert-butyl (3R,4R)-4-[[3-(2,4-dioxohexahydropyrimidin-1-yl)-1-methyl-indazol-6-yl]amino]-3-methyl-piperidine-1-carboxylate and 2-chloro-4-[(1-methyl-2-oxo-indolin-5-yl)amino]pyrimidine-5-carbonitrile as the starting materials. The crude residue was purified by preparative HPLC (BEH column, C18) using a gradient of 25-55% MeCN and 10 mM sodium bicarbonate in water to afford title compound (6.7 mg, 7%) as a solid. LCMS $C_{32}H_{33}N_{11}O_3$ requires 619.3, found 620.7 $[M+H]^+$; $^1H$ NMR (400 MHz, DMSO-$d_6$) δ 10.45 (s, 1H), 9.28 (s, 1H), 8.40 (s, 1H), 7.54-7.40 (m, 2H), 7.26 (d, J=8.8 Hz, 1H), 6.94 (d, J=4.6 Hz, 1H), 6.51 (dd, J=8.8, 1.9 Hz, 1H), 6.43 (s, 1H), 5.75 (d, J=8.9 Hz, 1H), 4.66 (br s, 1H), 4.44 (s, 1H), 3.85 (t, J=6.7 Hz, 2H), 3.81 (s, 3H), 3.53 (s, 2H), 3.18-3.03 (m, 3H), 2.85-2.75 (m, 1H), 2.72 (t, J=6.7 Hz, 2H), 2.14-2.06 (m, 1H), 1.58 (s, 1H), 1.23 (s, 3H), 0.97 (d, J=6.4 Hz, 3H).

Example S133. Synthesis of 1-(6-(4-((5-chloro-4-((1-methyl-2-oxoindolin-5-yl)amino)pyrimidin-2-yl)amino)piperidin-1-yl)-1-methyl-1H-indazol-3-yl)dihydropyrimidine-2,4(1H,3H)-dione (133)

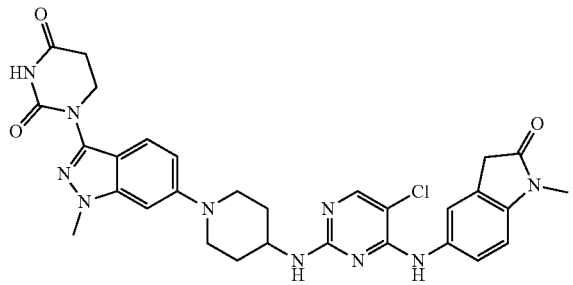

Step 1: Synthesis of 1-(6-(4-((5-chloro-4-((1-methyl-2-oxoindolin-5-yl)amino)pyrimidin-2-yl)amino)piperidin-1-yl)-1-methyl-1H-indazol-3-yl)dihydropyrimidine-2,4(1H,3H)-dione. The title compound was synthesized analogously to Example S133 using tert-butyl N-(4-piperidyl)carbamate as the reactant in Step 6. LCMS $C_{32}H_{33}N_{11}O_3$ requires 614.2, found 615.3 [M+H]$^+$; $^1$H NMR (500 MHz, DMSO-d$_6$) δ 10.50 (br s, 1H), 8.53 (br s, 1H), 7.94 (s, 1H), 7.74 (br s, 1H), 7.56 (s, 1H), 7.44 (d, J=9.0 Hz, 1H), 7.00 (br s, 1H), 6.92 (d, J=8.8 Hz, 2H), 6.83 (s, 1H), 3.92-3.88 (m, 2H), 3.88 (s, 3H), 3.82 (d, J=12.7 Hz, 2H), 3.69 (br s, 1H), 3.55 (s, 2H), 3.10 (s, 3H), 2.82 (t, J=11.8 Hz, 2H), 2.73 (t, J=6.7 Hz, 2H), 1.95 (br d, J=10.5 Hz, 2H), 1.59 (br dd, J=21.8, 10.6 Hz, 2H).

Example S134. Synthesis of 1-(6-(1-(5-chloro-4-((1-methyl-2-oxoindolin-5-yl)amino)pyrimidin-2-yl)piperidin-4-yl)-1-methyl-1H-indazol-3-yl)dihydropyrimidine-2,4(1H,3H)-dione (134)

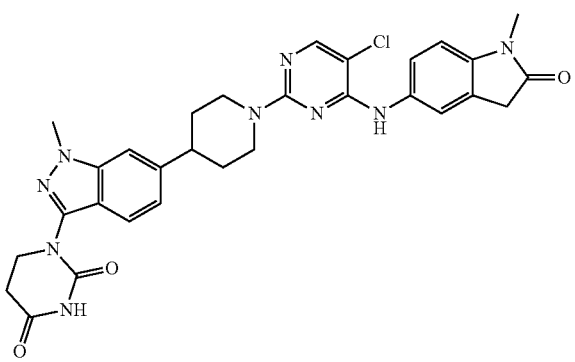 [SMILES: CN1C(=O)Cc2cc(Nc3nc(N4CCC(c5ccc6c(N7CCC(=O)NC7=O)nn(C)c6c5)CC4)ncc3Cl)ccc21]

Step 1: Synthesis of tert-Butyl N-(6-bromo-1-methyl-indazol-3-yl)carbamate. To a solution of 6-bromo-1-methyl-indazol-3-amine (1.0 g, 4.42 mmol) in 1,4-dioxane (25 mL) was added Boc$_2$O (1.16 g, 5.31 mmol), and the reaction mixture was heated to 100° C. for 16 h and then cooled to rt. The volatiles were evaporated under reduced pressure and the residue was purified by column chromatography on silica gel using a gradient of 0-100% EtOAc in hexanes to afford the title compound (1.18 g, 82%) as a solid. MS (ESI) [M-tBu]$^+$271.0. $^1$H NMR (400 MHz, DMSO-d$_6$) δ 9.62 (s, 1H), 7.89 (s, 1H), 7.67 (dd, J=8.6, 2.4 Hz, 1H), 7.20 (dd, J=8.7, 1.6 Hz, 1H), 3.91 (s, 3H), 1.47 (s, 9H).

Step 2: Synthesis of tert-Butyl N-(6-bromo-1-methyl-indazol-3-yl)-N-(2-cyanoethyl)carbamate. To a solution of tert-butyl N-(6-bromo-1-methyl-indazol-3-yl)carbamate (1.18 g, 3.61 mmol) in MeCN (15 mL) were added sequentially KF (429.4 mg, 7.39 mmol), acrylonitrile (0.83 mL, 12.6 mmol) and Al$_2$O$_3$ (1.29 g, 12.6 mmol), and the reaction mixture was heated to reflux for 18 h and then cooled to rt. The mixture was filtered on Celite and washed with MeCN (20 mL). The filtrate was concentrated under reduced pressure to afford the title compound (1.0 g, 73%) as an oil, which was used in the next step without further purification. MS (ESI) [M-tBu]$^+$324.6.

Step 3: Synthesis of tert-Butyl N-(3-amino-3-oxo-propyl)-N-(6-bromo-1-methyl-indazol-3-yl)carbamate. To a solution of tert-butyl N-(6-bromo-1-methyl-indazol-3-yl)-N-(2-cyanoethyl)carbamate (12 g, 31.6 mmol) in MeOH (90 mL) at 0° C. were added sequentially 30% H$_2$O$_2$ (128 mL, 1.23 mol) and NH$_4$OH (118 mL, 0.92 mol), and the reaction mixture was warmed to rt and stirred for 6 h. Water (500 mL) and DCM (500 mL) were added and the layers were separated. The organic layer was washed with a saturated aqueous solution of Na$_2$SO$_3$ (200 mL), dried (Na$_2$SO$_4$), filtered and concentrated under reduced pressure. The residue was purified by column chromatography on silica gel using a gradient of 0-100% EtOAc in hexanes followed by a second purification using and 0-20% MeOH in DCM to afford the title compound (10.6 g, 84%) as a solid. MS (ESI) [M+H]$^+$ 397.1.

Step 4: Synthesis of 1-(6-Bromo-1-methyl-indazol-3-yl)hexahydropyrimidine-2,4-dione. To a solution of tert-butyl N-(3-amino-3-oxo-propyl)-N-(6-bromo-1-methyl-indazol-3-yl)carbamate (10.6 g, 26.7 mmol) in THF (125 mL) was added KOtBu (6.0 g, 53.4 mmol), and the reaction mixture was stirred at 0° C. for 2 h. EtOAc (100 mL) and 1N HCl (40 mL) were added and the layers were separated. The organic layer was washed with brine (40 mL), dried (Na$_2$SO$_4$), filtered and concentrated under reduced pressure. The residue was purified by column chromatography on silica gel using a gradient of 0-100% EtOAc in hexane to afford the title compound (2.1 g, 24%) as a solid. MS (ESI) [M+H]$^+$ 323.1.

Step 5: Synthesis of tert-Butyl 4-[3-(2,4-dioxohexahydro-pyrimidin-1-yl)-1-methyl-indazol-6-yl]-3,6-dihydro-2H-pyridine-1-carboxylate. A mixture of 1-(6-bromo-1-methyl-indazol-3-yl)hexahydropyrimidine-2,4-dione (600 mg, 1.86 mmol), tert-butyl 4-(4,4,5,5-tetramethyl-1,3,2-dioxaborolan-2-yl)-3,6-dihydro-2H-pyridine-1-carboxylate (603 mg, 1.95 mmol), Pd(dppf)Cl$_2$-DCM (75.8 mg, 90 µmol) and K$_3$PO$_4$ (1.18 g, 5.57 mmol) in 1,4-dioxane (16 mL) and water (4 mL) was heated to 90° C. for 4 h and then cooled to rt. Volatiles were removed and the residue was purified by reverse phase chromatography (C18) with a gradient of 20-100% MeCN and 10 mM ammonium formate in water to afford the title compound (200 mg, 25%) as a solid. MS (ESI) [M−H]$^-$424.3. $^1$H NMR (500 MHz, DMSO-d$_6$) δ 10.54 (s, 1H), 7.62-7.57 (m, 2H), 7.26 (dd, J=8.6, 1.4 Hz, 1H), 6.29 (s, 1H), 4.07-4.02 (m, 2H), 3.99 (s, 3H), 3.92 (t, J=6.7 Hz, 2H), 3.61-3.55 (m, 2H), 2.76 (t, J=6.7 Hz, 2H), 2.61-2.55 (m, 2H), 1.44 (s, 9H).

Step 6: Synthesis of 1-(6-(1-(5-chloro-4-((1-methyl-2-oxoindolin-5-yl)amino)pyrimidin-2-yl)piperidin-4-yl)-1-methyl-1H-indazol-3-yl)dihydropyrimidine-2,4(1H,3H)-dione. The title compound was synthesized according to General Procedures 4, 5, and 6 using tert-Butyl 4-[3-(2,4-dioxohexahydropyrimidin-1-yl)-1-methyl-indazol-6-yl]-3,6-dihydro-2H-pyridine-1-carboxylate as the starting material. LCMS $C_{30}H_{30}ClN_9O_3$ requires 599.2, found 600.3 [M+H]$^+$; $^1$H NMR (500 MHz, DMSO-d$_6$) δ 10.52 (s, 1H), 8.64 (s, 1H), 8.02 (d, J=3.7 Hz, 1H), 7.56-7.51 (m, 3H), 7.44 (s, 1H), 7.04 (dd, J=8.6, 1.2 Hz, 1H), 6.94 (d, J=8.4 Hz, 1H), 4.72-4.62 (m, 2H), 3.95 (s, 3H), 3.90 (t, J=6.7 Hz, 2H), 3.53 (s, 2H), 3.10 (s, 3H), 2.98-2.88 (m, 3H), 2.74 (t, J=6.7 Hz, 2H), 1.90-1.83 (m, 2H), 1.71-1.58 (m, 2H).

Example S135. Synthesis of 1-(6-((1-(5-chloro-4-((1-methyl-2-oxoindolin-5-yl)amino)pyrimidin-2-yl)piperidin-4-yl)amino)-1-methyl-1H-indazol-3-yl)dihydropyrimidine-2,4(1H,3H)-dione (135)

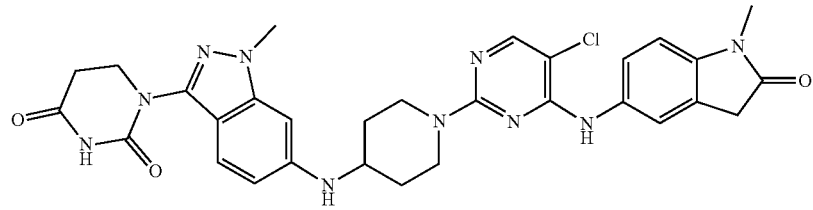 [SMILES: CN1C(=O)Cc2cc(Nc3nc(N4CCC(Nc5ccc6c(N7CCC(=O)NC7=O)nn(C)c6c5)CC4)ncc3Cl)ccc21]

Step 1: Synthesis of tert-butyl 4-[[3-(2,4-dioxohexahydropyrimidin-1-yl)-1-methyl-indazol-6-yl]amino]piperidine-1-carboxylate. To a stirred solution of 1-(6-amino-1-methyl-indazol-3-yl)hexahydropyrimidine-2,4-dione (200 mg, 0.77 mmol) and tert-butyl 4-oxopiperidine-1-carboxylate (307 mg, 1.54 mmol) in DCM (5 mL) were added acetic acid (10 mg, 0.77 mmol) with the pH adjusted to 6 and added sodium triacetoxyborohydride (490 mg, 2.31 mmol) in portions at RT under nitrogen atmosphere. The resulting mixture was stirred for 2 h at RT under nitrogen atmosphere. The reaction was monitored by LCMS. The reaction mixture was purified by flash to afford the title compound (240 mg, 70%) as a yellow solid.

Step 2: Synthesis of 1-(6-((1-(5-chloro-4-((1-methyl-2-oxoindolin-5-yl)amino)pyrimidin-2-yl)piperidin-4-yl)amino)-1-methyl-1H-indazol-3-yl)dihydropyrimidine-2,4(1H,3H)-dione The title compound was synthesized according to General Procedures 4, 5, and 6 using tert-butyl 4-[[3-(2,4-dioxohexahydropyrimidin-1-yl)-1-methyl-indazol-6-yl]amino]piperidine-1-carboxylate as starting material. LCMS $C_{30}H_{31}ClN_{10}O_3$ requires 614, found 615 [M+H]$^+$; $^1$H NMR (300 MHz, DMSO-d$_6$) δ 8.64 (s, 1H), 8.01 (s, 1H), 7.57-7.47 (m, 2H), 7.27 (d, J=8.8 Hz, 1H), 6.93 (d, J=9.1 Hz, 1H), 6.55-6.44 (m, 2H), 4.38 (d, J=13.1 Hz, 2H), 3.83 (d, J=11.9 Hz, 5H), 3.62-3.53 (m, 3H), 3.16-3.12 (m, 5H), 2.73-2.70 (m, 3H), 2.09-1.94 (m, 2H), 1.36-1.20 (m, 2H).

Example S136. Synthesis of 1-(6-((1-(5-chloro-4-((2-oxo-1-(2,2,2-trifluoroethyl)indolin-5-yl)amino)pyrimidin-2-yl)piperidin-4-yl)amino)-1-methyl-1H-indazol-3-yl)dihydropyrimidine-2,4(1H,3H)-dione (136)

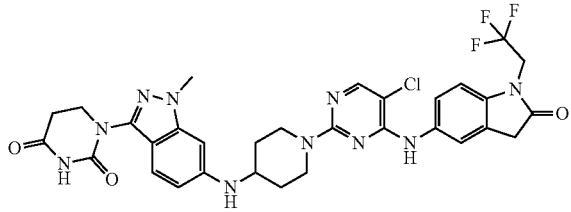 [SMILES: Cn1nc(N2CCC(=O)NC2=O)c2ccc(NC3CCN(c4ncc(Cl)c(Nc5ccc6c(c5)CC(=O)N6CC(F)(F)F)n4)CC3)cc21]

Step 1: Synthesis of 1-(6-((1-(5-chloro-4-((2-oxo-1-(2,2,2-trifluoroethyl)indolin-5-yl)amino)pyrimidin-2-yl)piperidin-4-yl)amino)-1-methyl-1H-indazol-3-yl)dihydropyrimidine-2,4(1H,3H)-dione. The title compound was synthesized according to General Procedures 1 and 6 using 5-amino-1-(2,2,2-trifluoroethyl)indolin-2-one and 1-[1-Methyl-6-(4-piperidylamino) indazol-3-yl]hexahydropyrimidine-2,4-dione as starting materials. LCMS $C_{31}H_{30}ClF_3N_{10}O_3$ requires 682.2, found 683.3 [M+H]$^+$; $^1$H NMR (500 MHz, DMSO) δ 10.45 (s, 1H), 8.69 (s, 1H), 8.03 (s, 1H), 7.58 (d, J=1.8 Hz, 1H), 7.54 (dd, J=8.6, 2.1 Hz, 1H), 7.27 (d, J=8.8 Hz, 1H), 7.11 (d, J=8.6 Hz, 1H), 6.51 (dd, J=8.9, 1.8 Hz, 1H), 6.44 (d, J=1.4 Hz, 1H), 5.82 (d, J=8.2 Hz, 1H), 4.58 (q, J=9.4 Hz, 2H), 4.43-4.33 (m, 2H), 3.86 (t, J=6.7 Hz, 2H), 3.82 (s, 3H), 3.70 (s, 2H), 3.68-3.60 (m, 1H), 3.16-3.07 (m, 2H), 2.72 (t, J=6.7 Hz, 2H), 2.03-1.96 (m, 2H), 1.38-1.27 (m, 2H).

Example S137. Synthesis of 1-(6-((1-(5-chloro-4-((1-(2-hydroxyethyl)-2-oxoindolin-5-yl)amino)pyrimidin-2-yl)piperidin-4-yl)amino)-1-methyl-1H-indazol-3-yl)dihydropyrimidine-2,4(1H,3H)-dione (137)

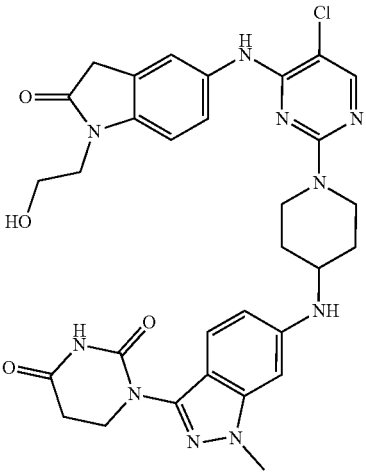 [SMILES: Cn1nc(N2CCC(=O)NC2=O)c2ccc(NC3CCN(c4ncc(Cl)c(Nc5ccc6c(c5)CC(=O)N6CCO)n4)CC3)cc21]

Step 1: Synthesis of 1-(6-((1-(5-chloro-4-((1-(2-hydroxyethyl)-2-oxoindolin-5-yl)amino)pyrimidin-2-yl)piperidin-4-yl)amino)-1-methyl-1H-indazol-3-yl)dihydropyrimidine-2,4(1H,3H)-dione. The title compound was synthesized according to General Procedures 1 and 6 using 5-amino-1-

(2-hydroxyethyl)indolin-2-one and 1-[1-methyl-6-(4-piperidylamino) indazol-3-yl]hexahydropyrimidine-2,4-dione as starting materials. LCMS $C_{31}H_{33}ClN_{10}O_4$ requires 644.2, found 645.3 [M+H]$^+$; $^1$H NMR (500 MHz, DMSO) δ 10.45 (s, 1H), 8.63 (s, 1H), 8.01 (s, 1H), 7.53 (s, 1H), 7.49 (d, J=8.4 Hz, 1H), 7.27 (d, J=8.8 Hz, 1H), 6.99 (d, J=8.5 Hz, 1H), 6.51 (dd, J=8.9, 1.7 Hz, 1H), 6.44 (s, 1H), 5.82 (d, J=8.3 Hz, 1H), 4.79 (bs, 1H), 4.44-4.32 (m, 2H), 3.86 (t, J=6.7 Hz, 2H), 3.82 (s, 3H), 3.70 (t, J=5.9 Hz, 2H), 3.68-3.60 (m, 1H), 3.57 (t, J=5.8 Hz, 2H), 3.53 (s, 2H), 3.16-3.07 (m, 2H), 2.72 (t, J=6.7 Hz, 2H), 2.04-1.96 (m, 2H), 1.38-1.26 (m, 2H).

Example S138. Synthesis of 2-(4-((3-(2,4-dioxotetrahydropyrimidin-1(2H)-yl)-1-methyl-1H-indazol-6-yl)amino)piperidin-1-yl)-4-((1-methyl-2-oxoindolin-5-yl)amino)pyrimidine-5-carbonitrile (138)

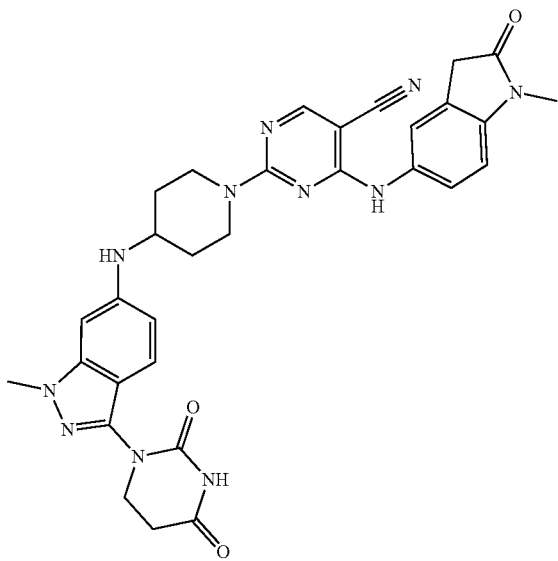

Step 1: Synthesis of 2-(4-((3-(2,4-dioxotetrahydropyrimidin-1(2H)-yl)-1-methyl-1H-indazol-6-yl)amino)piperidin-1-yl)-4-((1-methyl-2-oxoindolin-5-yl)amino)pyrimidine-5-carbonitrile. The title compound was synthesized according to General Procedures 1 and 6 using 2,4-dichloropyrimidine-5-carbonitrile and 1-[1-methyl-6-(4-piperidylamino) indazol-3-yl]hexahydropyrimidine-2,4-dione; hydrochloride as starting materials. LCMS $C_{31}H_{31}N_{11}O_3$ requires 605.3, found 606.5 [M+H]$^+$; $^1$H NMR (500 MHz, DMSO) δ 10.45 (s, 1H), 9.28 (s, 1H), 8.45 (s, 1H), 8.40 (s, 1H), 7.52-7.40 (m, 2H), 7.28 (d, J=8.8 Hz, 1H), 6.98-6.81 (m, 1H), 6.51 (dd, J=8.9, 1.7 Hz, 1H), 6.45 (s, 1H), 5.84 (d, J=8.2 Hz, 1H), 4.67-4.50 (m, 1H), 4.41-4.27 (m, 1H), 3.86 (t, J=6.7 Hz, 2H), 3.82 (s, 3H), 3.72-3.62 (m, 1H), 3.54 (s, 2H), 3.26-3.15 (m, 2H), 3.10 (s, 3H), 2.72 (t, J=6.7 Hz, 2H), 2.03 (d, J=10.1 Hz, 2H), 1.32 (td, J=13.6, 4.0 Hz, 2H). MS (ESI) [M+H]$^+$.

Example S139. Synthesis of 1-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)pyrimidine-2,4(1H,3H)-dione (139)

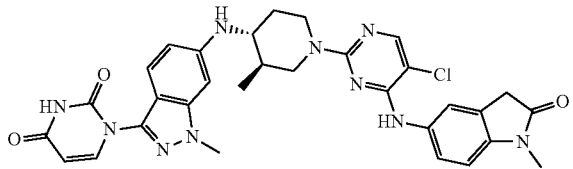 [SMILES: C[C@@H]1CN(c2ncc(Cl)c(Nc3ccc4c(c3)CC(=O)N4C)n2)CC[C@H]1Nc1ccc2c(-n3ccc(=O)[nH]c3=O)nn(C)c2c1]

Step 1: Synthesis of 1-(6-bromo-1-methyl-1H-indazol-3-yl) urea. To a stirred a solution of 6-bromo-1-methyl-1H-indazol-3-amine (10 g, 44.2 mmol) in acetonitrile (100 mL) was added isocyanatotrimethylsilane (20.4 g, 177 mmol) in a sealed tube. The reaction mixture was heated to 65° C. and stirred for 16 h. The reaction mixture cooled to 25° C. and concentrated under reduced pressure to obtain the crude product. The crude product was purified by column chromatography on silica gel with 10% methanol/DCM to afford the title compound (4.0 g, 13.7 mmol, 30% yield) as a brown solid.

Step 2: Synthesis of 1-(6-bromo-1-methyl-1H-indazol-3-yl)pyrimidine-2,4(1H,3H)-dione. To a stirred solution of 1-(6-bromo-1-methyl-1H-indazol-3-yl) urea (4.0 g, 13.67 mmol) in DMF (10 mL) at 0° C. was added methyl 3,3-dimethoxypropionate (2.431 g, 16.40 mmol) under nitrogen at 0° C. The reaction mixture was heated to 90° C. and stirred for 3 h. The reaction mixture was cooled to room temperature and treated with ice cold water to obtain solid. The solid was filtered and washed with water to afford the title compound (4.1 g, 4.63 mmol, 33% yield) as yellow solid. LCMS: 320.9 [M+H]$^+$.

Step 3: Synthesis of 1-(6-bromo-1-methyl-1H-indazol-3-yl)-3-(4-methoxybenzyl)pyrimidine-2,4(1H,3H)-dione. To a stirred solution of 1-(6-bromo-1-methyl-1H-indazol-3-yl)pyrimidine-2,4(1H,3H)-dione (4.0 g, 12.46 mmol) in DMF (20 mL) was added cesium carbonate (6.09 g, 18.68 mmol) and 1-(bromomethyl)-4-methoxybenzene (3.76 g, 18.68 mmol). The reaction mixture was slowly heated to 80° C. and stirred for 3 h. The reaction mixture was poured in water and extracted with ethyl acetate (3×50 mL). The combined organic layer was dried over sodium sulphate, filtered, and concentrated under reduced pressure to obtain crude. The crude product was purified by flash column chromatography on silica gel with 30% ethyl acetate/pet ether to afford the title compound (2.05 g, 3.58 mmol, 28% yield).

Step 4: Synthesis of tert-butyl (3R,4R)-4-((3-(3-(4-methoxybenzyl)-2,4-dioxo-3,4-dihydropyrimidin-1(2H)-yl)-1-methyl-1H-indazol-6-yl)amino)-3-methylpiperidine-1-carboxylate. To a stirred solution of 1-(6-bromo-1H-indazol-3-yl)-3-(4-methoxybenzyl)pyrimidine-2,4(1H,3H)-dione (500 mg, 0.872 mmol) in 1,4-dioxane (10 mL) was added cesium carbonate (710 mg, 2.181 mmol) and tert-butyl (3R,4R)-4-amino-3-methylpiperidine-1-carboxylate (280 mg 1.30 mmol) degassed with nitrogen for 10 min. Then CPhos-Pd-G3 (703 mg, 0.872 mmol) was added. The reaction mixture was heated to 90° C. and stirred for 18 h. The reaction mixture was filtered through celite pad and the celite pad was washed with ethyl acetate. The filtrate was concentrated under reduced pressure to obtain the crude. The crude product was purified by flash column chromatography on silica gel with 30% ethyl acetate/pet ether to afford the title compound (301 mg, 0.426 mmol, 48% yield) as a light-yellow solid.

Step 5: Synthesis of 1-(1-methyl-6-(((3R,4R)-3-methylpiperidin-4-yl)amino)-1H-indazol-3-yl)pyrimidine-2,4(1H,3H)-dione. To a stirred solution of tert-butyl (3R,4R)-4-((3-(3-(4-methoxybenzyl)-2,4-dioxo-3,4-dihydropyrimidin-1(2H)-yl)-1-methyl-1H-indazol-6-yl)amino)-3-methylpiperidine-1-carboxylate (300 mg, 0.42 mmol) in 1,4-dioxane (10 mL) was added TFA (5.0 mL). The reaction mixture heated to 80° C. and stirred for 48 h. The reaction mixture was concentrated under reduced pressure and triturated by diethyl ether to afford the title compound (301 mg, 0.426 mmol, 48% yield) as a brown gummy solid. The crude product was used for the next step without further purification.

Step 6: Synthesis of 1-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl) pyrimidine-2,4(1H,3H)-dione. To a stirred solution of 1-(1-methyl-6-(((3R,4R)-3-methylpiperidin-4-yl)amino)-1H-indazol-3-yl)pyrimidine-2,4(1H,3H)-dione (100 mg, 0.172 mmol) in DMSO (2.0 mL) was added 5-((5-chloro-2-fluoropyrimidin-4-yl)amino)-1-methylindolin-2-one (50.3 mg, 0.172 mmol) and DIPEA (0.15 mL, 0.85 mmol) at 25° C. The reaction mixture was heated to 80° C. and stirred for 6 h. The reaction mixture was cooled to room temperature and purified by preparative HPLC to afford the title compound (7.0 mg, 0.01 mmol 5% yield) as an off-white solid. Prep method: Rt 10.5 min, Column: X-select C18 (150×19) mm, 5.0 μm, 0.1% formic acid in water/acetonitrile; Flow rate: 15.0 mL/min. LCMS $C_{31}H_{31}N_{10}O_3$ requires 626.2, found 627.2 [M+H]$^+$; $^1$H NMR (400 MHz, DMSO-$d_6$): δ 11.55 (s, 1H), 8.68 (s, 1H), 8.03 (s, 1H), 7.74 (d, J=7.60 Hz, 1H), 7.57-7.52 (m, 2H), 7.23 (d, J=8.80 Hz, 1H), 6.95 (d, J=8.00 Hz, 1H), 6.58 (d, J=8.0 Hz, 1H), 6.5 (s, 1H), 5.90 (d, J=8.80 Hz, 1H), 5.71 (d, J=7.60 Hz, 1H), 4.52-4.46 (m, 2H), 3.88 (s, 3H), 3.54 (s, 2H), 3.11 (s, 3H), 3.06-2.99 (m, 1H), 2.72-2.69 (m, 1H), 2.33-2.29 (m, 1H), 2.09-2.07 (m, 1H), 1.62-1.58 (m, 1H), 1.31-1.17 (m, 2H), 0.98 (d, J=5.60 Hz, 3H).

Example S140. Synthesis of 1-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)-5-fluoropyrimidine-2,4(1H,3H)-dione (140)

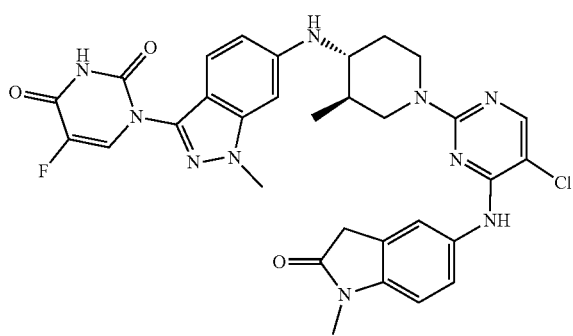 [SMILES: C[C@@H]1CN(c2ncc(Cl)c(Nc3ccc4c(c3)CC(=O)N4C)n2)CC[C@H]1Nc1ccc2c(-n3cc(F)c(=O)[nH]c3=O)nn(C)c2c1]

Step 1: Synthesis of 5-fluoro-3-(4-methoxybenzyl)pyrimidine-2,4(1H,3H)-dione. To a stirred solution of 5-fluoropyrimidine-2,4(1H,3H)-dione (5.0 g, 38.4 mmol) in DMF (100 mL) was added triethylamine (5.36 mL, 38.4 mmol) at 25° C., under nitrogen. The reaction mixture was cooled to 0° C. and methyl chloroformate (2.98 mL, 38.4 mmol) was added dropwise and stirred for 3 h. Then Et$_3$N (8.04 ml, 57.6 mmol) and 4-methoxybenzylchloride (7.82 mL, 57.7 mmol) were added at 0° C. The reaction mixture was slowly warmed to 25° C. and stirred for 6 h. The reaction mixture was treated with ice cold water (100 mL) and extracted with ethyl acetate (2×100 mL). The combined organic layer was dried over anhydrous sodium sulphate and concentrated under reduced pressure to afford crude. The crude was dissolved in a 1:1 mixture of MeOH and DCM (50 mL) and added 30% H$_2$O$_2$ (4.32 mL, 42.3 mmol) followed by 6.0N NaOH (0.1 mL) at 0° C. The reaction mixture was stirred for 1 h and treated ice-cold water (100 mL) and extracted with dichloromethane (2×100 mL). The combined organic layer was washed with water, dried over anhydrous sodium sulphate, and concentrated under reduced pressure to afford the crude product. The crude product was purified by flash column chromatography on silica gel with 50% ethyl acetate/pet ether to afford the title compound (5.10 g, 17.58 mmol, 46% yield) as an off-white solid. $^1$H NMR (400 MHz, DMSO-$d_6$): δ 11.16 (d, J=5.6 Hz, 1H), 7.87 (t, J=6.0 Hz, 1H), 7.26-7.23 (m, 2H), 6.88-6.86 (m, 2H), 4.88 (s, 2H), 3.72 (s, 3H).

Step 2: Synthesis of 1-(6-bromo-1-methyl-1H-indazol-3-yl)-5-fluoro-3-(4-methoxybenzyl)pyrimidine-2,4(1H,3H)-dione. To a stirred solution of 6-bromo-1-methyl-3-(4,4,5,5-tetramethyl-1,3,2-dioxaborolan-2-yl)-1H-indazole (3.0 g, 8.90 mmol) and molecular sieves (0.5 g) in DCM (40 mL) was added compound 5-fluoro-3-(4-methoxybenzyl)pyrimidine-2,4(1H,3H)-dione (5.06 g, 17.80 mmol), Et$_3$N (2.481 mL, 17.80 mmol) and copper (II) acetate (1.617 g, 8.90 mmol) at 25° C. The reaction mixture was stirred for 16 h under oxygen. The reaction mixture was filtered through celite pad and the filtrate was concentrated under vacuum to afford crude compound. The crude product was purified by flash column chromatography on silica gel with 35-45% ethyl acetate/pet ether to afford the title compound (1.2 g, 2.61 mmol, 29% yield) as an off-white solid. $^1$H NMR (400 MHz, DMSO-$d_6$): δ 8.38 (d, J=6.0 Hz, 1H), 8.11 (d, J=1.2 Hz, 1H), 7.65 (dd, J=0.4 Hz and 8.8 Hz, 1H), 7.37 (dd, J=1.2 Hz and 8.4 Hz, 1H), 7.33-7.30 (m, 2H), 6.91-6.88 (m, 2H), 5.00 (s, 2H), 4.07 (s, 3H), 3.73 (s, 3H).

Step 3: Synthesis of tert-butyl (3R,4R)-4-((3-(5-fluoro-3-(4-methoxybenzyl)-2,4-dioxo-3,4-dihydropyrimidin-1(2H)-yl)-1-methyl-1H-indazol-6-yl)amino)-3-methylpiperidine-1-carboxylate. A stirred solution of compound 1-(6-bromo-1-methyl-1H-indazol-3-yl)-5-fluoro-3-(4-methoxybenzyl) pyrimidine-2,4(1H,3H)-dione (1.10 g, 2.395 mmol) and tert-butyl (3R,4R)-4-amino-3-methylpiperidine-1-carboxylate (513 mg, 2.395 mmol) in 1,4-dioxane (30.0 mL) was degassed with nitrogen for 5 min. Then CPhos-Pd-G3 (97 mg, 0.120 mmol) and Cs$_2$CO$_3$ (1.171 g, 3.59 mmol) were added. The reaction mixture was heated to 100° C. and stirred for 10 h. The reaction mixture was cooled to 25° C., treated with water (100 mL) and extracted with ethyl acetate (2×100 mL). The combined organic layer was dried over anhydrous sodium sulphate and concentrated under reduced pressure to afford the crude product. The crude product was purified by flash column chromatography on silica gel with 80-100% ethyl acetate/pet ether to afford the title compound (400 mg, 0.621 mmol, 26% yield) as an off white solid. LCMS: 593.2 (M+H), Rt 3.467 min Step 4: Synthesis of 5-fluoro-1-(1-methyl-6-(((3R,4R)-3-methyl-1-(2,2,2-trifluoroacetyl)-1l4-piperidin-4-yl)amino)-1H-indazol-3-yl)pyrimidine-2,4(1H,3H)-dione. To a stirred solution of compound 6 (500 mg, 0.844 mmol) in TFA (0.65 mL, 8.44 mmol) was added CF₃SO₃H (0.375 mL, 4.22 mmol) at 25° C. The reaction mixture was heated to 50° C. and stirred for 8 h. The reaction mixture was concentrated under vacuum to afford the crude product. The crude compound was triturated with diethyl ether and dried under reduced pressure to afford the title compound (400 mg, 0.782 mmol, 93% yield) as a brown solid. The crude product was used for the next step without further purification. LCMS: 372.7 [M+H]⁺.

Step 5: Synthesis of 1-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)-5-fluoropyrimidine-2,4 (1H,3H)-dione. To a stirred solution of 5-fluoro-1-(1-methyl-6-(((3R,4R)-3-methyl-1-(2,2,2-trifluoroacetyl)-114-piperidin-4-yl)amino)-1H-indazol-3-yl)pyrimidine-2,4(1H,3H)-dione (100 mg, 0.195 mmol) and 5-((5-chloro-2-fluoropyrimidin-4-yl)amino)-1-methylindolin-2-one (58.1 mg, 0.195 mmol) in DMSO (2.0 mL) was added DIPEA (0.102 mL, 0.586 mmol) in DMSO (2.0 mL) at 25° C. The reaction mixture was heated to 80° C. and stirred for 4 h. The reaction mixture was cooled to room temperature and purified by preparative HPLC to afford the title compound (30 mg, 0.045 mmol, 23% yield) as an off-white solid. LCMS $C_{31}H_{30}ClFN_{10}O_3$ requires 644.2, found 645.2 [M+H]⁺; ¹H NMR (400 MHz, DMSO-d₆): δ 12.05 (s, 1H), 8.69 (s, 1H), 8.20 (d, J=6.4 Hz, 1H), 8.03 (s, 1H), 7.58 (s, 1H), 7.52 (dd, J=1.6 Hz and 8.8 Hz, 1H), 7.27 (d, J=8.8 Hz, 1H), 6.94 (d, J=8.4 Hz, 1H), 6.59 (dd, J=1.6 Hz and 9.2 Hz, 1H), 6.51 (s, 1H), 5.90 (d, J=9.2 Hz, 1H), 4.49-4.46 (m, 2H), 3.88 (s, 3H), 3.54 (s, 2H), 3.14 (s, 3H), 3.11-3.00 (m, 1H), 2.73-2.67 (m, 1H), 2.09-2.07 (m, 1H), 1.56-1.63 (m, 1H), 1.24-1.15 (m, 1H), 0.98 (d, J=6.4 Hz, 3H).

Examples S141-S144. Synthesis of Compounds 141-144

Examples in Table 4 below have been made according to the general procedures outlined in the table beginning with their respective commercial starting materials and intermediates found within this document.

TABLE 4

| Compound | General Procedure No. | MS Data | NMR Data |
|---|---|---|---|
| Example S141<br>1-(6-(((3R,4R)-1-(5-chloro-4-((1-methyl-2-oxoindolin-5-yl)amino)pyrimidin-2-yl)-3-methylpiperidin-4-yl)amino)-1-methyl-1H-indazol-3-yl)dihydropyrimidine-2,4(1H,3H)-dione (141) | 6 | Requires 628.2, found 629.3 [M + H]⁺ | ¹H NMR (400 MHz, DMSO-d₆) δ 10.41 (br s, 1H), 8.61 (s, 1H), 7.98 (s, 1H), 7.56-7.47 (m, 2H), 7.21 (d, J = 9.0 Hz, 1H), 6.89 (d, J = 8.5 Hz, 1H), 6.46 (dd, J = 8.8, 1.9 Hz, 1H), 6.38 (d, J = 1.2 Hz, 1H), 5.69 (d, J = 8.9 Hz, 1H), 4.50-4.30 (m, 2H), 3.81 (t, J = 6.7 Hz, 2H), 3.77 (s, 3H), 3.49 (s, 2H), 3.02 (d, J = 32.4 Hz, 5H), 2.68 (t, J = 6.7 Hz, 2H), 2.11-1.99 (m, 1H),1.59-1.51 (m, 1H), 1.25-0.99 (m, 2H), 0.93 (d, J = 6.4 Hz, 3H) |
| Example S142<br>1-(6-(((3R,4R)-1-(5-chloro-4-((4-fluoro-1-methyl-2-oxoindolin-5-yl)amino)pyrimidin-2-yl)-3-methylpiperidin-4-yl)amino)-1-methyl-1H-indazol-3-yl)dihydropyrimidine-2,4(1H,3H)-dione (142) | 1, 6 | Requires 646.2, found 648.0 [M + H]⁺ | ¹H NMR (DMSO-d6, 400 MHz) δ 10.3-10.4 (m, 1H), 8.5-8.7 (m, 1H), 7.8-8.1 (m, 1H), 7.2-7.4 (m, 1H), 7.1-7.2 (m, 1H), 6.7-6.9 (m, 1H), 6.4-6.5 (m, 1H), 6.2-6.4 (m, 1H), 5.58-5.8 (m, 3H), 4.2-4.4 (m, 2H), 3.8-3.8 (m, 2H), 3.72 (s, 3H), 3.5-3.6 (m, 2H), 3.1-3.1 (m, 1H), 3.06 (s, 2H), 2.6-2.7 (m, 3H), 1.8-2.0 (m, 1H), 1.3-1.5 (m, 1H), 0.9-1.1 (m, 1H), 0.6-0.9 (m, 3H) |

TABLE 4-continued

| Compound | General Procedure No. | MS Data | NMR Data |
|---|---|---|---|
| Example S143<br>1-(6-(((3R,4R)-1-(5-chloro-4-((1-methyl-2-oxo-2,3-dihydro-1H-pyrrolo[2,3-b]pyridin-5-yl)amino)pyrimidin-2-yl)-3-methylpiperidin-4-yl)amino)-1-methyl-1H-indazol-3-yl)dihydropyrimidine-2,4(1H,3H)-dione (143) | 6 | Requires 629.2, found 630.4 [M + H]⁺ | ¹H NMR (400 MHz, DMSO-d6) δ ppm 10.45 (s, 1 H), 8.85 (s, 1 H), 8.35 (d, J = 2.20 Hz, 1 H), 8.05 (s, 1 H), 7.86 (s, 1 H), 7.25 (d, J = 8.80 Hz, 1 H), 6.50 (dd, J = 8.93, 1.83 Hz, 1 H), 6.42 (s, 1 H), 5.73 (d, J = 9.05 Hz, 1 H), 4.34-4.55 (m, 2 H), 3.85 (t, J = 6.66 Hz, 2 H), 3.81 (s, 3 H), 3.59-3.67 (m, 2 H), 3.12 (s, 3 H), 2.96-3.07 (m, 1 H), 2.72 (t, J = 6.66 Hz, 2 H), 1.94-2.12 (m, 2 H), 1.50-1.67 (m, 1 H), 1.10-1.19 (m, 1 H), 0.95 (d, J = 6.60 Hz, 3 H), 0.80-0.89 (m, 1 H) |
| Example S144<br>1-(6-((1-(5-chloro-4-((1-ethyl-2-oxoindolin-5-yl)amino)pyrimidin-2-yl)piperidin-4-yl)amino)-1-methyl-1H-indazol-3-yl)dihydropyrimidine-2,4(1H,3H)-dione (144) | 1, 6 | Required 628.2, Found 629.3 [M + H]⁺ | ¹H NMR (500 MHz, DMSO) δ 10.48 (s, 1H), 8.15 (s, 1H), 7.51-7.48 (m, 1H), 7.48-7.44 (m, 1H), 7.41-7.34 (m, 1H), 7.04 (d, J = 8.4 Hz, 1H), 6.73-6.57 (m, 2H), 4.33-4.26 (m, 2H), 3.88 (t, J = 6.6 Hz, 2H), 3.85 (s, 3H), 3.74-3.71 (m, 1H), 3.68 (q, J = 7.1 Hz, 2H), 3.57 (s, 2H), 3.26-3.15 (m, 2H), 2.73 (t, J = 6.7 Hz, 2H), 2.08-2.00 (m, 2H), 1.51-1.40 (m, 2H), 1.13 (t, J = 7.2 Hz, 3H). 2 exchangeable protons were not observed. |

Example S145. Synthesis of 2-((3R,4R)-4-((3-(2,6-dioxopiperidin-3-yl)-1-methyl-1H-indazol-6-yl)amino)-3-methoxypiperidin-1-yl)-4-((1-methyl-2-oxoindolin-5-yl)amino) pyrimidine-5-carbonitrile (145)

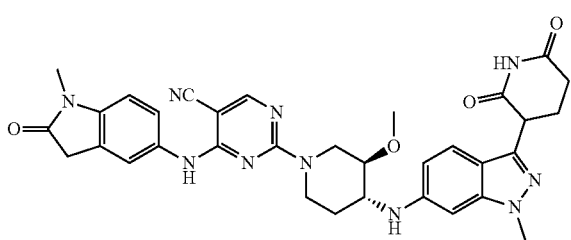 [SMILES: CO[C@@H]1CN(c2ncc(C#N)c(Nc3ccc4c(c3)CC(=O)N4C)n2)CC[C@H]1Nc1ccc2c(C3CCC(=O)NC3=O)nn(C)c2c1]

Step 1: Synthesis of tert-butyl (3R,4R)-4-(((benzyloxy)carbonyl)amino)-3-hydroxypiperidine-1-carboxylate. To a stirred solution of tert-butyl (3R,4R)-4-amino-3-hydroxypiperidine-1-carboxylate (2.5 g, 11.6 mmol) in DCM (10 mL) at 0° C., Cbz-Cl (1.97 g, 11.6 mmol) and saturated aqueous sodium carbonate solution (10 mL) were added. The reaction mixture was warmed up to 25° C. and stirred for 2 h. The reaction mixture was quenched with water (50 mL) and extracted with DCM (3×50 mL). The combined organic layers were washed with water (50 mL), dried over anhydrous sodium sulfate, filtered, and concentrated under reduced pressure to afford the crude product. The crude residue was purified by flash column chromatography on silica with 40% ethyl acetate/pet ether to afford the title compound (3.3 g, 9.42 mmol, 81% yield) as an off-white solid.

Step 2: Synthesis of tert-butyl (3R,4R)-4-(((benzyloxy)carbonyl)amino)-3-methoxypiperidine-1-carboxylate. To a stirred solution of silver (I) oxide (10.9 g, 47.1 mmol) and tert-butyl (3R,4R)-4-(((benzyloxy) carbonyl)amino)-3-hydroxypiperidine-1-carboxylate (3.3 g, 9.42 mmol) in ACN (50 mL), methyl iodide (14.7 mL, 235 mmol) was added dropwise. The reaction mixture was stirred at 25° C. for 16 h. The reaction mixture was filtered through a celite pad and the celite pad was washed with methanol (3×50 mL). The filtrate was concentrated under reduced pressure to afford the crude product. The crude residue was purified by flash column chromatography on silica with 25% ethyl acetate/pet ether to afford the title compound (3.1 g, 8.45 mmol, 90% yield) as a colorless liquid.

Step 3: Synthesis of tert-butyl (3R,4R)-4-amino-3-methoxypiperidine-1-carboxylate. To a stirred solution of tert-butyl (3R,4R)-4-(((benzyloxy) carbonyl)amino)-3-methoxypiperidine-1-carboxylate (3.0 g, 8.23 mmol) in methanol (20 mL) was added 10% palladium on carbon (1.0 g) under nitrogen. The reaction mixture was stirred under 1 atm of hydrogenation pressure at 25° C. for 3 h. The reaction mixture was filtered through a pad of celite and the celite pad was washed with methanol (200 mL). The filtrate was concentrated under reduced pressure to afford the title compound (1.7 g, 7.38 mmol, 90% yield) as crude product. The crude product was used in the next step without further purification.

Step 4: Synthesis of tert-butyl (3R,4R)-4-((3-(2,6-bis(benzyloxy)pyridin-3-yl)-1-methyl-1H-indazol-6-yl)amino)-3-methoxypiperidine-1-carboxylate. A stirred solution of tert-butyl (3R,4R)-4-amino-3-methoxypiperidine-1-carboxylate (200 mg, 0.87 mmol) and 3-(2,6-bis(benzyloxy)pyridin-3-yl)-6-bromo-1-methyl-1H-indazole (435 mg, 0.87 mmol) in toluene (10 mL) was degassed for 10 min. Then NaO'Bu (167 mg, 1.74 mmol), Pd$_2$dba$_3$ (80 mg, 0.09 mmol) and CPhos (114 mg, 2.26 mmol) were added at 25° C. The reaction mixture was heated to 100° C. and stirred for 12 h. The reaction mixture was poured into water (150 mL) and diluted with ethyl acetate (150 mL). The layers were separated, and the aqueous layer was extracted with ethyl acetate (3×150 mL). The combined organic layers were washed with brine (150 mL), dried over anhydrous sodium sulfate, filtered, and concentrated under reduced pressure to afford the crude product. The crude residue was purified by flash column chromatography on silica with 25% ethyl acetate/pet ether to afford the title compound (485 mg, 0.66 mmol, 76% yield) as a light-brown solid.

Step 5: Synthesis of tert-butyl (3R,4R)-4-((3-(2,6-dioxopiperidin-3-yl)-1-methyl-1H-indazol-6-yl)amino)-3-methoxypiperidine-1-carboxylate. To a stirred solution of tert-butyl (3R,4R)-4-((3-(2,6-bis(benzyloxy)pyridin-3-yl)-1-methyl-1H-indazol-6-yl)amino)-3-methoxypiperidine-1-carboxylate (485 mg, 0.66 mmol) and trifluoroacetic acid (0.05 mL, 0.66 mmol) in ethanol (4 mL) and THF (4 mL) was added 20% palladium hydroxide on carbon (150 mg) under nitrogen. The reaction mixture was stirred under 1 atm of hydrogenation pressure at 25° C. for 3 h. The reaction mixture was filtered through a pad of celite and the celite pad was washed with methanol (200 mL). The filtrate was concentrated under reduced pressure to afford the title compound (300 mg, 0.42 mmol, 64% yield) as crude product. The crude product was used in the next step without further purification.

Step 6: Synthesis of 3-(6-(((3R,4R)-3-methoxypiperidin-4-yl)amino)-1-methyl-1H-indazol-3-yl) piperidine-2,6-dione. The title compound was synthesized according to General Procedure 5 using tert-butyl (3R,4R)-4-((3-(2,6-dioxopiperidin-3-yl)-1-methyl-1H-indazol-6-yl)amino)-3-methoxypiperidine-1-carboxylate (250 mg, 0.53 mmol) as the starting material.

Step 7: Synthesis of 2-((3R,4R)-4-((3-(2,6-dioxopiperidin-3-yl)-1-methyl-1H-indazol-6-yl)amino)-3-methoxypiperidin-1-yl)-4-((1-methyl-2-oxoindolin-5-yl)amino) pyrimidine-5-carbonitrile. The synthesis of the title compound was accomplished using General Procedure 6 using 3-(6-(((3R,4R)-3-methoxypiperidin-4-yl)amino)-1-methyl-1H-indazol-3-yl) piperidine-2,6-dione (200 mg, 0.38 mmol) and 4-((1-methyl-2-oxoindolin-5-yl) amino)-2-(methylsulfonyl)pyrimidine-5-carbonitrile (149 mg, 0.38 mmol). The reaction mixture was filtered and purified by reverse-phased semi-preparative HPLC (10-100% acetonitrile+0.1% formic acid in water 0.1% formic acid, over 30 min). Fractions containing clean product were combined and lyophilized to give the title compound as a white solid (7.7 mg, 0.012 mmol, 8.23% yield). MS (ESI) m/z 635.2 [M+H]$^+$; $^1$H NMR (500 MHz, DMSO-d$_6$) δ ppm 10.82 (s, 1H), 9.29 (s, 1H), 8.39 (d, J=11.20 Hz, 1H), 7.50 (d, J=11.20 Hz, 2H), 7.44 (d, J=7.60 Hz, 1H), 6.93 (d, J=8.40 Hz, 1H), 6.58 (d, J=8.80 Hz, 1H), 6.47 (s, 1H), 5.90 (s, 1H), 4.21-4.07 (m, 2H), 4.21-4.07 (m, 3H), 3.92-3.83 (m, 1H), 3.82 (s, 3H), 3.81-3.60 (m, 2H), 3.54 (s, 3H), 3.53-3.48 (m, 1H), 3.10 (m, 3H), 2.62 (d, J=8.40 Hz, 2H), 2.30-2.00 (m, 3H), 1.36 (brs, 1H).

Example S146. Synthesis of 3-(6-(((3R,4R)-1-(5-chloro-4-((1-methyl-2-oxoindolin-5-yl)amino)pyrimidin-2-yl)-3-methoxypiperidin-4-yl)amino)-1-methyl-1H-indazol-3-yl)piperidine-2,6-dione (146)

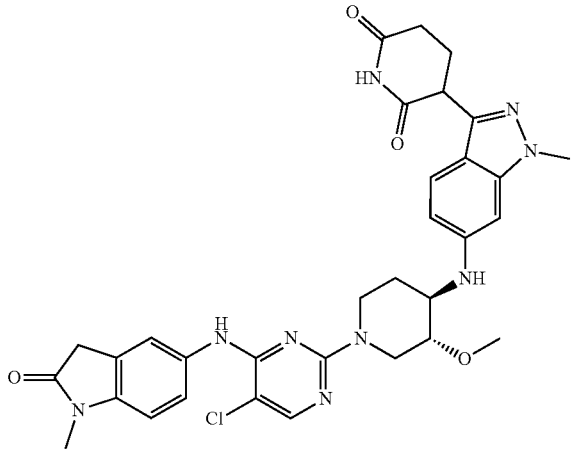

Step 1: Synthesis of tert-butyl (3R,4R)-4-((3-(2,6-bis(benzyloxy)pyridin-3-yl)-1-methyl-1H-indazol-6-yl)amino)-3-methoxypiperidine-1-carboxylate. A dioxane (35 mL) solution of 3-(2,6-bis(benzyloxy)pyridin-3-yl)-6-bromo-1-methyl-1H-indazole (1750 mg, 3.50 mmol) tert-butyl (3R,4R)-4-amino-3-methoxypiperidine-1-carboxylate (1007 mg, 4.37 mmol) and sodium tert-butoxide (504 mg, 5.25 mmol) was degassed for 15 min with nitrogen before addition of Josiphos Pd G3 (323 mg, 0.350 mmol). The reaction mixture was then heated at 100° C. for 16 hr. The mixture was then cooled to RT and diluted with saturated sodium bicarbonate and extracted with EtOAc (3×). The combined organics were dried over magnesium sulfate and filtered through celite before being concentrated and purified with silica gel chromatography using 0 to 100% EtOAc in hexanes to provide the title compound (1.25 g, 1.92 mmol). $^1$H NMR (500 MHz, CDCl$_3$) δ ppm 7.92 (d, J=7.99 Hz, 1H), 7.54-7.29 (m, 11H), 7.28-7.25 (m, 1H), 6.51 (d, J=8.11 Hz, 1H), 6.47-6.41 (m, 2H), 5.49 (s, 2H), 5.41 (s, 2H), 4.00 (s, 4H), 3.96-3.73 (m, 2H), 3.49 (s, 4H), 3.22 (td, J=7.60, 3.87 Hz, 2H), 2.30-2.19 (m, 1H), 1.51 (s, 9H).

Step 2: Synthesis of 3-(6-(((3R,4R)-3-methoxypiperidin-4-yl)amino)-1-methyl-1H-indazol-3-yl)piperidine-2,6-dione hydrochloride. The synthesis of the title compound was accomplished using General Procedures 4 and 5 using tert-butyl (3R,4R)-4-((3-(2,6-bis(benzyloxy)pyridin-3-yl)-1-methyl-1H-indazol-6-yl)amino)-3-methoxypiperidine-1-carboxylate as the starting material.

Step 3: Synthesis of 3-(6-(((3R,4R)-1-(5-chloro-4-((1-methyl-2-oxoindolin-5-yl)amino)pyrimidin-2-yl)-3-methoxypiperidin-4-yl)amino)-1-methyl-1H-indazol-3-yl)piperidine-2,6-dione. The synthesis of the title compound was accomplished using General Procedure 6 using 3-(6-(((3R,4R)-3-methoxypiperidin-4-yl)amino)-1-methyl-1H-indazol-3-yl)piperidine-2,6-dione hydrochloride (65 mg, 0.159 mmol) and 5-((5-chloro-2-fluoropyrimidin-4-yl)amino)-1-methylindolin-2-one (46 mg, 0.159 mmol). The reaction mixture was filtered and purified by reverse-phased semi-preparative HPLC (10-100% acetonitrile+0.1% formic acid in water 0.1% formic acid, over 30 min). Fractions containing clean product were combined and lyophilized to give the title compound as a white solid (7.7 mg, 0.012 mmol, 8.23% yield). MS (ESI) m/z 644.6 [M+H]$^+$; $^1$H NMR (500 MHz, DMSO-d$_6$) δ ppm 10.82 (s, 1H), 8.67 (s, 1H), 8.03 (s, 1H), 7.64-7.47 (m, 2H), 7.33 (d, J=8.8 Hz, 1H), 6.93 (d, J=8.3 Hz, 1H), 6.56 (dd, J=1.7, 8.8 Hz, 1H), 6.46 (d, J=1.2 Hz, 1H), 5.85 (d, J=8.0 Hz, 1H), 4.29 (br d, J=11.4 Hz, 1H), 4.18 (dd, J=5.1, 8.8 Hz, 1H), 4.11-3.99 (m, 1H), 3.82 (s, 3H), 3.67-3.56 (m, 1H), 3.54 (s, 2H), 3.42-3.35 (m, 1H), 3.30 (s, 3H), 3.17 (dt, J=3.9, 7.4 Hz, 1H), 3.10 (s, 3H), 2.66-2.57 (m, 2H), 2.32-2.21 (m, 1H), 2.19-2.11 (m, 1H), 2.07-1.99 (m, 1H), 1.42-1.31 (m, 1H).

Example S147. Synthesis of rel-3-(6-(((3R,4S)-1-(5-chloro-4-((1-methyl-2-oxoindolin-5-yl)amino)pyrimidin-2-yl)-3-(trifluoromethyl)piperidin-4-yl)amino)-1-methyl-1H-indazol-3-yl)piperidine-2,6-dione, isomer 1 (147)

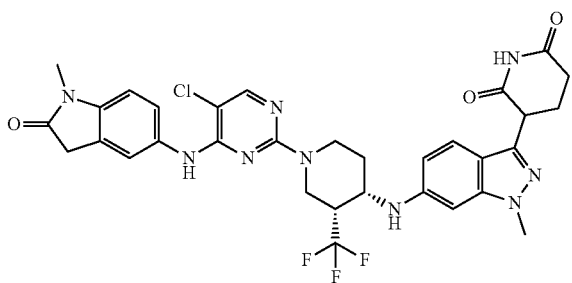 [SMILES: CN1C(=O)Cc2cc(Nc3nc(N4CC[C@H](Nc5ccc6c(C7CCC(=O)NC7=O)nn(C)c6c5)[C@H](C(F)(F)F)C4)ncc3Cl)ccc21]

Step 1: Synthesis of tert-butyl 4-((3-(2,6-bis(benzyloxy)pyridin-3-yl)-1-methyl-1H-indazol-6-yl)amino)-3-(trifluoromethyl)piperidine-1-carboxylate. 3-(2,6-bis(benzyloxy)pyridin-3-yl)-6-bromo-1-methyl-1H-indazole (300 mg, 0.600 mmol), cesium carbonate (391 mg, 1.199 mmol), tert-butyl 4-amino-3-(trifluoromethyl)piperidine-1-carboxylate (241 mg, 0.899 mmol), and XPhos Pd G3 (50.7 mg, 0.060 mmol) were added to a 1 dram vial equipped with a stir bar and purged with nitrogen for 1 min. Next, dioxane (5995 μl) was added, and the reaction mixture was stirred at 70° C. overnight. LCMS indicated significant product formation. The reaction was cooled to RT and poured into a separatory funnel with water, sat. potassium carbonate, and dichloromethane. The aqueous layer was extracted with dichloromethane 3×. The combined organic layers were dried over magnesium sulfate, filtered, and concentrated. The mixture was purified with 0-50% EA/hex and 1% MeOH. Fractions containing clean product were combined and lyophilized to give the title compound tert-butyl 4-((3-(2,6-bis(benzyloxy)pyridin-3-yl)-1-methyl-1H-indazol-6-yl)amino)-3-(trifluoromethyl)piperidine-1-carboxylate (354 mg, 0.515 mmol, 86% yield) as a yellow solid. The enantiomers were separated by chiral SFC using Method isocratic: 25B, where B is 0.1% FA in Methanol; Column: ChiralPack IC with a flow rate: 2 ml/min. This afforded the relative enantiomers rel-tert-butyl (3R,4S)-4-((3-(2,6-dioxopiperidin-3-yl)-1-methyl-1H-indazol-6-yl)amino)-3-(trifluoromethyl)piperidine-1-carboxylate, isomer 1 (90.1 mg, 24.5% yield) and rel-tert-butyl (3R,4S)-4-((3-(2,6-dioxopiperidin-3-yl)-1-methyl-1H-indazol-6-yl)amino)-3-(trifluoromethyl)piperidine-1-carboxylate, isomer 2 (87.4 mg, 24.5% yield). LC MS at t=3.89 (m+1=688.76) showed 688.311. $^1$H NMR (CHLOROFORM-d, 400 MHz) δ 7.8-8.0 (m, 1H), 7.3-7.5 (m, 8H), 6.4-6.6 (m, 1H), 6.3-6.4 (m, 2H), 5.3-5.5 (m, 4H), 4.0-4.1 (m, 3H), 4.0-4.0 (m, 3H), 3.5-3.7 (m, 2H), 2.17 (s, 3H), 2.0-2.1 (m, 1H), 1.6-1.8 (m, 2H), 1.5-1.5 (m, 9H).

Step 2: Synthesis of rel-tert-butyl (3R,4S)-4-((3-(2,6-dioxopiperidin-3-yl)-1-methyl-1H-indazol-6-yl)amino)-3-(trifluoromethyl)piperidine-1-carboxylate, isomer 1. tert-butyl 4-((3-(2,6-bis(benzyloxy)pyridin-3-yl)-1-methyl-1H-indazol-6-yl)amino)-3-(trifluoromethyl)piperidine-1-carboxylate, isomer 1 (90.1 mg, 0.131 mmol) and MeOH (1310 μl) were added to a 40 mL vial equipped with a stir bar. The reaction was purged with nitrogen and then palladium on carbon (27.9 mg, 0.013 mmol) was added. The vial was purged with nitrogen again and then a balloon of hydrogen was added. The vial was heated to 50° C. for 15 hours. The mixture was filtered over celite. The filtrate was concentrated to give the title compound (56 mg, 84% yield). LCMS at t=2.86 and 2.93 (m+1=510.2) showed 510.2. $^1$H NMR (CHLOROFORM-d, 500 MHz) δ 8.0-8.2 (m, 1H), 7.4-7.6 (m, 1H), 6.5-6.6 (m, 1H), 6.3-6.4 (m, 1H), 4.2-4.3 (m, 1H), 4.0-4.2 (m, 2H), 3.9-4.0 (m, 4H), 3.8-3.8 (m, 1H), 3.4-3.5 (m, 1H), 2.9-3.1 (m, 1H), 2.6-2.8 (m, 2H), 2.4-2.6 (m, 1H), 2.3-2.4 (m, 1H), 2.0-2.1 (m, 1H), 1.9-1.9 (m, 1H), 1.7-1.9 (m, 1H), 1.50 (s, 10H).

Step 3: Synthesis of 3-(1-methyl-6-(((3R,4S)-3-(trifluoromethyl)piperidin-4-yl)amino)-1H-indazol-3-yl)piperidine-2,6-dione, isomer 1. A round bottom flask was charged with rel-tert-butyl (3R,4S)-4-((3-(2,6-dioxopiperidin-3-yl)-1-methyl-1H-indazol-6-yl)amino)-3-(trifluoromethyl)piperidine-1-carboxylate (56.0 mg, 0.110 mmol) in DCM (1099 μL). Then HCl (55.0 μL, 0.220 mmol) was added and the solution stirred for 1 hour at room temperature. Next, the solution was concentrated to give the title compound as an HCl salt (49 mg, 0.110 mmol, 100% yield) as a white solid, which was used without further purification in the next step. LCMS at t=141 and 1.53 (m+1=410.2) showed 410.2.

Step 4: Synthesis of rel-3-(6-(((3R,4S)-1-(5-chloro-4-((1-methyl-2-oxoindolin-5-yl)amino)pyrimidin-2-yl)-3-(trifluoromethyl)piperidin-4-yl)amino)-1-methyl-1H-indazol-3-yl)piperidine-2,6-dione, isomer 1. To a stirred solution of 3-(1-methyl-6-(((3R,4S)-3-(trifluoromethyl)piperidin-4-yl)amino)-1H-indazol-3-yl)piperidine-2,6-dione, Isomer 1 (28 mg, 0.075 mmol) and 5-((5-chloro-2-fluoropyrimidin-4-yl)amino)-1-methylindolin-2-one (28.6 mg, 0.075 mmol) in DMSO (1 mL) was added DIPEA (0.053 mL, 0.302 mmol). The reaction mixture was stirred at 80° C. for 4 hours. The reaction mixture was filtered and purified by reverse-phased semi-preparative HPLC (10-100% acetonitrile+0.1% formic acid in water 0.1% formic acid, over 30 min). Fraction containing clean product were combined and lyophilized to give the title compound (3.2 mg, 4.69 μmol, 4.26% yield). ¹H NMR (CHLOROFORM-d, 400 MHz) δ 8.0-8.1 (m, 1H), 7.8-7.9 (m, 1H), 7.4-7.6 (m, 3H), 6.9-7.0 (m, 1H), 6.7-6.8 (m, 1H), 6.5-6.7 (m, 1H), 6.2-6.4 (m, 1H), 4.5-4.6 (m, 1H), 4.1-4.3 (m, 4H), 3.91 (s, 3H), 3.6-3.7 (m, 1H), 3.52 (s, 3H), 3.22 (s, 3H), 2.9-3.1 (m, 1H), 2.6-2.8 (m, 2H), 2.3-2.6 (m, 2H), 2.0-2.2 (m, 1H), 2.0-2.0 (m, 1H), 1.7-1.8 (m, 1H). LC MS at t=2.49 (m+1=682.1) showed 682.3.

Example S148. Synthesis of 3-(6-(((3S,4R)-1-(5-chloro-4-((1-methyl-2-oxoindolin-5-yl)amino)pyrimidin-2-yl)-3-(trifluoromethyl)piperidin-4-yl)amino)-1-methyl-1H-indazol-3-yl)piperidine-2,6-dione (148)

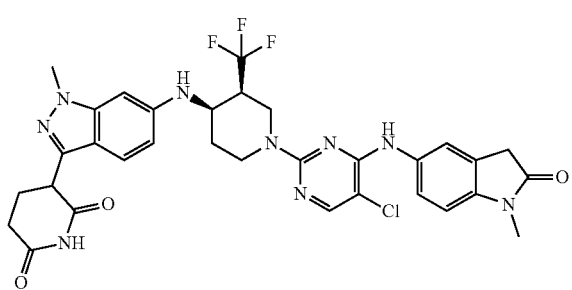 [SMILES: CN1C(=O)Cc2cc(Nc3nc(N4CC[C@@H](Nc5ccc6c(C7CCC(=O)NC7=O)nn(C)c6c5)[C@@H](C(F)(F)F)C4)ncc3Cl)ccc21]

Step 1: Synthesis of 3-(6-(((3S,4R)-1-(5-chloro-4-((1-methyl-2-oxoindolin-5-yl)amino)pyrimidin-2-yl)-3-(trifluoromethyl)piperidin-4-yl)amino)-1-methyl-1H-indazol-3-yl)piperidine-2,6-dione, isomer 2. The title compound was synthesized analogously to Example S147 using the second eluting isomer from Example S147, Step 1. To a stirred solution of 3-(1-methyl-6-(((3S,4R)-3-(trifluoromethyl)piperidin-4-yl)amino)-1H-indazol-3-yl)piperidine-2,6-dione, Isomer 2 (56 mg, 0.137 mmol) and 5-((5-chloro-2-fluoropyrimidin-4-yl)amino)-1-methylindolin-2-one (40.0 mg, 0.137 mmol) in DMSO (1 mL) was added N-ethyl-N-isopropylpropan-2-amine (0.096 mL, 0.547 mmol). The reaction stirred at 80° C. for 4 hours. The reaction mixture was filtered and purified by reverse-phased semi-preparative HPLC (10-100% acetonitrile+0.1% formic acid in water 0.1% formic acid, over 30 min). Fractions containing clean product were combined and lyophilized to give the title compound (21.7 mg, 0.031 mmol, 23.03% yield). ¹H NMR (CDCl₃, 400 MHz) δ 8.0-8.1 (m, 1H), 7.8-7.9 (m, 1H), 7.4-7.6 (m, 3H), 6.9-7.0 (m, 1H), 6.7-6.8 (m, 1H), 6.5-6.7 (m, 1H), 6.2-6.4 (m, 1H), 4.5-4.6 (m, 1H), 4.1-4.3 (m, 4H), 3.91 (s, 3H), 3.6-3.7 (m, 1H), 3.52 (s, 3H), 3.22 (s, 3H), 2.9-3.1 (m, 1H), 2.6-2.8 (m, 2H), 2.3-2.6 (m, 2H), 2.0-2.2 (m, 1H), 2.0-2.0 (m, 1H), 1.7-1.8 (m, 1H). LCMS [M+1=682.1] showed 682.3.

Example S149. Synthesis of 3-(6-((4R,5S)-4-((5-chloro-4-((1-methyl-2-oxoindolin-5-yl)amino)pyrimidin-2-yl)(methyl)amino)-5-methyl-2-oxopiperidin-1-yl)-1-methyl-1H-indazol-3-yl)piperidine-2,6-dione (149)

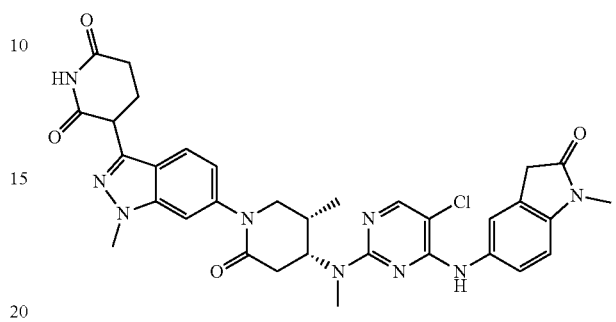

Step 1: Synthesis of tert-butyl (S)-(3-(2,2-dimethyl-4,6-dioxo-1,3-dioxan-5-yl)-2-methyl-3-oxopropyl) carbamate. To a stirred solution of (S)-3-((tert-butoxycarbonyl)amino)-2-methylpropanoic acid (10.00 g, 46.7 mmol) and 2,2-dimethyl-1,3-dioxane-4,6-dione (7.41 g, 51.4 mmol) in DCM (160 mL), EDC (13.44 g, 70.1 mmol) and DMAP (8.57 g, 70.1 mmol) were added. The reaction mixture was stirred at 25° C. for 16 h. The reaction mixture was diluted with DCM (300 mL), washed with 10% aqueous sodium bisulfate solution (3×100 mL), dried over anhydrous sodium sulfate, filtered, and concentrated under reduced pressure to afford the crude title compound (16.2 g, 27.5 mmol, 59% yield) as a yellow solid. The crude product was used in the next step without further purification.

Step 2: Synthesis of tert-butyl (S)-5-methyl-2,4-dioxopiperidine-1-carboxylate. A solution of tert-butyl (S)-(3-(2,2-dimethyl-4,6-dioxo-1,3-dioxan-5-yl)-2-methyl-3-oxopropyl) carbamate (16.2 g, 27.5 mmol) in ethyl acetate (150 mL) was refluxed at 80° C. and stirred for 8 h. The reaction mixture was cooled to room temperature and concentrated under reduced pressure to afford the crude compound. The crude material was purified by flash column chromatography on silica with 50% ethyl acetate/pet ether to afford the title compound (6.92 g, 27.4 mmol, quant. yield) as a white solid.

Step 3: Synthesis of (S)-5-methylpiperidine-2,4-dione. Trifluoroacetic acid (21.1 mL, 274 mmol) was added dropwise at 0° C. to a stirred solution of tert-butyl (S)-5-methyl-2,4-dioxopiperidine-1-carboxylate (6.92 g, 27.4 mmol) in DCM (100 mL). The resulting solution was warmed up to 25° C. and stirred for 16 h. The reaction mixture was concentrated under reduced pressure, dissolved in acetonitrile (100 mL), and basified by solid sodium bicarbonate until the pH of the solution was greater than 8. The mixture was stirred for another hour, dried over anhydrous sodium sulfate, filtered, and concentrated under reduced pressure to afford the crude title compound (8.5 g, 26.9 mmol, 98% yield) as a yellow oil. The crude product was used in the next step without further purification.

Step 4: Synthesis of (S)-4-(benzyl(methyl)amino)-5-methyl-5,6-dihydropyridin-2(1H)-one. To a stirred solution of (S)-5-methylpiperidine-2,4-dione (8.5 g, 26.9 mmol) and N-methyl-1-phenylmethanamine (6.52 g, 53.8 mmol) in MeOH (150 mL), AcOH (2.3 mL, 40.4 mmol) was added. The reaction mixture was stirred at 60° C. for 16 h. The reaction mixture was concentrated under reduced pressure to afford the title compound, which was used without further purification (20 g, 26.4 mmol, 98% yield).

Step 5: Synthesis of (4R,5S)-5-methyl-4-(methylamino) piperidin-2-one. To a solution of (S)-4-(benzyl(methyl) amino)-5-methyl-5,6-dihydropyridin-2(1H)-one (20 g, 26.4 mmol) in methanol (150 mL), platinum (IV) oxide (3.0 g) was added. The reaction mixture was stirred under 7 atm of hydrogenation pressure at 25° C. for 72 h. The reaction mixture was filtered through a pad of celite and the celite pad was washed with methanol (3×100 mL). The filtrate was concentrated under reduced pressure. This material was purified by preparative HPLC to afford the title compound (3.8 g, 26.3 mmol, 99% yield) as a white solid. Prep-HPLC method: Rt 5.4 min; Column: XSelect C18 (300×30) mm, 10.0 µm; 0.1% TFA in water/acetonitrile; Flow Rate: 20.0 mL/min.

Step 6: Synthesis of tert-butyl methyl((4R,5S)-5-methyl-2-oxopiperidin-4-yl) carbamate. To a stirred solution of (4R,5S)-5-methyl-4-(methylamino) piperidin-2-one (3.8 g, 26.3 mmol) in THF (38 mL), Et$_3$N (9.2 mL, 65.8 mmol) and boc-anhydride (6.32 g, 28.9 mmol) were added sequentially. The reaction mixture was stirred at 25° C. for 16 h. The reaction mixture was diluted with ethyl acetate (30 mL) and quenched with water (20 mL). The layers were separated, and the aqueous layer was extracted with ethyl acetate (3×30 mL). The combined organic layers were washed with water (20 mL) and brine (20 mL), dried over anhydrous sodium sulfate, filtered, and concentrated under reduced pressure to afford the title compound (1.32 g, 4.15 mmol, 16% yield), which was used without further purification.

Step 7: Synthesis of tert-butyl ((4R,5S)-1-(3-(2,6-bis(benzyloxy)pyridin-3-yl)-1-methyl-1H-indazol-6-yl)-5-methyl-2-oxopiperidin-4-yl)(methyl)carbamate. A stirred solution of 3-(2,6-bis(benzyloxy)pyridin-3-yl)-6-bromo-1-methyl-1H-indazole (1.32 g, 2.64 mmol) and tert-butyl methyl((4R,5S)-5-methyl-2-oxopiperidin-4-yl) carbamate (0.7 g, 2.20 mmol) in toluene (25 mL) was degassed with nitrogen for 5 min. Then cesium carbonate (2.87 g, 8.80 mmol), Pd$_2$(dba)$_3$ (0.20 g, 0.22 mmol) and xantphos (0.51 g, 0.88 mmol) were added. The reaction mixture was heated to 120° C. and stirred for 16 h. The reaction mixture was cooled to room temperature, diluted with ethyl acetate (50 mL) and quenched with water (50 mL). The layers were separated, and the aqueous layer was extracted with ethyl acetate (3×50 mL). The combined organic layers were washed with water (3×50 mL) and brine (50 mL), dried over anhydrous sodium sulfate, filtered, and concentrated under reduced pressure to afford the crude compound which was purified by preparative HPLC to afford the title compound (0.86 g, 1.23 mmol, 56% yield) as a light-yellow solid. Prep-HPLC method: Rt 7.4 min; Column: XSelect C18 (300×30) mm, 10.0 µm; 0.1% TFA in water/acetonitrile; Flow Rate: 20.0 mL/min.

Step 8: Synthesis of tert-butyl ((4R,5S)-1-(3-(2,6-dioxopiperidin-3-yl)-1-methyl-1H-indazol-6-yl)-5-methyl-2-oxopiperidin-4-yl)(methyl)carbamate. To a stirred solution of tert-butyl ((4R,5S)-1-(3-(2,6-bis(benzyloxy)pyridin-3-yl)-1-methyl-1H-indazol-6-yl)-5-methyl-2-oxopiperidin-4-yl)(methyl)carbamate (860 mg, 1.23 mmol) and trifluoroacetic acid (0.10 mL, 1.23 mmol) in ethanol (7.5 mL) and THF (7.5 mL) was added 20% palladium hydroxide on carbon (400 mg) under nitrogen. The reaction mixture was stirred under 4 atm of hydrogenation pressure at 50° C. for 4 h. The reaction mixture was filtered through a pad of celite and the celite pad was washed with ethanol/THF (1:1, 200 mL). The filtrate was concentrated under reduced pressure to afford the title compound (510 mg, 0.70 mmol, 57% yield) as a crude product. The crude product was used in the next step without further purification.

Step 9: Synthesis of 3-(6-(((4R,5S)-4-((5-chloro-4-((1-methyl-2-oxoindolin-5-yl)amino) pyrimidin-2-yl)(methyl) amino)-5-methyl-2-oxopiperidin-1-yl)-1-methyl-1H-indazol-3-yl) piperidine-2,6-dione. The title compound was synthesized according to General Procedures 5 and 6 using tert-butyl ((4R,5S)-1-(3-(2,6-dioxopiperidin-3-yl)-1-methyl-1H-indazol-6-yl)-5-methyl-2-oxopiperidin-4-yl) (methyl)carbamate (400 mg, 0.55 mmol) as the starting material. LCMS [M+H]$^+$ found 656.2; $^1$H NMR (400 MHz, DMSO-d$_6$): δ 10.92 (s, 1H), 8.67 (s, 1H), 8.05 (s, 1H), 7.70 (d, J=8.40 Hz, 1H), 7.58-7.52 (m, 3H), 6.99-6.95 (m, 2H), 5.05 (brs, 1H), 4.41-4.37 (m, 1H), 3.99 (s, 3H), 3.70-3.65 (m, 1H), 3.57 (s, 3H), 3.33-3.25 (m, 3H), 3.08 (s, 3H), 2.83-2.63 (m, 5H), 2.40-2.34 (m, 1H), 2.21-2.17 (m, 1H), 0.99 (d, J=6.80 Hz, 3H).

Example S150. Synthesis of 3-(6-(((2R,4S)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2, 6-dione (150)

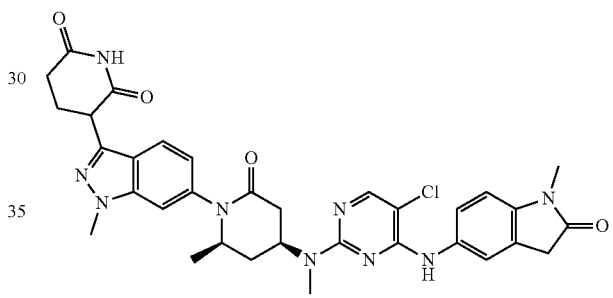

Step 1: Synthesis of tert-butyl methyl((4R,5S)-5-methyl-2-oxopiperidin-4-yl) carbamate. The title compound was synthesized according to Steps 1-6, Example 5149 using (R)-3-((tert-butoxycarbonyl)amino) butanoic acid as the original starting material.

Step 2: Synthesis of tert-butyl ((2R,4S)-1-(3-(2,6-bis(benzyloxy)pyridin-3-yl)-1-methyl-1H-indazol-6-yl)-2-methyl-6-oxopiperidin-4-yl)(methyl)carbamate. To a stirred solution of 3-(2,6-bis(benzyloxy)pyridin-3-yl)-6-bromo-1-methyl-1H-indazole (4.13 g, 8.25 mmol) and tert-butyl methyl((4R,5S)-5-methyl-2-oxopiperidin-4-yl) carbamate (2.0 g, 8.25 mmol) in dioxane (40 mL), potassium phosphate (5.26 g, 49.5 mmol), CuI (4.72 g, 24.8 mmol) and DMEDA (4.37 g, 49.5 mmol) were added. The reaction mixture was heated to 120° C. and stirred for 48 h. The reaction mixture was cooled down to room temperature, quenched with saturated aqueous ammonium chloride solution (100 mL) and extracted with ethyl acetate (3×200 mL). The combined organic layers were washed with water (3×100 mL) and brine (100 mL), dried over anhydrous sodium sulfate, filtered, and concentrated under reduced pressure to afford the crude compound which was purified by preparative HPLC to afford the title compound (0.41 g, 0.62 mmol, 8% yield, peak 1) as an off-white solid. Prep-HPLC method: Rt 15.0 min and 15.4 min; Column: YMC C18 Phenyl (250×21) mm, 5.0 µm; 0.1% TFA in water/acetonitrile; Flow Rate: 15.0 mL/min.

Step 3: Synthesis of tert-butyl ((2R,4S)-1-(3-(2,6-di-oxopiperidin-3-yl)-1-methyl-1H-indazol-6-yl)-2-methyl-6-oxopiperidin-4-yl)(methyl)carbamate. To a stirred solution of tert-butyl ((2R,4S)-1-(3-(2,6-bis(benzyloxy)pyridin-3-yl)-1-methyl-1H-indazol-6-yl)-2-methyl-6-oxopiperidin-4-yl)(methyl)carbamate (410 mg, 0.62 mmol, peak 1) and trifluoroacetic acid (0.05 mL, 0.62 mmol) in ethanol (3 mL) and THF (3 mL) was added 20% palladium hydroxide on carbon (250 mg) under nitrogen. The reaction mixture was stirred under 4 atm of hydrogenation pressure at 50° C. for 4 h. The reaction mixture was filtered through a pad of celite and the celite pad was washed with ethanol/THF (1:1, 150 mL). The filtrate was concentrated under reduced pressure to afford the title compound (300 mg, 0.61 mmol, 99% yield) as a crude product. The crude product was used in the next step without further purification.

Step 4: Synthesis of 3-(6-((2R,4S)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione. The title compound was synthesized according to General Procedures 5 and 6 using tert-butyl ((2R,4S)-1-(3-(2,6-dioxopiperidin-3-yl)-1-methyl-1H-indazol-6-yl)-2-methyl-6-oxopiperidin-4-yl)(methyl)carbamate (300 mg, 0.61 mmol) as the starting material. LCMS [M+H]$^+$ found 656.2; $^1$H NMR (400 MHz, DMSO-d$_6$): δ 10.92 (s, 1H), 8.68 (s, 1H), 8.05 (s, 1H), 7.70 (d, J=8.80 Hz, 1H), 7.60 (s, 1H), 7.51-7.46 (m, 2H), 6.93 (d, J=8.40 Hz, 1H), 6.85 (s, 1H), 5.00 (brs, 1H), 4.42-4.38 (m, 1H), 4.05-4.00 (m, 1H), 3.99 (s, 3H), 3.54-3.52 (m, 2H), 3.09 (s, 3H), 2.99 (s, 3H), 2.66-2.64 (m, 3H), 2.45-2.41 (m, 2H), 2.22-2.08 (m, 2H), 1.98-1.95 (m, 1H), 0.93 (d, J=6.00 Hz, 3H).

Example S151. Synthesis of 3-(6-((2R,4R)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione (151)

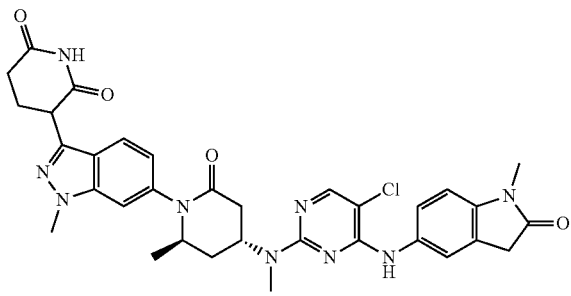

Step 1: Synthesis of tert-butyl ((2R,4R)-1-(3-(2,6-di-oxopiperidin-3-yl)-1-methyl-1H-indazol-6-yl)-2-methyl-6-oxopiperidin-4-yl)(methyl)carbamate. To a stirred solution of tert-butyl ((2R,4R)-1-(3-(2,6-bis(benzyloxy)pyridin-3-yl)-1-methyl-1H-indazol-6-yl)-2-methyl-6-oxopiperidin-4-yl)(methyl)carbamate (170 mg, 0.26 mmol, peak 2 from Example S150, Step 2) and trifluoroacetic acid (0.02 mL, 0.26 mmol) in ethanol (1 mL) and THF (1 mL) was added 20% palladium hydroxide on carbon (100 mg) under nitrogen. The reaction mixture was stirred under 4 atm of hydrogenation pressure at 50° C. for 4 h. The reaction mixture was filtered through a pad of celite and the celite pad was washed with ethanol/THF (1:1, 50 mL). The filtrate was concentrated under reduced pressure to afford the title compound (135 mg, 0.26 mmol, 99% yield) as a crude product. The crude product was used in the next step without further purification.

Step 2: Synthesis of 3-(6-((2R,4R)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione. The title compound was synthesized according to General Procedures 5 and 6 using tert-butyl ((2R,4R)-1-(3-(2,6-dioxopiperidin-3-yl)-1-methyl-1H-indazol-6-yl)-2-methyl-6-oxopiperidin-4-yl)(methyl)carbamate (135 mg, 0.26 mmol) as the starting material. LCMS [M+H]$^+$ found 656.2; $^1$H NMR (400 MHz, DMSO-d$_6$): δ 10.91 (s, 1H), 8.74 (s, 1H), 8.05 (s, 1H), 7.71 (d, J=8.80 Hz, 1H), 7.56 (s, 1H), 7.46 (s, 2H), 6.97 (d, J=8.40 Hz, 1H), 6.89 (d, J=7.60 Hz, 1H), 5.14 (brs, 1H), 4.42-4.38 (m, 1H), 4.13-4.10 (m, 1H), 4.01 (s, 3H), 3.57 (s, 2H), 3.14 (s, 3H), 2.98 (s, 3H), 2.61-2.60 (m, 4H), 2.44-2.33 (m, 2H), 2.23-2.17 (m, 1H), 1.81-1.79 (m, 1H), 0.98 (s, 3H).

Example S152. Synthesis of 3-(6-((2S,4R)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione (152)

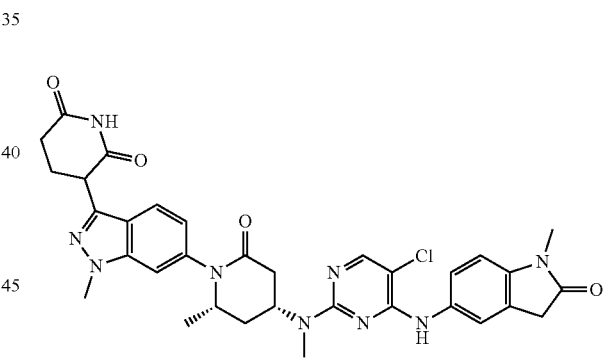

Step 1: Synthesis of 3-(6-((2S,4R)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione. The title compound was synthesized analogously to Example S150 using (R)-3-((tert-butoxycarbonyl)amino) butanoic acid (10.00 g, 49.2 mmol) as the original starting material. LCMS [M+H]$^+$ found 656.2; $^1$H NMR (400 MHz, DMSO-d$_6$): δ 10.91 (s, 1H), 8.67 (s, 1H), 8.05 (s, 1H), 7.71-7.69 (m, 1H), 7.61 (s, 1H), 7.51-7.47 (m, 2H), 6.95-6.86 (m, 2H), 5.11-5.10 (m, 1H), 4.41-4.38 (m, 1H), 3.99 (s, 3H), 3.55-3.52 (m, 2H), 3.13 (s, 3H), 3.03 (s, 3H), 2.80-2.60 (m, 3H), 2.49-2.38 (m, 3H), 2.32-2.10 (m, 2H), 2.02-1.92 (m, 1H), 0.93 (d, J=6.4 Hz, 3H).

Example S153. Synthesis of 3-(6-((2S,4S)-4-((5-chloro-4-((1-methyl-2-oxoindolin-5-yl)amino)pyrimidin-2-yl)(methyl)amino)-2-methyl-6-oxopiperidin-1-yl)-1-methyl-1H-indazol-3-yl) piperidine-2,6-dione (153)

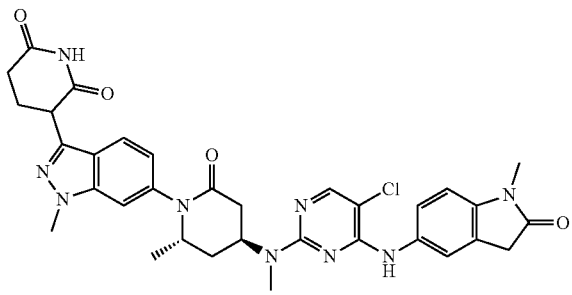

Step 1: Synthesis of 3-(6-((2S,4S)-4-((5-chloro-4-((1-methyl-2-oxoindolin-5-yl)amino) pyrimidin-2-yl)(methyl)amino)-2-methyl-6-oxopiperidin-1-yl)-1-methyl-1H-indazol-3-yl) piperidine-2,6-dione. The title compound was synthesized analogously to Example S151. LCMS [M+H]+ found 656.2; 1H NMR (400 MHz, DMSO-d6): δ 10.91 (s, 1H), 8.72-8.68 (m, 1H), 8.05 (d, J=2.0 Hz, 1H), 7.71 (dd, J=4.40, 8.60 Hz, 1H), 7.60 (s, 1H), 7.56-7.46 (m, 2H), 6.98-6.88 (m, 2H), 5.21-5.10 (m, 1H), 4.39-4.35 (m, 1H), 4.19-4.11 (m, 1H), 4.00 (d, J=4.80 Hz, 3H), 3.55-3.52 (m, 2H), 3.13 (d, J=17.60 Hz, 3H), 3.03 (d, J=4.00 Hz, 3H), 2.80-2.67 (m, 2H), 2.62-2.60 (m, 1H), 2.47-2.38 (m, 2H), 2.30-2.28 (m, 2H), 2.05-2.00 (m, 1H), 1.02 (d, J=6.40 Hz, 3H).

Example S154. Synthesis of 3-(6-(((3R,4R)-1-(5-chloro-4-((1-methyl-2-oxoindolin-5-yl)amino)pyrimidin-2-yl)-3-methoxypiperidin-4-yl)amino)-1-methyl-1H-indazol-3-yl)-3-methylpiperidine-2,6-dione (154)

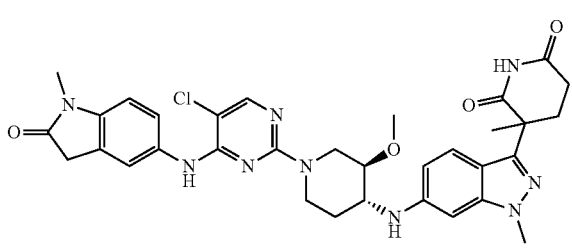 [SMILES: CO[C@@H]1CN(c2ncc(Cl)c(Nc3ccc4c(c3)CC(=O)N4C)n2)CC[C@H]1Nc1ccc2c(C3(C)CCC(=O)NC3=O)nn(C)c2c1]

Step 1: Synthesis of tert-butyl (3R,4R)-4-((3-(5-(tert-butoxy)-2-cyano-5-oxopentan-2-yl)-1-methyl-1H-indazol-6-yl)amino)-3-methoxypiperidine-1-carboxylate. A stirred solution of tert-butyl 4-(6-bromo-1-methyl-1H-indazol-3-yl)-4-cyanopentanoate (300 mg, 0.77 mmol) and tert-butyl (3R,4R)-4-amino-3-methoxypiperidine-1-carboxylate (176 mg, 0.77 mmol) in toluene (10 mL) was degassed for 5 min. Then NaOtBu (110 mg, 1.15 mmol), Pd2dba3 (70.0 mg, 0.08 mmol) and BINAP (47.6 mg, 0.08 mmol) were added at 25° C. The reaction mixture was heated to 100° C. and stirred for 6 h. The reaction mixture was quenched with water (20 mL) and diluted with ethyl acetate (50 mL). The layers were separated, and the aqueous layer was extracted with ethyl acetate (2×50 mL). The combined organic layers were dried over anhydrous sodium sulfate, filtered, and concentrated under reduced pressure to afford the crude product. The crude residue was purified by flash column chromatography on silica with 100% ethyl acetate/pet ether to afford the title compound (300 mg, 0.41 mmol, 54% yield) as an off-white solid.

Step 2: Synthesis of tert-butyl (3R,4R)-3-methoxy-4-((1-methyl-3-(3-methyl-2,6-dioxopiperidin-3-yl)-1H-indazol-6-yl)amino) piperidine-1-carboxylate. To a stirred solution of tert-butyl (3R,4R)-4-((3-(5-(tert-butoxy)-2-cyano-5-oxopentan-2-yl)-1-methyl-1H-indazol-6-yl)amino)-3-methoxypiperidine-1-carboxylate (300 mg, 0.55 mmol) in acetic acid (5 mL), sulfuric acid (0.03 mL, 0.55 mmol) was added. The reaction mixture was heated to 60° C. and stirred for 6 h. The reaction mixture was concentrated under reduced pressure and the resulting crude mixture was dissolved in acetonitrile (5 mL), followed by the addition of DIPEA (0.27 mL, 1.56 mmol) and BOC-anhydride (0.15 mL, 0.62 mmol). The reaction mixture was stirred at 25° C. for 16 h. The reaction mixture was quenched with water (20 mL) and diluted with ethyl acetate (30 mL). The layers were separated, and the aqueous layer was extracted with ethyl acetate (2×30 mL). The combined organic layers were dried over anhydrous sodium sulfate, filtered, and concentrated under reduced pressure to afford the crude product. The crude residue was purified by flash column chromatography on silica with 100% ethyl acetate/pet ether to afford the title compound (180 mg, 0.27 mmol, 49% yield over 2 steps) as an off-white solid.

Step 3: Synthesis of 3-(6-(((3R,4R)-3-methoxypiperidin-4-yl)amino)-1-methyl-1H-indazol-3-yl)-3-methylpiperidine-2,6-dione. The title compound was synthesized according to General Procedure 5 using tert-butyl (3R,4R)-3-methoxy-4-((1-methyl-3-(3-methyl-2,6-dioxopiperidin-3-yl)-1H-indazol-6-yl)amino) piperidine-1-carboxylate (180 mg, 0.37 mmol) as the starting material.

Step 4: Synthesis of 3-(6-(((3R,4R)-1-(5-chloro-4-((1-methyl-2-oxoindolin-5-yl)amino) pyrimidin-2-yl)-3-methoxypiperidin-4-yl)amino)-1-methyl-1H-indazol-3-yl)-3-methylpiperidine-2,6-dione. The title compound was synthesized according to General Procedure 6 using 3-(6-(((3R,4R)-3-methoxypiperidin-4-yl)amino)-1-methyl-1H-indazol-3-yl)-3-methylpiperidine-2,6-dione (100 mg, 0.20 mmol) and 5-((5-chloro-2-fluoropyrimidin-4-yl)amino)-1-methylindolin-2-one (59 mg, 0.20 mmol) as starting materials. LCMS [M+H]+ found 658.3; 1H NMR (400 MHz, DMSO-d6): δ 10.74 (s, 1H), 9.00 (s, 1H), 8.08 (s, 1H), 7.53-7.44 (m, 3H), 6.96-6.94 (m, 1H), 6.58-6.56 (m, 1H), 6.49-6.47 (m, 1H), 6.13-5.61 (m, 1H), 4.20 (br d, J=12.5 Hz, 2H), 4.02-3.91 (m, 2H), 3.81 (s, 3H), 3.65-3.59 (m, 1H), 3.47-3.34 (m, 2H), 3.29 (s, 3H), 3.23-3.18 (m, 1H), 3.11 (s, 3H), 2.48-2.45 (m, 1H), 2.42-2.39 (m, 1H), 2.13-1.99 (m, 2H), 1.59 (s, 3H), 1.44-1.31 (m, 1H).

Example S155. Synthesis of 2-((3R,4R)-3-methoxy-4-((1-methyl-3-(3-methyl-2,6-dioxopiperidin-3-yl)-1H-indazol-6-yl)amino) piperidin-1-yl)-4-((1-methyl-2-oxoindolin-5-yl)amino) pyrimidine-5-carbonitrile (155)

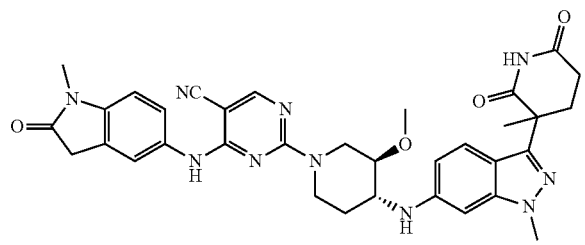 [SMILES: CO[C@@H]1CN(c2ncc(C#N)c(Nc3ccc4c(c3)CC(=O)N4C)n2)CC[C@H]1Nc1ccc2c(C3(C)CCC(=O)NC3=O)nn(C)c2c1]

Step 1: Synthesis of 2-((3R,4R)-3-methoxy-4-((1-methyl-3-(3-methyl-2,6-dioxopiperidin-3-yl)-1H-indazol-6-yl) amino) piperidin-1-yl)-4-((1-methyl-2-oxoindolin-5-yl) amino) pyrimidine-5-carbonitrile. The title compound was synthesized according to General Procedure 6 using 3-(6-(((3R,4R)-3-methoxypiperidin-4-yl)amino)-1-methyl-1H-indazol-3-yl)-3-methylpiperidine-2,6-dione (150 mg, 0.30 mmol) and 2-fluoro-4-((1-methyl-2-oxoindolin-5-yl)amino) pyrimidine-5-carbonitrile (103 mg, 0.30 mmol) as starting materials. LCMS [M+H]$^+$ found 649.2; $^1$H NMR (400 MHz, DMSO-d$_6$): δ 10.77 (s, 1H), 9.30 (s, 1H), 8.40 (br s, 1H), 7.48-7.42 (m, 3H), 6.96-6.91 (m, 1H), 6.58 (br d, J=8.0 Hz, 1H), 6.46 (s, 1H), 4.14-4.04 (m, 1H), 3.82-3.77 (m, 3H), 3.67-3.59 (m, 2H), 3.58-3.49 (m, 5H), 3.23 (br s, 2H), 3.10 (s, 3H), 2.58-2.53 (m, 2H), 2.48-2.45 (m, 1H), 2.43-2.37 (m, 1H), 2.13-1.98 (m, 2H), 1.59 (s, 3H), 1.45-1.37 (m, 1H).

Example S156. Synthesis of 1-(6-(((3R,4R)-1-(5-chloro-4-((1-methyl-2-oxoindolin-5-yl)amino) pyrimidin-2-yl)-3-methoxypiperidin-4-yl)amino)-1-methyl-1H-indazol-3-yl) dihydropyrimidine-2,4(1H,3H)-dione (156)

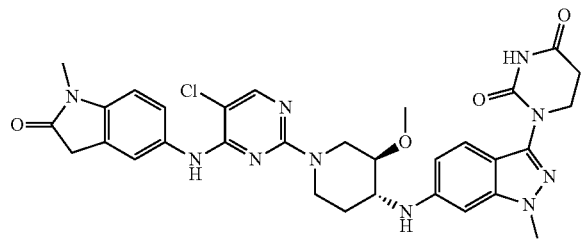 [SMILES: CO[C@@H]1CN(c2ncc(Cl)c(Nc3ccc4c(c3)CC(=O)N4C)n2)CC[C@H]1Nc1ccc2c(N3CCC(=O)NC3=O)nn(C)c2c1]

Step 1: Synthesis of tert-butyl (3R,4R)-3-methoxy-4-((3-(3-(4-methoxybenzyl)-2,4-dioxotetrahydropyrimidin-1(2H)-yl)-1-methyl-1H-indazol-6-yl)amino) piperidine-1-carboxylate. A stirred solution of 1-(6-bromo-1-methyl-1H-indazol-3-yl)-3-(4-methoxybenzyl) dihydropyrimidine-2,4 (1H,3H)-dione (1.00 g, 2.26 mmol) and tert-butyl (3R,4R)-4-amino-3-methoxypiperidine-1-carboxylate (0.52 g, 2.26 mmol) in toluene (3 mL) was degassed for 10 min. Then Cs$_2$CO$_3$ (1.47 g, 4.51 mmol) and Pd-Ruphos-G3 (0.19 g, 0.23 mmol) were added at 25° C. The reaction mixture was heated to 120° C. and stirred for 12 h. The reaction mixture was poured into water (150 mL) and diluted with ethyl acetate (150 mL). The layers were separated, and the aqueous layer was extracted with ethyl acetate (3×150 mL). The combined organic layers were washed with brine (150 mL), dried over anhydrous sodium sulfate, filtered, and concentrated under reduced pressure to afford the crude product. The crude residue was purified by flash column chromatography on silica with 70% ethyl acetate/pet ether to afford the title compound (0.80 g, 1.27 mmol, 56% yield) as a pale-yellow solid.

Step 2: Synthesis of 1-(6-(((3R,4R)-3-methoxypiperidin-4-yl)amino)-1-methyl-1H-indazol-3-yl)dihydropyrimidine-2,4(1H,3H)-dione. The title compound was synthesized according to General Procedure 5 using tert-butyl (3R,4R)-3-methoxy-4-((3-(3-(4-methoxybenzyl)-2,4-dioxotetrahydropyrimidin-1(2H)-yl)-1-methyl-1H-indazol-6-yl)amino) piperidine-1-carboxylate (800 mg, 1.27 mmol) as the starting material.

Step 3: Synthesis of 1-(6-(((3R,4R)-1-(5-chloro-4-((1-methyl-2-oxoindolin-5-yl)amino) pyrimidin-2-yl)-3-methoxypiperidin-4-yl)amino)-1-methyl-1H-indazol-3-yl) dihydropyrimidine-2,4(1H,3H)-dione. The title compound was synthesized according to General Procedure 6 using 3-(6-(((3R,4R)-3-methoxypiperidin-4-yl)amino)-1-methyl-1H-indazol-3-yl)-3-methylpiperidine-2,6-dione (150 mg, 0.30 mmol) and 2-fluoro-4-((1-methyl-2-oxoindolin-5-yl)amino)pyrimidine-5-carbonitrile (103 mg, 0.30 mmol) as starting materials. LCMS [M+H]$^+$ found 634.2; $^1$H NMR (400 MHz, DMSO-d$_6$): δ 10.45 (s, 1H), 8.68 (s, 1H), 8.02 (s, 1H), 7.54-7.50 (m, 2H), 7.28 (d, J=8.80 Hz, 1H), 6.93 (d, J=8.40 Hz, 1H), 6.55 (dd, J=1.60, 8.80 Hz, 1H), 6.45 (d, J=1.20 Hz, 1H), 5.90 (d, J=8.00 Hz, 1H), 4.32 (d, J=10.80 Hz, 1H), 4.07 (brs, 1H), 3.86 (t, J=6.80 Hz, 2H), 3.81 (s, 3H), 3.63-3.59 (m, 2H), 3.38-3.26 (m, 5H) 3.18-3.13 (m, 2H), 3.10 (s, 3H), 2.73 (t, J=6.80 Hz, 2H), 2.07-2.02 (m, 1H), 1.35 (d, J=9.60 Hz, 1H).

Example S157. Synthesis of 2-((3R,4R)-4-((3-(2,4-dioxotetrahydropyrimidin-1(2H)-yl)-1-methyl-1H-indazol-6-yl)amino)-3-methoxypiperidin-1-yl)-4-((1-methyl-2-oxoindolin-5-yl)amino) pyrimidine-5-carbonitrile (157)

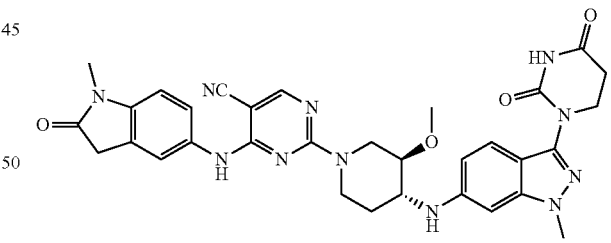

Step 1: Synthesis of 4-((1-methyl-2-oxoindolin-5-yl)amino)-2-(methylthio) pyrimidine-5-carbonitrile. To a stirred solution of 5-amino-1-methylindolin-2-one (1.0 g, 6.17 mmol) and 4-chloro-2-(methylthio)pyrimidine-5-carbonitrile (1.15 g, 6.17 mmol) in THF (10 mL), DIPEA (2.7 mL, 15.4 mmol) was added. The reaction mixture was stirred at 25° C. for 16 h. The reaction mixture was filtered, and the precipitated solids were washed with water (4×50 mL) to afford the title compound (1.77 g, 5.58 mmol, 91% yield) as a yellow solid.

Step 2: Synthesis of 4-((1-methyl-2-oxoindolin-5-yl)amino)-2-(methylsulfonyl)pyrimidine-5-carbonitrile. To a stirred solution of 4-((1-methyl-2-oxoindolin-5-yl)amino)-

2-(methylthio)pyrimidine-5-carbonitrile (750 mg, 2.41 mmol) in DCM (25 mL), mCPBA (1.25 g, 7.23 mmol) was added. The reaction mixture was stirred at 25° C. for 3 h. The reaction mixture was quenched with saturated aqueous sodium bicarbonate solution (25 mL) and diluted with ethyl acetate (50 mL). The layers were separated, and the aqueous layer was extracted with ethyl acetate (3×50 mL). The combined organic layers were washed with brine (50 mL), dried over anhydrous sodium sulfate, filtered, and concentrated under reduced pressure to afford the title compound (715 mg, 1.57 mmol, 65% yield) as a yellow solid.

Step 3: Synthesis of 2-((3R,4R)-4-((3-(2,4-dioxotetrahydropyrimidin-1(2H)-yl)-1-methyl-1H-indazol-6-yl)amino)-3-methoxypiperidin-1-yl)-4-((1-methyl-2-oxoindolin-5-yl)amino) pyrimidine-5-carbonitrile. The title compound was synthesized according to General Procedure 6 using 3-(6-(((3R,4R)-3-methoxypiperidin-4-yl)amino)-1-methyl-1H-indazol-3-yl)-3-methylpiperidine-2,6-dione (100 mg, 0.26 mmol) and 4-((1-methyl-2-oxoindolin-5-yl)amino)-2-(methylsulfonyl)pyrimidine-5-carbonitrile (103 mg, 0.26 mmol) as starting materials. LCMS [M+H]$^+$ found 636.2; $^1$H NMR (400 MHz, DMSO-d$_6$): δ 10.46 (s, 1H), 9.29 (s, 1H), 8.40 (s, 1H), 7.48-7.43 (m, 2H), 7.30 (d, J=8.80 Hz, 1H), 6.93 (d, J=8.80 Hz, 1H), 6.57 (d, J=8.80 Hz, 1H), 6.45 (s, 1H), 5.94 (s, 1H), 4.30-4.12 (m, 2H), 3.86 (t, J=6.80 Hz, 2H), 3.81 (s, 3H), 3.65 (brs, 2H), 3.54 (s, 3H), 3.40-3.30 (m, 2H), 3.25-3.12 (m, 2H), 3.10 (s, 3H), 2.73 (t, J=6.40 Hz, 2H), 2.08 (brs, 1H), 1.41 (brs, 1H).

Example S158. Synthesis of 1-(6-(((3R,4R)-1-(5-chloro-4-fluoro-6-((1-methyl-2-oxoindolin-5-yl)amino)pyrimidin-2-yl)-3-methoxypiperidin-4-yl)amino)-1-methyl-1H-indazol-3-yl) dihydropyrimidine-2,4(1H,3H)-dione (158)

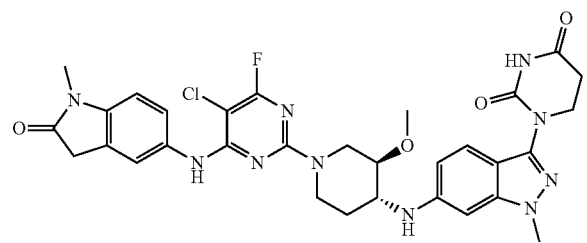 [SMILES: CO[C@@H]1CN(c2nc(F)c(Cl)c(Nc3ccc4c(c3)CC(=O)N4C)n2)CC[C@H]1Nc1ccc2c(N3CCC(=O)NC3=O)nn(C)c2c1]

Step 1: Synthesis of 5-((5-chloro-2,6-difluoropyrimidin-4-yl)amino)-1-methylindolin-2-one. To a stirred solution of 5-amino-1-methylindolin-2-one (500 mg, 3.08 mmol) and 5-chloro-2,4,6-trifluoropyrimidine (519 mg, 3.08 mmol) in ACN (25 mL), DIPEA (0.5 mL, 3.08 mmol) was added at 0° C. The reaction mixture was stirred at 0° C. for 2 h. The reaction mixture was quenched with water (10 mL) and extracted with DCM (3×25 mL). The combined organic layers were dried over anhydrous sodium sulfate, filtered, and concentrated under reduced pressure to afford the title compound (550 mg, 1.59 mmol, 52% yield) as an off-white solid.

Step 2: Synthesis of 1-(6-(((3R,4R)-1-(5-chloro-4-fluoro-6-((1-methyl-2-oxoindolin-5-yl)amino)pyrimidin-2-yl)-3-methoxypiperidin-4-yl)amino)-1-methyl-1H-indazol-3-yl) dihydropyrimidine-2,4(1H,3H)-dione. The title compound was synthesized according to General Procedure 6 using 1-(6-(((3R,4R)-3-methoxypiperidin-4-yl)amino)-1-methyl-1H-indazol-3-yl)dihydropyrimidine-2,4(1H,3H)-dione (150 mg, 0.39 mmol) and 5-((5-chloro-2,6-difluoropyrimidin-4-yl)amino)-1-methylindolin-2-one (148 mg, 0.43 mmol) as starting materials. LCMS [M+H]$^+$ found 663.2; $^1$H NMR (400 MHz, DMSO-d$_6$): δ 10.45 (s, 1H), 8.99 (s, 1H), 7.45-7.49 (m, 2H), 7.29 (d, J=8.80 Hz, 1H), 6.93 (d, J=8.40 Hz, 1H), 6.56 (q, J=1.60 Hz, 1H), 6.44 (d, J=1.20 Hz, 1H), 5.91 (d, J=8.00 Hz, 1H), 4.12 (d, J=12.40 Hz, 1H), 3.86 (t, J=6.80 Hz, 3H), 3.81 (s, 3H), 3.60-3.63 (m, 1H), 3.53 (s, 2H), 3.41-3.47 (m, 2H), 3.31-3.28 (m, 3H), 3.19 (s, 1H), 3.10 (s, 3H), 2.72 (t, J=6.80 Hz, 2H), 2.01-2.07 (m, 1H), 1.50-1.60 (m, 1H).

Example S159. Synthesis of Synthesis of 3-(6-(((3R,4R)-1-(5-chloro-4-fluoro-6-((1-methyl-2-oxoindolin-5-yl)amino)pyrimidin-2-yl)-3-methoxypiperidin-4-yl)amino)-1-methyl-1H-indazol-3-yl)-3-methylpiperidine-2,6-dione (159)

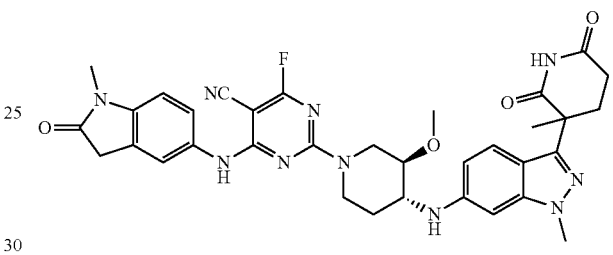

Step 1: Synthesis of 3-(6-(((3R,4R)-1-(5-chloro-4-fluoro-6-((1-methyl-2-oxoindolin-5-yl)amino)pyrimidin-2-yl)-3-methoxypiperidin-4-yl)amino)-1-methyl-1H-indazol-3-yl)-3-methylpiperidine-2,6-dione. The title compound was synthesized according to General Procedure 6 using 3-(6-(((3R,4R)-3-methoxypiperidin-4-yl)amino)-1-methyl-1H-indazol-3-yl)-3-methylpiperidine-2,6-dione (150 mg, 0.30 mmol) and 5-((5-chloro-2,6-difluoropyrimidin-4-yl)amino)-1-methylindolin-2-one (93 mg, 0.30 mmol) as starting materials. LCMS [M+H]$^+$ found 676.2; $^1$H NMR (400 MHz, DMSO-d$_6$): δ 10.77 (s, 1H), 9.00 (s, 1H), 7.52-7.44 (m, 3H), 6.98-6.91 (m, 1H), 6.62-6.55 (m, 1H), 6.50-6.41 (m, 1H), 6.02-5.83 (m, 1H), 4.12-4.07 (m, 1H), 3.92-3.84 (m, 1H), 3.80 (s, 3H), 3.52-3.47 (m, 5H) 3.35-3.25 (m, 3H), 3.25-3.14 (m, 2H), 3.11 (s, 3H), 2.48-2.39 (m, 2H), 2.11-1.98 (m, 2H), 1.59 (s, 3H), 1.45-1.35 (m, 1H).

BIOLOGICAL EXAMPLES

Example B1. BCL6_HiBiT Degradation Assay

A DHL-4 cell line with HiBiT-tag knocked into endogenous BCL6 locus using CRISPR was generated. The DHL-4_BCL6_HiBiT cells were dispensed into 384-well plates (Corning no. 3570) that were pre-spotted with compounds. Compounds were dispensed by an acoustic dispenser (ATS acoustic transfer system from EDC Biosystems) into a 384-well plate in a 10-point dose response curve using 3-fold dilutions starting at 1-10 μM and going down to 0.0015-0.00015 μM. 25 μL of media (RPMI-1640+10% heat inactivated FBS+1×Pen/Strep) containing 2500 of DHL-4 was dispensed per well. Assay plates were incubated at 37° C. with 5% CO$_2$ for 2 hours. After incubation, 25 μL of the Nano-Glo HiBiT lytic detection working solution (Promega, catalogue no. N3040, Madison, WI) was added to each well and incubated at room temperature for 15-30 min, protected from light. After 30 min, luminescence was read on an Envision or PHERAstar luminescence reader. To determine the $EC_{50}$ value (the half-maximum effective concentration) and the level of the gradation (Yconstant) of a BCL6 degrader, luminescent signal normalized by DMSO control (Y) and compound concentration (x) was fitted using a four-parameter dose-response model $(Y=(A+((B-A)/1+((C/x)^{\wedge}D))$ in Dotmatics. Fitted value C is the degradation $EC_{50}$ and the minimum value A is the Y constant.

The degradation of BCL6 at 2 h in DHL-4 results are shown in Table 5, where $EC_{50}$ is the half maximal effect and $Y_{con}$ is the % remaining maximal effect.

TABLE 5

| Compound No. | $EC_{50}$ | $Y_{Con}$ |
|---|---|---|
| 1 | ** | ^^ |
| 2 | * | ^^^ |
| 3 | ** | ^ |
| 4 | * | ^^^ |
| 5 | * | ^ |
| 6 | * | ^ |
| 7 | *** | ^ |
| 8 | * | ^ |
| 9 | * | ^ |
| 10 | ** | ^^ |
| 11 | * | ^ |
| 12 | * | ^^^ |
| 13 | *** | ^ |
| 14 | * | ^ |
| 15 | ** | ^ |
| 16 | * | ^^ |
| 17 | *** | ^ |
| 18 | *** | ^ |
| 19 | * | ^^ |
| 20 | * | ^^ |
| 21 | *** | ^ |
| 22 | *** | ^ |
| 23 | ** | ^ |
| 24 | *** | ^ |
| 25 | *** | ^ |
| 26 | *** | ^ |
| 27 | *** | ^ |
| 28 | *** | ^ |
| 29 | * | ^^^ |
| 30 | *** | ^ |
| 31 | *** | ^ |
| 32 | *** | ^ |
| 33 | * | ^^^ |
| 34 | *** | ^ |
| 35 | *** | ^ |
| 36 | * | ^ |
| 37 | *** | ^ |
| 38 | *** | ^ |
| 39 | *** | ^ |
| 40 | * | ^ |
| 41 | * | ^^ |
| 42 | * | ^^ |
| 43 | * | ^ |
| 44 | *** | ^ |
| 45 | * | ^^ |
| 46 | *** | ^ |
| 47 | *** | ^ |
| 48 | *** | ^ |
| 49 | *** | ^ |
| 50 | *** | ^ |
| 51 | ** | ^^ |
| 52 | * | ^^ |
| 53 | * | ^^ |
| 54 | * | ^ |
| 55 | * | ^^ |
| 56 | * | ^^^ |
| 57 | * | ^ |
| 58 | * | ^^ |
| 59 | *** | ^ |
| 60 | *** | ^ |
| 61 | * | ^^^ |
| 62 | * | ^^^ |
| 63 | * | ^ |
| 64 | * | ^ |
| 65 | * | ^ |
| 66 | *** | ^ |
| 67 | * | ^^ |
| 68 | * | ^^ |
| 69 | * | ^^^ |
| 70 | * | ^^^ |
| 71 | * | ^^^ |
| 72 | * | ^^^ |
| 73 | * | ^^^ |
| 74 | * | ^^ |
| 75 | * | ^^^ |
| 76 | * | ^^^ |
| 77 | * | ^^^ |
| 78 | * | ^^ |
| 79 | * | ^^^ |
| 80 | ** | ^ |
| 81 | * | ^^^ |
| 82 | * | ^^^ |
| 83 | * | ^^ |
| 84 | * | ^ |
| 85 | * | ^^^ |
| 86 | * | ^^^ |
| 87 | * | ^ |
| 88 | * | ^ |
| 89 | * | ^ |
| 90 | * | ^ |
| 91 | * | ^ |
| 92 | * | ^^^ |
| 93 | * | ^^^ |
| 94 | * | ^^^ |
| 95 | * | ^^^ |
| 96 | * | ^^^ |
| 97 | * | ^^^ |
| 98 | * | ^^^ |
| 99 | * | ^^^ |
| 100 | * | ^^^ |
| 101 | * | ^^^ |
| 102 | * | ^^^ |
| 103 | * | ^^^ |
| 104 | * | ^^^ |
| 105 | * | ^^^ |
| 106 | * | ^^^ |
| 107 | * | ^^^ |
| 108 | * | ^^^ |
| 109 | ** | ^^^ |
| 110 | * | ^^^ |
| 111 | * | ^^^ |
| 112 | * | ^^^ |
| 113 | * | ^^^ |
| 114 | * | ^^^ |
| 115 | * | ^^^ |
| 116 | * | ^^^ |
| 117 | * | ^^^ |
| 118 | * | ^^^ |
| 119 | * | ^^^ |
| 120 | * | ^^^ |
| 121 | * | ^^^ |
| 122 | * | ^^^ |
| 123 | * | ^^^ |
| 124 | *** | ^ |
| 125 | *** | ^ |
| 126 | ** | ^^ |
| 127 | * | ^^ |
| 128 | * | ^^ |
| 129 | * | ^^ |
| 130 | * | ^ |
| 131 | * | ^^^ |
| 132 | * | ^^^ |
| 133 | *** | ^ |
| 134 | *** | ^ |
| 135 | * | ^ |
| 136 | * | ^ |
| 137 | ** | ^^ |
| 138 | * | ^ |
| 139 | ** | ^^^ |
| 140 | ** | ^^^ |

TABLE 5-continued

| Compound No. | EC$_{50}$ | Y$_{Con}$ |
|---|---|---|
| 141 | * | ^^^ |
| 142 | * | ^^^ |
| 143 | * | ^^^ |
| 144 | * | ^ |
| 145† | * | ^^ |
| 146 | * | ^^ |
| 147 | * | ^ |
| 148 | * | ^ |
| 149 | * | ^^ |
| 150† | ** | ^^ |
| 151† | * | ^^^ |
| 152† | ** | ^ |
| 153† | * | ^^^ |
| 154 | * | ^^ |
| 155 | * | ^^ |
| 156 | * | ^^ |
| 157 | ** | ^^ |
| 158 | * | ^^ |
| 159 | * | ^^ |

\* <0.1 μM
\*\* 0.1 to 1 μM
\*\*\* >1 μM
^ >60%
^^ 20-60%
^^^ <20%
†Data from 24 h degradation assay Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of the following structural formula:

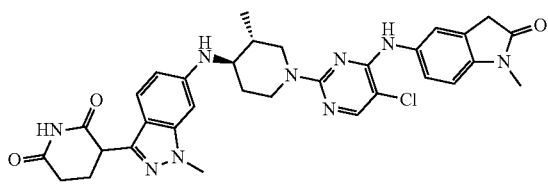 [SMILES: C[C@@H]1CN(c2ncc(Cl)c(Nc3ccc4c(c3)CC(=O)N4C)n2)CC[C@H]1Nc1ccc2c(C3CCC(=O)NC3=O)nn(C)c2c1]

or a pharmaceutically acceptable salt thereof.

2. A compound of the following structural formula:

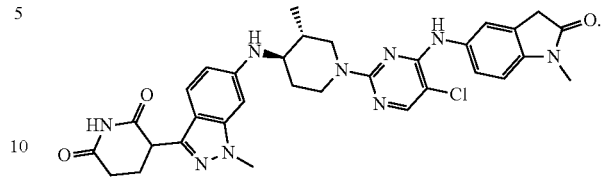

3. A pharmaceutical composition comprising the compound of claim 1, or a pharmaceutically acceptable salt thereof, and a pharmaceutically acceptable excipient.

4. A pharmaceutical composition comprising the compound of claim 2 and a pharmaceutically acceptable excipient.

5. A method of treating Non-Hodgkin's lymphoma in a subject in need thereof, comprising administering to the subject an effective amount of the compound of claim 1 or a pharmaceutically acceptable salt thereof.

6. A method of treating Diffuse Large B-cell Lymphoma in a subject in need thereof, comprising administering to the subject an effective amount of the compound of claim 1 or a pharmaceutically acceptable salt thereof.

7. A method of treating follicular lymphoma in a subject in need thereof, comprising administering to the subject an effective amount of the compound of claim 1 or a pharmaceutically acceptable salt thereof.

8. A method of treating Non-Hodgkin's lymphoma in a subject in need thereof, comprising administering to the subject an effective amount of the compound of claim 2.

9. A method of treating Diffuse Large B-cell Lymphoma in a subject in need thereof, comprising administering to the subject an effective amount of the compound of claim 2.

10. A method of treating follicular lymphoma in a subject in need thereof, comprising administering to the subject an effective amount of the compound of claim 2.

\* \* \* \* \*

UNITED STATES PATENT AND TRADEMARK OFFICE
CERTIFICATE OF CORRECTION

| | | |
|---|---|---|
| PATENT NO. | : 12,404,239 B2 | Page 1 of 1 |
| APPLICATION NO. | : 18/140129 | |
| DATED | : September 2, 2025 | |
| INVENTOR(S) | : Dehua Huang et al. | |

It is certified that error appears in the above-identified patent and that said Letters Patent is hereby corrected as shown below:

On the Title Page

Column 2, Item (56) "Other Publications", Line 14, please replace "2007" with --2017--.

Signed and Sealed this
Twenty-eighth Day of October, 2025

John A. Squires
*Director of the United States Patent and Trademark Office*